United States Patent
Yamagishi et al.

(10) Patent No.: US 9,051,296 B2
(45) Date of Patent: Jun. 9, 2015

(54) ARYL CARBOXAMIDE DERIVATIVES AS TTX-S BLOCKERS

(75) Inventors: Tatsuya Yamagishi, Aichi (JP); Yoshimasa Arano, Aichi (JP); Mikio Morita, Aichi (JP); Tadashi Inoue, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 49 days.

(21) Appl. No.: 13/509,442

(22) PCT Filed: Nov. 16, 2010

(86) PCT No.: PCT/JP2010/006723
§ 371 (c)(1),
(2), (4) Date: May 23, 2012

(87) PCT Pub. No.: WO2011/058766
PCT Pub. Date: May 19, 2011

(65) Prior Publication Data
US 2012/0232052 A1 Sep. 13, 2012

Related U.S. Application Data

(60) Provisional application No. 61/272,893, filed on Nov. 16, 2009, provisional application No. 61/282,181, filed on Dec. 28, 2009.

(51) Int. Cl.

| | | |
|---|---|---|
| *A61K 31/435* | (2006.01) | |
| *A01N 43/40* | (2006.01) | |
| *C07D 221/04* | (2006.01) | |
| *C07D 401/06* | (2006.01) | |
| *A61K 31/44* | (2006.01) | |
| *A61K 31/445* | (2006.01) | |
| *A61K 31/4525* | (2006.01) | |
| *A61K 31/4535* | (2006.01) | |
| *A61K 31/454* | (2006.01) | |
| *A61K 31/4545* | (2006.01) | |
| *A61K 31/4709* | (2006.01) | |
| *A61K 31/4725* | (2006.01) | |
| *A61K 31/4745* | (2006.01) | |
| *A61K 31/498* | (2006.01) | |
| *A61K 31/4985* | (2006.01) | |
| *A61K 31/506* | (2006.01) | |

(Continued)

(52) U.S. Cl.
CPC ............ *C07D 401/06* (2013.01); *A61K 31/435* (2013.01); *A61K 31/44* (2013.01); *A61K 31/445* (2013.01); *A61K 31/4525* (2013.01); *A61K 31/4535* (2013.01); *A61K 31/454* (2013.01); *A61K 31/4545* (2013.01); *A61K 31/4709* (2013.01); *A61K 31/4725* (2013.01); *A61K 31/4745* (2013.01); *A61K 31/498* (2013.01); *A61K 31/4985* (2013.01); *A61K 31/506* (2013.01); *A61K 31/519* (2013.01); *A61K 31/5383* (2013.01); *C07D 211/46* (2013.01); *C07D 401/10* (2013.01); *C07D 401/12* (2013.01); *C07D 401/14* (2013.01); *C07D 405/06* (2013.01); *C07D 405/12* (2013.01); *C07D 405/14* (2013.01); *C07D 409/06* (2013.01); *C07D 413/06* (2013.01); *C07D 417/06* (2013.01); *C07D 417/10* (2013.01); *C07D 455/04* (2013.01); *C07D 471/04* (2013.01); *C07D 471/06* (2013.01); *C07D 487/04* (2013.01); *C07D 491/048* (2013.01); *C07D 495/04* (2013.01); *C07D 498/04* (2013.01); *C07D 513/04* (2013.01)

(58) Field of Classification Search
USPC ............ 514/277; 546/100; 548/400; 549/400
See application file for complete search history.

(56) References Cited

U.S. PATENT DOCUMENTS

| | | |
|---|---|---|
| 4,889,864 A | 12/1989 | Ehrhardt et al. |
| 4,956,359 A | 9/1990 | Taylor, Jr. et al. |

(Continued)

FOREIGN PATENT DOCUMENTS

| | | |
|---|---|---|
| EP | 0 194 112 | 9/1986 |
| EP | 0 270 074 | 6/1988 |

(Continued)

OTHER PUBLICATIONS

Banker et al (1997).*

(Continued)

*Primary Examiner* — Paul V Ward
(74) *Attorney, Agent, or Firm* — Wenderoth, Lind & Ponack, L.L.P.

(57) ABSTRACT

The present invention relates to aryl carboxamide derivatives of formula (I), wherein $Ar^1$ is phenyl; $Ar^2$ is aryl; n is 1-4; X is —O—, —S—, —SO— or —SO$_2$—, a prodrug thereof or a pharmaceutically acceptable salt thereof, which have blocking activities of voltage gated sodium channels as the TTX-S channels, and which are useful in the treatment or prevention of such disorders and diseases as pain in which voltage gated sodium channels are involved. The invention also relates to pharmaceutical compositions comprising these compounds and the use of these compounds and compositions in the prevention or treatment of such diseases as pain in which voltage gated sodium channels are involved.

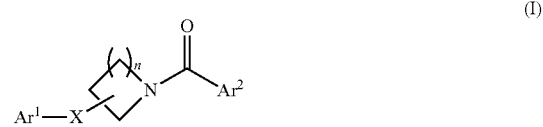

(I)

6 Claims, No Drawings

(51) Int. Cl.

| | | |
|---|---|---|
| *A61K 31/519* | (2006.01) | |
| *A61K 31/5383* | (2006.01) | |
| *C07D 211/46* | (2006.01) | |
| *C07D 401/10* | (2006.01) | |
| *C07D 401/12* | (2006.01) | |
| *C07D 401/14* | (2006.01) | |
| *C07D 405/06* | (2006.01) | |
| *C07D 405/12* | (2006.01) | |
| *C07D 405/14* | (2006.01) | |
| *C07D 409/06* | (2006.01) | |
| *C07D 413/06* | (2006.01) | |
| *C07D 417/06* | (2006.01) | |
| *C07D 417/10* | (2006.01) | |
| *C07D 455/04* | (2006.01) | |
| *C07D 471/04* | (2006.01) | |
| *C07D 471/06* | (2006.01) | |
| *C07D 487/04* | (2006.01) | |
| *C07D 491/048* | (2006.01) | |
| *C07D 495/04* | (2006.01) | |
| *C07D 498/04* | (2006.01) | |
| *C07D 513/04* | (2006.01) | |

(56) References Cited

U.S. PATENT DOCUMENTS

| | | |
|---|---|---|
| 4,977,165 A | 12/1990 | Oinuma et al. |
| 5,068,231 A | 11/1991 | Taylor, Jr. et al. |
| 5,082,850 A | 1/1992 | Oinuma et al. |
| 5,151,418 A | 9/1992 | Taylor, Jr. et al. |
| 5,162,347 A | 11/1992 | Oinuma et al. |
| 5,183,902 A | 2/1993 | Taylor, Jr. et al. |
| 5,246,946 A | 9/1993 | Oinuma et al. |
| 6,335,445 B1 | 1/2002 | Chabrier de Lassauniere et al. |
| 2002/0007062 A1 | 1/2002 | Chabrier de Lassauniere et al. |
| 2002/0042511 A1 | 4/2002 | Chabrier de Lassauniere et al. |
| 2002/0045753 A1 | 4/2002 | Chabrier de Lassauniere et al. |
| 2003/0078420 A1 | 4/2003 | Chabrier de Lassauniere et al. |
| 2005/0043397 A1 | 2/2005 | Chabrier de Lassauniere et al. |
| 2005/0187272 A1 | 8/2005 | De Lassauniere et al. |
| 2006/0035938 A1 | 2/2006 | Bladh et al. |
| 2007/0027163 A1 | 2/2007 | Bissantz et al. |
| 2008/0021022 A1 | 1/2008 | Bartberger et al. |
| 2008/0027050 A1 | 1/2008 | Terauchi et al. |
| 2008/0182993 A1 | 7/2008 | Chabrier de Lassauniere et al. |
| 2009/0012118 A1 | 1/2009 | Borza et al. |
| 2009/0143358 A1 | 6/2009 | Marron et al. |
| 2009/0192156 A1 | 7/2009 | Menear et al. |
| 2009/0197859 A1 | 8/2009 | Collantes et al. |
| 2010/0143341 A1 | 6/2010 | Taylor et al. |
| 2010/0160280 A1 | 6/2010 | Allen et al. |
| 2010/0204265 A1 | 8/2010 | Baskaran et al. |
| 2010/0222357 A1 | 9/2010 | Bissantz et al. |
| 2010/0234351 A1 | 9/2010 | Seto et al. |
| 2010/0292206 A1 | 11/2010 | Kasai et al. |
| 2011/0263571 A1 | 10/2011 | Ishibuchi et al. |

FOREIGN PATENT DOCUMENTS

| | | |
|---|---|---|
| EP | 0 304 888 | 3/1989 |
| EP | 2 065 369 | 6/2009 |
| GB | 2 310 660 | 9/1997 |
| JP | 10-17564 | 1/1998 |
| WO | 95/02405 | 1/1995 |
| WO | 98/58934 | 12/1998 |
| WO | 01/21598 | 3/2001 |
| WO | 02/34718 | 5/2002 |
| WO | 2004/043924 | 5/2004 |
| WO | 2005/105760 | 11/2005 |
| WO | 2006/010967 | 2/2006 |
| WO | 2006/136402 | 12/2006 |
| WO | 2007/014851 | 2/2007 |
| WO | 2007/097470 | 8/2007 |
| WO | 2008/011453 | 1/2008 |
| WO | 2008/029084 | 3/2008 |
| WO | 2008-118758 | 10/2008 |
| WO | 2009/023179 | 2/2009 |
| WO | 2009/051244 | 4/2009 |
| WO | 2009/093032 | 7/2009 |
| WO | 2009/098576 | 8/2009 |
| WO | 2009/105722 | 8/2009 |
| WO | 2009/112845 | 9/2009 |
| WO | 2010/050461 | 5/2010 |
| WO | 2010/074588 | 7/2010 |
| WO | 2010/077992 | 7/2010 |
| WO | 2010/091409 | 8/2010 |
| WO | 2010/124082 | 10/2010 |
| WO | 2010/124086 | 10/2010 |
| WO | 2010/124108 | 10/2010 |
| WO | 2010/124112 | 10/2010 |
| WO | 2010/124114 | 10/2010 |
| WO | 2010/124116 | 10/2010 |
| WO | 2010/124119 | 10/2010 |
| WO | 2010/137351 | 12/2010 |

OTHER PUBLICATIONS

Wolff et al. (1997).*

English translation of the International Preliminary Report on Patentability and Written Opinion dated May 22, 2012.

International Search Report issued Dec. 21, 2010 in International (PCT) Application No. PCT/JP2010/006723 along with the Written Opinion.

P. Ghosh et al., "Comparative QSAR Studies of Nitrofuranyl Amide Derivatives using Theoretical Structural Properties", Molecular Simulation, vol. 35, Nos. 14-15, pp. 1185-1200, Dec. 2009, Abstract, p. 1187, N-3.

K. E. Hevener et al., "Quantitative Structure-Activity Relationship Studies on Nitrofuranyl Anti-Tubercular Agents", Bioorganic & Medicinal Chemistry, vol. 16, No. 17, pp. 8042-8053, 2008, Abstract, p. 8049, Figure 6.

N. R. Budha et al., "Pharmacokinetically-Guided Lead Optimization of Nitrofuranylamide Anti-Tuberculosis Agents", The APPS Journal, vol. 10, No. 1, pp. 157-165, Mar. 2008, Abstract, p. 162, Fig. 3.

I. Borza et al., "Selective NR1/2B N-Methyl-D-Aspartate Receptor Antagonists Among Indole-2-Carboxamides and Benzimidazole-2-Carboxamides", J. Med. Chem., vol. 50, No. 5, pp. 901-914, 2007, Abstract, p. 906, Table 6, p. 908, Table. 8.

I. Borza et al., "Kynurenic Acid Amides as Novel NR2B Selective NMDA Receptor Antagonists", Bioorganic & Medicinal Chemistry Letters, vol. 17, No. 2, pp. 406-409, 2007, Abstract, p. 408, Table 1.

I. Borza et al., "Benzimidazole-2-Carboxamides as Novel NR2B Selective NMDA Receptor Antagonists", Bioorganic & Medicinal Chemistry Letters, vol. 16, No. 17, pp. 4638-4640, 2006, Abstract, p. 4640, Table 1.

* cited by examiner

ARYL CARBOXAMIDE DERIVATIVES AS TTX-S BLOCKERS

This application is a U.S. national stage of International Application No. PCT/JP2010/006723 filed Nov. 16, 2010, which claims the benefit of U.S. provisional application Ser. No. 61/272,893 filed Nov. 16, 2009 and Ser. No. 61/282,181 filed Dec. 28, 2009.

TECHNICAL FIELD

The present invention relates to aryl carboxamide derivatives compounds which are tetrodotoxin-sensitive (TTX-S) blockers over the $Na_{v1.5}$ channel, and which are useful in the treatment or prevention of neurological and psychiatric disorders and diseases in which TTX-S channels are involved. The invention also relates to pharmaceutical compositions comprising these compounds and the use of these compounds and compositions in the prevention or treatment of such diseases in which TTX-S sodium channels are involved.

BACKGROUND ART

The aryl carboxamide derivatives of the present invention are sodium channel blockers and have a number of therapeutic applications, particularly in the treatment of pain.

More particularly, the aryl carboxamide derivatives of the invention are selective tetrodotoxin-sensitive (TTX-S) blockers. In the discussion that follows, the invention is exemplified by reference to the inhibition of $Na_{v1.3}$ or $Na_{v1.7}$ channel as the TTX-S channels. They show the affinity for $Na_{v1.3}$ or $Na_{v1.7}$ channel which is significantly greater than their affinity for $Na_{v1.5}$ channel as the tetrodotoxin-resistant (TTX-R) sodium channels. Aryl carboxamide derivatives of the invention show good selectivity for the $Na_{v1.3}$ or $Na_{v1.7}$ channel as compared with $Na_{v1.5}$ channel.

The rat $Na_{v1.3}$ channel and the human $Na_{v1.3}$ channel have been cloned in 1988 and 1998/2000 respectively (FEBS Lett. 228 (1), 187-194, 1988; J. Mol. Neurosci., 10 (1), 67-70, 1998; Eur. J. Neurosci. 12 (12), 4281-4289, 2000). The $Na_{v1.3}$ channel was formerly known as brain type III sodium channel. $Na_{v1.3}$ is present at relatively high levels in the nervous system of rat embryos but is barely detectable in adult rats. $Na_{v1.3}$ is up-regulated following axotomy in the Spinal Nerve Ligation (SNL), Chronic Constriction Injury (CCI), and diabetic neuropathy models (J Neurophysiol 82, 2776-2785, 1999. J. A. Black et al.; Ann Neurol 52, 786-792, 2002. M. J. Cranner et al.; Pain 83, 591-600, 1999. S. Dib-Hajj et al.; J Biol Chem 279, 29341-29350, 2004. S. Hong et al.; Mol Brain Res 95, 153-161, 2001. C. H. Kim et al.). The up-regulation of $Na_{v1.3}$ channel contributes to rapidly repriming sodium current in small dorsal root ganglion (DRG) neurons (J Neurophysiol 82, 2776-2785, 1999. J. A. Black et al.). These observations suggest that $Na_{v1.3}$ may make a key contribution to neuronal hyperexcitability.

In order to validate the contribution of $Na_{v1.3}$ sodium channel in the pain states, specific antisense oligonucleotides (ASO) were used in animal pain models. $Na_{v1.3}$ sodium channel ASO treatment significantly attenuated pain-related behaviors after CCI operation (J. Neurosci. 24, 4832-4839, 2004, Haim, B. C. et al.). These finding suggest that $Na_{v1.3}$ sodium channel antagonist is useful to treat neuropathic pain conditions.

The $Na_{v1.7}$ channel appears to be the best 'validated' pain target. The most exciting findings with respect to $Na_{v1.7}$ have come from human genetic studies. Cox et al. (Nature 444, 894-898, 2006) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both TTX-R and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (Trends in Pharm. Sci 22, 27-31, 2001, Baker, M. D. et al.). In rats, application of a very low dose of TTX to the DRG of the injured segment of the L5 spinal nerve significantly reduces mechanical allodynic behavior (Brain Res 871, 98-103, 2000, Lyu, Y. S. et al.). This suggests that TTX-S subtypes of sodium channels play an important role in maintaining allodynic behaviors in an animal model of neuropathic pain.

The $Na_{v1.5}$ channel is also a member of TTX-resistant sodium channels. The $Na_{v1.5}$ channel is almost exclusively expressed in cardiac tissue and has been shown to underlie a variety of cardiac arrhythmias and conduction disorders.

SUMMARY OF INVENTION

It is an objective of the invention to provide new TTX-S blockers that are good drug candidates. Preferred compounds should bind potently to the TTX-S ($Na_{v1.3}$ and $Na_{v1.7}$) channels whilst showing little affinity for other sodium channels, particularly the $Na_{v1.5}$ channel. They should be well absorbed from the gastrointestinal tract, be metabolically stable and possess favorable pharmacokinetic properties. They should be non-toxic and demonstrate few side-effects. Furthermore, the ideal drug candidate will exist in a physical form that is stable, non-hygroscopic and easily formulated.

In particular, the aryl carboxamide derivatives of the present invention are selective for the TTX-S channels over the $Na_{v1.5}$ channel, leading to improvements in the side-effect profile.

The aryl carboxamide derivatives of the present invention are therefore useful in the treatment of a wide range of disorders, particularly pain, acute pain, chronic pain, neuropathic pain, inflammatory pain, visceral pain, nociceptive pain including postsurgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the aryl carboxamide derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

Although WO 2003/037274 discloses pyrazol amide compounds which have sodium channel blocking activities, the phenoxy group is not included in the patent. WO 2003/084948 also discloses compounds which have sodium channel blocking activities. The compounds of the invention, which are represented by the formula $A^1-X^1-X^2-Z^1-X^3-X^4-A^2$ in claim 1, involve an extremely large number of compounds. However the compounds which are disclosed in the meaning of Article 5 of the PCT and are supported by the description in the meaning of Article 6 of the PCT are limited to an extremely small part of the compounds claimed. Especially an amide moiety is formally included in the said broad formula in claim 1, but neither actual working examples nor embodiments in the specification. In addition, the representative compound, Example 198 (3-((4-(phenoxymethyl)piperidin-1-yl)methyl)pyrazin-2(1H)-one), in WO 2003/084948 showed >30 microM and 15 microM against $Na_{v1.3}$ and $Na_{v1.7}$, respectively in FRET Assay (Method A) described in the present patent application, whereas the compounds of this invention showed <5 microM.

The compounds of this invention characterized by having phenoxy, phenylthio, phenylsulfoxy, or phenylsulfonyl group and amide group are novel, and are quite different from the prior arts. In addition the compounds of this invention with an amide group greatly contribute improving the selectivity for the $Na_{v1.3}$ or $Na_{v1.7}$ channel as compared with $Na_{v1.5}$ channel. Furthermore the compounds with an amide group surprisingly reduced the dofetilide binding activities, which reduce the risk of cardiovascular adverse events.

Structurally close compounds are disclosed in WO 2002/34718, WO 2006/010967, US 2007/0027163, WO 2007/082079 and WO2009/105722, which are not for sodium channel blockers of this invention but for quite different biological targets. Particularly although WO 2007/082079 discloses 4-pyridyl compounds as protein kinase inhibitors, the 4-pyridyl compounds of this invention with terminal chloro, trifluoromethyl, trifluoromethoxy, trifluoroethoxy or ethoxy phenyl ring showed excellent sodium channel blocking activities.

With respect to other compounds disclosed in the art, the compounds of the present invention may show less toxicity, good absorption, distribution, good solubility, less plasma protein binding, less drug-drug interaction, good metabolic stability, reduced inhibitory activity at HERG channel, and reduced QT prolongation.

The present invention is directed to aryl carboxamide derivatives compounds which are TTX-S blockers over the $Na_{v1.5}$ channel, and which are useful in the treatment or prevention of neurological and psychiatric disorders and diseases in which TTX-S channels are involved. The invention is also directed to pharmaceutical compositions comprising these compounds and the use of these compounds and compositions in the prevention or treatment of such diseases in which TTX-S sodium channels are involved.

[1] The present invention provides a use of a compound of the following formula (I) for the manufacture of a medicament for the treatment of a condition or disorder in which TTX-S channel blockers are involved:

[Chem.1]

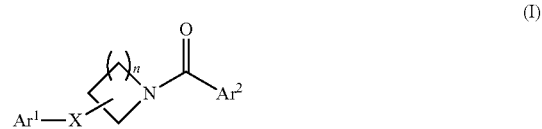

(I)

wherein
$Ar^1$ is phenyl which may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$— (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C$(=O)—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C$(=O)NH—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro;

$Ar^2$ is aryl which may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$— (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C$(=O)—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C$(=O)NH—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro;

n is 1, 2, 3 or 4;

i is 0 or 1;

k is 0 or 1;

$R^1$ and $R^2$ are independently selected from the group consisting of:

(1) hydrogen, (2) $C_{1-6}$ alkyl, (3) hydroxy $C_1$-$C_4$ alkyl, (4) $C_1$-$C_4$ alkoxy $C_1$-$C_4$ alkyl, (5) amino $C_1$-$C_4$ alkyl, (6) $C_1$-$C_4$ haloalkyl, (7) $C_1$-$C_4$ haloalkoxy, (8) $C_{3-6}$ alkenyl, (9) $C_{3-8}$ cycloalkyl $C_{0-6}$ alkyl, (10) phenyl, which is unsubstituted or substituted with $R^3$, and (11) 5 to 10 membered aryl $C_0$-$C_4$ alkyl; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, and nitro;

or $R^1$ and $R^2$ taken together with the nitrogen atom to which they are attached form a 3 to 8 membered ring, where the ring may contain one to four heteroatom(s) independently selected from nitrogen, oxygen, and sulfur; where the ring may be saturated or partially saturated or unsaturated; and the ring is unsubstituted or substituted one or more substituents selected from $R^3$;

$R^3$ is selected from the group consisting of:

(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocyclic group, (10) —$CO_2$H, and (11) —CN;

X is —O—, —S—, —SO—, or —$SO_2$—;

or a prodrug thereof or a pharmaceutically acceptable salt thereof, each as described herein, for the manufacture of a medicament for the treatment of a condition or disorder mediated by TTX-S channel; in particular, $Na_{V1.3}$ channels blocking activity. In order to use the compounds of formula (I), prodrugs thereof, and pharmaceutically acceptable salts thereof in therapy, they will normally be formulated into a pharmaceutical composition in accordance with standard pharmaceutical practice.

[2] This invention provides the use of a compound as described in formula (I) wherein Are is aryl selected from benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, chromanyl, cinnolinyl, 2,3-dioxoindolyl, furanyl, furopyridyl, furopyrrolyl, imidazolyl, imidazopyrazinyl, imidazopyridinyl, imidazopyrimidinyl, imidazothiazolyl, indazolyl, indolinyl, indolyl, isochromanyl, isoquinolyl, isoxazolopyridyl, isoxazolyl, isothiazolyl, naphthyridinyl, oxadiazolyl, oxazolyl, 2-oxoindolyl, oxoisoindolyl, phthalazyl, pyrazolyl, pyrazolopyridyl, pyrazolopyrimidinyl, pyrazinyl, pyridopyrimidinyl, pyridyl, pyrimidyl, pyridazinyl, pyrrolopyridyl, pyrrolyl, quinazolinyl, quinolyl, quinoxalinyl, thiazolyl, thiophenyl, thienopyrazinyl, thienopyrazolyl, thienopyridyl, thienopyrrolyl, triazolopyrimidinyl, triazolyl, 3,4-dihydro-2H-pyrido[3,2-b][1,4]oxazinyl, 1-methyl-4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 2-oxo-2,5,6,7-tetrahydro-1H-cyclopentapyridyl, 4,5,6,7-tetrahydro-indazolyl, 4-oxo-1,4-dihydro-1,8-naphthyridyl, and 5,6,7,8-tetrahydro-1,6-naphthyridyl;

and the other descriptors are the same as in the definition described in [1]; or a prodrug thereof or a pharmaceutically acceptable salt thereof.

[3] The present invention also provides the use as described in [1] or [2], wherein the condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia; and combinations thereof.

[4] The present invention provides a compound of formula (I) as described in [1] wherein $Ar^1$ is phenyl which may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(═O)—, (16) HO—C(═O)—, (17) $C_1$-$C_4$ alkyl-O—C(═O)—, (18) $R^1N(R^2)$C(═O)—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(═O)N($R^2$)—$C_{0-4}$ alkyl-$O_k$—, (21) $NH_2$(HN═)C—, (22) $NH_2$C(═O)NH—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$C(═O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(═O)—, $C_1$-$C_4$ alkyl-$SO_2$—NH—, and nitro;

$Ar^2$ is selected from; 3-benzofuranyl, 4-benzofuranyl, 5-benzofuranyl, 6-benzofuranyl, 7-benzofuranyl, benzofurazanyl, benzimidazolonyl, 3-benzoimidazolyl, 4-benzoimidazolyl, 5-benzoimidazolyl, 6-benzoimidazolyl, 7-benzoimidazolyl, benzoisothiazolyl, benzoisoxazolyl, benzothiadiazolyl, 3-benzothiazolyl, 4-benzothiazolyl, 5-benzothiazolyl, 6-benzothiazolyl, 7-benzothiazolyl, benzoxadiazolyl, benzoxazolonyl, 3-benzoxazolyl, 4-benzoxazolyl, 5-benzoxazolyl, 6-benzoxazolyl, 7-benzoxazolyl, 3-benzothiophenyl, 4-benzothiophenyl, 5-benzothiophenyl, 6-benzothiophenyl, 7-benzothiophenyl, benzotriazolyl, chromanyl, cinnolinyl, 2,3-dioxoindolyl, furanyl, furopyridyl, furopyrrolyl, imidazolyl, imidazopyrazinyl, imidazopyridinyl, imidazopyrimidinyl, imidazothiazolyl, indazolyl, indolinyl, 4-indolyl, 5-indolyl, 6-indolyl, 7-indolyl, isochromanyl, isoquinolyl, isoxazolopyridyl, isoxazolyl, isothiazolyl, naphthyridinyl, oxadiazolyl, oxazolyl, 2-oxoindolyl, oxoisoindolyl, phthalazyl, pyrazolyl, pyrazolopyridyl, pyrazolopyrimidinyl, pyrazinyl, pyridopyrimidinyl, 2-pyridyl, 3-pyridyl, 5-pyridyl, 6-pyridyl, pyrimidyl, pyridazinyl, pyrrolopyridyl, pyrrolyl, quinazolinyl, quinolyl, quinoxalinyl, thiazolyl, thiophenyl, thienopyrazinyl, thienopyrazolyl, thienopyridyl, thienopyrrolyl, triazolopyrimidinyl, triazolyl, 3,4-dihydro-2H-pyrido[3,2-b][1,4]oxazinyl, 1-methyl-4-oxo-1,4-dihydroquinolyl, 4-oxo-1,4-dihydropyrimidyl, 2-oxo-1,2-dihydroquinolyl, 4-oxo-4H-pyrido[1,2-a]pyrimidyl, 2-oxo-2,5,6,7-tetrahydro-1H-cyclopentapyridyl, 4,5,6,7-tetrahydroindazolyl, 4-oxo-1,4-dihydro-1,8-naphthyridyl, and 5,6,7,8-tetrahydro-1,6-naphthyridyl wherein said 3-benzofuranyl, 4-benzofuranyl, 5-benzofuranyl, 6-benzofuranyl, 7-benzofuranyl, benzofurazanyl, benzimidazolonyl, 3-benzoimidazolyl, 4-benzoimidazolyl, 5-benzoimidazolyl, 6-benzoimidazolyl, 7-benzoimidazolyl, benzoisothiazolyl, benzoisoxazolyl, benzothiadiazolyl, 3-benzothiazolyl, 4-benzothiazolyl, 5-benzothiazolyl, 6-benzothiazolyl, 7-benzothiazolyl, benzoxadiazolyl, benzoxazolonyl, 3-benzoxazolyl, 4-benzoxazolyl, 5-benzoxazolyl, 6-benzoxazolyl, 7-benzoxazolyl, 3-benzothiophenyl, 4-benzothiophenyl, 5-benzothiophenyl, 6-benzothiophenyl, 7-benzothiophenyl, benzotriazolyl, chromanyl, cinnolinyl, 2,3-dioxoindolyl, furanyl, furopyridyl, furopyrrolyl, imidazolyl, imidazopyrazinyl, imidazopyridinyl, imidazopyrimidinyl, imidazothiazolyl, indazolyl, indolinyl, 4-indolyl, 5-indolyl, 6-indolyl, 7-indolyl, isochromanyl, isoquinolyl, isoxazolopyridyl, isoxazolyl, isothiazolyl, naphthyridinyl, oxadiazolyl, oxazolyl, 2-oxoindolyl, oxoisoindolyl, phthalazyl, pyrazolyl, pyrazolopyridyl, pyrazolopyrimidinyl, pyrazinyl, pyridopyrimidinyl, 2-pyridyl, 3-pyridyl, 5-pyridyl, 6-pyridyl, pyrimidyl, pyridazinyl, pyrrolopyridyl, pyrrolyl, quinazolinyl, quinoxalinyl, thiazolyl, thiophenyl, thienopyrazinyl, thienopyrazolyl, thienopyridyl, thienopyrrolyl, triazolopyrimidinyl, triazolyl, 3,4-dihydro-2H-pyrido[3,2-b][1,4]oxazinyl, 1-methyl-4-oxo-1,4-dihydroquinolyl, 4-oxo-1,4-dihydropyrimidyl, 2-oxo-1,2-dihydroquinolyl, 4-oxo-4H-pyrido[1,2-a]pyrimidyl, 2-oxo-2,5,6,7-tetrahydro-1H-cyclopentapyridyl, 4,5,6,7-tetrahydro-indazolyl, 4-oxo-1,4-dihydro-1,8-naphthyridyl, and 5,6,7,8-tetrahydro-1,6-naphthyridyl may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_1$-$C_4$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C(=O)$—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C(=O)NH$—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, 12'N($R^2$)C(=O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2) C(=O)$—, $C_1$-$C_4$ alkyl-$SO_2$—NH—, and nitro;

said quinolyl may be optionally substituted with 1 to 4 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) 2-hydroxyl, (6) 3-hydroxyl, (7) 5-hydroxyl, (8) 6-hydroxyl, (9) 7-hydroxyl, (10) 8-hydroxyl, (11) $C_3$-$C_8$ cycloalkyl-$C_1$-$C_4$ alkyl-$O_i$—, (12) $C_1$-$C_4$ alkylthio, (13) nitro, (14) $R^1N(R^2)$—$C_{0-4}$ alkyl-$O_i$— (15) cyano, (16) hydroxy $C_1$-$C_4$ alkyl-$O_i$—, (17) $C_1$-$C_4$ alkyl-$O_i$—, (18) $C_1$-$C_4$ alkylsulfonyl, (19) $R^1N(R^2)$—$SO_2$—$C_{0-4}$ alkyl-$O_i$—, (20) $C_1$-$C_4$ alkyl C(=O)—, (21) HO—C(=O)—, (22) $C_1$-$C_4$ alkyl-O—C(=O)—, (23) $R^1N(R^2)C(=O)$—$C_{0-4}$ alkyl-$O_i$—, (24) $C_1$-$C_4$ alkyl-$SO_2$—NH—$C_{0-4}$ alkyl-$O_i$—, (25) $R^1$—O, —C(=O)N($R^2$)—$C_{0-4}$ alkyl-$O_k$—, (26) $NH_2$(HN=)C—, (27) $NH_2C(=O)NH$—, (28) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro; and (29) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro;

n is 1, 2, 3, or 4;

i is 0 or 1;

k is 0 or 1;

$R^1$ and $R^2$ are independently selected from the group consisting of:

(1) hydrogen, (2) $C_{1-6}$ alkyl, (3) hydroxy $C_1$-$C_4$ alkyl, (4) $C_1$-$C_4$ alkoxy $C_1$-$C_4$ alkyl, (5) amino $C_1$-$C_4$ alkyl, (6) $C_1$-$C_4$ haloalkyl, (7) $C_1$-$C_4$ haloalkoxy, (8) $C_{3-6}$ alkenyl, (9) $C_{3-8}$ cycloalkyl $C_{0-6}$ alkyl, (10) phenyl, which is unsubstituted or substituted with $R^3$, and (11) 5 to 10 membered aryl $C_0$-$C_4$ alkyl; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, and nitro;

or $R^1$ and $R^2$ taken together with the nitrogen atom to which they are attached form a 3 to 8 membered ring, where the ring may contain one to four heteroatom(s) independently selected from nitrogen, oxygen, and sulfur; where the ring may be saturated or partially saturated or unsaturated; and the ring is unsubstituted or substituted one or more substituents selected from $R^3$;

$R^3$ is selected from the group consisting of:
(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocyclic group, (10) —$CO_2H$, and (11) —CN;

X is —O—, —S—, —SO—, or —$SO_2$—;

or a prodrug thereof or a pharmaceutically acceptable salt thereof.

[5] The present invention provides a compound of formula (I) as described in [1]

wherein $Ar^1$ is phenyl which is substituted with chloro, trifluoromethyl, trifluoromethoxy, trifluoroethoxy or ethoxy; and which may be substituted with 1 to 2 substituents independently selected from:

(1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C(=O)$—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C(=O)NH$—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro;

$Ar^2$ is 4-pyridyl which may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C(=O)$—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C(=O)NH$—, (23) 5 to 10 membered aryl-$O_i$—$C_0$-$C_4$ alkyl-$O_k$—; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$C(=O)—, $C_1$-$C_4$ alkyl-$SO_2$—NH—, and nitro; and (24) heterocyclic group-$O_i$—$C_0$-$C_4$ alkyl-$O_k$—; wherein said heterocyclic group may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)$ C(=O)—, $C_1$-$C_4$ alkyl-$SO_2$—NH—, and nitro;

n is 1, 2, 3, or 4;

i is 0 or 1;

k is 0 or 1;

$R^1$ and $R^2$ are independently selected from the group consisting of:

(1) hydrogen, (2) $C_{1-6}$ alkyl, (3) hydroxy $C_1$-$C_4$ alkyl, (4) $C_1$-$C_4$ alkoxy $C_1$-$C_4$ alkyl, (5) amino $C_1$-$C_4$ alkyl, (6) $C_1$-$C_4$ haloalkyl, (7) $C_1$-$C_4$ haloalkoxy, (8) $C_{3-6}$ alkenyl, (9) $C_{3-8}$ cycloalkyl $C_{0-6}$ alkyl, (10) phenyl, which is unsubstituted or substituted with $R^3$, and (11) 5 to 10 membered aryl $C_0$-$C_4$ alkyl; wherein said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, and nitro;

or $R^1$ and $R^2$ taken together with the nitrogen atom to which they are attached form a 3 to 8 membered ring, where the ring may contain one to four heteroatom(s) independently selected from nitrogen, oxygen, and sulfur; where the ring may be saturated or partially saturated or unsaturated; and the ring is unsubstituted or substituted one or more substituents selected from $R^3$;

$R^3$ is selected from the group consisting of:

(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocyclic group, (10) —$CO_2H$, and (11) —CN;

X is —O—, —S—, —SO—, or —$SO_2$—;

or a prodrug thereof or a pharmaceutically acceptable salt thereof.

[6] Suitable individual compounds of the invention are:

(4-(4-chlorophenoxy)piperidin-1-yl)(8-hydroxyquinolin-2-yl)methanone;

(4-(2-chlorophenoxy)piperidin-1-yl)(8-hydroxyquinolin-2-yl)methanone;

(4-(3-chlorophenoxy)piperidin-1-yl)(8-hydroxyquinolin-2-yl)methanone;

(8-hydroxyquinolin-2-yl)(4-(o-tolyloxy)piperidin-1-yl)methanone;

(8-hydroxyquinolin-2-yl)(4-(m-tolyloxy)piperidin-1-yl)methanone;

(8-hydroxyquinolin-2-yl)(4-(p-tolyloxy)piperidin-1-yl)methanone;

(4-(4-chlorophenoxy)piperidin-1-yl)(quinolin-2-yl)methanone;

(4-(4-chlorophenoxy)piperidin-1-yl)(4-hydroxyquinolin-2-yl)methanone;

(4-(4-chlorophenoxy)piperidin-1-yl)(quinolin-6-yl)methanone;

(4-(4-chlorophenoxy)piperidin-1-yl)(quinolin-3-yl)methanone;

(4-(4-chlorophenoxy)piperidin-1-yl)(isoquinolin-3-yl)methanone;

(4-(4-chlorophenoxy)piperidin-1-yl)(1,6-naphthyridin-2-yl)methanone;

(4-(4-chlorophenoxy)piperidin-1-yl)(isoquinolin-1-yl)methanone;
(4-(4-chlorophenoxy)piperidin-1-yl)(quinolin-4-yl)methanone;
(4-(4-chlorophenoxy)piperidin-1-yl)(6-(2,2,2-trifluoroethoxy)pyridin-3-yl)methanone;
(4-(4-chlorophenoxy)piperidin-1-yl)(6-methylpyridin-2-yl)methanone;
(4-(4-chlorophenoxy)piperidin-1-yl)(3,5-difluoropyridin-2-yl)methanone;
(4-(4-chlorophenoxy)piperidin-1-yl)(5-methylpyridin-3-yl)methanone;
(4-(4-chlorophenoxy)piperidin-1-yl)(quinoxalin-6-yl)methanone;
(4-(4-chlorophenoxy)piperidin-1-yl)(6-phenoxypyridin-3-yl)methanone;
(4-(4-chlorophenoxy)piperidin-1-yl)(quinolin-8-yl)methanone;
benzo[c]isoxazol-3-yl(4-(4-chlorophenoxy)piperidin-1-yl)methanone;
(4-(4-chlorophenoxy)piperidin-1-yl)(1-isopropyl-1H-benzo[d][1,2,3]triazol-5-yl)methanone;
(4-(4-chlorophenoxy)piperidin-1-yl)(5-fluoro-1H-indol-2-yl)methanone;
(4-(4-chlorophenoxy)piperidin-1-yl)(6-fluoro-1H-indol-2-yl)methanone;
(4-(4-chlorophenoxy)piperidin-1-yl)(5-isobutylisoxazol-3-yl)methanone;
(4-(4-chlorophenoxy)piperidin-1-yl)(2-methyl-5-phenylfuran-3-yl)methanone;
(4-(4-chlorophenoxy)piperidin-1-yl)(3-(2-methylthiazol-4-yl)phenyl)methanone;
(4-(4-chlorophenoxy)piperidin-1-yl)(5-methoxy-1H-indol-2-yl)methanone;
(4-(4-chlorophenoxy)piperidin-1-yl)(1H-indol-4-yl)methanone;
(3-(1H-pyrazol-1-yl)phenyl)(4-(4-chlorophenoxy)piperidin-1-yl)methanone;
(4-(1H-1,2,4-triazol-1-yl)phenyl)(4-(4-chlorophenoxy)piperidin-1-yl)methanone;
(4-(4-chlorophenoxy)piperidin-1-yl)(5-methyl-2-phenyl-2H-1,2,3-triazol-4-yl)methanone;
(4-(4-chlorophenoxy)piperidin-1-yl)(4,5-dichloroisothiazol-3-yl)methanone;
benzofuran-2-yl(4-(4-chlorophenoxy)piperidin-1-yl)methanone; benzo[b]thiophen-2-yl(4-(4-chlorophenoxy)piperidin-1-yl)methanone;
(8-hydroxyquinolin-2-yl)(4-(2-methoxyphenoxy)piperidin-1-yl)methanone;
(4-(4-chlorophenoxy)piperidin-1-yl)(4-methyl-2-phenylpyrimidin-5-yl)methanone;
(4-(4-chlorophenoxy)piperidin-1-yl)(6-phenylpyrimidin-4-yl)methanone;
(4-(4-chlorophenoxy)piperidin-1-yl)(4-methoxyquinolin-2-yl)methanone;
(4-(4-chlorophenoxy)piperidin-1-yl)(quinoxalin-2-yl)methanone; benzo[d]thiazol-6-yl(4-(4-chlorophenoxy)piperidin-1-yl)methanone;
(4-(4-chlorophenoxy)piperidin-1-yl)(1H-indol-3-yl)methanone;
(4-(4-chlorophenoxy)piperidin-1-yl)(1H-indol-2-yl)methanone;
(4-(4-chlorophenoxy)piperidin-1-yl)(1-methyl-1H-indol-3-yl)methanone;
(4-(4-chlorophenoxy)piperidin-1-yl)(1-methyl-1H-indol-2-yl)methanone;
(4-(4-chlorophenoxy)piperidin-1-yl)(2,3-dimethyl-1H-indol-5-yl)methanone;
(4-(4-chlorophenoxy)piperidin-1-yl)(1H-indol-6-yl)methanone;
(4-(4-chlorophenoxy)piperidin-1-yl)(2-methyl-1H-benzo[d]imidazol-5-yl)methanone;
(4-(4-chlorophenoxy)piperidin-1-yl)(imidazo[1,2-a]pyridin-2-yl)methanone;
(4-(4-chlorophenoxy)piperidin-1-yl)(2-methylimidazo[1,2-a]pyridin-3-yl)methanone;
(4-(4-chlorophenoxy)piperidin-1-yl)(5-methyl-1-phenyl-1H-pyrazol-4-yl)methanone;
(4-(tert-butyl)phenyl)(4-(4-chlorophenoxy)piperidin-1-yl)methanone;
(4-(4-chlorophenoxy)piperidin-1-yl)(4-chlorophenyl)methanone;
(4-(4-chlorophenoxy)piperidin-1-yl)(4-fluorophenyl)methanone;
(4-(4-chlorophenoxy)piperidin-1-yl)(3-(5-fluoro-1H-benzo[d]imidazol-2-yl)phenyl)methanone;
(4-(4-chlorophenoxy)piperidin-1-yl)(3-(1-methyl-1H-benzo[d]imidazol-2-yl)phenyl)methanone;
(4-(2-fluorophenoxy)piperidin-1-yl)(8-hydroxyquinolin-2-yl)methanone;
(4-(3-fluorophenoxy)piperidin-1-yl)(8-hydroxyquinolin-2-yl)methanone;
(4-(4-fluorophenoxy)piperidin-1-yl)(8-hydroxyquinolin-2-yl)methanone;
(8-hydroxyquinolin-2-yl)(4-(3-methoxyphenoxy)piperidin-1-yl)methanone;
2-((1-(8-hydroxyquinoline-2-carbonyl)piperidin-4-yl)oxy)benzonitrile;
4-((1-(8-hydroxyquinoline-2-carbonyl)piperidin-4-yl)oxy)benzonitrile;
3-((1-(8-hydroxyquinoline-2-carbonyl)piperidin-4-yl)oxy)benzonitrile;
(4-(4-chlorophenoxy)piperidin-1-yl)(8-methoxyquinolin-2-yl)methanone;
(4-(4-chlorophenoxy)piperidin-1-yl)(1-methyl-1H-indol-7-yl)methanone;
(4-(4-chlorophenoxy)piperidin-1-yl)(1-methyl-1H-indol-4-yl)methanone;
(4-(4-chlorophenoxy)piperidin-1-yl)(1,8-naphthyridin-2-yl)methanone;
(8-hydroxyquinolin-2-yl)(4-phenoxypiperidin-1-yl)methanone;
(8-hydroxyquinolin-2-yl)(4-(2-(trifluoromethyl)phenoxy)piperidin-1-yl)methanone;
(8-hydroxyquinolin-2-yl)(4-(3-(trifluoromethyl)phenoxy)piperidin-1-yl)methanone;
(5-(tert-butyl)isoxazol-3-yl)(4-(4-chlorophenoxy)piperidin-1-yl)methanone;
(4-(4-chlorophenoxy)piperidin-1-yl)(5-phenylisoxazol-3-yl)methanone;
(4-(4-chlorophenoxy)piperidin-1-yl)(5-cyclopropylisoxazol-3-yl)methanone;
(4-(4-chlorophenoxy)piperidin-1-yl)(3,5-dimethylisoxazol-4-yl)methanone;
(4-(4-chlorophenoxy)piperidin-1-yl)(1-methyl-1H-indazol-3-yl)methanone;
(4-(4-chlorophenoxy)piperidin-1-yl)(2-methyl-2H-indazol-3-yl)methanone;
(4-(4-chlorophenoxy)piperidin-1-yl)(cinnolin-4-yl)methanone;
(4-(4-chlorophenoxy)piperidin-1-yl)(2-methyl-4-phenylpyrimidin-5-yl)methanone;

(4-(4-chlorophenoxy)piperidin-1-yl)(6-methylpyridin-3-yl)
methanone;
(4-(4-chlorophenoxy)piperidin-1-yl)(pyridin-4-yl)metha-
none;
[1,2,4]triazolo[1,5-a]pyrimidin-2-yl(4-(4-chlorophenoxy)
piperidin-1-yl)methanone;
(4-(4-chlorophenoxy)piperidin-1-yl)(1,2,3-trimethyl-1H-in-
dol-5-yl)methanone;
(4-(4-chlorophenoxy)piperidin-1-yl)(1-methyl-1H-indol-6-
yl)methanone;
(4-(4-chlorophenoxy)piperidin-1-yl)(2-methylthiazol-4-yl)
methanone;
(4-(4-chlorophenoxy)piperidin-1-yl)(6-methoxypyridin-3-
yl)methanone;
(4-(4-chlorophenoxy)piperidin-1-yl)(2-phenoxypyridin-3-
yl)methanone;
(4-(4-chlorophenoxy)piperidin-1-yl)(1H-indol-7-yl)metha-
none;
7-(4-(4-chlorophenoxy)piperidine-1-carbonyl)indoline-2,3-
dione;
(4-(4-chlorophenoxy)piperidin-1-yl)(3-methylpyridin-2-yl)
methanone;
(4-(4-chlorophenoxy)piperidin-1-yl)(6-hydroxypyridin-2-
yl)methanone;
(4-(4-chlorophenoxy)piperidin-1-yl)(2,4-dimethylthiazol-5-
yl)methanone;
(4-(4-chlorophenoxy)piperidin-1-yl)(5-methyl-1,3,4-oxa-
diazol-2-yl)methanone;
(4-(4-chlorophenoxy)piperidin-1-yl)(1H-indazol-3-yl)
methanone;
(4-(4-chlorophenoxy)piperidin-1-yl)(4,5,6,7-tetrahydro-1H-
indazol-3-yl)methanone;
(4-(4-chlorophenoxy)piperidin-1-yl)(6-methoxypyridin-2-
yl)methanone;
(4-(4-chlorophenoxy)piperidin-1-yl)(2-methyl-4,5,6,7-tet-
rahydro-2H-indazol-3-yl)methanone;
(4-(4-chlorophenoxy)piperidin-1-yl)(isoquinolin-4-yl)
methanone;
(4-(4-chlorophenoxy)piperidin-1-yl)(4-methylpyridin-2-yl)
methanone;
(4-(4-chlorophenoxy)piperidin-1-yl)(6-methoxyquinolin-2-
yl)methanone;
(4-(4-chlorophenoxy)piperidin-1-yl)(6-methoxy-2-meth-
ylquinolin-3-yl)methanone;
(3-(4-chlorophenoxy)azetidin-1-yl)(8-hydroxyquinolin-2-
yl)methanone;
benzo[d]isoxazol-3-yl(4-(4-chlorophenoxy)piperidin-1-yl)
methanone;
(4-(4-chlorophenoxy)piperidin-1-yl)(2-(trifluoromethyl)-
1H-benzo[d]imidazol-5-yl)methanone;
(4-(4-chlorophenoxy)piperidin-1-yl)(1,5-naphthyridin-2-yl)
methanone;
(3-(4-chlorophenoxy)pyrrolidin-1-yl)(8-hydroxyquinolin-2-
yl)methanone;
(4-(4-chlorophenoxy)piperidin-1-yl)(2-methyl-6-phenylpy-
ridin-3-yl)methanone;
(4-(4-chlorophenoxy)piperidin-1-yl)(1,5-dimethyl-1H-in-
dol-3-yl)methanone;
(4-(4-chlorophenoxy)piperidin-1-yl)(5-fluoro-1-methyl-1H-
indol-3-yl)methanone;
(5-chloro-1-methyl-1H-indol-3-yl)(4-(4-chlorophenoxy)pi-
peridin-1-yl)methanone;
(4-(4-chlorophenoxy)piperidin-1-yl)(5-methoxy-1-methyl-
1H-indol-3-yl)methanone;
(4-(4-chlorophenoxy)piperidin-1-yl)(1,6-dimethyl-1H-in-
dol-3-yl)methanone;
(4-(4-chlorophenoxy)piperidin-1-yl)(6-fluoro-1-methyl-1H-
indol-3-yl)methanone;
(6-chloro-1-methyl-1H-indol-3-yl)(4-(4-chlorophenoxy)pi-
peridin-1-yl)methanone;
(4-(4-chlorophenoxy)piperidin-1-yl)(6-methoxy-1-methyl-
1H-indol-3-yl)methanone;
(4-(4-chlorophenoxy)piperidin-1-yl)(5-fluoro-1-methyl-1H-
indol-2-yl)methanone;
(4-(4-chlorophenoxy)piperidin-1-yl)(5-methoxy-1-methyl-
1H-indol-2-yl)methanone;
(4-(4-chlorophenoxy)piperidin-1-yl)(3-fluorophenyl)metha-
none;
(4-(4-chlorophenoxy)piperidin-1-yl)(p-tolyl)methanone;
(4-(4-chlorophenoxy)piperidin-1-yl)(4-methoxyphenyl)
methanone;
4-(4-(4-chlorophenoxy)piperidine-1-carbonyl)benzonitrile;
(4-(4-chlorophenoxy)piperidin-1-yl)(6-methylimidazo[1,2-
a]pyridin-2-yl)methanone;
(6-chloroimidazo[1,2-a]pyridin-2-yl)(4-(4-chlorophenoxy)
piperidin-1-yl)methanone;
(4-(4-chlorophenoxy)piperidin-1-yl)(2-methylpyridin-3-yl)
methanone;
(4-(4-chlorophenoxy)piperidin-1-yl)(4-isopropoxyphenyl)
methanone;
(4-(4-chlorophenoxy)piperidin-1-yl)(4-(trifluoromethoxy)
phenyl)methanone;
(4-(4-chlorophenoxy)piperidin-1-yl)(4-(methylsulfonyl)
phenyl)methanone;
(4-(4-chlorophenoxy)piperidin-1-yl)(3-methoxyphenyl)
methanone;
(4-(4-chlorophenoxy)piperidin-1-yl)(pyridin-2-yl)metha-
none;
(4-(4-chlorophenoxy)piperidin-1-yl)(5-methylisoxazol-3-
yl)methanone;
(4-(4-chlorophenoxy)piperidin-1-yl)(oxazol-4-yl)metha-
none;
(4-(4-chlorophenoxy)piperidin-1-yl)(4-methylthiazol-5-yl)
methanone;
(4-(4-chlorophenoxy)piperidin-1-yl)(5-methylpyrazin-2-yl)
methanone;
(4-(4-chlorophenoxy)piperidin-1-yl)(6-fluoro-1-methyl-1H-
indol-2-yl)methanone;
4-(4-(4-chlorophenoxy)piperidine-1-carbonyl)-N,N-dimeth-
ylbenzenesulfonamide;
4-(4-(4-chlorophenoxy)piperidine-1-carbonyl)benzamide;
(4-(4-chlorophenoxy)piperidin-1-yl)(5-fluoro-1H-indazol-
3-yl)methanone;
(5-chloro-1H-indazol-3-yl)(4-(4-chlorophenoxy)piperidin-
1-yl)methanone;
(6-chloro-1H-indazol-3-yl)(4-(4-chlorophenoxy)piperidin-
1-yl)methanone;
(4-(4-chlorophenoxy)piperidin-1-yl)(4-(2-hydroxypropan-
2-yl)phenyl)methanone;
(4-(4-chlorophenoxy)piperidin-1-yl)(2,6-dimethoxypyridin-
3-yl)methanone;
(4-(4-chlorophenoxy)piperidin-1-yl)(6-methoxy-1-methyl-
1H-indol-2-yl)methanone;
(4-(4-chlorophenoxy)piperidin-1-yl)(1-methyl-5-(trifluo-
romethoxy)-1H-indol-2-yl)methanone;
2-(4-(4-chlorophenoxy)piperidine-1-carbonyl)-1-methyl-
1H-indole-5-carbonitrile;
(4-(4-chlorophenoxy)piperidin-1-yl)(1-methyl-5-(methyl-
sulfonyl)-1H-indol-2-yl)methanone;
(4-(4-chlorophenoxy)piperidin-1-yl)(4-methylpyridin-3-yl)
methanone;
3-(4-(4-chlorophenoxy)piperidine-1-carbonyl)-5,6-dimeth-
ylpyridin-2(1H)-one;

(4-(4-chlorophenoxy)piperidin-1-yl)(quinolin-5-yl)methanone;
(4-(4-fluorophenoxy)piperidin-1-yl)(2-methyl-2H-indazol-3-yl)methanone;
(4-(4-fluorophenoxy)piperidin-1-yl)(6-methoxypyridin-3-yl)methanone;
(4-(4-chlorophenoxy)piperidin-1-yl)(3-methoxy-4-methylphenyl)methanone;
(5-chloro-4-methoxythiophen-3-yl)(4-(4-chlorophenoxy)piperidin-1-yl)methanone;
(4-phenoxypiperidin-1-yl)(quinolin-8-yl)methanone;
(4-(4-fluorophenoxy)piperidin-1-yl)(imidazo[1,2-a]pyridin-2-yl)methanone;
(4-(4-fluorophenoxy)piperidin-1-yl)(quinolin-8-yl)methanone;
(6-aminopyridin-3-yl)(4-(4-chlorophenoxy)piperidin-1-yl)methanone;
(5-bromopyridin-3-yl)(4-(4-chlorophenoxy)piperidin-1-yl)methanone;
(5-bromopyridin-2-yl)(4-(4-chlorophenoxy)piperidin-1-yl)methanone;
1-(4-(4-(4-chlorophenoxy)piperidine-1-carbonyl)phenyl)ethanone;
(4-(4-chlorophenoxy)piperidin-1-yl)(3,4-dimethoxyphenyl)methanone;
(4-(4-chlorophenoxy)piperidin-1-yl)(isoquinolin-5-yl)methanone;
(4-(4-chlorophenoxy)piperidin-1-yl)(phenyl)methanone;
(4-(4-chlorophenoxy)piperidin-1-yl)(m-tolyl)methanone;
(4-(4-chlorophenoxy)piperidin-1-yl)(2-methoxyphenyl)methanone;
(4-(4-chlorophenoxy)piperidin-1-yl)(3-(trifluoromethoxy)phenyl)methanone;
(1H-benzo[d]imidazol-5-yl)(4-(4-chlorophenoxy)piperidin-1-yl)methanone;
(4-(4-chlorophenoxy)piperidin-1-yl)(1,5-dimethyl-1H-pyrazol-3-yl)methanone;
(4-(4-chlorophenoxy)piperidin-1-yl)(1,3-dimethyl-1H-pyrazol-5-yl)methanone;
(3-(tert-butyl)-1-methyl-1H-pyrazol-5-yl)(4-(4-chlorophenoxy)piperidin-1-yl)methanone;
(4-(4-chlorophenoxy)piperidin-1-yl)(1-methyl-5-(trifluoromethyl)-1H-pyrazol-3-yl)methanone;
(4-(4-chlorophenoxy)piperidin-1-yl)(1-(4-methoxyphenyl)-5-methyl-1H-pyrazol-4-yl)methanone;
(4-(4-chlorophenoxy)piperidin-1-yl)(1-(2-methoxyphenyl)-1H-pyrazol-4-yl)methanone
(4-(4-chlorophenoxy)piperidin-1-yl)(3,5-dimethyl-1H-pyrazol-4-yl)methanone;
(4-(4-chlorophenoxy)piperidin-1-yl)(1H-1,2,4-triazol-3-yl)methanone;
(4-(4-chlorophenoxy)piperidin-1-yl)(5-isopropyl-1H-pyrazol-3-yl)methanone;
(4-(4-chlorophenoxy)piperidin-1-yl)(imidazo[2,1-b]thiazol-6-yl)methanone;
(4-(3-methoxyphenoxy)piperidin-1-yl)(quinolin-8-yl)methanone;
imidazo[1,2-a]pyridin-2-yl(4-(3-methoxyphenoxy)piperidin-1-yl)methanone;
(4-(3-fluorophenoxy)piperidin-1-yl)(quinolin-8-yl)methanone;
(4-(3-fluorophenoxy)piperidin-1-yl)(imidazo[1,2-a]pyridin-2-yl)methanone;
(4-(4-chlorophenoxy)piperidin-1-yl)(5-chloropyridin-3-yl)methanone;
(4-(4-chlorophenoxy)piperidin-1-yl)(5-methoxypyridin-3-yl)methanone;
3-(4-(4-chlorophenoxy)piperidine-1-carbonyl)benzonitrile;
(4-(4-chlorophenoxy)piperidin-1-yl)(2-ethoxypyridin-3-yl)methanone;
(4-(4-chlorophenoxy)piperidin-1-yl)(2-methoxypyridin-4-yl)methanone;
(4-(4-chlorophenoxy)piperidin-1-yl)(isoquinolin-8-yl)methanone;
(4-(4-chlorophenoxy)piperidin-1-yl)(2-methylthiazol-5-yl)methanone;
(4-((4-chlorophenyl)thio)piperidin-1-yl)(quinolin-8-yl)methanone;
(4-((4-chlorophenyl)thio)piperidin-1-yl)(6-methylpyridin-3-yl)methanone;
(4-((4-chlorophenyl)sulfonyl)piperidin-1-yl)(quinolin-8-yl)methanone;
1-(3-((1-(quinoline-8-carbonyl)piperidin-4-yl)oxy)phenyl)ethanone;
(4-(3,5-dimethoxyphenoxy)piperidin-1-yl)(quinolin-8-yl)methanone;
quinolin-8-yl(4-(3-(trifluoromethoxy)phenoxy)piperidin-1-yl)methanone;
(4-(4-chlorophenoxy)piperidin-1-yl)(3-methylisoxazol-5-yl)methanone;
(4-(4-chlorophenoxy)piperidin-1-yl)(1-isopropyl-1H-pyrazol-4-yl)methanone;
5-(4-(4-chlorophenoxy)piperidine-1-carbonyl)picolinonitrile;
(4-(4-chlorophenoxy)piperidin-1-yl)(2-hydroxyquinolin-4-yl)methanone;
(4-(4-chlorophenoxy)piperidin-1-yl)(5-(trifluoromethyl)-1H-pyrazol-3-yl)methanone;
(4-(4-chlorophenoxy)piperidin-1-yl)(5-cyclopropyl-1H-pyrazol-3-yl)methanone;
(4-(4-chlorophenoxy)piperidin-1-yl)(5-(2-methoxyphenyl)-1H-pyrazol-3-yl)methanone
(4-(4-chlorophenoxy)piperidin-1-yl)(3-isopropyl-1-methyl-1H-pyrazol-5-yl)methanone
(4-(4-chlorophenoxy)piperidin-1-yl)(3-ethyl-1-methyl-1H-pyrazol-5-yl)methanone;
(4-(4-chlorophenoxy)piperidin-1-yl)(1-ethyl-3-methyl-1H-pyrazol-5-yl)methanone;
(4-(4-chlorophenoxy)piperidin-1-yl)(2-methyloxazol-4-yl)methanone;
(4-(4-chlorophenoxy)piperidin-1-yl)(thieno[3,2-b]pyridin-2-yl)methanone;
(4-(4-chlorophenoxy)piperidin-1-yl)(imidazo[1,2-a]pyridin-6-yl)methanone;
(4-(4-chlorophenoxy)piperidin-1-yl)(1-methyl-1H-indazol-6-yl)methanone;
(4-(4-chlorophenoxy)piperidin-1-yl)(6-(trifluoromethoxy)-1H-indazol-3-yl)methanone;
(4-(4-chlorophenoxy)piperidin-1-yl)(1-methyl-6-(trifluoromethoxy)-1H-indazol-3-yl)methanone;
(4-(4-chlorophenoxy)piperidin-1-yl)(2,4-dimethyloxazol-5-yl)methanone;
(4-(4-chlorophenoxy)piperidin-1-yl)(5-methoxypyridin-2-yl)methanone;
(4-(4-chlorophenoxy)piperidin-1-yl)(imidazo[1,2-a]pyridin-7-yl)methanone;
(4-(4-chlorophenoxy)piperidin-1-yl)(imidazo[1,2-a]pyrazin-2-yl)methanone;
(4-(4-chlorophenoxy)piperidin-1-yl)(2-methyl-2H-indazol-6-yl)methanone;
(4-(4-chlorophenoxy)piperidin-1-yl)(6-(pyrrolidin-1-yl)pyridin-2-yl)methanone;
(4-(4-chlorophenoxy)piperidin-1-yl)(5-(pyrrolidin-1-yl)pyridin-2-yl)methanone;

(4-(4-chlorophenoxy)piperidin-1-yl)(4-fluoro-3-methoxyphenyl)methanone;
(4-(4-chlorophenoxy)piperidin-1-yl)(4-methyl-3,4-dihydro-2H-pyrido[3,2-b][1,4]oxazin-7-yl)methanone;
(4-(4-chlorophenoxy)piperidin-1-yl)(6-(piperidin-1-yl)pyridin-3-yl)methanone;
3-(4-(4-chlorophenoxy)piperidine-1-carbonyl)quinolin-2(1H)-one;
(4-(4-chlorophenoxy)piperidin-1-yl)(imidazo[1,2-a]pyridin-8-yl)methanone;
(4-(4-chlorophenoxy)piperidin-1-yl)(pyrazolo[1,5-a]pyridin-7-yl)methanone;
(4-(4-chlorophenoxy)piperidin-1-yl)(4-(trifluoromethyl)pyridin-3-yl)methanone;
(4-(4-chlorophenoxy)piperidin-1-yl)(1-methyl-1H-imidazol-2-yl)methanone;
(4-(4-chlorophenoxy)piperidin-1-yl)(1-(2-(trifluoromethyl)phenyl)-1H-imidazol-2-yl)methanone;
3-(4-(4-chlorophenoxy)piperidine-1-carbonyl)-1-methylquinolin-4(1H)-one;
(3-(4-chlorophenoxy)azetidin-1-yl)(quinolin-8-yl)methanone;
(3-(4-chlorophenoxy)azetidin-1-yl)(6-methylpyridin-3-yl)methanone;
(4-(4-chlorophenoxy)piperidin-1-yl)(pyrimidin-4-yl)methanone;
(4-(4-chlorophenoxy)piperidin-1-yl)(5-chloropyridin-2-yl)methanone;
(4-(4-chlorophenoxy)piperidin-1-yl)(2-methoxyquinolin-4-yl)methanone;
(4-(4-chlorophenoxy)piperidin-1-yl)(5-hydroxypyridin-3-yl)methanone;
(4-(4-chlorophenoxy)piperidin-1-yl)(6-(trifluoromethyl)pyridin-3-yl)methanone;
(5-aminopyridin-3-yl)(4-(4-chlorophenoxy)piperidin-1-yl)methanone;
(4-(4-chlorophenoxy)piperidin-1-yl)(imidazo[1,2-a]pyrimidin-2-yl)methanone;
N-(5-(4-(4-chlorophenoxy)piperidine-1-carbonyl)pyridin-3-yl)acetamide;
(4-(4-chlorophenoxy)piperidin-1-yl)(chroman-6-yl)methanone;
(4-(4-chlorophenoxy)piperidin-1-yl)(1-methyl-1H-pyrazolo[3,4-b]pyridin-3-yl)methan one;
(4-(4-chlorophenoxy)piperidin-1-yl)(1-methyl-1H-indol-5-yl)methanone;
(4-(4-chlorophenoxy)piperidin-1-yl)(3-(pyridin-2-yloxy)phenyl)methanone;
(4-(4-chlorophenoxy)piperidin-1-yl)(1-methyl-1H-benzo[d]imidazol-5-yl)methanone;
(4-(4-chlorophenoxy)piperidin-1-yl)(4-((tetrahydro-2H-pyran-4-yl)oxy)phenyl)methan one;
(4-(4-chlorophenoxy)piperidin-1-yl)(pyrazolo[1,5-a]pyridin-2-yl)methanone;
1-(3-(4-(4-chlorophenoxy)piperidine-1-carbonyl)-1H-pyrazol-5-yl)ethanone;
(4-(4-chlorophenoxy)piperidin-1-yl)(1,3,5-trimethyl-1H-pyrazol-4-yl)methanone;
(4-(4-chlorophenoxy)piperidin-1-yl)(1H-pyrrolo[2,3-b]pyridin-2-yl)methanone;
4-(4-(4-chlorophenoxy)piperidine-1-carbonyl)-1-methylquinolin-2(1H)-one;
5-(4-(4-chlorophenoxy)piperidine-1-carbonyl)-1H-benzo[d]imidazol-2(3H)-one;
(4-(4-chlorophenoxy)piperidin-1-yl)(5-methoxypyrazin-2-yl)methanone;
5-(4-(4-chlorophenoxy)piperidine-1-carbonyl)-1,3-dimethyl-1H-benzo[d]imidazol-2(3H)-one;
(4-(4-chlorophenoxy)piperidin-1-yl)(1-methyl-1H-imidazol-4-yl)methanone;
(4-(4-chlorophenoxy)piperidin-1-yl)(2-phenyl-1H-imidazol-4-yl)methanone;
(4-(4-chlorophenoxy)piperidin-1-yl)(1,3-dimethyl-1H-pyrazol-4-yl)methanone;
(4-(4-chlorophenoxy)piperidin-1-yl)(1,5-dimethyl-1H-pyrazol-4-yl)methanone;
(4-(4-chlorophenoxy)piperidin-1-yl)(3-isobutyl-1-methyl-1H-pyrazol-5-yl)methanone;
(4-chloro-5-methyl-1H-pyrazol-3-yl)(4-(4-chlorophenoxy)piperidin-1-yl)methanone;
3-(4-(4-chlorophenoxy)piperidine-1-carbonyl)-1-isopropyl-6,7-dihydro-1H-cyclopenta[b]pyridin-2(5H)-one;
5-(4-(4-chlorophenoxy)piperidine-1-carbonyl)-2-methoxybenzonitrile;
(4-(4-chlorophenoxy)piperidin-1-yl)(2-isopropylthiazol-4-yl)methanone;
(4-(4-chlorophenoxy)piperidin-1-yl)(5,6-dimethoxy-1H-indol-2-yl)methanone;
(4-(4-chlorophenoxy)piperidin-1-yl)(2,7-dimethylpyrazolo[1,5-a]pyrimidin-6-yl)methanone;
(4-(4-chlorophenoxy)piperidin-1-yl)(1H-pyrrolo[2,3-b]pyridin-3-yl)methanone;
(4-(4-chlorophenoxy)piperidin-1-yl)(1-methyl-1H-pyrrolo[2,3-b]pyridin-2-yl)methanone;
(4-(4-chlorophenoxy)piperidin-1-yl)(5,6-dimethoxy-1-methyl-1H-indol-2-yl)methanone;
(4-(4-chlorophenoxy)piperidin-1-yl)(1-methyl-1H-pyrrolo[2,3-b]pyridin-3-yl)methanone;
3-(4-(4-chlorophenoxy)piperidine-1-carbonyl)-1-isopropyl-4-methylquinolin-2(1H)-one;
(4-(4-chlorophenoxy)piperidin-1-yl)(4-methyl-4H-furo[3,2-b]pyrrol-5-yl)methanone;
(4-(4-chlorophenoxy)piperidin-1-yl)(4-methyl-4H-thieno[3,2-b]pyrrol-5-yl)methanone;
(4-(4-chlorophenoxy)piperidin-1-yl)(1,3-dimethyl-1H-thieno[2,3-c]pyrazol-5-yl)methanone;
2-(4-(4-chlorophenoxy)piperidine-1-carbonyl)-6,7-dihydropyrido[3,2,1-ij]quinolin-3 (5H)-one;
5-(4-(4-chlorophenoxy)piperidine-1-carbonyl)-1H-pyrrolo[3,2,1-ij]quinolin-4(2H)-one;
3-(4-(4-chlorophenoxy)piperidine-1-carbonyl)-1-ethyl-7-methyl-1,8-naphthyridin-4(1H)-one;
(4-(4-chlorophenoxy)piperidin-1-yl)(isoquinolin-6-yl)methanone;
(4-(4-chlorophenoxy)piperidin-1-yl)(5-methylpyridin-2-yl)methanone;
(4-(4-chlorophenoxy)piperidin-1-yl)(5-(2,2,2-trifluoroethoxy)pyridin-3-yl)methanone;
(4-(4-chlorophenoxy)piperidin-1-yl)(3-methylisoxazolo[5,4-b]pyridin-5-yl)methanone;
(4-(4-chlorophenoxy)piperidin-1-yl)(1,3,6-trimethyl-1H-pyrazolo[3,4-b]pyridin-4-yl)methanone;
(4-(4-chlorophenoxy)piperidin-1-yl)(thieno[2,3-b]pyridin-2-yl)methanone;
(4-(4-chlorophenoxy)piperidin-1-yl)(thieno[2,3-b]pyrazin-6-yl)methanone;
(4-(4-chlorophenoxy)piperidin-1-yl)(pyrazolo[1,5-a]pyrimidin-3-yl)methanone;
(4-(4-chlorophenoxy)piperidin-1-yl)(2-(pyrrolidin-1-yl)pyrimidin-5-yl)methanone;
(1H-benzo[d]imidazol-4-yl)(4-(4-chlorophenoxy)piperidin-1-yl)methanone;

benzo[d][1,2,3]thiadiazol-7-yl(4-(4-chlorophenoxy)piperidin-1-yl)methanone;
3-(4-(4-chlorophenoxy)piperidine-1-carbonyl)-1-methylquinolin-2(1H)-one;
(4-(4-chlorophenoxy)piperidin-1-yl)(1-methyl-1H-benzo[d]imidazol-2-yl)methanone;
(4-(4-chlorophenoxy)piperidin-1-yl)(pyrazolo[1,5-a]pyrimidin-2-yl)methanone;
(4-(4-chlorophenoxy)piperidin-1-yl)(2-methoxypyrimidin-5-yl)methanone;
(1H-benzo[d][1,2,3]triazol-4-yl)(4-(4-chlorophenoxy)piperidin-1-yl)methanone;
(4-(4-chlorophenoxy)piperidin-1-yl)(6-methylimidazo[2,1-b]thiazol-5-yl)methanone;
benzo[c][1,2,5]thiadiazol-4-yl(4-(4-chlorophenoxy)piperidin-1-yl)methanone;
(4-(4-chlorophenoxy)piperidin-1-yl)(1-(2-methoxyethyl)-1H-indol-5-yl)methanone;
(4-(4-chlorophenoxy)piperidin-1-yl)(1-(2-methoxyethyl)-1H-indol-6-yl)methanone;
(3-amino-1-methyl-1H-pyrazol-5-yl)(4-(4-chlorophenoxy)piperidin-1-yl)methanone;
(4-(4-chlorophenoxy)piperidin-1-yl)(5-cyclopropyl-1-methyl-1H-pyrazol-3-yl)methan one;
(4-(4-chlorophenoxy)piperidin-1-yl)(3-cyclopropyl-1-methyl-1H-pyrazol-5-yl)methan one;
1-benzyl-3-(4-(4-chlorophenoxy)piperidine-1-carbonyl)pyridin-2(1H)-one;
(1-benzyl-1H-pyrazol-4-yl)(4-(4-chlorophenoxy)piperidin-1-yl)methanone;
(4-(4-chlorophenoxy)piperidin-1-yl)(1-(2-methoxyethyl)-1H-indol-2-yl)methanone;
(4-(4-chlorophenoxy)piperidin-1-yl)(1-(2-methoxyethyl)-1H-indol-4-yl)methanone;
(4-(4-chlorophenoxy)piperidin-1-yl)(3,6-dimethylisoxazolo[5,4-b]pyridin-4-yl)methan one;
4-(4-(4-chlorophenoxy)piperidine-1-carbonyl)-1-methylpyridin-2(1H)-one;
3-(4-(4-chlorophenoxy)piperidine-1-carbonyl)-4H-pyrido[1,2-a]pyrimidin-4-one;
3-(4-(4-chlorophenoxy)piperidine-1-carbonyl)isoquinolin-1(2H)-one;
(4-(4-chlorophenoxy)piperidin-1-yl)(2-(3,5-dimethyl-1H-pyrazol-4-yl)phenyl)methanone;
benzo[c][1,2,5]oxadiazol-5-yl(4-(4-chlorophenoxy)piperidin-1-yl)methanone;
(6-aminopyridin-2-yl)(4-(4-chlorophenoxy)piperidin-1-yl)methanone;
3-(4-(4-chlorophenoxy)piperidine-1-carbonyl)-1,6-dimethylpyridin-2(1H)-one;
(4-(4-chlorophenoxy)piperidin-1-yl)(3-propoxypyridin-2-yl)methanone;
(4-(4-chlorophenoxy)piperidin-1-yl)(6-((tetrahydro-2H-pyran-4-yl)oxy)pyridin-3-yl)methanone;
(4-(4-chlorophenoxy)piperidin-1-yl)(6-((tetrahydro-2H-pyran-4-yl)oxy)pyridin-2-yl)methanone;
(4-(4-chlorophenoxy)piperidin-1-yl)(5-((tetrahydro-2H-pyran-4-yl)oxy)pyridin-3-yl)methanone;
(4-(4-chlorophenoxy)piperidin-1-yl)(3-hydroxy-4-methoxyphenyl)methanone;
(4-chloro-2-hydroxyphenyl)(4-(4-chlorophenoxy)piperidin-1-yl)methanone;
(4-(4-chlorophenoxy)piperidin-1-yl)(4-hydroxy-3-methylphenyl)methanone;
(4-(4-chlorophenoxy)piperidin-1-yl)(6-morpholinopyridin-2-yl)methanone;
(4-(4-chlorophenoxy)piperidin-1-yl)(2-morpholinopyridin-4-yl)methanone;
(4-(4-chlorophenoxy)piperidin-1-yl)(1-methyl-3-(trifluoromethyl)-1H-pyrazol-5-yl)methanone;
(4-(4-chlorophenoxy)piperidin-1-yl)(2-hydroxy-4-(trifluoromethyl)phenyl)methanone;
(4-(4-chlorophenoxy)piperidin-1-yl)(3-hydroxy-4-methylphenyl)methanone;
tert-butyl ((2-(4-(4-chlorophenoxy)piperidine-1-carbonyl)pyridin-4-yl)methyl)carbamate;
(4-(aminomethyl)pyridin-2-yl)(4-(4-chlorophenoxy)piperidin-1-yl)methanone;
N-((2-(4-(4-chlorophenoxy)piperidine-1-carbonyl)pyridin-4-yl)methyl)pivalamide;
N-((2-(4-(4-chlorophenoxy)piperidine-1-carbonyl)pyridin-4-yl)methyl)-4-fluorobenzamide;
N-((2-(4-(4-chlorophenoxy)piperidine-1-carbonyl)pyridin-4-yl)methyl)-4-fluorobenzenesulfonamide;
tert-butyl 2-(4-(4-chlorophenoxy)piperidine-1-carbonyl)-7,8-dihydro-1,6-naphthyridine-6(5H)-carboxylate;
(4-(4-chlorophenoxy)piperidin-1-yl)(6-(methylsulfonyl)-5,6,7,8-tetrahydro-1,6-naphthyridin-2-yl)methanone;
N-(tert-butyl)-4-(4-(4-chlorophenoxy)piperidine-1-carbonyl)benzamide;
N-(tert-butyl)-4-(4-(4-chlorophenoxy)piperidine-1-carbonyl)-N-methylbenzamide;
4-(4-(4-chlorophenoxy)piperidine-1-carbonyl)-N-(2,2,2-trifluoroethyl)benzamide;
(4-(4-chlorophenoxy)piperidin-1-yl)(4-(2-methoxyethoxy)phenyl)methanone;
(4-(4-chlorophenoxy)piperidin-1-yl)(4-(2-hydroxyethoxy)phenyl)methanone;
N-(4-(4-(4-chlorophenoxy)piperidine-1-carbonyl)benzyl)pivalamide;
4-(4-(4-chlorophenoxy)piperidine-1-carbonyl)picolinamide;
(4-(4-chlorophenoxy)piperidin-1-yl)(5-morpholinopyridin-3-yl)methanone;
(4-(4-chlorophenoxy)piperidin-1-yl)(6-(piperidin-1-yl)pyrimidin-4-yl)methanone;
(3-(1H-imidazol-1-yl)phenyl)(4-(4-chlorophenoxy)piperidin-1-yl)methanone;
(2-(1H-pyrazol-1-yl)phenyl)(4-(4-chlorophenoxy)piperidin-1-yl)methanone;
(4-(4-chlorophenoxy)piperidin-1-yl)(2-(2-methyl-1H-imidazol-1-yl)phenyl)methanone
(4-(4-chlorophenoxy)piperidin-1-yl)(2-(3-methyl-1,2,4-oxadiazol-5-yl)phenyl)methanone;
(4-(4-chlorophenoxy)piperidin-1-yl)(3-methyl-1H-pyrazol-5-yl)methanone;
(4-(4-chlorophenoxy)piperidin-1-yl)(6-(piperidine-1-carbonyl)pyridin-2-yl)methanone;
(4-(4-chlorophenoxy)piperidin-1-yl)(2-hydroxy-4-methoxyphenyl)methanone;
(4-(4-chlorophenoxy)piperidin-1-yl)(4-hydroxy-3-methoxyphenyl)methanone;
N-(5-chloro-2-(4-(4-chlorophenoxy)piperidine-1-carbonyl)phenyl)methanesulfonamide;
N-(4-chloro-2-(4-(4-chlorophenoxy)piperidine-1-carbonyl)phenyl)methanesulfonamide;
(4-(4-chlorophenoxy)piperidin-1-yl)(2'-(hydroxymethyl)-[1,1'-biphenyl]-4-yl)methanone;
(4-(4-chlorophenoxy)piperidin-1-yl)(2'-(methylsulfonyl)-[1,1'-biphenyl]-4-yl)methanone;
(3-chloro-4-hydroxyphenyl)(4-(4-chlorophenoxy)piperidin-1-yl)methanone;

3-(tert-butyl)-5-(4-(4-chlorophenoxy)piperidine-1-carbonyl)benzamide;
3-(tert-butyl)-5-(4-(4-chlorophenoxy)piperidine-1-carbonyl)-N,N-dimethylbenzamide;
(3-(tert-butyl)-5-(4-(4-chlorophenoxy)piperidine-1-carbonyl)phenyl)(morpholino)methanone;
4'-(4-(4-chlorophenoxy)piperidine-1-carbonyl)-[1,1'-biphenyl]-3-carboxamide;
(4-(4-chlorophenoxy)piperidin-1-yl)(1-(2-morpholinoethyl)-1H-indol-5-yl)methanone;
2-(5-(4-(4-chlorophenoxy)piperidine-1-carbonyl)-1H-indol-1-yl)-N,N-dimethylacetamide;
(4-(4-chlorophenoxy)piperidin-1-yl)(1-(2-hydroxyethyl)-1H-indol-5-yl)methanone;
(4-(4-chlorophenoxy)piperidin-1-yl)(4-morpholinopyridin-2-yl)methanone;
(4-(4-chlorophenoxy)piperidin-1-yl)(4-(piperidin-1-yl)pyridin-2-yl)methanone;
2-(3-(4-(4-chlorophenoxy)piperidine-1-carbonyl)-1H-indol-1-yl)-N,N-dimethylacetamide;
(4-(4-chlorophenoxy)piperidin-1-yl)(1-(2-hydroxyethyl)-1H-indol-3-yl)methanone;
(4-(4-chlorophenoxy)piperidin-1-yl)(1-(2-morpholinoethyl)-1H-indol-3-yl)methanone;
(4-(4-chlorophenoxy)piperidin-1-yl)(1-(2-(piperidin-1-yl)ethyl)-1H-indol-3-yl)methan one;
2-(4-(4-(4-chlorophenoxy)piperidine-1-carbonyl)phenyl)-2-methylpropanenitrile;
(4-(4-chlorophenoxy)piperidin-1-yl)(3-fluoro-4-hydroxyphenyl)methanone;
2-chloro-5-(4-(4-chlorophenoxy)piperidine-1-carbonyl)benzenesulfonamide;
4'-(4-(4-chlorophenoxy)piperidine-1-carbonyl)-[1,1'-biphenyl]-4-carboxamide;
4'-(4-(4-chlorophenoxy)piperidine-1-carbonyl)-[1,1'-biphenyl]-2-carboxamide;
(5-chloro-2-hydroxyphenyl)(4-(4-chlorophenoxy)piperidin-1-yl)methanone;
(4-(4-chlorophenoxy)piperidin-1-yl)(2-hydroxy-4-methylphenyl)methanone;
(4-(4-chlorophenoxy)piperidin-1-yl)(5-fluoro-2-hydroxyphenyl)methanone;
(4-(4-chlorophenoxy)piperidin-1-yl)(2-hydroxy-3-methylphenyl)methanone;
(4-(4-chlorophenoxy)piperidin-1-yl)(2-hydroxy-3-isopropylphenyl)methanone;
(4-(4-chlorophenoxy)piperidin-1-yl)(2-hydroxy-6-methoxyphenyl)methanone;
(4-(4-chlorophenoxy)piperidin-1-yl)(2-fluoro-6-hydroxyphenyl)methanone;
(4-(4-chlorophenoxy)piperidin-1-yl)(3-hydroxy-2-methylphenyl)methanone;
(2-chloro-4-hydroxyphenyl)(4-(4-chlorophenoxy)piperidin-1-yl)methanone;
(4-(4-chlorophenoxy)piperidin-1-yl)(2-fluoro-4-hydroxyphenyl)methanone;
N-(4-(4-(4-chlorophenoxy)piperidine-1-carbonyl)-2-methylphenyl)methanesulfonamide;
(4-(4-chlorophenoxy)piperidin-1-yl)(4-fluoro-3-hydroxyphenyl)methanone;
(4-(4-chlorophenoxy)piperidin-1-yl)(2-hydroxy-5-methylphenyl)methanone;
(4-(4-chlorophenoxy)piperidin-1-yl)(2-hydroxy-3-methoxyphenyl)methanone;
(4-(4-chlorophenoxy)piperidin-1-yl)(4-fluoro-2-hydroxyphenyl)methanone;
(4-(4-chlorophenoxy)piperidin-1-yl)(3,5-dihydroxyphenyl)methanone;
N-(3-(4-(4-chlorophenoxy)piperidine-1-carbonyl)phenyl)acetamide;
(4-(4-chlorophenoxy)piperidin-1-yl)(1-((4-hydroxytetrahydro-2H-pyran-4-yl)methyl)-1H-indol-5-yl)methanone;
(1-(2-aminoethyl)-1H-indol-5-yl)(4-(4-chlorophenoxy)piperidin-1-yl)methanone;
N-(2-(5-(4-(4-chlorophenoxy)piperidine-1-carbonyl)-1H-indol-1-yl)ethyl)acetamide;
N-(2-(5-(4-(4-chlorophenoxy)piperidine-1-carbonyl)-1H-indol-1-yl)ethyl)methanesulfonamide;
2-(5-(4-(4-chlorophenoxy)piperidine-1-carbonyl)-1H-indol-1-yl)-1-morpholinoethanone;
(4-(4-chlorophenoxy)piperidin-1-yl)(3'-(methylsulfonyl)-[1,1'-biphenyl]-4-yl)methanone;
(4-(4-chlorophenoxy)piperidin-1-yl)(3'-(hydroxymethyl)-[1,1'-biphenyl]-4-yl)methanone;
N-(4'-(4-(4-chlorophenoxy)piperidine-1-carbonyl)-[1,1'-biphenyl]-2-yl)methanesulfonamide;
N-(4'-(4-(4-chlorophenoxy)piperidine-1-carbonyl)-[1,1'-biphenyl]-3-yl)methanesulfonamide;
4'-(4-(4-chlorophenoxy)piperidine-1-carbonyl)-N-methyl-[1,1'-biphenyl]-3-carboxamide;
4'-(4-(4-chlorophenoxy)piperidine-1-carbonyl)-N,N-dimethyl-[1,1'-biphenyl]-3-carboxamide;
(4-(4-chlorophenoxy)piperidin-1-yl)(3'-(morpholine-4-carbonyl)-[1,1'-biphenyl]-4-yl) methanone;
(4-chloro-3-hydroxyphenyl)(4-(4-chlorophenoxy)piperidin-1-yl)methanone;
N-(5-(4-(4-chlorophenoxy)piperidine-1-carbonyl)-2-methylphenyl)methanesulfonamide;
1-(3-(4-(4-chlorophenoxy)piperidine-1-carbonyl)phenyl)ethanone;
(4-(4-chlorophenoxy)piperidin-1-yl)(1-(2-hydroxyethyl)-2-methyl-1H-benzo[d]imidazol-5-yl)methanone;
(4-(4-chlorophenoxy)piperidin-1-yl)(6-ethoxypyridin-2-yl)methanone;
(4-(4-chlorophenoxy)piperidin-1-yl)(4-hydroxy-7-methyl-1,8-naphthyridin-3-yl)methanone;
N-(6-(4-(4-chlorophenoxy)piperidine-1-carbonyl)pyridin-2-yl)acetamide;
N-(4-(4-(4-chlorophenoxy)piperidine-1-carbonyl)pyridin-2-yl)acetamide;
N-(5-(4-(4-chlorophenoxy)piperidine-1-carbonyl)pyridin-2-yl)acetamide;
(4-(4-chlorophenoxy)piperidin-1-yl)(3-hydroxypyridin-2-yl)methanone;
(4-bromo-1-methoxynaphthalen-2-yl)(4-(4-chlorophenoxy)piperidin-1-yl)methanone;
6-(4-(4-chlorophenoxy)piperidine-1-carbonyl)isoindolin-1-one;
(4-(4-chlorophenoxy)piperidin-1-yl)(quinoxalin-5-yl)methanone;
(4-(4-chlorophenoxy)piperidin-1-yl)(1,6-naphthyridin-5-yl)methanone;
(4-(4-chlorophenoxy)piperidin-1-yl)(4-hydroxyphenyl)methanone;
(4-(4-chlorophenoxy)piperidin-1-yl)(4-ethoxy-2-hydroxyphenyl)methanone;
(4-(4-chlorophenoxy)piperidin-1-yl)(3-hydroxyphenyl)methanone;
(4-(4-chlorophenoxy)piperidin-1-yl)(2-hydroxyphenyl)methanone;
(4-(4-chlorophenoxy)piperidin-1-yl)(4-hydroxy-3,5-dimethoxyphenyl)methanone;

(4-(4-chlorophenoxy)piperidin-1-yl)(4-hydroxy-2-methylphenyl)methanone;
(4-(4-chlorophenoxy)piperidin-1-yl)(5-hydroxy-2-methylphenyl)methanone;
(3-chloro-2-hydroxyphenyl)(4-(4-chlorophenoxy)piperidin-1-yl)methanone;
(4-(4-chlorophenoxy)piperidin-1-yl)(3-fluoro-2-hydroxyphenyl)methanone;
2-(5-(4-(4-chlorophenoxy)piperidine-1-carbonyl)-2-methylphenoxy)acetamide;
2-(2-(4-(4-chlorophenoxy)piperidine-1-carbonyl)-5-methylphenoxy)acetamide;
(4-(4-chlorophenoxy)piperidin-1-yl)(2,6-dihydroxyphenyl)methanone;
(4-(4-chlorophenoxy)piperidin-1-yl)(2-fluoro-3-hydroxyphenyl)methanone;
(4-(4-chlorophenoxy)piperidin-1-yl)(2-fluoro-5-hydroxyphenyl)methanone;
(2-chloro-5-hydroxyphenyl)(4-(4-chlorophenoxy)piperidin-1-yl)methanone;
(3-(tert-butyl)-1-methyl-1H-pyrazol-5-yl)(4-(4-fluorophenoxy)piperidin-1-yl)methanone;
(4-fluoro-3-methoxyphenyl)(4-(4-fluorophenoxy)piperidin-1-yl)methanone;
(4-((4-chlorophenyl)sulfonyl)piperidin-1-yl)(2-methyl-2H-indazol-3-yl)methanone;
(4-(4-fluorophenoxy)piperidin-1-yl)(4-fluorophenyl)methanone;
(5-(tert-butyl)isoxazol-3-yl)(4-(4-fluorophenoxy)piperidin-1-yl)methanone;
(4-(4-fluorophenoxy)piperidin-1-yl)(1-methyl-5-(trifluoromethyl)-1H-pyrazol-3-yl)methanone;
(4-(4-fluorophenoxy)piperidin-1-yl)(1-methyl-1H-indazol-3-yl)methanone;
(4-(4-fluorophenoxy)piperidin-1-yl)(quinoxalin-2-yl)methanone;
(4-(4-fluorophenoxy)piperidin-1-yl)(4-methoxyquinolin-2-yl)methanone;
(4-(4-fluorophenoxy)piperidin-1-yl)(6-methoxyquinolin-2-yl)methanone;
(4-(4-fluorophenoxy)piperidin-1-yl)(isoquinolin-1-yl)methanone;
(4-(4-fluorophenoxy)piperidin-1-yl)(isoquinolin-4-yl)methanone;
(4-(4-fluorophenoxy)piperidin-1-yl)(quinolin-4-yl)methanone;
(5-aminopyridin-2-yl)(4-(4-chlorophenoxy)piperidin-1-yl)methanone;
(6-(tert-butyl)pyridin-3-yl)(4-(4-chlorophenoxy)piperidin-1-yl)methanone;
(6-(tert-butyl)pyridin-3-yl)(4-(4-fluorophenoxy)piperidin-1-yl)methanone;
N-(6-(4-(4-chlorophenoxy)piperidine-1-carbonyl)pyridin-3-yl)acetamide;
(6-methylpyridin-3-yl)(4-(3-(trifluoromethoxy)phenoxy)piperidin-1-yl)methanone;
(1,3-dimethyl-1H-pyrazol-5-yl)(4-(3-(trifluoromethoxy)phenoxy)piperidin-1-yl)methanone;
(3,5-dimethylisoxazol-4-yl)(4-(3-(trifluoromethoxy)phenoxy)piperidin-1-yl)methanone
(6-hydroxypyridin-2-yl)(4-(3-(trifluoromethoxy)phenoxy)piperidin-1-yl)methanone;
(3-methylpyridin-2-yl)(4-(3-(trifluoromethoxy)phenoxy)piperidin-1-yl)methanone;
(5-methoxypyridin-3-yl)(4-(3-(trifluoromethoxy)phenoxy)piperidin-1-yl)methanone;
(5-aminopyridin-3-yl)(4-(3-(trifluoromethoxy)phenoxy)piperidin-1-yl)methanone;
(6-methoxypyridin-3-yl)(4-(3-(trifluoromethoxy)phenoxy)piperidin-1-yl)methanone;
4-(4-(3-(trifluoromethoxy)phenoxy)piperidine-1-carbonyl)picolinamide;
(3-methylisoxazol-5-yl)(4-(3-(trifluoromethoxy)phenoxy)piperidin-1-yl)methanone;
(2-methylthiazol-5-yl)(4-(3-(trifluoromethoxy)phenoxy)piperidin-1-yl)methanone;
(1-methyl-1H-imidazol-4-yl)(4-(3-(trifluoromethoxy)phenoxy)piperidin-1-yl)methanone;
(2-hydroxy-6-methoxyphenyl)(4-(3-(trifluoromethoxy)phenoxy)piperidin-1-yl)methan one;
(2,4-dimethylthiazol-5-yl)(4-(3-(trifluoromethoxy)phenoxy)piperidin-1-yl)methanone;
(2-methyl-2H-indazol-3-yl)(4-(3-(trifluoromethoxy)phenoxy)piperidin-1-yl)methanone
(2-methyl-2H-indazol-6-yl)(4-(3-(trifluoromethoxy)phenoxy)piperidin-1-yl)methanone imidazo[1,2-a]pyridin-8-yl(4-(3-(trifluoromethoxy)phenoxy)piperidin-1-yl)methanone;
(1,8-naphthyridin-2-yl)(4-(3-(trifluoromethoxy)phenoxy)piperidin-1-yl)methanone;
(1,5-naphthyridin-2-yl)(4-(3-(trifluoromethoxy)phenoxy)piperidin-1-yl)methanone;
(2-hydroxyquinolin-4-yl)(4-(3-(trifluoromethoxy)phenoxy)piperidin-1-yl)methanone;
1,6-dimethyl-3-(4-(3-(trifluoromethoxy)phenoxy)piperidine-1-carbonyl)pyridin-2(1H)-one;
benzo[d]thiazol-6-yl(4-(4-fluorophenoxy)piperidin-1-yl)methanone;
(4-(4-fluorophenoxy)piperidin-1-yl)(2-methyl-1H-benzo[d]imidazol-5-yl)methanone;
(4-(4-fluorophenoxy)piperidin-1-yl)(1-methyl-1H-benzo[d]imidazol-5-yl)methanone;
(4-(4-fluorophenoxy)piperidin-1-yl)(5-methoxypyridin-2-yl)methanone;
(4-(4-fluorophenoxy)piperidin-1-yl)(4-methyl-2-phenylpyrimidin-5-yl)methanone;
(4-(4-fluorophenoxy)piperidin-1-yl)(1-methyl-1H-benzo[d]imidazol-2-yl)methanone;
(4-(4-chlorophenoxy)piperidin-1-yl)(6-ethoxypyridin-3-yl)methanone;
(4-(4-chlorophenoxy)piperidin-1-yl)(6-(dimethylamino)pyridin-3-yl)methanone;
(4-((4-chlorophenyl)sulfonyl)piperidin-1-yl)(quinolin-2-yl)methanone;
(4-((4-chlorophenyl)sulfonyl)piperidin-1-yl)(quinolin-3-yl)methanone;
(4-((4-chlorophenyl)sulfonyl)piperidin-1-yl)(5-methyl-1-phenyl-1H-pyrazol-4-yl)methanone;
(4-((4-chlorophenyl)sulfonyl)piperidin-1-yl)(4-methoxyquinolin-2-yl)methanone;
(4-((4-chlorophenyl)sulfonyl)piperidin-1-yl)(6-ethoxypyridin-2-yl)methanone;
(6-methoxypyridin-2-yl)(4-(3-(trifluoromethoxy)phenoxy)piperidin-1-yl)methanone;
(5-methoxypyrazin-2-yl)(4-(3-(trifluoromethoxy)phenoxy)piperidin-1-yl)methanone;
(2-hydroxy-3-methoxyphenyl)(4-(3-(trifluoromethoxy)phenoxy)piperidin-1-yl)methan one;
(2-methyloxazol-4-yl)(4-(3-(trifluoromethoxy)phenoxy)piperidin-1-yl)methanone;
(4-(2-hydroxypropan-2-yl)phenyl)(4-(3-(trifluoromethoxy)phenoxy)piperidin-1-yl)methanone;

(6-ethoxypyridin-2-yl)(4-(3-(trifluoromethoxy)phenoxy)piperidin-1-yl)methanone;
(1H-benzo[d]imidazol-6-yl)(4-(3-(trifluoromethoxy)phenoxy)piperidin-1-yl)methanone;
imidazo[1,2-a]pyrazin-2-yl(4-(3-(trifluoromethoxy)phenoxy)piperidin-1-yl)methanone;
(4-hydroxy-7-methyl-1,8-naphthyridin-3-yl)(4-(3-(trifluoromethoxy)phenoxy)piperidin-1-yl)methanone;
N-(4-(4-(3-(trifluoromethoxy)phenoxy)piperidine-1-carbonyl)pyridin-2-yl)acetamide;
N-(6-(4-(3-(trifluoromethoxy)phenoxy)piperidine-1-carbonyl)pyridin-2-yl)acetamide;
(4-((4-chlorophenyl)sulfonyl)piperidin-1-yl)(p-tolyl)methanone;
(4-((4-chlorophenyl)sulfonyl)piperidin-1-yl)(4-methoxyphenyl)methanone;
(4-chlorophenyl)(4-((4-chlorophenyl)sulfonyl)piperidin-1-yl)methanone;
(4-((4-chlorophenyl)sulfonyl)piperidin-1-yl)(1,5-naphthyridin-2-yl)methanone;
(4-((4-chlorophenyl)sulfonyl)piperidin-1-yl)(6-methoxy-1-methyl-1H-indol-2-yl)methanone;
quinolin-8-yl(44(3-(trifluoromethyl)phenyl)sulfonyl)piperidin-1-yl)methanone;
quinolin-8-yl(4-tosylpiperidin-1-yl)methanone;
(4-((4-chlorophenyl)sulfonyl)piperidin-1-yl)(isoquinolin-3-yl)methanone;
4-(4-(3-(trifluoromethoxy)phenoxy)piperidine-1-carbonyl)benzamide;
3-(4-(3-(trifluoromethoxy)phenoxy)piperidine-1-carbonyl)benzamide;
3-(4-(4-chlorophenoxy)piperidine-1-carbonyl)benzamide;
3-(4-(4-chlorophenoxy)piperidine-1-carbonyl)-N-methylbenzamide;
4-(4-(4-chlorophenoxy)piperidine-1-carbonyl)-N-methylbenzamide;
(4-hydroxyquinolin-2-yl)(4-(3-(trifluoromethoxy)phenoxy)piperidin-1-yl)methanone;
(3-hydroxyquinoxalin-2-yl)(4-(3-(trifluoromethoxy)phenoxy)piperidin-1-yl)methanone
(6-(hydroxymethyl)pyridin-2-yl)(4-(3-(trifluoromethoxy)phenoxy)piperidin-1-yl)methanone;
(1-(2-hydroxyethyl)-2-methyl-1H-benzo[d]imidazol-5-yl)(4-(3-(trifluoromethoxy)phen oxy)piperidin-1-yl)methanone;
(2-hydroxy-6-methylpyridin-4-yl)(4-(3-(trifluoromethoxy)phenoxy)piperidin-1-yl)methanone;
1-methyl-4-(4-(3-(trifluoromethoxy)phenoxy)piperidine-1-carbonyl)pyridin-2(1H)-one
(2-hydroxy-6-methylpyridin-3-yl)(4-(3-(trifluoromethoxy)phenoxy)piperidin-1-yl)methanone;
3-(4-(3-(trifluoromethoxy)phenoxy)piperidine-1-carbonyl)quinolin-2(1H)-one;
(1H-1,2,4-triazol-3-yl)(4-(3-(trifluoromethoxy)phenoxy)piperidin-1-yl)methanone;
2-cyclopropyl-6-methyl-5-(4-(3-(trifluoromethoxy)phenoxy)piperidine-1-carbonyl)pyrimidin-4(1H)-one;
5,6-dimethyl-3-(4-(3-(trifluoromethoxy)phenoxy)piperidine-1-carbonyl)pyridin-2(1H)-one;
(4-(3-(trifluoromethoxy)phenoxy)piperidin-1-yl)(1,3,6-trimethyl-1H-pyrazolo[3,4-b]pyridin-4-yl)methanone;
4-(4-(3-(trifluoromethoxy)phenoxy)piperidine-1-carbonyl)-1H-benzo[d]imidazol-2(3H)-one;
(4-(4-chloro-2-methoxyphenoxy)piperidin-1-yl)(quinolin-8-yl)methanone;
1-(5-chloro-2-((1-(quinoline-8-carbonyl)piperidin-4-yl)oxy)phenyl)ethanone;
5-chloro-2-((1-(quinoline-8-carbonyl)piperidin-4-yl)oxy)benzonitrile;
(4-((4-chlorophenyl)sulfonyl)piperidin-1-yl)(quinoxalin-2-yl)methanone;
(4-((4-chlorophenyl)sulfonyl)piperidin-1-yl)(6-methoxyquinolin-2-yl)methanone;
(4-((4-chlorophenyl)sulfonyl)piperidin-1-yl)(4-methyl-2-phenylpyrimidin-5-yl)methan one;
(4-((4-chlorophenyl)sulfonyl)piperidin-1-yl)(6-(pyrrolidin-1-yl)pyridin-2-yl)methanone;
(5-(tert-butyl)isoxazol-3-yl)(4-((4-chlorophenyl)sulfonyl)piperidin-1-yl)methanone;
(4-((4-chlorophenyl)sulfonyl)piperidin-1-yl)(6-(2,2,2-trifluoroethoxy)pyridin-3-yl)methanone;
(4-((4-chlorophenyl)sulfonyl)piperidin-1-yl)(1-methyl-1H-indol-5-yl)methanone;
(4-((4-chlorophenyl)sulfonyl)piperidin-1-yl)(1-methyl-1H-indol-2-yl)methanone;
(4-(3-fluorophenoxy)piperidin-1-yl)(4-fluorophenyl)methanone;
(4-((4-chlorophenyl)sulfonyl)piperidin-1-yl)(1-methyl-1H-indol-6-yl)methanone;
3-(4-(3-(trifluoromethyl)phenoxy)piperidine-1-carbonyl)benzamide;
4-(4-(3-(trifluoromethyl)phenoxy)piperidine-1-carbonyl)benzamide;
4-(4-(3-(trifluoromethyl)phenoxy)piperidine-1-carbonyl)picolinamide;
(4-((4-chlorophenyl)sulfonyl)piperidin-1-yl)(2-methoxyquinolin-4-yl)methanone;
(4-((4-chlorophenyl)sulfonyl)piperidin-1-yl)(6-phenoxypyridin-3-yl)methanone;
3-(4-((4-chlorophenyl)sulfonyl)piperidine-1-carbonyl)quinolin-2(1H)-one;
3-(4-((4-chlorophenyl)sulfonyl)piperidine-1-carbonyl)-1-methylquinolin-2(1H)-one;
(4-(4-fluorophenoxy)piperidin-1-yl)(5-methyl-1-phenyl-1H-pyrazol-4-yl)methanone;
4-(4-(4-chlorophenoxy)piperidine-1-carbonyl)-N-(2-methoxyethyl)-N-methylbenzamide;
4-(4-(4-chlorophenoxy)piperidine-1-carbonyl)-N-(2-methoxyethyl)benzamide;
4-(4-(4-chlorophenoxy)piperidine-1-carbonyl)-N-(1-((1-hydroxycyclohexyl)methyl)piperidin-4-yl)benzamide;
(S)-4-(4-(4-chlorophenoxy)piperidine-1-carbonyl)-N-(2-hydroxy-1-phenylethyl)benzamide;
(S)-4-(4-(4-chlorophenoxy)piperidine-1-carbonyl)-N-(2-hydroxy-2-phenylethyl)benzamide;
(S)-4-(4-(4-chlorophenoxy)piperidine-1-carbonyl)-N-(1-hydroxy-3-phenylpropan-2-yl)benzamide;
(S)—N-(1-amino-1-oxo-3-phenylpropan-2-yl)-4-(4-(4-chlorophenoxy)piperidine-1-carbonyl)benzamide;
(4-((4-chlorophenyl)sulfonyl)piperidin-1-yl)(1-methyl-1H-indol-4-yl)methanone;
4-(4-((4-chlorophenyl)thio)piperidine-1-carbonyl)picolinamide;
6-(4-(3-(trifluoromethoxy)phenoxy)piperidine-1-carbonyl)picolinamide;
4-(4-(4-chlorophenoxy)piperidine-1-carbonyl)-N-(2-oxo-2-phenylethyl)benzamide;
(2-(methylsulfonyl)phenyl)(4-(3-(trifluoromethoxy)phenoxy)piperidin-1-yl)methanone;
(3-(methylsulfonyl)phenyl)(4-(3-(trifluoromethoxy)phenoxy)piperidin-1-yl)methanone;
(4-((4-chlorophenyl)sulfonyl)piperidin-1-yl)(5-fluoro-1-methyl-1H-indol-2-yl)methanone;

(4-((4-chlorophenyl)sulfonyl)piperidin-1-yl)(6-fluoro-1-methyl-1H-indol-2-yl)methanone;
(4-(3-ethoxyphenoxy)piperidin-1-yl)(quinolin-8-yl)methanone;
(4-((4-chlorophenyl)sulfonyl)piperidin-1-yl)(3-(2-methylthiazol-4-yl)phenyl)methanone;
N-methyl-3-(4-(3-(trifluoromethoxy)phenoxy)piperidine-1-carbonyl)benzamide;
3-(4-(3-(trifluoromethoxy)phenoxy)piperidine-1-carbonyl)benzenesulfonamide;
4-(4-(3-(trifluoromethoxy)phenoxy)piperidine-1-carbonyl)benzenesulfonamide;
(4-(4-fluorophenoxy)piperidin-1-yl)(1,5-naphthyridin-2-yl)methanone;
(4-(4-fluorophenoxy)piperidin-1-yl)(quinolin-2-yl)methanone;
(4-(3-fluorophenoxy)piperidin-1-yl)(4-methoxyquinolin-2-yl)methanone;
(1H-benzo[d][1,2,3]triazol-7-yl)(4-(3-(trifluoromethoxy)phenoxy)piperidin-1-yl)methanone;
2-(2-(4-(4-chlorophenoxy)piperidine-1-carbonyl)phenoxy)acetamide;
2-(4-(4-(4-chlorophenoxy)piperidine-1-carbonyl)phenoxy)acetamide;
2-(2-(4-(3-(trifluoromethoxy)phenoxy)piperidine-1-carbonyl)phenoxy)acetamide;
2-(3-(4-(3-(trifluoromethoxy)phenoxy)piperidine-1-carbonyl)phenoxy)acetamide;
2-(4-(4-(3-(trifluoromethoxy)phenoxy)piperidine-1-carbonyl)phenoxy)acetamide;
(8-hydroxyquinolin-2-yl)(4-((3-(trifluoromethoxy)phenyl)sulfonyl)piperidin-1-yl)methanone;
quinolin-8-yl(44(3-(trifluoromethoxy)phenyl)sulfonyl)piperidin-1-yl)methanone;
quinolin-2-yl(4-((3-(trifluoromethoxy)phenyl)sulfonyl)piperidin-1-yl)methanone;
(4-((4-chlorophenyl)sulfonyl)piperidin-1-yl)(5-phenylisoxazol-3-yl)methanone;
(6-methoxyquinolin-2-yl)(4-((3-(trifluoromethoxy)phenyl)sulfonyl)piperidin-1-yl)methanone;
(5-methyl-2-phenyl-2H-1,2,3-triazol-4-yl)(4-((3-(trifluoromethoxy)phenyl)sulfonyl)piperidin-1-yl)methanone;
(5-fluoro-1-methyl-1H-indol-2-yl)(4-((3-(trifluoromethoxy)phenyl)sulfonyl)piperidin-1-yl)methanone;
(6-fluoro-1-methyl-1H-indol-2-yl)(4-((3-(trifluoromethoxy)phenyl)sulfonyl)piperidin-1-yl)methanone;
(4-hydroxyquinolin-8-yl)(4-(3-(trifluoromethoxy)phenoxy)piperidin-1-yl)methanone;
(1,8-naphthyridin-4-yl)(4-(3-(trifluoromethoxy)phenoxy)piperidin-1-yl)methanone;
(1,6-naphthyridin-8-yl)(4-(3-(trifluoromethoxy)phenoxy)piperidin-1-yl)methanone;
[1,2,4]triazolo[1,5-a]pyrimidin-2-yl(4-(3-(trifluoromethoxy)phenoxy)piperidin-1-yl)methanone;
(5-methyl-1H-pyrazol-3-yl)(4-(3-(trifluoromethoxy)phenoxy)piperidin-1-yl)methanone;
2-chloro-5-(4-(3-(trifluoromethoxy)phenoxy)piperidine-1-carbonyl)benzenesulfonamide;
(S)-3-(4-(4-chlorophenoxy)piperidine-1-carbonyl)-N-(2-hydroxy-2-phenylethyl)benzamide;
(S)-3-(4-(4-chlorophenoxy)piperidine-1-carbonyl)-N-(2-hydroxy-1-phenylethyl)benzamide;
(S)-3-(4-(4-chlorophenoxy)piperidine-1-carbonyl)-N-(1-hydroxy-3-phenylpropan-2-yl)benzamide;
(S)—N-(1-amino-1-oxo-3-phenylpropan-2-yl)-3-(4-(4-chlorophenoxy)piperidine-1-carbonyl)benzamide;
(4-((3-ethoxyphenyl)sulfonyl)piperidin-1-yl)(8-hydroxyquinolin-2-yl)methanone;
(4-((4-chlorophenyl)sulfonyl)piperidin-1-yl)(4-methyl-2-phenylthiazol-5-yl)methanone;
(4-((4-chlorophenyl)sulfonyl)piperidin-1-yl)(2-phenylthiazol-4-yl)methanone;
(4-chloro-2-(methylsulfonyl)phenyl)(4-(3-(trifluoromethoxy)phenoxy)piperidin-1-yl)methanone;
(5-fluoro-2-(methylsulfonyl)phenyl)(4-(3-(trifluoromethoxy)phenoxy)piperidin-1-yl)methanone;
N,N-dimethyl-4-(4-(3-(trifluoromethoxy)phenoxy)piperidine-1-carbonyl)benzenesulfonamide;
N-(2-(4-(4-(3-(trifluoromethoxy)phenoxy)piperidine-1-carbonyl)phenoxy)ethyl)acetamide;
(2-phenyl-1H-imidazol-5-yl)(4-((3-(trifluoromethoxy)phenyl)sulfonyl)piperidin-1-yl)methanone;
(3-(2-methylthiazol-4-yl)phenyl)(4-((3-(trifluoromethoxy)phenyl)sulfonyl)piperidin-1-yl)methanone;
N-(4-(4-(3-ethoxyphenoxy)piperidine-1-carbonyl)pyridin-2-yl)acetamide;
(4-(3-ethoxyphenoxy)piperidin-1-yl)(2-(methylsulfonyl)phenyl)methanone;
3-(4-(3-ethoxyphenoxy)piperidine-1-carbonyl)benzenesulfonamide;
N-(6-(4-(3-ethoxyphenoxy)piperidine-1-carbonyl)pyridin-2-yl)acetamide;
(4-(3-ethoxyphenoxy)piperidin-1-yl)(2-methyl-2H-indazol-3-yl)methanone;
(4-(3-ethoxyphenoxy)piperidin-1-yl)(1,5-naphthyridin-2-yl)methanone;
(8-hydroxyquinolin-2-yl)(4-((4-(trifluoromethoxy)phenyl)sulfonyl)piperidin-1-yl)methanone;
quinolin-8-yl(4-((4-(trifluoromethoxy)phenyl)sulfonyl)piperidin-1-yl)methanone;
quinolin-2-yl(4-((4-(trifluoromethoxy)phenyl)sulfonyl)piperidin-1-yl)methanone;
N-(3-(4-(3-(trifluoromethoxy)phenoxy)piperidine-1-carbonyl)phenyl)methanesulfonamide;
(2-(ethylsulfonyl)phenyl)(4-(3-(trifluoromethoxy)phenoxy)piperidin-1-yl)methanone;
(3-fluoro-4-(methylsulfonyl)phenyl)(4-(3-(trifluoromethoxy)phenoxy)piperidin-1-yl)methanone;
ethyl (4-(4-(3-(trifluoromethoxy)phenoxy)piperidine-1-carbonyl)pyridin-2-yl)carbamate;
2-(4-(3-(trifluoromethoxy)phenoxy)piperidine-1-carbonyl)thiazole-4-carboxamide;
N,N-dimethyl-2-(4-(3-(trifluoromethoxy)phenoxy)piperidine-1-carbonyl)benzenesulfonamide;
(4-(4-(3-(trifluoromethoxy)phenoxy)piperidine-1-carbonyl)phenyl)methanesulfonamide;
4-methoxy-3-(4-(3-(trifluoromethoxy)phenoxy)piperidine-1-carbonyl)benzenesulfonamide;
2-((2-(4-(3-(trifluoromethoxy)phenoxy)piperidine-1-carbonyl)pyridin-3-yl)oxy)acetamide;
(4-(aminomethyl)pyridin-2-yl)(4-(3-(trifluoromethoxy)phenoxy)piperidin-1-yl)methan one;
N-((2-(4-(3-(trifluoromethoxy)phenoxy)piperidine-1-carbonyl)pyridin-4-yl)methyl)methanesulfonamide;
ethyl ((2-(4-(3-(trifluoromethoxy)phenoxy)piperidine-1-carbonyl)pyridin-4-yl)methyl)carb a mate;
N-(2-(4-(3-(trifluoromethoxy)phenoxy)piperidine-1-carbonyl)benzyl)acetamide;
N-(2-(4-(3-(trifluoromethoxy)phenoxy)piperidine-1-carbonyl)benzyl)methanesulfonamide;
ethyl 2-(4-(3-(trifluoromethoxy)phenoxy)piperidine-1-carbonyl)benzylcarbamate;

(2-(methylsulfonyl)phenyl)(4-(3-(2,2,2-trifluoroethoxy) phenoxy)piperidin-1-yl)methan one;
N-(4-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)picolinamide;
3-(4-(3-(2,2,2-trifluoroethoxy)phenoxy)piperidine-1-carbonyl)benzamide;
3-(4-(3-(2,2,2-trifluoroethoxy)phenoxy)piperidine-1-carbonyl)benzenesulfonamide;
2-(2-(4-(3-(2,2,2-trifluoroethoxy)phenoxy)piperidine-1-carbonyl)phenoxy)acetamide;
quinolin-8-yl(4-(3-(2,2,2-trifluoroethoxy)phenoxy)piperidin-1-yl)methanone;
(1,5-naphthyridin-2-yl)(4-(3-(2,2,2-trifluoroethoxy)phenoxy)piperidin-1-yl)methanone
(2-methyl-2H-indazol-3-yl)(4-(3-(2,2,2-trifluoroethoxy) phenoxy)piperidin-1-yl)methanone;
(1,3-dimethyl-1H-pyrazol-5-yl)(4-(3-(2,2,2-trifluoroethoxy) phenoxy)piperidin-1-yl)methanone;
N-(6-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)benzamide;
(3,5-dimethylisoxazol-4-yl)(4-(3-(2,2,2-trifluoroethoxy) phenoxy)piperidin-1-yl)methanone;
(3-(methylsulfonyl)phenyl)(4-(3-(2,2,2-trifluoroethoxy) phenoxy)piperidin-1-yl)methan one;
(1,6-naphthyridin-8-yl)(4-(3-(2,2,2-trifluoroethoxy)phenoxy)piperidin-1-yl)methanone
(3-methyl-1H-pyrazol-5-yl)(4-(3-(2,2,2-trifluoroethoxy) phenoxy)piperidin-1-yl)methanone;
2-(3-(4-(3-(2,2,2-trifluoroethoxy)phenoxy)piperidine-1-carbonyl)phenoxy)acetamide;
(5-((tetrahydro-2H-pyran-4-yl)oxy)pyridin-3-yl)(4-(3-(trifluoromethoxy)phenoxy)piperidin-1-yl)methanone;
1-(3-(4-(3-(trifluoromethoxy)phenoxy)piperidine-1-carbonyl)phenyl)urea;
1-(4-(4-(3-(trifluoromethoxy)phenoxy)piperidine-1-carbonyl)phenyl)urea;
(1H-1,2,4-triazol-3-yl)(4-(3-(2,2,2-trifluoroethoxy)phenoxy)piperidin-1-yl)methanone;
(4-(3-ethoxyphenoxy)piperidin-1-yl)(3-(methylsulfonyl) phenyl)methanone;
(4-(3-ethoxyphenoxy)piperidin-1-yl)(3-methyl-1H-pyrazol-5-yl)methanone;
N,N-dimethyl-3-(4-(3-(trifluoromethoxy)phenoxy)piperidine-1-carbonyl)benzenesulfonamide;
N-(2-(4-(3-(trifluoromethoxy)phenoxy)piperidine-1-carbonyl)phenyl)methanesulfonamide;
(6-aminopyridin-2-yl)(4-(3-(trifluoromethoxy)phenoxy)piperidin-1-yl)methanone;
2-(methyl(3-(4-(3-(trifluoromethoxy)phenoxy)piperidine-1-carbonyl)benzyl)amino)acetamide;
2-(methyl(4-(4-(3-(trifluoromethoxy)phenoxy)piperidine-1-carbonyl)benzyl)amino)acetamide;
N,N-dimethyl-2-(2-(4-(3-(trifluoromethoxy)phenoxy)piperidine-1-carbonyl)phenoxy)acetamide;
(1,3-dimethyl-1H-pyrazol-5-yl)(4-(3-(trifluoromethyl)phenoxy)piperidin-1-yl)methanone;
(2-(methylsulfonyl)phenyl)(4-(3-(trifluoromethyl)phenoxy) piperidin-1-yl)methanone;
N-(6-(4-(3-(trifluoromethoxy)phenoxy)piperidine-1-carbonyl)pyridin-2-yl)acetamide;
3-(4-(3-(trifluoromethyl)phenoxy)piperidine-1-carbonyl) benzenesulfonamide;
(3,5-dimethylisoxazol-4-yl)(4-(3-(trifluoromethyl)phenoxy) piperidin-1-yl)methanone;
(1,6-naphthyridin-8-yl)(4-(3-(trifluoromethyl)phenoxy)piperidin-1-yl)methanone;
(3-methyl-1H-pyrazol-5-yl)(4-(3-(trifluoromethyl)phenoxy) piperidin-1-yl)methanone;
2-(2-(4-(3-(trifluoromethyl)phenoxy)piperidine-1-carbonyl) phenoxy)acetamide;
2-(4-(4-(3-(trifluoromethyl)phenoxy)piperidine-1-carbonyl) phenoxy)acetamide;
2-(3-(4-(3-(trifluoromethyl)phenoxy)piperidine-1-carbonyl) phenoxy)acetamide;
(1H-1,2,4-triazol-3-yl)(4-(3-(trifluoromethyl)phenoxy)piperidin-1-yl)methanone;
N-(2-(2-(4-(3-(trifluoromethoxy)phenoxy)piperidine-1-carbonyl)phenoxy)ethyl)acetamide;
N-(2-(2-(4-(3-(trifluoromethoxy)phenoxy)piperidine-1-carbonyl)phenoxy)ethyl)methanesulfonamide;
ethyl (2-(2-(4-(3-(trifluoromethoxy)phenoxy)piperidine-1-carbonyl)phenoxy)ethyl)carbamate;
N-(2-(2-(4-(3-(trifluoromethoxy)phenoxy)piperidine-1-carbonyl)phenoxy)ethyl)cyclopropane-1,1-dicarboxamide;
(3-(2-aminoethoxy)phenyl)(4-(3-(trifluoromethoxy)phenoxy)piperidin-1-yl)methanone;
N-(2-(3-(4-(3-(trifluoromethoxy)phenoxy)piperidine-1-carbonyl)phenoxy)ethyl)acetamide;
N-(2-(3-(4-(3-(trifluoromethoxy)phenoxy)piperidine-1-carbonyl)phenoxy)ethyl)methanesulfonamide;
ethyl (2-(3-(4-(3-(trifluoromethoxy)phenoxy)piperidine-1-carbonyl)phenoxy)ethyl)carbamate;
N-(2-(3-(4-(3-(trifluoromethoxy)phenoxy)piperidine-1-carbonyl)phenoxy)ethyl)cyclopropane-1,1-dicarboxamide;
N-(3-(4-(3-(trifluoromethoxy)phenoxy)piperidine-1-carbonyl)pyridin-2-yl)acetamide;
N-(1-methyl-5-(4-(3-(trifluoromethoxy)phenoxy)piperidine-1-carbonyl)-1H-pyrazol-3-yl)acetamide;
(2-(ethylsulfonyl)phenyl)(4-(3-(trifluoromethyl)phenoxy) piperidin-1-yl)methanone;
(4-(3-ethoxyphenoxy)piperidin-1-yl)(2-(ethylsulfonyl)phenyl)methanone;
(2-(ethylsulfonyl)phenyl)(4-(3-(2,2,2-trifluoroethoxy)phenoxy)piperidin-1-yl)methanone;
N-(2-(4-(3-(trifluoromethoxy)phenoxy)piperidine-1-carbonyl)pyridin-3-yl)acetamide;
2-(4-(4-(3-chlorophenoxy)piperidine-1-carbonyl)phenoxy) acetamide;
2-(2-(4-((4-chlorophenyl)thio)piperidine-1-carbonyl)phenoxy)acetamide;
2-(3-(4-((4-chlorophenyl)thio)piperidine-1-carbonyl)phenoxy)acetamide;
(4-((4-chlorophenyl)thio)piperidin-1-yl)(2-(methylsulfonyl) phenyl)methanone;
2-(methyl(2-(4-(3-(trifluoromethoxy)phenoxy)piperidine-1-carbonyl)benzyl)amino)acetamide;
1-morpholino-2-(2-(4-(3-(trifluoromethoxy)phenoxy)piperidine-1-carbonyl)phenoxy)ethanone;
1-(piperidin-1-yl)-2-(2-(4-(3-(trifluoromethoxy)phenoxy) piperidine-1-carbonyl)phenoxy)ethanone;
(2-(2-methoxyethoxy)phenyl)(4-(3-(trifluoromethoxy)phenoxy)piperidin-1-yl)methanone;
(3-(methylsulfonyl)phenyl)(4-(3-(trifluoromethyl)phenoxy) piperidin-1-yl)methanone;
(4-(3-chlorophenoxy)piperidin-1-yl)(3-(methylsulfonyl) phenyl)methanone;
(4-(4-chlorophenoxy)piperidin-1-yl)(3-(methylsulfonyl) phenyl)methanone;

(4-(4-chlorophenoxy)piperidin-1-yl)(2-(ethylsulfonyl)phenyl)methanone;
N,N-dimethyl-3-(4-(3-(trifluoromethyl)phenoxy)piperidine-1-carbonyl)benzenesulfonamide;
3-(4-(4-chlorophenoxy)piperidine-1-carbonyl)-N,N-dimethylbenzenesulfonamide;
N,N-dimethyl-3-(4-(3-(2,2,2-trifluoroethoxy)phenoxy)piperidine-1-carbonyl)benzenesulfonamide;
N,N-dimethyl-2-(4-(3-(trifluoromethyl)phenoxy)piperidine-1-carbonyl)benzenesulfonamide;
2-(4-(4-chlorophenoxy)piperidine-1-carbonyl)-N,N-dimethylbenzenesulfonamide;
N,N-dimethyl-2-(4-(3-(2,2,2-trifluoroethoxy)phenoxy)piperidine-1-carbonyl)benzenesulfonamide;
(4-(3-(2-methoxyethoxy)phenoxy)piperidin-1-yl)(quinolin-8-yl)methanone;
(4-(3-(2-methoxyethoxy)phenoxy)piperidin-1-yl)(quinolin-2-yl)methanone;
(4-(3-(2-methoxyethoxy)phenoxy)piperidin-1-yl)(2-methyl-2H-indazol-3-yl)methanone;
2-((2-(4-(3-(trifluoromethoxy)phenoxy)piperidine-1-carbonyl)phenyl)thio)acetamide;
2-((2-(4-(4-chlorophenoxy)piperidine-1-carbonyl)phenyl)thio)acetamide;
4-(4-(3-(2,2,2-trifluoroethoxy)phenoxy)piperidine-1-carbonyl)-1H-benzo[d]imidazol-2(3H)-one;
(4-(3-ethoxyphenoxy)piperidin-1-yl)(1-methyl-1H-benzo[d]imidazol-2-yl)methanone;
(4-(3-fluorophenoxy)piperidin-1-yl)(1-methyl-1H-benzo[d]imidazol-2-yl)methanone;
(1H-pyrrolo[2,3-b]pyridin-2-yl)(4-(3-(2,2,2-trifluoroethoxy)phenoxy)piperidin-1-yl)methanone;
(4-(3-ethoxyphenoxy)piperidin-1-yl)(1H-pyrrolo[2,3-b]pyridin-2-yl)methanone;
(1H-pyrrolo[2,3-b]pyridin-2-yl)(4-(3-(trifluoromethoxy)phenoxy)piperidin-1-yl)methanone;
(4-(3-ethoxyphenoxy)piperidin-1-yl)(1-methyl-1H-pyrazolo[3,4-b]pyridin-3-yl)methan one;
(4-(3-ethoxyphenoxy)piperidin-1-yl)(1H-pyrrolo[2,3-b]pyridin-3-yl)methanone;
(4-(3-ethoxyphenoxy)piperidin-1-yl)(pyrazolo[1,5-a]pyrimidin-3-yl)methanone;
(1,3-dimethyl-1H-thieno[2,3-c]pyrazol-5-yl)(4-(3-ethoxyphenoxy)piperidin-1-yl)methanone;
(4-(3-fluorophenoxy)piperidin-1-yl)(4-methyl-3,4-dihydro-2H-pyrido[3,2-b][1,4]oxazin-7-yl)methanone;
(3,5-dimethyl-1H-pyrazol-4-yl)(4-(3-(2,2,2-trifluoroethoxy)phenoxy)piperidin-1-yl)methanone;
N-(2-hydroxyethyl)-N-methyl-2-(4-(3-(trifluoromethoxy)phenoxy)piperidine-1-carbon yl)benzenesulfonamide;
N-(2-methoxyethyl)-N-methyl-2-(4-(3-(trifluoromethoxy)phenoxy)piperidine-1-carbon yl)benzenesulfonamide;
(2-(morpholinosulfonyl)phenyl)(4-(3-(trifluoromethoxy)phenoxy)piperidin-1-yl)methanone;
2-(N-methyl-2-(4-(3-(trifluoromethoxy)phenoxy)piperidine-1-carbonyl)phenylsulfonamido)acetamide;
N-methyl-3-(4-(3-(2,2,2-trifluoroethoxy)phenoxy)piperidine-1-carbonyl)benzenesulfonamide;
3-(4-(3-ethoxyphenoxy)piperidine-1-carbonyl)-N-methylbenzenesulfonamide;
N-methyl-3-(4-(3-(trifluoromethoxy)phenoxy)piperidine-1-carbonyl)benzenesulfonamide;
(1,5-naphthyridin-2-yl)(4-(3-(trifluoromethyl)phenoxy)piperidin-1-yl)methanone;
3-(4-((4-chlorophenyl)thio)piperidine-1-carbonyl)benzenesulfonamide;
(4-((4-chlorophenyl)thio)piperidin-1-yl)(1,5-naphthyridin-2-yl)methanone;
N-(6-(4-((4-chlorophenyl)thio)piperidine-1-carbonyl)pyridin-2-yl)acetamide;
(4-((4-chlorophenyl)thio)piperidin-1-yl)(1,6-naphthyridin-8-yl)methanone;
2-(4-(4-(3,4-difluorophenoxy)piperidine-1-carbonyl)phenoxy)acetamide;
(4-(3,4-difluorophenoxy)piperidin-1-yl)(1,5-naphthyridin-2-yl)methanone;
2-(4-(4-(2,4-difluorophenoxy)piperidine-1-carbonyl)phenoxy)acetamide;
N-(4-(4-(3-(trifluoromethoxy)phenoxy)piperidine-1-carbonyl)pyridin-2-yl)pivalamide;
(2-(1H-imidazol-1-yl)pyridin-4-yl)(4-(3-(trifluoromethoxy)phenoxy)piperidin-1-yl)methanone;
N-(4-(4-(3-ethoxyphenoxy)piperidine-1-carbonyl)pyridin-2-yl)pivalamide;
1-(3-(4-(3-(trifluoromethoxy)phenoxy)piperidine-1-carbonyl)phenyl)pyrrolidin-2-one;
1-(3-(4-(3-(trifluoromethoxy)phenoxy)piperidine-1-carbonyl)phenyl)imidazolidin-2-one; and
(5-amino-1H-pyrazol-3-yl)(4-(3-(trifluoromethoxy)phenoxy)piperidin-1-yl)methanone;
or a prodrug thereof or a pharmaceutically acceptable salt thereof.

[7] More suitable individual compounds of the invention are:
(4-(4-chlorophenoxy)piperidin-1-yl)(quinoxalin-6-yl)methanone;
(4-(4-chlorophenoxy)piperidin-1-yl)(quinolin-8-yl)methanone;
(4-(1H-1,2,4-triazol-1-yl)phenyl)(4-(4-chlorophenoxy)piperidin-1-yl)methanone;
(4-(4-chlorophenoxy)piperidin-1-yl)(3,5-dimethylisoxazol-4-yl)methanone; (4-(4-chlorophenoxy)piperidin-1-yl)(2-methyl-2H-indazol-3-yl)methanone;
(4-(4-chlorophenoxy)piperidin-1-yl)(6-methylpyridin-3-yl)methanone;
(4-(4-chlorophenoxy)piperidin-1-yl)(6-methoxypyridin-3-yl)methanone;
(4-(4-chlorophenoxy)piperidin-1-yl)(3-methylpyridin-2-yl)methanone;
(4-(4-chlorophenoxy)piperidin-1-yl)(2,4-dimethylthiazol-5-yl)methanone;
(4-(4-chlorophenoxy)piperidin-1-yl)(4,5,6,7-tetrahydro-1H-indazol-3-yl)methanone;
(4-(4-chlorophenoxy)piperidin-1-yl)(6-methoxypyridin-2-yl)methanone;
(4-(4-chlorophenoxy)piperidin-1-yl)(2-methyl-4,5,6,7-tetrahydro-2H-indazol-3-yl)methanone;
(4-(4-chlorophenoxy)piperidin-1-yl)(1,5-naphthyridin-2-yl)methanone;
4-(4-(4-chlorophenoxy)piperidine-1-carbonyl)benzamide;
(4-(4-chlorophenoxy)piperidin-1-yl)(4-(2-hydroxypropan-2-yl)phenyl)methanone;
(4-(4-chlorophenoxy)piperidin-1-yl)(quinolin-5-yl)methanone;
(4-(4-fluorophenoxy)piperidin-1-yl)(2-methyl-2H-indazol-3-yl)methanone;
(4-phenoxypiperidin-1-yl)(quinolin-8-yl)methanone;
(4-(4-fluorophenoxy)piperidin-1-yl)(quinolin-8-yl)methanone;
(4-(4-chlorophenoxy)piperidin-1-yl)(phenyl)methanone;
(1H-benzo[d]imidazol-5-yl)(4-(4-chlorophenoxy)piperidin-1-yl)methanone;

(4-(4-chlorophenoxy)piperidin-1-yl)(1,3-dimethyl-1H-pyrazol-5-yl)methanone;
(4-(3-methoxyphenoxy)piperidin-1-yl)(quinolin-8-yl)methanone;
(4-(3-fluorophenoxy)piperidin-1-yl)(quinolin-8-yl)methanone;
(4-(4-chlorophenoxy)piperidin-1-yl)(2-methylthiazol-5-yl)methanone;
1-(3-((1-(quinoline-8-carbonyl)piperidin-4-yl)oxy)phenyl)ethanone;
(4-(4-chlorophenoxy)piperidin-1-yl)(3-methylisoxazol-5-yl)methanone;
(4-(4-chlorophenoxy)piperidin-1-yl)(1-isopropyl-1H-pyrazol-4-yl)methanone;
(4-(4-chlorophenoxy)piperidin-1-yl)(3-isopropyl-1-methyl-1H-pyrazol-5-yl)methanone;
(4-(4-chlorophenoxy)piperidin-1-yl)(3-ethyl-1-methyl-1H-pyrazol-5-yl)methanone;
(4-(4-chlorophenoxy)piperidin-1-yl)(imidazo[1,2-a]pyrazin-2-yl)methanone;
(4-(4-chlorophenoxy)piperidin-1-yl)(4-methyl-3,4-dihydro-2H-pyrido[3,2-b][1,4]oxazin-7-yl)methanone;
(4-(4-chlorophenoxy)piperidin-1-yl)(pyrazolo[1,5-a]pyridin-7-yl)methanone;
(4-(4-chlorophenoxy)piperidin-1-yl)(1-methyl-1H-imidazol-2-yl)methanone;
(4-(4-chlorophenoxy)piperidin-1-yl)(1-methyl-1H-imidazol-4-yl)methanone;
(4-chloro-5-methyl-1H-pyrazol-3-yl)(4-(4-chlorophenoxy)piperidin-1-yl)methanone;
(4-(4-chlorophenoxy)piperidin-1-yl)(4-methyl-4H-furo[3,2-b]pyrrol-5-yl)methanone;
(4-(4-chlorophenoxy)piperidin-1-yl)(pyrazolo[1,5-a]pyrimidin-3-yl)methanone;
(4-(4-chlorophenoxy)piperidin-1-yl)(2-(pyrrolidin-1-yl)pyrimidin-5-yl)methanone;
(1H-benzo[d][1,2,3]triazol-4-yl)(4-(4-chlorophenoxy)piperidin-1-yl)methanone;
3-(4-(4-chlorophenoxy)piperidine-1-carbonyl)-1,6-dimethylpyridin-2(1H)-one;
(4-(4-chlorophenoxy)piperidin-1-yl)(1-methyl-3-(trifluoromethyl)-1H-pyrazol-5-yl)methanone;
(4-(4-chlorophenoxy)piperidin-1-yl)(4-(2-hydroxyethoxy)phenyl)methanone;
(4-(4-chlorophenoxy)piperidin-1-yl)(2-hydroxy-4-methoxyphenyl)methanone;
2-(3-(4-(4-chlorophenoxy)piperidine-1-carbonyl)-1H-indol-1-yl)-N,N-dimethylacetamide;
(4-(4-chlorophenoxy)piperidin-1-yl)(3-fluoro-4-hydroxyphenyl)methanone;
2-chloro-5-(4-(4-chlorophenoxy)piperidine-1-carbonyl)benzenesulfonamide;
(4-(4-chlorophenoxy)piperidin-1-yl)(2-hydroxy-6-methoxyphenyl)methanone;
(4-(4-chlorophenoxy)piperidin-1-yl)(2-fluoro-4-hydroxyphenyl)methanone;
(4-(4-chlorophenoxy)piperidin-1-yl)(4-fluoro-3-hydroxyphenyl)methanone;
(4-(4-chlorophenoxy)piperidin-1-yl)(2-hydroxy-3-methoxyphenyl)methanone;
N-(3-(4-(4-chlorophenoxy)piperidine-1-carbonyl)phenyl)acetamide;
(4-(4-chlorophenoxy)piperidin-1-yl)(1-((4-hydroxytetrahydro-2H-pyran-4-yl)methyl)-1H-indol-5-yl)methanone;
N-(6-(4-(4-chlorophenoxy)piperidine-1-carbonyl)pyridin-2-yl)acetamide;
N-(4-(4-(4-chlorophenoxy)piperidine-1-carbonyl)pyridin-2-yl)acetamide;
(4-(4-chlorophenoxy)piperidin-1-yl)(1,6-naphthyridin-5-yl)methanone;
(4-(4-chlorophenoxy)piperidin-1-yl)(3-hydroxyphenyl)methanone;
(4-(4-chlorophenoxy)piperidin-1-yl)(2-fluoro-3-hydroxyphenyl)methanone;
(3-(tert-butyl)-1-methyl-1H-pyrazol-5-yl)(4-(4-fluorophenoxy)piperidin-1-yl)methanone;
(4-fluoro-3-methoxyphenyl)(4-(4-fluorophenoxy)piperidin-1-yl)methanone;
(4-((4-chlorophenyl)sulfonyl)piperidin-1-yl)(2-methyl-2H-indazol-3-yl)methanone;
(4-(4-fluorophenoxy)piperidin-1-yl)(1-methyl-1H-indazol-3-yl)methanone;
(4-(4-fluorophenoxy)piperidin-1-yl)(4-methoxyquinolin-2-yl)methanone;
(4-(4-fluorophenoxy)piperidin-1-yl)(isoquinolin-1-yl)methanone;
(5-aminopyridin-2-yl)(4-(4-chlorophenoxy)piperidin-1-yl)methanone;
(1,3-dimethyl-1H-pyrazol-5-yl)(4-(3-(trifluoromethoxy)phenoxy)piperidin-1-yl)methanone;
(3,5-dimethylisoxazol-4-yl)(4-(3-(trifluoromethoxy)phenoxy)piperidin-1-yl)methanone
(3-methylpyridin-2-yl)(4-(3-(trifluoromethoxy)phenoxy)piperidin-1-yl)methanone;
4-(4-(3-(trifluoromethoxy)phenoxy)piperidine-1-carbonyl)picolinamide;
(1-methyl-1H-imidazol-4-yl)(4-(3-(trifluoromethoxy)phenoxy)piperidin-1-yl)methanone;
(2-hydroxy-6-methoxyphenyl)(4-(3-(trifluoromethoxy)phenoxy)piperidin-1-yl)methan one;
(2,4-dimethylthiazol-5-yl)(4-(3-(trifluoromethoxy)phenoxy)piperidin-1-yl)methanone;
(2-methyl-2H-indazol-3-yl)(4-(3-(trifluoromethoxy)phenoxy)piperidin-1-yl)methanone;
1,6-dimethyl-3-(4-(3-(trifluoromethoxy)phenoxy)piperidine-1-carbonyl)pyridin-2(1H)-one;
benzo[d]thiazol-6-yl(4-(4-fluorophenoxy)piperidin-1-yl)methanone;
(4-(4-fluorophenoxy)piperidin-1-yl)(1-methyl-1H-benzo[d]imidazol-2-yl)methanone;
(2-methyloxazol-4-yl)(4-(3-(trifluoromethoxy)phenoxy)piperidin-1-yl)methanone;
N-(4-(4-(3-(trifluoromethoxy)phenoxy)piperidine-1-carbonyl)pyridin-2-yl)acetamide;
N-(6-(4-(3-(trifluoromethoxy)phenoxy)piperidine-1-carbonyl)pyridin-2-yl)acetamide;
3-(4-(3-(trifluoromethoxy)phenoxy)piperidine-1-carbonyl)benzamide;
(6-(hydroxymethyl)pyridin-2-yl)(4-(3-(trifluoromethoxy)phenoxy)piperidin-1-yl)methanone;
5,6-dimethyl-3-(4-(3-(trifluoromethoxy)phenoxy)piperidine-1-carbonyl)pyridin-2(1H)-one;
4-(4-(3-(trifluoromethoxy)phenoxy)piperidine-1-carbonyl)-1H-benzo[d]imidazol-2(3H)-one;
(4-(4-chloro-2-methoxyphenoxy)piperidin-1-yl)(quinolin-8-yl)methanone;
3-(4-(3-(trifluoromethyl)phenoxy)piperidine-1-carbonyl)benzamide;
4-(4-(3-(trifluoromethyl)phenoxy)piperidine-1-carbonyl)picolinamide;
(4-(4-fluorophenoxy)piperidin-1-yl)(5-methyl-1-phenyl-1H-pyrazol-4-yl)methanone;

4-(4-(4-chlorophenoxy)piperidine-1-carbonyl)-N-(2-methoxyethyl)-N-methylbenzamide;
(S)-4-(4-(4-chlorophenoxy)piperidine-1-carbonyl)-N-(2-hydroxy-2-phenylethyl)benzamide;
4-(4-((4-chlorophenyl)thio)piperidine-1-carbonyl)picolinamide;
6-(4-(3-(trifluoromethoxy)phenoxy)piperidine-1-carbonyl)picolinamide;
(2-(methylsulfonyl)phenyl)(4-(3-(trifluoromethoxy)phenoxy)piperidin-1-yl)methanone;
(4-(3-ethoxyphenoxy)piperidin-1-yl)(quinolin-8-yl)methanone;
N-methyl-3-(4-(3-(trifluoromethoxy)phenoxy)piperidine-1-carbonyl)benzamide;
3-(4-(3-(trifluoromethoxy)phenoxy)piperidine-1-carbonyl)benzenesulfonamide;
4-(4-(3-(trifluoromethoxy)phenoxy)piperidine-1-carbonyl)benzenesulfonamide;
(4-(4-fluorophenoxy)piperidin-1-yl)(1,5-naphthyridin-2-yl)methanone;
(4-(4-fluorophenoxy)piperidin-1-yl)(quinolin-2-yl)methanone;
(4-(3-fluorophenoxy)piperidin-1-yl)(4-methoxyquinolin-2-yl)methanone;
(1H-benzo[d][1,2,3]triazol-7-yl)(4-(3-(trifluoromethoxy)phenoxy)piperidin-1-yl)methanone;
2-(2-(4-(4-chlorophenoxy)piperidine-1-carbonyl)phenoxy)acetamide;
2-(2-(4-(3-(trifluoromethoxy)phenoxy)piperidine-1-carbonyl)phenoxy)acetamide;
(4-((4-chlorophenyl)sulfonyl)piperidin-1-yl)(5-phenylisoxazol-3-yl)methanone;
(4-hydroxyquinolin-8-yl)(4-(3-(trifluoromethoxy)phenoxy)piperidin-1-yl)methanone;
(1,8-naphthyridin-4-yl)(4-(3-(trifluoromethoxy)phenoxy)piperidin-1-yl)methanone;
(1,6-naphthyridin-8-yl)(4-(3-(trifluoromethoxy)phenoxy)piperidin-1-yl)methanone;
[1,2,4]triazolo[1,5-a]pyrimidin-2-yl(4-(3-(trifluoromethoxy)phenoxy)piperidin-1-yl)methanone;
(5-methyl-1H-pyrazol-3-yl)(4-(3-(trifluoromethoxy)phenoxy)piperidin-1-yl)methanone;
2-chloro-5-(4-(3-(trifluoromethoxy)phenoxy)piperidine-1-carbonyl)benzenesulfonamide;
(S)-3-(4-(4-chlorophenoxy)piperidine-1-carbonyl)-N-(2-hydroxy-2-phenylethyl)benzamide;
(S)—N-(1-amino-1-oxo-3-phenylpropan-2-yl)-3-(4-(4-chlorophenoxy)piperidine-1-carbonyl)benzamide;
(4-((4-chlorophenyl)sulfonyl)piperidin-1-yl)(2-phenylthiazol-4-yl)methanone;
(5-fluoro-2-(methylsulfonyl)phenyl)(4-(3-(trifluoromethoxy)phenoxy)piperidin-1-yl)methanone;
N,N-dimethyl-4-(4-(3-(trifluoromethoxy)phenoxy)piperidine-1-carbonyl)benzenesulfonamide;
N-(2-(4-(4-(3-(trifluoromethoxy)phenoxy)piperidine-1-carbonyl)phenoxy)ethyl)acetamide;
N-(4-(4-(3-ethoxyphenoxy)piperidine-1-carbonyl)pyridin-2-yl)acetamide;
3-(4-(3-ethoxyphenoxy)piperidine-1-carbonyl)benzenesulfonamide;
N-(6-(4-(3-ethoxyphenoxy)piperidine-1-carbonyl)pyridin-2-yl)acetamide;
(4-(3-ethoxyphenoxy)piperidin-1-yl)(1,5-naphthyridin-2-yl)methanone;
quinolin-8-yl(4-((4-(trifluoromethoxy)phenyl)sulfonyl)piperidin-1-yl)methanone;
quinolin-2-yl(4-((4-(trifluoromethoxy)phenyl)sulfonyl)piperidin-1-yl)methanone;
(2-(ethylsulfonyl)phenyl)(4-(3-(trifluoromethoxy)phenoxy)piperidin-1-yl)methanone;
2-(4-(3-(trifluoromethoxy)phenoxy)piperidine-1-carbonyl)thiazole-4-carboxamide;
(4-(4-(3-(trifluoromethoxy)phenoxy)piperidine-1-carbonyl)phenyl)methanesulfonamide;
4-methoxy-3-(4-(3-(trifluoromethoxy)phenoxy)piperidine-1-carbonyl)benzenesulfonamide;
2-((2-(4-(3-(trifluoromethoxy)phenoxy)piperidine-1-carbonyl)pyridin-3-yl)oxy)acetamide;
(4-(aminomethyl)pyridin-2-yl)(4-(3-(trifluoromethoxy)phenoxy)piperidin-1-yl)methanone;
N-((2-(4-(3-(trifluoromethoxy)phenoxy)piperidine-1-carbonyl)pyridin-4-yl)methyl)methanesulfonamide;
ethyl ((2-(4-(3-(trifluoromethoxy)phenoxy)piperidine-1-carbonyl)pyridin-4-yl)methyl)carbamate;
N-(2-(4-(3-(trifluoromethoxy)phenoxy)piperidine-1-carbonyl)benzyl)acetamide;
N-(2-(4-(3-(trifluoromethoxy)phenoxy)piperidine-1-carbonyl)benzyl)methanesulfonamide;
(2-(methylsulfonyl)phenyl)(4-(3-(2,2,2-trifluoroethoxy)phenoxy)piperidin-1-yl)methanone;
N-(4-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)picolinamide;
3-(4-(3-(2,2,2-trifluoroethoxy)phenoxy)piperidine-1-carbonyl)benzamide;
2-(2-(4-(3-(2,2,2-trifluoroethoxy)phenoxy)piperidine-1-carbonyl)phenoxy)acetamide;
(1,5-naphthyridin-2-yl)(4-(3-(2,2,2-trifluoroethoxy)phenoxy)piperidin-1-yl)methanone;
(2-methyl-2H-indazol-3-yl)(4-(3-(2,2,2-trifluoroethoxy)phenoxy)piperidin-1-yl)methanone;
(1,3-dimethyl-1H-pyrazol-5-yl)(4-(3-(2,2,2-trifluoroethoxy)phenoxy)piperidin-1-yl)methanone;
N-(6-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)benzamide;
(3,5-dimethylisoxazol-4-yl)(4-(3-(2,2,2-trifluoroethoxy)phenoxy)piperidin-1-yl)methanone;
(3-(methylsulfonyl)phenyl)(4-(3-(2,2,2-trifluoroethoxy)phenoxy)piperidin-1-yl)methanone;
(1,6-naphthyridin-8-yl)(4-(3-(2,2,2-trifluoroethoxy)phenoxy)piperidin-1-yl)methanone;
(3-methyl-1H-pyrazol-5-yl)(4-(3-(2,2,2-trifluoroethoxy)phenoxy)piperidin-1-yl)methanone;
2-(3-(4-(3-(2,2,2-trifluoroethoxy)phenoxy)piperidine-1-carbonyl)phenoxy)acetamide;
1-(4-(4-(3-(trifluoromethoxy)phenoxy)piperidine-1-carbonyl)phenyl)urea;
(1H-1,2,4-triazol-3-yl)(4-(3-(2,2,2-trifluoroethoxy)phenoxy)piperidin-1-yl)methanone;
(4-(3-ethoxyphenoxy)piperidin-1-yl)(3-(methylsulfonyl)phenyl)methanone;
(4-(3-ethoxyphenoxy)piperidin-1-yl)(3-methyl-1H-pyrazol-5-yl)methanone;
N,N-dimethyl-3-(4-(3-(trifluoromethoxy)phenoxy)piperidine-1-carbonyl)benzenesulfonamide;
N-(2-(4-(3-(trifluoromethoxy)phenoxy)piperidine-1-carbonyl)phenyl)methanesulfonamide;
(6-aminopyridin-2-yl)(4-(3-(trifluoromethoxy)phenoxy)piperidin-1-yl)methanone;

N,N-dimethyl-2-(2-(4-(3-(trifluoromethoxy)phenoxy)piperidine-1-carbonyl)phenoxy)acetamide;
(1,3-dimethyl-1H-pyrazol-5-yl)(4-(3-(trifluoromethyl)phenoxy)piperidin-1-yl)methanone;
(2-(methylsulfonyl)phenyl)(4-(3-(trifluoromethyl)phenoxy)piperidin-1-yl)methanone;
N-(6-(4-(3-(trifluoromethyl)phenoxy)piperidine-1-carbonyl)pyridin-2-yl)acetamide;
3-(4-(3-(trifluoromethyl)phenoxy)piperidine-1-carbonyl)benzenesulfonamide;
(3,5-dimethylisoxazol-4-yl)(4-(3-(trifluoromethyl)phenoxy)piperidin-1-yl)methanone;
(1,6-naphthyridin-8-yl)(4-(3-(trifluoromethyl)phenoxy)piperidin-1-yl)methanone;
(3-methyl-1H-pyrazol-5-yl)(4-(3-(trifluoromethyl)phenoxy)piperidin-1-yl)methanone;
2-(2-(4-(3-(trifluoromethyl)phenoxy)piperidine-1-carbonyl)phenoxy)acetamide;
2-(3-(4-(3-(trifluoromethyl)phenoxy)piperidine-1-carbonyl)phenoxy)acetamide;
(1H-1,2,4-triazol-3-yl)(4-(3-(trifluoromethyl)phenoxy)piperidin-1-yl)methanone;
N-(2-(2-(4-(3-(trifluoromethoxy)phenoxy)piperidine-1-carbonyl)phenoxy)ethyl)methanesulfonamide;
N-(2-(2-(4-(3-(trifluoromethoxy)phenoxy)piperidine-1-carbonyl)phenoxy)ethyl)cyclopropane-1,1-dicarboxamide;
N-(2-(3-(4-(3-(trifluoromethoxy)phenoxy)piperidine-1-carbonyl)phenoxy)ethyl)methanesulfonamide;
N-(3-(4-(3-(trifluoromethoxy)phenoxy)piperidine-1-carbonyl)pyridin-2-yl)acetamide;
N-(1-methyl-5-(4-(3-(trifluoromethoxy)phenoxy)piperidine-1-carbonyl)-1H-pyrazol-3-yl)acetamide;
(2-(ethylsulfonyl)phenyl)(4-(3-(trifluoromethyl)phenoxy)piperidin-1-yl)methanone;
(2-(ethylsulfonyl)phenyl)(4-(3-(2,2,2-trifluoroethoxy)phenoxy)piperidin-1-yl)methanone;
N-(2-(4-(3-(trifluoromethoxy)phenoxy)piperidine-1-carbonyl)pyridin-3-yl)acetamide;
(3-(methylsulfonyl)phenyl)(4-(3-(trifluoromethyl)phenoxy)piperidin-1-yl)methanone;
(4-(3-chlorophenoxy)piperidin-1-yl)(3-(methylsulfonyl)phenyl)methanone;
(4-(4-chlorophenoxy)piperidin-1-yl)(3-(methylsulfonyl)phenyl)methanone;
(4-(4-chlorophenoxy)piperidin-1-yl)(2-(ethylsulfonyl)phenyl)methanone;
N,N-dimethyl-3-(4-(3-(trifluoromethyl)phenoxy)piperidine-1-carbonyl)benzenesulfonamide;
3-(4-(4-chlorophenoxy)piperidine-1-carbonyl)-N,N-dimethylbenzenesulfonamide;
(4-(3-(2-methoxyethoxy)phenoxy)piperidin-1-yl)(quinolin-8-yl)methanone;
(4-(3-(2-methoxyethoxy)phenoxy)piperidin-1-yl)(quinolin-2-yl)methanone;
(4-(3-(2-methoxyethoxy)phenoxy)piperidin-1-yl)(2-methyl-2H-indazol-3-yl)methanone;
2-((2-(4-(3-(trifluoromethoxy)phenoxy)piperidine-1-carbonyl)phenyl)thio)acetamide;
2-((2-(4-(4-chlorophenoxy)piperidine-1-carbonyl)phenyl)thio)acetamide;
4-(4-(3-(2,2,2-trifluoroethoxy)phenoxy)piperidine-1-carbonyl)-1H-benzo[d]imidazol-2(3H)-one;
(4-(3-ethoxyphenoxy)piperidin-1-yl)(1-methyl-1H-benzo[d]imidazol-2-yl)methanone;
(4-(3-fluorophenoxy)piperidin-1-yl)(1-methyl-1H-benzo[d]imidazol-2-yl)methanone;
(4-(3-ethoxyphenoxy)piperidin-1-yl)(1-methyl-1H-pyrazolo[3,4-b]pyridin-3-yl)methanone;
(4-(3-ethoxyphenoxy)piperidin-1-yl)(pyrazolo[1,5-a]pyrimidin-3-yl)methanone;
(4-(3-fluorophenoxy)piperidin-1-yl)(4-methyl-3,4-dihydro-2H-pyrido[3,2-b][1,4]oxazin-7-yl)methanone;
(3,5-dimethyl-1H-pyrazol-4-yl)(4-(3-(2,2,2-trifluoroethoxy)phenoxy)piperidin-1-yl)methanone;
N-(2-hydroxyethyl)-N-methyl-2-(4-(3-(trifluoromethoxy)phenoxy)piperidine-1-carbonyl)benzenesulfonamide;
(2-(morpholinosulfonyl)phenyl)(4-(3-(trifluoromethoxy)phenoxy)piperidin-1-yl)methanone;
2-(N-methyl-2-(4-(3-(trifluoromethoxy)phenoxy)piperidine-1-carbonyl)phenylsulfonamido)acetamide;
N-methyl-3-(4-(3-(2,2,2-trifluoroethoxy)phenoxy)piperidine-1-carbonyl)benzenesulfonamide;
3-(4-(3-ethoxyphenoxy)piperidine-1-carbonyl)-N-methylbenzenesulfonamide;
N-methyl-3-(4-(3-(trifluoromethoxy)phenoxy)piperidine-1-carbonyl)benzenesulfonamide;
(4-((4-chlorophenyl)thio)piperidin-1-yl)(1,5-naphthyridin-2-yl)methanone;
N-(6-(4-((4-chlorophenyl)thio)piperidine-1-carbonyl)pyridin-2-yl)acetamide;
2-(4-(4-(3,4-difluorophenoxy)piperidine-1-carbonyl)phenoxy)acetamide;
(4-(3,4-difluorophenoxy)piperidin-1-yl)(1,5-naphthyridin-2-yl)methanone;
2-(4-(4-(2,4-difluorophenoxy)piperidine-1-carbonyl)phenoxy)acetamide;
N-(4-(4-(3-(trifluoromethoxy)phenoxy)piperidine-1-carbonyl)pyridin-2-yl)pivalamide; and
(5-amino-1H-pyrazol-3-yl)(4-(3-(trifluoromethoxy)phenoxy)piperidin-1-yl)methanone;
or a prodrug thereof or a pharmaceutically acceptable salt thereof.

[8] The present invention provides a method for the treatment of a condition or disorder in which TTX-S channel blockers are involved, in a mammalian subject, including a human, which comprises administering to a mammal in need of such treatment a therapeutically effective amount of the compound or the prodrug thereof or the pharmaceutically acceptable salt thereof, as described in any one of [1] to [7].

[9] The present invention provides the method as described in [8], wherein said condition or disorder is selected from the group consisting of: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia; and combinations thereof.

[10] The present invention provides a pharmaceutical composition comprising the compound or the prodrug thereof or the pharmaceutically acceptable salt thereof, as described in any one of [4] to [7], together with a pharmaceutically acceptable carrier.

[11] The present invention provides a pharmaceutical composition as described in [10], further comprising another pharmacologically active agent.

[12] The present invention provides a compound of formula (I) described in [1] or a prodrug thereof or a pharmaceutically acceptable salt, solvate or composition thereof for use in the treatment of a condition or disorder in which TTX-S channel blockers are involved.

[13] Also, the present invention provides a process for preparing a pharmaceutical composition, the process comprising mixing a compound described in any one of [4] to [7] or a prodrug thereof or a pharmaceutically acceptable salt thereof and a pharmaceutically acceptable carrier or excipient.

[14] Also, the present invention provides an intermediate in a process for preparing a compound of formula (I) or a prodrug thereof or a pharmaceutically acceptable salt thereof.

Examples of conditions or disorders mediated by TTX-S channels blocking activity include, but are not limited to, TTX-S channels related diseases. The compounds of the present invention show the TTX-S channels blocking activity. The compounds of the present invention may show less toxicity, good absorption, distribution, good solubility, less protein binding affinity other than TTX-S channels, less drug-drug interaction, and good metabolic stability.

DESCRIPTION OF EMBODIMENTS

As appreciated by those of skill in the art, "halogen" or "halo" as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-8}$ alkyl specifically includes methyl, ethyl, n-propyl, isopropyl, n-butyl, iso-butyl, tert-butyl, pentyl, and hexyl. Similarly, $C_{2-6}$ alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents.

The term "alkenyl", as used herein, means a hydrocarbon radical having at least one double bond including, but not limited to, ethenyl, propenyl, 1-butenyl, 2-butenyl and the like.

The term "cycloalkyl", as used herein, means a mono- or bicyclic ring, but not limited to, cyclopropyl, cyclobutyl, cyclopentyl, cyclohexyl, cycloheptyl, norboranyl, and adamantyl groups and the like.

The term "aryl", as used herein, means mono- or bi-carbocyclic or mono- or bi-heterocyclic group which may contain 0-4 heteroatoms selected from O, N and S, but not limited to, phenyl, naphthyl, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, frazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazoleyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof, and wherein the saturated heterocyclic moieties include tetrahydrothienyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, and N-oxides thereof and S-oxides thereof and the said rings which are fully or partially saturated and the like.

The term "heterocyclic group" as used herein includes both unsaturated and saturated heterocyclic moieties, wherein the unsaturated heterocyclic moieties include benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, frazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazoleyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, triazolopyrimidyl, tetrahydrothienyl, 3,4-dihydro-2H-pyrido[3,2-b][1,4]oxazinyl, 2-oxo-2,5,6,7-tetrahydro-1H-cyclopentapyridyl, 4,5,6,7-tetrahydro-indazolyl, 5,6,7,8-tetrahydro-1,6-naphthyridyl, and N-oxides thereof and S-oxides thereof.

The term "$C_0$", as used herein, means direct bond.

The term "protecting group", as used herein, means a amino or carboxyl protecting group which is selected from typical amino or carboxyl protecting groups described in Protective Groups in Organic Synthesis edited by T. W. Greene et al. (John Wiley & Sons, 2007).

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. ScL, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl.

(ii) where the compound of the formula (I) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

The compounds of formula (I) may have polymorphs in crystalline form, which are within the scope of the present invention.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{13}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, Isotopically labeled compounds of the invention can generally be prepared by carrying out the procedures disclosed in the Schemes and/or in the Examples below, then substituting a readily available isotopically labeled reagent for a non-isotopically labeled reagent.

The compounds of formula (I), being $Na_{V1.3}$ channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The aryl carboxamide derivatives of formula (I) are also expected to be useful in the treatment of multiple sclerosis.

The invention also relates to therapeutic use of the aryl carboxamide derivatives of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a prodrug thereof or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-

(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitryptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. alphaR,9R)-7-[3,5-bis (trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[R2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;

a vanilloid receptor agonist (e.g. resinferatoxin) or antagonist (e.g. capsazepine);

a transient receptor potential cation channel subtype (V1, V2, V3, V4, M8, A1) agonists and antagonists;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol(registered trademark);

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazin o[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-yrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1 alpha,3alpha,5alpha)(3-aminomethyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan(registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethyl-venlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4- chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[{2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-meth yl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonists;

a voltage-gated sodium-dependent channel blockers ($Na_{v1.3}$, $Na_{v1.7}$, $Na_{v1.8}$);

a voltage dependent calcium channel blockers (N-type, T-type);

a P2X (ion channel type ATP receptor) antagonists;

an acid-sensing ion channel (ASIC1a, ASIC3) antagonists;

and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or prodrug thereof or pharmaceutically acceptable salt thereof.

For parenteral administration, fluid unit dosage forms are prepared utilising a compound of formula (I) or prodrug thereof or pharmaceutically acceptable salt thereof and a sterile vehicle. Formulations for injection may be presented in unit dosage form e.g. in ampoules or in multi-dose, utilising a compound of formula (I) or prodrug thereof or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or prodrugs thereof or pharmaceutically acceptable salts thereof may also be formulated in rectal compositions such as suppositories or retention enemas, e.g. containing conventional suppository bases such as cocoa butter or other glycerides.

The compounds of formula (I) or prodrugs thereof or pharmaceutically acceptable salts may also be formulated as depot preparations. Such long acting formulations may be administered by implantation (for example subcutaneously or intramuscularly) or by intramuscular injection. Thus, for example, the compounds of formula (I) or prodrugs thereof or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or prodrugs thereof or pharmaceutically acceptable salts thereof may be formulated as solutions for administration via a suitable metered or unitary dose device or alternatively as a powder mix with a suitable carrier for administration using a suitable delivery device. Thus compounds of formula (I) or prodrugs thereof or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) or prodrugs thereof or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

DMF: N,N-dimethylformamide
DMSO: Dimethyl sulfoxide
EDC: 1-Ethyl-3-(3-dimethylaminopropyl)carbodiimide Hydrochloride
HOBT: 1-Hydroxybenztriazole
HBTU: O-(Benzotriazol-1-yl)-N,N,N',N'-tetramethyluronium Hexafluorophosphate
HPLC: High pressure liquid chromatography
LC: liquid chromatography
tR: Retention time
MHz: Megahertz
NMR: Nuclear Magnetic Resonance
TFA: Trifluoroacetic acid
THF: Tetrahydrofuran
TLC: Thin layer chromatography The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMSO, THF, diethylether, diisopropylether, dimethoxyethane, acetonitrile, dichloromethane, dichloroethane and chloroform are preferred.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; the structure and purity of all isolated compounds were assured by at least one of the following techniques: tlc (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography was carried out using Merck silica gel 60 (230-400 mesh ASTM) or Fuji Silysia Chromatorex(registered trademark) DU3050 (Amino Type, 30-50 micrometer) or Biotage silica (32-63 mm, KP-Sil) or Biotage amino bounded silica (35-75 mm, KP-NH). The purification of compounds using HPLC (preparative LC-MS) was performed by the following apparatus and conditions.

Apparatus; Waters MS-trigger AutoPurification™ system
Column; Waters XTerra C18, 19×50 mm, 5 mm particle
Condition A: Methanol or acetonitrile/0.01% (v/v) ammonia aqueous solution
Condition B: Methanol or acetonitrile/0.05% (v/v) formic acid aqueous solution Low-resolution mass spectral data (ESI) were obtained by the following apparatus and conditions: Apparatus; Waters Alliance HPLC system on ZQ or ZMD mass spectrometer and UV detector. NMR data were determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; microL (microliter(s)), microg (microgram(s)), M (mol(s) per liter), L (liter(s)), mL (milliliter(s)), g (gram(s)), mg (milligram(s)), mol (moles), mmol (millimoles).

Conditions for Determining HPLC Retention Time:
Method A:
Apparatus: Waters ACQUITY Ultra Parformance LC with TUV Detector and ZQ mass spectrometer
Column: Waters ACQUITY C18, 2.1×100 mm, 1.7 micrometer particle size
Column Temperature: 60° C.
Flow rate: 0.7 mL/min Run time: 3 min UV detection: 210 nm MS detection: ESI positive/negative mode Mobile Phases:

A1: 10 mM Ammonium acetate

B1: acetonitrile

TABLE 1

| Gradient program: (QC_neutral_full_3min) | | |
|---|---|---|
| Time (min) | A1 (%) | B1 (%) |
| 0 | 95 | 5 |
| 0.1 | 95 | 5 |
| 1.8 | 5 | 95 |
| 2.3 | 95 | 5 |

Method B:

Apparatus: Waters 2795 Alliance HPLC with ZQ 2000 mass spectrometer and 2996 PDA detector Column: Waters XBridge C18 4.6×50 mm, 5 micrometer Column Temperature: 40° C.

Flow rate: 1.2 mL/min

Run time: 4.5 min

UV detection: 210-400 nm scan

MS detection: ESI positive/negative mode

Mobile Phases:

A1: $H_2O$ (Milli-Q water)

B1: acetonitrile

C: 1% aq.HCOOH

D: 1% aq.$NH_3$

TABLE 2

| Gradient program: (QC_neutral_4pt5min) | | | | |
|---|---|---|---|---|
| Time (min) | A1 (%) | B1 (%) | C (%) | D (%) |
| 0 | 85 | 10 | 2.5 | 2.5 |
| 0.2 | 85 | 10 | 2.5 | 2.5 |
| 3.2 | 0 | 95 | 2.5 | 2.5 |
| 3.7 | 0 | 95 | 2.5 | 2.5 |
| 3.71 | 85 | 10 | 2.5 | 2.5 |

All of the aryl carboxamide derivatives of the formula (I) can be prepared by the procedures described in the general methods presented below or by the specific methods described in the Examples section and the Preparations section, or by routine modifications thereof. The present invention also encompasses any one or more of these processes for preparing the aryl carboxamide derivatives of formula (I), in addition to any novel intermediates used therein.

In the following general methods, descriptors are as previously defined for aryl carboxamide derivatives of the formula (I) unless otherwise stated.

<Scheme-A>

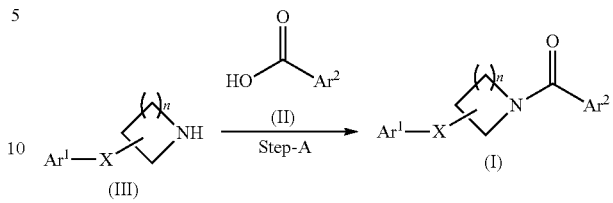

[Chem. 2]

In Step-A, a compound of formula (I) can be prepared from a compound of formula (III) by amidation with a compound of formula (II) using a suitable condensation agent such as HBTU and EDC-HOBT, preferably under the presence of a base such as triethylamine and N,N-diisopropylethylamine in a suitable solvent such as N,N-dimethylformamide and dichloromethane at a temperature of from about 5 to 60° C. for about 1-24 hours. In addition, a compound of formula (I) can be also prepared from a compound of formula (III) by amidation with an acid chloride prepared from a compound of formula (II) using thionylchloride, preferably under the presence of a base such as triethylamine, pyridine, and N,N-diisopropylethylamine in a suitable solvent such as dichloromethane at a temperature of from about 5 to 40° C. for about 1-24 hours.

In order to obtain some other compounds of formula (I), the appropriate conversion reaction of the substituents will be used.

For example, N-acyl/N-sulfonyl/N-alkoxycarbonyl substituted derivative can be prepared from a compound of the corresponding amine with using a suitable acid chloride/sulfonyl chloride/alkyl chloroformate using a suitable base such as pyridine and N,N-diisopropylethylamine, and a suitable solvent such as N,N-dimethylacetamide and dichloromethane at a temperature of from about 5 to 40° C. for about 1-24 hours, respectively. In addition, the corresponding amine for preparation of N-acyl/N-sulfonyl/N-alkoxycarbonyl substituted derivative can be prepared by de-protection of N-tert-butoxycarbonyl group (protecting group) under acidic condition using a suitable agent such as trifluoroacetic acid and a suitable solvent such as dichloromethane at a temperature of from about 5 to 40° C. for about 0.5-12 hours; N-alkyl substituted indole derivatives can be prepared from a compound of the corresponding 1H-indole using a suitable alkyl halide, a suitable base such as sodium hydride and a suitable solvent such as N,N-dimethylformamide at a temperature of from about 5 to 120° C. for about 1-24 hours; amide derivatives can be prepared from a compound of the corresponding carboxylic acid and a suitable amine by amidation according to the similar method described in Step-A. In addition, the corresponding carboxylic acid for amidation can be prepared from the ester (protecting group) by hydrolysis using a suitable agent such as aqueous sodium hydroxide solution and a suitable solvent such as methanol, tetrahydrofuran at a temperature of from about 5 to 60° C. for about 1-24 hours.

All starting materials in the following general syntheses may be commercially available or obtained by conventional methods known to those skilled in the art, otherwise noted in the intermediate synthesis part.

Intermediate Synthesis Part

Amine Part

Intermediate-1: 1-(3-(Piperidin-4-yloxy)phenyl)ethanone hydrochloride

<Step-1> tert-Butyl 4-(3-acetylphenoxy)piperidine-1-carboxylate

To a stirred solution of tert-butyl 4-hydroxypiperidine-1-carboxylate (4.00 g, 19.9 mmol), 1-(3-hydroxyphenyl)ethanone (2.71 g, 19.9 mmol), and triphenylphosphine (5.73 g, 21.9 mmol) in tetrahydrofuran (100 mL) was added slowly diisopropyl azodicarboxylate (4.25 mL, 21.9 mmol) at 0° C. under Nitrogen. The resulting mixture was stirred at room temperature for 17 hours. The mixture was poured into water (200 mL) and extracted with ethyl acetate (200 mL). The organic layer was washed with water (200 mL) and dried over sodium sulfate. After removal of the solvent, the residue was purified by column chromatography on silica gel eluting with n-hexane/ethyl acetate (4:1) to give 4.70 g (74%) of the title compound as colorless oil.
$^1$H-NMR (300 MHz, CDCl$_3$) δ 7.56-7.48 (2H, m), 7.37 (1H, t, J=8.1 Hz), 7.12 (1H, ddd, J=8.1, 2.6, 1.1 Hz), 4.60-4.51 (1H, m), 3.76-3.65 (2H, m), 3.41-3.30 (2H, m), 2.60 (3H, s), 1.99-1.87 (2H, m), 1.83-1.68 (2H, m), 1.47 (9H, s).

<Step-2> 1-(3-(Piperidin-4-yloxy)phenyl)ethanone hydrochloride tert-Butyl 4-(3-acetylphenoxy)piperidine-1-carboxylate (4.70 g, 14.7 mmol, Step-1) was dissolved in 4M hydrochloric acid ethyl acetate solution (30 mL). The mixture was stirred at room temperature for 2 hours. After concentration under reduced pressure, the residue was crystallized from diisopropylether to give 3.37 g (89%) of the title compound as a white solid.
$^1$H-NMR (300 MHz, CDCl$_3$) δ 9.71 (2H, br.s), 7.61-7.55 (1H, m), 7.51-7.45 (1H, m), 7.41 (1H, t, J=8.1 Hz), 7.12 (1H, ddd, J=8.1, 2.6, 1.1 Hz), 4.81-4.72 (1H, m), 3.56-3.23 (4H, m), 2.60 (3H, s), 2.42-2.26 (2H, m), 2.24-2.10 (2H, m), MS (ESI) m/z: 220 (M+H)$^+$.

Intermediate-2: 4-(3-(2,2,2-Trifluoroethoxy)phenoxy)piperidine hydrochloride <Step-1> tert-Butyl 4-(3-(2,2,2-trifluoroethoxy)phenoxy)piperidine-1-carboxylate To a stirred solution of tert-butyl 4-(3-hydroxyphenoxy)piperidine-1-carboxylate (2.00 g, 6.82 mmol) and cesium carbonate (4.44 g, 13.6 mmol) in N,N-dimethylformamide (25 mL) was added 2,2,2-trifluoroethyl trifluoromethane-sulfonate (1.74 g, 7.50 mmol) at room temperature. After stirring at room temperature for 2 hours, the mixture was poured into water (100 mL) and extracted with ethyl acetate (100 mL). The organic layer was washed with water (100 mL) and dried over sodium sulfate. After removal of the solvent, the residue was purified by column chromatography on silica gel eluting with n-hexane/ethyl acetate (4:1) to give 2.42 g (95%) of the title compound as colorless oil.
$^1$H-NMR (300 MHz, CDCl$_3$) δ 7.21 (1H, q, J=8.8 Hz), 6.63-6.58 (1H, m), 6.55-6.49 (2H, m), 4.50-4.41 (1H, m), 4.33 (2H, q, J=8.1 Hz), 3.75-3.64 (2H, m), 3.39-3.28 (2H, m), 1.98-1.85 (2H, m), 1.81-1.67 (2H, m), 1.47 (9H, s).

<Step-2> 4-(3-(2,2,2-Trifluoroethoxy)phenoxy)piperidine hydrochloride

The title compound was prepared in 96% yield (1.94 g, a white solid) from tert-butyl 4-(3-(2,2,2-trifluoroethoxy)phenoxy)piperidine-1-carboxylate (2.42 g, 6.44 mmol, Step-1) by the similar manner in Step-2 of Intermediate-1.
$^1$H-NMR (300 MHz, DMSO-d$_6$) δ 9.15 (2H, br.s), 7.24 (1H, t, J=8.1 Hz), 6.75-6.61 (3H, m), 4.74 (2H, q, J=8.8 Hz), 4.75-4.64 (1H, m), 3.27-3.15 (2H, m), 3.11-2.98 (2H, m), 2.17-2.04 (2H, m), 1.93-1.77 (2H, m), MS (ESI) m/z: 276 (M+H)

Intermediate-3: 4-(3-(2-Methoxyethoxy)phenoxy)piperidine hydrochloride

<Step-1> tert-Butyl 4-(3-(2-methoxyethoxy)phenoxy)piperidine-1-carboxylate

The title compound was prepared in 96% yield (355 mg, colorless syrup) from tert-butyl 4-(3-hydroxyphenoxy)piperidine-1-carboxylate (300 mg, 1.02 mmol) and 1-bromo-2-methoxyethane (171 mg, 1.23 mmol) at a reaction temperature of 60° C. by the similar manner in Step-1 of Intermediate-2.
$^1$H-NMR (300 MHz, CDCl$_3$) δ 7.19-7.13 (1H, m), 6.53-6.50 (3H, m), 4.45-4.39 (1H, m), 4.12-4.08 (2H, m), 3.76-3.66 (4H, m), 3.45 (3H, s), 3.35-3.27 (2H, m), 1.96-1.85 (2H, m), 1.79-1.64 (2H, m), 1.47 (9H, s).

<Step-2> 4-(3-(2-Methoxyethoxy)phenoxy)piperidine hydrochloride

The title compound was prepared in 94% yield (272 mg, a white solid) from tert-butyl 4-(3-(2-methoxyethoxy)phenoxy)piperidine-1-carboxylate (355 mg, 1.01 mmol, Step-1) by the similar manner in Step-2 of Intermediate-1.
$^1$H-NMR (300 MHz, DMSO-d$_6$) δ 8.93 (1H, br.s), 7.21-7.15 (1H, m), 6.58-6.53 (3H, m), 4.67-4.62 (1H, m), 4.07-4.04 (2H, m), 3.65-3.62 (2H, m), 3.36 (3H, s), 3.30-3.18 (2H, m), 3.09-3.01 (2H, m), 2.14-2.04 (2H, m), 1.87-1.77 (2H, m), MS (ESI) m/z: 252 (M+H)$^+$.

Intermediate-4: 4-((3-(Trifluoromethoxy)phenyl)sulfonyl)piperidine hydrochloride <Step-1> tert-Butyl 4-((3-(trifluoromethoxy)phenyl)thio)piperidine-1-carboxylate A mixture of tert-butyl 4-((methylsulfonyl)oxy)piperidine-1-carboxylate (1.34 g, 4.79 mmol), 3-(trifluoromethoxy)benzenethiol (1.12 g, 5.75 mmol) and potassium carbonate (1.99 g, 14.4 mmol) in N,N-dimethylformamide (50 mL) at 90° C. for 20 hours. The mixture was poured into water (200 mL) and extracted with ethyl acetate (200 mL). The organic layer was washed with water (200 mL) and dried over sodium sulfate. After removal of the solvent, the residue was purified by column chromatography on silica gel eluting with n-hexane/ethyl acetate (20:1) to give 1.34 g (74%) of the title compound as colorless oil.

¹H-NMR (300 MHz, CDCl₃) δ 7.36-7.25 (3H, m), 7.11-7.09 (1H, m), 3.99-3.95 (2H, m), 3.32-3.22 (1H, m), 2.99-2.92 (2H, m), 1.97-1.91 (2H, m), 1.59-1.48 (2H, m), 1.45 (9H, s)

<Step-2> tert-Butyl 4-((3-(trifluoromethoxy)phenyl)sulfonyl)piperidine-1-carboxylate To a stirred solution of tert-butyl 4-((3-(trifluoromethoxy)phenyl)thio)piperidine-1-carboxylate (1.34 g, 3.54 mmol, Step-1) in dichloromethane (30 mL) was added m-chloroperbenzoic acid (1.95 g, 7.79 mmol) at 0° C. After stirring at 0° C. for 1 hour, the reaction mixture was filtered. The filtrate was washed with saturated sodium thiosulfate aqueous solution (30 mL) and saturated sodium hydrogen carbonate aqueous solution (30 mL). The organic layer was dried over sodium sulfate and concentrated in vacuo. The residue was purified by column chromatography on silica gel eluting with n-hexane/ethyl acetate (3:1) to give 1.35 g (93%) of the title compound as a white solid.
¹H-NMR (300 MHz, CDCl₃) δ 7.82 (1H, dd, J=7.3, 1.5 Hz), 7.73 (1H, s), 7.66 (1H, t, J=8.1 Hz), 7.54 (1H, dd, J=8.1, 1.5 Hz), 4.31-4.18 (2H, m), 3.11-3.01 (1H, m), 2.74-2.60 (2H, m), 2.01-1.97 (2H, m), 1.69-1.55 (2H, m), 1.44 (9H, s).

<Step-3> 4-((3-(Trifluoromethoxy)phenyl)sulfonyl)piperidine hydrochloride

The title compound was prepared in 96% yield (1.09 g, a white solid) from tert-butyl 4-((3-(trifluoromethoxy)phenyl)sulfonyl)piperidine-1-carboxylate (1.35 g, 3.29 mmol, Step-2) by the similar manner in Step-2 of Intermediate-1.
¹H-NMR (300 MHz, DMSO-d₆) δ 8.95 (1H, br.s), 7.94-7.87 (3H, m), 7.80 (1H, s), 3.80-3.68 (1H, m), 3.40-3.32 (2H, m), 2.90-2.78 (2H, m), 2.04-1.98 (2H, m), 1.83-1.69 (2H, m), MS (ESI) m/z: 310 (M+H)⁺.

Intermediate-5:
4-((4-(Trifluoromethoxy)phenyl)sulfonyl)piperidine hydrochloride <Step-1> tert-Butyl 4-((4-(trifluoromethoxy)phenyl)thio)piperidine-1-carboxylate The title compound was prepared in 41% yield (0.66 g, colorless oil) from tert-butyl 4-((methylsulfonyl)oxy)piperidine-1-carboxylate (1.20 g, 4.30 mmol) and 4-(trifluoromethoxy)benzenethiol (1.00 g, 5.15 mmol) by the similar manner in Step-1 of Intermediate-4.
¹H-NMR (300 MHz, CDCl₃) δ 7.47-7.40 (2H, m), 7.19-7.13 (2H, m), 4.05-3.89 (2H, m), 3.24-3.13 (1H, m), 2.99-2.85 (2H, m), 1.96-1.86 (2H, m), 1.60-1.48 (2H, m), 1.45 (9H, s), MS (ESI) m/z: 378 (M+H)⁺.

<Step-2> tert-Butyl 4-((4-(trifluoromethoxy)phenyl)sulfonyl)piperidine-1-carboxylate The title compound was prepared in 80% yield (578 mg, a white solid) from tert-butyl 4-((4-(trifluoromethoxy)phenyl)thio)piperidine-1-carboxylate (662 mg, 1.75 mmol, Step-1) by the similar manner in Step-2 of Intermediate-4.
¹H-NMR (300 MHz, CDCl₃) δ 7.96-7.89 (2H, m), 7.44-7.38 (2H, m), 4.34-4.15 (2H, m), 3.11-2.99 (1H, m), 2.76-2.55 (2H, m), 2.06-1.91 (2H, m), 1.69-1.52 (2H, m), 1.43 (9H, s).

<Step-3> 4-((4-(Trifluoromethoxy)phenyl)sulfonyl)piperidine hydrochloride

The title compound was prepared in 99% yield (482 mg, a white solid) from tert-butyl 4-((4-(trifluoromethoxy)phenyl)sulfonyl)piperidine-1-carboxylate (578 mg, 1.41 mmol, Step-2) by the similar manner in Step-2 of Intermediate-1.
¹H-NMR (300 MHz, DNSO-d₆) δ 8.75 (1H, br.s), 8.04-7.99 (2H, m), 7.75-7.68 (2H, m), 3.95-3.60 (1H, m), 3.45-3.26 (2H, m), 2.91-2.79 (2H, m), 2.08-1.96 (2H, m), 1.87-1.64 (2H, m), MS (ESI) m/z: 310 (M+H)⁺.

Intermediate-6:
4-((3-Ethoxyphenyl)sulfonyl)piperidine hydrochloride

<Step-1> tert-Butyl 4-((3-ethoxyphenyl)thio)piperidine-1-carboxylate

The title compound was prepared in 67% yield (1.29 g, yellow oil) from tert-butyl 4-((methylsulfonyl)oxy)piperidine-1-carboxylate (1.60 g, 5.73 mmol) and 3-ethoxybenzenethiol (1.06 g, 6.87 mmol) by the similar manner in Step-1 of Intermediate-4.
¹H-NMR (300 MHz, CDCl₃) δ 7.20 (1H, t, J=8.1 Hz), 7.00-6.94 (2H, m), 6.78 (1H, ddd, J=8.1, 2.6, 1.1 Hz), 4.02 (2H, q, J=7.0 Hz), 4.06-3.89 (2H, m), 3.29-3.16 (1H, m), 3.00-2.85 (2H, m), 2.00-1.86 (2H, m), 1.61-1.49 (2H, m), 1.45 (9H, s), 1.42 (3H, t, J=7.0 Hz), MS (ESI) m/z: 338 (M+H)⁺.

<Step-2> tert-Butyl 4-((3-ethoxyphenyl)sulfonyl)piperidine-1-carboxylate

The title compound was prepared in 83% yield (1.16 g, a white solid) from tert-butyl 4-((3-ethoxyphenyl)thio)piperidine-1-carboxylate (1.29 g, 3.81 mmol, Step-1) by the similar manner in Step-2 of Intermediate-4.
¹H-NMR (300 MHz, CDCl₃) δ 7.46 (1H, q, J=8.1 Hz), 7.45-7.39 (1H, m), 7.36-7.32 (1H, m), 7.20-7.14 (1H, m), 4.30-4.15 (2H, m), 4.09 (2H, q, J=7.0 Hz), 3.12-2.94 (1H, m), 2.75-2.56 (2H, m), 2.05-1.88 (2H, m), 1.70-1.52 (2H, m), 1.45 (3H, t, J=7.0 Hz), 1.43 (9H, s).

<Step-3> 4-((3-Ethoxyphenyl)sulfonyl)piperidine hydrochloride

The title compound was prepared in 98% yield (0.95 g, a white solid) from tert-butyl 4-((3-ethoxyphenyl)sulfonyl)piperidine-1-carboxylate (1.16 g, 3.15 mmol, Step-2) by the similar manner in Step-2 of Intermediate-1.
¹H-NMR (300 MHz, DMSO-d₆) δ 7.62 (1H, t, J=8.1 Hz), 7.44-7.33 (2H, m), 7.30-7.26 (1H, m), 4.13 (2H, q, J=7.0 Hz), 3.71-3.58 (1H, m), 3.43-3.28 (2H, m), 2.93-2.73 (2H, m), 2.06-1.93 (2H, m), 1.82-1.65 (2H, m), 1.36 (3H, t, J=7.0 Hz), MS (ESI) m/z: 270 (M+H)⁺.

Intermediate Synthesis Part

Carboxylic Acid Part

Intermediate-7:
3-(5-Fluoro-1H-benzo[d]imidazol-2-yl)benzoic acid

A mixture of 3-formylbenzoic acid (500 mg, 3.33 mmol) and 4-fluorobenzene-1,2-diamine (420 mg, 3.33 mmol) in ethanol (10 mL) was refluxed for 5 hours. After cooling to room temperature, the precipitate was collected by filtration and dried to give 311 mg (36%) of the title compound as a brown solid.
MS (ESI) m/z: 257 (M+H)⁺.

Intermediate-8: 3-(1-Methyl-1H-benzo[d]imidazol-2-yl)benzoic acid

The title compound was prepared in 51% yield (428 g, a slight brown solid) from 3-formylbenzoic acid (500 mg, 3.33 mmol) and N1-methylbenzene-1,2-diamine (407 mg, 3.33 mmol) by the similar manner in Intermediate-7.
MS (ESI) m/z: 253 (M+H)$^+$.

Intermediate-9: 1-(2-Methoxyethyl)-1H-indole-5-carboxylic acid

<Step-1> Methyl 1-(2-methoxyethyl)-1H-indole-5-carboxylate

To a stirred solution of methyl 1H-indole-5-carboxylate (200 mg, 1.14 mmol) and sodium hydride (60% in oil, 39 mg, 1.71 mmol) in N,N-dimethylformamide (3 mL) was added 1-bromo-2-methoxyethane (190 mg, 1.37 mmol) at room temperature. Then the mixture was stirred at 60° C. for 2 hours. The mixture was poured into water (20 mL) and extracted with ethyl acetate (20 mL). The organic layer was washed with water (20 mL) and dried over sodium sulfate. After removal of the solvent, the residue was purified by column chromatography on silica gel eluting with n-hexane/ethyl acetate (2:1) to give 132 mg (50%) of the title compound as colorless syrup.
MS (ESI) m/z: 234 (M+H)$^+$.

<Step-2> 1-(2-Methoxyethyl)-1H-indole-5-carboxylic acid

A mixture of methyl 1-(2-methoxyethyl)-1H-indole-5-carboxylate (132 mg, 0.57 mmol, Step-1), 2M aqueous sodium hydroxide solution (2 mL), and methanol (2 mL) was stirred at 60° C. for 2 hours. The mixture was acidified with 2M aqueous hydrochloric acid solution, and the organic solvent was concentrated under reduced pressure. The precipitate was collected by filtration and dried to give 118 mg (95%) of the title compound as a white solid.
MS (ESI) m/z: 220 (M+H)$^+$.

Intermediate-10: 1-(2-Methoxyethyl)-1H-indole-6-carboxylic acid

<Step-1> Methyl 1-(2-methoxyethyl)-1H-indole-6-carboxylate

The title compound was prepared in 30% yield (79 mg, colorless syrup) from methyl 1H-indole-6-carboxylate (200 mg, 1.14 mmol) and 1-bromo-2-methoxyethane (190 mg, 1.37 mmol) by the similar manner in Step-1 of Intermediate-9.
MS (ESI) m/z: 234 (M+H)$^+$.

<Step-2> 1-(2-Methoxyethyl)-1H-indole-6-carboxylic acid

The title compound was prepared in 81% yield (60 mg, a white solid) from methyl 1-(2-methoxyethyl)-1H-indole-6-carboxylate (79 mg, 0.34 mmol, Step-1) by the similar manner in Step-2 of Intermediate-9.
MS (ESI) m/z: 220 (M+H)$^+$.

Intermediate-11: 5-(2,2,2-Trifluoroethoxy)nicotinic acid

<Step-1> Methyl 5-(2,2,2-trifluoroethoxy)nicotinate

The title compound was prepared in >99% yield (307 mg, a red solid) from methyl 5-hydroxynicotinate (200 mg, 1.31 mmol) by the similar manner in Step-1 of Intermediate-2.

$^1$H-NMR (300 MHz, CDCl$_3$) δ 8.91 (1H, d, J=1.5 Hz), 8.53 (1H, d, J=2.9 Hz), 7.80 (1H, dd, J=2.9, 1.5 Hz), 4.44 (2H, q, J=8.0 Hz), 3.94 (3H, s), MS (ESI) m/z: 236 (M+H)$^+$.

<Step-2> 5-(2,2,2-Trifluoroethoxy)nicotinic acid

The title compound was prepared in 75% yield (233 mg, a white solid) from methyl 5-(2,2,2-trifluoroethoxy)nicotinate (307 mg, 1.31 mmol, Step-1) by the similar manner in Step-2 of Intermediate-9.
$^1$H-NMR (300 MHz, DMSO-d$_6$) δ 8.77-8.73 (1H, m), 8.65-8.55 (1H, m), 7.93-7.88 (1H, m), 4.96 (2H, q, J=8.8 Hz), MS (ESI) m/z: 222 (M+H)$^+$.

Example Synthesis Part

Example 1

(4-(4-Chlorophenoxy)piperidin-1-yl)(8-hydroxyquinolin-2-yl)methanone

To a solution of 8-hydroxyquinoline-2-carboxylic acid (15 mg, 0.079 mmol), 4-(4-chlorophenoxy)piperidine (20 mg, 0.096 mmol), and triethylamine (0.044 mL, 0.32 mmol) in DMF was added HBTU (46 mg, 0.12 mol) at room temperature. The reaction mixture was stirred at 60° C. for 2 hours. The mixture was diluted with ethyl acetate (3 mL) and washed with water (1.5 mL). The organic layer was dried over sodium sulfate, and concentrated by N$_2$-flow. The residue was diluted with methanol and applied onto a strong cation exchange cartridge (BondElute(registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated by N$_2$-flow. The residue was purified by preparative LC-MS to give 6.6 mg (22% yield) of the title compound.

The following examples, Example 2-102, 104-320, 325, 327-348, 352, 356-383, 389-534, 542-544, 546-577, 582-608, 615-654, 664-725 were prepared according to the procedure similar to that described in Example 1, using the appropriate amino acids and carboxylic acids (see Table 3). In addition, non-basic compounds (e.g., neutral compounds) were purified by silica-gel column chromatography (NH-gel, eluting with ethyl acetate) instead of a strong cation exchange cartridge (BondElute(registered trademark) SCX), and then preparative LC-MS. The reactants were used commercially available material or obtained by conventional methods known to those skilled in the art, otherwise noted in the intermediate synthesis part.

Example 103

Benzo[d]isoxazol-3-yl(4-(4-chlorophenoxy)piperidin-1-yl)methanone

To a solution of 4-(4-chlorophenoxy)piperidine (26 mg, 0.12 mmol), and N,N-diisopropylethylamine (0.086 mL, 0.49 mmol) in dichloromethane (0.5 mL) was added dropwise a solution of benzo[d]isoxazole-3-carbonyl chloride (22 mg, 0.12 mmol) in dichloromethane (0.5 mL) at room temperature. The reaction mixture was stirred at room temperature for 1 hour. The mixture was diluted with ethyl acetate (3 mL) and washed with water (1.5 mL). The organic layer was dried over sodium sulfate, and concentrated under reduced pressure. The residue was purified by silica-gel column chromatography (NH-gel, eluting with ethyl acetate) and then preparative LC-MS to give 16.3 mg (37% yield) of the title compound.

Example 321

(4-(Aminomethyl)pyridin-2-yl)(4-(4-chlorophenoxy)piperidin-1-yl)methanone

<Step-1> tert-Butyl ((2-(4-(4-chlorophenoxy)piperidine-1-carbonyl)pyridin-4-yl)methyl)carbamate To a stirred solution of 4-(4-chlorophenoxy)piperidine hydrochloride (98 mg, 0.34 mmol), 4-(((tert-butoxycarbonyl)amino)methyl)picolinic acid (100 mg, 0.34 mmol), and N,N-diisopropylethylamine (0.14 mL, 0.79 mmol) in N,N-dimethylformamide (2 mL) was add HBTU (225 mg, 0.60 mmol) at room temperature. After stirring at 60° C. for 2 hours, the mixture was poured into water (5 mL). This was extracted with ethyl acetate (5 mL) and washed with water (5 mL). The organic layer was dried over sodium sulfate, and concentrated under reduced pressure. The residue was purified by silica-gel column chromatography (NH-gel, eluting with ethyl acetate) to give 177 mg (>99% yield) of the title compound as slight brown syrup.
MS (ESI) m/z: 446 (M+H)$^+$.

<Step-2> (4-(Aminomethyl)pyridin-2-yl)(4-(4-chlorophenoxy)piperidin-1-yl)methanone A mixture of tert-butyl ((2-(4-(4-chlorophenoxy)piperidine-1-carbonyl)pyridin-4-yl)methyl)carbamate (165 mg, 0.37 mmol, Step-1), trifluoroacetic acid (2 mL), and dichloromethane (2 mL) was stirred at room temperature for 1 hour. After removal of the solvent, the residue was purified by a strong cation exchange cartridge (BondElute(registered trademark) SCX) to give 128 mg (>99%) of the title compound as colorless syrup. 25 mg of this material was further purified by preparative LC-MS to give 16.9 mg (68% yield) of the title compound.

Example 322

N-((2-(4-(4-Chlorophenoxy)piperidine-1-carbonyl)pyridin-4-yl)methyl)pivalamide

To a stirred solution of (4-(aminomethyl)pyridin-2-yl)(4-(4-chlorophenoxy)piperidin-1-yl)methanone (25 mg, 0.072 mmol. Example 321), N,N-diisopropylethylamine (0.038 mL, 0.22 mmol) in dichloromethane (1 mL) was added pivaloyl chloride (0.011 mL, 0.087 mmol) at room temperature. After stirring at room temperature for 2 hours, the mixture was poured into water (3 mL). This was extracted with ethyl acetate (4 mL) and washed with water (3 mL). The organic layer was dried over sodium sulfate, and concentrated under reduced pressure. The residue was purified by silica-gel column chromatography (NH-gel, eluting with ethyl acetate) and then preparative LC-MS to give 14.0 mg (45% yield) of the title compound.

Example 323-324 were prepared according to the procedure similar to that described in Example 322, using 4-fluorobenzoyl chloride, 4-fluorobenzenesulfonyl chloride instead of pivaloyl chloride, respectively.

Example 326 was prepared from Example 325 according to the procedures similar to those described in Step-2 in Example 321 and Example 322, using methanesulfonyl chloride instead of pivaloyl chloride.

Example 349

3-(tert-Butyl)-5-(4-(4-chlorophenoxy)piperidine-1-carbonyl)benzamide

<Step-1> 3-(tert-Butyl)-5-(4-(4-chlorophenoxy)piperidine-1-carbonyl)benzoic acid To a stirred solution of 4-(4-chlorophenoxy)piperidine hydrochloride (100 mg, 0.40 mmol), 5-(tert-butyl)isophthalic acid (358 mg, 1.61 mmol), and N,N-diisopropylethylamine (0.28 mL, 1.61 mmol) in N,N-dimethylformamide (3 mL) was add HBTU (183 mg, 0.48 mmol) at room temperature. After stirring at 60° C. for 2 hours, the mixture was poured into water (5 mL). This was extracted with ethyl acetate (5 mL) and washed with water (5 mL). The organic layer was dried over sodium sulfate, and concentrated under reduced pressure. The residue was purified by silica-gel column chromatography (eluting with dichloromethane/methanol=7:1) to give 121 mg (72% yield) of the title compound as a white solid.
MS (ESI) m/z: 416 (M+H)$^+$.

<Step-2> 3-(tert-Butyl)-5-(4-(4-chlorophenoxy)piperidine-1-carbonyl)benzamide

To a stirred solution of 3-(tert-butyl)-5-(4-(4-chlorophenoxy)piperidine-1-carbonyl)benzoic acid (30 mg, 0.072 mmol, Step-1), EDC (21 mg, 0.11 mmol), HOBT (17 mg, 0.11 mmol), and N,N-diisopropylethylamine (0.28 mL, 1.61 mmol) in N,N-dimethylformamide (3 mL) was add 25% ammonium water (1 mL) at room temperature. After stirring at 60° C. for 2 hours, the mixture was poured into water (5 mL). This was extracted with ethyl acetate (5 mL) and washed with water (5 mL). The organic layer was dried over sodium sulfate, and concentrated under reduced pressure. The residue was purified by silica-gel column chromatography (NH-gel, eluting with ethyl acetate) and then preparative LC-MS to give 10.4 mg (35% yield) of the title compound.

Example 350 and 351 were prepared from 3-(tert-butyl)-5-(4-(4-chlorophenoxy)piperidine-1-carbonyl)benzoic acid (Step-1 of Example 349) according to the procedure similar to that described in Step-2 of Example 349, using 2M dimethylamie THF solution, morpholine instead of 25% ammonium water, respectively.

Example 353

(4-(4-Chlorophenoxy)piperidin-1-yl)(1-(2-morpholinoethyl)-1H-indol-5-yl)methanone <Step-1> (4-(4-Chlorophenoxy)piperidin-1-yl)(1H-indol-5-yl)methanone To a stirred solution of 4-(4-chlorophenoxy)piperidine hydrochloride (300 mg, 1.21 mmol), 1H-indole-5-carboxylic acid (195 mg, 1.21 mmol), and N,N-diisopropylethylamine (0.85 mL, 4.84 mmol) in N,N-dimethylformamide (10 mL) was add HBTU (688 mg, 1.81 mmol) at room temperature. After stirring at 60° C. for 2 hours, the mixture was poured into water (50 mL). This was extracted with ethyl acetate (50 mL) and washed with water (50 mL). The organic layer was dried over sodium sulfate, and concentrated under reduced pressure. The residue was purified by silica-gel column chromatography (NH-gel, eluting with n-hexane/ethyl acetate=1/1) to give 403 mg (94% yield) of the title compound as a white solid.
$^1$H-NMR (300 MHz, CDCl$_3$) δ 8.52 (1H, br.s), 7.74 (1H, s), 7.38 (1H, d, J=8.1 Hz), 7.34-7.09 (4H, m), 6.93-6.76 (2H, m), 6.58 (1H, s), 4.64-4.43 (1H, m), 4.05-3.30 (4H, m), 2.14-1.72 (4H, m), MS (ESI) m/z: 355 (M+H)$^+$.

<Step-2> (4-(4-Chlorophenoxy)piperidin-1-yl)(1-(2-morpholinoethyl)-1H-indol-5-yl)methanone To a stirred solution of (4-(4-chlorophenoxy)piperidin-1-yl)(1H-indol-5-yl)methanone (30 mg, 0.085 mmol, Step-1) and sodium hydride (60% in oil, 6 mg, 0.25 mmol) in N,N-dimethylformamide (1.5 mL) was added 4-(2-chloroethyl)morpholine hydrochloride (35 mg, 0.19 mmol) at room temperature. Then the mixture was stirred at 70° C. for 2 hours. The mixture was poured into water (20 mL) and extracted with ethyl acetate (20 mL). The organic layer was washed with water (20 mL), and dried over sodium sulfate. After removal of the solvent, the residue was purified by silica-gel column chromatography (NH-gel, eluting with ethyl acetate) and then preparative LC-MS to give 11.9 mg (30% yield) of the title compound.

Example 354, 384, and 388 were prepared from (4-(4-chlorophenoxy)piperidin-1-yl)(1H-indol-5-yl)methanone (Step-1 of Example 353) according to the procedure similar to that described in Step-2 of Example 353, using 2-chloro-N,N-dimethylacetamide, 4-(iodomethyl)tetrahydro-2H-pyran-4-ol, and 2-chloro-1-morpholinoethanone instead of 4-(2-chloroethyl)morpholine hydrochloride, respectively.

Example 355

(4-(4-Chlorophenoxy)piperidin-1-yl)(1-(2-hydroxyethyl)-1H-indol-5-yl)methanone

To a stirred solution of (4-(4-chlorophenoxy)piperidin-1-yl)(1H-indol-5-yl)methanone (30 mg, 0.085 mmol, Step-1 of Example 353) and sodium hydride (60% in oil, 4 mg, 0.17 mmol) in N,N-dimethylformamide (1.5 mL) was added (2-bromoethoxy)(tert-butyl)dimethylsilane (24 mg, 0.10 mmol) at room temperature. After stirring at room temperature for 2 hours, the mixture was poured into water (20 mL) and extracted with ethyl acetate (20 mL). The organic layer was washed with water (20 mL), and dried over sodium sulfate. After removal of the solvent, the residue was purified by silica-gel column chromatography (NH-gel, eluting with ethyl acetate) to give 43 mg (>99% yield) of (1-(2-((tert-butyldimethylsilyl)oxy)ethyl)-1H-indol-5-yl)(4-(4-chlorophenoxy)piperidin-1-yl)methanone as orange oil. This material was treated with 2M aqueous hydrochloric acid solution (0.4 mL) and tetrahydrofuran (1.5 mL) at room temperature for 1 hour. The mixture was neutralized by saturated sodium hydrogen carbonate aqueous solution and extracted with ethyl acetate (3 mL). The organic layer was dried over sodium sulfate. After removal of the solvent, the residue was purified by silica-gel column chromatography (NH-gel, eluting with ethyl acetate) and then preparative LC-MS to give 7.1 mg (18% yield) of the title compound.

Example 385

(1-(2-Aminoethyl)-1H-indol-5-yl)(4-(4-chlorophenoxy)piperidin-1-yl)methanone

<Step-1> tert-Butyl (2-(5-(4-(4-chlorophenoxy)piperidine-1-carbonyl)-1H-indol-1-yl)ethyl)carbamate To a stirred solution of (4-(4-chlorophenoxy)piperidin-1-yl)(1H-indol-5-yl)methanone (80 mg, 0.23 mmol, Step-1 of Example 353) and sodium hydride (60% in oil, 27 mg, 1.13 mmol) in N,N-dimethylformamide (5 mL) was added tert-butyl (2-bromoethyl)carbamate (76 mg, 0.34 mmol) at room temperature. Then the mixture was stirred at 70° C. for 3 hours. The mixture was poured into water (30 mL) and extracted with ethyl acetate (30 mL). The organic layer was washed with water (30 mL), and dried over sodium sulfate. After removal of the solvent, the residue was purified by silica-gel column chromatography (eluting with n-hexane/ethyl acetate=2/1) to give 112 mg (>99% yield) of the title compound as brown oil.

$^1$H-NMR (300 MHz, CDCl$_3$) δ 7.72 (1H, s), 7.37 (1H, d, J=8.8 Hz), 7.31-7.20 (3H, m), 7.14 (1H, d, J=3.3 Hz), 6.93-6.86 (2H, d, J=8.8 Hz), 6.55 (1H, d, J=3.3 Hz), 4.63-4.46 (2H, m), 4.33-4.24 (2H, m), 3.98-3.75 (1H, m), 3.55-3.43 (2H, m), 2.07-1.61 (6H, m), 1.43 (9H, s), MS (ESI) m/z: 498 (M+H)$^+$.

<Step-2> (1-(2-Aminoethyl)-1H-indol-5-yl)(4-(4-chlorophenoxy)piperidin-1-yl)methanone A mixture of tert-butyl (2-(5-(4-(4-chlorophenoxy)piperidine-1-carbonyl)-1H-indol-1-yl)ethyl)carbamate (112 mg, 0.23 mmol, Step-1), trifluoroacetic acid (1.5 mL), and dichloromethane (1.5 mL) was stirred at room temperature for 1 hour. After concentration in vacuo, the residue was purified by a strong cation exchange cartridge (BondElute(registered trademark) SCX) to give 83 mg (83% yield) of the title compound as yellow oil. 13 mg of this material was further purified by preparative LC-MS to give 6.6 mg (51% yield) of the title compound.

Example 386

N-(2-(5-(4-(4-Chlorophenoxy)piperidine-1-carbonyl)-1H-indol-1-yl)ethyl)acetamide To a stirred solution of (1-(2-aminoethyl)-1H-indol-5-yl)(4-(4-chlorophenoxy)piperidin-1-yl)methanone (30 mg, 0.075 mmol, Example 385) and pyridine (1 mL) was added acetic anhydride (0.0085 mL, 0.090 mmol) at room temperature. After stirring at room temperature for 2 hours, the mixture was poured into 1M aqueous hydrochloric acid solution (5 mL). This was extracted with ethyl acetate (5 mL) and washed with saturated sodium hydrogen carbonate aqueous solution (5 mL) and brine (5 mL). The organic layer was dried over sodium sulfate, and concentrated under reduced pressure. The residue was purified by silica-gel column chromatography (NH-gel, eluting with ethyl acetate) and then preparative LC-MS to give 8.9 mg (27% yield) of the title compound.

Example 387 was prepared from Example 385 according to the procedure similar to that described in Example 386, using methanesulfonyl chloride instead of acetic anhydride.

Example 535

4-(4-(4-chlorophenoxy)piperidine-1-carbonyl)-N-(2-methoxyethyl)-N-methylbenzamide <Step-1> Methyl 4-(4-(4-chlorophenoxy)piperidine-1-carbonyl)benzoate To a stirred solution of 4-(4-chlorophenoxy)piperidine hydrochloride (250 mg, 1.01 mmol), and triethylamine (0.56 mL, 4.03 mmol) in dichloromethane (10 mL) was added methyl 4-(chlorocarbonyl)benzoate (220 mg, 1.11 mmol) at room temperature. After stirring at room temperature for 2 hours, the mixture was poured into water (30 mL). This was extracted with dichloromethane (30 mL) and washed with water (30 mL). The organic layer was dried over sodium sulfate, and concentrated under reduced pressure. The residue was purified by silica-gel column chromatography (eluting with n-hexane/ethyl acetate=3/1) to give 329 mg (87% yield) of the title compound as a white solid.

$^1$H-NMR (300 MHz, CDCl$_3$) δ 8.13-8.07 (2H, m), 7.52-7.44 (2H, m), 7.31-7.20 (2H, m), 6.90-6.81 (2H, m), 4.60-4.51 (1H, m), 3.94 (3H, s), 3.97-3.80 (2H, m), 3.68-3.50 (1H, m), 3.40-3.23 (1H, m), 2.11-1.72 (4H, m), MS (ESI) m/z: 374 (M+H)$^+$.

<Step-2> 4-(4-(4-Chlorophenoxy)piperidine-1-carbonyl)benzoic acid

A mixture of methyl methyl 4-(4-(4-chlorophenoxy)piperidine-1-carbonyl)benzoate (329 mg, 0.88 mmol, Step-1), 2M sodium hydroxide aqueous solution (2 mL), tetrahydrofuran (2.5 mL), and methanol (5 mL) was stirred at 50° C. for 1 hour. The mixture was acidified by 1M aqueous hydrochloric acid solution and extracted with ethyl acetate (30 mL). The organic layer was dried over sodium sulfate and concentrated under reduced pressure. The residue was crystallized from diisopropylether to give 265 mg (84% yield) of the title compound as a white solid.
$^1$H-NMR (300 MHz, DMSO-$d_6$) δ 8.01-7.93 (2H, m), 7.52-7.45 (2H, m), 7.32-7.24 (2H, m), 7.02-6.94 (2H, m), 4.71-4.49 (1H, m), 4.05-3.63 (2H, m), 3.55-3.37 (1H, m), 3.35-3.08 (1H, m), 2.06-1.80 (2H, m), 1.71-1.47 (2H, m), MS (ESI) m/z: 360 (M+H)$^+$.

<Step-3> 4-(4-(4-chlorophenoxy)piperidine-1-carbonyl)-N-(2-methoxyethyl)-N-methylbenzamide The title compound was prepared in 51% yield (10.1 mg) prepared from 4-(4-(4-chlorophenoxy)piperidine-1-carbonyl)benzoic acid (Step-2) according to the procedure similar to that described in Step-2 of Example 349, using 2-methoxy-N-methylethanamine instead of 25% ammonium water.
Example 536-541 and 545 were prepared from 4-(4-(4-chlorophenoxy)piperidine-1-carbonyl)benzoic acid (Step-2 of Example 535) according to the procedure similar to that described in Step-2 of Example 349, using 2-methoxyethanamine, 1-((4-aminopiperidin-1-yl)methyl)cyclohexanol, (S)-2-amino-2-phenylethanol, (S)-2-amino-1-phenylethanol, (S)-2-amino-3-phenylpropan-1-ol, (S)-2-amino-3-phenylpropanamide, and 2-amino-1-phenylethanone hydrochloride instead of 25% ammonium water, respectively.

Example 578

(S)-3-(4-(4-Chlorophenoxy)piperidine-1-carbonyl)-N-(2-hydroxy-2-phenylethyl)benzamide <Step-1> Methyl 3-(4-(4-chlorophenoxy)piperidine-1-carbonyl)benzoate To a stirred solution of 4-(4-chlorophenoxy)piperidine hydrochloride (200 mg, 0.81 mmol), 3-(methoxycarbonyl)benzoic acid (145 mg, 0.81 mmol), and N,N-diisopropylethylamine (0.56 mL, 3.22 mmol) in N,N-dimethylformamide (4 mL) was add HBTU (458 mg, 1.21 mmol) at room temperature. After stirring at 60° C. for 2 hours, the mixture was poured into water (20 mL). This was extracted with ethyl acetate (20 mL) and washed with water (20 mL). The organic layer was dried over sodium sulfate, and concentrated under reduced pressure. The residue was purified by silica-gel column chromatography (NH-gel, eluting with ethyl acetate) to give 301 mg (>99% yield) of the title compound as yellow syrup.
MS (ESI) m/z: 374 (M+H)$^+$.

<Step-2> 3-(4-(4-Chlorophenoxy)piperidine-1-carbonyl)benzoic acid

A mixture of methyl 3-(4-(4-chlorophenoxy)piperidine-1-carbonyl)benzoate (301 mg, 0.81 mmol, Step-1), 2M sodium hydroxide aqueous solution (2 mL), tetrahydrofuran (2 mL), and methanol (2 mL) was stirred at 60° C. for 2 hours. The mixture was acidified by 2M aqueous hydrochloric acid solution and extracted with ethyl acetate (10 mL). The organic layer was dried over sodium sulfate, and concentrated under reduced pressure to give 270 mg (93% yield) of the title compound as a white solid.
MS (ESI) m/z: 360 (M+H)$^+$.

<Step-3> (S)-3-(4-(4-Chlorophenoxy)piperidine-1-carbonyl)-N-(2-hydroxy-2-phenylethyl)benzamide The title compound was prepared in 51% yield (10.1 mg) prepared from 3-(4-(4-chlorophenoxy)piperidine-1-carbonyl)benzoic acid (Step-2) according to the procedure similar to that described in Step-2 of Example 349, using (S)-2-amino-1-phenylethanol instead of 25% ammonium water.
Example 579-581 were prepared from 3-(tert-butyl)-5-(4-(4-chlorophenoxy)piperidine-1-carbonyl)benzamide (Step-2 of Example 578) according to the procedure similar to that described in Step-2 of Example 349, using (S)-2-amino-2-phenylethanol, (S)-2-amino-3-phenylpropan-1-ol, and (S)-2-amino-3-phenylpropanamide instead of 25% ammonium water, respectively.
Example 609 was prepared from 4-(3-(trifluoromethoxy)phenoxy)piperidine hydrochloride and 4-(((tert-butoxycarbonyl)amino)methyl)picolinic acid according to the procedures similar to those described in Example 321.
Example 610-611 were prepared from Example 609 according to the procedure similar to that described in Example 386, using methanesulfonyl chloride, ethyl chloroformate instead of acetic anhydride, respectively.
Example 612 was prepared from 4-(3-(trifluoromethoxy)phenoxy)piperidine hydrochloride and 2-(((tert-butoxycarbonyl)amino)methyl)benzoic acid according to the procedures similar to those described in Example 321 and Example 386.
Example 613 and 614 were prepared from 4-(3-(trifluoromethoxy)phenoxy)piperidine hydrochloride and 2-(((tert-butoxycarbonyl)amino)methyl)benzoic acid according to the procedures similar to those described in Example 321 and Example 386, using methanesulfonyl chloride, ethyl chloroformate instead of acetic anhydride, respectively.
Example 655 was prepared from 4-(3-(trifluoromethoxy)phenoxy)piperidine hydrochloride and 2-(2-((tert-butoxycarbonyl)amino)ethoxy)benzoic acid according to the procedures similar to those described in Example 321 and Example 386.
Example 656-657 were prepared from 4-(3-(trifluoromethoxy)phenoxy)piperidine hydrochloride and 2-(2-((tert-butoxycarbonyl)amino)ethoxy)benzoic acid according to the procedures similar to those described in Example 321 and Example 386, using methanesulfonyl chloride, ethyl chloroformate instead of acetic anhydride, respectively.
Example 658 was prepared from 4-(3-(trifluoromethoxy)phenoxy)piperidine hydrochloride and 2-(2-((tert-butoxycarbonyl)amino)ethoxy)benzoic acid according to the procedures similar to those described in Example 321 and Step-2 of Example 349, using 1-carbamoylcyclopropanecarboxylic acid.
Example 659 was prepared from 4-(3-(trifluoromethoxy)phenoxy)piperidine hydrochloride and 3-(2-((tert-butoxycarbonyl)amino)ethoxy)benzoic acid according to the procedures similar to those described in Example 321.
Example 660-663 were prepared from Example 659 according to the procedures similar to those described in Example 655-658, respectively.
The observed MS, Retention time and Method by HPLC of all examples are described in Table 3. $^1$H-NMR data of Example 21, 80, 92, 191, 403, 451, 561 and 574 are described in Table 4.

TABLE 3

| Example | Name | Structure | Structure of amine part | Structure of carboxylic acid part | Observed MS | Retention time | QC Method |
|---|---|---|---|---|---|---|---|
| Example 1 | (4-(4-chlorophenoxy)piperidin-1-yl)(8-hydroxyquinolin-2-yl)methanone | 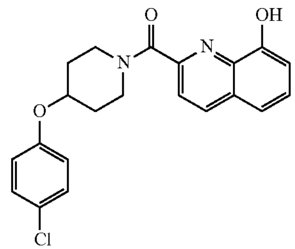 | | | 382.9 | 1.90 min. | Method A |
| Example 2 | (4-(2-chlorophenoxy)piperidin-1-yl)(8-hydroxyquinolin-2-yl)methanone | 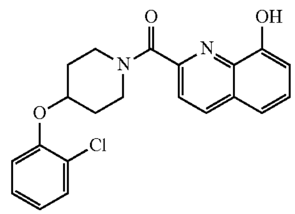 [SMILES: O=C(c1ccc2cccc(O)c2n1)N1CCC(Oc2ccccc2Cl)CC1] | | | 382.9 | 1.87 min. | Method A |
| Example 3 | (4-(3-chlorophenoxy)piperidin-1-yl)(8-hydroxyquinolin-2-yl)methanone | 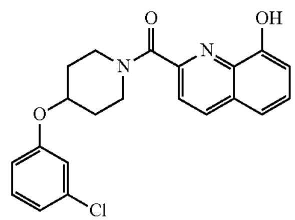 [SMILES: O=C(c1ccc2cccc(O)c2n1)N1CCC(Oc2cccc(Cl)c2)CC1] | | | 382.9 | 1.91 min. | Method A |
| Example 4 | (8-hydroxyquinolin-2-yl)(4-(o-tolyloxy)piperidin-1-yl)methanone | 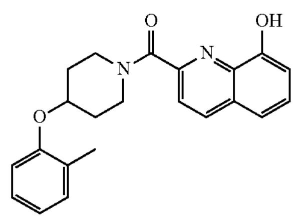 [SMILES: Cc1ccccc1OC1CCN(C(=O)c2ccc3cccc(O)c3n2)CC1] | | | 363 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 5 | (8-hydroxyquinolin-2-yl)(4-(m-tolyloxy)piperidin-1-yl)methanone | 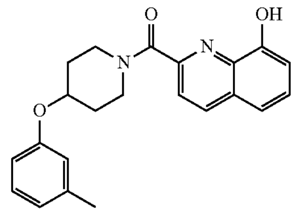 [SMILES: Cc1cccc(OC2CCN(C(=O)c3ccc4cccc(O)c4n3)CC2)c1] | | | 363 | 1.87 min. | Method A |
| Example 6 | (8-hydroxyquinolin-2-yl)(4-(p-tolyloxy)piperidin-1-yl)methanone | 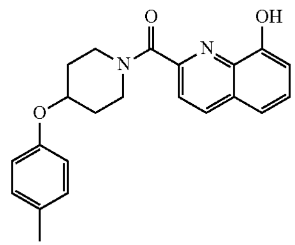 [SMILES: Cc1ccc(OC2CCN(C(=O)c3ccc4cccc(O)c4n3)CC2)cc1] | | | 363 | 1.88 min. | Method A |
| Example 7 | (4-(4-chlorophenoxy)piperidin-1-yl)(quinolin-2-yl)methanone | 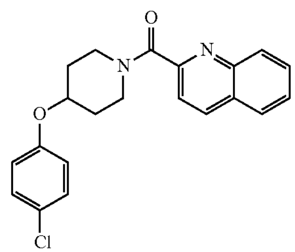 | | | 366.9 | 1.92 min. | Method A |
| Example 8 | (4-(4-chlorophenoxy)piperidin-1-yl)(4-hydroxyquinolin-2-yl)methanone | 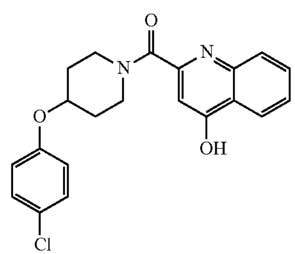 [SMILES: O=C(c1cc(O)c2ccccc2n1)N1CCC(Oc2ccc(Cl)cc2)CC1] | | | 382.9 | 1.53 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 9 | (4-(4-chlorophenoxy) piperidin-1-yl)(quinolin-6-yl) methanone | 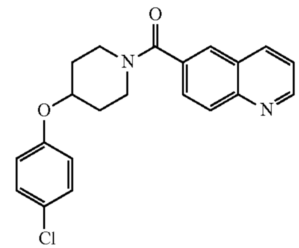 [SMILES: O=C(c1ccc2ncccc2c1)N1CCC(Oc2ccc(Cl)cc2)CC1] | | | 366.9 | 1.73 min. | Method A |
| Example 10 | (4-(4-chlorophenoxy) piperidin-1-yl)(quinolin-3-yl) methanone | 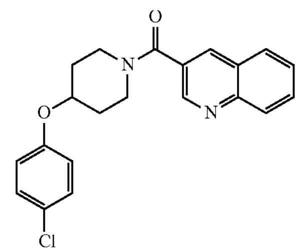 [SMILES: O=C(c1cnc2ccccc2c1)N1CCC(Oc2ccc(Cl)cc2)CC1] | | | 366.9 | 1.80 min. | Method A |
| Example 11 | (4-(4-chlorophenoxy) piperidin-1-yl)(isoquinolin-3-yl) methanone | 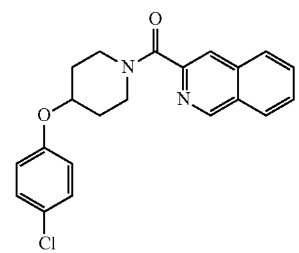 [SMILES: O=C(c1cc2ccccc2cn1)N1CCC(Oc2ccc(Cl)cc2)CC1] | | | 366.9 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 12 | (4-(4-chlorophenoxy) piperidin-1-yl)(1,6-naphthyridin-2-yl)methanone | 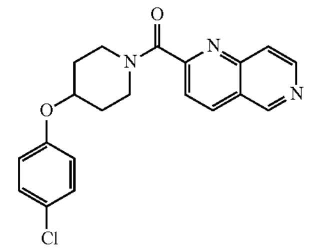 [SMILES: O=C(c1ccc2cnccc2n1)N1CCC(Oc2ccc(Cl)cc2)CC1] | | | 367.9 | 1.65 min. | Method A |
| Example 13 | (4-(4-chlorophenoxy) piperidin-1-yl)(isoquinolin-1-yl) methanone | 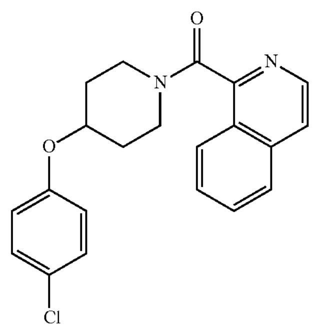 | | | 366.9 | 1.84 min. | Method A |
| Example 14 | (4-(4-chlorophenoxy) piperidin-1-yl)(quinolin-4-yl) methanone | 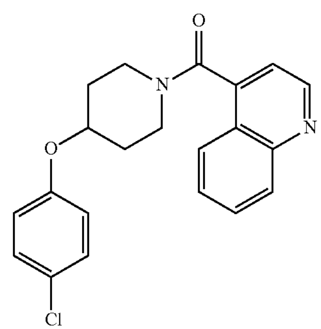 | | | 366.9 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 15 | (4-(4-chlorophenoxy)piperidin-1-yl)(6-(2,2,2-trifluoroethoxy)pyridin-3-yl)methanone | 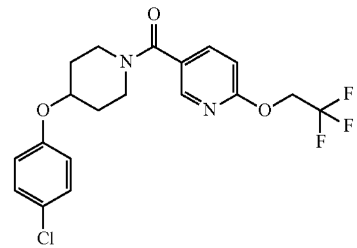 [SMILES: O=C(c1ccc(OCC(F)(F)F)nc1)N1CCC(Oc2ccc(Cl)cc2)CC1] | | | 414.9 | 1.97 min. | Method A |
| Example 16 | (4-(4-chlorophenoxy)piperidin-1-yl)(6-methylpyridin-2-yl)methanone | 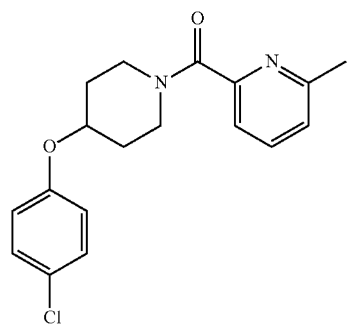 | | | 331 | 1.75 min. | Method A |
| Example 17 | (4-(4-chlorophenoxy)piperidin-1-yl)(3,5-difluoropyridin-2-yl)methanone | 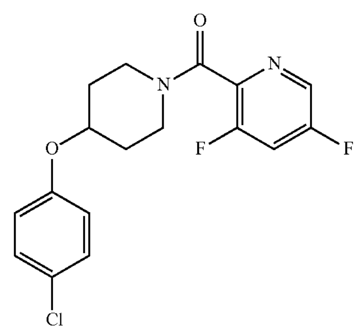 [SMILES: O=C(c1ncc(F)cc1F)N1CCC(Oc2ccc(Cl)cc2)CC1] | | | 352.9 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 18 | (4-(4-chlorophenoxy) piperidin-1-yl)(5-methylpyridin-3-yl) methanone | 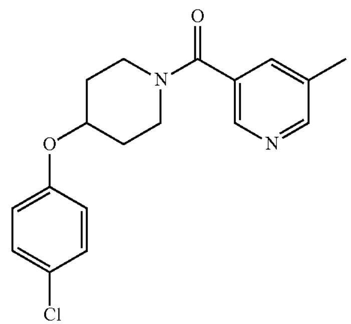 | | | 331 | 1.68 min. | Method A |
| Example 19 | (4-(4-chlorophenoxy) piperidin-1-yl)(quinoxalin-6-yl) methanone | 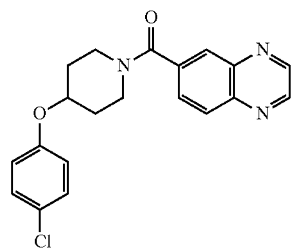 [SMILES: O=C(c1ccc2nccnc2c1)N1CCC(Oc2ccc(Cl)cc2)CC1] | | | 367.9 | 1.69 min. | Method A |
| Example 20 | (4-(4-chlorophenoxy) piperidin-1-yl)(6-phenoxypyridin-3-yl)methanone | 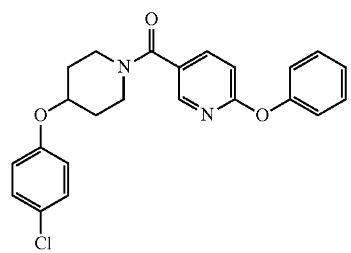 [SMILES: O=C(c1ccc(Oc2ccccc2)nc1)N1CCC(Oc2ccc(Cl)cc2)CC1] | | | 408.9 | 1.96 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 21 | (4-(4-chlorophenoxy) piperidin-1-yl)(quinolin-8-yl) methanone | 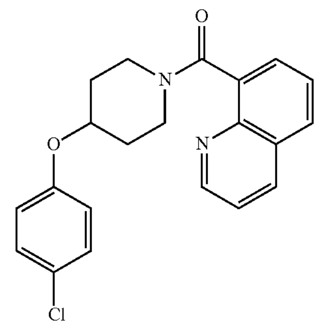 | | | 366.9 | 1.79 min. | Method A |
| Example 22 | benzo[c]isoxazol-3-yl (4-(4-chlorophenoxy) piperidin-1-yl)methanone | 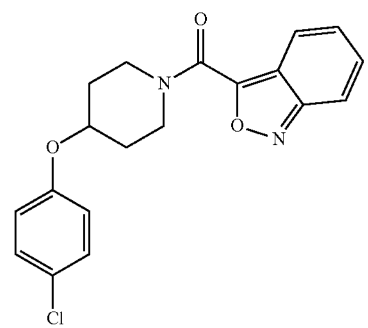 [SMILES: O=C(c1onc2ccccc12)N1CCC(Oc2ccc(Cl)cc2)CC1] | | | 356.9 | 1.97 min. | Method A |
| Example 23 | (4-(4-chlorophenoxy) piperidin-1-yl)(1-isopropyl-1H-benzo[d][1,2,3]triazol-5-yl)methanone | 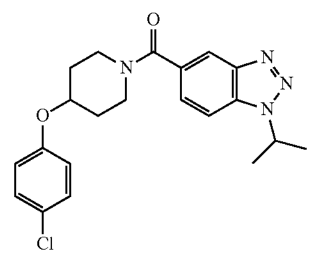 [SMILES: CC(C)n1nnc2cc(C(=O)N3CCC(Oc4ccc(Cl)cc4)CC3)ccc21] | | | 399 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 24 | (4-(4-chlorophenoxy)piperidin-1-yl)(5-fluoro-1H-indol-2-yl)methanone | 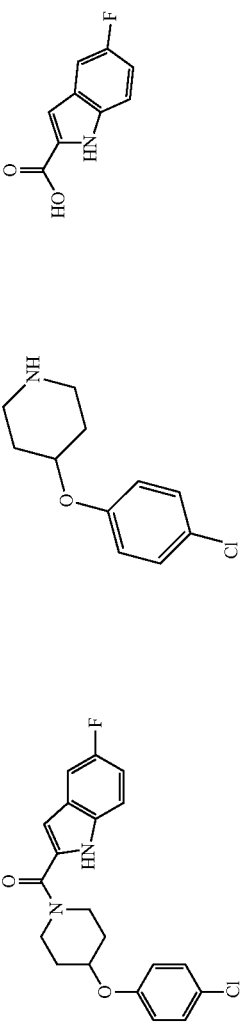 | 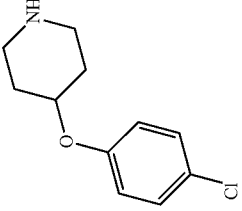 | 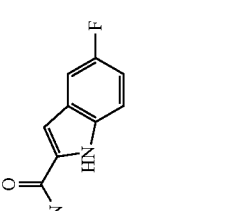 | 372.9 | 1.97 min. | Method A |
| Example 25 | (4-(4-chlorophenoxy)piperidin-1-yl)(6-fluoro-1H-indol-2-yl)methanone | 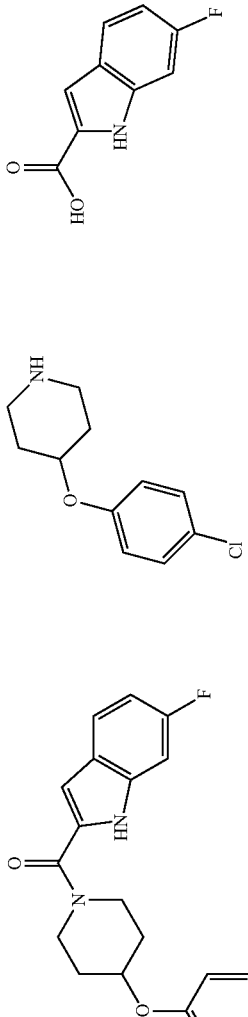 | 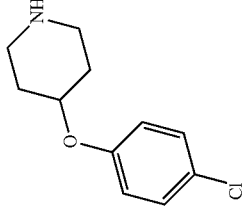 | 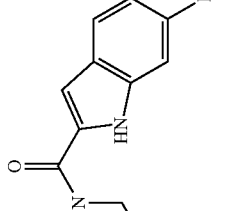 | 372.9 | 1.98 min. | Method A |
| Example 26 | (4-(4-chlorophenoxy)piperidin-1-yl)(5-isobutylisoxazol-3-yl)methanone | 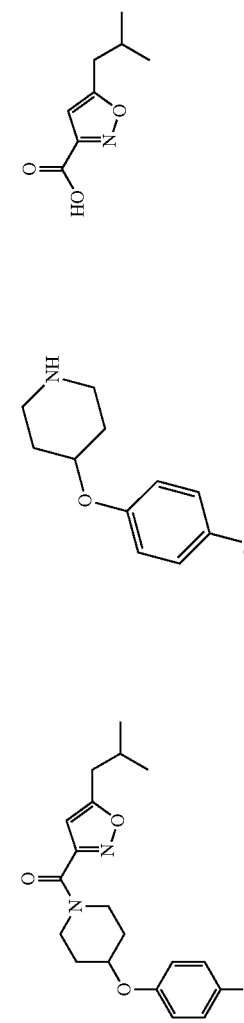 | 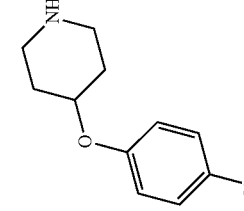 | 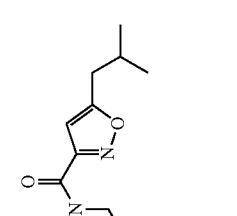 | 363 | 2.07 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 27 | (4-(4-chlorophenoxy)piperidin-1-yl)(2-methyl-5-phenylfuran-3-yl)methanone | 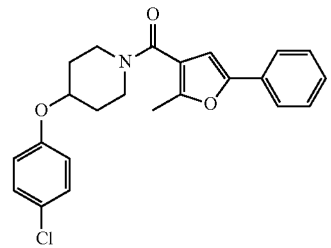 [SMILES: Cc1oc(-c2ccccc2)cc1C(=O)N1CCC(Oc2ccc(Cl)cc2)CC1] | | | 395.9 | 2.12 min. | Method A |
| Example 28 | (4-(4-chlorophenoxy)piperidin-1-yl)(3-(2-methylthiazol-4-yl)phenyl)methanone | 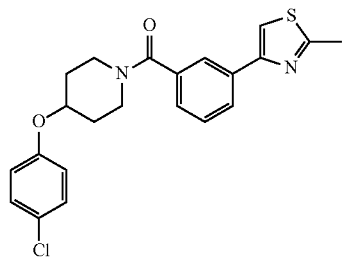 [SMILES: Cc1nc(-c2cccc(C(=O)N3CCC(Oc4ccc(Cl)cc4)CC3)c2)cs1] | | | 412.9 | 1.98 min. | Method A |
| Example 29 | (4-(4-chlorophenoxy)piperidin-1-yl)(5-methoxy-1H-indol-2-yl)methanone | 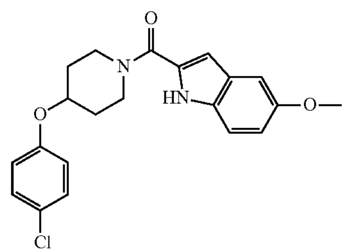 [SMILES: COc1ccc2[nH]c(C(=O)N3CCC(Oc4ccc(Cl)cc4)CC3)cc2c1] | | | 385 | 1.92 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 30 | (4-(4-chlorophenoxy) piperidin-1-yl)(1H-indol-4-yl) methanone | 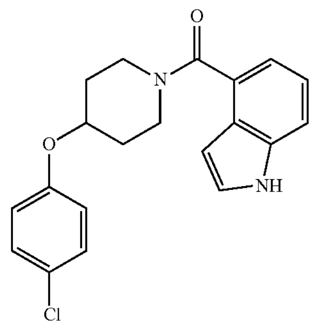 [SMILES: O=C(c1cccc2[nH]ccc12)N1CCC(Oc2ccc(Cl)cc2)CC1] | | | 354.9 | 1.79 min. | Method A |
| Example 31 | (3-(1H-pyrazol-1-yl) phenyl)(4-(4-chlorophenoxy) piperidin-1-yl)methanone | 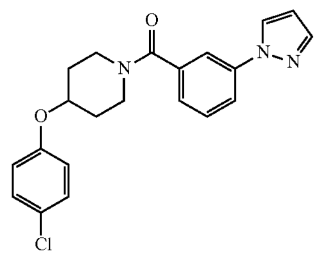 [SMILES: O=C(c1cccc(-n2cccn2)c1)N1CCC(Oc2ccc(Cl)cc2)CC1] | | | 381.9 | 1.87 min. | Method A |
| Example 32 | (4-(1H-1,2,4-triazol-1-yl) phenyl)(4-(4-chlorophenoxy) piperidin-1-yl)methanone | 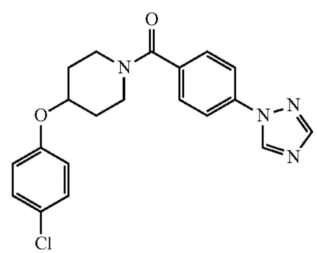 [SMILES: O=C(c1ccc(-n2cncn2)cc1)N1CCC(Oc2ccc(Cl)cc2)CC1] | | | 382.9 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 33 | (4-(4-chlorophenoxy)piperidin-1-yl)(5-methyl-2-phenyl-2H-1,2,3-triazol-4-yl)methanone | 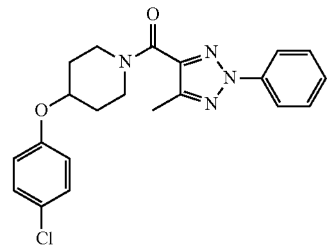 [SMILES: Cc1nn(-c2ccccc2)nc1C(=O)N1CCC(Oc2ccc(Cl)cc2)CC1] | | | 396.9 | 2.15 min. | Method A |
| Example 34 | (4-(4-chlorophenoxy)piperidin-1-yl)(4,5-dichloroisothiazol-3-yl)methanone | 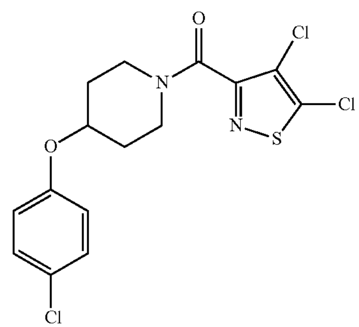 [SMILES: O=C(c1nsc(Cl)c1Cl)N1CCC(Oc2ccc(Cl)cc2)CC1] | | | 390.8 | 2.05 min. | Method A |
| Example 35 | benzofuran-2-yl(4-(4-chlorophenoxy)piperidin-1-yl)methanone | 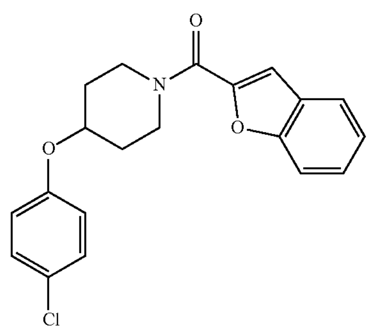 [SMILES: O=C(c1cc2ccccc2o1)N1CCC(Oc2ccc(Cl)cc2)CC1] | | | 355.9 | 2.02 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 36 | benzo[b]thiophen-2-yl (4-(4-chlorophenoxy)piperidin-1-yl)methanone | 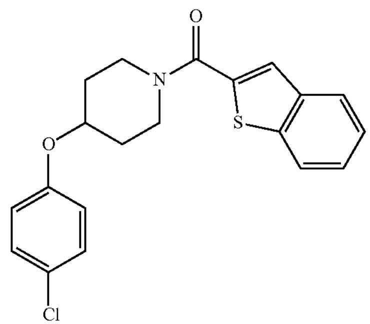 [SMILES: O=C(c1cc2ccccc2s1)N1CCC(Oc2ccc(Cl)cc2)CC1] | | | 371.9 | 2.07 min. | Method A |
| Example 37 | (8-hydroxyquinolin-2-yl) (4-(2-methoxyphenoxy)piperidin-1-yl)methanone | 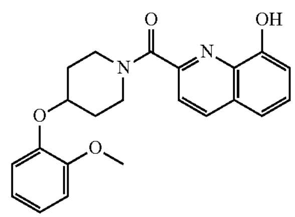 [SMILES: COc1ccccc1OC1CCN(C(=O)c2ccc3cccc(O)c3n2)CC1] | | | 378.9 | 1.70 min. | Method A |
| Example 38 | (4-(4-chlorophenoxy)piperidin-1-yl)(4-methyl-2-phenylpyrimidin-5-yl)methanone | 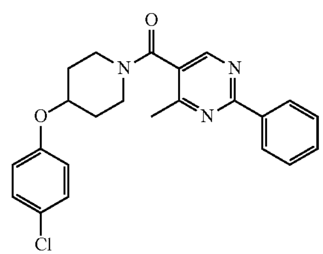 [SMILES: Cc1nc(-c2ccccc2)ncc1C(=O)N1CCC(Oc2ccc(Cl)cc2)CC1] | | | 408 | 2.04 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 39 | (4-(4-chlorophenoxy)piperidin-1-yl)(6-phenylpyrimidin-4-yl)methanone | 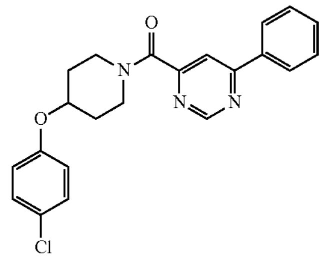 [SMILES: O=C(c1cc(-c2ccccc2)ncn1)N1CCC(Oc2ccc(Cl)cc2)CC1] | | | 393.9 | 1.96 min. | Method A |
| Example 40 | (4-(4-chlorophenoxy)piperidin-1-yl)(4-methoxyquinolin-2-yl)methanone | 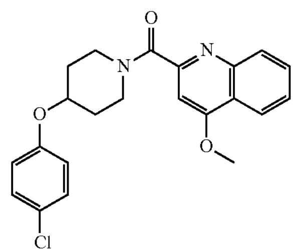 [SMILES: COc1cc(C(=O)N2CCC(Oc3ccc(Cl)cc3)CC2)nc2ccccc12] | | | 396.9 | 1.96 min. | Method A |
| Example 41 | (4-(4-chlorophenoxy)piperidin-1-yl)quinoxalin-2-yl)methanone | 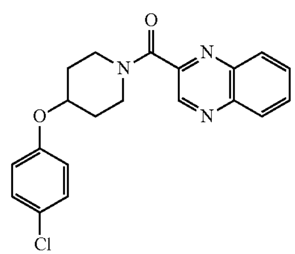 [SMILES: O=C(c1cnc2ccccc2n1)N1CCC(Oc2ccc(Cl)cc2)CC1] | | | 367.9 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 42 | benzo[d]thiazol-6-yl (4-(4-chlorophenoxy) pipeidin-1-yl)methanone | 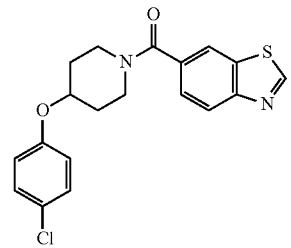 [SMILES: O=C(c1ccc2ncsc2c1)N1CCC(Oc2ccc(Cl)cc2)CC1] | | | 372.9 | 1.77 min. | Method A |
| Example 43 | (4-(4-chlorophenoxy) piperidin-1-yl)(1H-indol-3-yl) methanone | 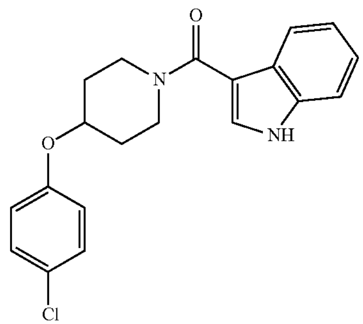 | | | 354.9 | 1.81 min. | Method A |
| Example 44 | (4-(4-chlorophenoxy) piperidin-1-yl)(1H-indol-2-yl) methanone | 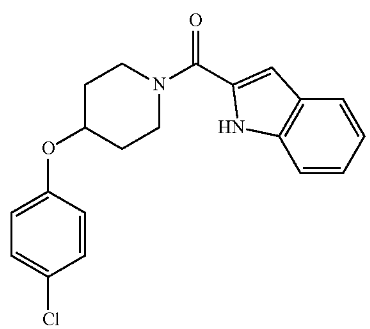 [SMILES: O=C(c1cc2ccccc2[nH]1)N1CCC(Oc2ccc(Cl)cc2)CC1] | | | 354.9 | 1.97 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 45 | (4-(4-chlorophenoxy) piperidin-1-yl)(1-methyl-1H-indol-3-yl)methanone | 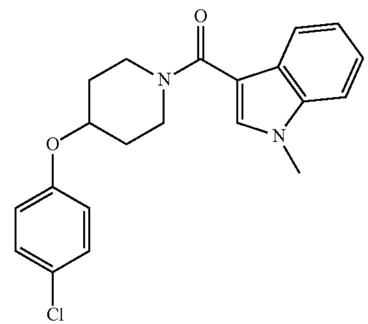 | | | 368.9 | 1.93 min. | Method A |
| Example 46 | (4-(4-chlorophenoxy) piperidin-1-yl)(1-methyl-1H-indol-2-yl)methanone | 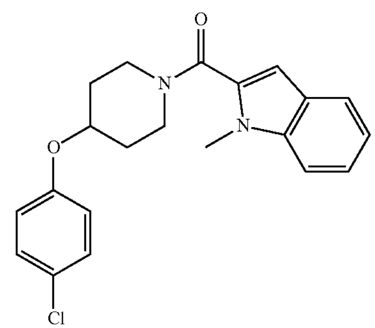 [SMILES: Cn1c(C(=O)N2CCC(Oc3ccc(Cl)cc3)CC2)cc2ccccc21] | | | 368.9 | 2.05 min. | Method A |
| Example 47 | (4-(4-chlorophenoxy) piperidin-1-yl)(2,3-dimethyl-1H-indol-5-yl)methanone | 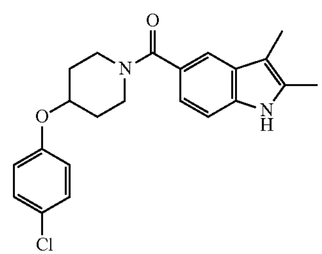 [SMILES: Cc1[nH]c2ccc(C(=O)N3CCC(Oc4ccc(Cl)cc4)CC3)cc2c1C] | | | 382.9 | 1.94 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 48 | (4-(4-chlorophenoxy) piperidin-1-yl)(1H-indol-6-yl) methanone | 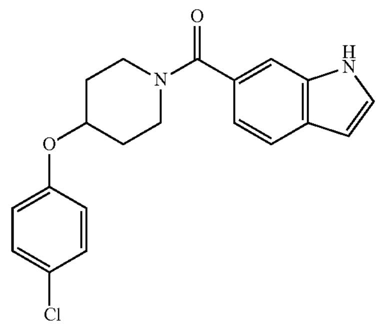 [SMILES: O=C(c1ccc2cc[nH]c2c1)N1CCC(Oc2ccc(Cl)cc2)CC1] | | | 354.9 | 1.84 min. | Method A |
| Example 49 | (4-(4-chlorophenoxy) piperidin-1-yl)(2-methyl-1H-benzo[d]imidazol-5-yl)methanone | 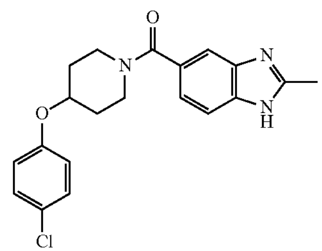 [SMILES: Cc1nc2cc(C(=O)N3CCC(Oc4ccc(Cl)cc4)CC3)ccc2[nH]1] | | | 370 | 1.54 min. | Method A |
| Example 50 | (4-(4-chlorophenoxy) piperidin-1-yl)(imidazo[1,2-a]pyridin-2-yl)methanone | 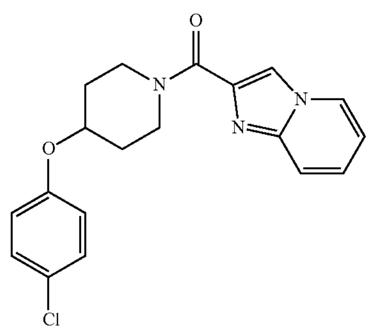 | | | 355.9 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 51 | (4-(4-chlorophenoxy)piperidin-1-yl)(2-methylimidazo[1,2-a]pyridin-3-yl)methanone | 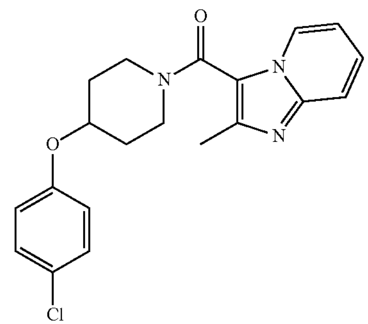 [SMILES: Cc1nc2ccccn2c1C(=O)N1CCC(Oc2ccc(Cl)cc2)CC1] | | | 370 | 1.69 min. | Method A |
| Example 52 | (4-(4-chlorophenoxy)piperidin-1-yl)(5-methyl-1-phenyl-1H-pyrazol-4-yl)methanone | 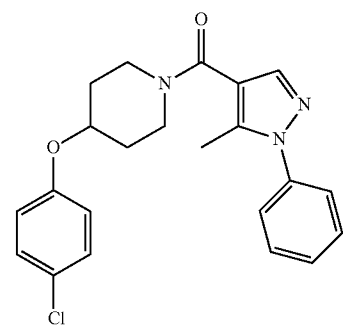 [SMILES: Cc1c(C(=O)N2CCC(Oc3ccc(Cl)cc3)CC2)cnn1-c1ccccc1] | | | 395.9 | 1.87 min. | Method A |
| Example 53 | (4-(tert-butyl)phenyl)(4-(4-chlorophenoxy)piperidin-1-yl)methanone | 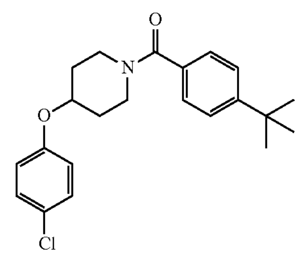 [SMILES: CC(C)(C)c1ccc(C(=O)N2CCC(Oc3ccc(Cl)cc3)CC2)cc1] | | | 372 | 2.18 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 54 | (4-(4-chlorophenoxy) piperidin-1-yl)(4-chlorophenyl) methanone | 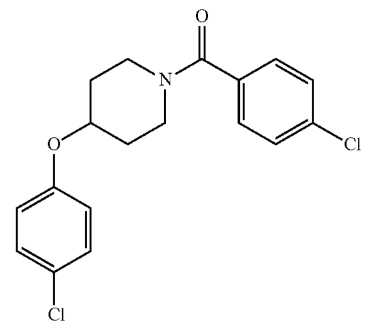 [SMILES: O=C(c1ccc(Cl)cc1)N1CCC(Oc2ccc(Cl)cc2)CC1] | | | 349.9 | 2.00 min. | Method A |
| Example 55 | (4-(4-chlorophenoxy) piperidin-1-yl)(4-fluorophenyl) methanone | 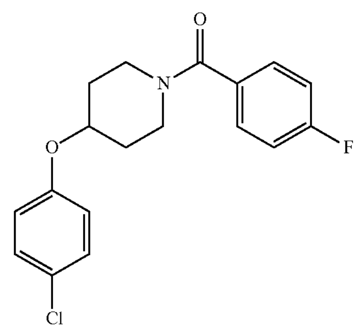 [SMILES: O=C(c1ccc(F)cc1)N1CCC(Oc2ccc(Cl)cc2)CC1] | | | 333.9 | 1.89 min. | Method A |
| Example 56 | (4-(4-chlorophenoxy) piperidin-1-yl)(3-(5-fluoro-1H-benzo[d]imidazol-2-yl)phenyl)methanone | 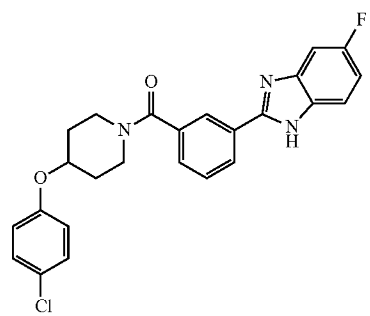 [SMILES: O=C(c1cccc(-c2nc3cc(F)ccc3[nH]2)c1)N1CCC(Oc2ccc(Cl)cc2)CC1] | | | 448.1 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 57 | (4-(4-chlorophenoxy)piperidin-1-yl)(3-(1-methyl-1H-benzo[d]imidazol-2-yl)phenyl)methanone | 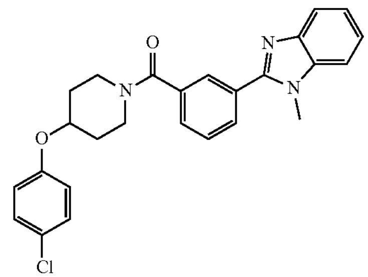 [SMILES: Cn1c(-c2cccc(C(=O)N3CCC(Oc4ccc(Cl)cc4)CC3)c2)nc2ccccc21] | | | 446 | 1.85 min. | Method A |
| Example 58 | (4-(2-fluorophenoxy)piperidin-1-yl)(8-hydroxyquinolin-2-yl)methanone | 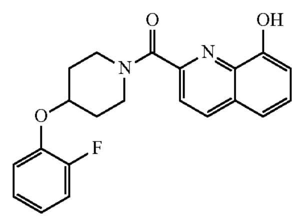 | | | 365.2 | 1.77 min. | Method A |
| Example 59 | (4-(3-fluorophenoxy)piperidin-1-yl)(8-hydroxyquinolin-2-yl)methanone | 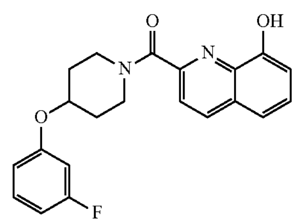 | | | 365.2 | 1.79 min. | Method A |
| Example 60 | (4-(4-fluorophenoxy)piperidin-1-yl)(8-hydroxyquinolin-2-yl)methanone | 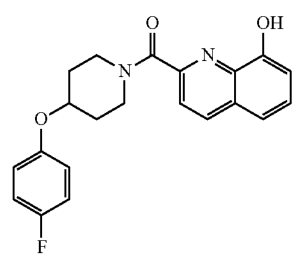 [SMILES: O=C(c1ccc2cccc(O)c2n1)N1CCC(Oc2ccc(F)cc2)CC1] | | | 365.2 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 61 | (8-hydroxyquinolin-2-yl)(4-(3-methoxyphenoxy)piperidin-1-yl)methanone | 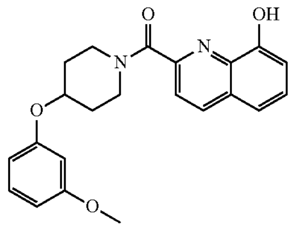 [SMILES: COc1cccc(OC2CCN(C(=O)c3ccc4cccc(O)c4n3)CC2)c1] | | | 377.2 | 1.75 min. | Method A |
| Example 62 | 2-((1-(8-hydroxyquinoline-2-carbonyl)piperidin-4-yl)oxy)benzonitrile | 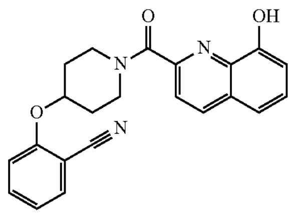 [SMILES: N#Cc1ccccc1OC1CCN(C(=O)c2ccc3cccc(O)c3n2)CC1] | | | 372.2 | 1.65 min. | Method A |
| Example 63 | 4-((1-(8-hydroxyquinoline-2-carbonyl)piperidin-4-yl)oxy)benzonitrile | 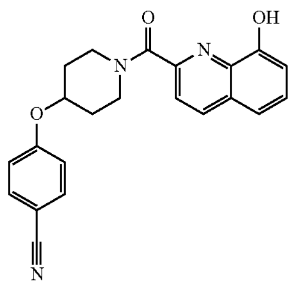 [SMILES: N#Cc1ccc(OC2CCN(C(=O)c3ccc4cccc(O)c4n3)CC2)cc1] | | | 372.2 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 64 | 3-((1-(8-hydroxyquinoline-2-carbonyl)piperidin-4-yl)oxy)benzonitrile | 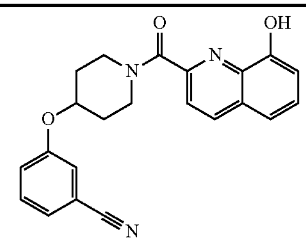 | | | 372.2 | 1.69 min. | Method A |
| Example 65 | (4-(4-chlorophenoxy)piperidin-1-yl)(8-methoxyquinolin-2-yl)methanone | 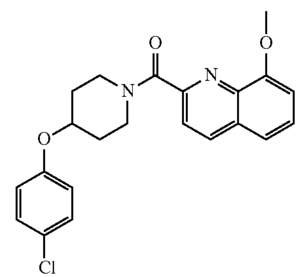 [SMILES: COc1cccc2ccc(C(=O)N3CCC(Oc4ccc(Cl)cc4)CC3)nc12] | | | 396.9 | 1.85 min. | Method A |
| Example 66 | (4-(4-chlorophenoxy)piperidin-1-yl)(1-methyl-1H-indol-7-yl)methanone | 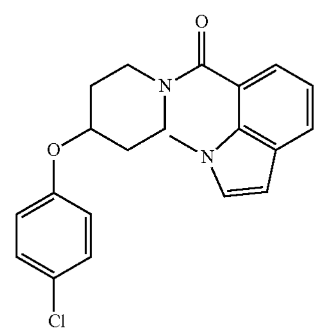 [SMILES: Cn1ccc2cccc(C(=O)N3CCC(Oc4ccc(Cl)cc4)CC3)c21] | | | 368.9 | 1.97 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 67 | (4-(4-chlorophenoxy) piperidin-1-yl)(1-methyl-1H-indol-4-yl)methanone | 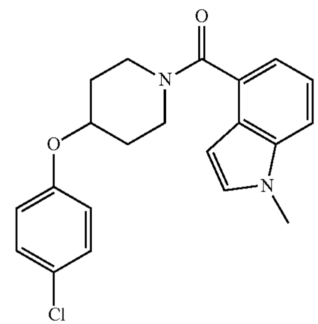 [SMILES: Cn1ccc2c(C(=O)N3CCC(Oc4ccc(Cl)cc4)CC3)cccc21] | | | 369 | 1.91 min. | Method A |
| Example 68 | (4-(4-chlorophenoxy) piperidin-1-yl)(1,8-naphthyridin-2-yl)methanone | 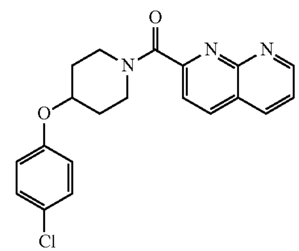 [SMILES: O=C(c1ccc2cccnc2n1)N1CCC(Oc2ccc(Cl)cc2)CC1] | | | 367.9 | 1.59 min. | Method A |
| Example 69 | (8-hydroxyquinolin-2-yl) (4-phenoxypiperidin-1-yl) methanone | 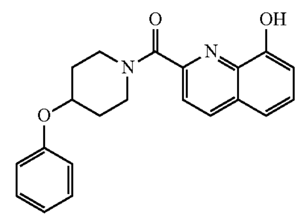 [SMILES: O=C(c1ccc2cccc(O)c2n1)N1CCC(Oc2ccccc2)CC1] | | | 347.1 | 1.76 min. | Method A |

| Example | Name | Structure | Structure of amine part | Structure of carboxylic acid part | Observed MS | Retention time | QC Method |
|---|---|---|---|---|---|---|---|
| Example 70 | (8-hydroxyquinolin-2-yl)(4-(2-(trifluoromethyl)phenoxy)piperidin-1-yl)methanone | 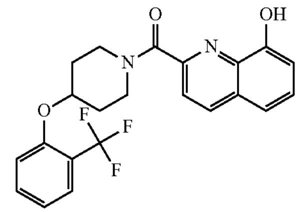 [SMILES: O=C(c1ccc2cccc(O)c2n1)N1CCC(Oc2ccccc2C(F)(F)F)CC1] | | | 415.1 | 1.89 min. | Method A |
| Example 71 | (8-hydroxyquinolin-2-yl)(4-(3-(trifluoromethyl)phenoxy)piperidin-1-yl)methanone | 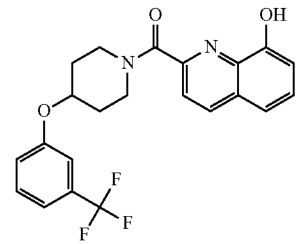 [SMILES: O=C(c1ccc2cccc(O)c2n1)N1CCC(Oc2cccc(C(F)(F)F)c2)CC1] | | | 415.1 | 1.91 min. | Method A |
| Example 72 | (5-(tert-butyl)isoxazol-3-yl)(4-(4-chlorophenoxy)piperidin-1-yl)methanone | 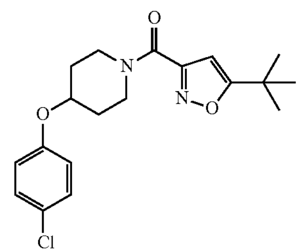 | | | 362.9 | 2.06 min. | Method A |
| Example 73 | (4-(4-chlorophenoxy)piperidin-1-yl)(5-phenylioxazol-3-yl)methanone | 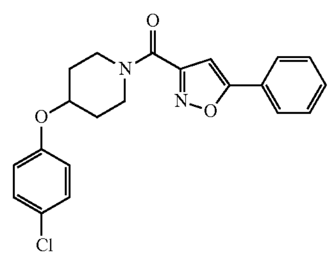 [SMILES: O=C(c1cc(-c2ccccc2)on1)N1CCC(Oc2ccc(Cl)cc2)CC1] | | | 382.9 | 2.04 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 74 | (4-(4-chlorophenoxy) piperidin-1-yl)(5-cyclopropylisoxazol-3-yl)methanone | 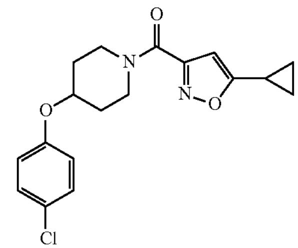 [SMILES: O=C(c1cc(C2CC2)on1)N1CCC(Oc2ccc(Cl)cc2)CC1] | | | 347 | 1.91 min. | Method A |
| Example 75 | (4-(4-chlorophenoxy) piperidin-1-yl)(3,5-dimethylisoxazol-4-yl)methanone | 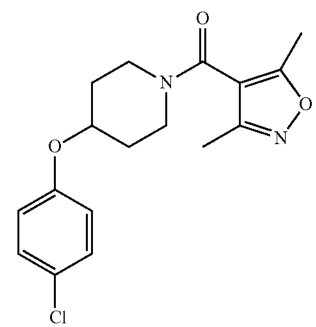 [SMILES: Cc1noc(C)c1C(=O)N1CCC(Oc2ccc(Cl)cc2)CC1] | | | 334.9 | 1.73 min. | Method A |
| Example 76 | (4-(4-chlorophenoxy) piperidin-1-yl)(1-methyl-1H-indazol-3-yl)methanone | 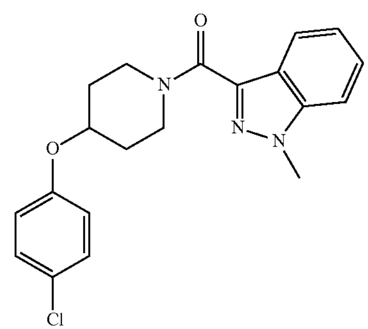 | | | 370 | 1.94 min. | Method A |

TABLE 3-continued
| Example | Name | Structure | Structure of amine part | Structure of carboxylic acid part | Observed MS | Retention time | QC Method |
|---|---|---|---|---|---|---|---|
| Example 77 | (4-(4-chlorophenoxy) piperidin-1-yl)(2-methyl-2H-indazol-3-yl)methanone | 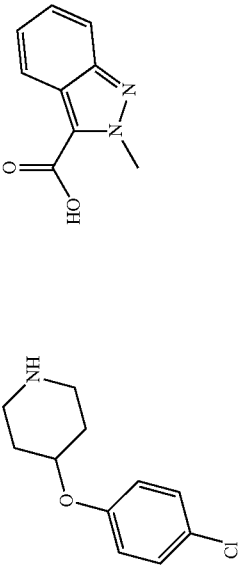 | 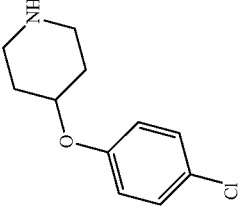 | 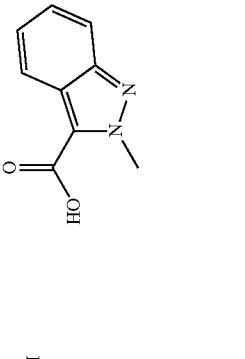 | 370 | 1.85 min. | Method A |
| Example 78 | (4-(4-chlorophenoxy) piperidin-1-yl)(cinnolin-4-yl) methanone | 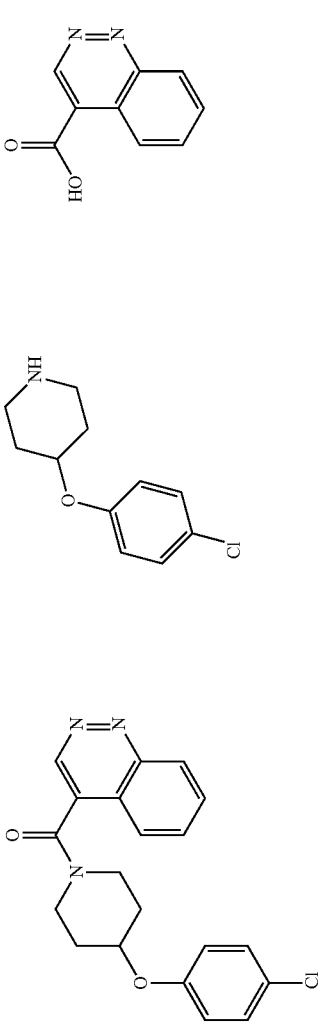 | 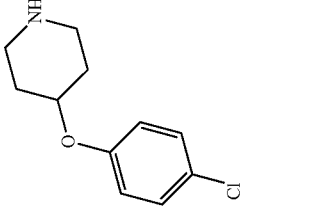 | 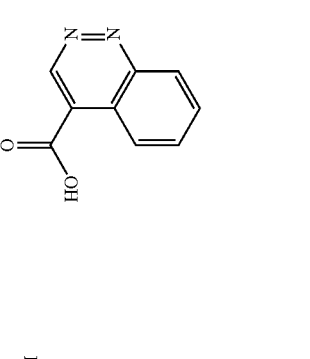 | 367.9 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 79 | (4-(4-chlorophenoxy) piperidin-1-yl)(2-methyl-4-phenylpyrimidin-5-yl)methanone | 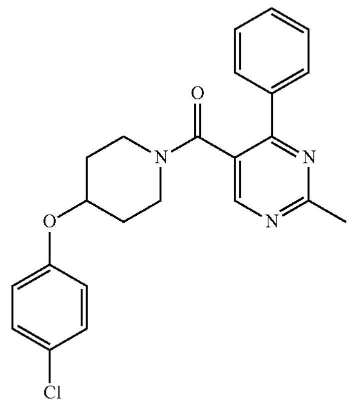 [SMILES: Cc1ncc(C(=O)N2CCC(Oc3ccc(Cl)cc3)CC2)c(-c2ccccc2)n1] | | | 408 | 1.86 min. | Method A |
| Example 80 | (4-(4-chlorophenoxy) piperidin-1-yl)(6-methylpyridin-3-yl) methanone | 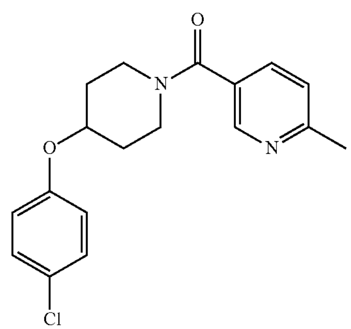 | | | 330.9 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 81 | (4-(4-chlorophenoxy)piperidin-1-yl)(pyridin-4-yl)methanone | 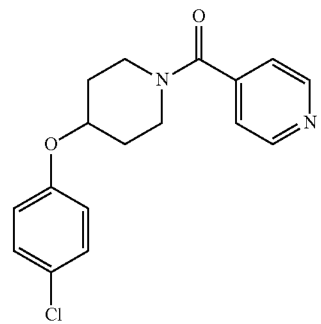 [SMILES: O=C(c1ccncc1)N1CCC(Oc2ccc(Cl)cc2)CC1] | | | 316.9 | 1.59 min. | Method A |
| Example 82 | [1,2,4]triazolo[1,5-a]pyrimidin-2-yl(4-(4-chlorophenoxy)piperidin-1-yl)methanone | 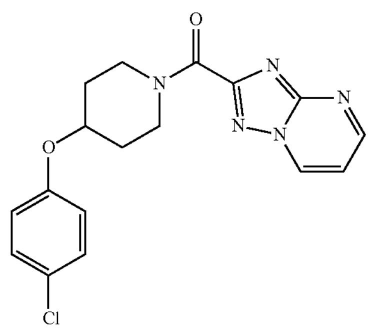 [SMILES: O=C(c1nc2ncccn2n1)N1CCC(Oc2ccc(Cl)cc2)CC1] | | | 357.9 | 1.52 min. | Method A |
| Example 83 | (4-(4-chlorophenoxy)piperidin-1-yl)(1,2,3-trimethyl-1H-indol-5-yl)methanone | 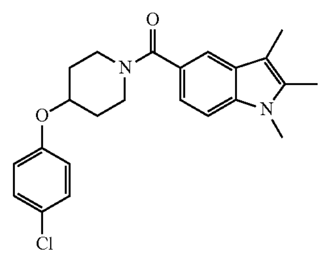 [SMILES: Cc1c(C)n(C)c2ccc(C(=O)N3CCC(Oc4ccc(Cl)cc4)CC3)cc12] | | | 396.9 | 2.06 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 84 | (4-(4-chlorophenoxy)piperidin-1-yl)(1-methyl-1H-indol-6-yl)methanone | 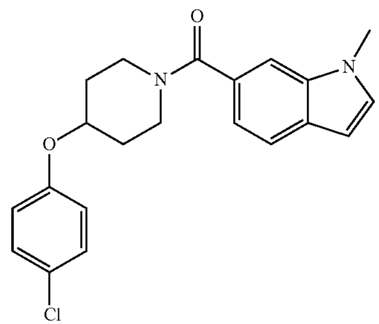 [SMILES: Cn1ccc2ccc(C(=O)N3CCC(Oc4ccc(Cl)cc4)CC3)cc21] | | | 368.9 | 1.93 min. | Method A |
| Example 85 | (4-(4-chlorophenoxy)piperidin-1-yl)(2-methylthiazol-4-yl)methanone | 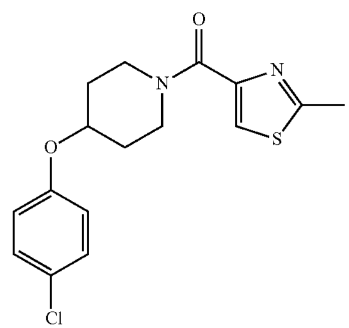 [SMILES: Cc1nc(C(=O)N2CCC(Oc3ccc(Cl)cc3)CC2)cs1] | | | 336.9 | 1.75 min. | Method A |
| Example 86 | (4-(4-chlorophenoxy)piperidin-1-yl)(6-methoxypyridin-3-yl)methanone | 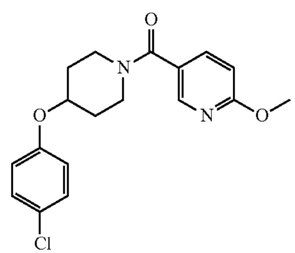 | | | 347 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 87 | (4-(4-chlorophenoxy)piperidin-1-yl)(2-phenoxypyridin-3-yl)methanone | 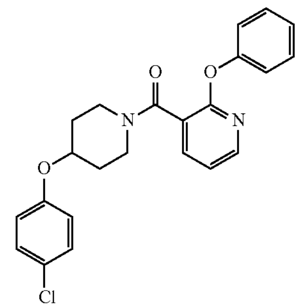 [SMILES: O=C(c1cccnc1Oc1ccccc1)N1CCC(Oc2ccc(Cl)cc2)CC1] | | | 408.9 | 1.93 min. | Method A |
| Example 88 | (4-(4-chlorophenoxy)piperidin-1-yl)(1H-indol-7-yl)methanone | 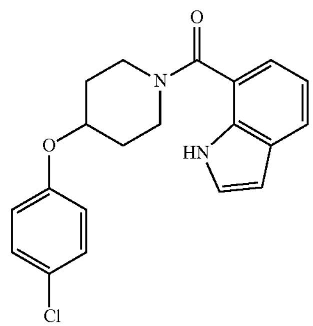 [SMILES: O=C(c1cccc2cc[nH]c12)N1CCC(Oc2ccc(Cl)cc2)CC1] | | | 353.1 | 1.94 min. | Method A |
| Example 89 | 7-(4-(4-chlorophenoxy)piperidine-1-carbonyl)indoline-2,3-dione | 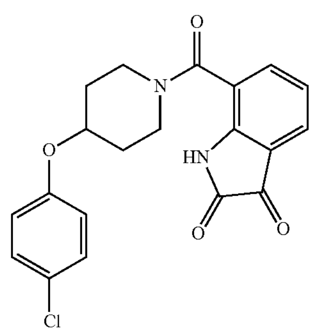 [SMILES: O=C1Nc2c(cccc2C(=O)N2CCC(Oc3ccc(Cl)cc3)CC2)C1=O] | | | 383.1 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 90 | (4-(4-chlorophenoxy) piperidin-1-yl)(3-methylpyridin-2-yl) methanone | 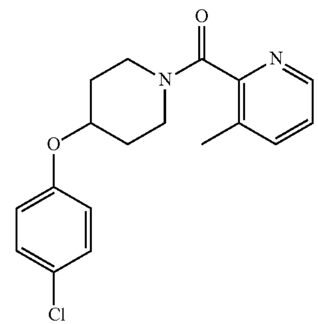 [SMILES: Cc1cccnc1C(=O)N1CCC(Oc2ccc(Cl)cc2)CC1] | | | 330.9 | 1.70 min. | Method A |
| Example 91 | (4-(4-chlorophenoxy) piperidin-1-yl)(6-hydroxypyridin-2-yl)methanone | 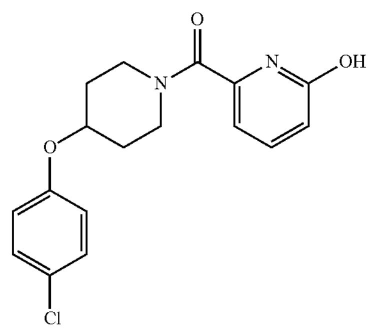 [SMILES: O=C(c1cccc(O)n1)N1CCC(Oc2ccc(Cl)cc2)CC1] | | | 331.1 | 1.48 min. | Method A |
| Example 92 | (4-(4-chlorophenoxy) piperidin-1-yl)(2,4-dimethylthiazol-5-yl)methanone | 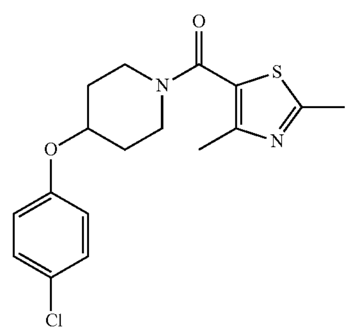 [SMILES: Cc1nc(C)c(C(=O)N2CCC(Oc3ccc(Cl)cc3)CC2)s1] | | | 350.9 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 93 | (4-(4-chlorophenoxy) piperidin-1-yl)(5-methyl-1,3,4-oxadiazol-2-yl)methanone | 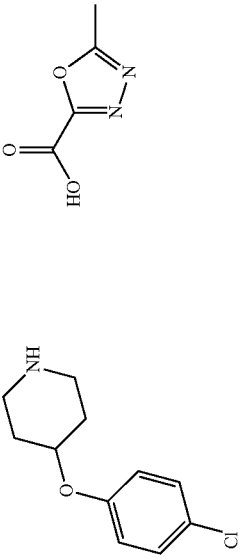 | 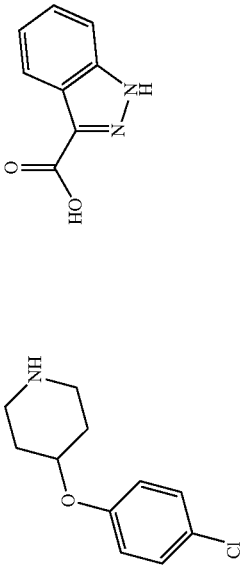 | 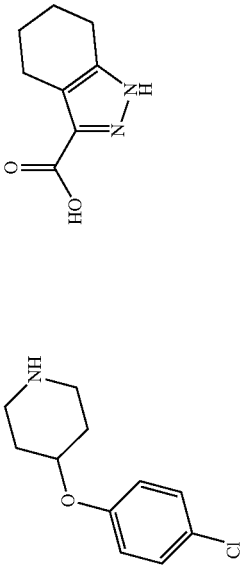 | 321.9 | 1.69 min. | Method A |
| Example 94 | (4-(4-chlorophenoxy) piperidin-1-yl)(1H-indazol-3-yl) methanone | 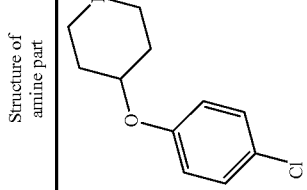 | 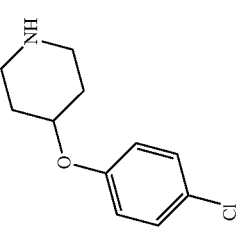 | 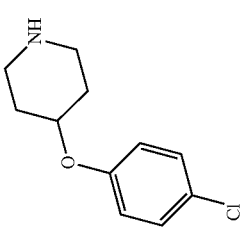 | 354.1 | 1.79 min. | Method A |
| Example 95 | (4-(4-chlorophenoxy) piperidin-1-yl)(4,5,6,7-tetrahydro-1H-indazol-3-yl)methanone | 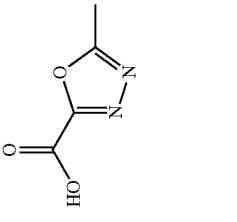 | 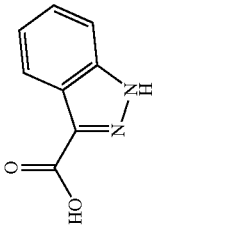 | 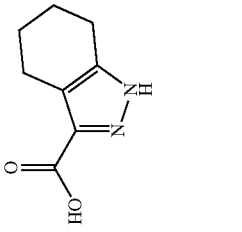 | 358.1 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 96 | (4-(4-chlorophenoxy) piperidin-1-yl)(6-methoxypyridin-2-yl)methanone | 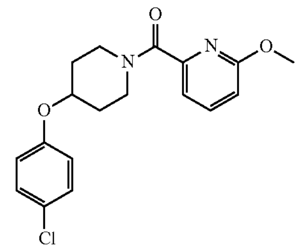 [SMILES: COc1cccc(C(=O)N2CCC(Oc3ccc(Cl)cc3)CC2)n1] | | | 347 | 1.90 min. | Method A |
| Example 97 | (4-(4-chlorophenoxy) piperidin-1-yl)(2-methyl-4,5,6,7-tetrahydro-2H-indazol-3-yl)methanone | 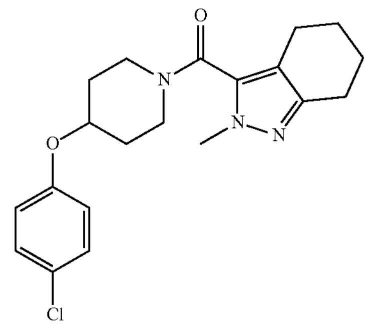 [SMILES: Cn1nc2c(c1C(=O)N1CCC(Oc3ccc(Cl)cc3)CC1)CCCC2] | | | 373.9 | 1.88 min. | Method A |
| Example 98 | (4-(4-chlorophenoxy) piperidin-1-yl)(isoquinolin-4-yl) methanone | 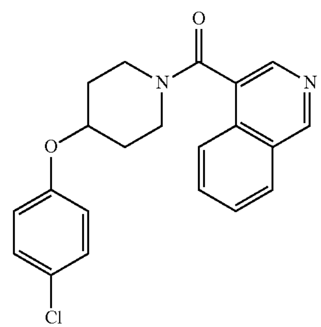 | | | 366.9 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 99 | (4-(4-chlorophenoxy)piperidin-1-yl)(4-methylpyridin-2-yl)methanone | 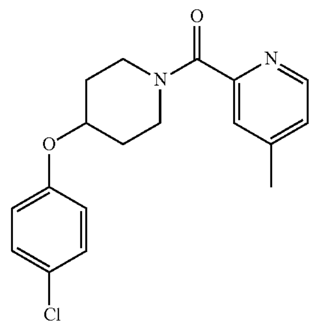 [SMILES: Cc1ccnc(C(=O)N2CCC(Oc3ccc(Cl)cc3)CC2)c1] | | | 330.9 | 1.73 min. | Method A |
| Example 100 | (4-(4-chlorophenoxy)piperidin-1-yl)(6-methoxyquinolin-2-yl)methanone | 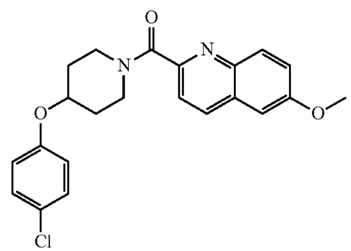 | | | 396.9 | 1.91 min. | Method A |
| Example 101 | (4-(4-chlorophenoxy)piperidin-1-yl)(6-methoxy-2-methylquinolin-3-yl)methanone | 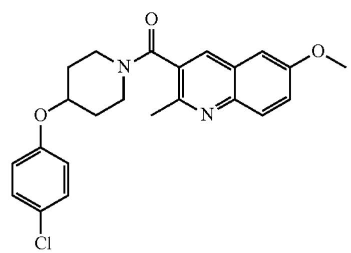 [SMILES: COc1ccc2nc(C)c(C(=O)N3CCC(Oc4ccc(Cl)cc4)CC3)cc2c1] | | | 410.9 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 102 | (3-(4-chlorophenoxy) azetidin-1-yl)(8-hydroxyquinolin-2-yl)methanone | 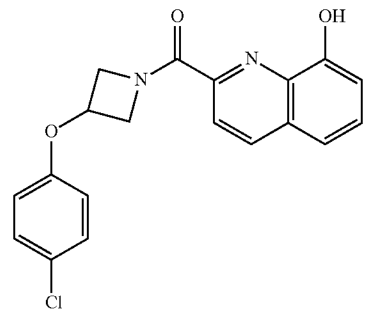 [SMILES: O=C(c1ccc2cccc(O)c2n1)N1CC(Oc2ccc(Cl)cc2)C1] | | | 353.1 | 1.83 min. | Method A |
| Example 103 | benzo[d]isoxazol-3-yl (4-(4-chlorophenoxy) piperidin-1-yl)methanone | 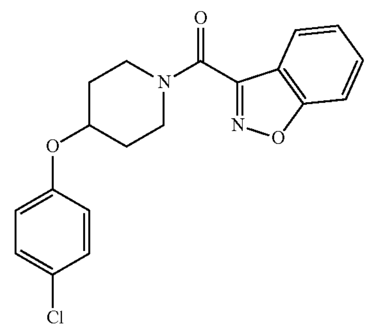 [SMILES: O=C(c1noc2ccccc12)N1CCC(Oc2ccc(Cl)cc2)CC1] | | | 356.9 | 1.99 min. | Method A |
| Example 104 | (4-(4-chlorophenoxy) piperidin-1-yl)(2-(trifluoromethyl)-1H-benzo[d]imidazol-5-yl)methanone | 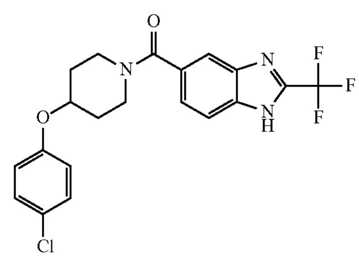 [SMILES: O=C(c1ccc2[nH]c(C(F)(F)F)nc2c1)N1CCC(Oc2ccc(Cl)cc2)CC1] | | | 422.1 | 1.73 min. | Method A |

TABLE 3-continued

| Example | Structure | Name | Structure of amine part | Structure of carboxylic acid part | Observed MS | Retention time | QC Method |
|---|---|---|---|---|---|---|---|
| Example 105 | 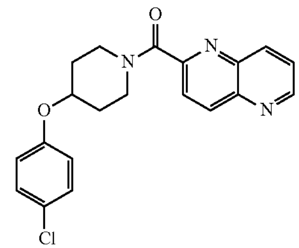 | (4-(4-chlorophenoxy)piperidin-1-yl)(1,5-naphthyridin-2-yl)methanone | | | 367.9 | 1.68 min. | Method A |
| Example 106 | 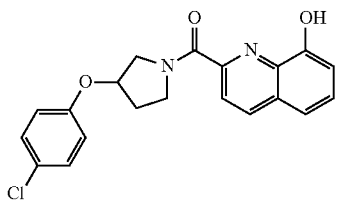 [SMILES: O=C(c1ccc2cccc(O)c2n1)N1CCC(Oc2ccc(Cl)cc2)C1] | (3-(4-chlorophenoxy)pyrrolidin-1-yl)(8-hydroxyquinolin-2-yl)methanone | | | 367.1 | 1.82 min. | Method A |
| Example 107 | 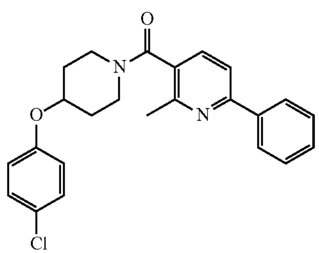 [SMILES: Cc1nc(-c2ccccc2)ccc1C(=O)N1CCC(Oc2ccc(Cl)cc2)CC1] | (4-(4-chlorophenoxy)piperidin-1-yl)(2-methyl-6-phenylpyridin-3-yl)methanone | | | 407 | 2.04 min. | Method A |

| Example | Name | Structure | Structure of amine part | Structure of carboxylic acid part | Observed MS | Retention time | QC Method |
|---|---|---|---|---|---|---|---|
| Example 108 | (4-(4-chlorophenoxy) piperidin-1-yl)(1,5-dimethyl-1H-indol-3-yl)methanone | 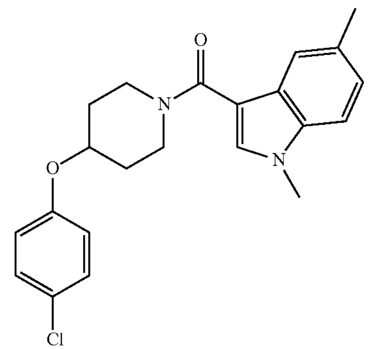 [SMILES: Cc1ccc2c(c1)c(C(=O)N1CCC(Oc3ccc(Cl)cc3)CC1)cn2C] | | | 382.9 | 2.01 min. | Method A |
| Example 109 | (4-(4-chlorophenoxy) piperidin-1-yl)(5-fluoro-1-methyl-1H-indol-3-yl)methanone | 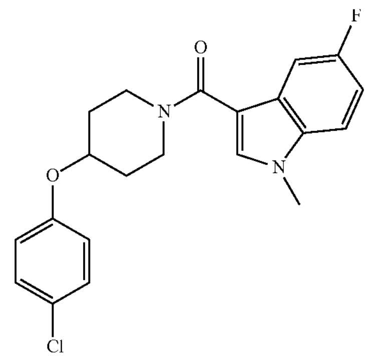 [SMILES: Cn1cc(C(=O)N2CCC(Oc3ccc(Cl)cc3)CC2)c2cc(F)ccc21] | | | 386.9 | 1.94 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 110 | (5-chloro-1-methyl-1H-indol-3-yl)(4-(4-chlorophenoxy)piperidin-1-yl)methanone | 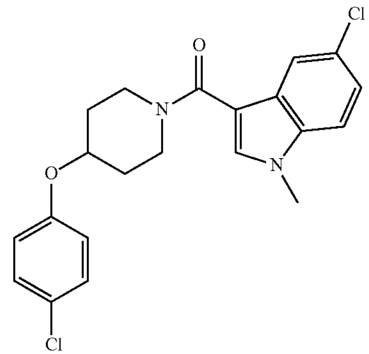 [SMILES: Cn1cc(C(=O)N2CCC(Oc3ccc(Cl)cc3)CC2)c2cc(Cl)ccc21] | | | 402.9 | 2.03 min. | Method A |
| Example 111 | (4-(4-chlorophenoxy)piperidin-1-yl)(5-methoxy-1-methyl-1H-indol-3-yl)methanone | 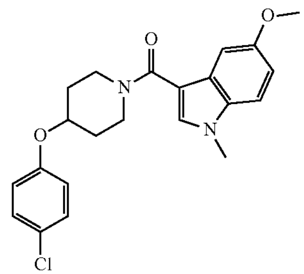 [SMILES: COc1ccc2c(c1)c(C(=O)N1CCC(Oc3ccc(Cl)cc3)CC1)cn2C] | | | 399 | 1.90 min. | Method A |
| Example 112 | (4-(4-chlorophenoxy)piperidin-1-yl)(1,6-dimethyl-1H-indol-3-yl)methanone | 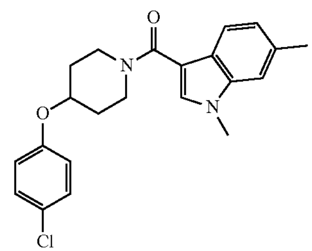 [SMILES: Cc1ccc2c(C(=O)N3CCC(Oc4ccc(Cl)cc4)CC3)cn(C)c2c1] | | | 382.9 | 2.02 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 113 | (4-(4-chlorophenoxy)piperidin-1-yl)(6-fluoro-1-methyl-1H-indol-3-yl)methanone | 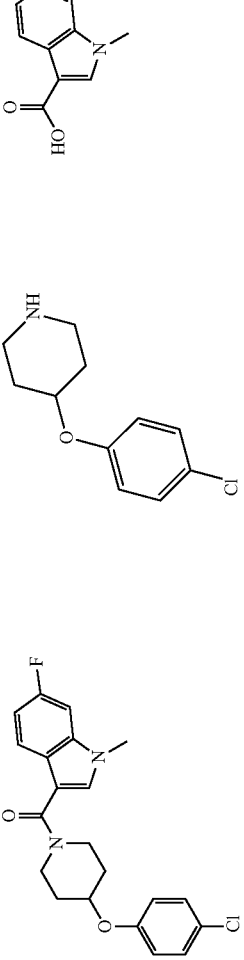 | 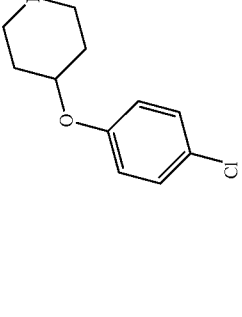 | 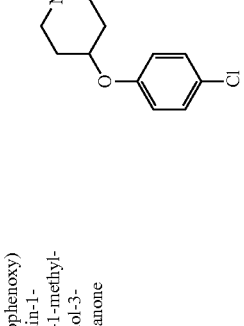 | 386.9 | 1.95 min. | Method A |
| Example 114 | (6-chloro-1-methyl-1H-indol-3-yl)(4-(4-chlorophenoxy)piperidin-1-yl)methanone | 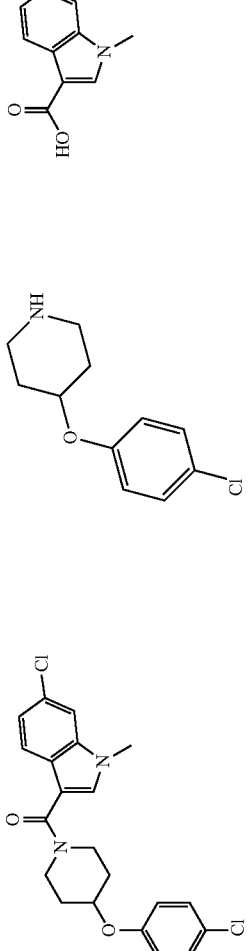 | 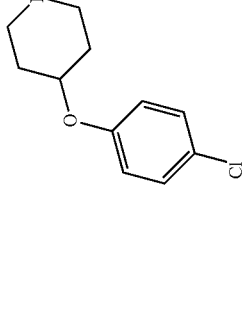 | 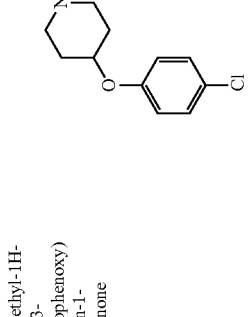 | 402.9 | 2.04 min. | Method A |
| Example 115 | (4-(4-chlorophenoxy)piperidin-1-yl)(6-methoxy-1-methyl-1H-indol-3-yl)methanone | 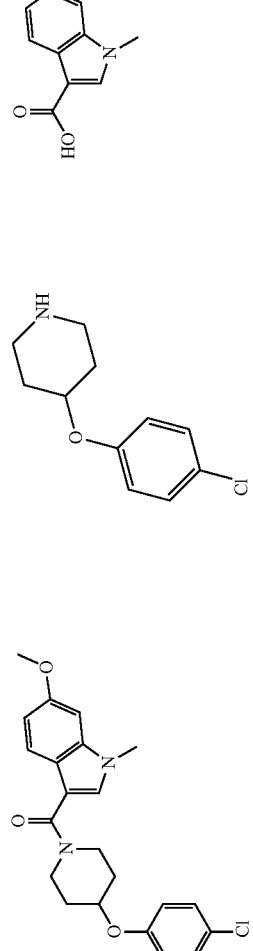 | 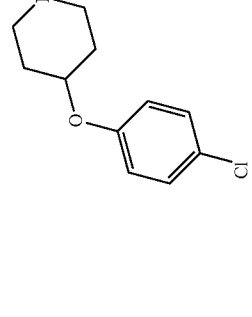 | 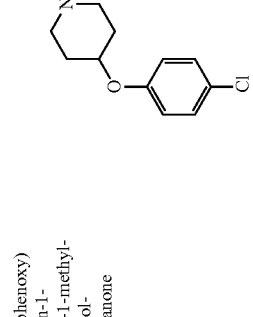 | 399 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 116 | (4-(4-chlorophenoxy) piperidin-1-yl)(5-fluoro-1-methyl-1H-indol-2-yl)methanone | 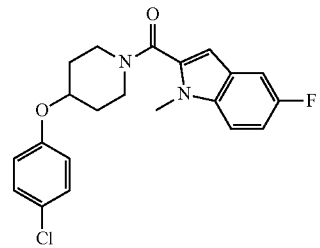 [SMILES: Cn1c(C(=O)N2CCC(Oc3ccc(Cl)cc3)CC2)cc2cc(F)ccc21] | | | 386.9 | 2.04 min. | Method A |
| Example 117 | (4-(4-chlorophenoxy) piperidin-1-yl)(5-methoxy-1-methyl-1H-indol-2-yl)methanone | 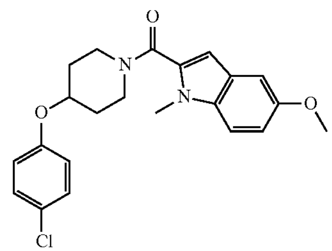 [SMILES: COc1ccc2c(c1)cc(C(=O)N1CCC(Oc3ccc(Cl)cc3)CC1)n2C] | | | 399 | 2.00 min. | Method A |
| Example 118 | (4-(4-chlorophenoxy) piperidin-1-yl)(3-fluorophenyl) methanone | 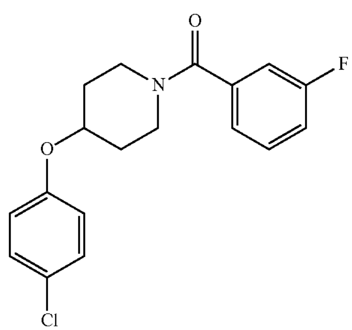 [SMILES: O=C(c1cccc(F)c1)N1CCC(Oc2ccc(Cl)cc2)CC1] | | | 334 | 1.91 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 119 | (4-(4-chlorophenoxy) piperidin-1-yl)(p-tolyl) methanone | 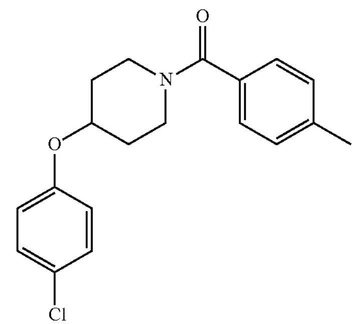 [SMILES: Cc1ccc(C(=O)N2CCC(Oc3ccc(Cl)cc3)CC2)cc1] | | | 330 | 1.97 min. | Method A |
| Example 120 | (4-(4-chlorophenoxy) piperidin-1-yl)(4-methoxyphenyl) methanone | 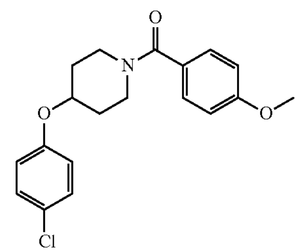 [SMILES: COc1ccc(C(=O)N2CCC(Oc3ccc(Cl)cc3)CC2)cc1] | | | 345.9 | 1.88 min. | Method A |
| Example 121 | 4-(4-(4-chlorophenoxy) piperidine-1-carbonyl) benzonitrile | 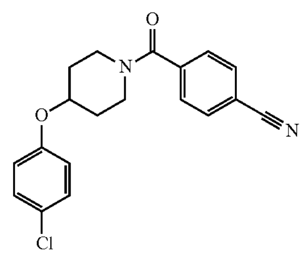 [SMILES: N#Cc1ccc(C(=O)N2CCC(Oc3ccc(Cl)cc3)CC2)cc1] | | | 340.9 | 1.81 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 122 | (4-(4-chlorophenoxy)piperidin-1-yl)(6-methylimidazo[1,2-a]pyridin-2-yl)methanone | 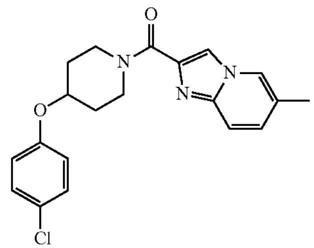 [SMILES: Cc1ccc2nc(C(=O)N3CCC(Oc4ccc(Cl)cc4)CC3)cn2c1] | | | 369.9 | 1.75 min. | Method A |
| Example 123 | (6-chloroimidazo[1,2-a]pyridin-2-yl)(4-(4-chlorophenoxy)piperidin-1-yl)methanone | 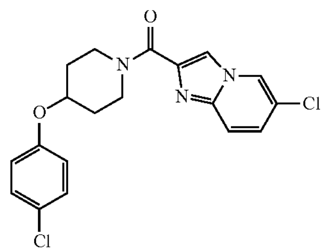 [SMILES: O=C(c1cn2cc(Cl)ccc2n1)N1CCC(Oc2ccc(Cl)cc2)CC1] | | | 389.8 | 1.81 min. | Method A |
| Example 124 | (4-(4-chlorophenoxy)piperidin-1-yl)(2-methylpyridin-3-yl)methanone | 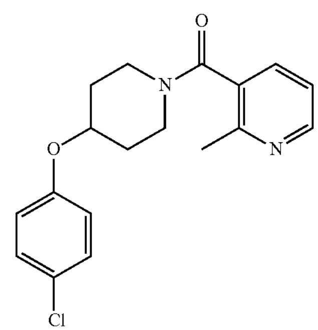 [SMILES: Cc1ncccc1C(=O)N1CCC(Oc2ccc(Cl)cc2)CC1] | | | 330.9 | 1.62 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 125 | (4-(4-chlorophenoxy)piperidin-1-yl)(4-isopropoxyphenyl)methanone | 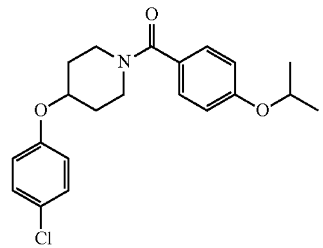 [SMILES: CC(C)Oc1ccc(C(=O)N2CCC(Oc3ccc(Cl)cc3)CC2)cc1] | | | 373.9 | 2.03 min. | Method A |
| Example 126 | (4-(4-chlorophenoxy)piperidin-1-yl)(4-(trifluoromethoxy)phenyl)methanone | 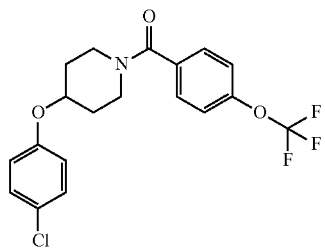 [SMILES: O=C(c1ccc(OC(F)(F)F)cc1)N1CCC(Oc2ccc(Cl)cc2)CC1] | | | 399.9 | 2.04 min. | Method A |
| Example 127 | (4-(4-chlorophenoxy)piperidin-1-yl)(4-(methylsulfonyl)phenyl)methanone | 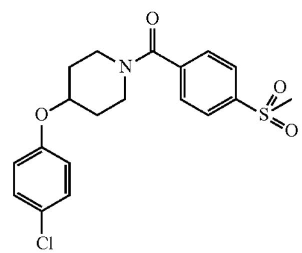 [SMILES: CS(=O)(=O)c1ccc(C(=O)N2CCC(Oc3ccc(Cl)cc3)CC2)cc1] | | | 393.8 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 128 | (4-(4-chlorophenoxy) piperidin-1-yl)(3-methoxyphenyl) methanone | 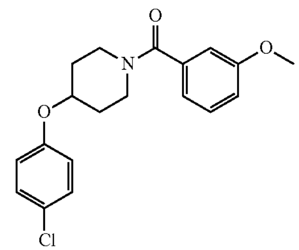 [SMILES: COc1cccc(C(=O)N2CCC(Oc3ccc(Cl)cc3)CC2)c1] | | | 345.9 | 1.89 min. | Method A |
| Example 129 | (4-(4-chlorophenoxy) piperidin-1-yl)(pyridin-2-yl) methanone | 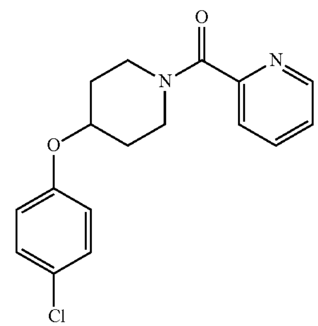 [SMILES: O=C(c1ccccn1)N1CCC(Oc2ccc(Cl)cc2)CC1] | | | 316.9 | 1.66 min. | Method A |
| Example 130 | (4-(4-chlorophenoxy) piperidin-1-yl)(5-methylisoxazol-3-yl)methanone | 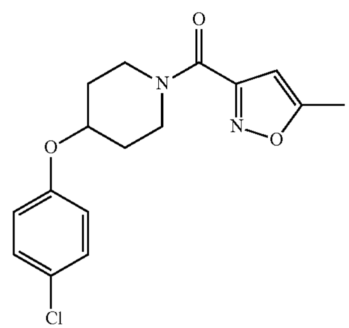 [SMILES: Cc1cc(C(=O)N2CCC(Oc3ccc(Cl)cc3)CC2)no1] | | | 320.9 | 1.81 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 131 | (4-(4-chlorophenoxy)piperidin-1-yl)(oxazol-4-yl)methanone | 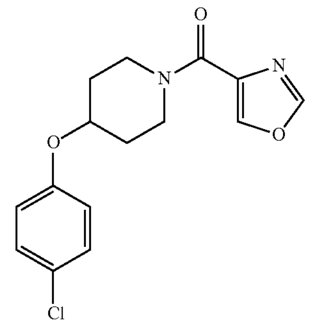 [SMILES: O=C(c1cocn1)N1CCC(Oc2ccc(Cl)cc2)CC1] | | | 306.9 | 1.64 min. | Method A |
| Example 132 | (4-(4-chlorophenoxy)piperidin-1-yl)(4-methylthiazol-5-yl)methanone | 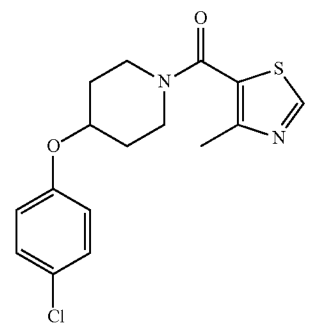 [SMILES: Cc1ncsc1C(=O)N1CCC(Oc2ccc(Cl)cc2)CC1] | | | 336.9 | 1.69 min. | Method A |
| Example 133 | (4-(4-chlorophenoxy)piperidin-1-yl)(5-methylpyrazin-2-yl)methanone | 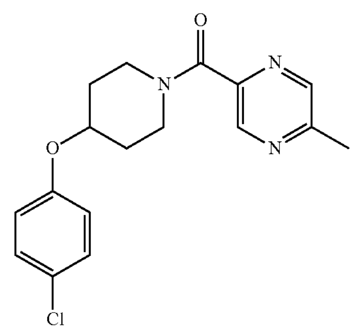 [SMILES: Cc1cnc(C(=O)N2CCC(Oc3ccc(Cl)cc3)CC2)cn1] | | | 332 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 134 | (4-(4-chlorophenoxy)piperidin-1-yl)(6-fluoro-1-methyl-1H-indol-2-yl)methanone | 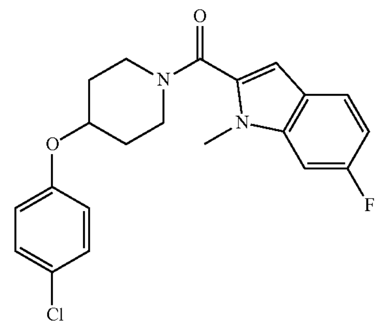 [SMILES: Cn1c(C(=O)N2CCC(Oc3ccc(Cl)cc3)CC2)cc2ccc(F)cc21] | | | 386.9 | 2.05 min. | Method A |
| Example 135 | 4-(4-(4-chlorophenoxy)piperidine-1-carbonyl)-N,N-dimethylbenzenesulfonamide | 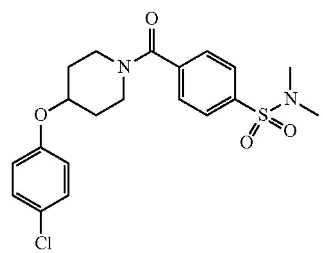 [SMILES: CN(C)S(=O)(=O)c1ccc(C(=O)N2CCC(Oc3ccc(Cl)cc3)CC2)cc1] | | | 422.9 | 1.80 min. | Method A |
| Example 136 | 4-(4-(4-chlorophenoxy)piperidine-1-carbonyl)benzamide | 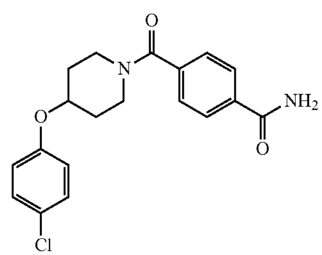 [SMILES: NC(=O)c1ccc(C(=O)N2CCC(Oc3ccc(Cl)cc3)CC2)cc1] | | | 357.1 | 1.53 min. | Method A |

| Example | Name | Structure | Structure of amine part | Structure of carboxylic acid part | Observed MS | Retention time | QC Method |
|---|---|---|---|---|---|---|---|
| Example 137 | (4-(4-chlorophenoxy)piperidin-1-yl)(5-fluoro-1H-indazol-3-yl)methanone | 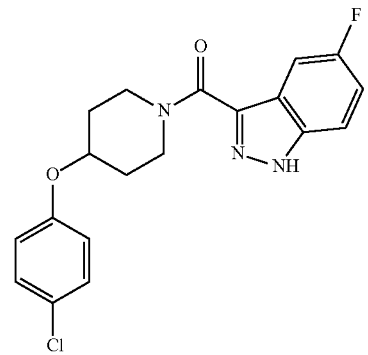 [SMILES: O=C(c1n[nH]c2ccc(F)cc12)N1CCC(Oc2ccc(Cl)cc2)CC1] | | | 372.1 | 1.83 min. | Method A |
| Example 138 | (5-chloro-1H-indazol-3-yl)(4-(4-chlorophenoxy)piperidin-1-yl)methanone | 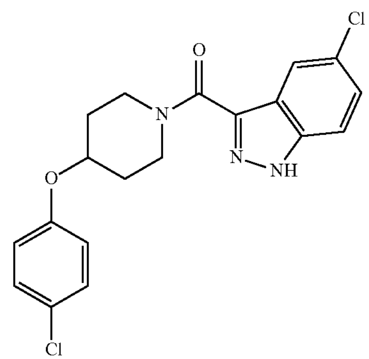 [SMILES: O=C(c1n[nH]c2ccc(Cl)cc12)N1CCC(Oc2ccc(Cl)cc2)CC1] | | | 388.1 | 1.92 min. | Method A |
| Example 139 | (6-chloro-1H-indazol-3-yl)(4-(4-chlorophenoxy)piperidin-1-yl)methanone | 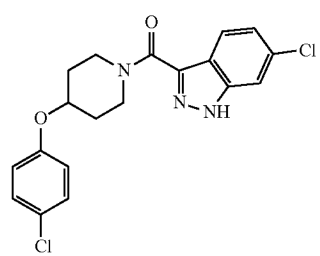 [SMILES: O=C(c1n[nH]c2cc(Cl)ccc12)N1CCC(Oc2ccc(Cl)cc2)CC1] | | | 388.1 | 1.91 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 140 | (4-(4-chlorophenoxy) piperidin-1-yl)(4-(2-hydroxypropan-2-yl)phenyl)methanone | 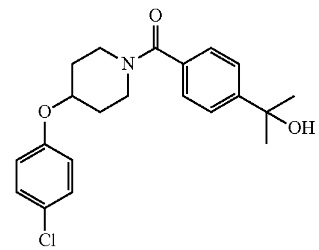 [SMILES: CC(C)(O)c1ccc(C(=O)N2CCC(Oc3ccc(Cl)cc3)CC2)cc1] | | | 373.9 | 1.75 min. | Method A |
| Example 141 | (4-(4-chlorophenoxy) piperidin-1-yl)(2,6-dimethoxypyridin-3-yl)methanone | 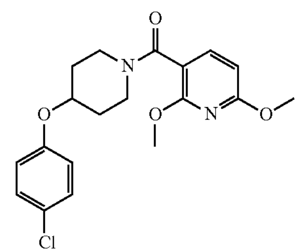 [SMILES: COc1ccc(C(=O)N2CCC(Oc3ccc(Cl)cc3)CC2)c(OC)n1] | | | 376.9 | 1.93 min. | Method A |
| Example 142 | (4-(4-chlorophenoxy) piperidin-1-yl)(6-methoxy-1-methyl-1H-indol-2-yl)methanone | 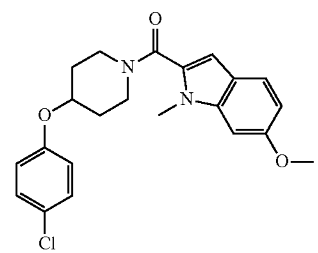 [SMILES: COc1ccc2cc(C(=O)N3CCC(Oc4ccc(Cl)cc4)CC3)n(C)c2c1] | | | 398.9 | 2.01 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 143 | (4-(4-chlorophenoxy) piperidin-1-yl)(1-methyl-5-(trifluoromethoxy)-1H-indol-2-yl)methanone | 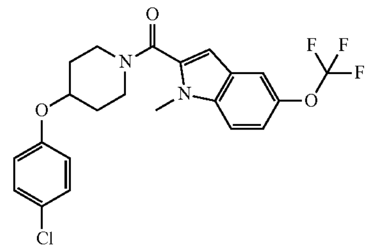 [SMILES: Cn1c(C(=O)N2CCC(Oc3ccc(Cl)cc3)CC2)cc2cc(OC(F)(F)F)ccc21] | | | 452.9 | 2.16 min. | Method A |
| Example 144 | 2-(4-(4-chlorophenoxy) piperidine-1-carbonyl)-1-methyl-1H-indole-5-carbonitrile | 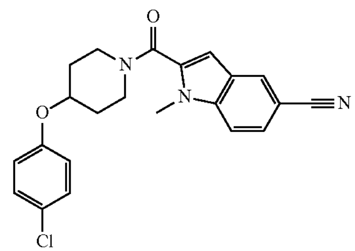 [SMILES: Cn1c(C(=O)N2CCC(Oc3ccc(Cl)cc3)CC2)cc2cc(C#N)ccc21] | | | 394 | 1.92 min. | Method A |
| Example 145 | (4-(4-chlorophenoxy) piperidin-1-yl)(1-methyl-5-(methylsulfonyl)-1H-indol-2-yl)methanone | 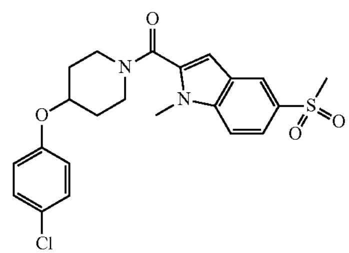 [SMILES: Cn1c(C(=O)N2CCC(Oc3ccc(Cl)cc3)CC2)cc2cc(S(C)(=O)=O)ccc21] | | | 446.9 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 146 | (4-(4-chlorophenoxy) piperidin-1-yl)(4-methylpyridin-3-yl) methanone | 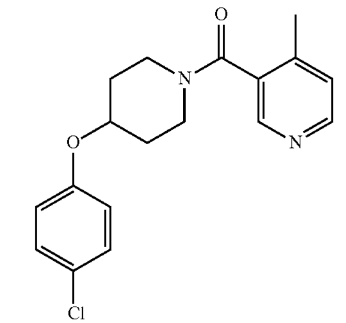 [SMILES: Cc1ccncc1C(=O)N1CCC(Oc2ccc(Cl)cc2)CC1] | | | 330.9 | 1.63 min. | Method A |
| Example 147 | 3-(4-(4-chlorophenoxy) piperidine-1-carbonyl)-5,6-dimethylpyridin-2(1H)-one | 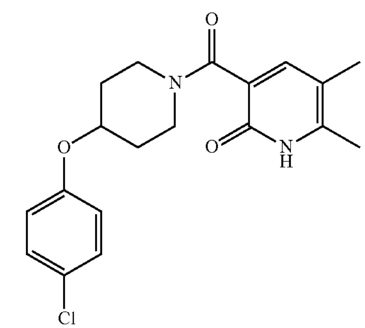 [SMILES: Cc1cc(C(=O)N2CCC(Oc3ccc(Cl)cc3)CC2)c(=O)[nH]c1C] | | | 359.1 | 1.51 min. | Method A |
| Example 148 | (4-(4-chlorophenoxy) piperidin-1-yl)(quinolin-5-yl) methanone | 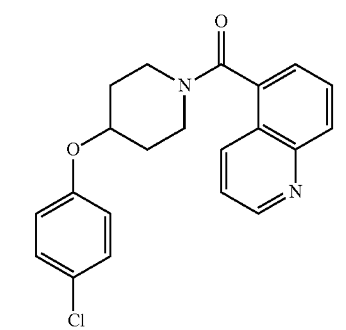 [SMILES: O=C(c1cccc2ncccc12)N1CCC(Oc2ccc(Cl)cc2)CC1] | | | 366.9 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 149 | (4-(4-fluorophenoxy)piperidin-1-yl)(2-methyl-2H-indazol-3-yl)methanone | 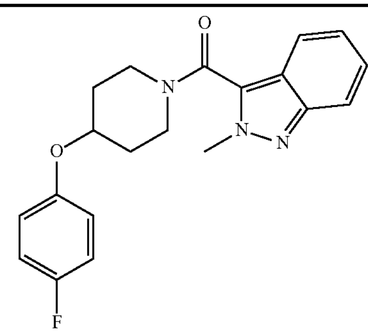 | | | 353.9 | 1.72 min. | Method A |
| Example 150 | (4-(4-fluorophenoxy)piperidin-1-yl)(6-methoxypyridin-3-yl)methanone | 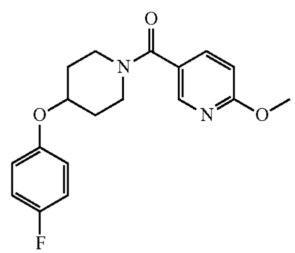 [SMILES: COc1ccc(C(=O)N2CCC(Oc3ccc(F)cc3)CC2)cn1] | | | 330.9 | 1.65 min. | Method A |
| Example 151 | (4-(4-chlorophenoxy)piperidin-1-yl)(3-methoxy-4-methylphenyl)methanone | 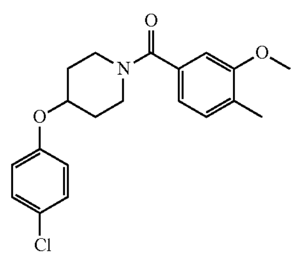 [SMILES: COc1cc(C(=O)N2CCC(Oc3ccc(Cl)cc3)CC2)ccc1C] | | | 359.9 | 2.01 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 152 | (5-chloro-4-methoxythiophen-3-yl)(4-(4-chlorophenoxy)piperidin-1-yl)methanone | 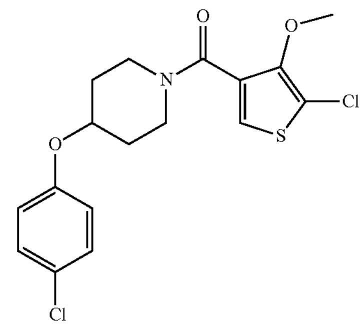 [SMILES: COc1c(C(=O)N2CCC(Oc3ccc(Cl)cc3)CC2)csc1Cl] | | | 385.8 | 1.99 min. | Method A |
| Example 153 | (4-phenoxypiperidin-1-yl)(quinolin-8-yl)methanone | 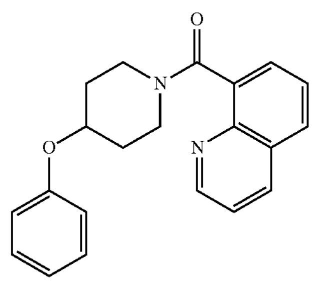 [SMILES: O=C(c1cccc2cccnc12)N1CCC(Oc2ccccc2)CC1] | | | 333 | 1.65 min. | Method A |
| Example 154 | (4-(4-fluorophenoxy)piperidin-1-yl)(imidazo[1,2-a]pyridin-2-yl)methanone | 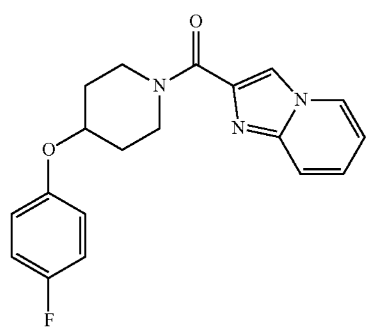 [SMILES: O=C(c1cn2ccccc2n1)N1CCC(Oc2ccc(F)cc2)CC1] | | | 339.9 | 1.53 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 155 | (4-(4-fluorophenoxy)piperidin-1-yl)(quinolin-8-yl)methanone | 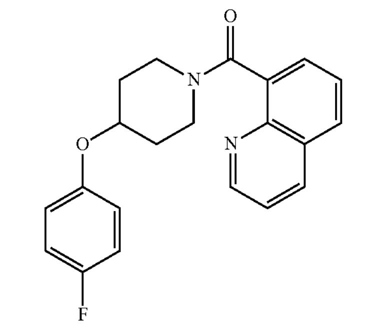 [SMILES: O=C(c1cccc2cccnc12)N1CCC(Oc2ccc(F)cc2)CC1] | | | 351 | 1.66 min. | Method A |
| Example 156 | (6-aminopyridin-3-yl)(4-(4-chlorophenoxy)piperidin-1-yl)methanone | 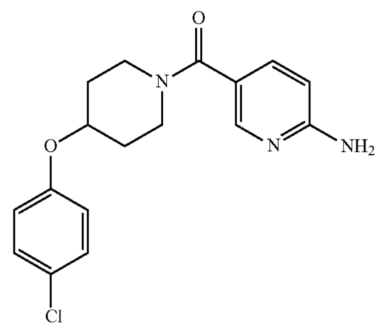 [SMILES: Nc1ccc(C(=O)N2CCC(Oc3ccc(Cl)cc3)CC2)cn1] | | | 331.9 | 1.53 min. | Method A |
| Example 157 | (5-bromopyridin-3-yl)(4-(4-chlorophenoxy)piperidin-1-yl)methanone | 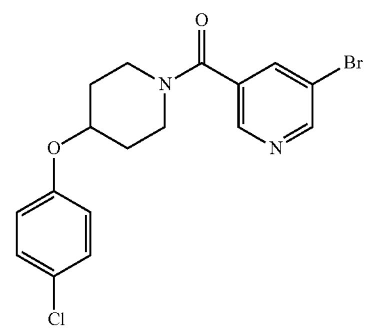 [SMILES: O=C(c1cncc(Br)c1)N1CCC(Oc2ccc(Cl)cc2)CC1] | | | 394.8 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 158 | (5-bromopyridin-2-yl)(4-(4-chlorophenoxy)piperidin-1-yl)methanone | 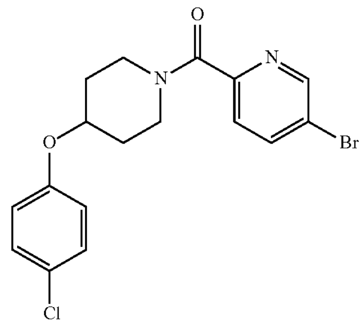 | | | 394.8 | 1.92 min. | Method A |
| Example 159 | 1-(4-(4-(4-chlorophenoxy)piperidine-1-carbonyl)phenyl)ethanone | 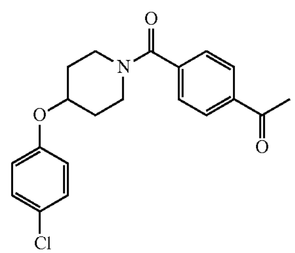 [SMILES: CC(=O)c1ccc(C(=O)N2CCC(Oc3ccc(Cl)cc3)CC2)cc1] | | | 357.9 | 1.83 min. | Method A |
| Example 160 | (4-(4-chlorophenoxy)piperidin-1-yl)(3,4-dimethoxyphenyl)methanone | 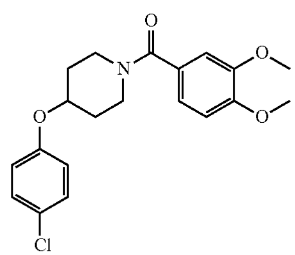 [SMILES: COc1ccc(C(=O)N2CCC(Oc3ccc(Cl)cc3)CC2)cc1OC] | | | 375.8 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 161 | (4-(4-chlorophenoxy)piperidin-1-yl)(isoquinolin-5-yl)methanone | 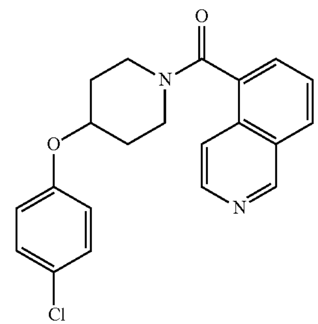 [SMILES: O=C(c1cccc2cnccc12)N1CCC(Oc2ccc(Cl)cc2)CC1] | | | 366.8 | 1.73 min. | Method A |
| Example 162 | (4-(4-chlorophenoxy)piperidin-1-yl)(phenyl)methanone | 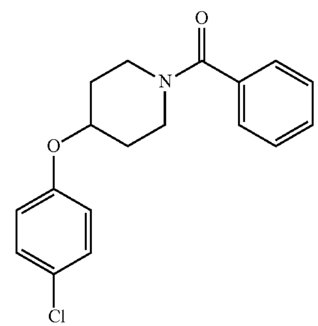 [SMILES: O=C(c1ccccc1)N1CCC(Oc2ccc(Cl)cc2)CC1] | | | 315.9 | 1.92 min. | Method A |
| Example 163 | (4-(4-chlorophenoxy)piperidin-1-yl)(m-tolyl)methanone | 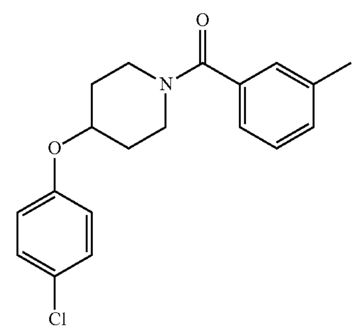 [SMILES: Cc1cccc(C(=O)N2CCC(Oc3ccc(Cl)cc3)CC2)c1] | | | 329.9 | 2.02 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 164 | (4-(4-chlorophenoxy) piperidin-1-yl)(2-methoxyphenyl) methanone | 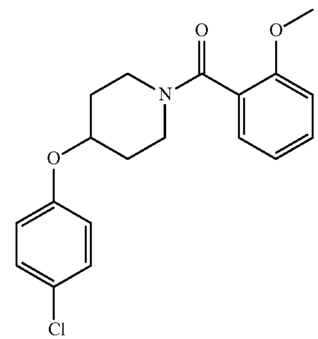 [SMILES: COc1ccccc1C(=O)N1CCC(Oc2ccc(Cl)cc2)CC1] | | | 345.9 | 1.92 min. | Method A |
| Example 165 | (4-(4-chlorophenoxy) piperidin-1-yl)(3-(trifluoromethoxy) phenyl)methanone | 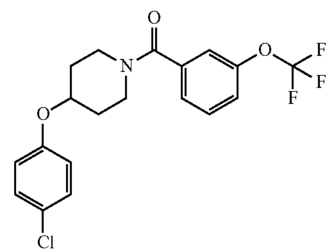 [SMILES: O=C(c1cccc(OC(F)(F)F)c1)N1CCC(Oc2ccc(Cl)cc2)CC1] | | | 399.8 | 2.10 min. | Method A |
| Example 166 | (1H-benzo[d]imidazol-5-yl) (4-(4-chlorophenoxy) piperidin-1-yl)methanone | 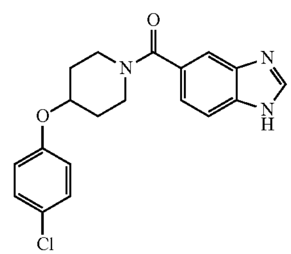 [SMILES: O=C(c1ccc2[nH]cnc2c1)N1CCC(Oc2ccc(Cl)cc2)CC1] | | | 354.1 | 1.54 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 167 | (4-(4-chlorophenoxy)piperidin-1-yl)(1,5-dimethyl-1H-pyrazol-3-yl)methanone | 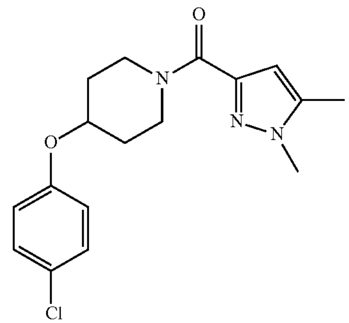 [SMILES: Cc1cc(C(=O)N2CCC(Oc3ccc(Cl)cc3)CC2)nn1C] | | | 333.9 | 1.72 min. | Method A |
| Example 168 | (4-(4-chlorophenoxy)piperidin-1-yl)(1,3-dimethyl-1H-pyrazol-5-yl)methanone | 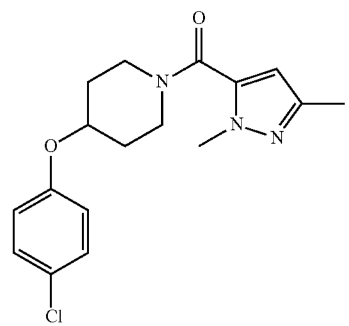 [SMILES: Cc1cc(C(=O)N2CCC(Oc3ccc(Cl)cc3)CC2)n(C)n1] | | | 333.9 | 1.73 min. | Method A |
| Example 169 | (3-(tert-butyl)-1-methyl-1H-pyrazol-5-yl)(4-(4-chlorophenoxy)piperidin-1-yl)methanone | 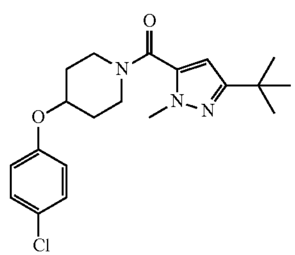 [SMILES: Cn1nc(C(C)(C)C)cc1C(=O)N1CCC(Oc2ccc(Cl)cc2)CC1] | | | 375.9 | 2.02 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 170 | (4-(4-chlorophenoxy) piperidin-1-yl)(1-methyl-5-(trifluoromethyl)-1H-pyrazol-3-yl)methanone | 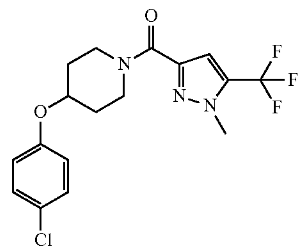 [SMILES: Cn1nc(C(=O)N2CCC(Oc3ccc(Cl)cc3)CC2)cc1C(F)(F)F] | | | 387.8 | 1.96 min. | Method A |
| Example 171 | (4-(4-chlorophenoxy) piperidin-1-yl)(1-(4-methoxyphenyl)-5-methyl-1H-pyrazol-4-yl)methanone | 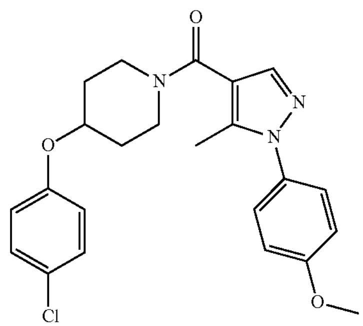 [SMILES: COc1ccc(-n2ncc(C(=O)N3CCC(Oc4ccc(Cl)cc4)CC3)c2C)cc1] | | | 425.9 | 1.88 min. | Method A |
| Example 172 | (4-(4-chlorophenoxy) piperidin-1-yl)(1-(2-methoxyphenyl)-1H-pyrazol-4-yl)methanone | 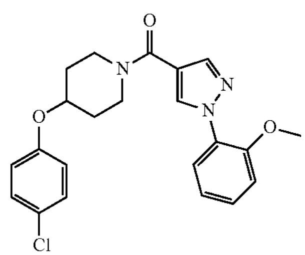 [SMILES: COc1ccccc1-n1cc(C(=O)N2CCC(Oc3ccc(Cl)cc3)CC2)cn1] | | | 411.8 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 173 | (4-(4-chlorophenoxy)piperidin-1-yl)(3,5-dimethyl-1H-pyrazol-4-yl)methanone | 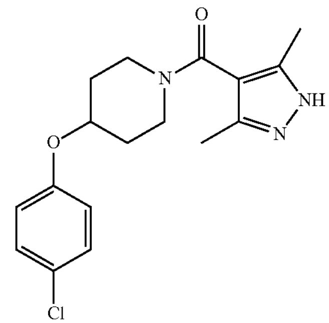 [SMILES: Cc1n[nH]c(C)c1C(=O)N1CCC(Oc2ccc(Cl)cc2)CC1] | | | 332.1 | 1.54 min. | Method A |
| Example 174 | (4-(4-chlorophenoxy)piperidin-1-yl)(1H-1,2,4-triazol-3-yl)methanone | 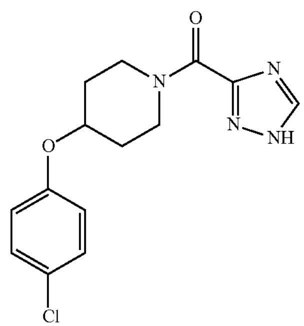 [SMILES: O=C(c1nc[nH]n1)N1CCC(Oc2ccc(Cl)cc2)CC1] | | | 305 | 1.47 min. | Method A |
| Example 175 | (4-(4-chlorophenoxy)piperidin-1-yl)(5-isopropyl-1H-pyrazol-3-yl)methanone | 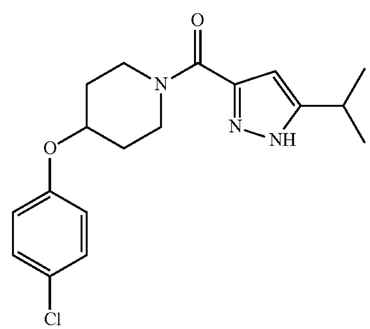 [SMILES: CC(C)c1cc(C(=O)N2CCC(Oc3ccc(Cl)cc3)CC2)n[nH]1] | | | 346.1 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 176 | (4-(4-chlorophenoxy)piperidin-1-yl)(imidazo[2,1-b]thiazol-6-yl)methanone | 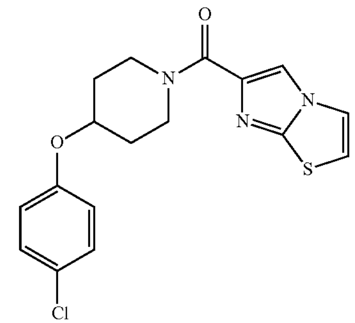 [SMILES: O=C(c1cn2ccsc2n1)N1CCC(Oc2ccc(Cl)cc2)CC1] | | | 361.8 | 1.71 min. | Method A |
| Example 177 | (4-(3-methoxyphenoxy)piperidin-1-yl)(quinolin-8-yl)methanone | 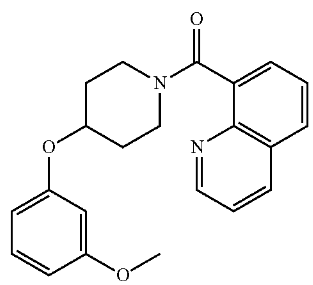 [SMILES: COc1cccc(OC2CCN(C(=O)c3cccc4cccnc34)CC2)c1] | | | 362.9 | 1.64 min. | Method A |
| Example 178 | Imidazo[1,2-a]pyridin-2-yl(4-(3-methoxyphenoxy)piperidin-1-yl)methanone | 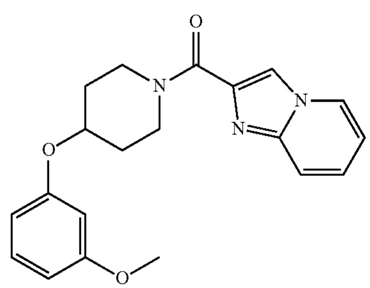 [SMILES: COc1cccc(OC2CCN(C(=O)c3cn4ccccc4n3)CC2)c1] | | | 351.9 | 1.52 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 179 | (4-(3-fluorophenoxy) piperidin-1-yl)(quinolin-8-yl) methanone | 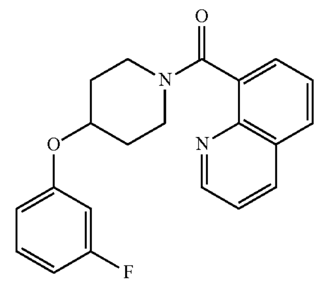 [SMILES: O=C(c1cccc2cccnc12)N1CCC(Oc2cccc(F)c2)CC1] | | | 350.9 | 1.69 min. | Method A |
| Example 180 | (4-(3-fluorophenoxy) piperidin-1-yl)(imidazo[1,2-a] pyridin-2-yl)methanone | 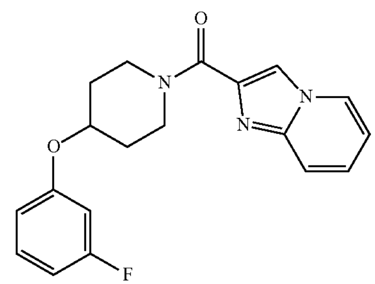 [SMILES: O=C(c1cn2ccccc2n1)N1CCC(Oc2cccc(F)c2)CC1] | | | 339.9 | 1.57 min. | Method A |
| Example 181 | (4-(4-chlorophenoxy) piperidin-1-yl)(5-chloropyridin-3-yl) methanone | 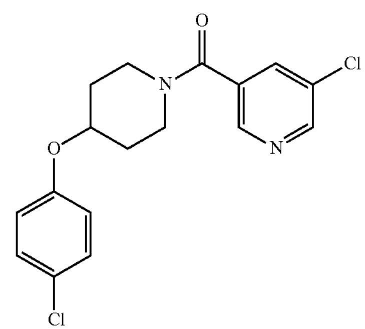 [SMILES: O=C(c1cncc(Cl)c1)N1CCC(Oc2ccc(Cl)cc2)CC1] | | | 350.9 | 1.81 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 182 | (4-(4-chlorophenoxy) piperidin-1-yl)(5-methoxypyridin-3-yl)methanone | 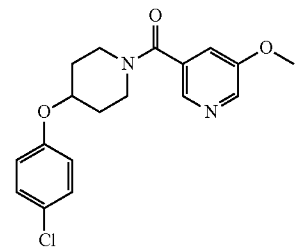 [SMILES: COc1cncc(C(=O)N2CCC(Oc3ccc(Cl)cc3)CC2)c1] | | | 346.9 | 1.69 min. | Method A |
| Example 183 | 3-(4-(4-chlorophenoxy) piperidine-1-carbonyl) benzonitrile | 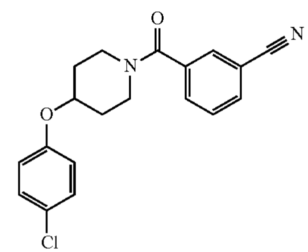 [SMILES: N#Cc1cccc(C(=O)N2CCC(Oc3ccc(Cl)cc3)CC2)c1] | | | 340.9 | 1.83 min. | Method A |
| Example 184 | (4-(4-chlorophenoxy) piperidin-1-yl)(2-ethoxypyridin-3-yl) methanone | 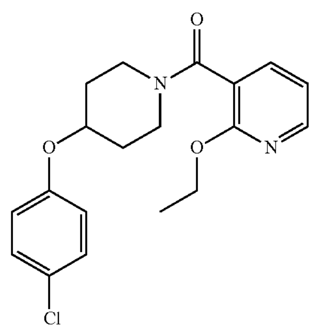 [SMILES: CCOc1ncccc1C(=O)N1CCC(Oc2ccc(Cl)cc2)CC1] | | | 360.8 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 185 | (4-(4-chlorophenoxy)piperidin-1-yl)(2-methoxypyridin-4-yl)methanone | 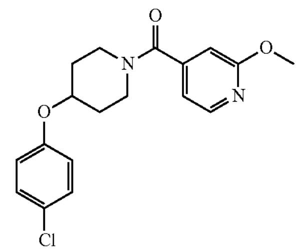 [SMILES: COc1cc(C(=O)N2CCC(Oc3ccc(Cl)cc3)CC2)ccn1] | | | 346.8 | 1.81 min. | Method A |
| Example 186 | (4-(4-chlorophenoxy)piperidin-1-yl)(isoquinolin-8-yl)methanone | 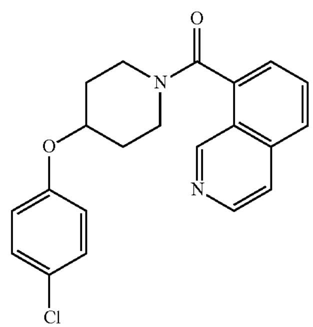 [SMILES: O=C(c1cccc2ccncc12)N1CCC(Oc2ccc(Cl)cc2)CC1] | | | 366.9 | 1.76 min. | Method A |
| Example 187 | (4-(4-chlorophenoxy)piperidin-1-yl)(2-methylthiazol-5-yl)methanone | 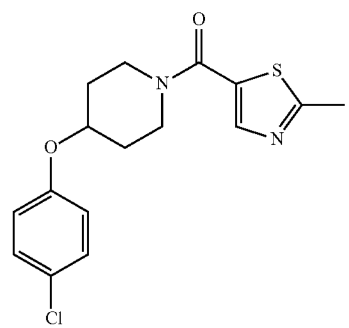 [SMILES: Cc1ncc(C(=O)N2CCC(Oc3ccc(Cl)cc3)CC2)s1] | | | 336.9 | 1.74 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 188 | (4-((4-chlorophenyl) thio)piperidin-1-yl)(quinolin-8-yl) methanone | 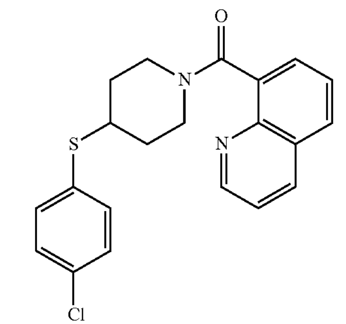 [SMILES: O=C(c1cccc2cccnc12)N1CCC(Sc2ccc(Cl)cc2)CC1] | | | 382.8 | 1.90 min. | Method A |
| Example 189 | (4-((4-chlorophenyl) thio)piperidin-1-yl)(6-methylpyridin-3-yl)methanone | 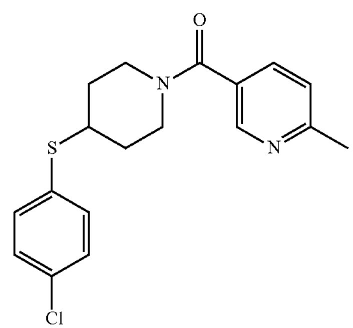 [SMILES: Cc1ccc(C(=O)N2CCC(Sc3ccc(Cl)cc3)CC2)cn1] | | | 346.9 | 1.77 min. | Method A |
| Example 190 | (4-((4-chlorophenyl) sulfonyl)piperidin-1-yl)(quinolin-8-yl) methanone | 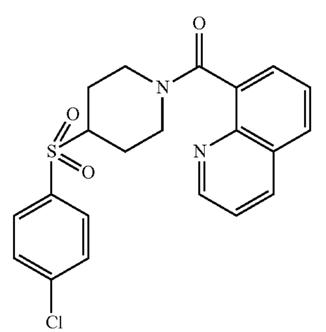 [SMILES: O=C(c1cccc2cccnc12)N1CCC(S(=O)(=O)c2ccc(Cl)cc2)CC1] | | | 414.8 | 1.54 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 191 | 1-(3-((1-(quinoline-8-carbonyl)piperidin-4-yl)oxy)phenyl)ethanone | 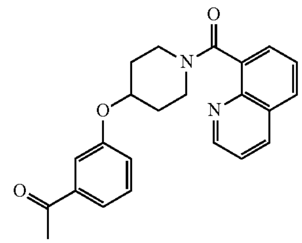 [SMILES: CC(=O)c1cccc(OC2CCN(C(=O)c3cccc4cccnc34)CC2)c1] | | | 374.9 | 1.54 min. | Method A |
| Example 192 | (4-(3,5-dimethoxyphenoxy)piperidin-1-yl)(quinolin-8-yl)methanone | 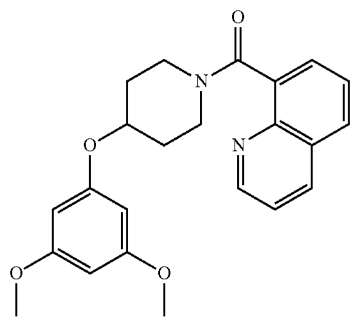 [SMILES: COc1cc(OC)cc(OC2CCN(C(=O)c3cccc4cccnc34)CC2)c1] | | | 392.9 | 1.65 min. | Method A |
| Example 193 | quinolin-8-yl(4-(3-(trifluoromethoxy)phenoxy)piperidin-1-yl)methanone | 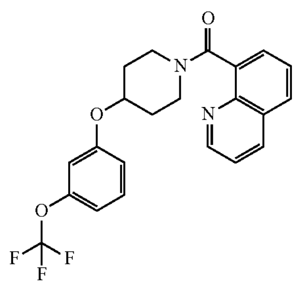 [SMILES: O=C(c1cccc2cccnc12)N1CCC(Oc2cccc(OC(F)(F)F)c2)CC1] | | | 416.9 | 1.88 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 194 | (4-(4-chlorophenoxy)piperidin-1-yl)(3-methylisoxazol-5-yl)methanone | 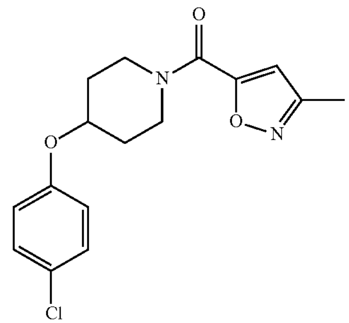 [SMILES: Cc1cc(C(=O)N2CCC(Oc3ccc(Cl)cc3)CC2)on1] | | | 320.9 | 1.80 min. | Method A |
| Example 195 | (4-(4-chlorophenoxy)piperidin-1-yl)(1-isopropyl-1H-pyrazol-4-yl)methanone | 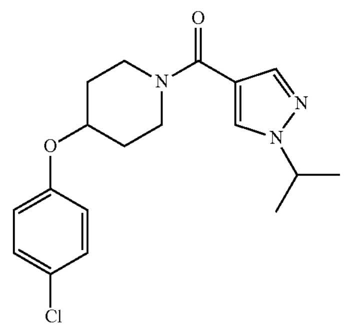 [SMILES: CC(C)n1cc(C(=O)N2CCC(Oc3ccc(Cl)cc3)CC2)cn1] | | | 347.9 | 1.74 min. | Method A |
| Example 196 | 5-(4-(4-chlorophenoxy)piperidine-1-carbonyl)picolinonitrile | 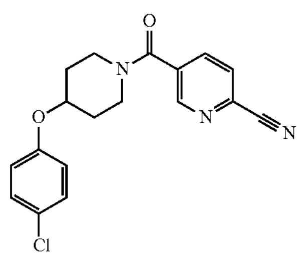 [SMILES: N#Cc1ccc(C(=O)N2CCC(Oc3ccc(Cl)cc3)CC2)cn1] | | | 340 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 197 | (4-(4-chlorophenoxy) piperidin-1-yl)(2-hydroxyquinolin-4-yl)methanone | 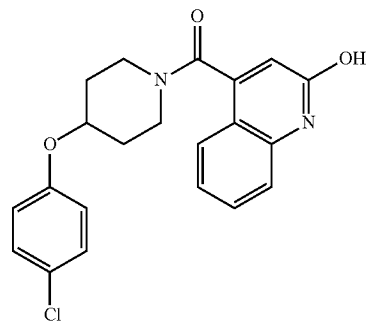 [SMILES: O=C(c1cc(O)nc2ccccc12)N1CCC(Oc2ccc(Cl)cc2)CC1] | | | 381.1 | 1.62 min. | Method A |
| Example 198 | (4-(4-chlorophenoxy) piperidin-1-yl)(5-(trifluoromethyl)-1H-pyrazol-3-yl)methanone | 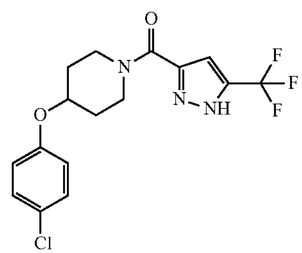 [SMILES: O=C(c1cc(C(F)(F)F)[nH]n1)N1CCC(Oc2ccc(Cl)cc2)CC1] | | | 372 | 1.86 min. | Method A |
| Example 199 | (4-(4-chlorophenoxy) piperidin-1-yl)(5-cyclopropyl-1H-pyrazol-3-yl)methanone | 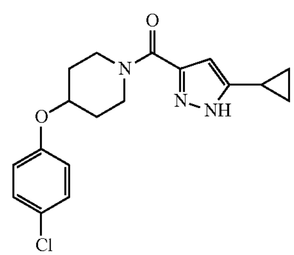 [SMILES: O=C(c1cc(C2CC2)[nH]n1)N1CCC(Oc2ccc(Cl)cc2)CC1] | | | 344.1 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 200 | (4-(4-chlorophenoxy)piperidin-1-yl)(5-(2-methoxyphenyl)-1H-pyrazol-3-yl)methanone | 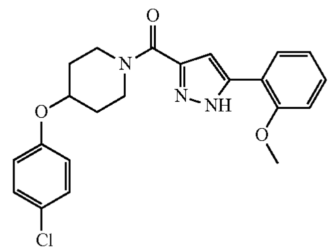 [SMILES: COc1ccccc1-c1cc(C(=O)N2CCC(Oc3ccc(Cl)cc3)CC2)n[nH]1] | | | 410.1 | 1.89 min. | Method A |
| Example 201 | (4-(4-chlorophenoxy)piperidin-1-yl)(3-isopropyl-1-methyl-1H-pyrazol-5-yl)methanone | 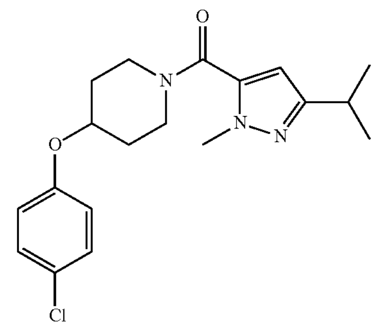 [SMILES: CC(C)c1cc(C(=O)N2CCC(Oc3ccc(Cl)cc3)CC2)n(C)n1] | | | 361.9 | 1.93 min. | Method A |
| Example 202 | (4-(4-chlorophenoxy)piperidin-1-yl)(3-ethyl-1-methyl-1H-pyrazol-5-yl)methanone | 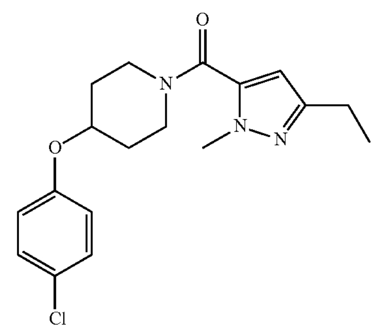 [SMILES: CCc1cc(C(=O)N2CCC(Oc3ccc(Cl)cc3)CC2)n(C)n1] | | | 347.9 | 1.84 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 203 | (4-(4-chlorophenoxy)piperidin-1-yl)(1-ethyl-3-methyl-1H-pyrazol-5-yl)methanone | 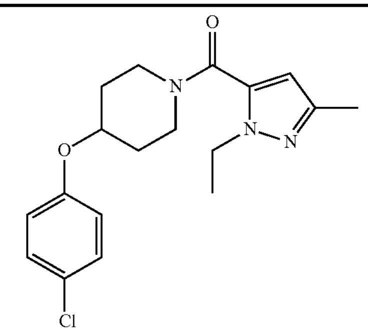 | | | 347.9 | 1.82 min. | Method A |
| Example 204 | (4-(4-chlorophenoxy)piperidin-1-yl)(2-methyloxazol-4-yl)methanone | 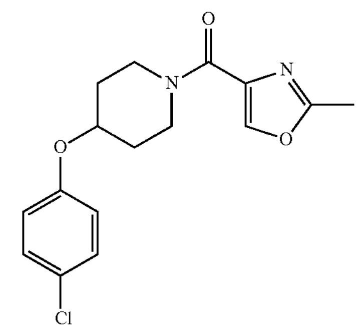 [SMILES: Cc1nc(C(=O)N2CCC(Oc3ccc(Cl)cc3)CC2)co1] | | | 320.9 | 1.71 min. | Method A |
| Example 205 | (4-(4-chlorophenoxy)piperidin-1-yl)(thieno[3,2-b]pyridin-2-yl)methanone | 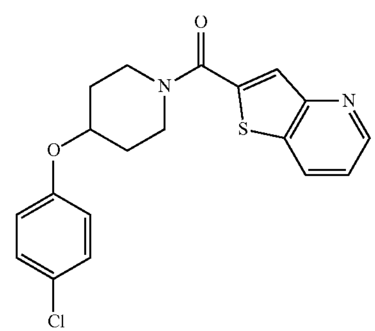 [SMILES: O=C(c1cc2ncccc2s1)N1CCC(Oc2ccc(Cl)cc2)CC1] | | | 372.8 | 1.81 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 206 | (4-(4-chlorophenoxy) piperidin-1-yl)imidazo[1,2-a] pyridin-6-yl)methanone | 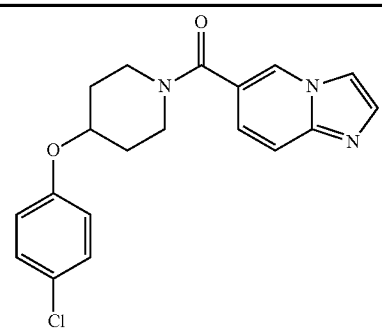 | | | 355.8 | 1.58 min. | Method A |
| Example 207 | (4-(4-chlorophenoxy) piperidin-1-yl)(1-methyl-1H-indazol-5-yl)methanone | 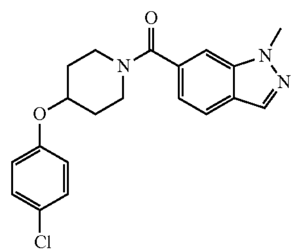 [SMILES: Cn1ncc2ccc(C(=O)N3CCC(Oc4ccc(Cl)cc4)CC3)cc21] | | | 369.8 | 1.80 min. | Method A |
| Example 208 | (4-(4-chlorophenoxy) piperidin-1-yl)(6-(trifluoromethoxy)-1H-indazol-3-yl) methanone | 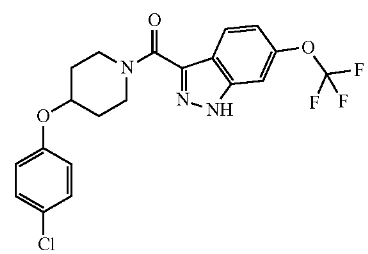 [SMILES: O=C(c1n[nH]c2cc(OC(F)(F)F)ccc12)N1CCC(Oc2ccc(Cl)cc2)CC1] | | | 438 | 2.00 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 209 | (4-(4-chlorophenoxy)piperidin-1-yl)(1-methyl-6-(trifluoromethoxy)-1H-indazol-3-yl)methanone | 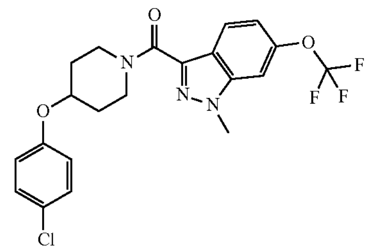 [SMILES: Cn1nc(C(=O)N2CCC(Oc3ccc(Cl)cc3)CC2)c2ccc(OC(F)(F)F)cc21] | | | 453.8 | 2.14 min. | Method A |
| Example 210 | (4-(4-chlorophenoxy)piperidin-1-yl)(2,4-dimethyloxazol-5-yl)methanone | 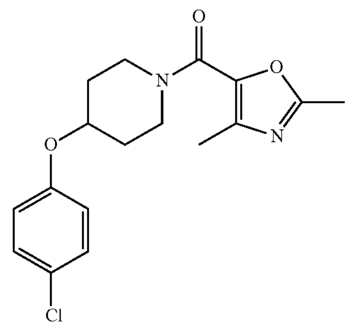 [SMILES: Cc1nc(C)c(C(=O)N2CCC(Oc3ccc(Cl)cc3)CC2)o1] | | | 334.9 | 1.73 min. | Method A |
| Example 211 | (4-(4-dichlorophenoxy)piperidin-1-yl)(5-methoxypyridin-2-yl)methanone | 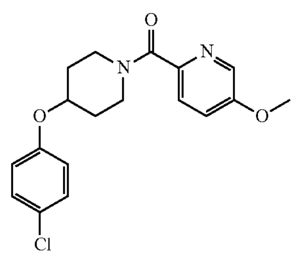 | | | 346.9 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 212 | (4-(4-chlorophenoxy)piperidin-1-yl)(imidazo[1,2-a]pyridin-7-yl)methanone | 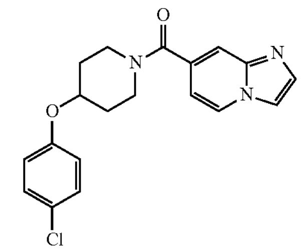 [SMILES: O=C(c1ccn2ccnc2c1)N1CCC(Oc2ccc(Cl)cc2)CC1] | | | 355.8 | 1.58 min. | Method A |
| Example 213 | (4-(4-chlorophenoxy)piperidin-1-yl)(imidazo[1,2-a]pyrazin-2-yl)methanone | 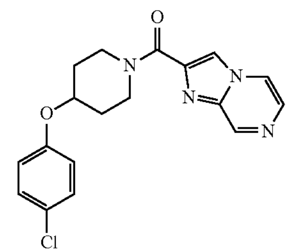 [SMILES: O=C(c1cn2ccncc2n1)N1CCC(Oc2ccc(Cl)cc2)CC1] | | | 356.8 | 1.56 min. | Method A |
| Example 214 | (4-(4-chlorophenoxy)piperidin-1-yl)(2-methyl-2H-indazol-6-yl)methanone | 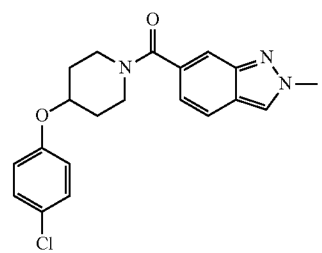 [SMILES: Cn1cc2ccc(C(=O)N3CCC(Oc4ccc(Cl)cc4)CC3)cc2n1] | | | 369.8 | 1.69 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 215 | (4-(4-chlorophenoxy)-piperidin-1-yl)(6-(pyrrolidin-1-yl)pyridin-2-yl)methanone | 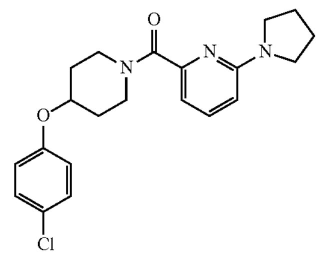 [SMILES: O=C(c1cccc(N2CCCC2)n1)N1CCC(Oc2ccc(Cl)cc2)CC1] | | | 385.8 | 2.07 min. | Method A |
| Example 216 | (4-(4-chlorophenoxy)-piperidin-1-yl)(5-(pyrrolidin-1-yl)pyridin-2-yl)methanone | 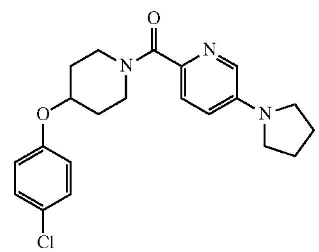 [SMILES: O=C(c1ccc(N2CCCC2)cn1)N1CCC(Oc2ccc(Cl)cc2)CC1] | | | 385.9 | 1.96 min. | Method A |
| Example 217 | (4-(4-chlorophenoxy)-piperidin-1-yl)(4-fluoro-3-methoxyphenyl)methanone | 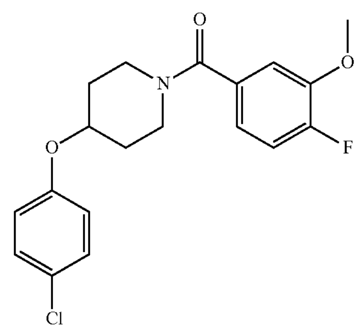 [SMILES: COc1cc(C(=O)N2CCC(Oc3ccc(Cl)cc3)CC2)ccc1F] | | | 363.9 | 1.91 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 218 | (4-(4-chlorophenoxy) piperidin-1-yl)(4-methyl-3,4-dihydro-2H-pyrido[3,2-b][1,4]oxazin-7-yl)methanone | 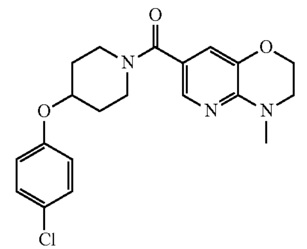 [SMILES: CN1CCOc2cc(C(=O)N3CCC(Oc4ccc(Cl)cc4)CC3)cnc21] | | | 387.9 | 1.78 min. | Method A |
| Example 219 | (4-(4-chlorophenoxy) piperidin-1-yl)(6-(piperidin-1-yl)pyridin-3-yl)methanone | 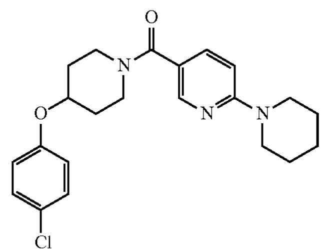 [SMILES: O=C(c1ccc(N2CCCCC2)nc1)N1CCC(Oc2ccc(Cl)cc2)CC1] | | | 399.9 | 2.05 min. | Method A |
| Example 220 | 3-(4-(4-chlorophenoxy) piperidine-1-carbonyl)quinolin-2(1H)-one | 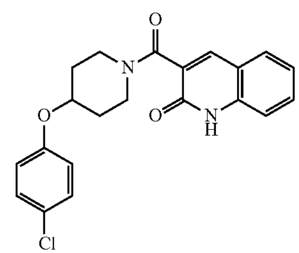 [SMILES: O=C(c1cc2ccccc2[nH]c1=O)N1CCC(Oc2ccc(Cl)cc2)CC1] | | | 381 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 221 | (4-(4-chlorophenoxy)piperidin-1-yl)(imidazo[1,2-a]pyridin-8-yl)methanone | 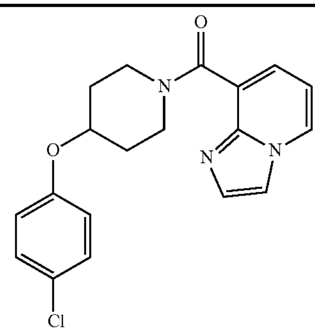 | | | 355.9 | 1.58 min. | Method A |
| Example 222 | (4-(4-chlorophenoxy)piperidin-1-yl)(pyrazolo[1,5-a]pyridin-7-yl)methanone | 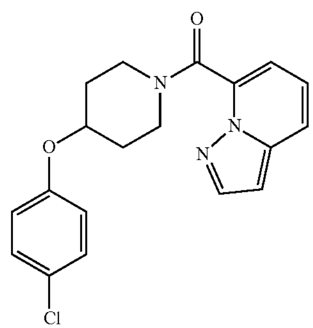 [SMILES: O=C(c1cccc2ccnn12)N1CCC(Oc2ccc(Cl)cc2)CC1] | | | 355.8 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 223 | (4-(4-chlorophenoxy) piperidin-1-yl)(4-(trifluoromethyl) pyridin-3-yl)methanone | 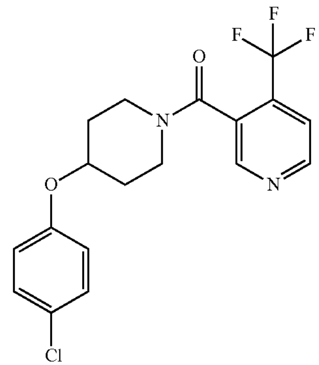 [SMILES: O=C(c1cnccc1C(F)(F)F)N1CCC(Oc2ccc(Cl)cc2)CC1] | | | 384.8 | 1.84 min. | Method A |
| Example 224 | (4-(4-chlorophenoxy) piperidin-1-yl)(1-methyl-1H-imidazol-2-yl)methanone | 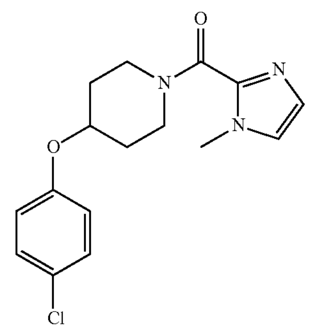 [SMILES: Cn1ccnc1C(=O)N1CCC(Oc2ccc(Cl)cc2)CC1] | | | 319.9 | 1.62 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 225 | (4-(4-chlorophenoxy)piperidin-1-yl)(1-(2-(trifluoromethyl)phenyl)-1H-imidazol-2-yl)methanone | 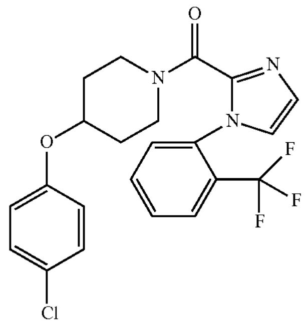 [SMILES: O=C(c1nccn1-c1ccccc1C(F)(F)F)N1CCC(Oc2ccc(Cl)cc2)CC1] | | | 449.8 | 2.00 min. | Method A |
| Example 226 | 3-(4-(4-chlorophenoxy)piperidine-1-carbonyl)-1-methylquinolin-4(1H)-one | 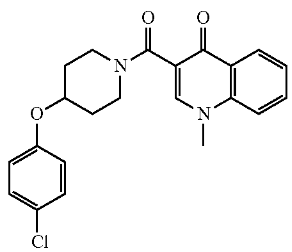 [SMILES: Cn1cc(C(=O)N2CCC(Oc3ccc(Cl)cc3)CC2)c(=O)c2ccccc21] | | | 396.8 | 1.59 min. | Method A |
| Example 227 | (3-(4-chlorophenoxy)azetidin-1-yl)(quinolin-8-yl)methanone | 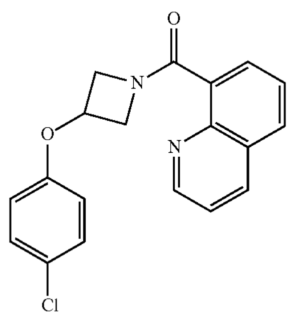 [SMILES: O=C(c1cccc2cccnc12)N1CC(Oc2ccc(Cl)cc2)C1] | | | 338.8 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 228 | (3-(4-chlorophenoxy) azetidin-1-yl)(6-methylpyridin-3-yl) methanone | 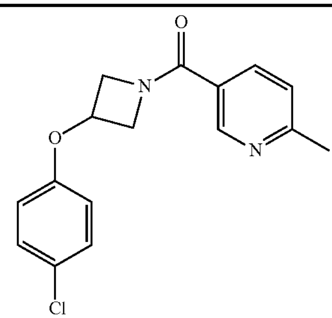 | | | 302.9 | 1.57 min. | Method A |
| Example 229 | (4-(4-chlorophenoxy) piperidin-1-yl)(pyrimidin-4-yl) methanone | 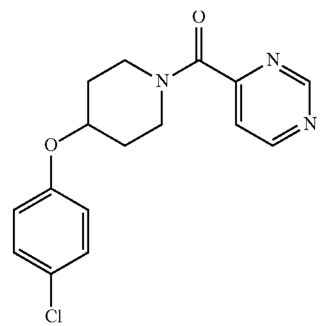 [SMILES: O=C(c1ccncn1)N1CCC(Oc2ccc(Cl)cc2)CC1] | | | 316.6 | 1.60 min. | Method A |
| Example 230 | (4-(4-chlorophenoxy) piperidin-1-yl)(5-chloropyridin-2-yl) methanone | 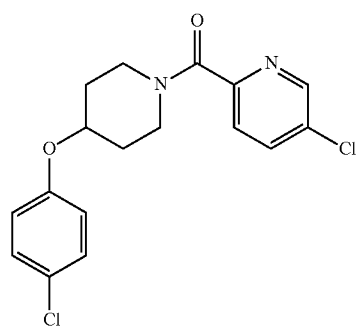 [SMILES: O=C(c1ccc(Cl)cn1)N1CCC(Oc2ccc(Cl)cc2)CC1] | | | 350.8 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 231 | (4-(4-chlorophenoxy)piperidin-1-yl)(2-methoxyquinolin-4-yl)methanone | 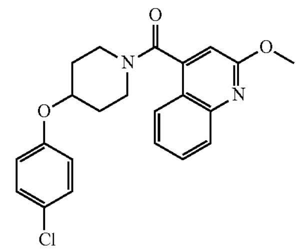 [SMILES: COc1cc(C(=O)N2CCC(Oc3ccc(Cl)cc3)CC2)c2ccccc2n1] | | | 396.8 | 2.05 min. | Method A |
| Example 232 | (4-(4-chlorophenoxy)piperidin-1-yl)(5-hydroxypyridin-3-yl)methanone | 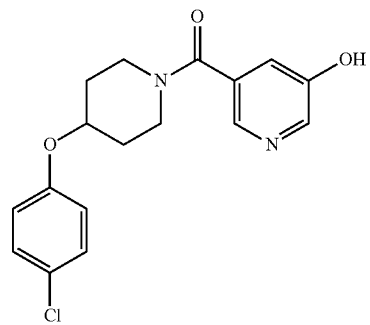 [SMILES: O=C(c1cncc(O)c1)N1CCC(Oc2ccc(Cl)cc2)CC1] | | | 331.1 | 1.52 min. | Method A |
| Example 233 | (4-(4-chlorophenoxy)piperidin-1-yl)(6-(trifluoromethyl)pyridin-3-yl)methanone | 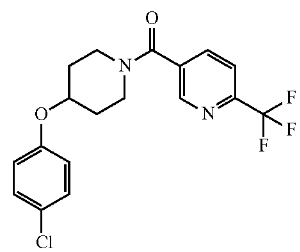 [SMILES: O=C(c1ccc(C(F)(F)F)nc1)N1CCC(Oc2ccc(Cl)cc2)CC1] | | | 384.8 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 234 | (5-aminopyridin-3-yl)(4-(4-chlorophenoxy)piperidin-1-yl)methanone | 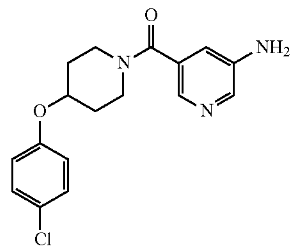 [SMILES: Nc1cncc(C(=O)N2CCC(Oc3ccc(Cl)cc3)CC2)c1] | | | 331.9 | 1.50 min. | Method A |
| Example 235 | (4-(4-chlorophenoxy)piperidin-1-yl)(imidazo[1,2-a]pyrimidin-2-yl)methanone | 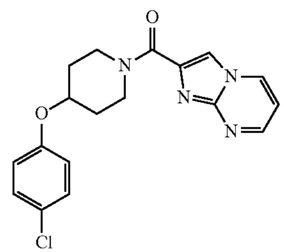 [SMILES: O=C(c1cn2cccnc2n1)N1CCC(Oc2ccc(Cl)cc2)CC1] | | | 356.8 | 1.51 min. | Method A |
| Example 236 | N-(5-(4-(4-chlorophenoxy)piperidine-1-carbonyl)pyridin-3-yl)acetamide | 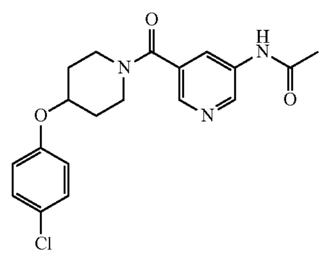 [SMILES: CC(=O)Nc1cncc(C(=O)N2CCC(Oc3ccc(Cl)cc3)CC2)c1] | | | 372.1 | 1.51 min. | Method A |

TABLE 3-continued

| Example | Name | Structure | Structure of carboxylic acid part | Structure of amine part | Observed MS | Retention time | QC Method |
|---|---|---|---|---|---|---|---|
| Example 237 | (4-(4-chlorophenoxy)piperidin-1-yl)(chroman-6-yl)methanone | 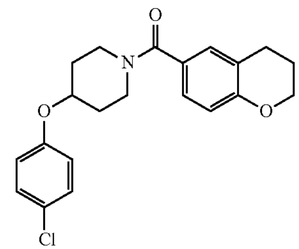 [SMILES: O=C(c1ccc2c(c1)CCCO2)N1CCC(Oc2ccc(Cl)cc2)CC1] | | | 371.8 | 1.97 min. | Method A |
| Example 238 | (4-(4-chlorophenoxy)piperidin-1-yl)(1-methyl-1H-pyrazolo[3,4-b]pyridin-3-yl)methanone | 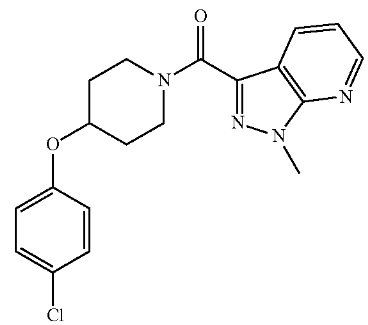 | | | 370.8 | 1.86 min. | Method A |
| Example 239 | (4-(4-chlorophenoxy)piperidin-1-yl)(1-methyl-1H-indol-5-yl)methanone | 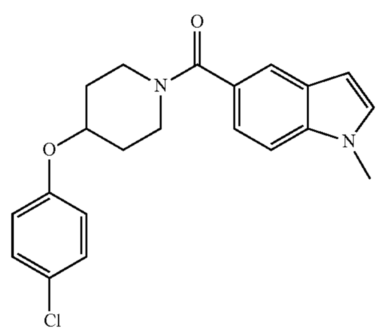 | | | 368.9 | 1.93 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 240 | (4-(4-chlorophenoxy)piperidin-1-yl)(3-(pyridin-2-yloxy)phenyl)methanone | 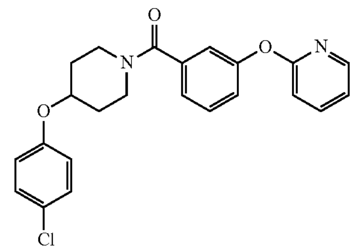 [SMILES: O=C(c1cccc(Oc2ccccn2)c1)N1CCC(Oc2ccc(Cl)cc2)CC1] | | | 408.8 | 1.94 min. | Method A |
| Example 241 | (4-(4-chlorophenoxy)piperidin-1-yl)(1-methyl-1H-benzo[d]imidazol-5-yl)methanone | 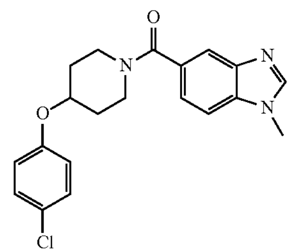 | | | 369.9 | 1.61 min. | Method A |
| Example 242 | (4-(4-chlorophenoxy)piperidin-1-yl)(4-((tetrahydro-2H-pyran-4-yl)oxy)phenyl)methanone | 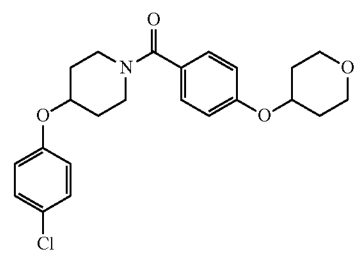 [SMILES: O=C(c1ccc(OC2CCOCC2)cc1)N1CCC(Oc2ccc(Cl)cc2)CC1] | | | 415.9 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 243 | (4-(4-chlorophenoxy) piperidin-1-yl)(pyrazolo[1,5-a]pyridin-2-yl)methanone | 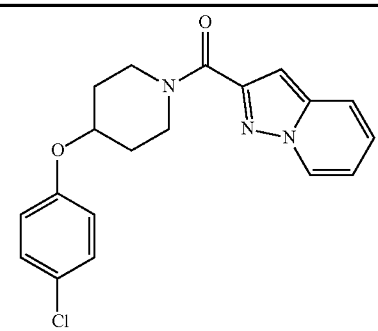 | | | 355.9 | 1.83 min. | Method A |
| Example 244 | 1-(3-(4-(4-chlorophenoxy) piperidine-1-carbonyl)-1H-pyrazol-5-yl)ethanone | 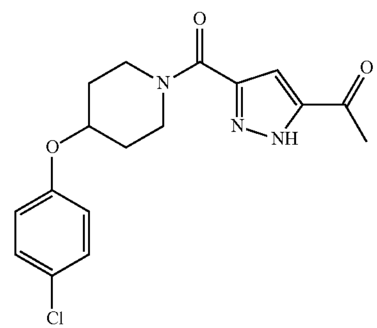 [SMILES: CC(=O)c1cc(C(=O)N2CCC(Oc3ccc(Cl)cc3)CC2)n[nH]1] | | | 346.1 | 1.63 min. | Method A |
| Example 245 | (4-(4-chlorophenoxy) piperidin-1-yl)(1,3,5-trimethyl-1H-pyrazol-4-yl)methanone | 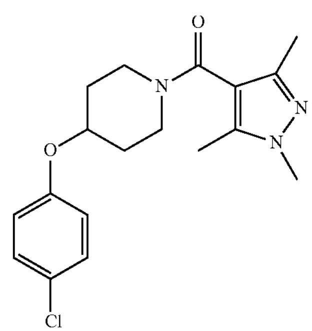 [SMILES: Cc1nn(C)c(C)c1C(=O)N1CCC(Oc2ccc(Cl)cc2)CC1] | | | 347.9 | 1.63 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 246 | (4-(4-chlorophenoxy) piperidin-1-yl)(1H-pyrrolo[2,3-b]pyridin-2-yl)methanone | 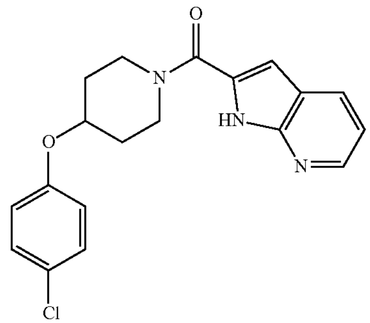 [SMILES: O=C(c1cc2cccnc2[nH]1)N1CCC(Oc2ccc(Cl)cc2)CC1] | | | 354.1 | 1.76 min. | Method A |
| Example 247 | 4-(4-(4-chlorophenoxy) piperidine-1-carbonyl)-1H-methylquinolin-2(1H)-one | 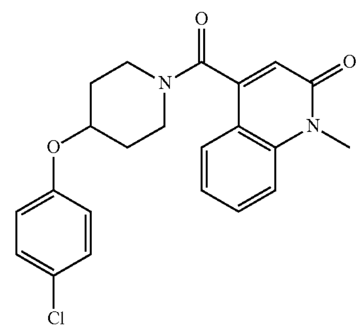 [SMILES: Cn1c(=O)cc(C(=O)N2CCC(Oc3ccc(Cl)cc3)CC2)c2ccccc21] | | | 396.9 | 1.74 min. | Method A |
| Example 248 | 5-(4-(4-chlorophenoxy) piperidine-1-carbonyl)-1H-benzo[d]imidazol-2(3H)-one | 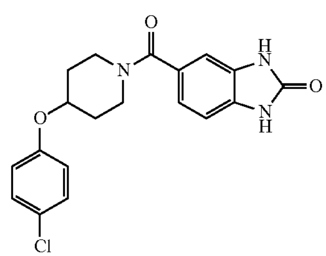 [SMILES: O=C(c1ccc2[nH]c(=O)[nH]c2c1)N1CCC(Oc2ccc(Cl)cc2)CC1] | | | 370.1 | 1.50 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 249 | (4-(4-chlorophenoxy) piperidin-1-yl)(5-methoxypyrazin-2-yl)methanone | 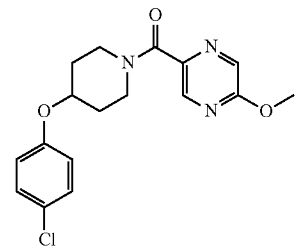 [SMILES: COc1cnc(C(=O)N2CCC(Oc3ccc(Cl)cc3)CC2)cn1] | | | 347.8 | 1.82 min. | Method A |
| Example 250 | 5-(4-(4-chlorophenoxy) piperidine-1-carbonyl)-1,3-dimethyl-1H-benzo[d]imidazol-2(3H)-one | 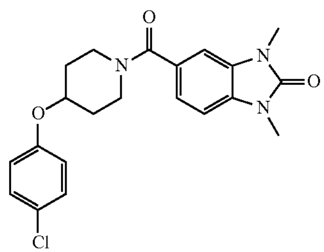 [SMILES: Cn1c(=O)n(C)c2cc(C(=O)N3CCC(Oc4ccc(Cl)cc4)CC3)ccc21] | | | 399.8 | 1.68 min. | Method A |
| Example 251 | (4-(4-chlorophenoxy) piperidin-1-yl)(1-methyl-1H-imidazol-4-yl)methanone | 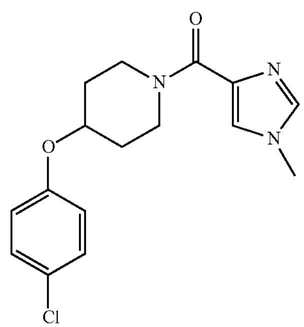 [SMILES: Cn1cnc(C(=O)N2CCC(Oc3ccc(Cl)cc3)CC2)c1] | | | 319.9 | 1.53 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 252 | (4-(4-chlorophenoxy)piperidin-1-yl)(2-phenyl-1H-imidazol-4-yl)methanone | 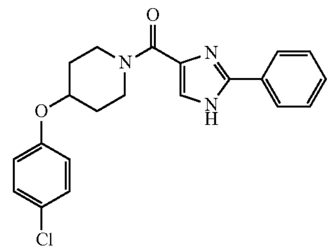 [SMILES: O=C(c1c[nH]c(-c2ccccc2)n1)N1CCC(Oc2ccc(Cl)cc2)CC1] | | | 380.1 | 1.81 min. | Method A |
| Example 253 | (4-(4-chlorophenoxy)piperidin-1-yl)(1,3-dimethyl-1H-pyrazol-4-yl)methanone | 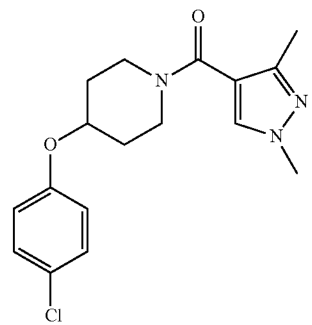 [SMILES: Cc1nn(C)cc1C(=O)N1CCC(Oc2ccc(Cl)cc2)CC1] | | | 333.9 | 1.60 min. | Method A |
| Example 254 | (4-(4-chlorophenoxy)piperidin-1-yl)(1,5-dimethyl-1H-pyrazol-4-yl)methanone | 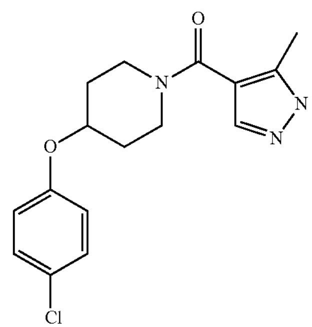 [SMILES: Cc1[nH]ncc1C(=O)N1CCC(Oc2ccc(Cl)cc2)CC1] | | | 333.9 | 1.61 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 255 | (4-(4-chlorophenoxy)piperidin-1-yl)(3-isobutyl-1-methyl-1H-pyrazol-5-yl)methanone | 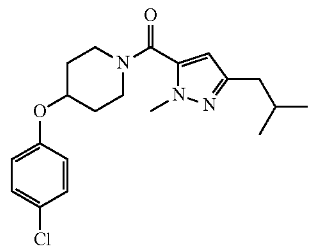 [SMILES: CC(C)Cc1cc(C(=O)N2CCC(Oc3ccc(Cl)cc3)CC2)n(C)n1] | | | 375.9 | 2.02 min. | Method A |
| Example 256 | (4-chloro-5-methyl-1H-pyrazol-3-yl)(4-(4-chlorophenoxy)piperidin-1-yl)methanone | 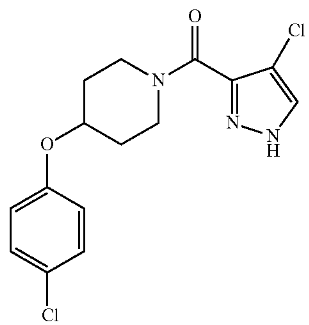 [SMILES: O=C(c1n[nH]cc1Cl)N1CCC(Oc2ccc(Cl)cc2)CC1] | | | 352 | 1.74 min. | Method A |
| Example 257 | 3-(4-(4-chlorophenoxy)piperidine-1-carbonyl)-1-isopropyl-6,7-dihydro-1H-cyclopenta[b]pyridin-2(5H)-one | 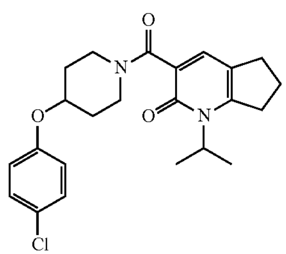 [SMILES: CC(C)n1c2c(cc(C(=O)N3CCC(Oc4ccc(Cl)cc4)CC3)c1=O)CCC2] | | | 413.1 | 1.87 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 258 | 5-(4-(4-chlorophenoxy)piperidine-1-carbonyl)-2-methoxybenzonitrile | 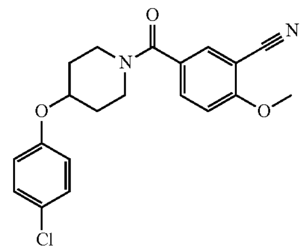 [SMILES: COc1ccc(C(=O)N2CCC(Oc3ccc(Cl)cc3)CC2)cc1C#N] | | | 370.8 | 1.83 min. | Method A |
| Example 259 | (4-(4-chlorophenoxy)piperidin-1-yl)(2-isopropylthiazol-4-yl)methanone | 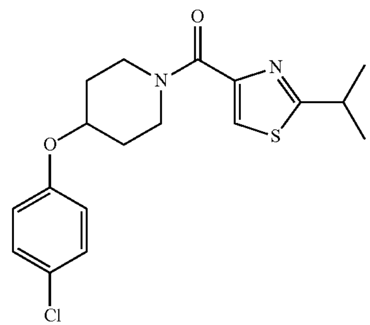 [SMILES: CC(C)c1nc(C(=O)N2CCC(Oc3ccc(Cl)cc3)CC2)cs1] | | | 364.8 | 2.03 min. | Method A |
| Example 260 | (4-(4-chlorophenoxy)piperidin-1-yl)(5,6-dimethoxy-1H-indol-2-yl)methanone | 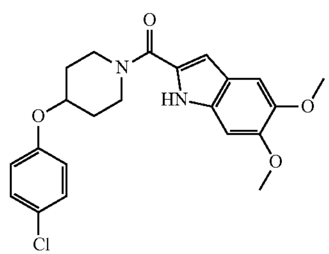 [SMILES: COc1cc2cc(C(=O)N3CCC(Oc4ccc(Cl)cc4)CC3)[nH]c2cc1OC] | | | 413.1 | 1.85 min. | Method A |

| Example | Name | Structure | Structure of amine part | Structure of carboxylic acid part | Observed MS | Retention time | QC Method |
|---|---|---|---|---|---|---|---|
| Example 261 | (4-(4-chlorophenoxy)piperidin-1-yl)(2,7-dimethylpyrazolo[1,5-a]pyrimidin-6-yl)methanone | 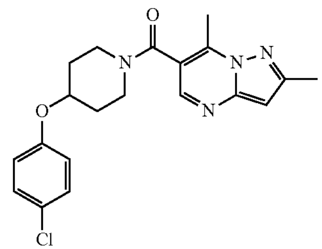 [SMILES: Cc1cc2ncc(C(=O)N3CCC(Oc4ccc(Cl)cc4)CC3)c(C)n2n1] | | | 383.1 | 1.73 min. | Method A |
| Example 262 | (4-(4-chlorophenoxy)piperidin-1-yl)(1H-pyrrolo[2,3-b]pyridin-3-yl)methanone | 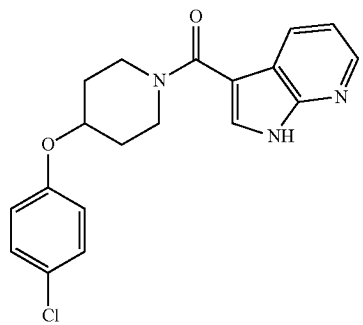 [SMILES: O=C(c1c[nH]c2ncccc12)N1CCC(Oc2ccc(Cl)cc2)CC1] | | | 354.1 | 1.64 min. | Method A |
| Example 263 | (4-(4-chlorophenoxy)piperidin-1-yl)(1-methyl-1H-pyrrolo[2,3-b]pyridin-2-yl)methanone | 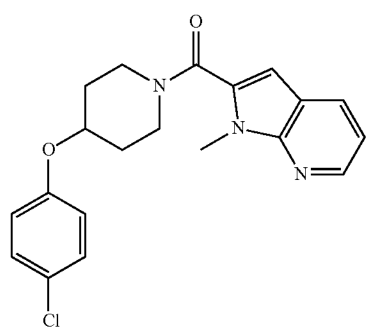 [SMILES: Cn1c(C(=O)N2CCC(Oc3ccc(Cl)cc3)CC2)cc2cccnc21] | | | 369.8 | 1.87 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 264 | (4-(4-chlorophenoxy) piperidin-1-yl)(5,6-dimethoxy-1-methyl-1H-indol-2-yl)methanone | 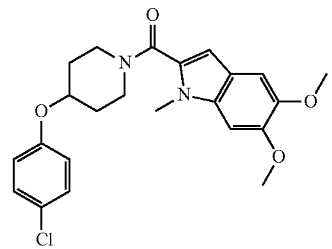 [SMILES: COc1cc2cc(C(=O)N3CCC(Oc4ccc(Cl)cc4)CC3)n(C)c2cc1OC] | | | 428.8 | 1.92 min. | Method A |
| Example 265 | (4-(4-chlorophenoxy) piperidin-1-yl)(1-methyl-1H-pyrrolo[2,3-b]pyridin-3-yl) methanone | 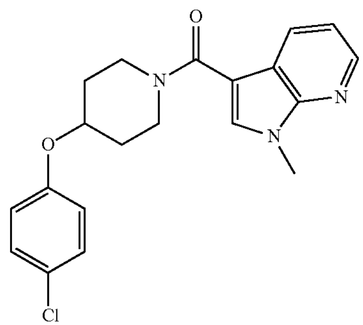 | | | 369.8 | 1.75 min. | Method A |
| Example 266 | 3-(4-(4-chlorophenoxy) piperidine-1-carbonyl)-1-isopropyl-4-methylquinolin-2(1H)-one | 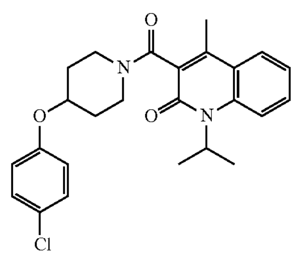 [SMILES: Cc1c(C(=O)N2CCC(Oc3ccc(Cl)cc3)CC2)c(=O)n(C(C)C)c2ccccc12] | | | 438.8 | 1.98 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 267 | (4-(4-chlorophenoxy) piperidin-1-yl)(4-methyl-1H-furo[3,2-b]pyrrol-5-yl)methanone | 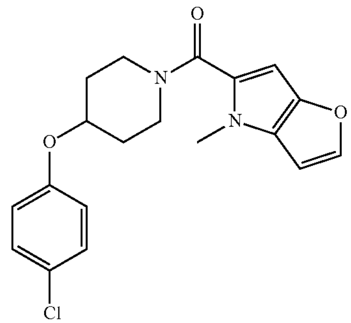 [SMILES: Cn1c(C(=O)N2CCC(Oc3ccc(Cl)cc3)CC2)cc2occc21] | | | 358.9 | 1.95 min. | Method A |
| Example 268 | (4-(4-chlorophenoxy) piperidin-1-yl)(4-methyl-1H-thieno[3,2-b]pyrrol-5-yl)methanone | 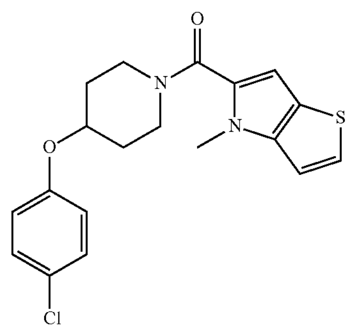 [SMILES: Cn1c(C(=O)N2CCC(Oc3ccc(Cl)cc3)CC2)cc2sccc21] | | | 374.8 | 2.04 min. | Method A |
| Example 269 | (4-(4-chlorophenoxy) piperidin-1-yl)(1,3-dimethyl-1H-thieno[2,3-c]pyrazol-5-yl)methanone | 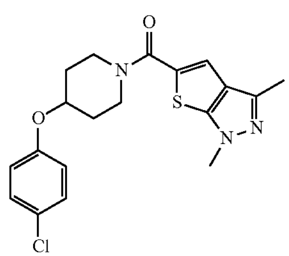 [SMILES: Cc1nn(C)c2sc(C(=O)N3CCC(Oc4ccc(Cl)cc4)CC3)cc12] | | | 389.8 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 270 | 2-(4-(4-chlorophenoxy)piperidine-1-carbonyl)-6,7-dihydropyrido[3,2,1-ij]quinolin-3(5H)-one | 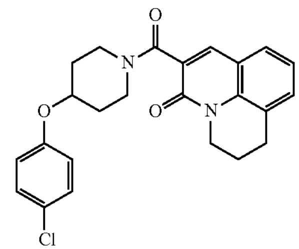 [SMILES: O=C(c1cc2cccc3c2n(c1=O)CCC3)N1CCC(Oc2ccc(Cl)cc2)CC1] | | | 422.8 | 1.85 min. | Method A |
| Example 271 | 5-(4-(4-chlorophenoxy)piperidine-1-carbonyl)-1H-pyrrolo[3,2,1-ij]quinolin-4(2H)-one | 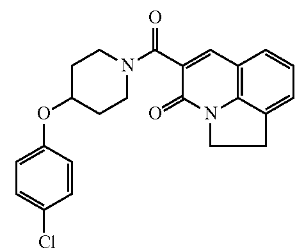 [SMILES: O=C(c1cc2cccc3c2n(c1=O)CC3)N1CCC(Oc2ccc(Cl)cc2)CC1] | | | 408.8 | 1.72 min. | Method A |
| Example 272 | 3-(4-(4-chlorophenoxy)piperidine-1-carbonyl)-1-ethyl-7-methyl-1,8-naphthyridin-4(1H)-one | 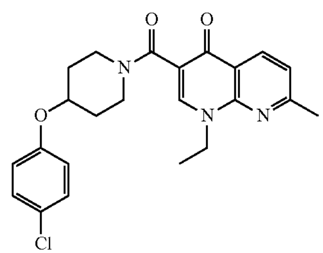 [SMILES: CCn1cc(C(=O)N2CCC(Oc3ccc(Cl)cc3)CC2)c(=O)c2ccc(C)nc21] | | | 424 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 273 | (4-(4-chlorophenoxy)piperidin-1-yl)(isoquinolin-6-yl)methanone | 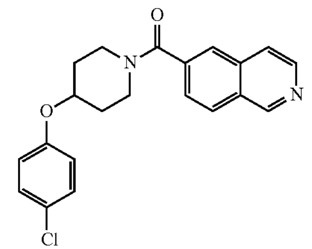 [SMILES: O=C(c1ccc2cnccc2c1)N1CCC(Oc2ccc(Cl)cc2)CC1] | | | 366.8 | 1.74 min. | Method A |
| Example 274 | (4-(4-chlorophenoxy)piperidin-1-yl)(5-methylpyridin-2-yl)methanone | 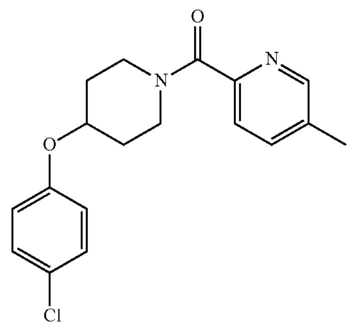 | | | 330.9 | 1.77 min. | Method A |
| Example 275 | (4-(4-chlorophenoxy)piperidin-1-yl)(5-(2,2,2-trifluoroethoxy)pyridin-3-yl)methanone | 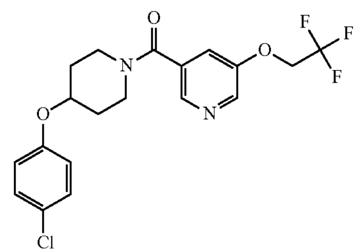 [SMILES: O=C(c1cncc(OCC(F)(F)F)c1)N1CCC(Oc2ccc(Cl)cc2)CC1] | | | 414.8 | 1.84 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 276 | (4-(4-chlorphenoxy)piperidin-1-yl)(3-methylisoxazolo[5,4-b]pyridin5-yl)methanone | 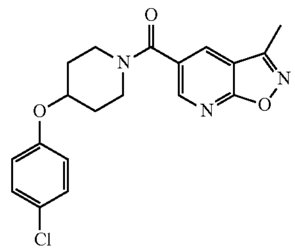 [SMILES: Cc1noc2ncc(C(=O)N3CCC(Oc4ccc(Cl)cc4)CC3)cc12] | | | 371.8 | 1.77 min. | Method A |
| Example 277 | (4-(4-chlorophenoxy)piperidin-1-yl)(1,3,6-trimethyl-1H-pyrazolo[3,4-b]pyridin-4-yl)methanone | 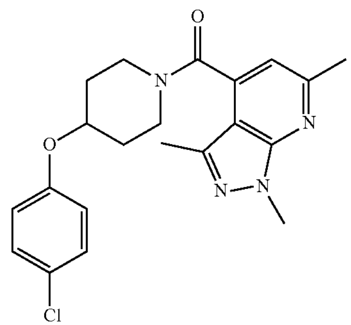 [SMILES: Cc1cc(C(=O)N2CCC(Oc3ccc(Cl)cc3)CC2)c2c(C)nn(C)c2n1] | | | 398.8 | 1.79 min. | Method A |
| Example 278 | (4-(4-chlorophenoxy)piperidin-1-yl)(thieno[2,3-b]pyridin-2-yl)methanone | 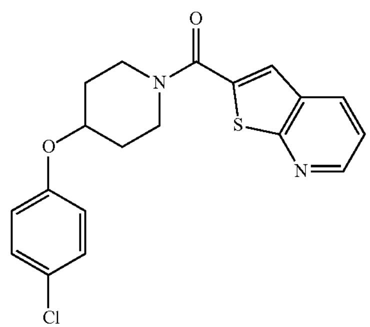 [SMILES: O=C(c1cc2cccnc2s1)N1CCC(Oc2ccc(Cl)cc2)CC1] | | | 372.8 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 279 | (4-(4-chlorophenoxy)piperidin-1-yl)(thieno[2,3-b]pyrazin-6-yl)methanone | 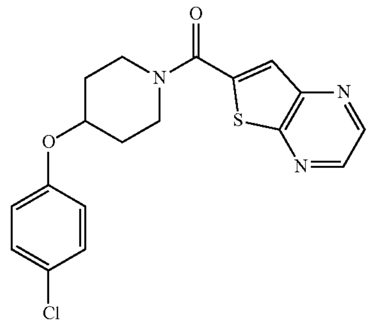 [SMILES: O=C(c1cc2nccnc2s1)N1CCC(Oc2ccc(Cl)cc2)CC1] | | | 373.8 | 1.82 min. | Method A |
| Example 280 | (4-(4-chlorophenoxy)piperidin-1-yl)(pyrazolo[1,5-a]pyrimidin-3-yl)methanone | 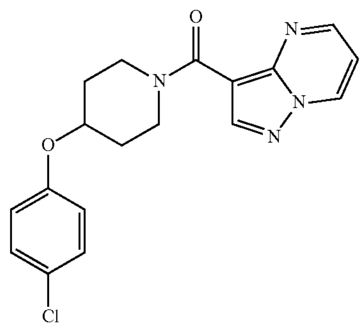 [SMILES: O=C(c1cnn2cccnc12)N1CCC(Oc2ccc(Cl)cc2)CC1] | | | 356.8 | 1.60 min. | Method A |
| Example 281 | (4-(4-chlorophenoxy)piperidin-1-yl)(2-(pyrrolidin-1-yl)pyrimidin-5-yl)methanone | 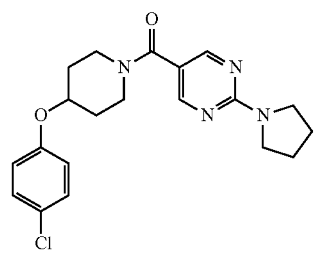 [SMILES: O=C(c1cnc(N2CCCC2)nc1)N1CCC(Oc2ccc(Cl)cc2)CC1] | | | 386.9 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 282 | (1H-benzo[d]imidazol-4-yl)(4-(4-chlorophenoxy)piperidin-1-yl)methanone | 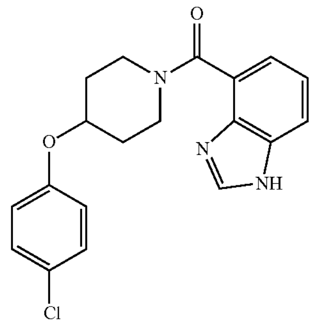 [SMILES: O=C(c1cccc2[nH]cnc12)N1CCC(Oc2ccc(Cl)cc2)CC1] | | | 354 | 1.57 min. | Method A |
| Example 283 | benzo[d][1,2,3]thiadiazol-7-yl(4-(4-chlorophenoxy)piperidin-1-yl)methanone | 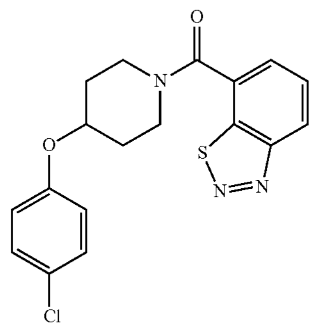 [SMILES: O=C(c1cccc2nnsc12)N1CCC(Oc2ccc(Cl)cc2)CC1] | | | 373.8 | 1.95 min. | Method A |
| Example 284 | 3-(4-(4-chlorophenoxy)piperidine-1-carbonyl)-1-methylquinolin-2(1H)-one | 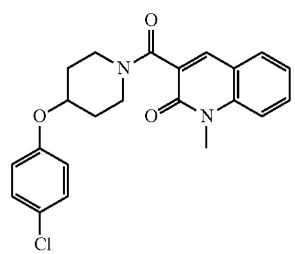 [SMILES: Cn1c(=O)c(C(=O)N2CCC(Oc3ccc(Cl)cc3)CC2)cc2ccccc21] | | | 396.8 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 285 | (4-(4-chlorophenoxy) piperidin-1-yl)(1-methyl-1H-benzo[d]imidazol-2-yl)methanone | 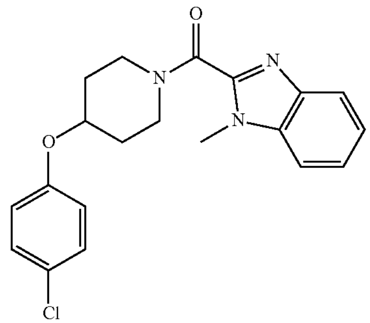 | | | 369.9 | 1.84 min. | Method A |
| Example 286 | (4-(4-chlorophenoxy) piperidin-1-yl)(pyrazolo[1,5-a]pyrimidin-2-yl)methanone | 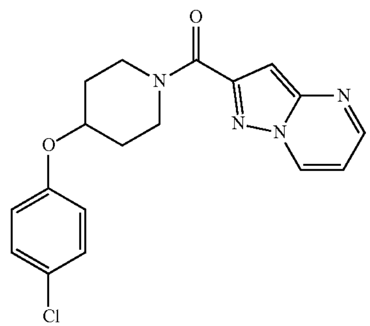 [SMILES: O=C(c1cc2ncccn2n1)N1CCC(Oc2ccc(Cl)cc2)CC1] | | | 355.1 | 1.65 min. | Method A |
| Example 287 | (4-(4-chlorophenoxy) piperidin-1-yl)(2-methoxypyrimidin-5-yl)methanone | 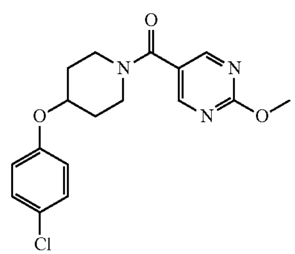 [SMILES: COc1ncc(C(=O)N2CCC(Oc3ccc(Cl)cc3)CC2)cn1] | | | 347.8 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 288 | (1H-benzo[d][1,2,3]triazol-4-yl)(4-(4-chlorophenoxy)piperidin-1-yl)methanone | 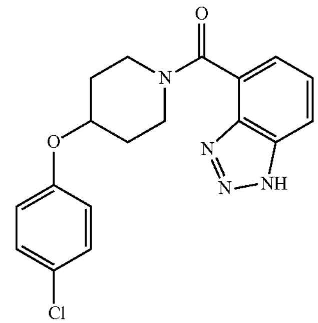 [SMILES: O=C(c1cccc2[nH]nnc12)N1CCC(Oc2ccc(Cl)cc2)CC1] | | | 355 | 1.60 min. | Method A |
| Example 289 | (4-(4-chlorophenoxy)piperidin-1-yl)(6-methylimidazo[2,1-b]thiazol-5-yl)methanone | 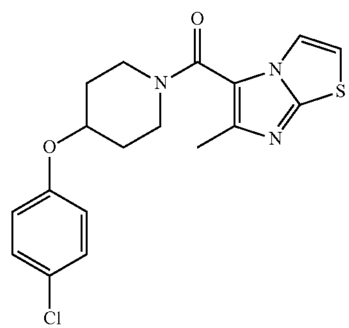 [SMILES: Cc1nc2sccn2c1C(=O)N1CCC(Oc2ccc(Cl)cc2)CC1] | | | 375.8 | 1.72 min. | Method A |
| Example 290 | benzo[d][1,2,5]thiadiazol-4-yl(4-(4-chlorophenoxy)piperidin-1-yl)methanone | 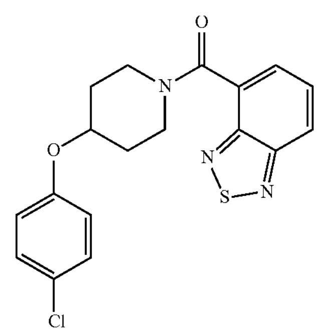 [SMILES: O=C(c1cccc2nsnc12)N1CCC(Oc2ccc(Cl)cc2)CC1] | | | 373.8 | 1.88 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 291 | (4-(4-chlorophenoxy) piperidin-1-yl)(1-(2-methoxyethyl)-1H-indol-5-yl)methanone | 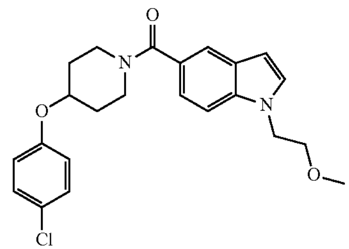 [SMILES: COCCn1ccc2cc(C(=O)N3CCC(Oc4ccc(Cl)cc4)CC3)ccc21] | | | 412.8 | 1.93 min. | Method A |
| Example 292 | (4-(4-chlorophenoxy) piperidin-1-yl)(1-(2-methoxyethyl)-1H-indol-5-yl)methanone | 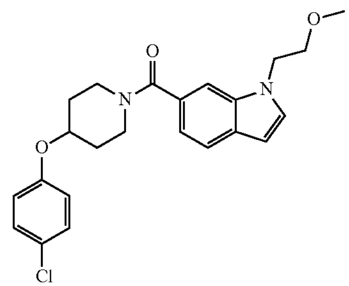 [SMILES: COCCn1ccc2ccc(C(=O)N3CCC(Oc4ccc(Cl)cc4)CC3)cc21] | | | 412.8 | 1.96 min. | Method A |
| Example 293 | (3-amino-1-methyl-1H-pyrazol-5-yl)(4-(4-chlorophenoxy) piperidin-1-yl)methanone | 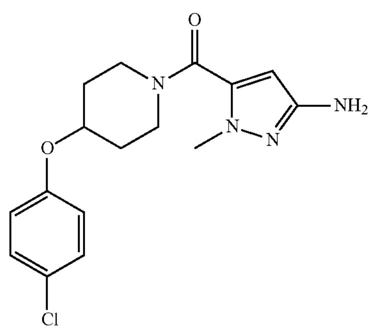 [SMILES: Cn1nc(N)cc1C(=O)N1CCC(Oc2ccc(Cl)cc2)CC1] | | | 334.9 | 1.51 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 294 | (4-(4-chlorophenoxy) piperidin-1-yl)(5-cyclopropyl-1-methyl-1H-pyrazol-3-yl) methanone | 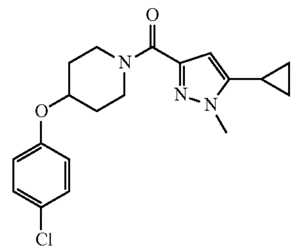 [SMILES: Cn1nc(C(=O)N2CCC(Oc3ccc(Cl)cc3)CC2)cc1C1CC1] | | | 359.9 | 1.86 min. | Method A |
| Example 295 | (4-(4-chlorophenoxy) piperidin-1-yl)(3-cyclopropyl-1-methyl-1H-pyrazol-5-yl) methanone | 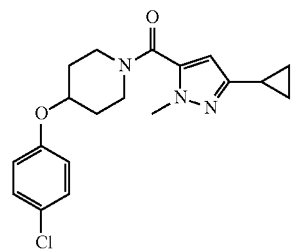 [SMILES: Cn1nc(C2CC2)cc1C(=O)N1CCC(Oc2ccc(Cl)cc2)CC1] | | | 359.9 | 1.86 min. | Method A |
| Example 296 | 1-benzyl-3-(4-(4-chlorophenoxy) piperidine-1-carbonyl)pyridin-2(1H)-one | 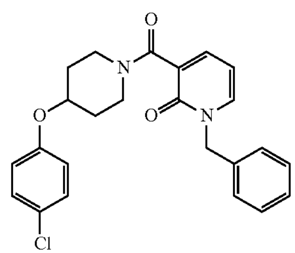 [SMILES: O=C(c1cccn(Cc2ccccc2)c1=O)N1CCC(Oc2ccc(Cl)cc2)CC1] | | | 422.8 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 297 | (1-benzyl-1H-pyrazol-4-yl)(4-(4-chlorophenoxy)piperidin-1-yl)methanone | 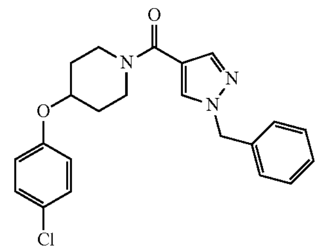 [SMILES: O=C(c1cnn(Cc2ccccc2)c1)N1CCC(Oc2ccc(Cl)cc2)CC1] | | | 395.9 | 1.85 min. | Method A |
| Example 298 | (4-(4-chlorophenoxy)piperidin-1-yl)(1-(2-methoxyethyl)-1H-indol-2-yl)methanone | 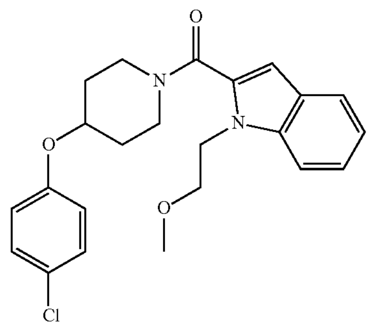 [SMILES: COCCn1c(C(=O)N2CCC(Oc3ccc(Cl)cc3)CC2)cc2ccccc21] | | | 412.8 | 2.09 min. | Method A |
| Example 299 | (4-(4-chlorophenoxy)piperidin-1-yl)(1-(2-methoxyethyl)-1H-indol-4-yl)methanone | 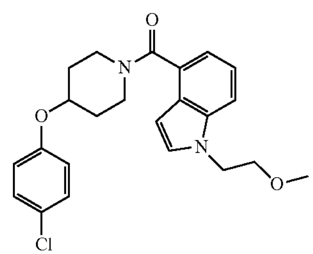 [SMILES: COCCn1ccc2c(C(=O)N3CCC(Oc4ccc(Cl)cc4)CC3)cccc21] | | | 412.8 | 1.93 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 300 | (4-(4-chlorophenoxy)piperidin-1-yl)(3,6-dimethylisoxazolo[5,4-b]pyridin-4-yl)methanone | 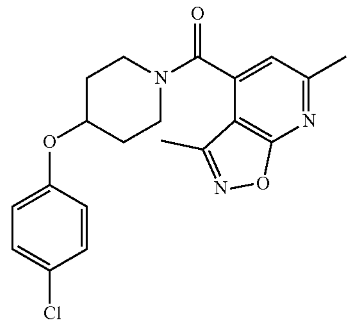 [SMILES: Cc1cc(C(=O)N2CCC(Oc3ccc(Cl)cc3)CC2)c2c(C)noc2n1] | | | 384 | 1.84 min. | Method A |
| Example 301 | 4-(4-(4-chlorophenoxy)piperidine-1-carbonyl)-1-methylpyridin-2(1H)-one | 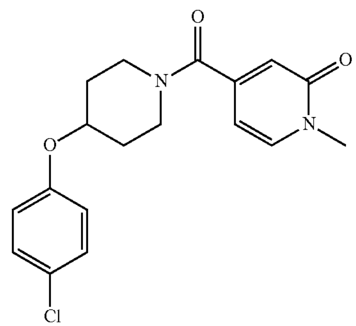 [SMILES: Cn1ccc(C(=O)N2CCC(Oc3ccc(Cl)cc3)CC2)cc1=O] | | | 346.8 | 1.49 min. | Method A |
| Example 302 | 3-(4-(4-chlorophenoxy)piperidine-1-carbonyl)-4H-pyrido[1,2-a]pyrimidin-4-one | 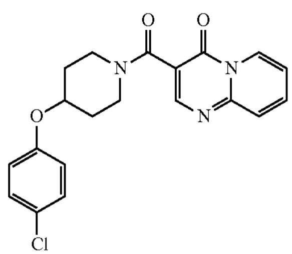 [SMILES: O=C(c1cnc2ccccn2c1=O)N1CCC(Oc2ccc(Cl)cc2)CC1] | | | 383.8 | 1.57 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 303 | 3-(4-(4-chlorophenoxy)piperidine-1-carbonyl)isoquinolin-1(2H)-one | 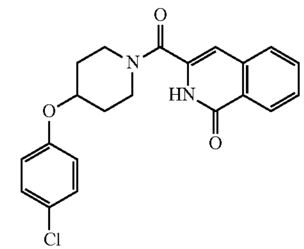 [SMILES: O=C(c1cc2ccccc2c(=O)[nH]1)N1CCC(Oc2ccc(Cl)cc2)CC1] | | | 381 | 1.73 min. | Method A |
| Example 304 | (4-(4-chlorophenoxy)piperidin-1-yl)(2-(3,5-dimethyl-1H-pyrazol-4-yl)phenyl)methanone | 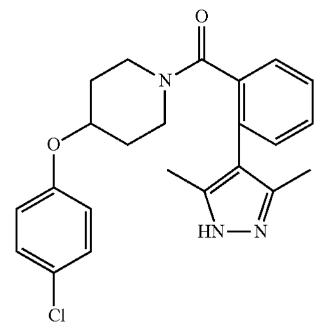 [SMILES: Cc1n[nH]c(C)c1-c1ccccc1C(=O)N1CCC(Oc2ccc(Cl)cc2)CC1] | | | 408 | 1.73 min. | Method A |
| Example 305 | benzo[d][1,2,5]oxadiazol-5-yl(4-(4-chlorophenoxy)piperidin-1-yl)methanone | 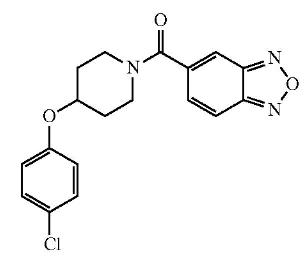 [SMILES: O=C(c1ccc2nonc2c1)N1CCC(Oc2ccc(Cl)cc2)CC1] | | | 357.8 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 306 | (6-aminopyridin-2-yl)(4-(4-chlorophenoxy)piperidin-1-yl)methanone | 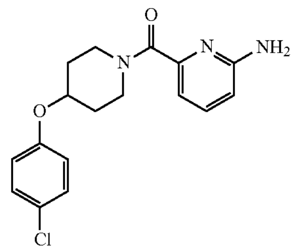 [SMILES: Nc1cccc(C(=O)N2CCC(Oc3ccc(Cl)cc3)CC2)n1] | | | 329.9 | 1.59 min. | Method A |
| Example 307 | 3-(4-(4-chlorophenoxy)piperidine-1-carbonyl)-1,6-dimethylpyridin-2(1H)-one | 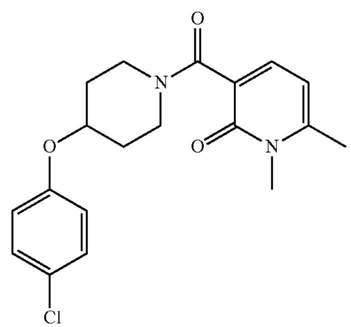 [SMILES: Cc1ccc(C(=O)N2CCC(Oc3ccc(Cl)cc3)CC2)c(=O)n1C] | | | 359 | 1.55 min. | Method A |
| Example 308 | (4-(4-chlorophenoxy)piperidin-1-yl)(3-propoxypyridin-2-yl)methanone | 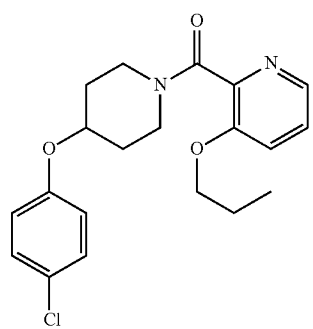 [SMILES: CCCOc1cccnc1C(=O)N1CCC(Oc2ccc(Cl)cc2)CC1] | | | 374.8 | 1.84 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 309 | (4-(4-chlorophenoxy)piperidin-1-yl)(6-((tetrahydro-2H-pyran-4-yl)oxy)pyridin-3-yl)methanone | 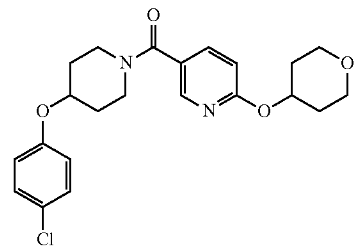 [SMILES: O=C(c1ccc(OC2CCOCC2)nc1)N1CCC(Oc2ccc(Cl)cc2)CC1] | | | 416.8 | 1.86 min. | Method A |
| Example 310 | (4-(4-chlorophenoxy)piperidin-1-yl)(6-((tetrahydro-2H-pyran-4-yl)oxy)pyridin-2-yl)methanone | 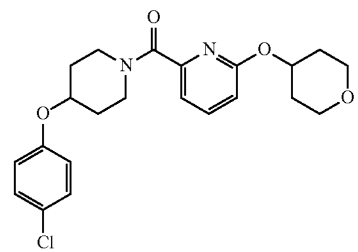 [SMILES: O=C(c1cccc(OC2CCOCC2)n1)N1CCC(Oc2ccc(Cl)cc2)CC1] | | | 416.8 | 1.90 min. | Method A |
| Example 311 | (4-(4-chlorophenoxy)piperidin-1-yl)(5-((tetrahydro-2H-pyran-4-yl)oxy)pyridin-3-yl)methanone | 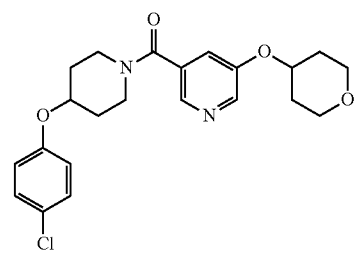 [SMILES: O=C(c1cncc(OC2CCOCC2)c1)N1CCC(Oc2ccc(Cl)cc2)CC1] | | | 416.8 | 1.71 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 312 | (4-(4-chlorophenoxy) piperidin-1-yl)(3-hydroxy-4-methoxyphenyl) methanone | 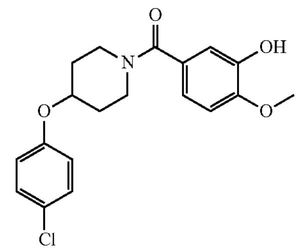 [SMILES: COc1ccc(C(=O)N2CCC(Oc3ccc(Cl)cc3)CC2)cc1O] | | | 360 | 1.70 min. | Method A |
| Example 313 | (4-chloro-2-hydroxyphenyl)(4-(4-chlorophenoxy) piperidin-1-yl)methanone | 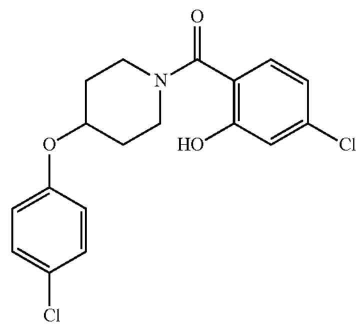 [SMILES: O=C(c1ccc(Cl)cc1O)N1CCC(Oc2ccc(Cl)cc2)CC1] | | | 364 | 1.88 min. | Method A |
| Example 314 | (4-(4-chlorophenoxy) piperidin-1-yl)(4-hydroxy-3-methylphenyl) methanone | 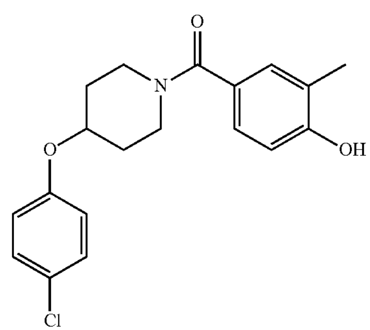 [SMILES: Cc1cc(C(=O)N2CCC(Oc3ccc(Cl)cc3)CC2)ccc1O] | | | 344 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 315 | (4-(4-chlorophenoxy)piperidin-1-yl)(6-morpholinopyridin-2-yl)methanone | 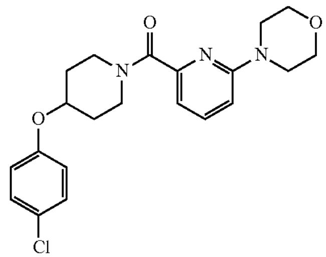 [SMILES: O=C(c1cccc(N2CCOCC2)n1)N1CCC(Oc2ccc(Cl)cc2)CC1] | | | 401.9 | 1.84 min. | Method A |
| Example 316 | (4-(4-chlorophenoxy)piperidin-1-yl)(2-morpholinopyridin-4-yl)methanone | 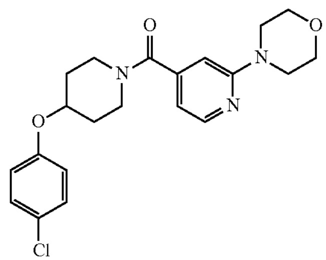 [SMILES: O=C(c1ccnc(N2CCOCC2)c1)N1CCC(Oc2ccc(Cl)cc2)CC1] | | | 401.9 | 1.77 min. | Method A |
| Example 317 | (4-(4-chlorophenoxy)piperidin-1-yl)(1-methyl-3-(trifluoromethyl)-1H-pyrazol-5-yl)methanone | 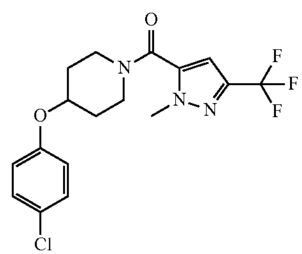 [SMILES: Cn1nc(C(F)(F)F)cc1C(=O)N1CCC(Oc2ccc(Cl)cc2)CC1] | | | 387.8 | 1.97 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 318 | (4-(4-chlorophenoxy)piperidin-1-yl)(2-hydroxy-4-(trifluoromethyl)phenyl)methanone | 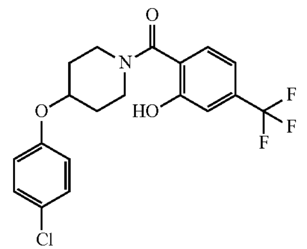 [SMILES: O=C(c1ccc(C(F)(F)F)cc1O)N1CCC(Oc2ccc(Cl)cc2)CC1] | | | 398 | 1.91 min. | Method A |
| Example 319 | (4-(4-chlorophenoxy)piperidin-1-yl)(3-hydroxy-4-methylphenyl)methanone | 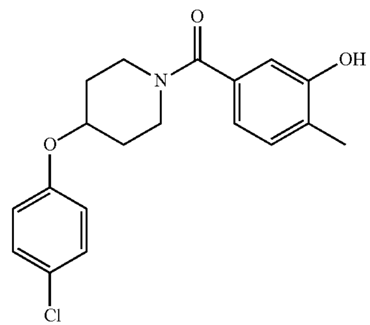 [SMILES: Cc1ccc(C(=O)N2CCC(Oc3ccc(Cl)cc3)CC2)cc1O] | | | 344.1 | 1.81 min. | Method A |
| Example 320 | tert-butyl ((2-(4-(4-chlorophenoxy)piperidine-1-carbonyl)pyridin-4-yl)methyl)carbamate | 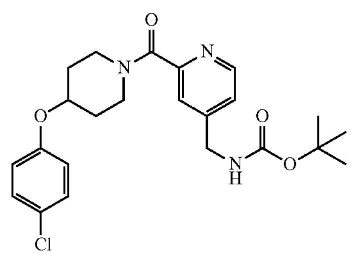 [SMILES: CC(C)(C)OC(=O)NCc1ccnc(C(=O)N2CCC(Oc3ccc(Cl)cc3)CC2)c1] | | | 444.1 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 321 | (4-(aminomethyl) pyridin-2-yl)(4-(4-chlorophenoxy)piperidin-1-yl)methanone | 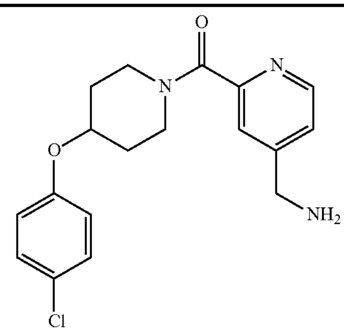 | Alternative route | | 345.9 | 1.39 min. | Method A |
| Example 322 | N-((2-(4-(4-chlorophenoxy) piperidine-1-carbonyl)pyridin-4-yl)methyl)pivalamide | 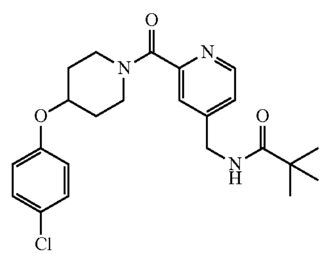 [SMILES: CC(C)(C)C(=O)NCc1ccnc(C(=O)N2CCC(Oc3ccc(Cl)cc3)CC2)c1] | Alternative route | | 428.1 | 1.69 min. | Method A |
| Example 323 | N-((2-(4-(4-chlorophenoxy) piperidine-1-carbonyl)pyridin-4-yl)methyl)-4-fluorobenzamide | 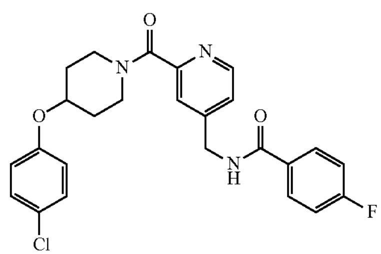 [SMILES: O=C(NCc1ccnc(C(=O)N2CCC(Oc3ccc(Cl)cc3)CC2)c1)c1ccc(F)cc1] | Alternative route | | 466.1 | 1.73 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 324 | N-((2-(4-(4-chlorophenoxy) piperidine-1-carbonyl)pyridin-4-yl) methyl)-4-fluorobenzenesulfonamide | 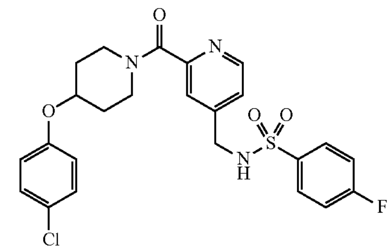 [SMILES: O=C(c1cc(CNS(=O)(=O)c2ccc(F)cc2)ccn1)N1CCC(Oc2ccc(Cl)cc2)CC1] | Alternative route | | 502 | 1.79 min. | Method A |
| Example 325 | tert-butyl 2-(4-(4-chlorophenoxy)piperidine-1-carbonyl)-7,8-dihydro-1,6-naphthyridine-6(5H)-carboxylate | 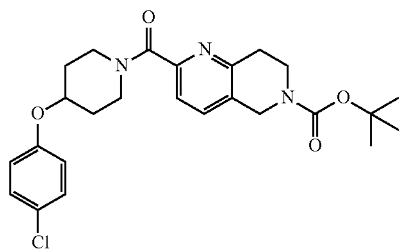 [SMILES: CC(C)(C)OC(=O)N1CCc2nc(C(=O)N3CCC(Oc4ccc(Cl)cc4)CC3)ccc2C1] | | | 471.9 | 1.99 min. | Method A |
| Example 326 | (4-(4-chlorophenoxy)piperidin-1-yl)(6-(methylsulfonyl)-5,6,7,8-tetrahydro-1,6-naphthyridin-2-yl)methanone | 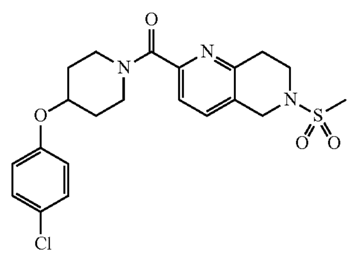 [SMILES: CS(=O)(=O)N1CCc2nc(C(=O)N3CCC(Oc4ccc(Cl)cc4)CC3)ccc2C1] | Alternative route | | 448.1 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 327 | N-(tert-butyl)-4-(4-(4-chlorophenoxy)piperidine-1-carbonyl)benzamide | 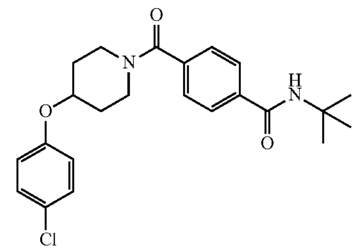 [SMILES: CC(C)(C)NC(=O)c1ccc(C(=O)N2CCC(Oc3ccc(Cl)cc3)CC2)cc1] | | | 413.1 | 1.87 min. | Method A |
| Example 328 | N-(tert-butyl)-4-(4-(4-chlorophenoxy)piperidine-1-carbonyl)-N-methylbenzamide | 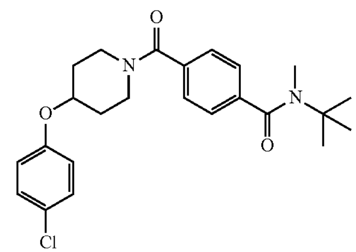 [SMILES: CN(C(=O)c1ccc(C(=O)N2CCC(Oc3ccc(Cl)cc3)CC2)cc1)C(C)(C)C] | | | 428.9 | 1.94 min. | Method A |
| Example 329 | 4-(4-(4-chlorophenoxy)piperidine-1-carbonyl)-N-(2,2,2-trifluoroethyl)benzamide | 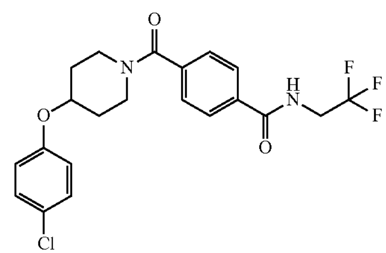 [SMILES: O=C(NCC(F)(F)F)c1ccc(C(=O)N2CCC(Oc3ccc(Cl)cc3)CC2)cc1] | | | 439 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 330 | (4-(4-chlorophenoxy)piperidin-1-yl)(4-(2-methoxyethoxy)phenyl)methanone | 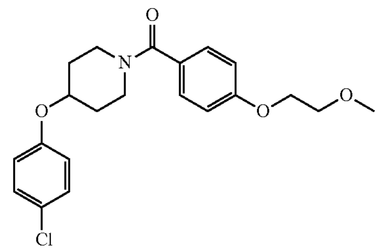 [SMILES: COCCOc1ccc(C(=O)N2CCC(Oc3ccc(Cl)cc3)CC2)cc1] | | | 389.9 | 1.86 min. | Method A |
| Example 331 | (4-(4-chlorophenoxy)piperidin-1-yl)(4-(2-hydroxyethoxy)phenyl)methanone | 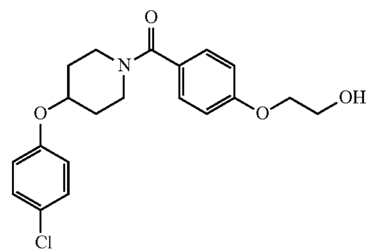 [SMILES: O=C(c1ccc(OCCO)cc1)N1CCC(Oc2ccc(Cl)cc2)CC1] | | | 375.8 | 1.65 min. | Method A |
| Example 332 | N-(4-(4-(4-chlorophenoxy)piperidine-1-carbonyl)benzyl)pivalamide | 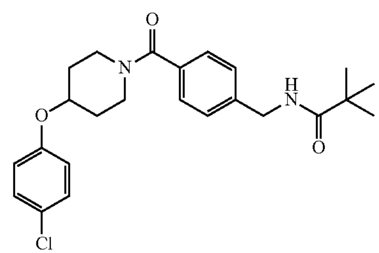 [SMILES: CC(C)(C)C(=O)NCc1ccc(C(=O)N2CCC(Oc3ccc(Cl)cc3)CC2)cc1] | | | 427.1 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 333 | 4-(4-(4-chlorophenoxy)piperidine-1-carbonyl)picolinamide | 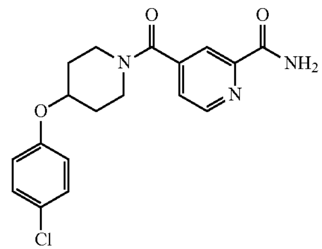 [SMILES: NC(=O)c1cc(C(=O)N2CCC(Oc3ccc(Cl)cc3)CC2)ccn1] | | | 358.1 | 1.55 min. | Method A |
| Example 334 | (4-(4-chlorophenoxy)piperidin-1-yl)(5-morpholinopyridin-3-yl)methanone | 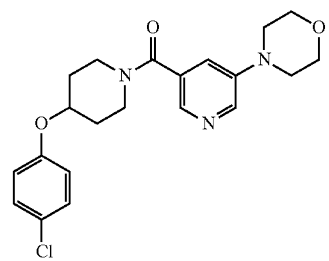 [SMILES: O=C(c1cncc(N2CCOCC2)c1)N1CCC(Oc2ccc(Cl)cc2)CC1] | | | 401.9 | 1.64 min. | Method A |
| Example 335 | (4-(4-chlorophenoxy)piperidin-1-yl)(6-(piperidin-1-yl)pyrimidin-4-yl)methanone | 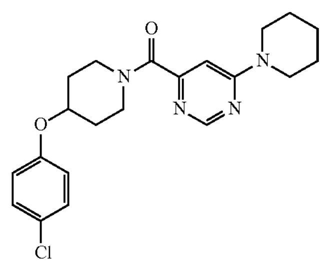 [SMILES: O=C(c1cc(N2CCCCC2)ncn1)N1CCC(Oc2ccc(Cl)cc2)CC1] | | | 400.9 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 336 | (3-(1H-imidazol-1-yl)phenyl)(4-(4-chlorophenoxy)piperidin-1-yl)methanone | 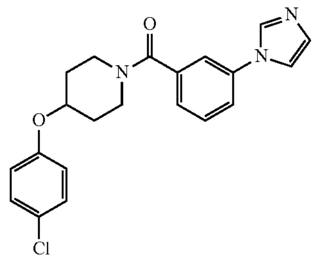 [SMILES: O=C(c1cccc(-n2ccnc2)c1)N1CCC(Oc2ccc(Cl)cc2)CC1] | | | 381.9 | 1.68 min. | Method A |
| Example 337 | (2-(1H-pyrazol-1-yl)phenyl)(4-(4-chlorophenoxy)piperidin-1-yl)methanone | 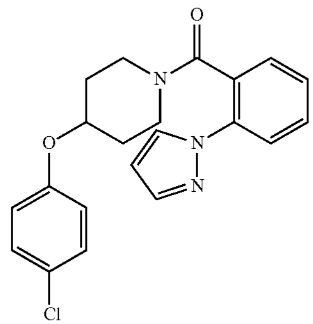 [SMILES: O=C(c1ccccc1-n1cccn1)N1CCC(Oc2ccc(Cl)cc2)CC1] | | | 381.9 | 1.87 min. | Method A |
| Example 338 | (4-(4-chlorophenoxy)piperidin-1-yl)(2-(2-methyl-1H-imidazol-1-yl)phenyl)methanone | 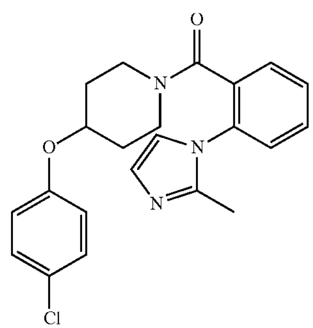 [SMILES: Cc1nccn1-c1ccccc1C(=O)N1CCC(Oc2ccc(Cl)cc2)CC1] | | | 395.9 | 1.68 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 339 | (4-(4-chlorophenoxy)piperidin-1-yl)(2-(3-methyl-1,2,4-oxadiazol-5-yl)phenyl)methanone | 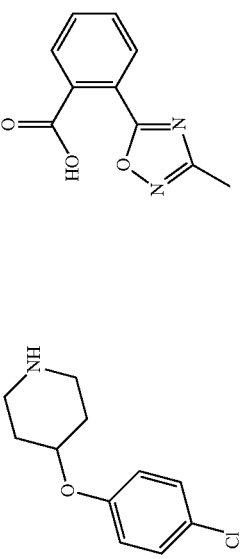 | 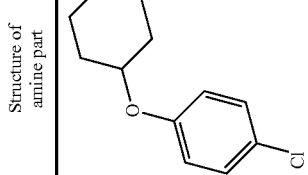 | 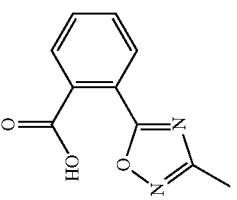 | 397.9 | 1.90 min. | Method A |
| Example 340 | (4-(4-chlorophenoxy)piperidin-1-yl)(3-methyl-1H-pyrazol-5-yl)methanone | 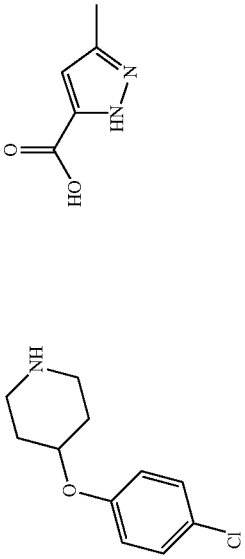 | 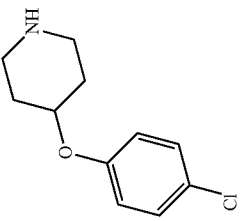 | 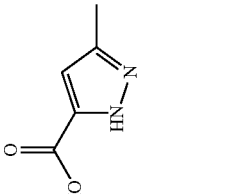 | 318.1 | 1.61 min. | Method A |
| Example 341 | (4-(4-chlorophenoxy)piperidin-1-yl)(6-(piperidine-1-carbonyl)pyridin-2-yl)methanone | 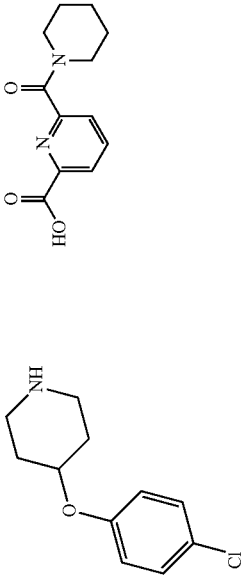 | 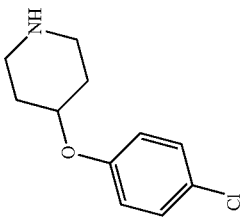 | 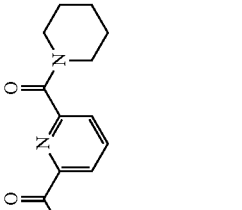 | 427.9 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 342 | (4-(4-chlorophenoxy) piperidin-1-yl)(2-hydroxy-4-methoxyphenyl) methanone | 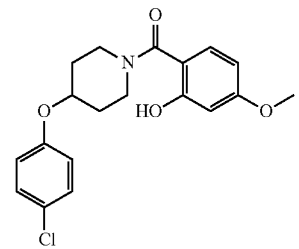 [SMILES: COc1ccc(C(=O)N2CCC(Oc3ccc(Cl)cc3)CC2)c(O)c1] | | | 360 | 1.83 min. | Method A |
| Example 343 | (4-(4-chlorophenoxy) piperidin-1-yl)(4-hydroxy-3-methoxyphenyl) methanone | 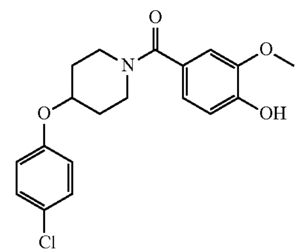 [SMILES: COc1cc(C(=O)N2CCC(Oc3ccc(Cl)cc3)CC2)ccc1O] | | | 360 | 1.70 min. | Method A |
| Example 344 | N-(5-chloro-2-(4-(4-chlorophenoxy) piperidine-1-carbonyl)phenyl) methanesulfonamide | 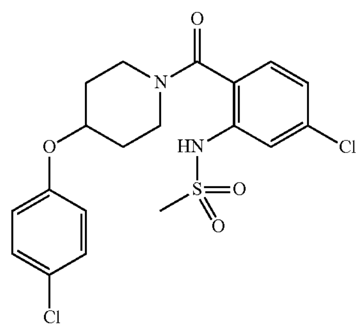 [SMILES: CS(=O)(=O)Nc1cc(Cl)ccc1C(=O)N1CCC(Oc2ccc(Cl)cc2)CC1] | | | 440.9 | 1.87 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 345 | N-(4-chloro-2-(4-(4-chlorophenoxy)piperidine-1-carbonyl)phenyl)methanesulfonamide | 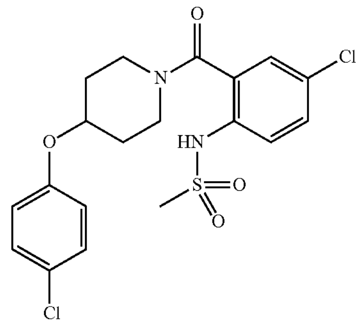 [SMILES: CS(=O)(=O)Nc1ccc(Cl)cc1C(=O)N1CCC(Oc2ccc(Cl)cc2)CC1] | | | 440.9 | 1.88 min. | Method A |
| Example 346 | (4-(4-chlorophenoxy)piperidin-1-yl)(2'-(hydroxymethyl-[1,1'-biphenyl]-4-yl)methanone | 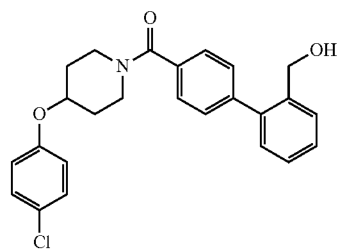 [SMILES: O=C(c1ccc(-c2ccccc2CO)cc1)N1CCC(Oc2ccc(Cl)cc2)CC1] | | | 421.8 | 1.89 min. | Method A |
| Example 347 | (4-(4-chlorophenoxy)piperidin-1-yl)(2'-(methylsulfonyl)-[1,1'-biphenyl]-4-yl)methanone | 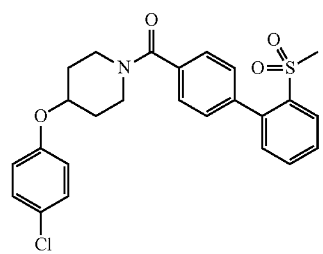 [SMILES: CS(=O)(=O)c1ccccc1-c1ccc(C(=O)N2CCC(Oc3ccc(Cl)cc3)CC2)cc1] | | | 469.7 | 1.88 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 348 | (3-chloro-4-hydroxyphenyl)(4-(4-chlorophenoxy)piperidin-1-yl)methanone | 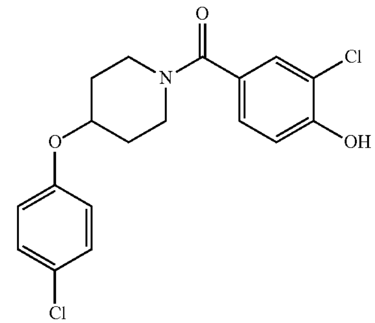 [SMILES: O=C(c1ccc(O)c(Cl)c1)N1CCC(Oc2ccc(Cl)cc2)CC1] | | | 364 | 1.77 min. | Method A |
| Example 349 | 3-(tert-butyl)-5-(4-(4-chlorophenoxy)piperidine-1-carbonyl)benzamide | 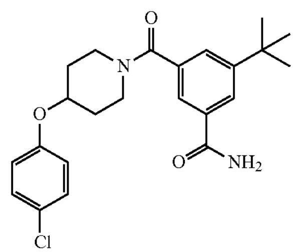 [SMILES: CC(C)(C)c1cc(C(N)=O)cc(C(=O)N2CCC(Oc3ccc(Cl)cc3)CC2)c1] | Alternative route | | 413.1 | 1.84 min. | Method A |
| Example 350 | (3-tert-butyl)-5-(4-(4-chlorophenoxy)piperidine-1-carbonyl)-N,N-dimethylbenzamide | 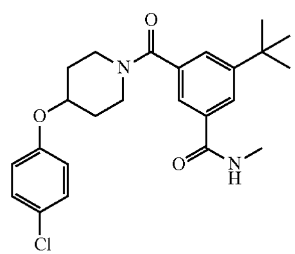 [SMILES: CNC(=O)c1cc(C(=O)N2CCC(Oc3ccc(Cl)cc3)CC2)cc(C(C)(C)C)c1] | Alternative route | | 442.9 | 1.95 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 351 | (3-(tert-butyl)-5-(4-(4-chlorophenoxy) piperidine-1-carbonyl)phenyl)(morpholino) methanone | 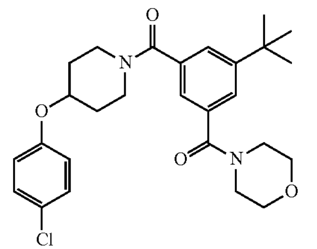 [SMILES: CC(C)(C)c1cc(C(=O)N2CCOCC2)cc(C(=O)N2CCC(Oc3ccc(Cl)cc3)CC2)c1] | Alternative route | | 484.8 | 1.93 min. | Method A |
| Example 352 | 4'-(4-(4-chlorophenoxy) piperidine-1-carbonyl)-[1,1'-biphenyl]-3-carboxamide | 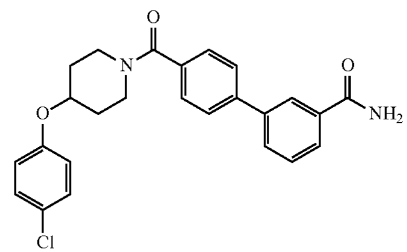 [SMILES: NC(=O)c1cccc(-c2ccc(C(=O)N3CCC(Oc4ccc(Cl)cc4)CC3)cc2)c1] | | | 433 | 1.73 min. | Method A |
| Example 353 | (4-(4-chlorophenoxy) piperidin-1-yl)(1-(2-morpholinoethyl)-1H-indol-5-yl)methanone | 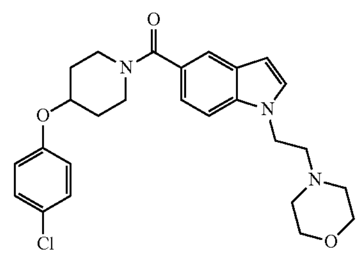 [SMILES: O=C(c1ccc2c(ccn2CCN2CCOCC2)c1)N1CCC(Oc2ccc(Cl)cc2)CC1] | Alternative route | | 467.8 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 354 | 2-(5-(4-(4-chlorophenoxy)piperidine-1-carbonyl)-1H-indol-1-yl)-N,N-dimethylacetamide | 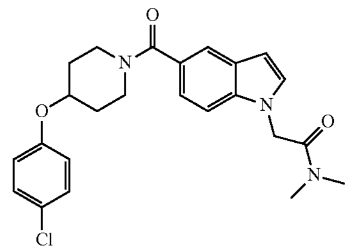 [SMILES: CN(C)C(=O)Cn1ccc2cc(C(=O)N3CCC(Oc4ccc(Cl)cc4)CC3)ccc21] | Alternative route | | 439.8 | 1.73 min. | Method A |
| Example 355 | (4-(4-chlorophenoxy)piperidin-1-yl)(1-(2-hydroxyethyl)-1H-indol-5-yl)methanone | 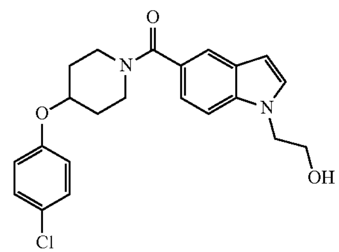 [SMILES: O=C(c1ccc2c(ccn2CCO)c1)N1CCC(Oc2ccc(Cl)cc2)CC1] | Alternative route | | 397 | 1.72 min. | Method A |
| Example 356 | (4-(4-chlorophenoxy)piperidin-1-yl)(4-morpholinopyridin-2-yl)methanone | 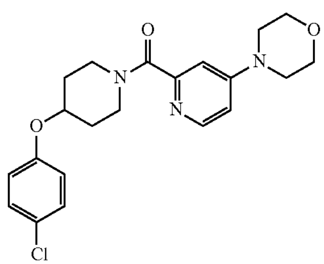 [SMILES: O=C(c1cc(N2CCOCC2)ccn1)N1CCC(Oc2ccc(Cl)cc2)CC1] | | | 400 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 357 | (4-(4-chlorophenoxy) piperidin-1-yl)(4-(piperidin-1-yl) pymidin-2-yl)methanone | 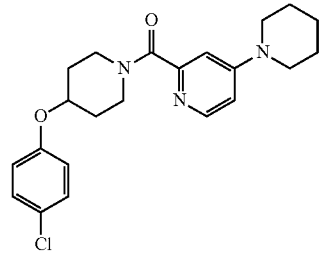 [SMILES: O=C(c1cc(N2CCCCC2)ccn1)N1CCC(Oc2ccc(Cl)cc2)CC1] | | | 399.8 | 1.90 min. | Method A |
| Example 358 | 2-(3-(4-(4-chlorophenoxy) piperidine-1-carbonyl)-1H-indol-1-yl)-N,N-dimethylacetamide | 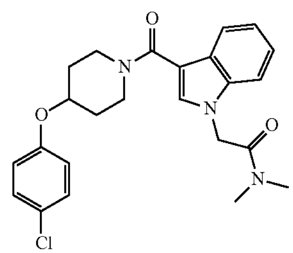 [SMILES: CN(C)C(=O)Cn1cc(C(=O)N2CCC(Oc3ccc(Cl)cc3)CC2)c2ccccc21] | | | 438.1 | 1.76 min. | Method A |
| Example 359 | (4-(4-chlorophenoxy)piperidin-1-yl)(1-(2-hydroxyethyl)-1H-indol-3-yl)methanone | 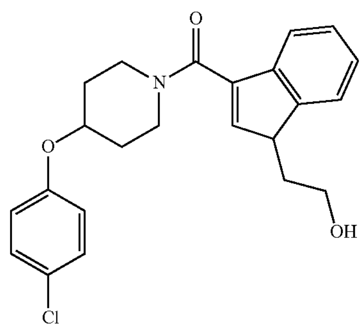 [SMILES: O=C(C1=CC(CCO)c2ccccc21)N1CCC(Oc2ccc(Cl)cc2)CC1] | | | 398.8 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 360 | (4-(4-chlorophenoxy) piperidin-1-yl)(1-(2-morpholinoethyl)-1H-indol-3-yl)methanone | 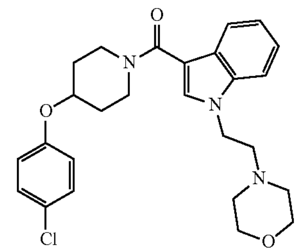 [SMILES: O=C(c1cn(CCN2CCOCC2)c2ccccc12)N1CCC(Oc2ccc(Cl)cc2)CC1] | | | 467.8 | 1.90 min. | Method A |
| Example 361 | (4-(4-chlorophenoxy) piperidin-1-yl)(1-(2-(piperidin-1-yl)ethyl)-1H-indol-3-yl)methanone | 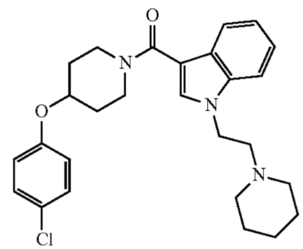 [SMILES: O=C(c1cn(CCN2CCCCC2)c2ccccc12)N1CCC(Oc2ccc(Cl)cc2)CC1] | | | 465.9 | 2.12 min. | Method A |
| Example 362 | 2-(4-(4-(4-chlorophenoxy)piperidine-1-carbonyl)phenyl)-2-methylpropanenitrile | 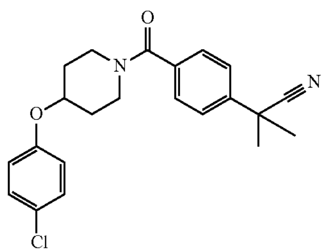 [SMILES: CC(C)(C#N)c1ccc(C(=O)N2CCC(Oc3ccc(Cl)cc3)CC2)cc1] | | | 382.8 | 1.96 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 363 | (4-(4-chlorophenoxy)piperidin-1-yl)(3-fluoro-4-hydroxyphenyl)methanone | 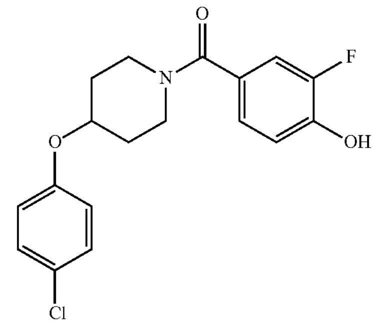 [SMILES: O=C(c1ccc(O)c(F)c1)N1CCC(Oc2ccc(Cl)cc2)CC1] | | | 348 | 1.70 min. | Method A |
| Example 364 | 2-chloro-5-(4-(4-chlorophenoxy)piperidine-1-carbonyl)benzenesulfonamide | 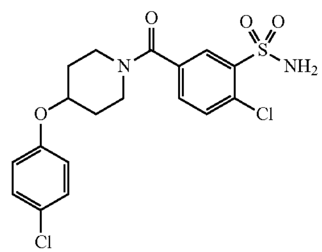 [SMILES: NS(=O)(=O)c1cc(C(=O)N2CCC(Oc3ccc(Cl)cc3)CC2)ccc1Cl] | | | 427 | 1.70 min. | Method A |
| Example 365 | 4'-(4-(4-chlorophenoxy)piperidine-1-carbonyl)-[1,1'-biphenyl]-4-carboxamide | 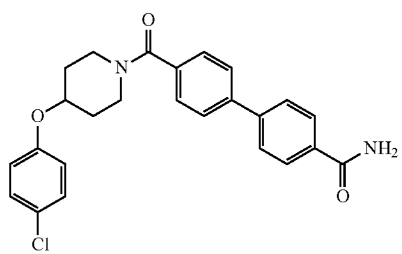 [SMILES: NC(=O)c1ccc(-c2ccc(C(=O)N3CCC(Oc4ccc(Cl)cc4)CC3)cc2)cc1] | | | 433.1 | 1.74 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 366 | 4'-(4-(4-chlorophenoxy) piperidine-1-carbonyl) [1,1'-biphenyl]-2-carboxamide | 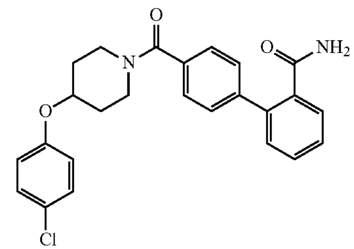 [SMILES: NC(=O)c1ccccc1-c1ccc(C(=O)N2CCC(Oc3ccc(Cl)cc3)CC2)cc1] | | | 433 | 1.76 min. | Method A |
| Example 367 | (5-chloro-2-hydroxyphenyl) (4-(4-chlorophenoxy) piperidin-1-yl)methanone | 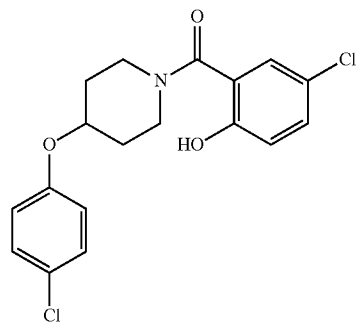 [SMILES: O=C(c1cc(Cl)ccc1O)N1CCC(Oc2ccc(Cl)cc2)CC1] | | | 364 | 1.92 min. | Method A |
| Example 368 | (4-(4-chlorophenoxy) piperidin-1-yl)(2-hydroxy-4-methylphenyl) methanone | 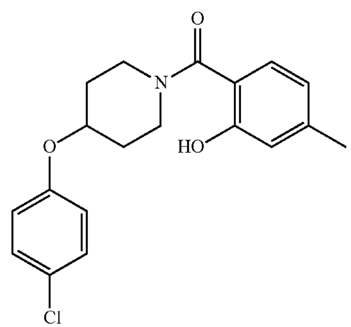 [SMILES: Cc1ccc(C(=O)N2CCC(Oc3ccc(Cl)cc3)CC2)c(O)c1] | | | 344.1 | 1.92 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 369 | (4-(4-chlorophenoxy)piperidin-1-yl)(5-fluoro-2-hydroxyphenyl)methanone | 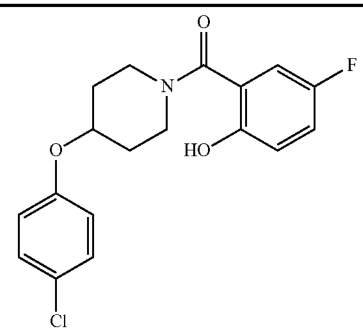 | | | 348 | 1.83 min. | Method A |
| Example 370 | (4-(4-chlorophenoxy)piperidin-1-yl)(2-hydroxy-3-methylphenyl)methanone | 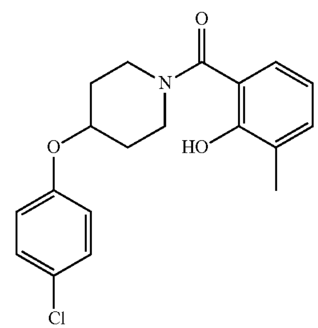 [SMILES: Cc1cccc(C(=O)N2CCC(Oc3ccc(Cl)cc3)CC2)c1O] | | | 346.1 | 3.45 min. | Method B |
| Example 371 | (4-(4-chlorophenoxy)piperidin-1-yl)(2-hydroxy-3-isopropylphenyl)methanone | 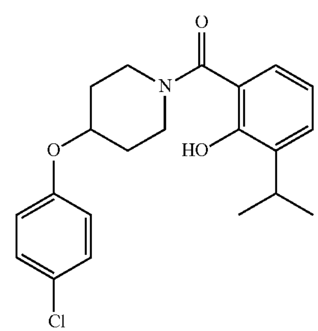 [SMILES: CC(C)c1cccc(C(=O)N2CCC(Oc3ccc(Cl)cc3)CC2)c1O] | | | 374.1 | 3.82 min. | Method B |

TABLE 3-continued

| Example | Name | Structure | Structure of amine part | Structure of carboxylic acid part | Observed MS | Retention time | QC Method |
|---|---|---|---|---|---|---|---|
| Example 372 | (4-(4-chlorophenoxy) piperidin-1-yl)(2-hydroxy-6-methoxyphenyl) methanone | 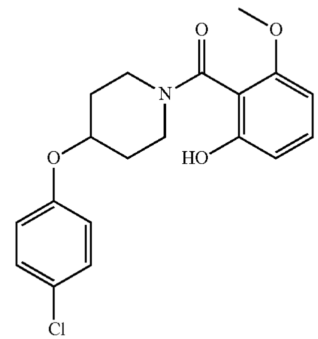 [SMILES: COc1cccc(O)c1C(=O)N1CCC(Oc2ccc(Cl)cc2)CC1] | | | 362.1 | 2.97 min. | Method B |
| Example 373 | (4-(4-chlorophenoxy) piperidin-1-yl)(2-fluoro-6-hydroxyphenyl) methanone | 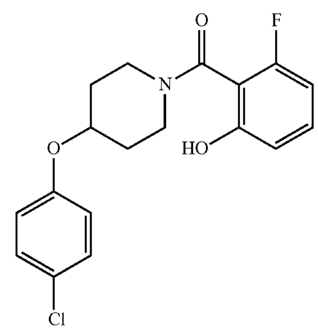 [SMILES: O=C(c1c(O)cccc1F)N1CCC(Oc2ccc(Cl)cc2)CC1] | | | 348.2 | 3.02 min. | Method B |
| Example 374 | (4-(4-chlorophenoxy) piperidin-1-yl)(3-hydroxy-2-methylphenyl) methanone | 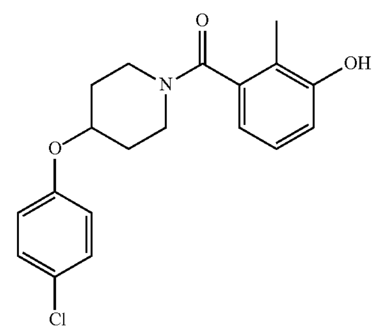 [SMILES: Cc1c(O)cccc1C(=O)N1CCC(Oc2ccc(Cl)cc2)CC1] | | | 344.2 | 3.02 min. | Method B |

TABLE 3-continued

| Example | Name | Structure | Structure of amine part | Structure of carboxylic acid part | Observed MS | Retention time | QC Method |
|---|---|---|---|---|---|---|---|
| Example 375 | (2-chloro-4-hydroxyphenyl)(4-(4-chlorophenoxy)piperidin-1-yl)methanone | 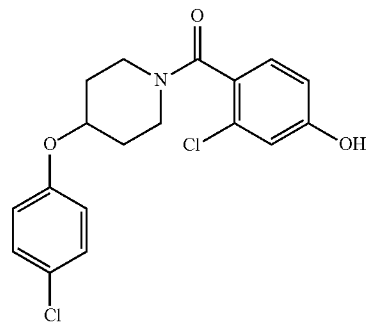 [SMILES: O=C(c1ccc(O)cc1Cl)N1CCC(Oc2ccc(Cl)cc2)CC1] | | | 364.1 | 3.02 min. | Method B |
| Example 376 | (4-(4-chlorophenoxy)piperidin-1-yl)(2-fluoro-4-hydroxyphenyl)methanone | 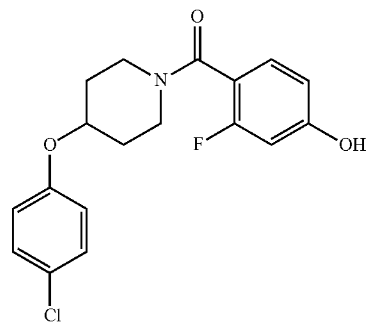 [SMILES: O=C(c1ccc(O)cc1F)N1CCC(Oc2ccc(Cl)cc2)CC1] | | | 348.2 | 2.95 min. | Method B |
| Example 377 | N-(4-(4-(4-chlorophenoxy)piperidine-1-carbonyl)-2-methylphenyl)methanesulfonamide | 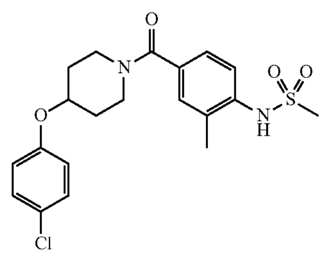 [SMILES: Cc1cc(C(=O)N2CCC(Oc3ccc(Cl)cc3)CC2)ccc1NS(C)(=O)=O] | | | 421.2 | 2.93 min. | Method B |

TABLE 3-continued

| Example | Name | Structure | Structure of amine part | Structure of carboxylic acid part | Observed MS | Retention time | QC Method |
|---|---|---|---|---|---|---|---|
| Example 378 | (4-(4-chlorophenoxy) piperidin-1-yl)(4-fluoro-3-hydroxyphenyl) methanone | 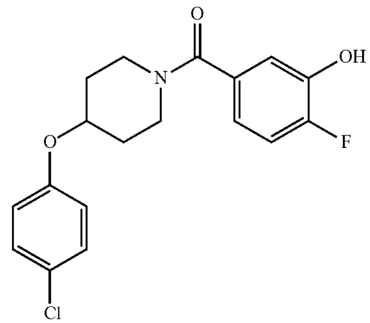 [SMILES: O=C(c1ccc(F)c(O)c1)N1CCC(Oc2ccc(Cl)cc2)CC1] | | | 348.1 | 1.73 min. | Method A |
| Example 379 | (4-(4-chlorophenoxy) piperidin-1-yl)(2-hydroxy-5-methylphenyl) methanone | 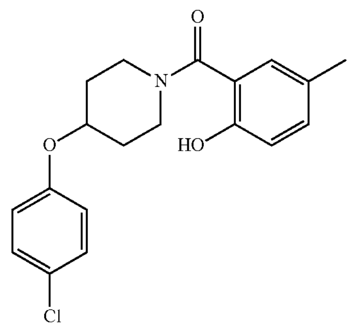 [SMILES: Cc1ccc(O)c(C(=O)N2CCC(Oc3ccc(Cl)cc3)CC2)c1] | | | 344.1 | 1.84 min. | Method A |
| Example 380 | (4-(4-chlorophenoxy) piperidin-1-yl)(2-hydroxy-3-methoxyphenyl) methanone | 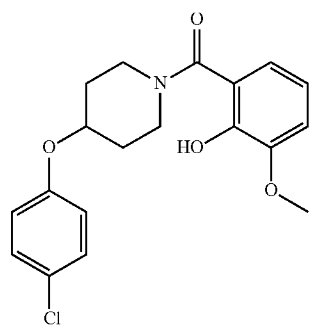 [SMILES: COc1cccc(C(=O)N2CCC(Oc3ccc(Cl)cc3)CC2)c1O] | | | 360.1 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 381 | (4-(4-chlorophenoxy)piperidin-1-yl)(4-fluoro-2-hydroxyphenyl)methanone | 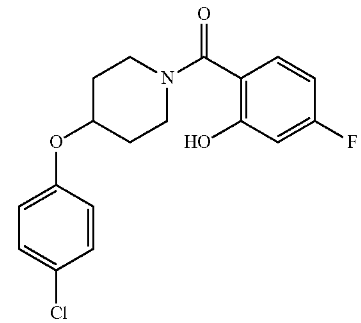 [SMILES: O=C(c1ccc(F)cc1O)N1CCC(Oc2ccc(Cl)cc2)CC1] | | | 348.1 | 1.80 min. | Method A |
| Example 382 | (4-(4-chlorophenoxy)piperidin-1-yl)(3,5-dihydroxyphenyl)methanone | 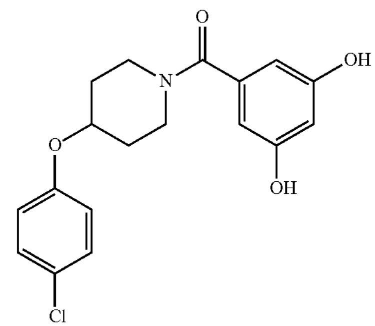 [SMILES: O=C(c1cc(O)cc(O)c1)N1CCC(Oc2ccc(Cl)cc2)CC1] | | | 346 | 1.55 min. | Method A |
| Example 383 | N-(3-(4-(4-chlorophenoxy)piperidine-1-carbonyl)phenyl)acetamide | 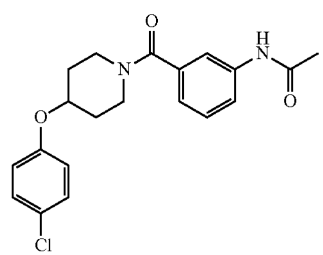 [SMILES: CC(=O)Nc1cccc(C(=O)N2CCC(Oc3ccc(Cl)cc3)CC2)c1] | | | 371.1 | 1.66 min. | Method A |

| Example | Name | Structure | Structure of amine part | Structure of carboxylic acid part | Observed MS | Retention time | QC Method |
|---|---|---|---|---|---|---|---|
| Example 384 | (4-(4-chlorophenoxy)piperidin-1-yl)(1-((4-hydroxytetrahydro-2H-pyran-4-yl)methyl)-1H-indol-5-yl)methanone | 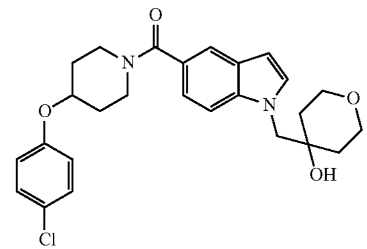 [SMILES: O=C(c1ccc2c(ccn2CC2(O)CCOCC2)c1)N1CCC(Oc2ccc(Cl)cc2)CC1] | Alternative route | | 467 | 1.75 min. | Method A |
| Example 385 | (1-(2-aminoethyl)-1H-indol-5-yl)(4-(4-chlorophenoxy)piperidin-1-yl)methanone | 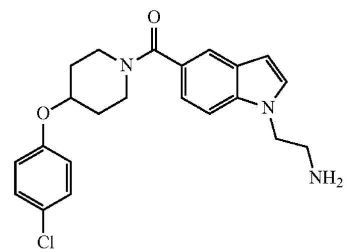 [SMILES: NCCn1ccc2cc(C(=O)N3CCC(Oc4ccc(Cl)cc4)CC3)ccc21] | Alternative route | | 397.8 | 1.57 min. | Method A |
| Example 386 | N-(2-(5-(4-(4-chlorophenoxy)piperidine-1-carbonyl)-1H-indol-1-yl)ethyl)acetamide | 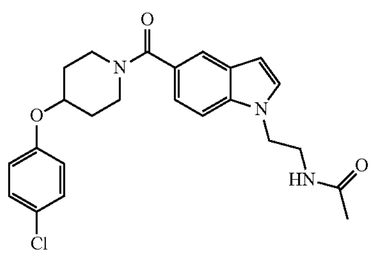 [SMILES: CC(=O)NCCn1ccc2cc(C(=O)N3CCC(Oc4ccc(Cl)cc4)CC3)ccc21] | Alternative route | | 438.1 | 1.67 min. | Method A |

| Example | Name | Structure | Structure of amine part | Structure of carboxylic acid part | Observed MS | Retention time | QC Method |
|---|---|---|---|---|---|---|---|
| Example 387 | N-(2-(5-(4-(4-chlorophenoxy)piperidine-1-carbonyl)-1H-indol-1-yl)ethyl)methanesulfonamide | 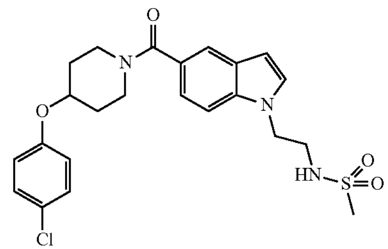 [SMILES: CS(=O)(=O)NCCn1ccc2cc(C(=O)N3CCC(Oc4ccc(Cl)cc4)CC3)ccc21] | Alternative route | | 474 | 1.74 min. | Method A |
| Example 388 | 2-(5-(4-(4-chlorophenoxy)piperidine-1-carbonyl)-1H-indol-1-yl)-1-morpholinoethanone | 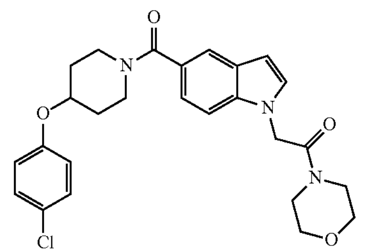 [SMILES: O=C(Cn1ccc2cc(C(=O)N3CCC(Oc4ccc(Cl)cc4)CC3)ccc21)N1CCOCC1] | Alternative route | | 480 | 1.72 min. | Method A |
| Example 389 | (4-(4-chlorophenoxy)piperidin-1-yl)(3'-methylsulfonyl)-[1,1'-biphenyl]-4-yl)methanone | 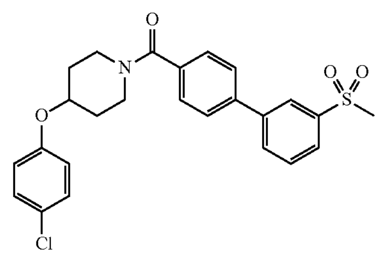 [SMILES: CS(=O)(=O)c1cccc(-c2ccc(C(=O)N3CCC(Oc4ccc(Cl)cc4)CC3)cc2)c1] | | | 469.7 | 1.87 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 390 | (4-(4-chlorophenoxy)piperidin-1-yl)(3'-(hydroxymethyl)-[1,1'-biphenyl]-4-yl)methanone | 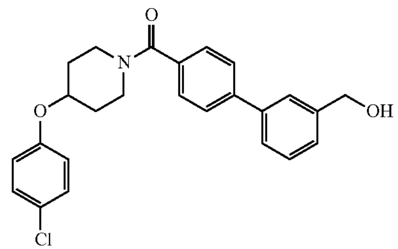 [SMILES: O=C(c1ccc(-c2cccc(CO)c2)cc1)N1CCC(Oc2ccc(Cl)cc2)CC1] | | | 419.9 | 1.86 min. | Method A |
| Example 391 | N-(4'-(4-(4-chlorophenoxy)piperidine-1-carbonyl)-[1,1'-biphenyl]-2-yl)methanesulfonamide | 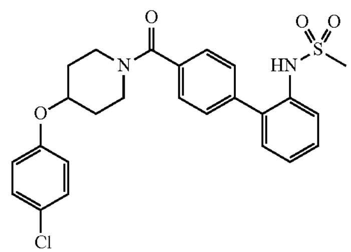 [SMILES: CS(=O)(=O)Nc1ccccc1-c1ccc(C(=O)N2CCC(Oc3ccc(Cl)cc3)CC2)cc1] | | | 483 | 1.88 min. | Method A |
| Example 392 | N-(4'-(4-(4-chlorophenoxy)piperidine-1-carbonyl)-[1,1'-biphenyl]-3-yl)methanesulfonamide | 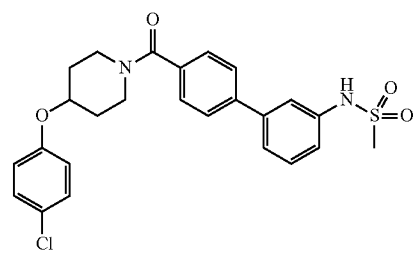 [SMILES: CS(=O)(=O)Nc1cccc(-c2ccc(C(=O)N3CCC(Oc4ccc(Cl)cc4)CC3)cc2)c1] | | | 483 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 393 | 4'-(4-(4-chlorophenoxy)piperidine-1-carbonyl)-N-methyl-[1,1'-biphenyl]-3-carboxamide | 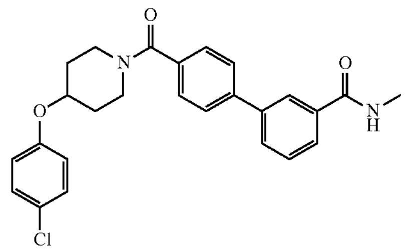 [SMILES: CNC(=O)c1cccc(-c2ccc(C(=O)N3CCC(Oc4ccc(Cl)cc4)CC3)cc2)c1] | | | 447 | 1.80 min. | Method A |
| Example 394 | 4'-(4-(4-chlorophenoxy)piperidine-1-carbonyl)-N,N-dimethyl-[1,1'-biphenyl]-3-carboxamide | 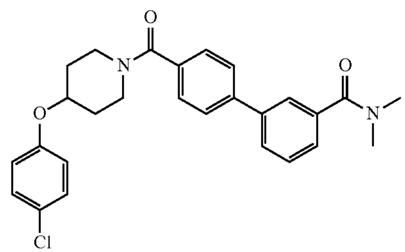 [SMILES: CN(C)C(=O)c1cccc(-c2ccc(C(=O)N3CCC(Oc4ccc(Cl)cc4)CC3)cc2)c1] | | | 462.8 | 1.86 min. | Method A |
| Example 395 | (4-(4-chlorophenoxy)piperidin-1-yl)(3'-(morpholine-4-carbonyl)-[1,1'-biphenyl]-4-yl)methanone | 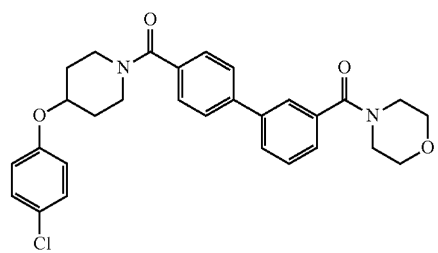 [SMILES: O=C(c1cccc(-c2ccc(C(=O)N3CCC(Oc4ccc(Cl)cc4)CC3)cc2)c1)N1CCOCC1] | | | 504.8 | 1.84 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 396 | (4-chloro-3-hydroxyphenyl)(4-(4-chlorophenoxy)piperidin-1-yl)methanone | 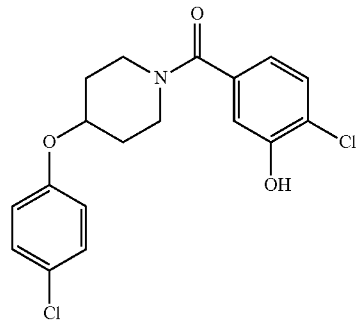 [SMILES: O=C(c1ccc(Cl)c(O)c1)N1CCC(Oc2ccc(Cl)cc2)CC1] | | | 364 | 1.81 min. | Method A |
| Example 397 | N-(5-(4-(4-chlorophenoxy)piperidine-1-carbonyl)-2-methylphenyl)methanesulfonamide | 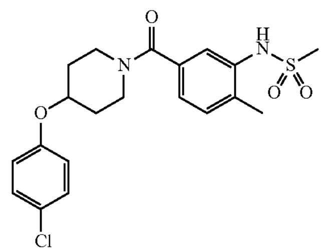 [SMILES: Cc1ccc(C(=O)N2CCC(Oc3ccc(Cl)cc3)CC2)cc1NS(C)(=O)=O] | | | 421 | 1.73 min. | Method A |
| Example 398 | 1-(3-(4-(4-chlorophenoxy)piperidine-1-carbonyl)phenyl)ethanone | 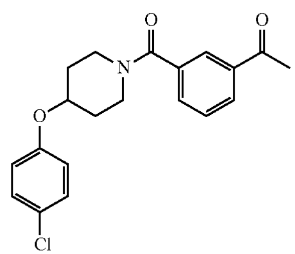 [SMILES: CC(=O)c1cccc(C(=O)N2CCC(Oc3ccc(Cl)cc3)CC2)c1] | | | 357.8 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 399 | (4-(4-chlorophenoxy)piperidin-1-yl)(1-(2-hydroxyethyl)-2-methyl-1H-benzo[d]imidazol-5-yl)methanone | 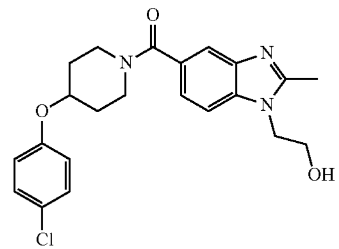 [SMILES: Cc1nc2cc(C(=O)N3CCC(Oc4ccc(Cl)cc4)CC3)ccc2n1CCO] | | | 413.8 | 1.52 min. | Method A |
| Example 400 | (4-(4-chlorophenoxy)piperidin-1-yl)(6-ethoxypyridin-2-yl)methanone | 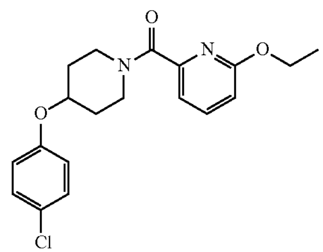 [SMILES: CCOc1cccc(C(=O)N2CCC(Oc3ccc(Cl)cc3)CC2)n1] | | | 360.8 | 1.99 min. | Method A |
| Example 401 | (4-(4-chlorophenoxy)piperidin-1-yl)(4-hydroxy-7-methyl-1,8-naphthyridin-3-yl)methanone | 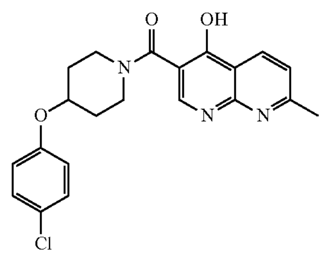 [SMILES: Cc1ccc2c(O)c(C(=O)N3CCC(Oc4ccc(Cl)cc4)CC3)cnc2n1] | | | 396 | 1.52 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 402 | N-(6-(4-(4-chlorophenoxy)piperidine-1-carbonyl)pyridin-2-yl)acetamide | 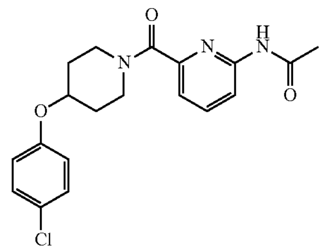 | | | 372 | 1.65 min. | Method A |
| Example 403 | N-(4-(4-(4-chlorophenoxy)piperidine-1-carbonyl)pyridin-2-yl)acetamide | 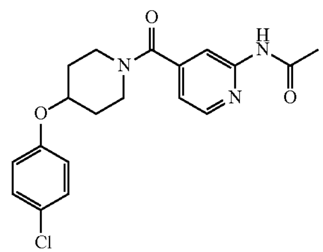 [SMILES: CC(=O)Nc1cc(C(=O)N2CCC(Oc3ccc(Cl)cc3)CC2)ccn1] | | | 372 | 1.60 min. | Method A |
| Example 404 | N-(5-(4-(4-chlorophenoxy)piperidine-1-carbonyl)pyridin-2-yl)acetamide | 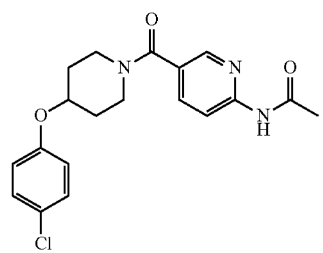 [SMILES: CC(=O)Nc1ccc(C(=O)N2CCC(Oc3ccc(Cl)cc3)CC2)cn1] | | | 372 | 1.60 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 405 | (4-(4-chlorophenoxy)piperidin-1-yl)(3-hydroxypyridin-2-yl)methanone | 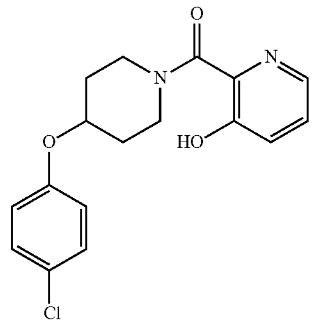 [SMILES: O=C(c1ncccc1O)N1CCC(Oc2ccc(Cl)cc2)CC1] | | | 331 | 1.65 min. | Method A |
| Example 406 | (4-bromo-1-methoxynaphthalen-2-yl)(4-(4-chlorophenoxy)piperidin-1-yl)methanone | 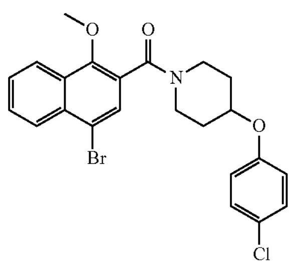 [SMILES: COc1c(C(=O)N2CCC(Oc3ccc(Cl)cc3)CC2)cc(Br)c2ccccc12] | | | 473.7 | 2.25 min. | Method A |
| Example 407 | 6-(4-(4-chlorophenoxy)piperidine-1-carbonyl)isoindolin-1-one | 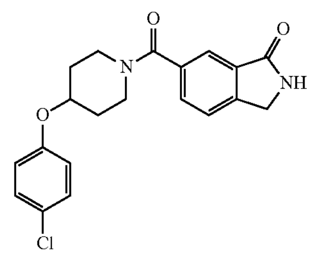 [SMILES: O=C1NCc2ccc(C(=O)N3CCC(Oc4ccc(Cl)cc4)CC3)cc21] | | | 369.1 | 1.55 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 408 | (4-(4-chlorophenoxy)piperidin-1-yl)(quinoxalin-5-yl)methanone | 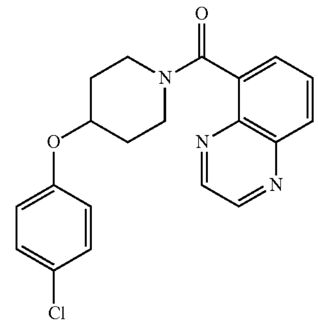 | | | 367.8 | 1.70 min. | Method A |
| Example 409 | (4-(4-chlorophenoxy)piperidin-1-yl)(1,6-naphthyridin-5-yl)methanone | 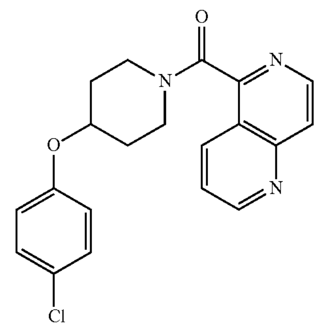 | | | 366.6 | 1.65 min. | Method A |
| Example 410 | (4-(4-chlorophenoxy)piperidin-1-yl)(4-hydroxyphenyl)methanone | 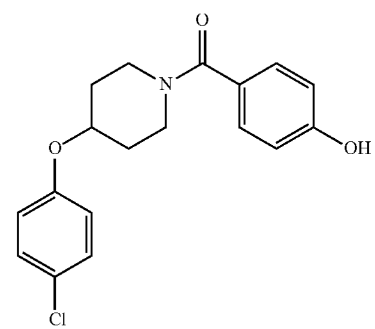 [SMILES: O=C(c1ccc(O)cc1)N1CCC(Oc2ccc(Cl)cc2)CC1] | | | 330.1 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 411 | (4-(4-chlorophenoxy) piperidin-1-yl)(4-ethoxy-2-hydroxyphenyl) methanone | 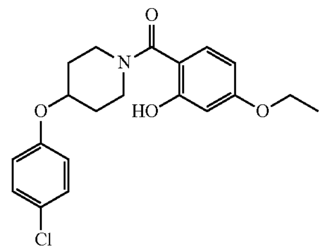 [SMILES: CCOc1ccc(C(=O)N2CCC(Oc3ccc(Cl)cc3)CC2)c(O)c1] | | | 374.1 | 1.92 min. | Method A |
| Example 412 | (4-(4-chlorophenoxy) piperidin-1-yl)(3-hydroxyphenyl) methanone | 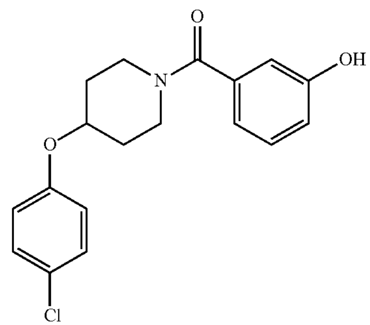 [SMILES: O=C(c1cccc(O)c1)N1CCC(Oc2ccc(Cl)cc2)CC1] | | | 330.1 | 1.70 min. | Method A |
| Example 413 | (4-(4-chlorophenoxy) piperidin-1-yl)(2-hydroxyphenyl) methanone | 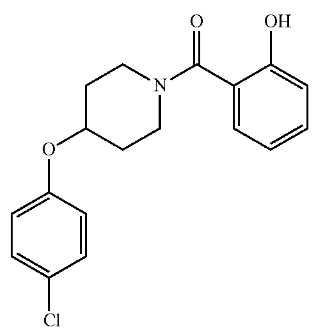 [SMILES: O=C(c1ccccc1O)N1CCC(Oc2ccc(Cl)cc2)CC1] | | | 330.1 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 414 | (4-(4-chlorophenoxy)piperidin-1-yl)(2,4-dihydroxyphenyl)methanone | 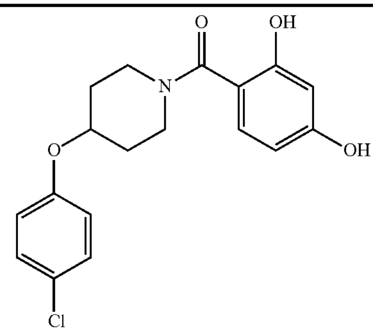 | | | 346.1 | 1.62 min. | Method A |
| Example 415 | (4-(4-chlorophenoxy)piperidin-1-yl)(4-hydroxy-3,5-dimethoxyphenyl)methanone | 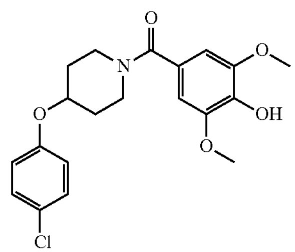 [SMILES: COc1cc(C(=O)N2CCC(Oc3ccc(Cl)cc3)CC2)cc(OC)c1O] | | | 390.1 | 1.69 min. | Method A |
| Example 416 | (4-(4-chlorophenoxy)piperidin-1-yl)(4-hydroxy-2-methylphenyl)methanone | 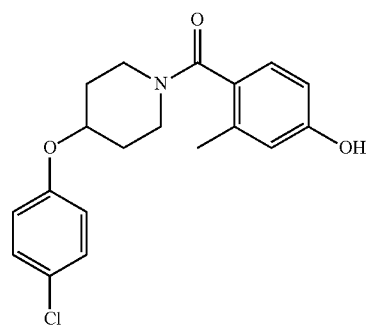 [SMILES: Cc1cc(O)ccc1C(=O)N1CCC(Oc2ccc(Cl)cc2)CC1] | | | 344.1 | 1.71 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 417 | (4-(4-chlorophenoxy)piperidin-1-yl)(5-hydroxy-2-methylphenyl)methanone | 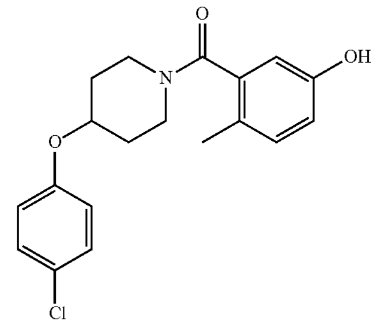 [SMILES: Cc1ccc(O)cc1C(=O)N1CCC(Oc2ccc(Cl)cc2)CC1] | | | 344.1 | 1.75 min. | Method A |
| Example 418 | (3-chloro-2-hydroxyphenyl)(4-(4-chlorophenoxy)piperidin-1-yl)methanone | 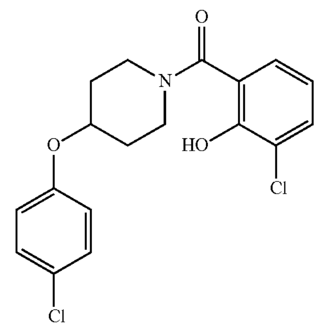 [SMILES: O=C(c1cccc(Cl)c1O)N1CCC(Oc2ccc(Cl)cc2)CC1] | | | 364 | 1.88 min. | Method A |
| Example 419 | (4-(4-chlorophenoxy)piperidin-1-yl)(3-fluoro-2-hydroxyphenyl)methanone | 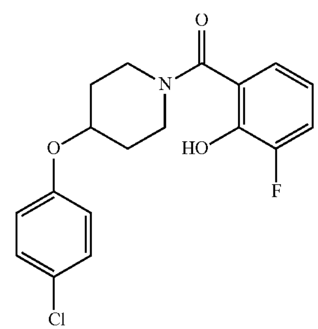 [SMILES: O=C(c1cccc(F)c1O)N1CCC(Oc2ccc(Cl)cc2)CC1] | | | 348.1 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 420 | 2-(5-(4-(4-chlorophenoxy)piperidine-1-carbonyl)-2-methylphenoxy)acetamide | 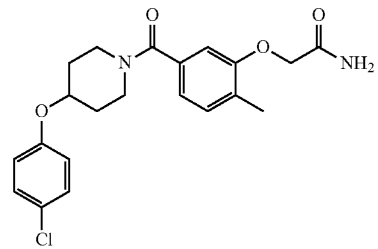 [SMILES: Cc1ccc(C(=O)N2CCC(Oc3ccc(Cl)cc3)CC2)cc1OCC(N)=O] | | | 401.1 | 1.68 min. | Method A |
| Example 421 | 2-(2-(4-(4-chlorophenoxy)piperidine-1-carbonyl)-5-methylphenoxy)acetamide | 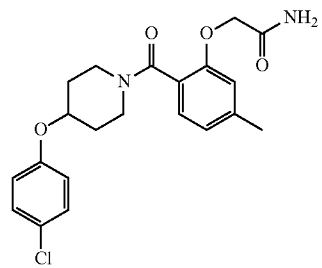 [SMILES: Cc1ccc(C(=O)N2CCC(Oc3ccc(Cl)cc3)CC2)c(OCC(N)=O)c1] | | | 401.1 | 1.72 min. | Method A |
| Example 422 | (4-(4-chlorophenoxy)piperidin-1-yl)(2,6-dihydroxyphenyl)methanone | 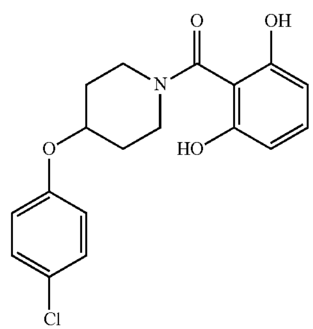 [SMILES: O=C(c1c(O)cccc1O)N1CCC(Oc2ccc(Cl)cc2)CC1] | | | 346.1 | 1.54 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 423 | (4-(4-chlorophenoxy)piperidin-1-yl)(2-fluoro-3-hydroxyphenyl)methanone | 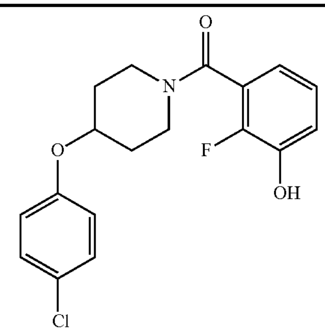 | | | 348 | 1.71 min. | Method A |
| Example 424 | (4-(4-chlorophenoxy)piperidin-1-yl)(2-fluoro-5-hydroxyphenyl)methanone | 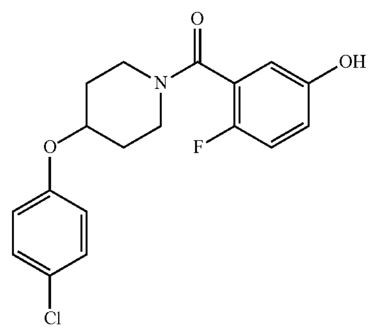 [SMILES: O=C(c1cc(O)ccc1F)N1CCC(Oc2ccc(Cl)cc2)CC1] | | | 348 | 1.75 min. | Method A |
| Example 425 | (2-chloro-5-hydroxyphenyl)(4-(4-chlorophenoxy)piperidin-1-yl)methanone | 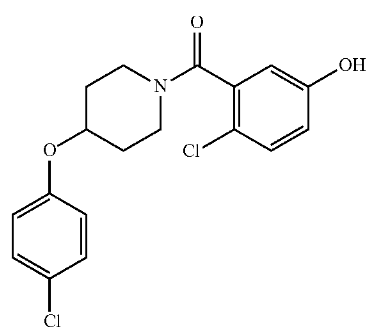 [SMILES: O=C(c1cc(O)ccc1Cl)N1CCC(Oc2ccc(Cl)cc2)CC1] | | | 364 | 1.80 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 426 | (3-(tert-butyl)-1-methyl-1H-pyrazol-5-yl)(4-(4-fluorophenoxy)piperidin-1-yl)methanone | 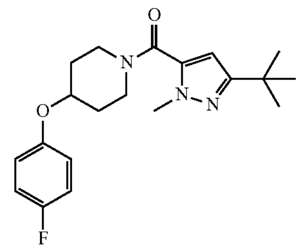 [SMILES: Cn1nc(C(C)(C)C)cc1C(=O)N1CCC(Oc2ccc(F)cc2)CC1] | | | 359.9 | 1.90 min. | Method A |
| Example 427 | (4-fluoro-3-methoxyphenyl)(4-(4-fluorophenoxy)piperidin-1-yl)methanone | 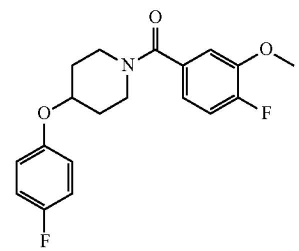 [SMILES: COc1cc(C(=O)N2CCC(Oc3ccc(F)cc3)CC2)ccc1F] | | | 347.8 | 1.79 min. | Method A |
| Example 428 | (4-((4-chlorophenyl)sulfonyl)piperidin-1-yl)(2-methyl-2H-indazol-3-yl)methanone | 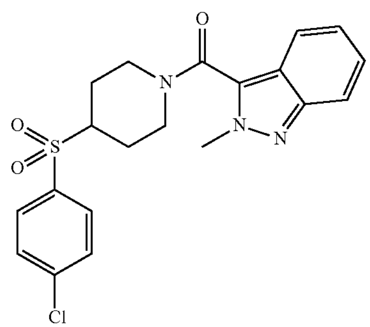 [SMILES: Cn1nc2ccccc2c1C(=O)N1CCC(S(=O)(=O)c2ccc(Cl)cc2)CC1] | | | 416 | 1.61 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 429 | (4-(4-fluorophenoxy) piperidin-1-yl)(4-fluorophenyl) methanone | 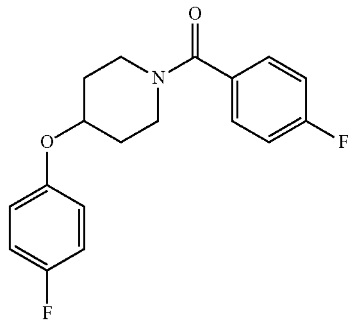 [SMILES: O=C(c1ccc(F)cc1)N1CCC(Oc2ccc(F)cc2)CC1] | | | 317.9 | 1.78 min. | Method A |
| Example 430 | (5-(tert-butyl)isoxazol-3-yl) (4-(4-fluorophenoxy) piperidin-1-yl)methanone | 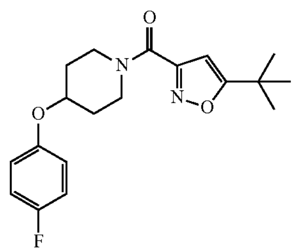 [SMILES: CC(C)(C)c1cc(C(=O)N2CCC(Oc3ccc(F)cc3)CC2)no1] | | | 346.9 | 1.97 min. | Method A |
| Example 431 | (4-(4-fluorophenoxy) piperidin-1-yl)(1-methyl-5-(trifluoromethyl)-1H-pyrazol-3-yl) methanone | 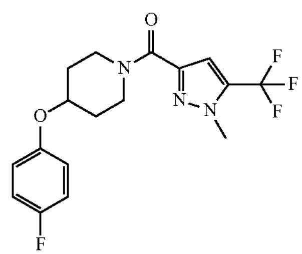 [SMILES: Cn1nc(C(=O)N2CCC(Oc3ccc(F)cc3)CC2)cc1C(F)(F)F] | | | 371.8 | 1.84 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 432 | (4-(4-fluorophenoxy)-piperidin-1-yl)(1-methyl-1H-indazol-3-yl)methanone | 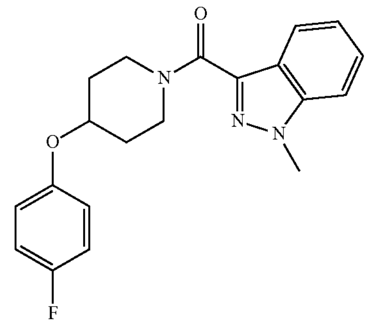 [SMILES: Cn1nc(C(=O)N2CCC(Oc3ccc(F)cc3)CC2)c2ccccc21] | | | 353.9 | 1.83 min. | Method A |
| Example 433 | (4-(4-fluorophenoxy)-piperidin-1-yl)(quinoxalin-2-yl)methanone | 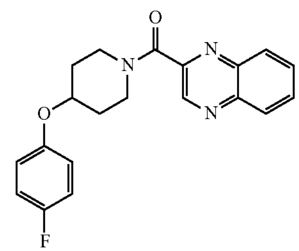 [SMILES: O=C(c1cnc2ccccc2n1)N1CCC(Oc2ccc(F)cc2)CC1] | | | 351.8 | 1.77 min. | Method A |
| Example 434 | (4-(4-fluorophenoxy)-piperidin-1-yl)(4-methoxyquinolin-2-yl)methanone | 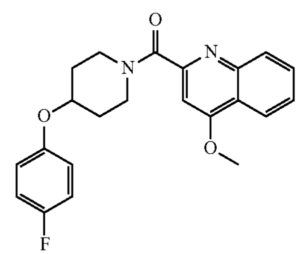 [SMILES: COc1cc(C(=O)N2CCC(Oc3ccc(F)cc3)CC2)nc2ccccc12] | | | 380.8 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 435 | (4-(4-fluorophenoxy) piperidin-1-yl)(6-methoxyquinolin-2-yl)methanone | 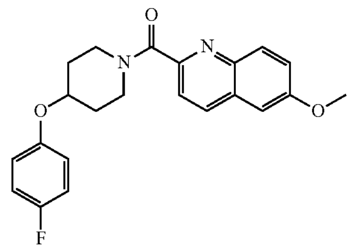 [SMILES: COc1ccc2nc(C(=O)N3CCC(Oc4ccc(F)cc4)CC3)ccc2c1] | | | 380.8 | 1.81 min. | Method A |
| Example 436 | (4-(4-fluorophenoxy) piperidin-1-yl)(isoquinolin-1-yl) methanone | 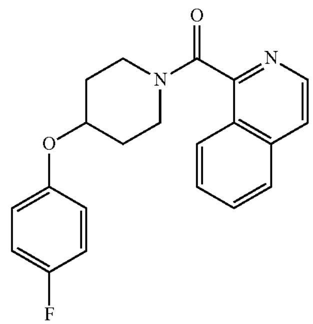 [SMILES: O=C(c1nccc2ccccc12)N1CCC(Oc2ccc(F)cc2)CC1] | | | 350.9 | 1.72 min. | Method A |
| Example 437 | (4-(4-fluorophenoxy) piperidin-1-yl)(isoquinolin-4-yl) methanone | 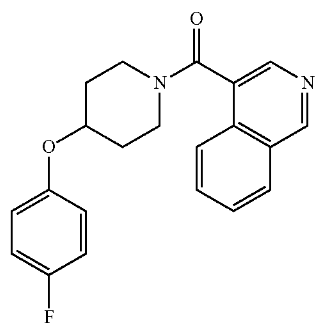 [SMILES: O=C(c1cncc2ccccc12)N1CCC(Oc2ccc(F)cc2)CC1] | | | 350.9 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 438 | (4-(4-fluorophenoxy) piperidin-1-yl)(quinolin-4-yl) methanone | 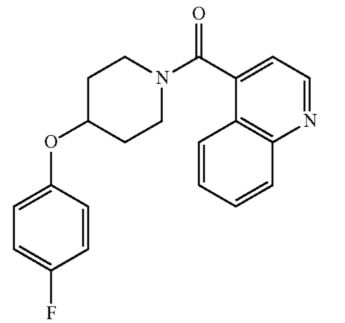 [SMILES: O=C(c1ccnc2ccccc12)N1CCC(Oc2ccc(F)cc2)CC1] | | | 350.9 | 1.65 min. | Method A |
| Example 439 | (5-aminopyridin-2-yl) (4-(4-chlorophenoxy) piperidin-1-yl)methanone | 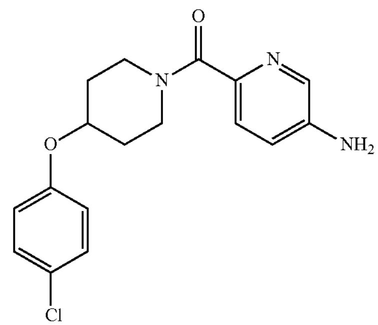 [SMILES: Nc1ccc(C(=O)N2CCC(Oc3ccc(Cl)cc3)CC2)nc1] | | | 330.1 | 1.55 min. | Method A |
| Example 440 | (6-(tert-butyl)pyridin-3-yl) (4-(4-chlorophenoxy) piperidin-1-yl)methanone | 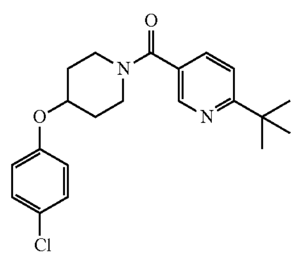 | | | 373.1 | 2.00 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 441 | (6-(tert-butyl)pyridin-3-yl)(4-(4-fluorophenoxy)piperidin-1-yl)methanone | 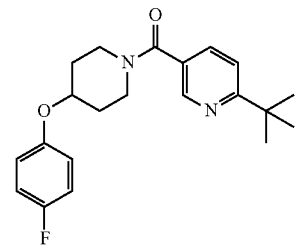 [SMILES: CC(C)(C)c1ccc(C(=O)N2CCC(Oc3ccc(F)cc3)CC2)cn1] | | | 357.1 | 1.88 min. | Method A |
| Example 442 | N-(6-(4-(4-chlorophenoxy)piperidine-1-carbonyl)pyridin-3-yl)acetamide | 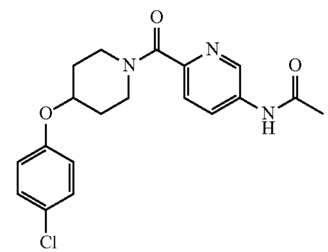 [SMILES: CC(=O)Nc1ccc(C(=O)N2CCC(Oc3ccc(Cl)cc3)CC2)nc1] | | | 372.1 | 1.54 min. | Method A |
| Example 443 | (6-methylpyridin-3-yl)(4-(3-(trifluoromethoxy)phenoxy)piperidin-1-yl)methanone | 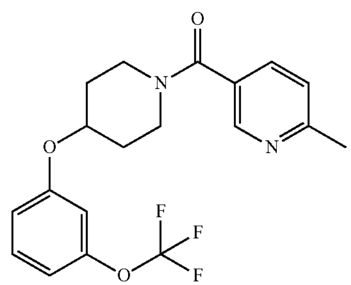 [SMILES: Cc1ccc(C(=O)N2CCC(Oc3cccc(OC(F)(F)F)c3)CC2)cn1] | | | 381 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 444 | (1,3-dimethyl-1H-pyrazol-5-yl)(4-(3-(trifluoromethoxy)phenoxy)piperidin-1-yl)methanone | 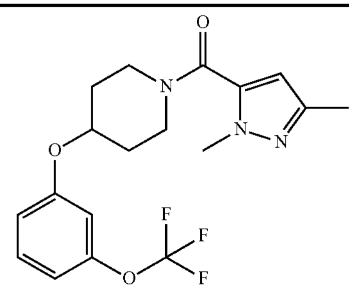 | | | 384 | 1.81 min. | Method A |
| Example 445 | (3,5-dimethylisoxazol-4-yl)(4-(3-(trifluoromethoxy)phenoxy)piperidin-1-yl)methanone | 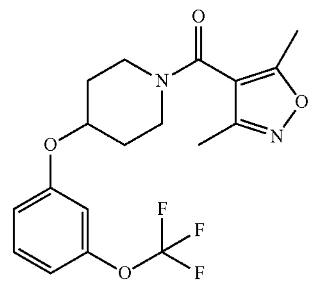 [SMILES: Cc1noc(C)c1C(=O)N1CCC(Oc2cccc(OC(F)(F)F)c2)CC1] | | | 383.3 | 1.83 min. | Method A |
| Example 446 | (6-hydroxypyridin-2-yl)(4-(3-(trifluoromethoxy)phenoxy)piperidin-1-yl)methanone | 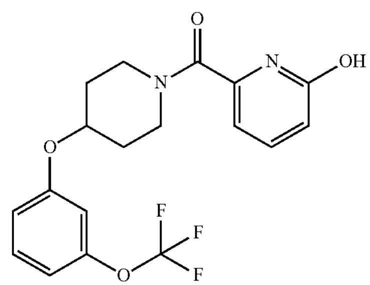 [SMILES: O=C(c1cccc(O)n1)N1CCC(Oc2cccc(OC(F)(F)F)c2)CC1] | | | 381.1 | 1.59 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 447 | (3-methylpyridin-2-yl)(4-(3-(trifluoromethoxy)phenoxy)piperidin-1-yl)methanone | 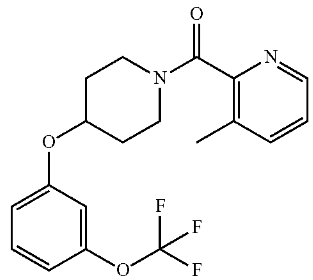 [SMILES: Cc1cccnc1C(=O)N1CCC(Oc2cccc(OC(F)(F)F)c2)CC1] | | | 381 | 1.79 min. | Method A |
| Example 448 | (5-methoxypyridin-3-yl)(4-(3-(trifluoromethoxy)phenoxy)piperidin-1-yl)methanone | 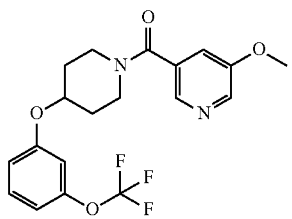 [SMILES: COc1cncc(C(=O)N2CCC(Oc3cccc(OC(F)(F)F)c3)CC2)c1] | | | 397 | 1.76 min. | Method A |
| Example 449 | (5-aminopyridin-3-yl)(4-(3-(trifluoromethoxy)phenoxy)piperidin-1-yl)methanone | 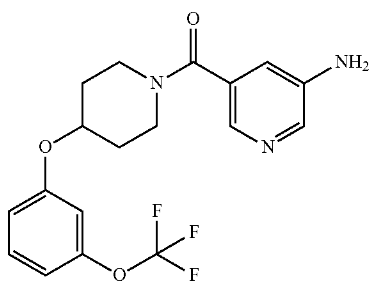 | | | 380.2 | 1.60 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 450 | (6-methoxypyridin-3-yl)(4-(3-(trifluoromethoxy)phenoxy)piperidin-1-yl)methanone | 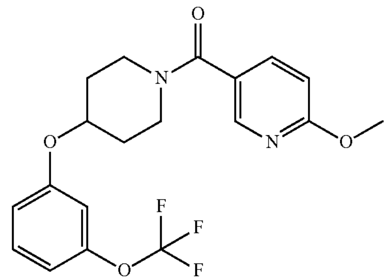 [SMILES: COc1ccc(C(=O)N2CCC(Oc3cccc(OC(F)(F)F)c3)CC2)cn1] | | | 397 | 1.88 min. | Method A |
| Example 451 | 4-(4-(3-(trifluoromethoxy)phenoxy)piperidine-1-carbonyl)picolinamide | 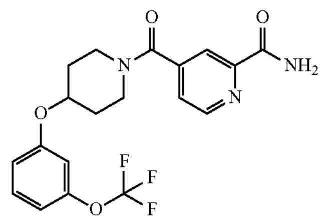 [SMILES: NC(=O)c1cc(C(=O)N2CCC(Oc3cccc(OC(F)(F)F)c3)CC2)ccn1] | | | 408.1 | 1.65 min. | Method A |
| Example 452 | (3-methylisoxazol-5-yl)(4-(3-(trifluoromethoxy)phenoxy)piperidin-1-yl)methanone | 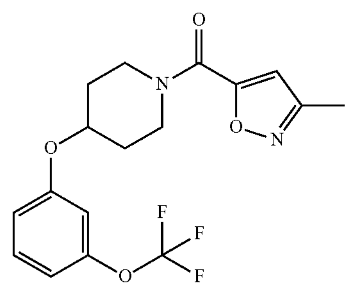 [SMILES: Cc1cc(C(=O)N2CCC(Oc3cccc(OC(F)(F)F)c3)CC2)on1] | | | 371.1 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 453 | (2-methylthiazol-5-yl)(4-(3-(trifluoromethoxy)phenoxy)piperidin-1-yl)methanone | 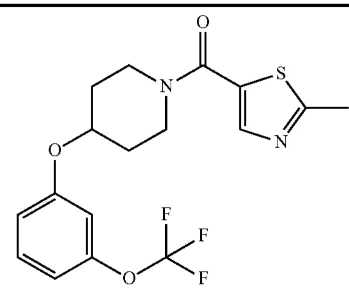 | | | 387 | 1.81 min. | Method A |
| Example 454 | (1-methyl-1H-imidazol-4-yl)(4-(3-(trifluoromethoxy)phenoxy)piperidin-1-yl)methanone | 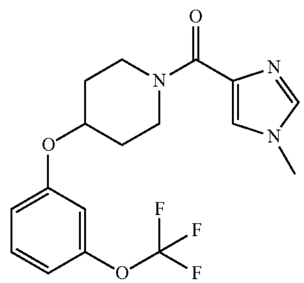 [SMILES: Cn1cnc(C(=O)N2CCC(Oc3cccc(OC(F)(F)F)c3)CC2)c1] | | | 370 | 1.64 min. | Method A |
| Example 455 | (2-hydroxy-6-methoxyphenyl)(4-(3-(trifluoromethoxy)phenoxy)piperidin-1-yl)methanone | 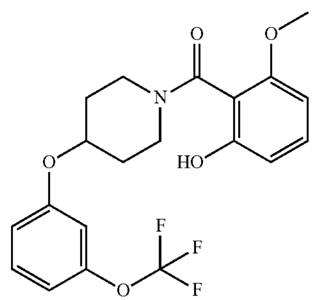 [SMILES: COc1cccc(O)c1C(=O)N1CCC(Oc2cccc(OC(F)(F)F)c2)CC1] | | | 410.1 | 1.78 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 456 | (2,4-dimethylthiazol-5-yl)(4-(3-(trifluoromethoxy)phenoxy)piperidin-1-yl)methanone | 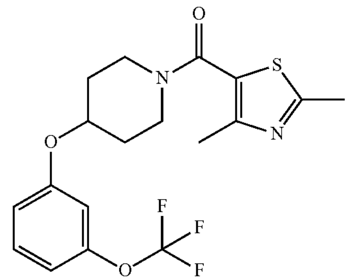 [SMILES: Cc1nc(C)c(C(=O)N2CCC(Oc3cccc(OC(F)(F)F)c3)CC2)s1] | | | 401 | 1.84 min. | Method A |
| Example 457 | (2-methyl-2H-indazol-3-yl)(4-(3-(trifluoromethoxy)phenoxy)piperidin-1-yl)methanone | 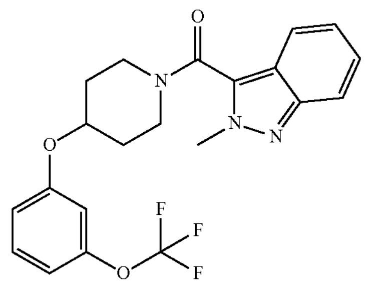 [SMILES: Cn1nc2ccccc2c1C(=O)N1CCC(Oc2cccc(OC(F)(F)F)c2)CC1] | | | 420.1 | 1.93 min. | Method A |
| Example 458 | (2-methyl-2H-indazol-6-yl)(4-(3-(trifluoromethoxy)phenoxy)piperidin-1-yl)methanone | 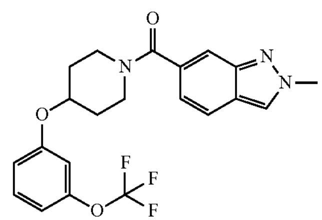 [SMILES: Cn1cc2ccc(C(=O)N3CCC(Oc4cccc(OC(F)(F)F)c4)CC3)cc2n1] | | | 420.1 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 459 | Imidazo[1,2-a]pyridin-8-yl(4-(3-(trifluoromethoxy)phenoxy)piperidin-1-yl)methanone | 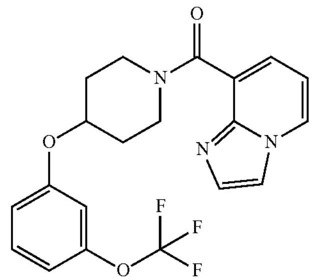 [SMILES: O=C(c1cccn2ccnc12)N1CCC(Oc2cccc(OC(F)(F)F)c2)CC1] | | | 406 | 1.68 min. | Method A |
| Example 460 | (1,8-naphthyridin-2-yl)(4-(3-(trifluoromethoxy)phenoxy)piperidin-1-yl)methanone | 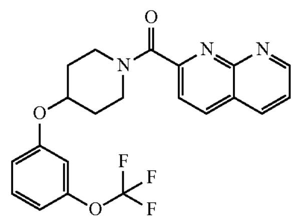 [SMILES: O=C(c1ccc2cccnc2n1)N1CCC(Oc2cccc(OC(F)(F)F)c2)CC1] | | | 418 | 1.70 min. | Method A |
| Example 461 | (1,5-naphthyridin-2-yl)(4-(3-(trifluoromethoxy)phenoxy)piperidin-1-yl)methanone | 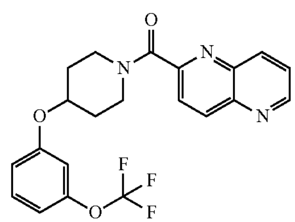 [SMILES: O=C(c1ccc2ncccc2n1)N1CCC(Oc2cccc(OC(F)(F)F)c2)CC1] | | | 418 | 1.78 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 462 | (2-hydroxyquinolin-4-yl)(4-(3-(trifluoromethoxy)phenoxy)piperidin-1-yl)methanone | | | | 431.1 | 1.71 min. | Method A |
| Example 463 | 1,6-dimethyl-3-(4-(3-(trifluoromethoxy)phenoxy)piperidine-1-carbonyl)pyridin-2(1H)-one | | | | 409.2 | 1.65 min. | Method A |
| Example 464 | benzo[d]thiazol-6-yl(4-(4-fluorophenoxy)piperidin-1-yl)methanone | | | | 355.3 | 1.65 min. | Method A |

| Example | Name | Structure | Structure of amine part | Structure of carboxylic acid part | Observed MS | Retention time | QC Method |
|---|---|---|---|---|---|---|---|
| Example 465 | (4-(4-fluorophenoxy)piperidin-1-yl)(2-methyl-1H-benzo[d]imidazol-5-yl)methanone | 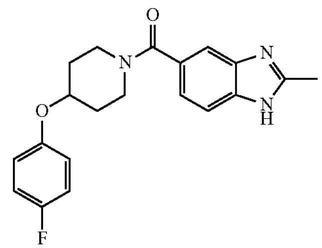 [SMILES: Cc1nc2cc(C(=O)N3CCC(Oc4ccc(F)cc4)CC3)ccc2[nH]1] | | | 352.2 | 1.44 min. | Method A |
| Example 466 | (4-(4-fluorophenoxy)piperidin-1-yl)(1-methyl-1H-benzo[d]imidazol-5-yl)methanone | 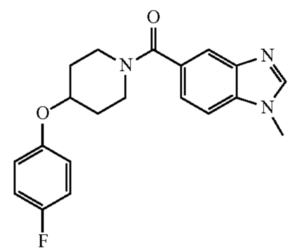 [SMILES: Cn1cnc2cc(C(=O)N3CCC(Oc4ccc(F)cc4)CC3)ccc21] | | | 354.1 | 1.50 min. | Method A |
| Example 467 | (4-(4-fluorophenoxy)piperidin-1-yl)(5-methoxypyridin-2-yl)methanone | 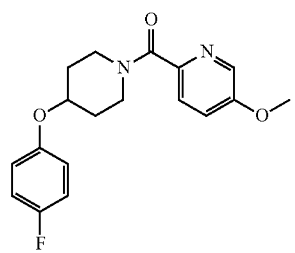 [SMILES: COc1ccc(C(=O)N2CCC(Oc3ccc(F)cc3)CC2)nc1] | | | 331.1 | 1.62 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 468 | (4-(4-fluorophenoxy)piperidin-1-yl)(4-methyl-2-phenylpyrimidin-5-yl)methanone | 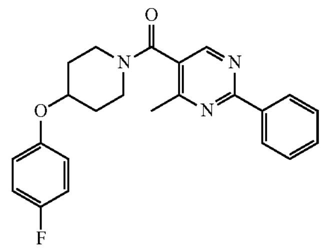 [SMILES: Cc1nc(-c2ccccc2)ncc1C(=O)N1CCC(Oc2ccc(F)cc2)CC1] | | | 390.2 | 1.93 min. | Method A |
| Example 469 | (4-(4-fluorophenoxy)piperidin-1-yl)(1-methyl-1H-benzo[d]imidazol-2-yl)methanone | 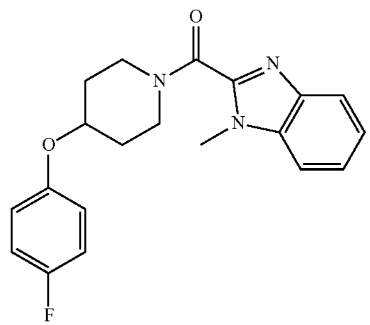 [SMILES: Cn1c(C(=O)N2CCC(Oc3ccc(F)cc3)CC2)nc2ccccc21] | | | 354.1 | 1.71 min. | Method A |
| Example 470 | (4-(4-chlorophenoxy)piperidin-1-yl)(6-ethoxypyridin-3-yl)methanone | 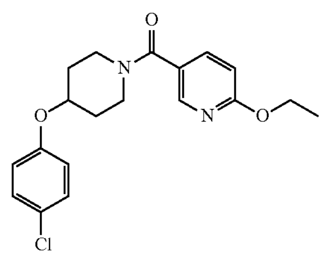 [SMILES: CCOc1ccc(C(=O)N2CCC(Oc3ccc(Cl)cc3)CC2)cn1] | | | 361.1 | 1.90 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 471 | (4-(4-chlorophenoxy)piperidin-1-yl)(6-(dimethylamino)pyridin-3-yl)methanone | 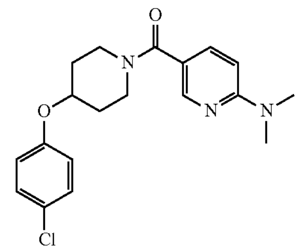 [SMILES: CN(C)c1ccc(C(=O)N2CCC(Oc3ccc(Cl)cc3)CC2)cn1] | | | 360.1 | 1.80 min. | Method A |
| Example 472 | (4-((4-chlorophenyl)sulfonyl)piperidin-1-yl)(quinolin-2-yl)methanone | 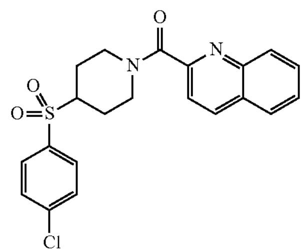 [SMILES: O=C(c1ccc2ccccc2n1)N1CCC(S(=O)(=O)c2ccc(Cl)cc2)CC1] | | | 413.5 | 1.65 min. | Method A |
| Example 473 | (4-((4-chlorophenyl)sulfonyl)piperidin-1-yl)(quinolin-3-yl)methanone | 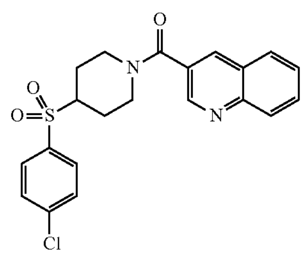 [SMILES: O=C(c1cnc2ccccc2c1)N1CCC(S(=O)(=O)c2ccc(Cl)cc2)CC1] | | | 413.2 | 1.57 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 474 | (4-((4-chlorophenyl)sulfonyl)piperidin-1-yl)(5-methyl-1-phenyl-1H-pyrazol-4-yl)methanone | 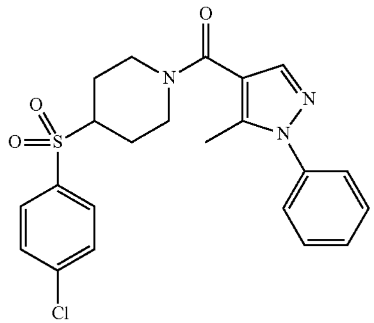 [SMILES: Cc1c(C(=O)N2CCC(S(=O)(=O)c3ccc(Cl)cc3)CC2)cnn1-c1ccccc1] | | | 444.1 | 1.64 min. | Method A |
| Example 475 | (4-((4-chlorophenyl)sulfonyl)piperidin-1-yl)(4-methyoxyquinolin-2-yl)methanone | 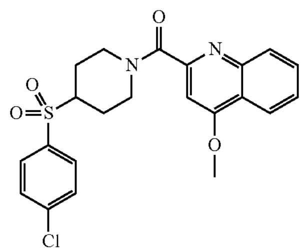 [SMILES: COc1cc(C(=O)N2CCC(S(=O)(=O)c3ccc(Cl)cc3)CC2)nc2ccccc12] | | | 445.1 | 1.71 min. | Method A |
| Example 476 | (4-((4-chlorophenyl)sulfonyl)piperidin-1-yl)(6-ethoxypyridin-2-yl)methanone | 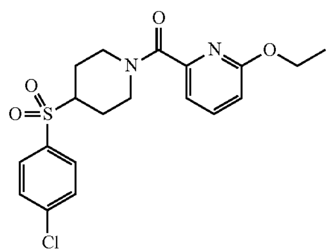 [SMILES: CCOc1cccc(C(=O)N2CCC(S(=O)(=O)c3ccc(Cl)cc3)CC2)n1] | | | 407.1 | 1.70 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 477 | (6-methoxypyridin-2-yl)(4-(3-(trifluoromethoxy)phenoxy)piperidin-1-yl)methanone | 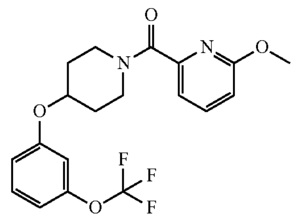 [SMILES: COc1cccc(C(=O)N2CCC(Oc3cccc(OC(F)(F)F)c3)CC2)n1] | | | 397.1 | 1.95 min. | Method A |
| Example 478 | (5-methoxypyrazin-2-yl)(4-(3-(trifluoromethoxy)phenoxy)piperidin-1-yl)methanone | 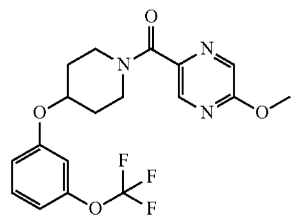 [SMILES: COc1cnc(C(=O)N2CCC(Oc3cccc(OC(F)(F)F)c3)CC2)cn1] | | | 398.1 | 1.89 min. | Method A |
| Example 479 | (2-hydroxy-3-methoxyphenyl)(4-(3-(trifluoromethoxy)phenoxy)piperidin-1-yl)methanone | 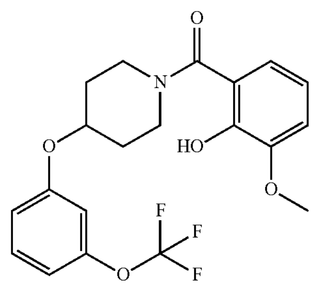 [SMILES: COc1cccc(C(=O)N2CCC(Oc3cccc(OC(F)(F)F)c3)CC2)c1O] | | | 410.3 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 480 | (2-methyloxazol-4-yl)(4-(3-(trifluoromethoxy)phenoxy)piperidin-1-yl)methanone | 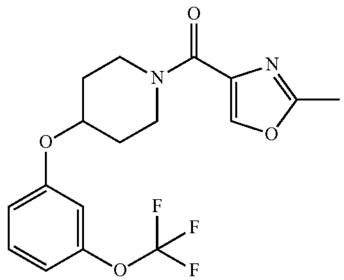 [SMILES: Cc1nc(C(=O)N2CCC(Oc3cccc(OC(F)(F)F)c3)CC2)co1] | | | 371.1 | 1.80 min. | Method A |
| Example 481 | (4-(2-hydroxypropan-2-yl)phenyl)(4-(3-(trifluoromethoxy)phenoxy)piperidin-1-yl)methanone | 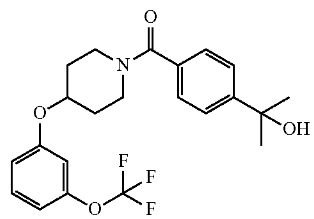 [SMILES: CC(C)(O)c1ccc(C(=O)N2CCC(Oc3cccc(OC(F)(F)F)c3)CC2)cc1] | | | 424.2 | 1.83 min. | Method A |
| Example 482 | (5-ethoxypyridin-2-yl)(4-(3-(trifluoromethoxy)phenoxy)piperidin-1-yl)methanone | 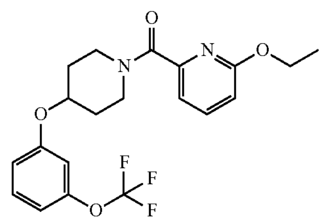 [SMILES: CCOc1cccc(C(=O)N2CCC(Oc3cccc(OC(F)(F)F)c3)CC2)n1] | | | 411.2 | 2.03 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 483 | (1H-benzo[d]imidazol-6-yl)(4-(3-(trifluoromethoxy)phenoxy)piperidin-1-yl)methanone | 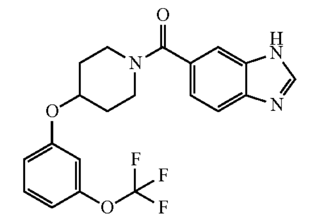 [SMILES: O=C(c1ccc2nc[nH]c2c1)N1CCC(Oc2cccc(OC(F)(F)F)c2)CC1] | | | 404.3 | 1.62 min. | Method A |
| Example 484 | Imidazo[1,2-a]pyrazin-2-yl(4-(3-(trifluoromethoxy)phenoxy)piperidin-1-yl)methanone | 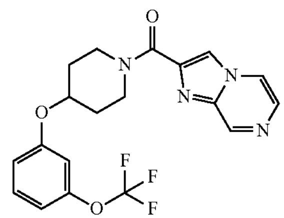 [SMILES: O=C(c1cn2ccncc2n1)N1CCC(Oc2cccc(OC(F)(F)F)c2)CC1] | | | 405.1 | 1.66 min. | Method A |
| Example 485 | (4-hydroxy-7-methyl-1,8-napthyridin-3-yl)(4-(3-(trifluoromethoxy)phenoxy)piperidin-1-yl)methanone | 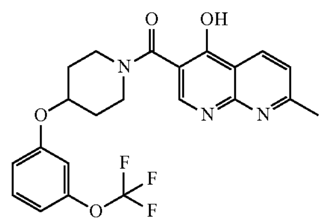 [SMILES: Cc1ccc2c(O)c(C(=O)N3CCC(Oc4cccc(OC(F)(F)F)c4)CC3)cnc2n1] | | | 446.3 | 1.62 min. | Method A |
| Example 486 | N-(4-(4-(3-(trifluoromethoxy)phenoxy)piperidine-1-carbonyl)pyridin-2-yl)acetamide | 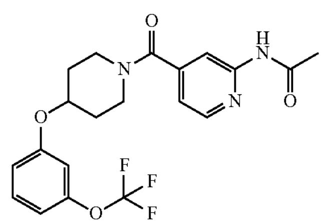 [SMILES: CC(=O)Nc1cc(C(=O)N2CCC(Oc3cccc(OC(F)(F)F)c3)CC2)ccn1] | | | 422.3 | 1.70 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 487 | N-(6-(4-(3-(trifluoromethoxy)phenoxy)piperidin-1-carbonyl)pyridin-2-yl)acetamide | 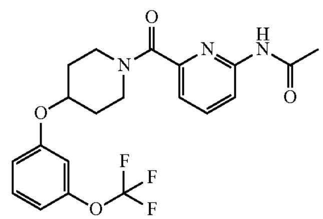 | | | 422.3 | 1.74 min. | Method A |
| Example 488 | (4-((4-chlorophenyl)sulfonyl)piperidin-1-yl)(p-tolyl)methanone | 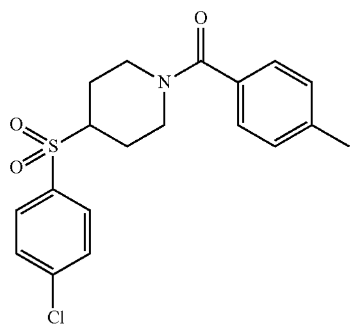 [SMILES: Cc1ccc(C(=O)N2CCC(S(=O)(=O)c3ccc(Cl)cc3)CC2)cc1] | | | 376.1 | 1.71 min. | Method A |
| Example 489 | (4-((4-chlorophenyl)sulfonyl)piperidin-1-yl)(4-methoxyphenyl)methanone | 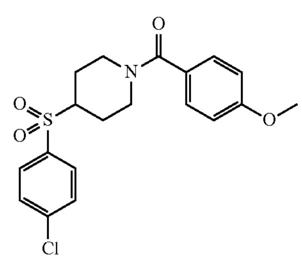 [SMILES: COc1ccc(C(=O)N2CCC(S(=O)(=O)c3ccc(Cl)cc3)CC2)cc1] | | | 394.1 | 1.63 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 490 | (4-chlorophenyl)(4-((4-chlorophenyl)sulfonyl)piperidin-1-yl)methanone | 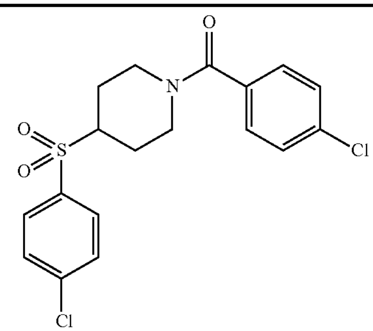 | | | 396.2 | 1.74 min. | Method A |
| Example 491 | (4-((4-chlorophenyl)sulfonyl)piperidin-1-yl)(1,5-naphthyridin-2-yl)methanone | 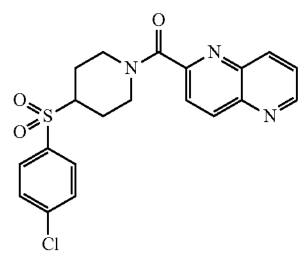 [SMILES: O=C(c1ccc2ncccc2n1)N1CCC(S(=O)(=O)c2ccc(Cl)cc2)CC1] | | | 413.9 | 1.45 min. | Method A |
| Example 492 | (4-((4-chlorophenyl)sulfonyl)piperidin-1-yl)(6-methoxy-1-methyl-1H-indol-2-yl)methanone | 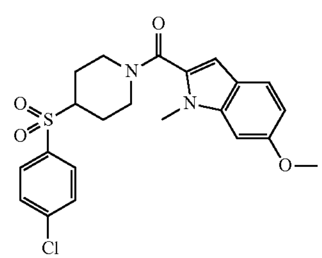 [SMILES: COc1ccc2cc(C(=O)N3CCC(S(=O)(=O)c4ccc(Cl)cc4)CC3)n(C)c2c1] | | | 445.9 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 493 | quinolin-8-yl(4-((3-(trifluoromethyl)phenyl)sulfonyl)piperidin-1-yl)methanone | 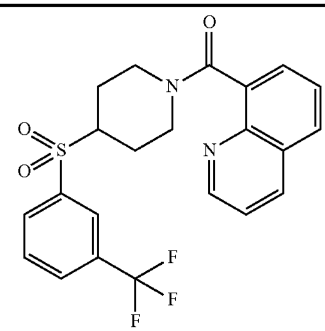 | | | 449 | 1.60 min. | Method A |
| Example 494 | quinolin-8-yl(4-tosylpiperidin-1-yl)methanone | 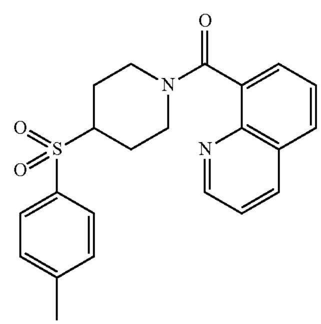 [SMILES: Cc1ccc(S(=O)(=O)C2CCN(C(=O)c3cccc4cccnc34)CC2)cc1] | | | 393.3 | 1.49 min. | Method A |
| Example 495 | (4-((4-chlorophenyl)sulfonyl)piperidin-1-yl)isoquinolin-3-yl)methanone | 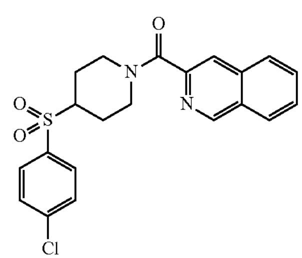 [SMILES: O=C(c1cc2ccccc2cn1)N1CCC(S(=O)(=O)c2ccc(Cl)cc2)CC1] | | | 415 | 1.61 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 496 | 4-(4-(3-(trifluoromethoxy)phenoxy)piperidine-1-carbonyl)benzamide | 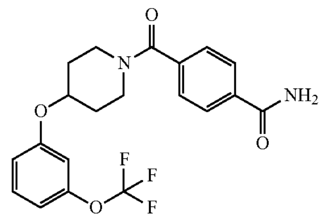 [SMILES: NC(=O)c1ccc(C(=O)N2CCC(Oc3cccc(OC(F)(F)F)c3)CC2)cc1] | | | 407.3 | 1.64 min. | Method A |
| Example 497 | 3-(4-(3-(trifluoromethoxy)phenoxy)piperidine-1-carbonyl)benzamide | 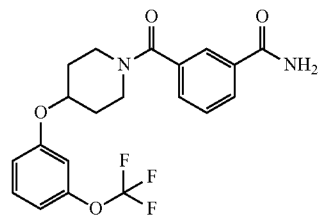 [SMILES: NC(=O)c1cccc(C(=O)N2CCC(Oc3cccc(OC(F)(F)F)c3)CC2)c1] | | | 407.2 | 1.65 min. | Method A |
| Example 498 | 3-(4-(3-chlorophenoxy)piperidine-1-carbonyl)benzamide | 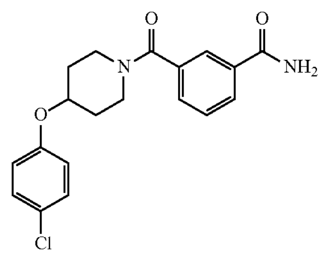 | | | 357.2 | 1.56 min. | Method A |
| Example 499 | 3-(4-(4-chlorophenoxy)piperidine-1-carbonyl)-N-methylbenzamide | 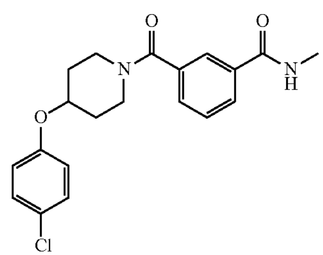 [SMILES: CNC(=O)c1cccc(C(=O)N2CCC(Oc3ccc(Cl)cc3)CC2)c1] | | | 371.2 | 1.62 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 500 | 4-(4-(4-chlorophenoxy)piperidine-1-carbonyl)-N-methylbenzamide | 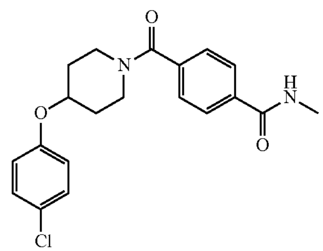 | | | 371.2 | 1.60 min. | Method A |
| Example 501 | (4-hydroxyquinolin-2-yl)(4-(3-(trifluoromethoxy)phenoxy)piperidin-1-yl)methanone | 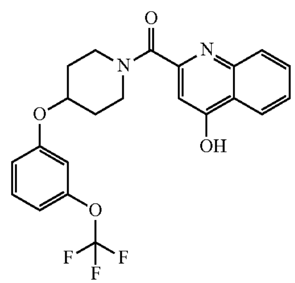 [SMILES: O=C(c1cc(O)c2ccccc2n1)N1CCC(Oc2cccc(OC(F)(F)F)c2)CC1] | | | 431.3 | 1.63 min. | Method A |
| Example 502 | (3-hydroxyquinoxalin-2-yl)(4-(3-(trifluoromethoxy)phenoxy)piperidin-1-yl)methanone | 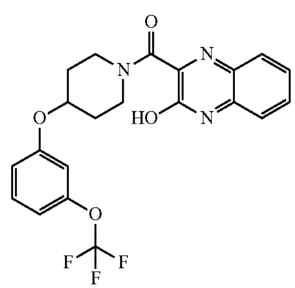 [SMILES: O=C(c1nc2ccccc2nc1O)N1CCC(Oc2cccc(OC(F)(F)F)c2)CC1] | | | 432.3 | 1.74 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 503 | (6-(hydroxymethyl)pyridin-2-yl)(4-(3-(trifluoromethoxy)phenoxy)piperidin-1-yl)methanone | 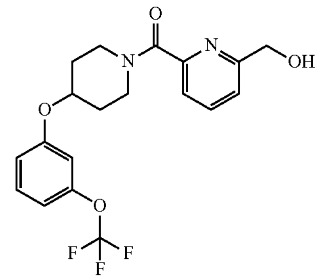 [SMILES: O=C(c1cccc(CO)n1)N1CCC(Oc2cccc(OC(F)(F)F)c2)CC1] | | | 395.3 | 1.64 min. | Method A |
| Example 504 | (1-(2-hydroxyethyl)-2-methyl-1H-benzo[d]imidazol-5-yl)(4-(3-(trifluoromethoxy)phenoxy)piperidin-1-yl)methanone | 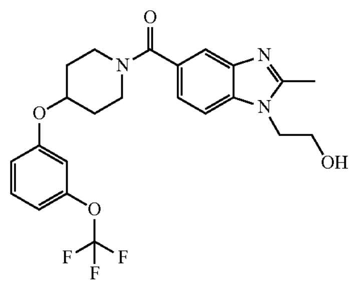 [SMILES: Cc1nc2cc(C(=O)N3CCC(Oc4cccc(OC(F)(F)F)c4)CC3)ccc2n1CCO] | | | 464.1 | 1.60 min. | Method A |
| Example 505 | (2-hydroxy-6-methylpyridin-4-yl)(4-(3-(trifluoromethoxy)phenoxy)piperidin-1-yl)methanone | 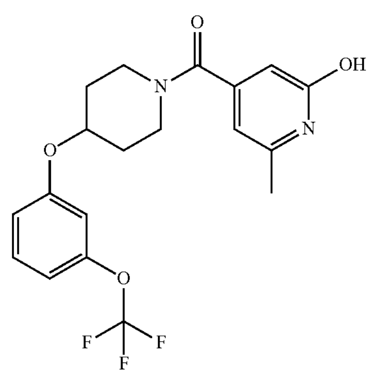 [SMILES: Cc1cc(C(=O)N2CCC(Oc3cccc(OC(F)(F)F)c3)CC2)cc(O)n1] | | | 395.3 | 1.57 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 506 | 1-methyl-4-(4-(3-(trifluoromethoxy)phenoxy)piperidine-1-carbonyl)pyridin-2(1H)-one | 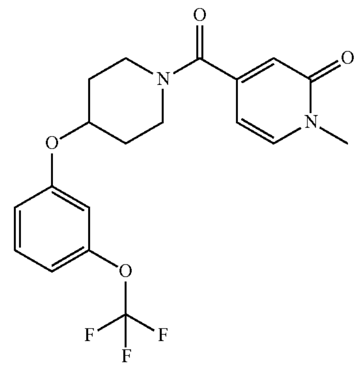 [SMILES: Cn1ccc(C(=O)N2CCC(Oc3cccc(OC(F)(F)F)c3)CC2)cc1=O] | | | 395.4 | 1.59 min. | Method A |
| Example 507 | (2-hydroxy-6-methylpyridin-3-yl)(4-(3-(trifluoromethoxy)phenoxy)piperidin-1-yl)methanone | 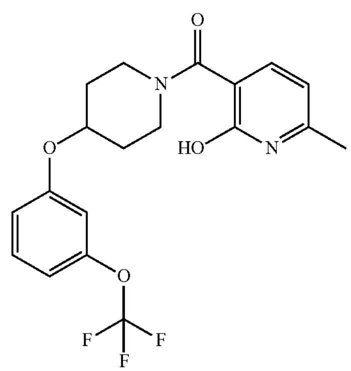 [SMILES: Cc1ccc(C(=O)N2CCC(Oc3cccc(OC(F)(F)F)c3)CC2)c(O)n1] | | | 395.3 | 1.56 min. | Method A |

| Example | Name | Structure | Structure of amine part | Structure of carboxylic acid part | Observed MS | Retention time | QC Method |
|---|---|---|---|---|---|---|---|
| Example 508 | 3-(4-(3-(trifluoromethoxy)phenoxy)piperidine-1-carbonyl)quinolin-2(1H)-one | 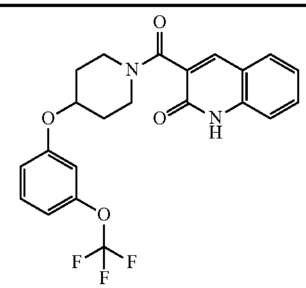 | | | 431.3 | 1.72 min. | Method A |
| Example 509 | (1H-1,2,4-triazol-3-yl)(4-(3-(trifluoromethoxy)phenoxy)piperidin-1-yl)methanone | 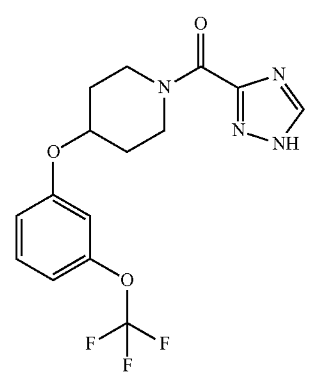 [SMILES: O=C(c1nc[nH]n1)N1CCC(Oc2cccc(OC(F)(F)F)c2)CC1] | | | 355.3 | 1.57 min. | Method A |
| Example 510 | 2-cyclopropyl-6-methyl-5-(4-(3-(trifluoromethoxy)phenoxy)piperidine-1-carbonyl)pyrimidin-4(1H)-one | 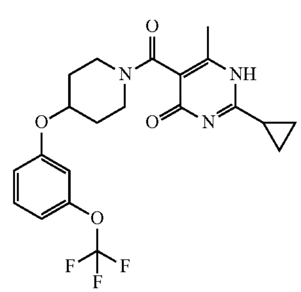 [SMILES: Cc1[nH]c(C2CC2)nc(=O)c1C(=O)N1CCC(Oc2cccc(OC(F)(F)F)c2)CC1] | | | 436.3 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 511 | 5,6-dimethyl-3-(4-(3-(trifluoromethoxy)phenoxy)piperidine-1-carbonyl)pyridin-2(1H)-one | 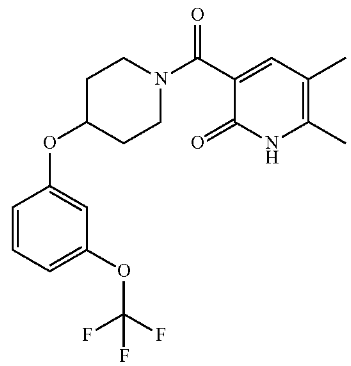 [SMILES: Cc1cc(C(=O)N2CCC(Oc3cccc(OC(F)(F)F)c3)CC2)c(=O)[nH]c1C] | | | 409.3 | 1.62 min. | Method A |
| Example 512 | (4-(3-(trifluoromethoxy)phenoxy)piperidin-1-yl)(1,3,6-trimethyl-1H-pyrazolo[3,4-b]pyridin-4-yl)methanone | 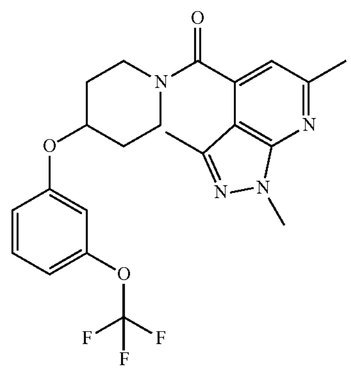 [SMILES: Cc1cc(C(=O)N2CCC(Oc3cccc(OC(F)(F)F)c3)CC2)c2c(C)nn(C)c2n1] | | | 449.1 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 513 | 4-(4-(3-(trifluoromethoxy)phenoxy)piperidine-1-carbonyl)-1H-benzo[d]imidazol-2(3H)-one | 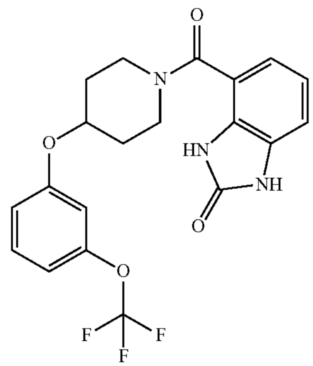 [SMILES: O=C(c1cccc2[nH]c(=O)[nH]c12)N1CCC(Oc2cccc(OC(F)(F)F)c2)CC1] | | | 420.2 | 1.65 min. | Method A |
| Example 514 | (4-(4-chloro-2-methoxyphenoxy)piperidin-1-yl)(quinolin-8-yl)methanone | 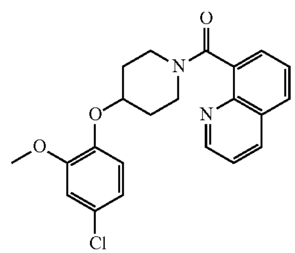 [SMILES: COc1cc(Cl)ccc1OC1CCN(C(=O)c2cccc3cccnc23)CC1] | | | 397.1 | 1.74 min. | Method A |
| Example 515 | 1-(5-chloro-2-((1-(quinoline-8-carbonyl)piperidin-4-yl)oxy)phenyl)ethanone | 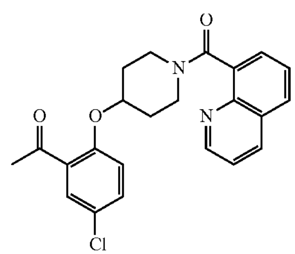 [SMILES: CC(=O)c1cc(Cl)ccc1OC1CCN(C(=O)c2cccc3cccnc23)CC1] | | | 409.1 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 516 | 5-chloro-2-((1-(quinoline-8-carbonyl)piperidin-4-yl)oxy)benzonitrile | 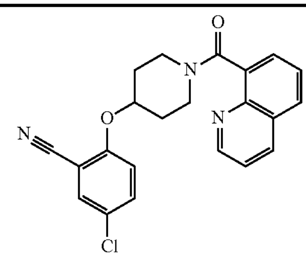 | | | 392.1 | 1.71 min. | Method A |
| Example 517 | (4-((4-chlorophenyl)sulfonyl)piperidin-1-yl)(quinoxalin-2-yl)methanone | 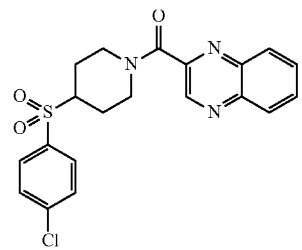 [SMILES: O=C(c1cnc2ccccc2n1)N1CCC(S(=O)(=O)c2ccc(Cl)cc2)CC1] | | | 416 | 1.63 min. | Method A |
| Example 518 | (4-((4-chlorophenyl)sulfonyl)piperidin-1-yl)(6-methoxyquinolin-2-yl)methanone | 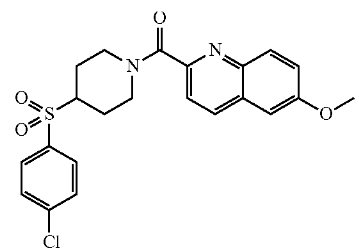 [SMILES: COc1ccc2nc(C(=O)N3CCC(S(=O)(=O)c4ccc(Cl)cc4)CC3)ccc2c1] | | | 445 | 1.68 min. | Method A |
| Example 519 | (4-((4-chlorophenyl)sulfonyl)piperidin-1-yl)(4-methyl-2-phenylpyrimidin-5-yl)methanone | 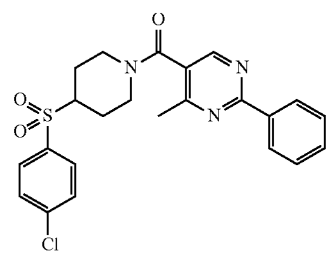 [SMILES: Cc1nc(-c2ccccc2)ncc1C(=O)N1CCC(S(=O)(=O)c2ccc(Cl)cc2)CC1] | | | 454.2 | 1.80 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 520 | (4-(4-chlorophenyl)sulfonyl)piperidin-1-yl)(6-(pyrrolidin-1-yl)pyridin-2-yl)methanone | 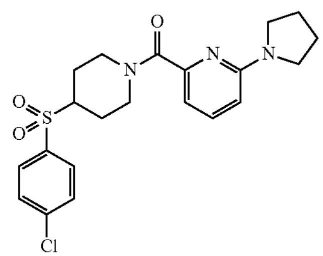 [SMILES: O=C(c1cccc(N2CCCC2)n1)N1CCC(S(=O)(=O)c2ccc(Cl)cc2)CC1] | | | 434.1 | 1.77 min. | Method A |
| Example 521 | (5-(tert-butyl)isoxazol-3-yl)(4-((4-chlorophenyl)sulfonyl)piperidin-1-yl)methanone | 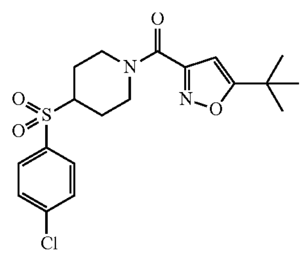 [SMILES: CC(C)(C)c1cc(C(=O)N2CCC(S(=O)(=O)c3ccc(Cl)cc3)CC2)no1] | | | 411.1 | 1.83 min. | Method A |
| Example 522 | (4-(4-chlorophenyl)sulfonyl)piperidin-1-yl)(6-(2,2,2-trifluoromethoxy)pyridin-3-yl)methanone | 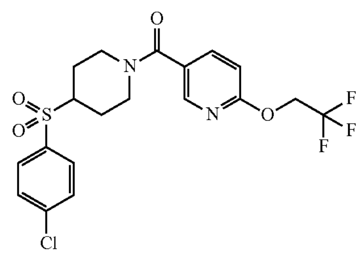 [SMILES: O=C(c1ccc(OCC(F)(F)F)nc1)N1CCC(S(=O)(=O)c2ccc(Cl)cc2)CC1] | | | 461.1 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 523 | (4-(4-chlorophenyl) sulfonyl)piperidin-1-yl)(1-methyl-1H-indol-5-yl)methanone | 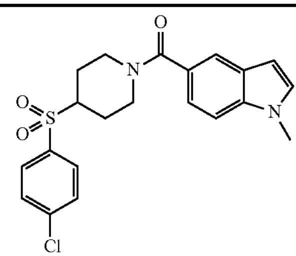 | | | 417 | 1.67 min. | Method A |
| Example 524 | (4-(4-chlorophenyl) sulfonyl)piperidin-1-yl)(1-methyl-1H-indol-2-yl)methanone | 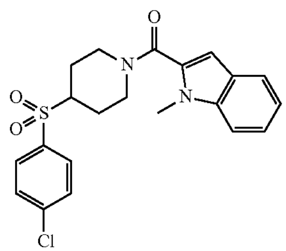 [SMILES: Cn1c(C(=O)N2CCC(S(=O)(=O)c3ccc(Cl)cc3)CC2)cc2ccccc21] | | | 415.1 | 1.80 min. | Method A |
| Example 525 | (4-(3-fluorophenoxy) piperidin-1-yl)(4-fluorophenyl) methanone | 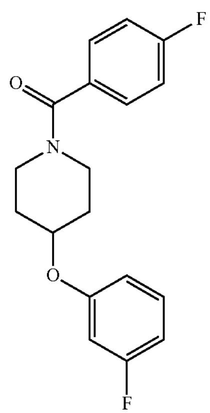 [SMILES: O=C(c1ccc(F)cc1)N1CCC(Oc2cccc(F)c2)CC1] | | | 318.1 | 1.81 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 526 | (4-((4-chlorophenyl)sulfonyl)piperidin-1-yl)(1-methyl-1H-indol-6-yl)methanone | 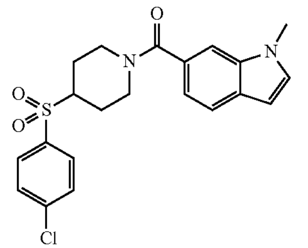 [SMILES: Cn1ccc2ccc(C(=O)N3CCC(S(=O)(=O)c4ccc(Cl)cc4)CC3)cc21] | | | 417 | 1.70 min. | Method A |
| Example 527 | 3-(4-(3-(trifluoromethoxy)phenoxy)piperidine-1-carbonyl)benzamide | 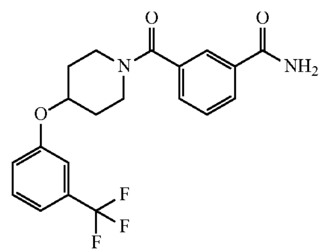 [SMILES: NC(=O)c1cccc(C(=O)N2CCC(Oc3cccc(C(F)(F)F)c3)CC2)c1] | | | 391.3 | 1.61 min. | Method A |
| Example 528 | 4-(4-(3-(trifluoromethoxy)phenoxy)piperidine-1-carbonyl)benzamide | 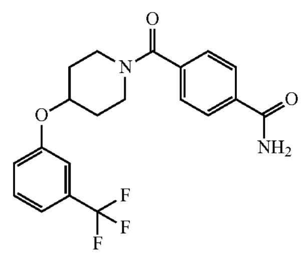 [SMILES: NC(=O)c1ccc(C(=O)N2CCC(Oc3cccc(C(F)(F)F)c3)CC2)cc1] | | | 391.3 | 1.60 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 529 | 4-(4-(3-(trifluoromethoxy)phenoxy)piperidine-1-carbonyl)picolinamide | 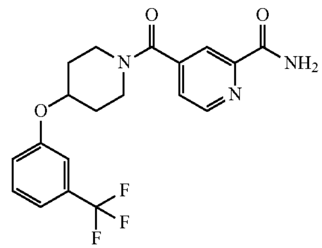 [SMILES: NC(=O)c1cc(C(=O)N2CCC(Oc3cccc(C(F)(F)F)c3)CC2)ccn1] | | | 392.2 | 1.61 min. | Method A |
| Example 530 | (4-((4-chlorophenyl)sulfonyl)piperidin-1-yl)(2-methoxyquinolin-4-yl)methanone | 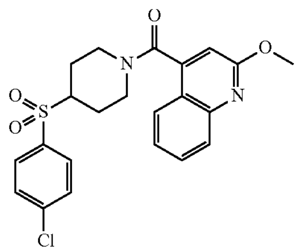 [SMILES: COc1cc(C(=O)N2CCC(S(=O)(=O)c3ccc(Cl)cc3)CC2)c2ccccc2n1] | | | 443.3 | 1.76 min. | Method A |
| Example 531 | (4-((4-chlorophenyl)sulfonyl)piperidin-1-yl)(6-phenoxypyridin-3-yl)methanone | 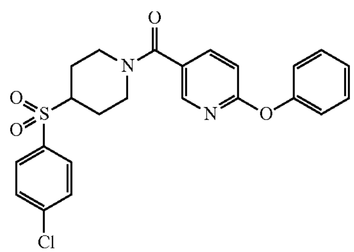 [SMILES: O=C(c1ccc(Oc2ccccc2)nc1)N1CCC(S(=O)(=O)c2ccc(Cl)cc2)CC1] | | | 455.3 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 532 | 3-(4-((4-chlorophenyl)sulfonyl)piperidine-1-carbonyl)quinolin-2(1H)-one | 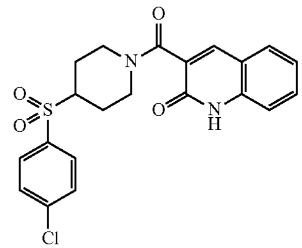 [SMILES: O=C(c1cc2ccccc2[nH]c1=O)N1CCC(S(=O)(=O)c2ccc(Cl)cc2)CC1] | | | 429.2 | 1.44 min. | Method A |
| Example 533 | 3-(4-((4-chlorophenyl)sulfonyl)piperidine-1-carbonyl)-1-methylquinolin-2(1H)-one | 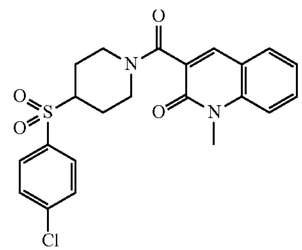 [SMILES: Cn1c(=O)c(C(=O)N2CCC(S(=O)(=O)c3ccc(Cl)cc3)CC2)cc2ccccc21] | | | 445.1 | 1.55 min. | Method A |
| Example 534 | (4-(4-fluorophenoxy)piperidin-1-yl)(5-methyl-1-phenyl-1H-pyrazol-4-yl)methanone | 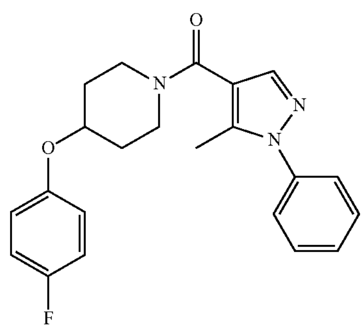 [SMILES: Cc1c(C(=O)N2CCC(Oc3ccc(F)cc3)CC2)cnn1-c1ccccc1] | | | 380.1 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 535 | 4-(4-(4-chlorophenoxy) piperidine-1-carbonyl)-N-(2-methoxyethyl)-N-methylbenzamide | 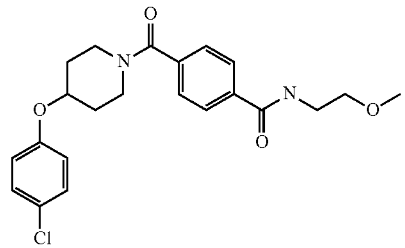 [SMILES: COCCNC(=O)c1ccc(C(=O)N2CCC(Oc3ccc(Cl)cc3)CC2)cc1] | Alternative route | | 431.1 | 1.69 min. | Method A |
| Example 536 | 4-(4-(4-chlorophenoxy) piperidine-1-carbonyl)-N-(2-methoxyethyl) benzamide | 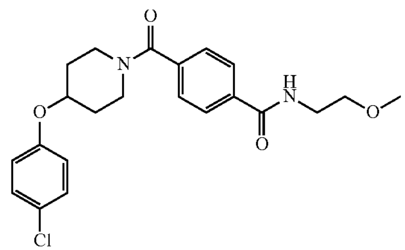 [SMILES: COCCNC(=O)c1ccc(C(=O)N2CCC(Oc3ccc(Cl)cc3)CC2)cc1] | Alternative route | | 415.3 | 1.64 min. | Method A |
| Example 537 | 4-(4-(4-chlorophenoxy) piperidine-4-carbonyl)-N-(1-((1-hydroxycyclohexyl) methyl)piperidin-1-yl)benzamide | 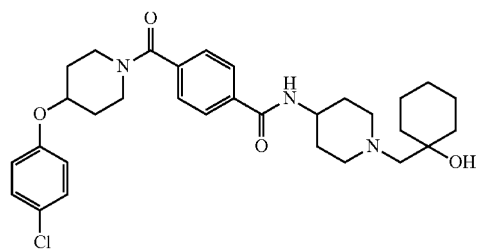 [SMILES: O=C(NC1CCN(CC2(O)CCCCC2)CC1)c1ccc(C(=O)N2CCC(Oc3ccc(Cl)cc3)CC2)cc1] | Alternative route | | 552.4 | 1.78 min. | Method A |
| Example 538 | (S)-4-(4-(4-chlorophenoxy) piperidine-1-carbonyl)-N-(2-hydroxy-1-phenylethyl) benzamide | 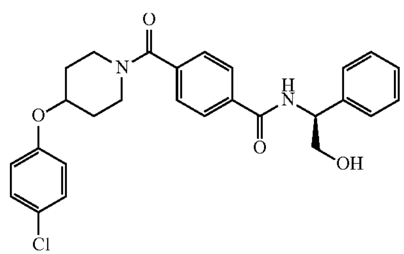 [SMILES: O=C(N[C@H](CO)c1ccccc1)c1ccc(C(=O)N2CCC(Oc3ccc(Cl)cc3)CC2)cc1] | Alternative route | | 477.4 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 539 | (S)-4-(4-(4-chlorophenoxy)piperidine-1-carbonyl)-N-(2-hydroxy-2-phenylethyl)benzamide | 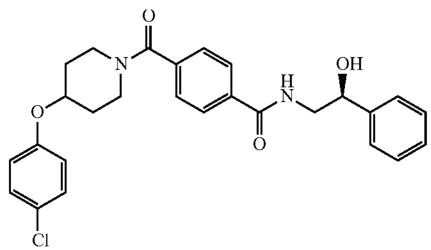 [SMILES: O=C(NC[C@@H](O)c1ccccc1)c1ccc(C(=O)N2CCC(Oc3ccc(Cl)cc3)CC2)cc1] | Alternative route | | 477.3 | 1.73 min. | Method A |
| Example 540 | (S)-4-(4-(4-chlorophenoxy)piperidine-1-carbonyl)-N-(1-hydroxy-3-phenylpropan-2-yl)benzamide | 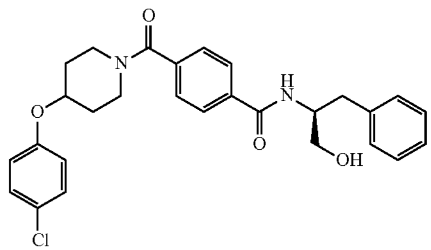 [SMILES: O=C(N[C@H](CO)Cc1ccccc1)c1ccc(C(=O)N2CCC(Oc3ccc(Cl)cc3)CC2)cc1] | Alternative route | | 491.4 | 1.75 min. | Method A |
| Example 541 | (S)-N-(1-amino-1-oxo-3-phenylpropan-2-yl)-4-(4-(4-chlorophenoxy)piperidine-1-carbonyl)benzamide | 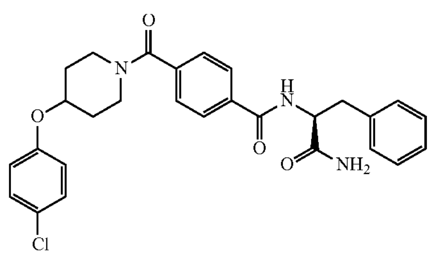 [SMILES: NC(=O)[C@H](Cc1ccccc1)NC(=O)c1ccc(C(=O)N2CCC(Oc3ccc(Cl)cc3)CC2)cc1] | Alternative route | | 504.3 | 1.70 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 542 | (4-((4-chlorophenyl)sulfonyl)piperidin-1-yl)(1-methyl-1H-indol-4-yl)methanone | 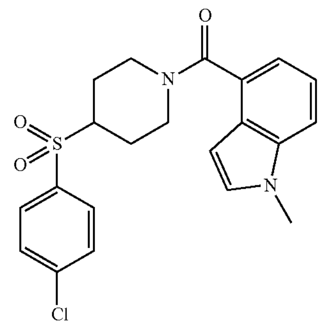 [SMILES: Cn1ccc2c(C(=O)N3CCC(S(=O)(=O)c4ccc(Cl)cc4)CC3)cccc21] | | | 417.1 | 1.66 min. | Method A |
| Example 543 | 4-(4-((4-chlorophenyl)thio)piperidine-1-carbonyl)picolinamide | 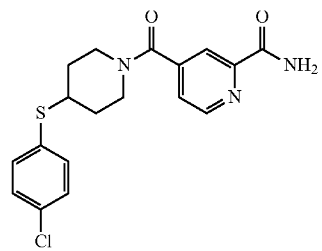 [SMILES: NC(=O)c1cc(C(=O)N2CCC(Sc3ccc(Cl)cc3)CC2)ccn1] | | | 374.3 | 1.64 min. | Method A |
| Example 544 | 6-(4-(3-(trifluoromethoxy)phenoxy)piperidine-1-carbonyl)picolinamide | 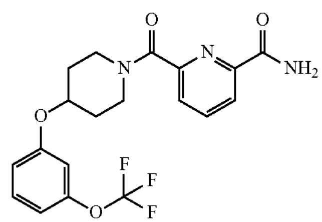 [SMILES: NC(=O)c1cccc(C(=O)N2CCC(Oc3cccc(OC(F)(F)F)c3)CC2)n1] | | | 410.1 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 545 | 4-(4-chlorophenoxy)-piperidine-1-carbonyl)-N-(2-oxo-2-phenylethyl)benzamide | 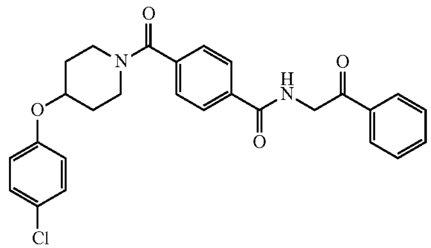 [SMILES: O=C(CNC(=O)c1ccc(C(=O)N2CCC(Oc3ccc(Cl)cc3)CC2)cc1)c1ccccc1] | Alternative route | | 475.3 | 1.80 min. | Method A |
| Example 546 | (2-(methylsulfonyl)phenyl)(4-(3-(trifluoromethoxy)phenoxy)piperidin-1-yl)methanone | 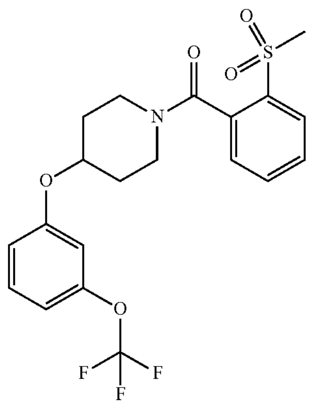 [SMILES: CS(=O)(=O)c1ccccc1C(=O)N1CCC(Oc2cccc(OC(F)(F)F)c2)CC1] | | | 444.1 | 1.83 min. | Method A |
| Example 547 | (3-(methylsulfonyl)phenyl)(4-(3-(trifluoromethoxy)phenoxy)piperidin-1-yl)methanone | 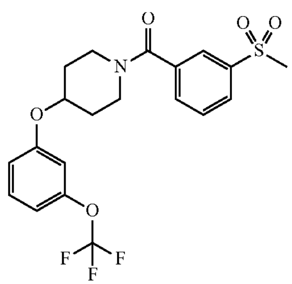 [SMILES: CS(=O)(=O)c1cccc(C(=O)N2CCC(Oc3cccc(OC(F)(F)F)c3)CC2)c1] | | | 442.3 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 548 | (4-((4-chlorophenyl)sulfonyl)piperidin-1-yl)(5-fluoro-1-methyl-1H-indol-2-yl)methanone | 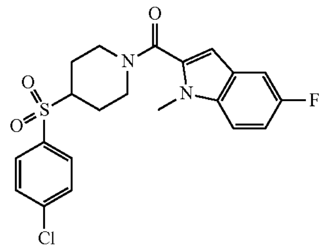 [SMILES: Cn1c(C(=O)N2CCC(S(=O)(=O)c3ccc(Cl)cc3)CC2)cc2cc(F)ccc21] | | | 433.3 | 1.78 min. | Method A |
| Example 549 | (4-((4-chlorophenyl)sulfonyl)piperidin-1-yl)(6-fluoro-1-methyl-1H-indol-2-yl)methanone | 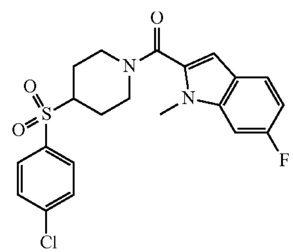 [SMILES: Cn1c(C(=O)N2CCC(S(=O)(=O)c3ccc(Cl)cc3)CC2)cc2ccc(F)cc21] | | | 433.3 | 1.79 min. | Method A |
| Example 550 | (4-(3-ethoxyphenoxy)piperidin-1-yl)(quinolin-8-yl)methanone | 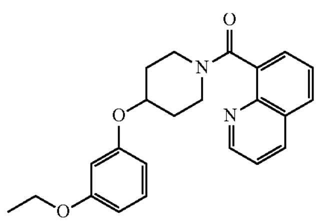 [SMILES: CCOc1cccc(OC2CCN(C(=O)c3cccc4cccnc34)CC2)c1] | | | 377.2 | 1.74 min. | Method A |
| Example 551 | (4-((4-chlorophenyl)sulfonyl)piperidin-1-yl)(3-(2-methylthiazol-4-yl)phenyl)methanone | 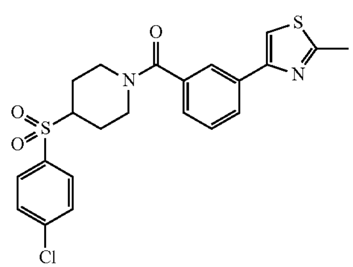 [SMILES: Cc1nc(-c2cccc(C(=O)N3CCC(S(=O)(=O)c4ccc(Cl)cc4)CC3)c2)cs1] | | | 461.1 | 1.71 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 552 | N-methyl-3-(4-(3-(trifluoromethoxy)phenoxy)piperidine-1-carbonyl)benzamide | 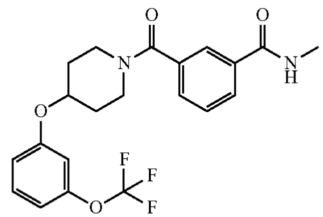 [SMILES: CNC(=O)c1cccc(C(=O)N2CCC(Oc3cccc(OC(F)(F)F)c3)CC2)c1] | | | 421.3 | 1.69 min. | Method A |
| Example 553 | 3-(4-(3-(trifluoromethoxy)phenoxy)piperidine-1-carbonyl)benzenesulfonamide | 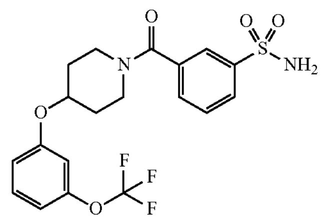 | | | 443.3 | 1.70 min. | Method A |
| Example 554 | 4-(4-(3-(trifluoromethoxy)phenoxy)piperidine-1-carbonyl)benzenesulfonamide | 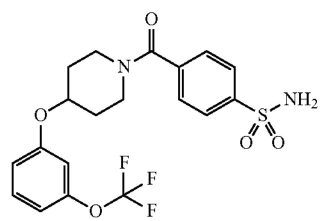 [SMILES: NS(=O)(=O)c1ccc(C(=O)N2CCC(Oc3cccc(OC(F)(F)F)c3)CC2)cc1] | | | 443.3 | 1.68 min. | Method A |
| Example 555 | (4-(4-fluorophenoxy)piperidin-1-yl)(1,5-naphthyridin-2-yl)methanone | 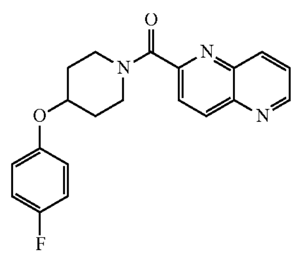 [SMILES: O=C(c1ccc2ncccc2n1)N1CCC(Oc2ccc(F)cc2)CC1] | | | 352.2 | 1.56 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 556 | (4-(4-fluorophenoxy)piperidin-1-yl)(quinolin-2-yl)methanone | 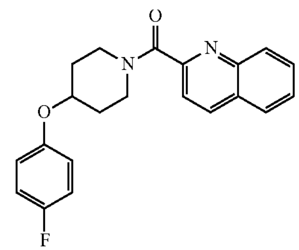 [SMILES: O=C(c1ccc2ccccc2n1)N1CCC(Oc2ccc(F)cc2)CC1] | | | 351.1 | 1.78 min. | Method A |
| Example 557 | (4-(3-fluorophenoxy)piperidin-1-yl)(4-methoxyquinolin-2-yl)methanone | 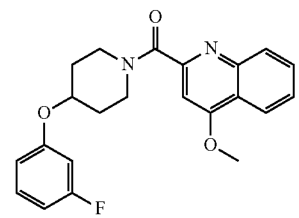 [SMILES: COc1cc(C(=O)N2CCC(Oc3cccc(F)c3)CC2)nc2ccccc12] | | | 381.2 | 1.85 min. | Method A |
| Example 558 | (1H-benzo[d][1,2,3]triazol-7-yl)(4-(3-(trifluoromethoxy)phenoxy)piperidin-1-yl)methanone | 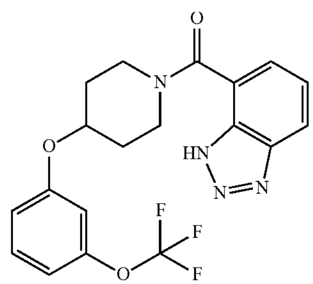 [SMILES: O=C(c1cccc2nn[nH]c12)N1CCC(Oc2cccc(OC(F)(F)F)c2)CC1] | | | 405.3 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 559 | 2-(2-(4-(4-chlorophenoxy)piperidine-1-carbonyl)phenoxy)acetamide | 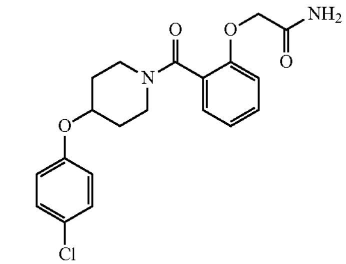 [SMILES: NC(=O)COc1ccccc1C(=O)N1CCC(Oc2ccc(Cl)cc2)CC1] | | | 387.4 | 1.63 min. | Method A |
| Example 560 | 2-(4-(4-(4-chlorophenoxy)piperidine-1-carbonyl)phenoxy)acetamide | 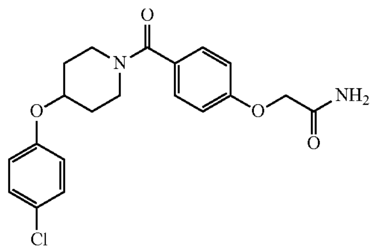 | | | 387.4 | 1.57 min. | Method A |
| Example 561 | 2-(2-(4-(3-(trifluoromethoxy)phenoxy)piperidine-1-carbonyl)phenoxy)acetamide | 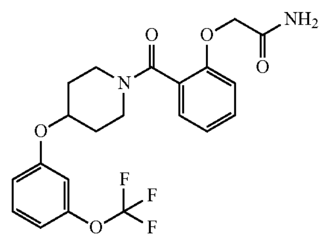 [SMILES: NC(=O)COc1ccccc1C(=O)N1CCC(Oc2cccc(OC(F)(F)F)c2)CC1] | | | 437.3 | 1.71 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 562 | 2-(3-(4-(3-(trifluoromethoxy)phenoxy)piperidine-1-carbonyl)phenoxy)acetamide | 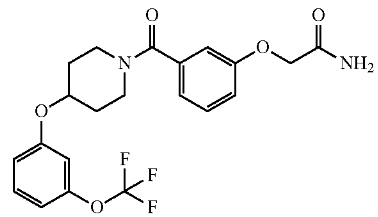 [SMILES: NC(=O)COc1cccc(C(=O)N2CCC(Oc3cccc(OC(F)(F)F)c3)CC2)c1] | | | 437.4 | 1.67 min. | Method A |
| Example 563 | 2-(4-(4-(3-(trifluoromethoxy)phenoxy)piperidine-1-carbonyl)phenoxy)acetamide | 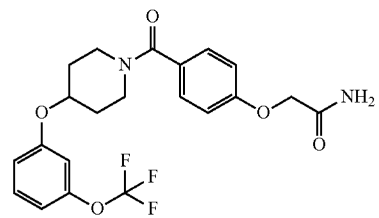 [SMILES: NC(=O)COc1ccc(C(=O)N2CCC(Oc3cccc(OC(F)(F)F)c3)CC2)cc1] | | | 437.4 | 1.65 min. | Method A |
| Example 564 | (8-hydroxyquinolin-2-yl)(4-((3-(trifluoromethoxy)phenyl)sulfonyl)piperidin-1-yl)methanone | 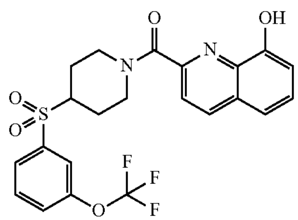 [SMILES: O=C(c1ccc2cccc(O)c2n1)N1CCC(S(=O)(=O)c2cccc(OC(F)(F)F)c2)CC1] | | | 479.3 | 1.73 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 565 | quinolin-8-yl(4-((3-(trifluoromethoxy)phenyl)sulfonyl)piperidin-1-yl)methanone | 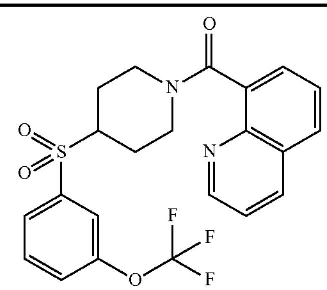 | | | 463.9 | 1.63 min. | Method A |
| Example 566 | quinolin-2-yl(4-((3-(trifluoromethoxy)phenyl)sulfonyl)piperidin-1-yl)methanone | 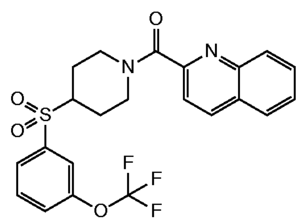 [SMILES: O=C(c1ccc2ccccc2n1)N1CCC(S(=O)(=O)c2cccc(OC(F)(F)F)c2)CC1] | | | 463.3 | 1.73 min. | Method A |
| Example 567 | (4-((4-chlorophenyl)sulfonyl)piperidin-1-yl)(5-phenylisoxazol-3-yl)methanone | 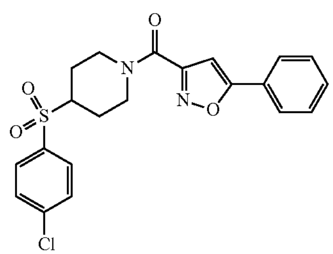 [SMILES: O=C(c1cc(-c2ccccc2)on1)N1CCC(S(=O)(=O)c2ccc(Cl)cc2)CC1] | | | 431.1 | 1.80 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 568 | (6-methoxyquinolin-2-yl)(4-((3-(trifluoromethoxy)phenyl)sulfonyl)piperidin-1-yl)methanone | 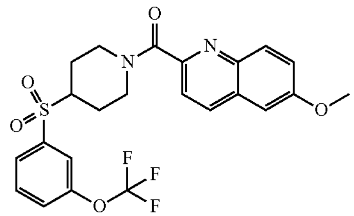 [SMILES: COc1ccc2nc(C(=O)N3CCC(S(=O)(=O)c4cccc(OC(F)(F)F)c4)CC3)ccc2c1] | | | 493.3 | 1.73 min. | Method A |
| Example 569 | (5-methyl-2-phenyl-2H-1,2,3-triazol-4-yl)(4-((3-(trifluoromethoxy)phenyl)sulfonyl)piperidin-1-yl)methanone | 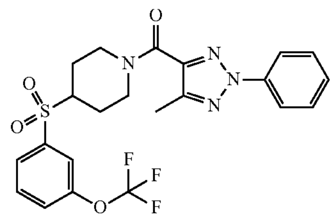 [SMILES: Cc1nn(-c2ccccc2)nc1C(=O)N1CCC(S(=O)(=O)c2cccc(OC(F)(F)F)c2)CC1] | | | 493.5 | 1.92 min. | Method A |
| Example 570 | (5-fluoro-1-methyl-1H-indol-2-yl)(4-((3-(trifluoromethoxy)phenyl)sulfonyl)piperidin-1-yl)methanone | 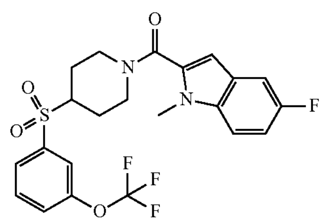 [SMILES: Cn1c(C(=O)N2CCC(S(=O)(=O)c3cccc(OC(F)(F)F)c3)CC2)cc2cc(F)ccc21] | | | 483.4 | 1.85 min. | Method A |
| Example 571 | (6-fluoro-1-methyl-1H-indol-2-yl)(4-((3-(trifluoromethoxy)phenoxy)sulfonyl)piperidin-1-yl)methanone | 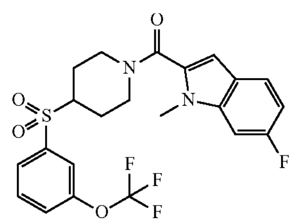 [SMILES: Cn1c(C(=O)N2CCC(S(=O)(=O)c3cccc(OC(F)(F)F)c3)CC2)cc2ccc(F)cc21] | | | 483.4 | 1.86 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 572 | (4-hydroxyquinolin-8-yl)(4-(3-(trifluoromethoxy)phenoxy)piperidin-1-yl)methanone | 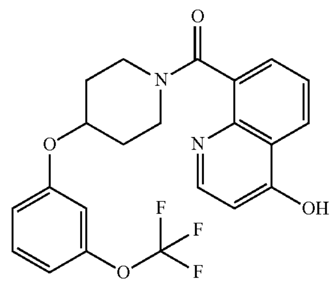 [SMILES: O=C(c1cccc2c(O)ccnc12)N1CCC(Oc2cccc(OC(F)(F)F)c2)CC1] | | | 431.4 | 1.62 min. | Method A |
| Example 573 | (1,8-naphthyridin-4-yl)(4-(3-(trifluoromethoxy)phenoxy)piperidin-1-yl)methanone | 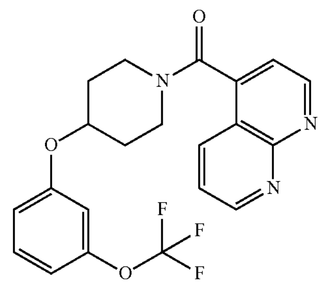 [SMILES: O=C(c1ccnc2ncccc12)N1CCC(Oc2cccc(OC(F)(F)F)c2)CC1] | | | 418.2 | 1.64 min. | Method A |
| Example 574 | (1,6-naphthyridin-8-yl)(4-(3-(trifluoromethoxy)phenoxy)piperidin-1-yl)methanone | 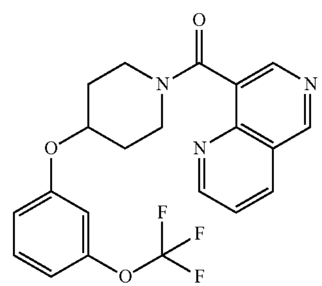 [SMILES: O=C(c1cncc2cccnc12)N1CCC(Oc2cccc(OC(F)(F)F)c2)CC1] | | | 418.2 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 575 | [1,2,4]triazolo[1,5-a]pyrimidin-2-yl(4-(3-(trifluoromethoxy)phenoxy)piperidin-1-yl)methanone | 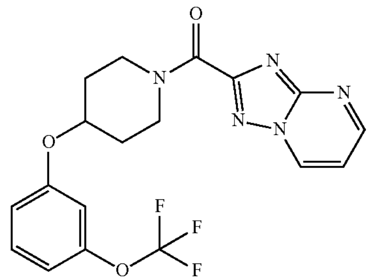 [SMILES: O=C(c1nc2ncccn2n1)N1CCC(Oc2cccc(OC(F)(F)F)c2)CC1] | | | 406.4 | 1.62 min. | Method A |
| Example 576 | (5-methyl-1H-pyrazol-3-yl)(4-(3-(trifluoromethoxy)phenoxy)piperidin-1-yl)methanone | 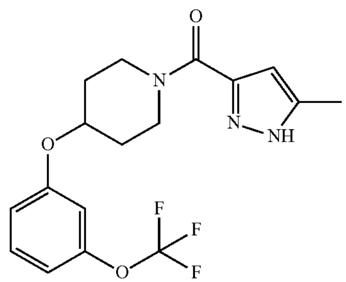 [SMILES: Cc1cc(C(=O)N2CCC(Oc3cccc(OC(F)(F)F)c3)CC2)n[nH]1] | | | 368.4 | 1.69 min. | Method A |
| Example 577 | 2-chloro-5-(4-(3-(trifluoromethoxy)phenoxy)piperidine-1-carbonyl)benzenesulfonamide | 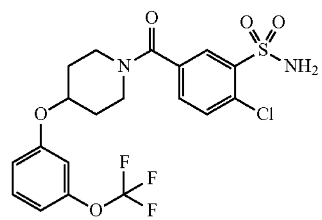 [SMILES: NS(=O)(=O)c1cc(C(=O)N2CCC(Oc3cccc(OC(F)(F)F)c3)CC2)ccc1Cl] | | | 477.3 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 578 | (S)-3-(4-(4-chlorophenoxy)piperidine-1-carbonyl)-N-(2-hydroxy-2-phenylethyl)benzamide | 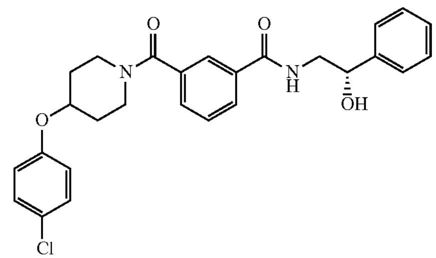 [SMILES: O=C(NC[C@@H](O)c1ccccc1)c1cccc(C(=O)N2CCC(Oc3ccc(Cl)cc3)CC2)c1] | Alternative route | | 477.4 | 1.72 min. | Method A |
| Example 579 | (S)-3-(4-(4-chlorophenoxy)piperidine-1-carbonyl)-N-(2-hydroxy-1-phenylethyl)benzamide | 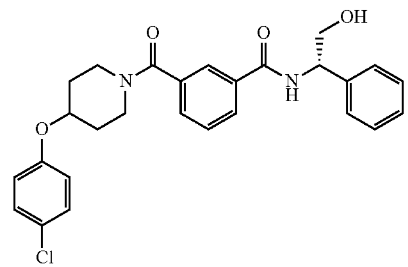 [SMILES: O=C(N[C@H](CO)c1ccccc1)c1cccc(C(=O)N2CCC(Oc3ccc(Cl)cc3)CC2)c1] | Alternative route | | 477.4 | 1.72 min. | Method A |
| Example 580 | (S)-3-(4-(4-chlorophenoxy)piperidine-1-carbonyl)-N-(1-hydroxy-3-phenylpropan-2-yl)benzamide | 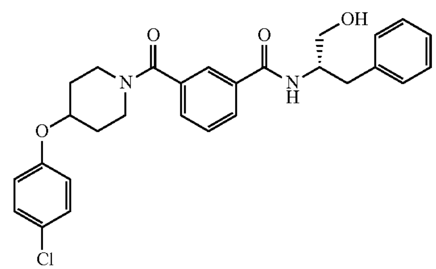 [SMILES: O=C(N[C@H](CO)Cc1ccccc1)c1cccc(C(=O)N2CCC(Oc3ccc(Cl)cc3)CC2)c1] | Alternative route | | 491.4 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 581 | (S)-N-(1-amino-1-oxo-3-phenylpropan-2-yl)-3-(4-(4-chlorophenoxy)piperidine-1-carbonyl)benzamide | 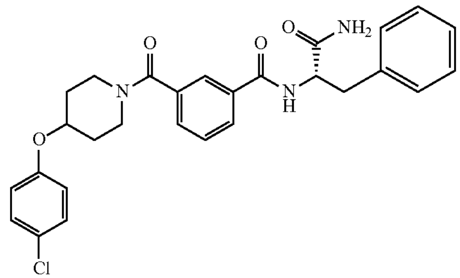 [SMILES: NC(=O)[C@H](Cc1ccccc1)NC(=O)c1cccc(C(=O)N2CCC(Oc3ccc(Cl)cc3)CC2)c1] | Alternative route | | 504.5 | 1.70 min. | Method A |
| Example 582 | (4-((3-ethoxyphenyl)sulfonyl)piperidin-1-yl)(8-hydroxyquinolin-2-yl)methanone | 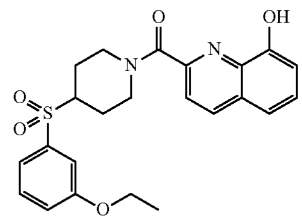 [SMILES: CCOc1cccc(S(=O)(=O)C2CCN(C(=O)c3ccc4cccc(O)c4n3)CC2)c1] | | | 439.4 | 1.64 min. | Method A |
| Example 583 | (4-((4-chlorophenyl)sulfonyl)piperidin-1-yl)(4-methyl-2-phenylthiazol-5-yl)methanone | 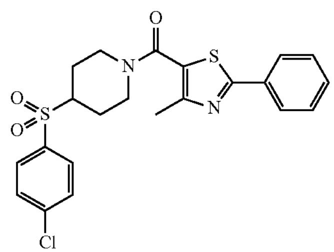 [SMILES: Cc1nc(-c2ccccc2)sc1C(=O)N1CCC(S(=O)(=O)c2ccc(Cl)cc2)CC1] | | | 459.1 | 1.80 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 584 | (4-((4-chlorophenyl)sulfonyl)piperidin-1-yl)(2-phenylthiazol-4-yl)methanone | 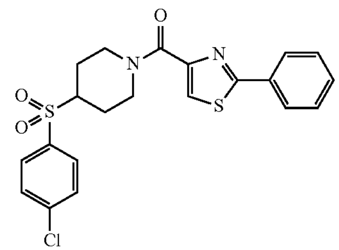 [SMILES: O=C(c1csc(-c2ccccc2)n1)N1CCC(S(=O)(=O)c2ccc(Cl)cc2)CC1] | | | 447.1 | 1.81 min. | Method A |
| Example 585 | (4-chloro-2-(methylsulfonyl)phenyl)(4-(3-(trifluoromethoxy)phenoxy)piperidin-1-yl)methanone | 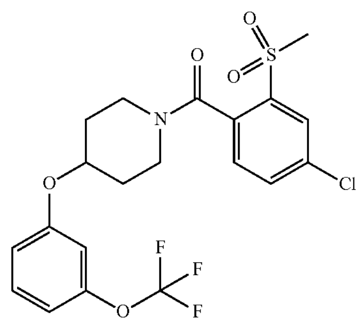 [SMILES: CS(=O)(=O)c1cc(Cl)ccc1C(=O)N1CCC(Oc2cccc(OC(F)(F)F)c2)CC1] | | | 478.1 | 1.95 min. | Method A |
| Example 586 | (5-fluoro-2-(methylsulfonyl)phenyl)(4-(3-(trifluoromethoxy)phenoxy)piperidin-1-yl)methanone | 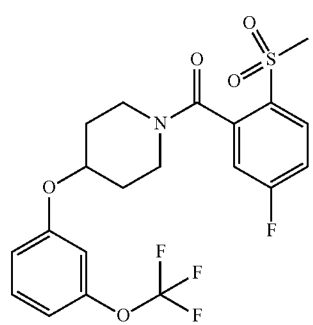 [SMILES: CS(=O)(=O)c1ccc(F)cc1C(=O)N1CCC(Oc2cccc(OC(F)(F)F)c2)CC1] | | | 460.4 | 1.87 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 587 | N,N-dimethyl-4-(4-(3-(trifluoromethoxy)phenoxy)piperidine-1-carbonyl)benzenesulfonamide | 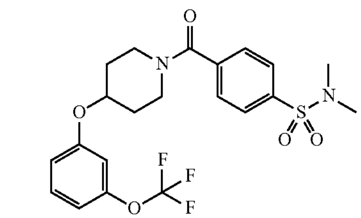 [SMILES: CN(C)S(=O)(=O)c1ccc(C(=O)N2CCC(Oc3cccc(OC(F)(F)F)c3)CC2)cc1] | | | 473.2 | 1.86 min. | Method A |
| Example 588 | N-(2-(4-(4-(3-(trifluoromethoxy)phenoxy)piperidine-1-carbonyl)phenoxy)ethyl)acetamide | 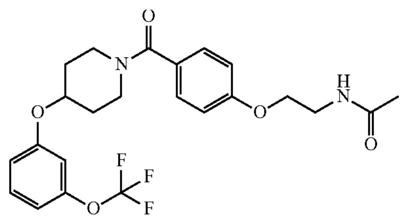 [SMILES: CC(=O)NCCOc1ccc(C(=O)N2CCC(Oc3cccc(OC(F)(F)F)c3)CC2)cc1] | | | 465.4 | 1.69 min. | Method A |
| Example 589 | (2-phenyl-1H-imidazol-5-yl)(4-((3-(trifluoromethoxy)phenyl)sulfonyl)piperidin-1-yl)methanone | 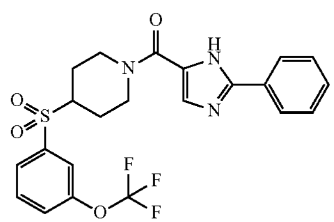 [SMILES: O=C(c1cnc(-c2ccccc2)[nH]1)N1CCC(S(=O)(=O)c2cccc(OC(F)(F)F)c2)CC1] | | | 478.3 | 1.64 min. | Method A |
| Example 590 | (3-(2-methylthiazol-4-yl)phenyl)(4-((3-(trifluoromethoxy)phenyl)sulfonyl)piperidin-1-yl)methanone | 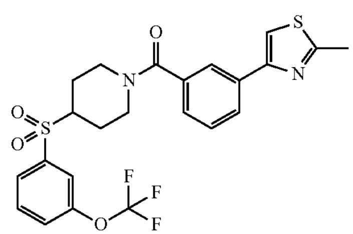 [SMILES: Cc1nc(-c2cccc(C(=O)N3CCC(S(=O)(=O)c4cccc(OC(F)(F)F)c4)CC3)c2)cs1] | | | 509.2 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 591 | N-(4-(4-(3-ethoxyphenoxy)piperidine-1-carbonyl)pyridin-2-yl)acetamide | 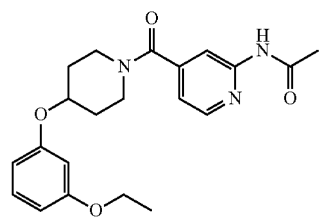 [SMILES: CCOc1cccc(OC2CCN(C(=O)c3ccnc(NC(C)=O)c3)CC2)c1] | | | 382.5 | 1.55 min. | Method A |
| Example 592 | (4-(3-ethoxyphenoxy)piperidin-1-yl)(2-(methylsulfonyl)phenyl)methanone | 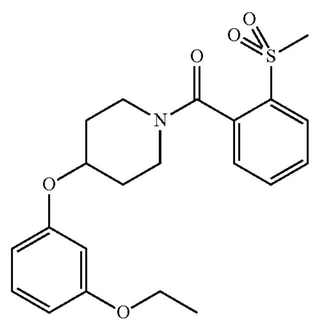 [SMILES: CCOc1cccc(OC2CCN(C(=O)c3ccccc3S(C)(=O)=O)CC2)c1] | | | 404.2 | 1.71 min. | Method A |
| Example 593 | 3-(4-(3-ethoxyphenoxy)piperidine-1-carbonyl)benzenesulfonamide | 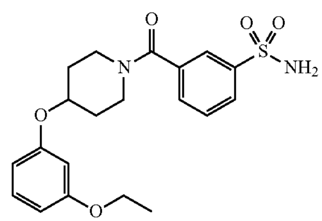 [SMILES: CCOc1cccc(OC2CCN(C(=O)c3cccc(S(N)(=O)=O)c3)CC2)c1] | | | 403.4 | 1.56 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 594 | N-(6-(4-(3-ethoxyphenoxy)piperidine-1-carbonyl)pyridin-2-yl)acetamide | 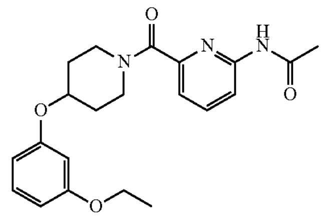 [SMILES: CCOc1cccc(OC2CCN(C(=O)c3cccc(NC(C)=O)n3)CC2)c1] | | | 382.5 | 1.59 min. | Method A |
| Example 595 | (4-(3-ethoxyphenoxy)piperidin-1-yl)(2-methyl-2H-indazol-3-yl)methanone | 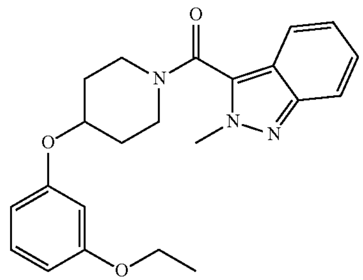 [SMILES: CCOc1cccc(OC2CCN(C(=O)c3c4ccccc4nn3C)CC2)c1] | | | 380.2 | 1.80 min. | Method A |
| Example 596 | (4-(3-ethoxyphenoxy)piperidin-1-yl)(1,5-naphthyridin-2-yl)methanone | 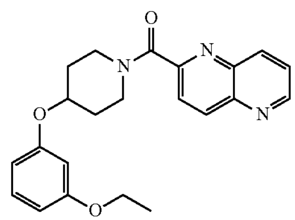 [SMILES: CCOc1cccc(OC2CCN(C(=O)c3ccc4ncccc4n3)CC2)c1] | | | 378.2 | 1.63 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 597 | (8-hydroxyquinolin-2-yl)(4-((4-(trifluoromethoxy)phenyl)sulfonyl)piperidin-1-yl)methanone | 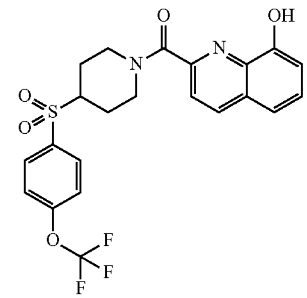 [SMILES: O=C(c1ccc2cccc(O)c2n1)N1CCC(S(=O)(=O)c2ccc(OC(F)(F)F)cc2)CC1] | | | 479.4 | 1.73 min. | Method A |
| Example 598 | quinolin-8-yl(4-((4-(trifluoromethoxy)phenyl)sulfonyl)piperidin-1-yl)methanone | 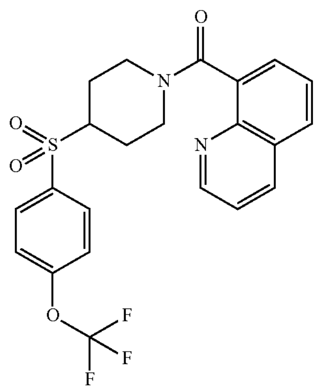 [SMILES: O=C(c1cccc2cccnc12)N1CCC(S(=O)(=O)c2ccc(OC(F)(F)F)cc2)CC1] | | | 463.5 | 1.63 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 599 | quinolin-2-yl(4-((4-(trifluoromethoxy)phenyl)sulfonyl)piperidin-1-yl)methanone | 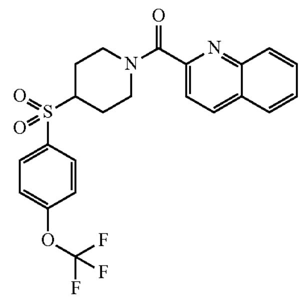 [SMILES: O=C(c1ccc2ccccc2n1)N1CCC(S(=O)(=O)c2ccc(OC(F)(F)F)cc2)CC1] | | | 463.3 | 1.73 min. | Method A |
| Example 600 | N-(3-(4-(3-(trifluoromethoxy)phenoxy)piperidine-1-carbonyl)phenyl)methanesulfonamide | 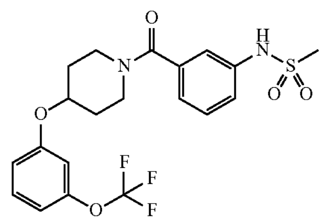 [SMILES: CS(=O)(=O)Nc1cccc(C(=O)N2CCC(Oc3cccc(OC(F)(F)F)c3)CC2)c1] | | | 457.4 | 1.75 min. | Method A |
| Example 601 | (2-(ethylsulfonyl)phenyl)(4-(3-(trifluoromethoxy)phenoxy)piperidin-1-yl)methanone | 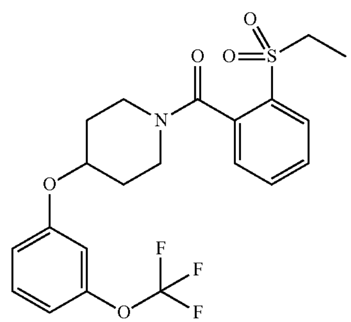 [SMILES: CCS(=O)(=O)c1ccccc1C(=O)N1CCC(Oc2cccc(OC(F)(F)F)c2)CC1] | | | 458.2 | 1.88 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 602 | (3-fluoro-4-(methylsulfonyl)phenyl)(4-(3-(trifluoromethoxy)phenoxy)piperidin-1-yl)methanone | 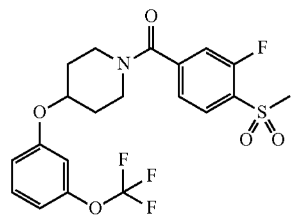 [SMILES: CS(=O)(=O)c1ccc(C(=O)N2CCC(Oc3cccc(OC(F)(F)F)c3)CC2)cc1F] | | | 462.1 | 1.80 min. | Method A |
| Example 603 | ethyl (4-(4-(3-(trifluoromethoxy)phenoxy)piperidine-1-carbonyl)pyridin-2-yl)carbamate | 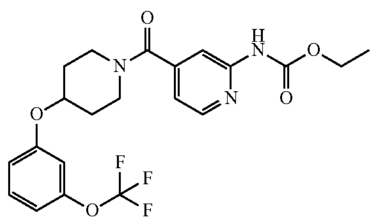 [SMILES: CCOC(=O)Nc1cc(C(=O)N2CCC(Oc3cccc(OC(F)(F)F)c3)CC2)ccn1] | | | 452.4 | 1.83 min. | Method A |
| Example 604 | 2-(4-(3-(trifluoromethoxy)phenoxy)piperidine-1-carbonyl)thiazole-4-carboxamide | 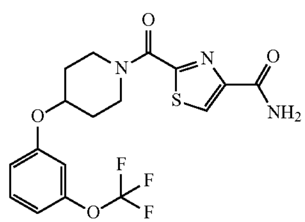 [SMILES: NC(=O)c1csc(C(=O)N2CCC(Oc3cccc(OC(F)(F)F)c3)CC2)n1] | | | 414.4 | 1.69 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 605 | N,N-dimethyl-2-(4-(3-(trifluoromethoxy)phenoxy)piperidine-1-carbonyl)benzenesulfonamide | 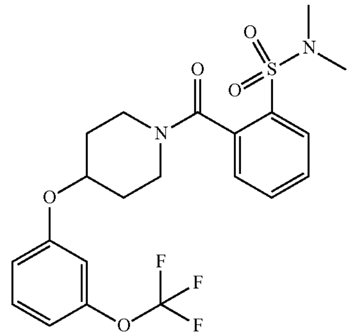 [SMILES: CN(C)S(=O)(=O)c1ccccc1C(=O)N1CCC(Oc2cccc(OC(F)(F)F)c2)CC1] | | | 473.3 | 1.89 min. | Method A |
| Example 606 | (4-(4-(3-(trifluoromethoxy)phenoxy)piperidine-1-carbonyl)phenyl)methanesulfonamide | 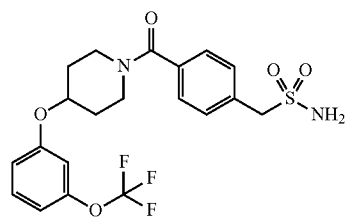 [SMILES: NS(=O)(=O)Cc1ccc(C(=O)N2CCC(Oc3cccc(OC(F)(F)F)c3)CC2)cc1] | | | 457.4 | 1.67 min. | Method A |
| Example 607 | 4-methoxy-3-(4-(3-(trifluoromethoxy)phenoxy)piperidine-1-carbonyl)benzenesulfonamide | 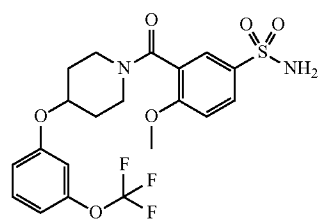 [SMILES: COc1ccc(S(N)(=O)=O)cc1C(=O)N1CCC(Oc2cccc(OC(F)(F)F)c2)CC1] | | | 473.4 | 1.69 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 608 | 2-((2-(4-(3-(trifluoromethoxy)phenoxy)piperidine-1-carbonyl)pyridin-3-yl)oxy)acetamide | 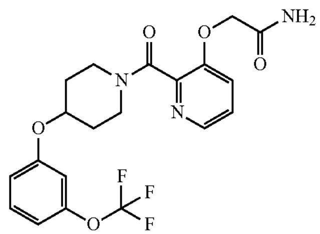 [SMILES: NC(=O)COc1cccnc1C(=O)N1CCC(Oc2cccc(OC(F)(F)F)c2)CC1] | | | 438.4 | 1.56 min. | Method A |
| Example 609 | (4-(aminomethyl)pyridin-2-yl)(4-(3-(trifluoromethoxy)phenoxy)piperidin-1-yl)methanone | 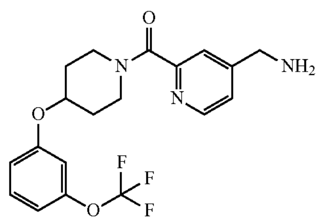 [SMILES: NCc1ccnc(C(=O)N2CCC(Oc3cccc(OC(F)(F)F)c3)CC2)c1] | Alternative route | | 396.2 | 1.52 min. | Method A |
| Example 610 | N-((2-(4-(3-(trifluoromethoxy)phenoxy)piperidine-1-carbonyl)pyridin-4-yl)methyl)methanesulfonamide | 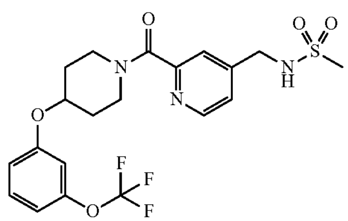 [SMILES: CS(=O)(=O)NCc1ccnc(C(=O)N2CCC(Oc3cccc(OC(F)(F)F)c3)CC2)c1] | Alternative route | | 472.4 | 1.63 min. | Method A |
| Example 611 | ethyl ((2-(4-(3-(trifluoromethoxy)phenoxy)piperidine-1-carbonyl)pyridin-4-yl)methyl)carbamate | 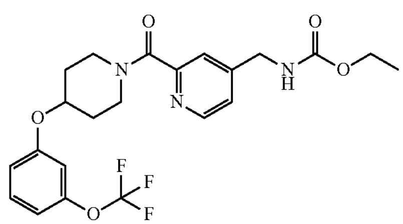 [SMILES: CCOC(=O)NCc1ccnc(C(=O)N2CCC(Oc3cccc(OC(F)(F)F)c3)CC2)c1] | Alternative route | | 466.5 | 1.74 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 612 | N-(2-(4-(3-(trifluoromethoxy)phenoxy)piperidine-1-carbonyl)benzyl)acetamide | 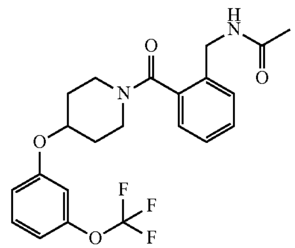 [SMILES: CC(=O)NCc1ccccc1C(=O)N1CCC(Oc2cccc(OC(F)(F)F)c2)CC1] | Alternative route | | 437.3 | 1.71 min. | Method A |
| Example 613 | N-(2-(4-(3-(trifluoromethoxy)phenoxy)piperidine-1-carbonyl)benzyl)methanesulfonamide | 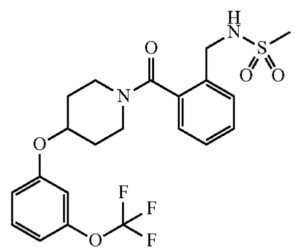 [SMILES: CS(=O)(=O)NCc1ccccc1C(=O)N1CCC(Oc2cccc(OC(F)(F)F)c2)CC1] | Alternative route | | 471.4 | 1.78 min. | Method A |
| Example 614 | ethyl 2-(4-(3-(trifluoromethoxy)phenoxy)piperidine-1-carbonyl)benzylcarbamate | 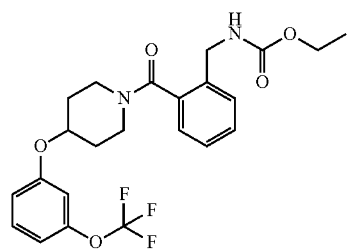 [SMILES: CCOC(=O)NCc1ccccc1C(=O)N1CCC(Oc2cccc(OC(F)(F)F)c2)CC1] | Alternative route | | 467.3 | 1.89 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 615 | (2-(methylsulfonyl)phenyl)(4-(3-(2,2,2-trifluoroethoxy)phenoxy)piperidin-1-yl)methanone | 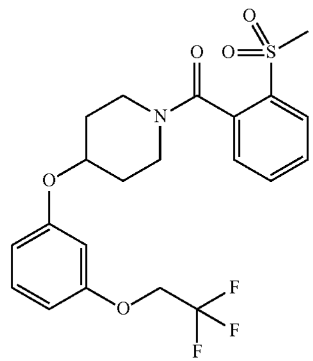 [SMILES: CS(=O)(=O)c1ccccc1C(=O)N1CCC(Oc2cccc(OCC(F)(F)F)c2)CC1] | | | 458.3 | 1.76 min. | Method A |
| Example 616 | N-(4-(4-(3-(2,2,2-trifluoroethoxy)phenoxy)piperidine-1-carbonyl)pyridin-2-yl)acetamide | 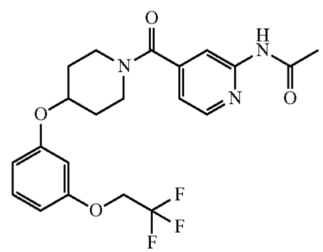 [SMILES: CC(=O)Nc1cc(C(=O)N2CCC(Oc3cccc(OCC(F)(F)F)c3)CC2)ccn1] | | | 436.5 | 1.61 min. | Method A |
| Example 617 | 4-(4-(3-(2,2,2-trifluoroethoxy)phenoxy)piperidine-1-carbonyl)picolinamide | 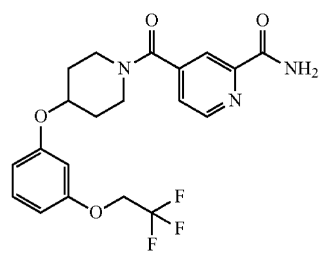 [SMILES: NC(=O)c1cc(C(=O)N2CCC(Oc3cccc(OCC(F)(F)F)c3)CC2)ccn1] | | | 422.5 | 1.57 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 618 | 3-(4-(3-(2,2,2-trifluoroethoxy)phenoxy)piperidine-1-carbonyl)benzamide | 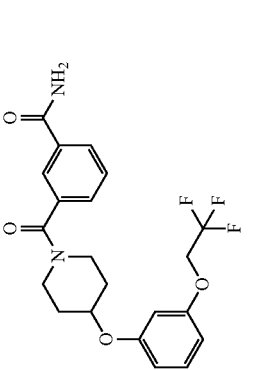 | 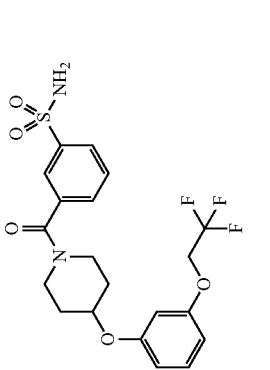 | 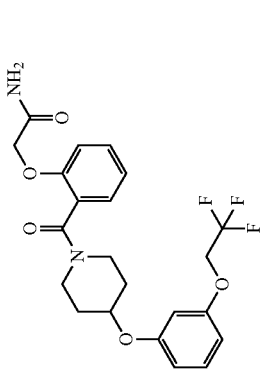 | 421.4 | 1.57 min. | Method A |
| Example 619 | 3-(4-(3-(2,2,2-trifluoroethoxy)phenoxy)piperidine-1-carbonyl)benzenesulfonamide | 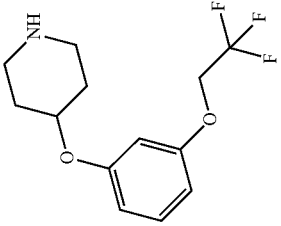 | 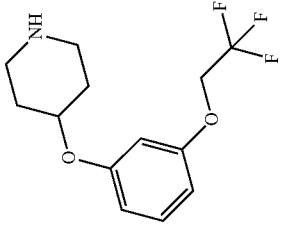 | 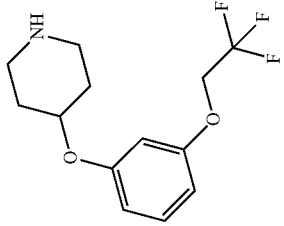 | 457.4 | 1.63 min. | Method A |
| Example 620 | 2-(2-(4-(3-(2,2,2-trifluoroethoxy)phenoxy)piperidine-1-carbonyl)phenoxy)acetamide | 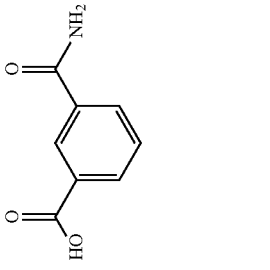 | 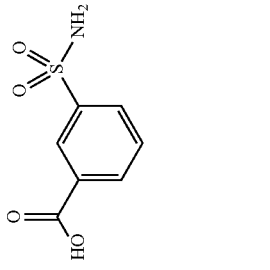 | 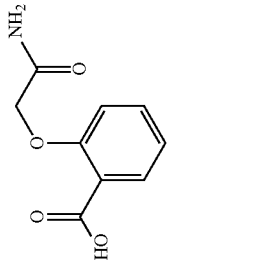 | 451.5 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 621 | quinolin-8-yl(4-(3-(2,2,2-trifluoroethoxy)phenoxy)piperidin-1-yl)methanone | 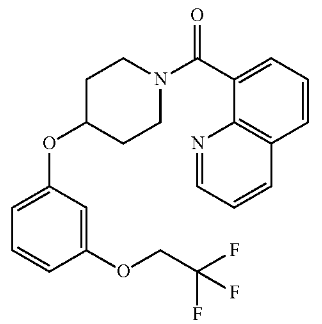 [SMILES: O=C(c1cccc2cccnc12)N1CCC(Oc2cccc(OCC(F)(F)F)c2)CC1] | | | 431.3 | 1.77 min. | Method A |
| Example 622 | (1,5-naphthyridin-2-yl)(4-(3-(2,2,2-trifluoroethoxy)phenoxy)piperidin-1-yl)methanone | 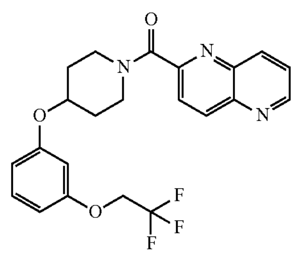 [SMILES: O=C(c1ccc2ncccc2n1)N1CCC(Oc2cccc(OCC(F)(F)F)c2)CC1] | | | 432.3 | 1.69 min. | Method A |
| Example 623 | (2-methyl-2H-indazol-3-yl)(4-(3-(2,2,2-trifluoroethoxy)phenoxy)piperidin-1-yl)methanone | 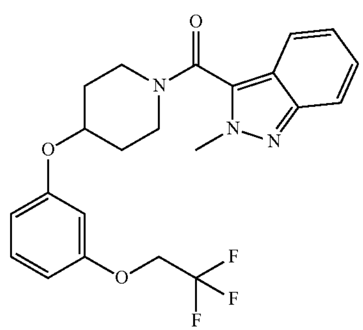 [SMILES: Cn1nc2ccccc2c1C(=O)N1CCC(Oc2cccc(OCC(F)(F)F)c2)CC1] | | | 434.3 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 624 | (1,3-dimethyl-1H-pyrazol-5-yl)(4-(3-(2,2,2-trifluoroethoxy)phenoxy)piperidin-1-yl)methanone | 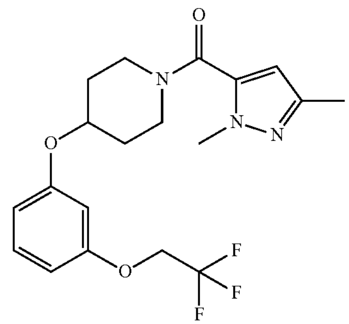 [SMILES: Cc1cc(C(=O)N2CCC(Oc3cccc(OCC(F)(F)F)c3)CC2)n(C)n1] | | | 398.3 | 1.72 min. | Method A |
| Example 625 | N-(6-(4-(3-(2,2,2-trifluoroethoxy)phenoxy)piperidine-1-carbonyl)pyridin-2-yl)acetamide | 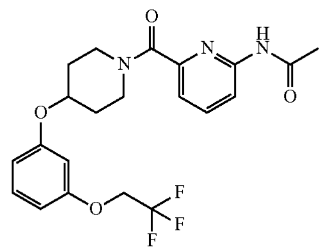 [SMILES: CC(=O)Nc1cccc(C(=O)N2CCC(Oc3cccc(OCC(F)(F)F)c3)CC2)n1] | | | 436.5 | 1.65 min. | Method A |
| Example 626 | 4-(4-(3-(2,2,2-trifluoroethoxy)phenoxy)piperidine-1-carbonyl)benzamide | 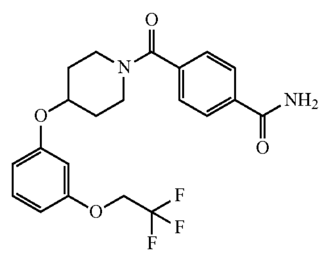 [SMILES: NC(=O)c1ccc(C(=O)N2CCC(Oc3cccc(OCC(F)(F)F)c3)CC2)cc1] | | | 421.4 | 1.56 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 627 | (3,5-dimethylisoxazol-4-yl)(4-(3-(2,2,2-trifluoroethoxy)phenoxy)piperidin-1-yl)methanone | 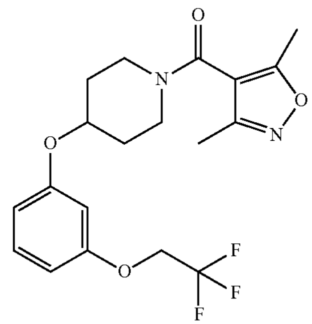 [SMILES: Cc1noc(C)c1C(=O)N1CCC(Oc2cccc(OCC(F)(F)F)c2)CC1] | | | 399.2 | 1.74 min. | Method A |
| Example 628 | (3-(methylsulfonyl)phenyl)(4-(3-(2,2,2-trifluoroethoxy)phenoxy)piperidin-1-yl)methanone | 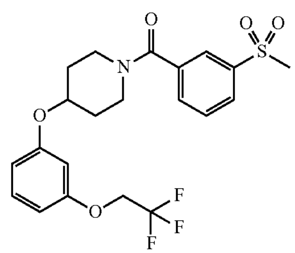 [SMILES: CS(=O)(=O)c1cccc(C(=O)N2CCC(Oc3cccc(OCC(F)(F)F)c3)CC2)c1] | | | 456.5 | 1.69 min. | Method A |
| Example 629 | (1,6-naphthyridin-8-yl)(4-(3-(2,2,2-trifluoroethoxy)phenoxy)piperidin-1-yl)methanone | 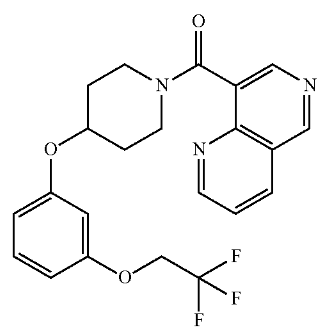 [SMILES: O=C(c1cncc2cccnc12)N1CCC(Oc2cccc(OCC(F)(F)F)c2)CC1] | | | 432.3 | 1.60 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 630 | (3-methyl-1H-pyrazol-5-yl)(4-(3-(2,2,2-trifluoroethoxy)phenoxy)piperidin-1-yl)methanone | 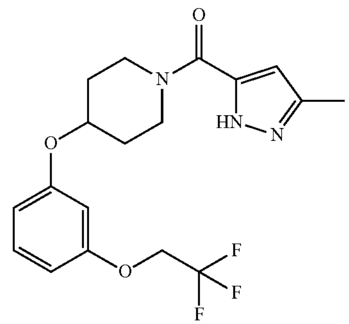 [SMILES: Cc1cc(C(=O)N2CCC(Oc3cccc(OCC(F)(F)F)c3)CC2)[nH]n1] | | | 382.5 | 1.62 min. | Method A |
| Example 631 | 2-(3-(4-(3-(2,2,2-trifluoroethoxy)phenoxy)piperidine-1-carbonyl)phenoxy)acetamide | 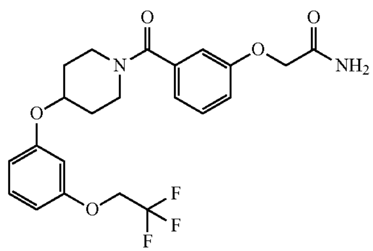 [SMILES: NC(=O)COc1cccc(C(=O)N2CCC(Oc3cccc(OCC(F)(F)F)c3)CC2)c1] | | | 451.5 | 1.60 min. | Method A |
| Example 632 | (5-((tetrahydro-2H-pyran-4-yl)oxy)pyridin-3-yl)(4-(3-(trifluoromethoxy)phenoxy)piperidin-1-yl)methanone | 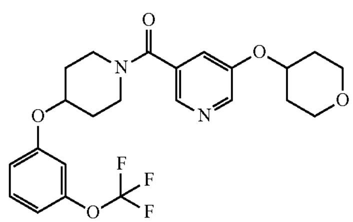 [SMILES: O=C(c1cncc(OC2CCOCC2)c1)N1CCC(Oc2cccc(OC(F)(F)F)c2)CC1] | | | 467.3 | 1.77 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 633 | 1-(3-(4-(3-(trifluoromethoxy)phenoxy)piperidine-1-carbonyl)phenyl)urea | 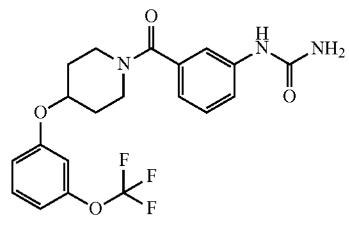 [SMILES: NC(=O)Nc1cccc(C(=O)N2CCC(Oc3cccc(OC(F)(F)F)c3)CC2)c1] | | | 422.4 | 1.63 min. | Method A |
| Example 634 | 1-(4-(4-(3-(trifluoromethoxy)phenoxy)piperidine-1-carbonyl)phenyl)urea | 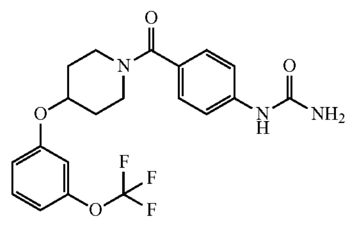 [SMILES: NC(=O)Nc1ccc(C(=O)N2CCC(Oc3cccc(OC(F)(F)F)c3)CC2)cc1] | | | 422.4 | 1.61 min. | Method A |
| Example 635 | (1H-1,2,4-triazol-3-yl)(4-(3-(2,2,2-trifluoroethoxy)phenoxy)piperidin-1-yl)methanone | 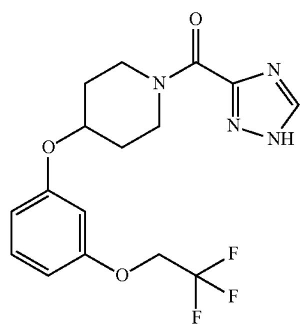 [SMILES: O=C(c1nc[nH]n1)N1CCC(Oc2cccc(OCC(F)(F)F)c2)CC1] | | | 369.4 | 1.51 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 636 | (4-(3-ethoxyphenoxy)piperidin-1-yl)(3-(methylsulfonyl)phenyl)methanone | 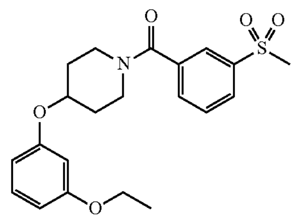 [SMILES: CCOc1cccc(OC2CCN(C(=O)c3cccc(S(C)(=O)=O)c3)CC2)c1] | | | 404.3 | 1.65 min. | Method A |
| Example 637 | (4-(3-ethoxyphenoxy)piperidin-1-yl)(3-methyl-1H-pyrazol-5-yl)methanone | 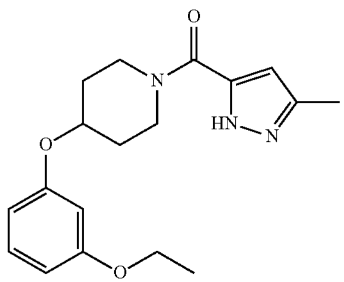 [SMILES: CCOc1cccc(OC2CCN(C(=O)c3cc(C)n[nH]3)CC2)c1] | | | 328.5 | 1.56 min. | Method A |
| Example 638 | N,N-dimethyl-3-(4-(3-(trifluoromethoxy)phenoxy)piperidine-1-carbonyl)benzenesulfonamide | 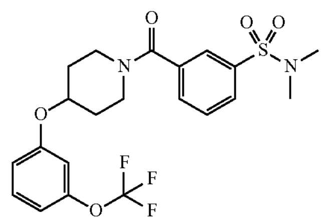 [SMILES: CN(C)S(=O)(=O)c1cccc(C(=O)N2CCC(Oc3cccc(OC(F)(F)F)c3)CC2)c1] | | | 473.3 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 639 | N-(2-(4-(3-(trifluoromethoxy)phenoxy)piperidine-1-carbonyl)phenyl)methanesulfonamide | 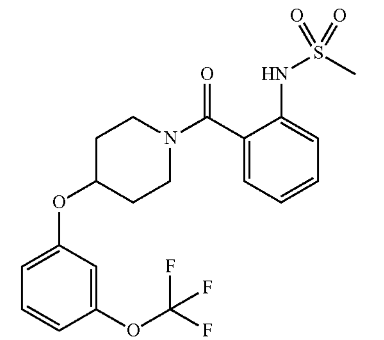 [SMILES: CS(=O)(=O)Nc1ccccc1C(=O)N1CCC(Oc2cccc(OC(F)(F)F)c2)CC1] | | | 457.4 | 1.82 min. | Method A |
| Example 640 | (6-aminopyridin-2-yl)(4-(3-(trifluoromethoxy)phenoxy)piperidin-1-yl)methanone | 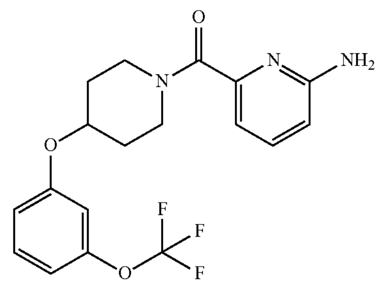 [SMILES: Nc1cccc(C(=O)N2CCC(Oc3cccc(OC(F)(F)F)c3)CC2)n1] | | | 380.4 | 1.68 min. | Method A |
| Example 641 | 2-(methyl(3-(4-(3-(trifluoromethoxy)phenoxy)piperidine-1-carbonyl)benzyl)amino)acetamide | 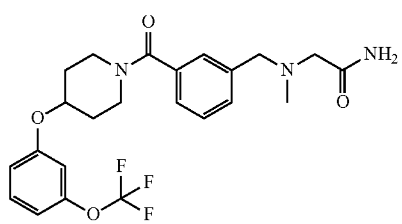 [SMILES: CN(CC(N)=O)Cc1cccc(C(=O)N2CCC(Oc3cccc(OC(F)(F)F)c3)CC2)c1] | | | 466.3 | 1.72 min. | Method A |

| Example | Name | Structure | Structure of amine part | Structure of carboxylic acid part | Observed MS | Retention time | QC Method |
|---|---|---|---|---|---|---|---|
| Example 642 | 2-(methyl(4-(4-(3-(trifluoromethoxy)phenoxy)piperidine-1-carbonyl)benzyl)amino)acetamide | 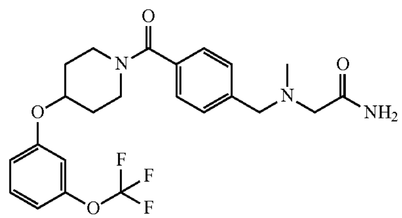 [SMILES: CN(CC(N)=O)Cc1ccc(C(=O)N2CCC(Oc3cccc(OC(F)(F)F)c3)CC2)cc1] | | | 464.5 | 1.71 min. | Method A |
| Example 643 | N,N-dimethyl-2-(2-(4-(3-(trifluoromethoxy)phenoxy)piperidine-1-carbonyl)phenoxy)acetamide | 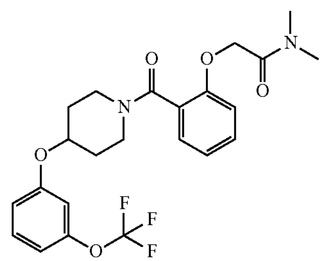 [SMILES: CN(C)C(=O)COc1ccccc1C(=O)N1CCC(Oc2cccc(OC(F)(F)F)c2)CC1] | | | 467.3 | 1.77 min. | Method A |
| Example 644 | (1,3-dimethyl-1H-pyrazol-5-yl)(4-(3-(trifluoromethyl)phenoxy)piperidin-1-yl)methanone | 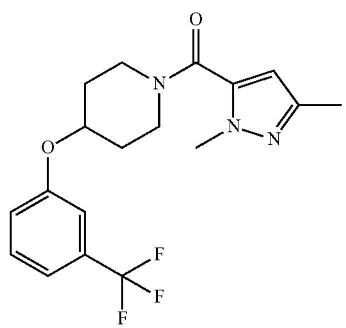 [SMILES: Cc1cc(C(=O)N2CCC(Oc3cccc(C(F)(F)F)c3)CC2)n(C)n1] | | | 368.2 | 1.75 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 645 | (2-(methylsulfonyl)phenyl)(4-(3-(trifluoromethyl)phenoxy)piperidin-1-yl)methanone | 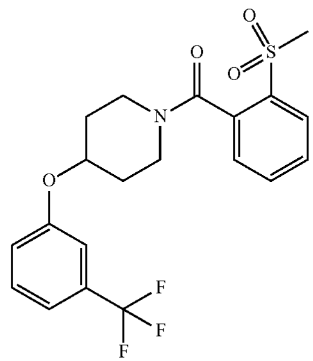 [SMILES: CS(=O)(=O)c1ccccc1C(=O)N1CCC(Oc2cccc(C(F)(F)F)c2)CC1] | | | 428.1 | 1.79 min. | Method A |
| Example 646 | N-(6-(4-(3-(trifluoromethyl)phenoxy)piperidine-1-carbonyl)pyridin-2-yl)acetamide | 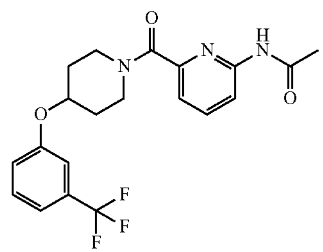 [SMILES: CC(=O)Nc1cccc(C(=O)N2CCC(Oc3cccc(C(F)(F)F)c3)CC2)n1] | | | 406.4 | 1.67 min. | Method A |
| Example 647 | 3-(4-(3-(trifluoromethyl)phenoxy)piperidine-1-carbonyl)benzenesulfonamide | 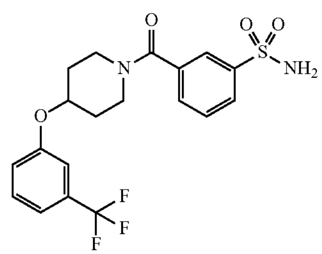 [SMILES: NS(=O)(=O)c1cccc(C(=O)N2CCC(Oc3cccc(C(F)(F)F)c3)CC2)c1] | | | 427.3 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 648 | (3,5-dimethylisoxazol-4-yl)(4-(3-(trifluoromethyl)phenoxy)piperidin-1-yl)methanone | 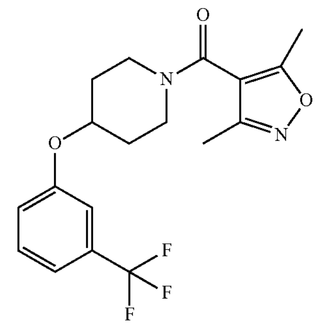 [SMILES: Cc1noc(C)c1C(=O)N1CCC(Oc2cccc(C(F)(F)F)c2)CC1] | | | 367.3 | 1.77 min. | Method A |
| Example 649 | (1,6-naphthyridin-8-yl)(4-(3-(trifluoromethyl)phenoxy)piperidin-1-yl)methanone | 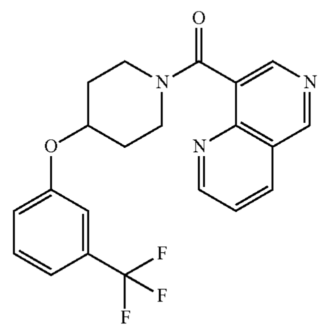 [SMILES: O=C(c1cncc2cccnc12)N1CCC(Oc2cccc(C(F)(F)F)c2)CC1] | | | 402.2 | 1.62 min. | Method A |
| Example 650 | (3-methyl-1H-pyrazol-5-yl)(4-(3-(trifluoromethyl)phenoxy)piperidin-1-yl)methanone | 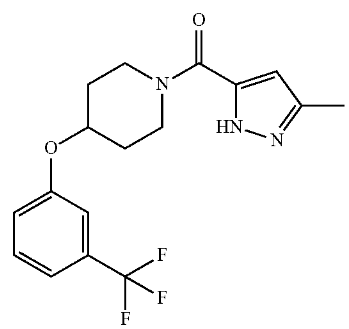 [SMILES: Cc1cc(C(=O)N2CCC(Oc3cccc(C(F)(F)F)c3)CC2)[nH]n1] | | | 352.4 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 651 | 2-(2-(4-(3-(trifluoromethyl)phenoxy)piperidine-1-carbonyl)phenoxy)acetamide | 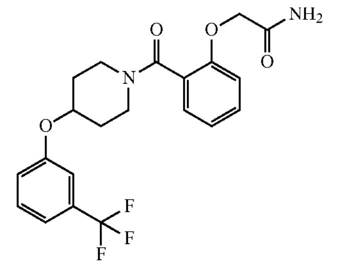 [SMILES: NC(=O)COc1ccccc1C(=O)N1CCC(Oc2cccc(C(F)(F)F)c2)CC1] | | | 421.4 | 1.65 min. | Method A |
| Example 652 | 2-(4-(4-(3-(trifluoromethyl)phenoxy)piperidine-1-carbonyl)phenoxy)acetamide | 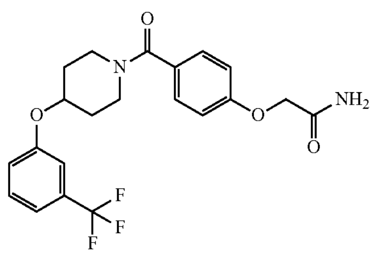 [SMILES: NC(=O)COc1ccc(C(=O)N2CCC(Oc3cccc(C(F)(F)F)c3)CC2)cc1] | | | 421.4 | 1.60 min. | Method A |
| Example 653 | 2-(3-(4-(3-(trifluoromethyl)phenoxy)piperidine-1-carbonyl)phenoxy)acetamide | 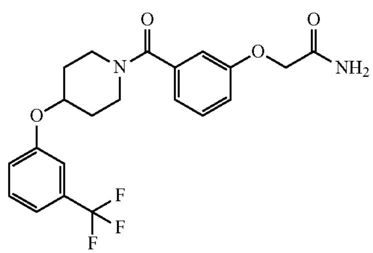 [SMILES: NC(=O)COc1cccc(C(=O)N2CCC(Oc3cccc(C(F)(F)F)c3)CC2)c1] | | | 421.4 | 1.62 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 654 | (1H-1,2,4-triazol-3-yl)(4-(3-(trifluoromethyl)phenoxy)piperidin-1-yl)methanone | 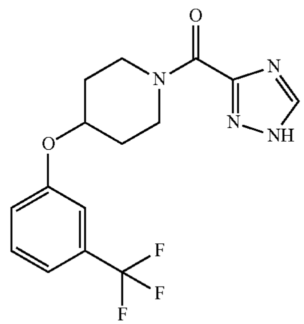 [SMILES: O=C(c1nc[nH]n1)N1CCC(Oc2cccc(C(F)(F)F)c2)CC1] | | | 339.3 | 1.51 min. | Method A |
| Example 655 | N-(2-(2-(4-(3-(trifluoromethoxy)phenoxy)piperidine-1-carbonyl)phenoxy)ethyl)acetamide | 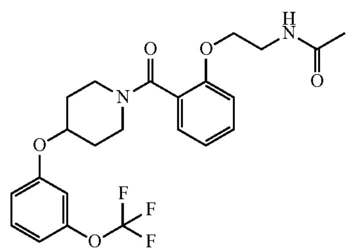 [SMILES: CC(=O)NCCOc1ccccc1C(=O)N1CCC(Oc2cccc(OC(F)(F)F)c2)CC1] | Alternative route | Alternative route | 467.2 | 1.73 min. | Method A |
| Example 656 | N-(2-(2-(4-(3-(trifluoromethoxy)phenoxy)piperidine-1-carbonyl)phenoxy)ethyl)methanesulfonamide | 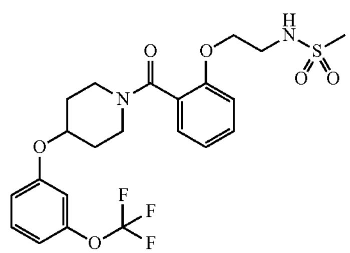 [SMILES: CS(=O)(=O)NCCOc1ccccc1C(=O)N1CCC(Oc2cccc(OC(F)(F)F)c2)CC1] | Alternative route | Alternative route | 501.3 | 1.80 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 657 | ethyl (2-(2-(4-(3-(trifluoromethoxy)phenoxy)piperidine-1-carbonyl)phenoxy)ethyl)carbamate | 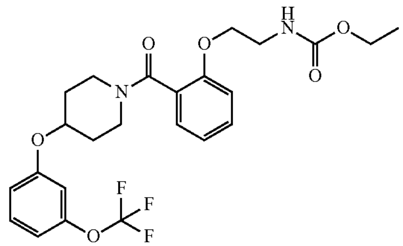 [SMILES: CCOC(=O)NCCOc1ccccc1C(=O)N1CCC(Oc2cccc(OC(F)(F)F)c2)CC1] | Alternative route | | 497.2 | 1.90 min. | Method A |
| Example 658 | N-(2-(2-(4-(3-(trifluoromethoxy)phenoxy)piperidine-1-carbonyl)phenoxy)ethyl)cyclopropane-1,1-dicarboxamide | 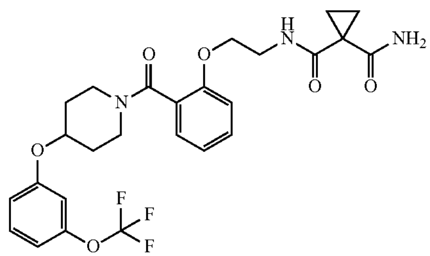 [SMILES: NC(=O)C1(C(=O)NCCOc2ccccc2C(=O)N2CCC(Oc3cccc(OC(F)(F)F)c3)CC2)CC1] | Alternative route | | 534.4 | 1.72 min. | Method A |
| Example 659 | (3-(2-aminomethoxy)phenyl)(4-(3-(trifluoromethoxy)phenoxy)piperidin-1-yl)methanone | 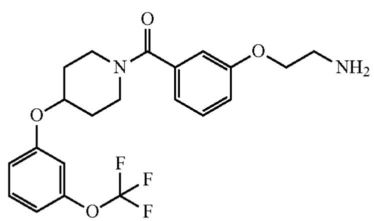 [SMILES: NCCOc1cccc(C(=O)N2CCC(Oc3cccc(OC(F)(F)F)c3)CC2)c1] | Alternative route | | 425.2 | 1.62 min. | Method A |
| Example 660 | N-(2-(3-(4-(3-(trifluoromethoxy)phenoxy)piperidine-1-carbonyl)phenoxy)ethyl)acetamide | 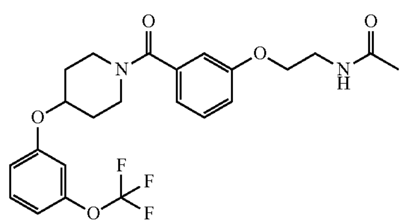 [SMILES: CC(=O)NCCOc1cccc(C(=O)N2CCC(Oc3cccc(OC(F)(F)F)c3)CC2)c1] | Alternative route | | 467.2 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 661 | N-(2-(3-(4-(3-(trifluoromethoxy)phenoxy)piperidine-1-carbonyl)phenoxy)ethyl)methanesulfonamide | 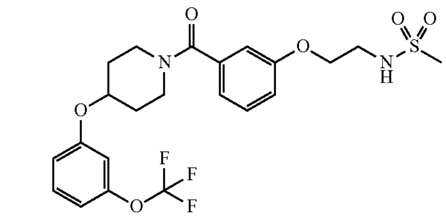 [SMILES: CS(=O)(=O)NCCOc1cccc(C(=O)N2CCC(Oc3cccc(OC(F)(F)F)c3)CC2)c1] | | Alternative route | 503.1 | 1.77 min. | Method A |
| Example 662 | ethyl (2-(3-(4-(3-(trifluoromethoxy)phenoxy)piperidine-1-carbonyl)phenoxy)ethyl)carbamate | 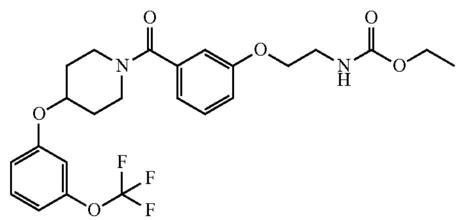 [SMILES: CCOC(=O)NCCOc1cccc(C(=O)N2CCC(Oc3cccc(OC(F)(F)F)c3)CC2)c1] | | Alternative route | 497.2 | 1.88 min. | Method A |
| Example 663 | N-(2-(3-(4-(3-(trifluoromethoxy)phenoxy)piperidine-1-carbonyl)phenoxy)ethyl)cyclopropane-1,1-dicarboxamide | 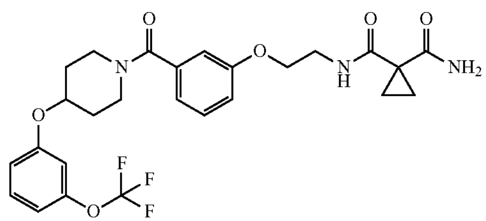 [SMILES: NC(=O)C1(C(=O)NCCOc2cccc(C(=O)N3CCC(Oc4cccc(OC(F)(F)F)c4)CC3)c2)CC1] | | Alternative route | 536.2 | 1.69 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 664 | N-(3-(4-(3-(trifluoromethoxy)phenoxy)piperidine-1-carbonyl)pyridin-2-yl)acetamide | 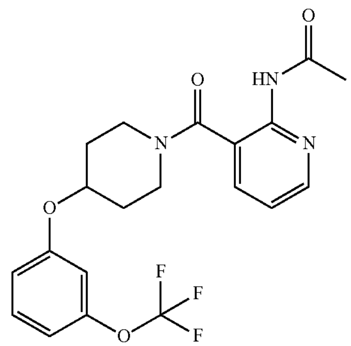 [SMILES: CC(=O)Nc1ncccc1C(=O)N1CCC(Oc2cccc(OC(F)(F)F)c2)CC1] | | | 424.1 | 1.61 min. | Method A |
| Example 665 | N-(1-methyl-5-(4-(3-(trifluoromethoxy)phenoxy)piperidine-1-carbonyl)-1H-pyrazol-3-yl)acetamide | 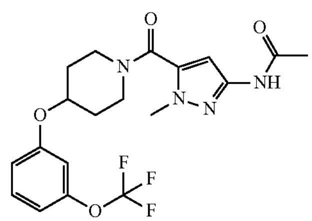 [SMILES: CC(=O)Nc1cc(C(=O)N2CCC(Oc3cccc(OC(F)(F)F)c3)CC2)n(C)n1] | | | 427.1 | 1.62 min. | Method A |
| Example 666 | (2-(ethylsulfonyl)phenyl)(4-(3-(trifluoromethyl)phenoxy)piperidin-1-yl)methanone | 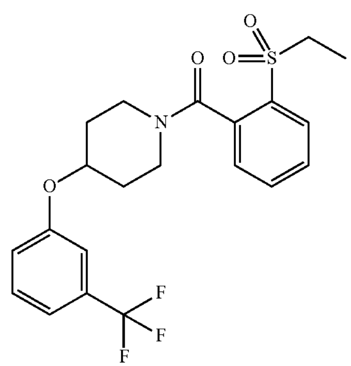 [SMILES: CCS(=O)(=O)c1ccccc1C(=O)N1CCC(Oc2cccc(C(F)(F)F)c2)CC1] | | | 442.1 | 1.85 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 667 | (4-(3-ethoxyphenoxy)piperidin-1-yl)(2-(ethylsulfonyl)phenyl)methanone | 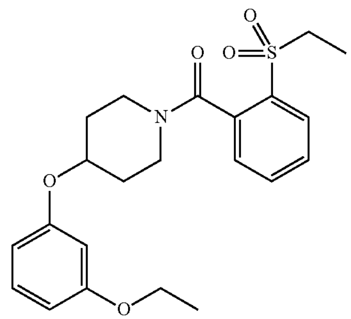 [SMILES: CCOc1cccc(OC2CCN(C(=O)c3ccccc3S(=O)(=O)CC)CC2)c1] | | | 418.1 | 1.77 min. | Method A |
| Example 668 | (2-(ethylsulfonyl)phenyl)(4-(3-(2,2,2-trifluoroethoxy)phenoxy)piperidin-1-yl)methanone | 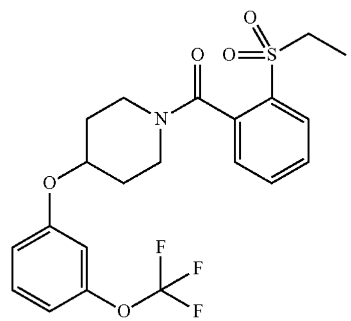 [SMILES: CCS(=O)(=O)c1ccccc1C(=O)N1CCC(Oc2cccc(OC(F)(F)F)c2)CC1] | | | 472.1 | 1.80 min. | Method A |
| Example 669 | N-(2-(4-(3-(trifluoromethoxy)phenoxy)piperidine-1-carbonyl)pyridin-3-yl)acetamide | 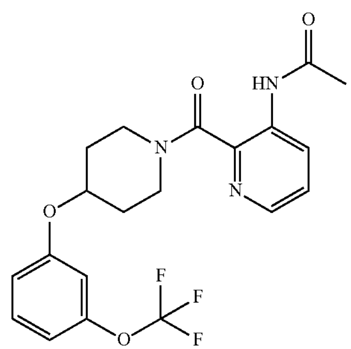 [SMILES: CC(=O)Nc1cccnc1C(=O)N1CCC(Oc2cccc(OC(F)(F)F)c2)CC1] | | | 424.1 | 1.65 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 670 | 2-(4-(4-(3-chlorophenoxy)piperidine-1-carbonyl)phenoxy)acetamide | 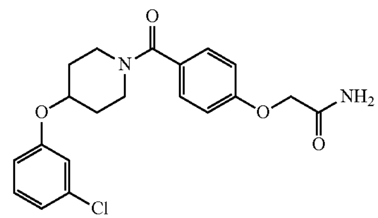 [SMILES: NC(=O)COc1ccc(C(=O)N2CCC(Oc3cccc(Cl)c3)CC2)cc1] | | | 389.1 | 1.57 min. | Method A |
| Example 671 | 2-(2-(4-((4-chlorophenyl)thio)piperidine-1-carbonyl)phenoxy)acetamide | 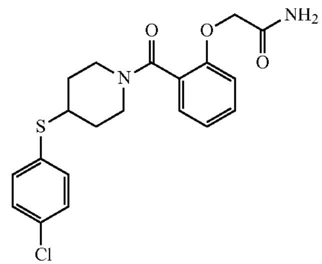 [SMILES: NC(=O)COc1ccccc1C(=O)N1CCC(Sc2ccc(Cl)cc2)CC1] | | | 405.1 | 1.70 min. | Method A |
| Example 672 | 2-(3-(4-((4-chlorophenyl)thio)piperidine-1-carbonyl)phenoxy)acetamide | 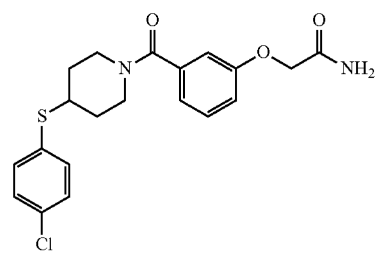 [SMILES: NC(=O)COc1cccc(C(=O)N2CCC(Sc3ccc(Cl)cc3)CC2)c1] | | | 405.1 | 1.67 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 673 | (4-(4-chlorophenyl)thio)piperidin-1-yl)(2-(methylsulfonyl)phenyl)methanone | 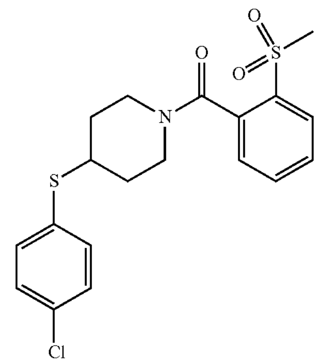 [SMILES: CS(=O)(=O)c1ccccc1C(=O)N1CCC(Sc2ccc(Cl)cc2)CC1] | | | 410.1 | 1.84 min. | Method A |
| Example 674 | 2-(methyl(2-(4-(3-(trifluoromethoxy)phenoxy)piperidine-1-carbonyl)benzyl)amino)acetamide | 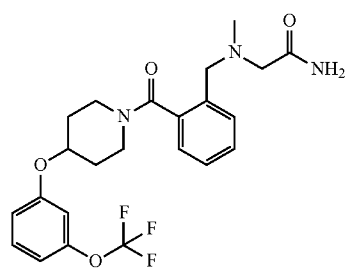 [SMILES: CN(CC(N)=O)Cc1ccccc1C(=O)N1CCC(Oc2cccc(OC(F)(F)F)c2)CC1] | | | 466.2 | 1.77 min. | Method A |
| Example 675 | 1-morpholino-2-(2-(4-(3-(trifluoromethoxy)phenoxy)piperidine-1-carbonyl)phenoxy)ethanone | 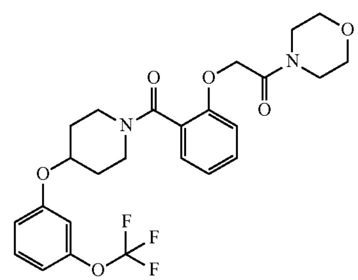 [SMILES: O=C(COc1ccccc1C(=O)N1CCC(Oc2cccc(OC(F)(F)F)c2)CC1)N1CCOCC1] | | | 509.2 | 1.76 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 676 | 1-(piperidin-1-yl)-2-(2-(4-(3-(trifluoromethoxy)phenoxy)piperidine-1-carbonyl)phenoxy)ethanone | 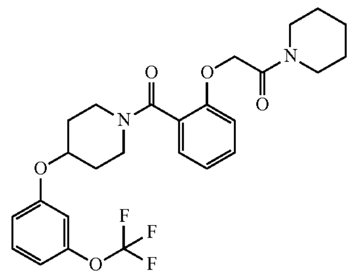 [SMILES: O=C(COc1ccccc1C(=O)N1CCC(Oc2cccc(OC(F)(F)F)c2)CC1)N1CCCCC1] | | | 507.2 | 1.91 min. | Method A |
| Example 677 | (2-(2-methoxyethoxy)phenyl)(4-(3-(trifluoromethoxy)phenoxy)piperidin-1-yl)methanone | 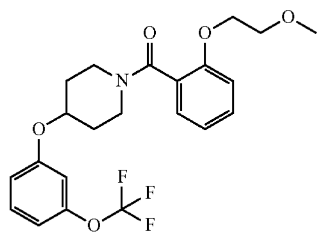 [SMILES: COCCOc1ccccc1C(=O)N1CCC(Oc2cccc(OC(F)(F)F)c2)CC1] | | | 440.1 | 1.92 min. | Method A |
| Example 678 | (3-(methylsulfonyl)phenyl)(4-(3-(trifluoromethyl)phenoxy)piperidin-1-yl)methanone | 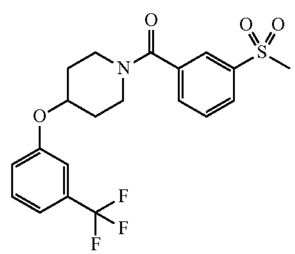 [SMILES: CS(=O)(=O)c1cccc(C(=O)N2CCC(Oc3cccc(C(F)(F)F)c3)CC2)c1] | | | 428.1 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 679 | (4-(3-chlorophenoxy)piperidin-1-yl)(3-(methylsulfonyl)phenyl)methanone | 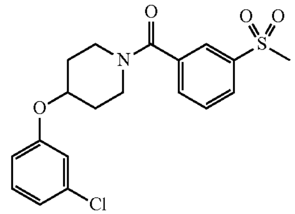 [SMILES: CS(=O)(=O)c1cccc(C(=O)N2CCC(Oc3cccc(Cl)c3)CC2)c1] | | | 394.1 | 1.69 min. | Method A |
| Example 680 | (4-(4-chlorophenoxy)piperidin-1-yl)(3-(methylsulfonyl)phenyl)methanone | 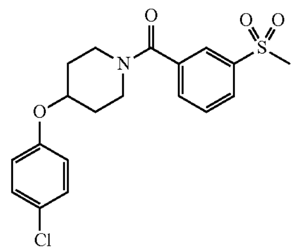 [SMILES: CS(=O)(=O)c1cccc(C(=O)N2CCC(Oc3ccc(Cl)cc3)CC2)c1] | | | 394.1 | 1.69 min. | Method A |
| Example 681 | (4-(4-chlorophenoxy)piperidin-1-yl)(2-(ethylsulfonyl)phenyl)methanone | 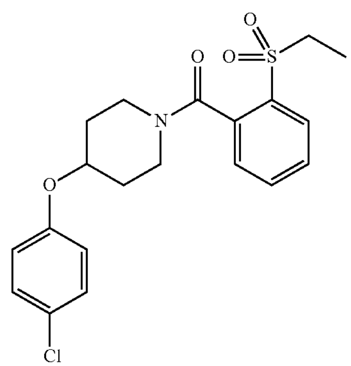 [SMILES: CCS(=O)(=O)c1ccccc1C(=O)N1CCC(Oc2ccc(Cl)cc2)CC1] | | | 408.2 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 682 | N,N-dimethyl-3-(4-(3-(trifluoromethyl)phenoxy)piperidine-1-carbonyl)benzenesulfonamide | 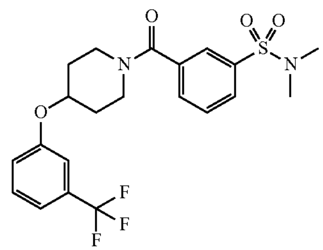 [SMILES: CN(C)S(=O)(=O)c1cccc(C(=O)N2CCC(Oc3cccc(C(F)(F)F)c3)CC2)c1] | | | 457.2 | 1.83 min. | Method A |
| Example 683 | 2-(4-(4-chlorophenoxy)piperidine-1-carbonyl-N,N-dimethylbenzenesulfonamide | 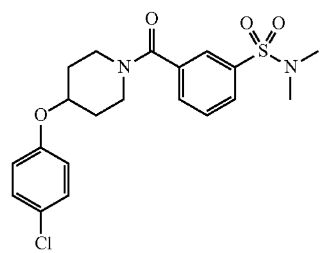 [SMILES: CN(C)S(=O)(=O)c1cccc(C(=O)N2CCC(Oc3ccc(Cl)cc3)CC2)c1] | | | 423.1 | 1.80 min. | Method A |
| Example 684 | N,N-dimethyl-3-(4-(3-(2,2,2-trifluoroethoxy)phenoxy)piperidine-1-carbonyl)benzenesulfonamide | 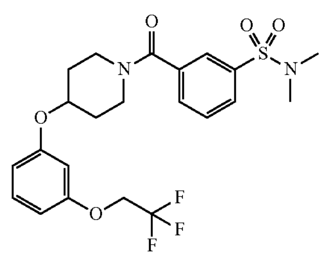 [SMILES: CN(C)S(=O)(=O)c1cccc(C(=O)N2CCC(Oc3cccc(OCC(F)(F)F)c3)CC2)c1] | | | 487.2 | 1.79 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 685 | N,N-dimethyl-2-(4-(3-(trifluoromethyl)phenoxy)piperidine-1-carbonyl)benzenesulfonamide | 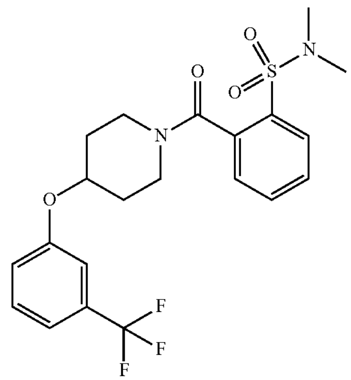 [SMILES: CN(C)S(=O)(=O)c1ccccc1C(=O)N1CCC(Oc2cccc(C(F)(F)F)c2)CC1] | | | 457.2 | 1.86 min. | Method A |
| Example 686 | 2-(4-(4-chlorophenoxy)piperidine-1-carbonyl)-N,N-dimethylbenzenesulfonamide | 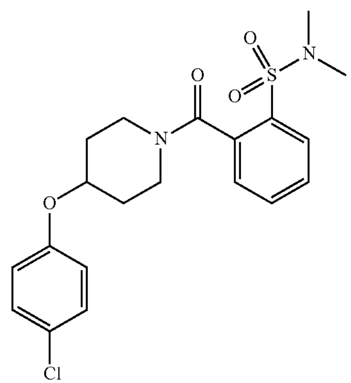 [SMILES: CN(C)S(=O)(=O)c1ccccc1C(=O)N1CCC(Oc2ccc(Cl)cc2)CC1] | | | 423.1 | 1.83 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 687 | N,N-dimethyl-2-(4-(3-(2,2,2-trifluoroethoxyphenoxy)piperidine-1-carbonyl)benzenesulfonamide | 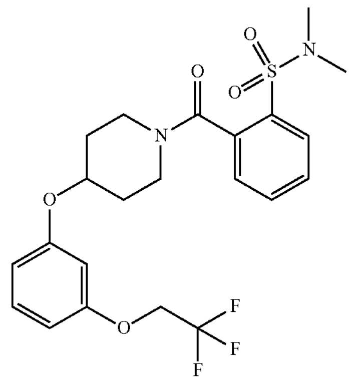 [SMILES: CN(C)S(=O)(=O)c1ccccc1C(=O)N1CCC(Oc2cccc(OCC(F)(F)F)c2)CC1] | | | 487.2 | 1.81 min. | Method A |
| Example 688 | (4-(3-(2-methoxyethoxy)phenoxy)piperidin-1-yl)(quinolin-8-yl)methanone | 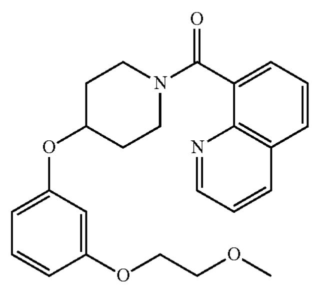 [SMILES: COCCOc1cccc(OC2CCN(C(=O)c3cccc4cccnc34)CC2)c1] | | | 407.2 | 1.59 min. | Method A |
| Example 689 | (4-(3-(2-methoxyethoxy)phenoxy)piperidin-1-yl)(quinolin-2-yl)methanone | 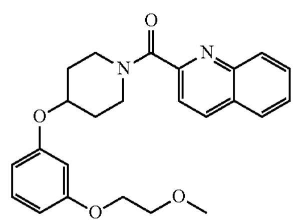 [SMILES: COCCOc1cccc(OC2CCN(C(=O)c3ccc4ccccc4n3)CC2)c1] | | | 407.2 | 1.71 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 690 | (4-(3-(2-methoxyethoxy)phenoxy)piperidin-1-yl)(2-methyl-2H-indazol-3-yl)methanone | 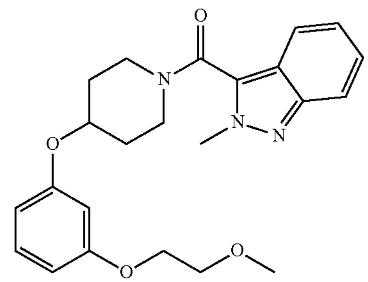 [SMILES: COCCOc1cccc(OC2CCN(C(=O)c3c4ccccc4nn3C)CC2)c1] | | | 410.2 | 1.67 min. | Method A |
| Example 691 | 2-((2-(4-(3-(trifluoromethoxy)phenoxy)piperidine-1-carbonyl)phenyl)thio)acetamide | 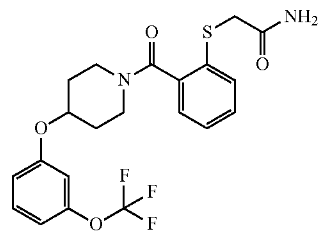 [SMILES: NC(=O)CSc1ccccc1C(=O)N1CCC(Oc2cccc(OC(F)(F)F)c2)CC1] | | | 455.1 | 1.71 min. | Method A |
| Example 692 | 2-((2-(4-(4-chlorophenoxy)piperidine-1-carbonyl)phenyl)thio)acetamide | 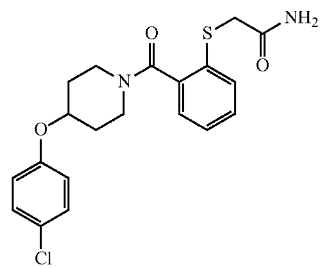 [SMILES: NC(=O)CSc1ccccc1C(=O)N1CCC(Oc2ccc(Cl)cc2)CC1] | | | 405.1 | 1.64 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 693 | 4-(4-(3-(2,2,2-trifluoroethoxy)phenoxy)piperidine-1-carbonyl)-1H-benzo[d]imidazol-2(3H)-one | 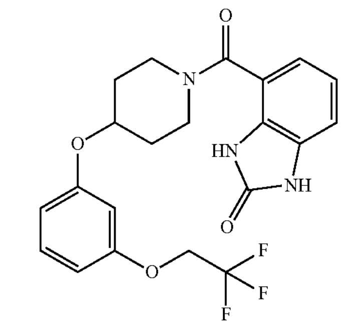 [SMILES: O=C(c1cccc2[nH]c(=O)[nH]c12)N1CCC(Oc2cccc(OCC(F)(F)F)c2)CC1] | | | 436.2 | 1.58 min. | Method A |
| Example 694 | (4-(3-ethoxyphenoxy)piperidin-1-yl)(1-methyl-1H-benzo[d]imidazol-2-yl)methanone | 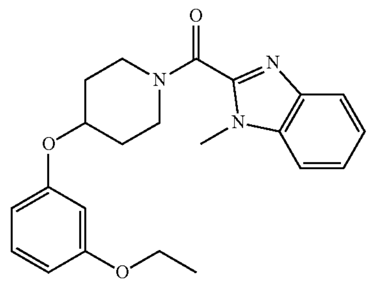 [SMILES: CCOc1cccc(OC2CCN(C(=O)c3nc4ccccc4n3C)CC2)c1] | | | 380.3 | 1.78 min. | Method A |
| Example 695 | (4-(3-fluorophenoxy)piperidin-1-yl)(1-methyl-1H-benzo[d]imidazol-2-yl)methanone | 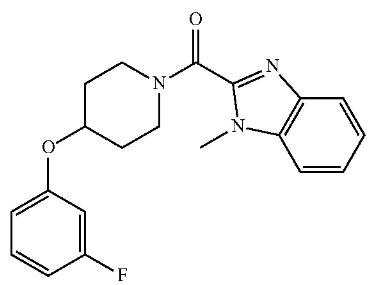 [SMILES: Cn1c(C(=O)N2CCC(Oc3cccc(F)c3)CC2)nc2ccccc21] | | | 354.3 | 1.72 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 696 | (1H-pyrrolo[2,3-b]pyridin-2-yl)(4-(3-(2,2,2-trifluoroethoxy)phenoxy)piperidin-1-yl)methanone | 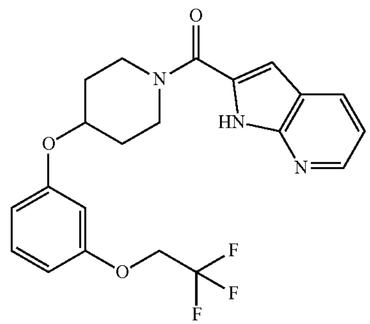 [SMILES: O=C(c1cc2cccnc2[nH]1)N1CCC(Oc2cccc(OCC(F)(F)F)c2)CC1] | | | 420.2 | 1.74 min. | Method A |
| Example 697 | (4-(3-ethoxyphenoxy)piperidin-1-yl)(1H-pyrrolo[2,3-b]pyridin-2-yl)methanone | 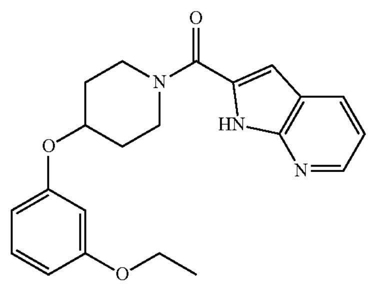 [SMILES: CCOc1cccc(OC2CCN(C(=O)c3cc4cccnc4[nH]3)CC2)c1] | | | 366.2 | 1.71 min. | Method A |
| Example 698 | (1H-pyrrolo[2,3-b]pyridin-2-yl)(4-(3-(trifluoromethoxy)phenoxy)piperidin-1-yl)methanone | 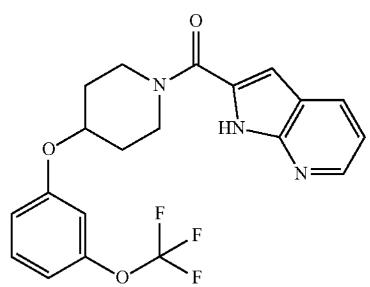 [SMILES: O=C(c1cc2cccnc2[nH]1)N1CCC(Oc2cccc(OC(F)(F)F)c2)CC1] | | | 406.1 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 699 | (4-(3-ethoxyphenoxy)piperidin-1-yl)(1-methyl-1H-pyrazolo[3,4-b]pyridin-3-yl)methanone | 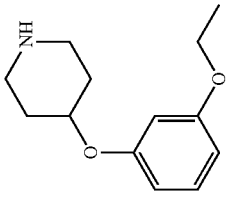 | 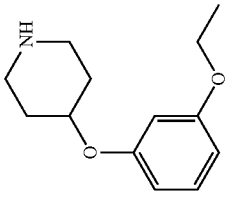 | 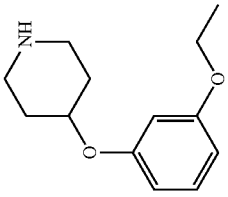 | 381.2 | 1.78 min. | Method A |
| Example 700 | (4-(3-ethoxyphenoxy)piperidin-1-yl)(1H-pyrrolo[2,3-b]pyridin-3-yl)methanone | 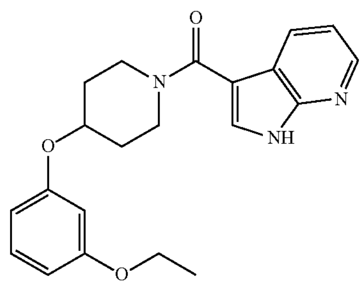 [SMILES: CCOc1cccc(OC2CCN(C(=O)c3c[nH]c4ncccc34)CC2)c1] | 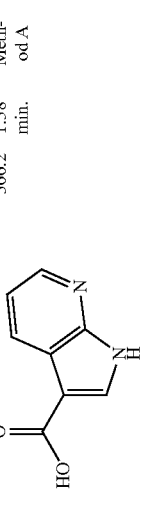 | 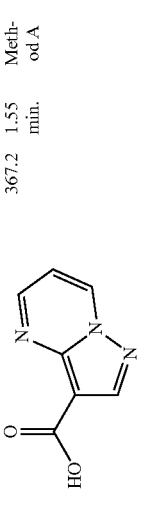 | 366.2 | 1.58 min. | Method A |
| Example 701 | (4-(3-ethoxyphenoxy)piperidin-1-yl)(pyrazolo[1,5-a]pyrimidin-3-yl)methanone | 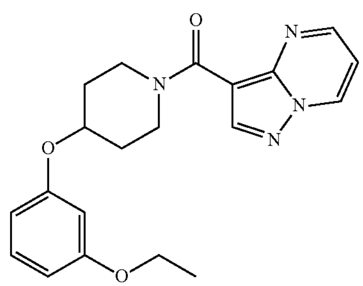 [SMILES: CCOc1cccc(OC2CCN(C(=O)c3cnn4cccnc34)CC2)c1] | 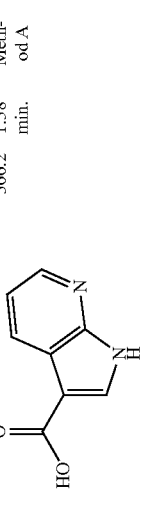 | 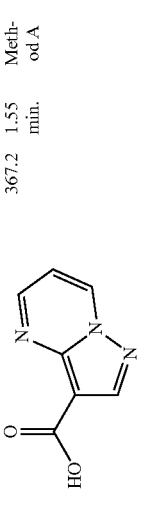 | 367.2 | 1.55 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 702 | (1,3-dimethyl-1H-benzo[2,3-c]pyrazol-5-yl)(4-(3-ethoxyphenoxy)piperidin-1-yl)methanone | 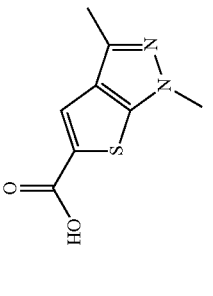 | 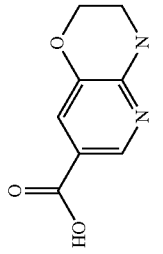 |  | 400.2 | 1.78 min. | Method A |
| Example 703 | (4-(3-fluorophenoxy)piperidin-1-yl)(4-methyl-3,4-dihydro-2H-pyrido[3,2-b][1,4]oxazin-7-yl)methanone | 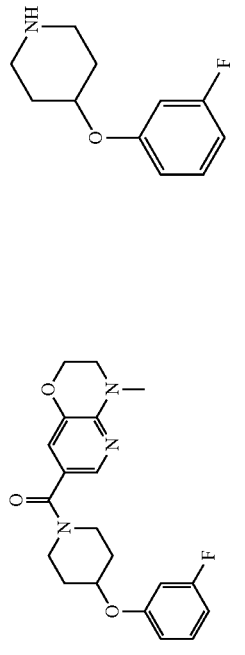 | 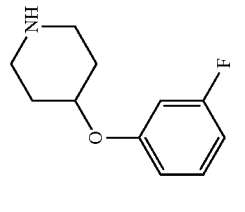 |  | 372.2 | 1.66 min. | Method A |
| Example 704 | (3,5-dimethyl-1H-pyrazol-4-yl)(4-(3-(2,2,2-trifluoroethoxy)phenoxy)piperidin-1-yl)methanone | 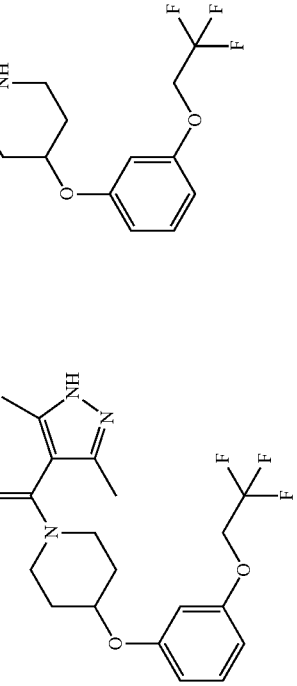 | 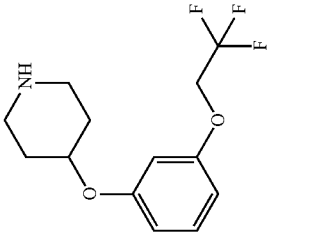 |  | 398.2 | 1.56 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 705 | N-(2-hydroxyethyl)-N-methyl-2-(4-(3-(trifluoromethoxy)phenoxy)piperidine-1-carbonyl)benzenesulfonamide | 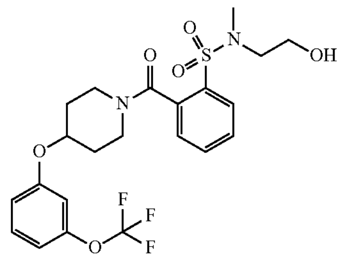 [SMILES: CN(CCO)S(=O)(=O)c1ccccc1C(=O)N1CCC(Oc2cccc(OC(F)(F)F)c2)CC1] | | | 503.2 | 1.78 min. | Method A |
| Example 706 | N-(2-methoxyethyl)-N-methyl-2-(4-(3-(trifluoromethoxy)phenoxy)piperidine-1-carbonyl)benzenesulfonamide | 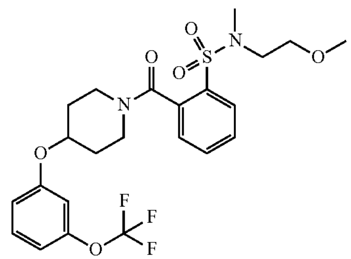 [SMILES: COCCN(C)S(=O)(=O)c1ccccc1C(=O)N1CCC(Oc2cccc(OC(F)(F)F)c2)CC1] | | | 517.2 | 1.91 min. | Method A |
| Example 707 | (2-(morpholinosulfonyl)phenyl)(4-(3-(trifluoromethoxy)phenoxy)piperidin-1-yl)methanone | 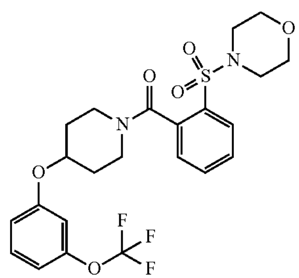 [SMILES: O=C(c1ccccc1S(=O)(=O)N1CCOCC1)N1CCC(Oc2cccc(OC(F)(F)F)c2)CC1] | | | 515.2 | 1.88 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 708 | 2-(N-methyl-2-(4-(3-(trifluoromethoxy)phenoxy)piperidine-1-carbonyl)phenylsulfonamide)acetamide | 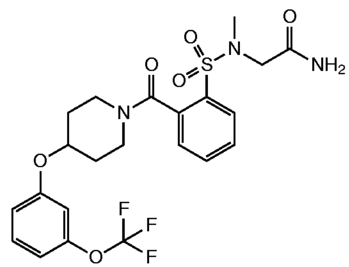 [SMILES: CN(CC(N)=O)S(=O)(=O)c1ccccc1C(=O)N1CCC(Oc2cccc(OC(F)(F)F)c2)CC1] | | | 516.2 | 1.72 min. | Method A |
| Example 709 | N-methyl-3-(4-(3-(2,2,2-trifluoroethoxy)phenoxy)piperidine-1-carbonyl)benzenesulfonamide | 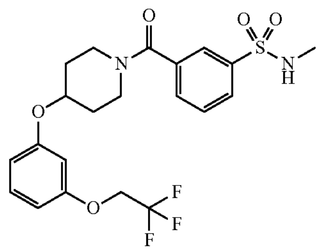 [SMILES: CNS(=O)(=O)c1cccc(C(=O)N2CCC(Oc3cccc(OCC(F)(F)F)c3)CC2)c1] | | | 473.2 | 1.70 min. | Method A |
| Example 710 | 3-(4-(3-ethoxyphenoxy)piperidine-1-carbonyl)-N-methylbenzenesulfonamide | 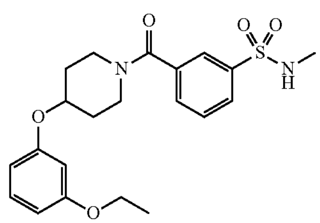 [SMILES: CCOc1cccc(OC2CCN(C(=O)c3cccc(S(=O)(=O)NC)c3)CC2)c1] | | | 419.2 | 1.66 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 711 | N-methyl-3-(4-(3-(trifluoromethoxy)phenoxy)piperidine-1-carbonyl)benzenesulfonamide | 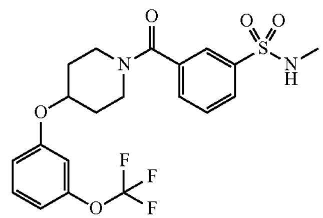 [SMILES: CNS(=O)(=O)c1cccc(C(=O)N2CCC(Oc3cccc(OC(F)(F)F)c3)CC2)c1] | | | 459.2 | 1.77 min. | Method A |
| Example 712 | (1,5-naphthyridin-2-yl)(4-(3-(trifluoromethoxy)phenoxy)piperidin-1-yl)methanone | 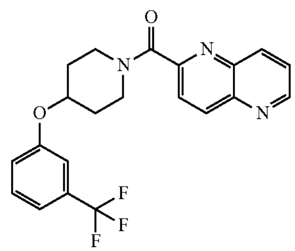 [SMILES: O=C(c1ccc2ncccc2n1)N1CCC(Oc2cccc(C(F)(F)F)c2)CC1] | | | 402.2 | 1.73 min. | Method A |
| Example 713 | 3-(4-((4-chlorophenyl)thio)piperidine-1-carbonyl)benzenesulfonamide | 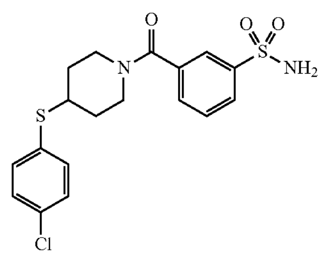 [SMILES: NS(=O)(=O)c1cccc(C(=O)N2CCC(Sc3ccc(Cl)cc3)CC2)c1] | | | 411.1 | 1.69 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 714 | (4-((4-chlorophenyl)thio)piperidin-1-yl)(1,5-naphthyridin-2-yl)methanone | 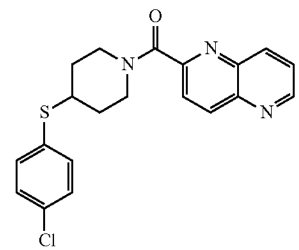 [SMILES: O=C(c1ccc2ncccc2n1)N1CCC(Sc2ccc(Cl)cc2)CC1] | | | 384.1 | 1.77 min. | Method A |
| Example 715 | N-(6-(4-((4-chlorophenyl)thio)piperidine-1-carbonyl)pyidin-2-yl)acetamide | 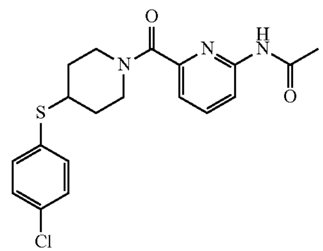 [SMILES: CC(=O)Nc1cccc(C(=O)N2CCC(Sc3ccc(Cl)cc3)CC2)n1] | | | 390.1 | 1.71 min. | Method A |
| Example 716 | (4-((4-chlorophenyl)thio)piperidin-1-yl)(1,6-naphthyridin-8-yl)methanone | 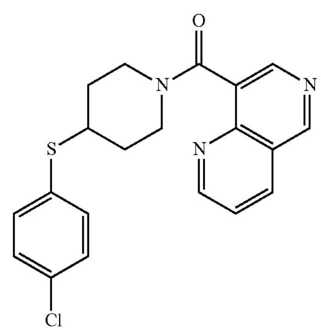 [SMILES: O=C(c1cncc2cccnc12)N1CCC(Sc2ccc(Cl)cc2)CC1] | | | 384.1 | 1.66 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 717 | 2-(4-(4-(3,4-difluorophenoxy)piperidine-1-carbonyl)phenoxy)acetamide | 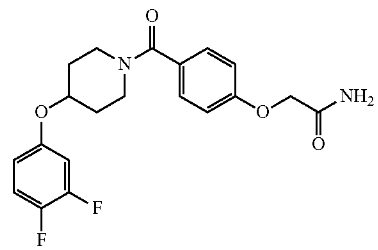 [SMILES: NC(=O)COc1ccc(C(=O)N2CCC(Oc3ccc(F)c(F)c3)CC2)cc1] | | | 391.2 | 1.49 min. | Method A |
| Example 718 | (4-(3,4-difluorophenoxy)piperidin-1-yl)(1,5-napthyridin-2-yl)methanone | 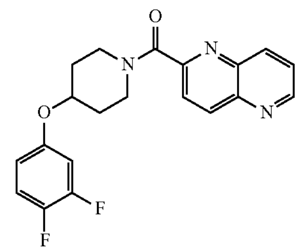 [SMILES: O=C(c1ccc2ncccc2n1)N1CCC(Oc2ccc(F)c(F)c2)CC1] | | | 370.2 | 1.61 min. | Method A |
| Example 719 | 2-(4-(4-(2,4-difluorophenoxy)piperidine-1-carbonyl)phenoxy)acetamide | 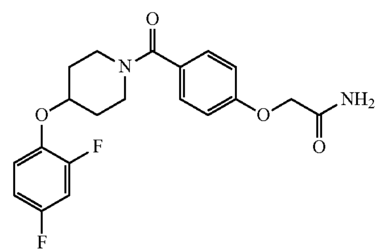 [SMILES: NC(=O)COc1ccc(C(=O)N2CCC(Oc3ccc(F)cc3F)CC2)cc1] | | | 391.2 | 1.48 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 720 | N-(4-(4-(3-(trifluoromethoxy)phenoxy)piperidine-1-carbonyl)pyridin-2-yl)pivalamide | 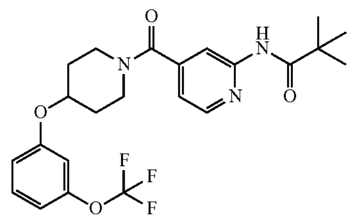 [SMILES: CC(C)(C)C(=O)Nc1cc(C(=O)N2CCC(Oc3cccc(OC(F)(F)F)c3)CC2)ccn1] | | | 464.5 | 1.92 min. | Method A |
| Example 721 | (2-(1H-imidazol-1-yl)pyridin-4-yl)(4-(3-(trifluoromethoxy)phenoxy)piperidin-1-yl)methanone | 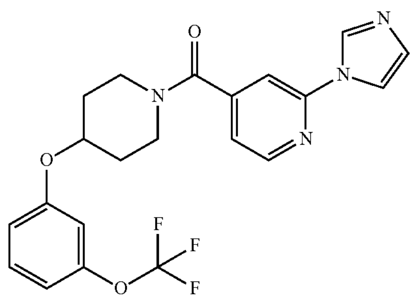 [SMILES: O=C(c1ccnc(-n2ccnc2)c1)N1CCC(Oc2cccc(OC(F)(F)F)c2)CC1] | | | 433.2 | 1.72 min. | Method A |
| Example 722 | N-(4-(4-(3-ethoxyphenoxy)piperidine-1-carbonyl)pyridin-2-yl)pivalamide | 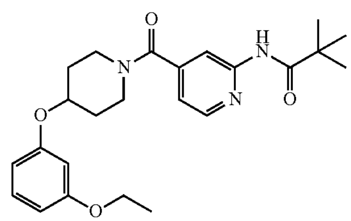 [SMILES: CCOc1cccc(OC2CCN(C(=O)c3ccnc(NC(=O)C(C)(C)C)c3)CC2)c1] | | | 424.5 | 1.82 min. | Method A |

TABLE 3-continued

| Example | Name | Structure | Structure of amine part | Structure of carboxylic acid part | Observed MS | Retention time | QC Method |
|---|---|---|---|---|---|---|---|
| Example 723 | 1-(3-(4-(3-(trifluoromethoxy)phenoxy)piperidine-1-carbonyl)phenyl)pyrrolidin-2-one | 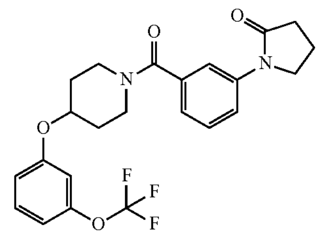 [SMILES: O=C(c1cccc(N2CCCC2=O)c1)N1CCC(Oc2cccc(OC(F)(F)F)c2)CC1] | | | 449.1 | 1.81 min. | Method A |
| Example 724 | 1-(3-(4-(3-(trifluoromethoxy)phenoxy)piperidine-1-carbonyl)phenyl)imidazolidin-2-one | 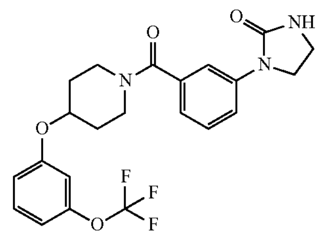 [SMILES: O=C(c1cccc(N2CCNC2=O)c1)N1CCC(Oc2cccc(OC(F)(F)F)c2)CC1] | | | 448.3 | 1.72 min. | Method A |
| Example 725 | (5-amino-1H-pyrazol-3-yl)(4-(3-(trifluoromethoxy)phenoxy)piperidin-1-yl)methanone | 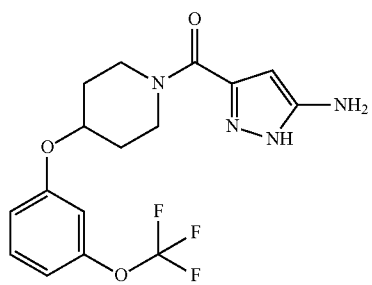 [SMILES: Nc1cc(C(=O)N2CCC(Oc3cccc(OC(F)(F)F)c3)CC2)n[nH]1] | | | 371.1 | 1.54 min. | Method A |

TABLE 4

| Example | $^1$H-NMR data (300 Mz, CDCl3) |
|---|---|
| Example 21 | δ 8.98-8.93 (1H, m), 8.18 (1H, d, J = 8.4 Hz), 7.87-7.85 (1H, m), 7.70-7.67 (1H, m), 7.60-7.55 (1H, m), 7.46-7.42 (1 H, m), 7.24-7.21 (2H, m), 6.85-6.83 (2H, m), 4.57-4.50 (1H, m), 4.16-3.96 (2H, m), 3.48-3.35 (1H, m), 3.17-3.04 (1H, m), 2.28-1.48 (4H, m) |
| Example 80 | δ 8.57 (1H, d, J = 1.5 Hz), 7.67 (1H, dd, J = 8.1, 2.2 Hz), 7.28-7.21 (3H, m), 6.88-6.83 (2H, m), 4.59-4.52 (1H, m), 3.94-3.32 (4H, m), 2.60 (3H, s), 2.08-1.70 (4H, m) |
| Example 92 | δ 7.28-7.21 (2H, m), 6.89-6.82 (2H, m), 4.58-4.50 (1H, m), 3.82-3.51 (4H, m), 2.68 (3H, s), 2.41 (3H, s), 2.01-1.79 (4H, m) |
| Example 191 | δ 8.99-8.95 (1H, m), 8.20-8.16 (1H, m), 7.88 (1H, d, J = 1.5 Hz), 7.86-7.84 (1H, m), 7.70-7.34 (5H, m), 7.14-7.10 (1H, m), 4.71-4.64 (1H, m), 4.20-3.96 (2H, m), 3.51-3.36 (1H, m), 3.20-3.05 (1H, m), 2.59 (3H, s), 2.32-1.56 (4H, m) |
| Example 403 | δ 8.33 (1H, d, J = 5.1 Hz), 8.23 (1H, s), 8.16 (1H, s), 7.26-7.20 (2H, m), 7.08-7.05 (1H, m), 6.87-6.81 (2H, m), 4.60-4.53 (1H, m), 3.97-3.74 (2H, m), 3.67-3.55 (1H, m), 3.91-3.76 (1H, m), 2.22 (3H, s), 2.09-1.75 (4H, m) |
| Example 451 | δ 8.68 (1H, d, J = 4.4 Hz), 8.19 (1H, s), 7.85 (1H, br.s), 7.50 (1H, dd, J = 5.1, 1.5 Hz), 7.33-7.27 (1H, m), 6.86-6.77 (3H, m), 5.72 (1H, br.s), 4.68-4.59 (1H, m), 4.02-3.77 (2H, m), 3.67-3.52 (1H, m), 3.39-3.28 (1H, m), 2.12-1.78 (4H, m) |
| Example 561 | δ 7.91-7.74 (1H, m), 7.45-7.20 (3H, m), 7.11-7.00 (2H, m), 6.90-6.75 (3H, m), 5.52 (1H, br.s), 4.76-4.55 (3H, m), 4.08-3.77 (2H, m), 3.67-3.55 (1H, m), 3.42-3.31 (1H, m), 2.10-1.76 (4H, m) |
| Example 574 | δ 9.32(1H, s), 9.20-9.13 (1H, m), 8.77 (1H, d, J = 1.5 Hz), 8.39-8.32 (1H, m), 7.61 (1H, dd, J = 8.4, 4.0 Hz), 7.28 (1H, t, J = 8.4 Hz), 6.89-6.73 (3H, m), 4.66-4.56 (1H, m), 4.19-3.96 (2H, m), 3.55-3.41 (1H, m), 3.25-3.09 (1H, m), 2.29-1.76 (4H, m) |

Pharmacological Assays

In Vitro Activities Against Human Voltage Gated Sodium Channels

The inhibitory activities of compounds against voltage gated sodium channels were determined by methodology well known in the art.

The ability of the aryl substituted carboxamid derivatives of the formula (I) to inhibit the $Na_{v1.3}$, $Na_{v1.7}$ and $Na_{v1.5}$ channels was measured by Fluorescence Resonance Energy Transfer (FRET) assay and electrophysiology assay described below.

FRET Assay (Method A)

This screen was used to determine the effects of compounds on human $Na_{v1.3}$, human $Na_{v1.7}$, and human $Na_{v1.5}$ channels, utilising the cell imaging technology by Hamamatsu Photonics's Functional Drug Screening System (FDSS). The change of membrane potential was monitored with fluorescent membrane potential dye pair, oxonol (DiS-BAC2(3)) and coumarin (CC2-DMPE), using FRET technology.

Cell Maintenance:

Each HEK293 cells expressing human $Na_{v1.3}$ channels and HEK293 cells expressing human $Na_{v1.5}$ channels were grown in T225 flasks, in a 5% $CO_2$ humidified incubator to about 80% confluence. Media composition consisted of Dulbecco's Modified Eagle Medium (high glucose), 10% fetal calf serum (FCS), 100 units/ml Penicillin, 100 microgram/ml Streptomycin and 500 microgram/ml Geneticine.

CHO cells expressing human $Na_{v1.7}$ channels were grown in T225 flasks, in a 5% $CO_2$ humidified incubator to about 80% confluence. Media composition consisted of HAM/F12 with Glutamax I, 10% FCS, 100 units/ml Penicillin and 100 microgram/ml Hygromycin.

Protocol:
Seeded each cell lines (1.5×10$^4$ cells/well) into poly-D-lysine coated 384-well plates prior to experimentation.
Incubated at 37° C. in 5% $CO_2$ for 24 hours.
Washed each well with buffer #1 (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice.
Added 1st loading solution containing 5 microM CC2-DMPE and 0.02% Pluronic F-127 in buffer #1.
Incubated the plate at room temperature in dark for 0.5 hours.
Washed each well with buffer #2 (160 mM Choline, 10 mM D-Glucose, 0.1 mM $CaCl_2$, 1 mM $MgCl_2$, 10 mM HEPES, pH 7.4 adjusted with KOH) twice.
Added 2nd loading solution containing 15 microM DiS-BAC2(3), 0.5 mM VABSC-1, 10 microM veratridine and 0.004% Pluronic F-127 in buffer #2.
Added compound solutions into the assay plate for 30 minutes under the dark at room temperature.
Measured the activity by FDSS.
The data were analyzed and reported as normalized ratios of intensities measured in the 465 nm and 575 nm channels. The process of calculating these ratios was performed as follows:
"FI465B"=the mean of fluorescence intensity as baseline (before Na+ ligand addition) at 465 nm
"FI575B"=the mean of fluorescence intensity as baseline (before Na+ ligand addition) at 575 nm
"FI465Max"=maximum fluorescence intensity at 465 nm after Na+ stimulation
"FI575 Min"=minimum fluorescence intensity at 575 nm after Na+ stimulation
"FR"=fluorescence ratio=(F1465Max/F1575 Min)−(FI465B/FI575B)

[Math. 1]

$$\text{Inhibition (\%)} = 100 - \frac{(FR \text{ of each well}) - (\text{median } FR \text{ in positive controls})}{(\text{median } FR \text{ in negative controls}) - (\text{median } FR \text{ in negative controls})} \times 100$$

This analysis was performed using a computerized specific program designed for FDSS generated data. Fluorescence ratio values were plotted using XLfit to determine an IC$_{50}$ value for each compound.

All tested compounds in this assay showed less than about 5 microM against either $Na_{v1.3}$ or $Na_{v1.7}$ in the above assays. Preferable compounds showed less than about 1 microM against either $Na_{v1.3}$ or $Na_{v1.7}$ in the above assays. In addition, all tested compounds showed higher IC$_{50}$ values in $Na_{v1.5}$ FRET Assay than IC$_{50}$ values in $Na_{v1.3}$ or $Na_{v1.7}$ FRET Assay.

Especially, Example 1, 2, 3, 4, 5, 6, 7, 9, 10, 11, 13, 14, 15, 16, 20, 21, 22, 26, 27, 28, 30, 31, 33, 34, 35, 36, 37, 38, 39, 40, 41, 42, 43, 45, 46, 47, 48, 49, 50, 52, 53, 54, 55, 57, 58, 59, 60, 61, 65, 66, 67, 69, 70, 71, 72, 73, 74, 76, 77, 78, 79, 80, 83, 84, 86, 87, 88, 92, 94, 95, 96, 97, 98, 100, 103, 104, 107, 109, 112, 113, 114, 115, 116, 117, 118, 119, 120, 122, 123, 125, 126, 128, 134, 137, 139, 141, 142, 143, 144, 151, 152, 159, 163, 168, 169, 170, 171, 172, 175, 176, 183, 185, 186, 188, 189, 190, 193, 197, 199, 200, 205, 207, 211, 212, 215, 216, 217, 218, 219, 220, 222, 226, 230, 231, 232, 233, 237, 238, 239, 240, 241, 242, 243, 246, 252, 256, 257, 258, 259, 263, 265, 266, 267, 268, 269, 270, 271, 278, 283, 284, 285, 290, 291, 292, 294, 296, 297, 298, 299, 303, 305, 312, 313, 314, 315, 318, 319, 320, 323, 324, 325, 328, 329, 330, 336, 337, 338, 339, 340, 342, 343, 345, 347, 348, 350, 353, 354, 355, 357, 360, 361, 362, 363, 367, 368, 369, 370, 371, 374, 375, 376, 378, 379, 380, 381, 382, 385, 389, 396, 398, 400, 401, 406, 410, 411, 412, 413, 414, 416, 417, 418, 419, 421, 423, 424, 434, 435, 440, 450, 451, 455, 459, 460, 461, 463, 470, 471, 472, 477, 478, 479, 481, 482, 483, 484, 485, 486, 487, 492, 493, 495, 496, 508, 512, 513, 514, 518, 520, 522, 539, and 540 of the invention have an IC$_{50}$ less than about 1 microM in the Na$_{v1.3}$ or Na$_{v1.7}$ FRET Assay.

FRET Assay (Method B)

This screen was used to determine the effects of compounds on human Na$_{v1.3}$, human Na$_{v1.7}$, and human Na$_{v1.5}$ channels, utilising electrical field stimulation (EFS) system in 96-well plate format on FDSS (Hamamatsu Photonics) platform. The change of membrane potential was monitored with FRET dye pair, oxonol (DiSBAC2(3)) and coumarin (CC2-DMPE).

Cell Maintenance:

Each HEK293 cells expressing human Na$_{v1.3}$ channels and HEK293 cells expressing human Na$_{v1.5}$ channels were grown in T225 flasks, in a 5% CO$_2$ humidified incubator to about 80% confluence. Media composition consisted of Dulbecco's Modified Eagle Medium (high glucose), 10% FCS, 100 units/ml Penicillin, 100 microgram/ml Streptomycin and 500 microgram/ml Geneticine.

CHO cells expressing human Na$_{v1.7}$ channels were grown in T225 flasks, in a 5% CO 2 humidified incubator to about 80% confluence. Media composition consisted of HAM/F12 with Glutamax I, 10% FCS, 100 units/ml Penicillin and 100 microgram/ml Hygromycin.

Protocol:

Seeded each cell lines (1×10$^5$ cells/well) into poly-D-lysine coated 96-well plates prior to experimentation.

Incubated at 37° C. in 5% CO$_2$ for 24 hours.

Washed each well with assay buffer (140 mM NaCl, 4.5 mM KCl, 10 mM D-Glucose, 2 mM CaCl$_2$, 1 mM MgCl$_2$, 10 mM HEPES, pH 7.4 adjusted with NaOH) twice.

Added 1st loading solution containing 10 microM CC2-DMPE and 0.06% Pluronic F-127 in assay buffer.

Incubated the plate at room temperature in dark for 1 hour.

Removed 1st loading solution and added 2nd loading solution containing 15 microM DiSBAC2(3), 0.555 mM VABSC-1 and 0.004% Pluronic F-127 in assay buffer.

Placed the plate under the dark at room temperature for 25 minutes.

Added compound solutions into the assay plate.

Set the assay plate in FDSS and placed an EFS device on the plate.

Measured EFS-induced fluorescent response by FDSS.

The data were analyzed and reported as normalized ratios of intensities measured at 440 nm. The process of calculating these ratios was performed as follows:

[Math. 2]

$$FIR = \text{Fluorescence Integration Ratio} =$$
$$\text{the integral of the ratio normalized by baseline (before } EFS\text{)}$$

$$\% \text{ inhibition} = \left\{ 1 - \frac{(FIR \text{ of each well} - \text{median } FIR \text{ in 100\% } Inh.)}{\left(\begin{array}{c}\text{median } FIR \text{ in 0\% } Inh. - \\ \text{median } FIR \text{ in 100\% } Inh.\end{array}\right)} \right\} \times 100$$

This analysis was performed using a computerized specific program designed for FDSS generated data. Fluorescence ratio values were plotted using XLfit to determine an IC$_{50}$ value for each compound.

All tested compounds in this assay showed less than about 5 microM against either Na$_{v1.3}$ or Na$_{v1.7}$ in the above assays. Preferable compounds showed less than about 3 microM against either Na$_{v1.3}$ or Na$_{v1.7}$ in the above assays.

Especially, Example 1, 21, 52, 90, 105, 136, 168, 187, 195, 331, 364, 395, 403, 404, 409, 434, 444, 445, 447, 450, 451, 454, 455, 456, 457, 463, 464, 469, 477, 478, 480, 482, 485, 486, 487, 503, 509, 513, 530, 546, 550, 553, 556, 557, 558, 560, 561, 562, 563, 564, 566, 567, 568, 570, 571, 574, 575, 576, 577, 578, 590, 593, 597, 599, 601, 602, 604, 605, 606, 609, 611, 612, 614, 615, 616, 617, 618, 619, 620, 621, 622, 623, 624, 625, 627, 628, 629, 630, 631, 636, 638, 639, 640, 641, 642, 643, 645, 648, 649, 650, 652, 654, 655, 656, 657, 658, 659, 660, 661, 662, 663, 665, 666, 667, 668, 669, 670, 671, 673, 674, 675, 676, 677, 678, 680, 681, 684, 685, 686, 687, 691, 693, 696, 697, 698, 699, 700, 702, 705, 707, 709, 710, 711, 712, 714, 715, 716, 720, 721, 723, and 725 of the invention have an IC$_{50}$ less than about 3 microM in the Na$_{v1.3}$ or Na$_{v1.7}$ EFS-FRET Assay. In addition, all tested compounds showed higher IC$_{50}$ values in Na$_{v1.5}$ FRET Assay than IC$_{50}$ values in Na$_{v1.3}$ or Na$_{v1.7}$ FRET Assay.

Electrophysiology Assay

Whole cell patch clamp recording was used to assess the efficacy or selectivity of Na channel blocker on human Na$_{v1.3}$ (hSCN3A) expressing HEK293 cells or human Na$_{v1.7}$ (hSCN9A) expressing CHO cells. Human Na$_{v1.3}$ expressing HEK293 cells were grown in growth media which comprised: DMEM, 10% heat-inactivated FBS (Hyclone Laboratories Inc), 100 microgram/ml Penicillin/100 U/ml Streptomycin, 150 microgram/ml Zeocin, 3 microgram/ml Geneticin. Human Na$_{v1.7}$ expressing CHO cells were grown in growth media which comprised: HAM/F-12, 9% heat-inactivated FBS (Hyclone Laboratories Inc), 100 microgram/ml Penicillin/100 U/ml Streptomycin, 100 microgram/ml Hygromycin.

Na channel expressing cells were dissociated by 0.05% Trypsine-EDTA, and then seeded on cover glass for 24-48 hr.

Glass pipettes were pulled to a tip diameter of 1-2 micrometer on a pipette puller. The pipettes were filled with the intracellular solution and a chloridized silver wire was inserted along its length, which was then connected to the headstage of the voltage-clamp amplifier (Axon Instruments or HEKA electronik). The extracellular recording solution consists of (mM): 140 NaCl, 5 KCl, 2 CaCl$_2$, 1 MgCl$_2$, 10 HEPES, 10 Glucose, pH 7.4 adjusted with NaOH. The internal solution consists of (mM): 120 CsF, 15 NaCl, 10 EGTA, 10 HEPES, pH 7.2 adjusted with CsOH; Upon insertion of the pipette tip into the bath, the pipette resistance was noted (acceptable range is between 1-3 megaohm). The junction potential between the pipette and bath solutions was zeroed on the amplifier. After establishing the whole-cell configuration, approximately 10 minutes were allowed for the pipette solution to equilibrate within the cell before beginning recording. Currents were lowpass filtered between 2-5 kHz and digitally sampled at 10 kHz.

The normalized steady-state inactivation curve was constructed using 2 sec (for vehicle) or 60 sec (for drugs) conditioning pulse to different potentials followed immediately by the test pulse to −10 mV. Peak currents were plotted as fraction of the maximum current at the conditioning potentials ranging from −120 mV to −40 mV for Na$_{v1.3}$ and from −130 mV to −60 mV for Na$_{v1.7}$. V1/2 or k values were estimated from Boltzmann fits. The affinity of drugs to resting state of Na channels (K$_{resting}$ or K$_r$) was assessed by 30 msec test pulse from a negative holding potential of −120 or −130 mV, where virtually all channels are in the resting state. $K_r$ value was calculated by a conventional 1:1 binding model:

$$K_{resting}(K_r) = \{[drug]I_{max}, drug/(I_{max}, control - I_{max}, drug)\}$$

where $K_{resting}$ (=$K_r$) is a dissociation constant for the resting state and [drug] is compound concentration. $I_{max}$,control and $I_{max}$,drug are peak currents in the absence and presence of compound, respectively.

The affinity of drug to inactivated state of Na channels ($K_{inact}$ or $K_i$) was estimated from the shift of the availability curve by compound. Interaction of the compound with the channel on inactivated state was evaluated by the following equation:

$$K_{inact}(K_i) = \{[drug]/((1+[drug]/Kr)*\exp(-\Delta V/k)-1)\} \quad [\text{Math.3}]$$

where $K_{inact}$ (=$K_i$) is a dissociation constant for the inactivated state. $\Delta V$ is the compound-induced voltage shift of half maximal voltage of Boltzmann curve and k is the slop factor on presense of compound.

All tested compounds of the invention showed potent activities in this model.

In Vivo Assay

Chronic Constriction Injury (CCI)-Induced Static Allodynia

Male Sprague-Dawley rats weighing 210-240 g were purchased from Charles River Japan, Inc. (Kanagawa, Japan). Animals were housed in groups of two per cage under a 12-h light/dark cycle (lights on at 07:00) with access to food and water ad libitum. CCI surgery was performed according to the method of Bennett G J and Xie Y K (Pain 1988, 33: 87-107). Animals were anesthetized with intraperitoneal injection of pentobarbital sodium. The left common sciatic nerve was exposed at the level of the middle of the thigh, freed of adhering tissue, and four ligatures were loosely tided around it by using 4-0 silk thread (Ethicon Inc., Brussels, Belgium) with approximately 1 mm apart. The incision was sutured, and the rats were allowed to recover. Sham operation was performed in the same manner except of sciatic nerve ligation. After 2 to 3 weeks, static allodynia was assessed using von Frey hairs (VFHs; North Coast Medical Inc., San Jose, Calif.) as described by Field M J et al. (Pain 1999, 83: 303-311). The animals were placed in grid bottom cages and allowed to acclimate for at least 30 min prior to the start of experiment. VFHs in ascending order of force (0.16, 0.4, 0.6, 1, 1.4, 2, 4, 6, 8, 10, 15 and 26 g) were applied to the plantar surface of the operated hind paw. Each VFH was applied to the paw for 6 sec, or until a withdrawal response occurred. Once a withdrawal response was happened, the paw was re-tested starting with the next descending VFH until no response occurred. The lowest amount of force required to elicit a response was defined as paw withdrawal threshold (PWT) in g. Animals showing <2 g of PWT in CCI were selected for evaluation and randomized to be nearly equal across all groups. The compounds of the invention or their vehicles were administered systemically. PWT was measured at the appropriated time after compound administration.

All tested compounds of the invention showed potent activities in this model.

Complete Freund's Adjuvant (CFA)-Induced Thermal Hyperalgesia

Male Sprague-Dawley rats weighing 200-250 g were purchased from Charles River Japan, Inc. (Kanagawa, Japan). Animals were housed under a 12-h light/dark cycle (lights on at 07:00) with access to food and water ad libitum. CFA-induced thermal hyperalgesia was assessed using the plantar test apparatus (Ugo Basile, Verse, Italy) as described by Hargreaves K et al. (Pain 1988, 32: 77-88). Animals were placed in an apparatus consisting of individual testing box on an elevated glass table and allowed to acclimate for at least 10 min. Following habituation, a mobile radiant heat source was located under the table and heat stimulation was applied to the plantar surface of the right hind paw. The latency to remove its hind paw was defined as paw withdrawal latency (PWL) in sec. The cut-off point was set at 30 sec to prevent tissue damage. CFA was prepared at a concentration of 200 microg/100 microl of Mycobacterium tuberculosis H37 RA (Difco Laboratories Inc.) in liquid paraffin and injected intra-plantarly with a 100 microl of CFA into the right hind paw. PWL was measured before and 2 days after CFA injection. Animals showing decrease of the PWL on day 2 were selected for evaluation and randomized to be nearly equal across all groups. The compounds of the invention or their vehicles were administered systemically. PWL was measured at the appropriated time after compound administration. All tested compounds of the invention showed potent activities in this model.

Human Dofetilide Binding Assay

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac). Binding assays were conducted in a total volume of 30 microL in 384-well plates. The activity was measured by PHERAstar (BMG LABTECH) using fluorescence polarization technology. Ten microL of test compounds were incubated with 10 microL of fluorescence ligand (6 nM Cy3B tagged dofetilide derivative) and 10 microL of membrane homogenate (6 microg protein) for 120 minutes at room temperature. Nonspecific binding was determined by 10 microM E4031 at the final concentration.

Examples showed higher IC$_{50}$ values in human dofetilide binding than IC$_{50}$ values in Na$_{v1.3}$ or Na$_{v1.7}$ FRET Assay (Method A and/or B). The high IC$_{50}$ values in human dofetilide binding activities lead to reducing the risk of cardiovascular adverse events.

As shown in the following table, the Example 10, which has amide group, is as good as the Example 726, which does not have amide group, in Na$_{v1.7}$ FRET assay. However in IC$_{50}$ value in the human dofetilide assay, the example 10 is much preferable to the example 270.

Example 726 was prepared from 4-(4-chlorophenoxy)piperidine and quinoline-3-carbaldehyde by reductive amination with sodium triacetoxyborohydride.

TABLE 5

| Example | Structure of Example (I) | IC$_{50}$ in the Na$_{v1.7}$ FRET Assay (μM) | IC$_{50}$ in the Human dofetilide binding Assay (μM) |
|---|---|---|---|
| 10 | (structure: piperidine N-acylated with quinoline-3-carbonyl, 4-O-(4-chlorophenyl)) | 0.36 | 7.91 |
| 726 | (structure: piperidine N-CH$_2$-quinolin-3-yl, 4-O-(4-chlorophenyl)) | 0.47 | 0.28 |

Metabolic Stability Assay:

Half-Life in Human Liver Microsomes (HLM)

Test compounds (1 microM) were incubated with 3.3 mM MgCl$_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. (NADPH generation system was also used instead of NADPH.) An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations: Half-life=ln 2/k The compounds of this invention showed preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound. More specifically, the assay is carried out as follows. The compounds (60 microM, 10 microL) were pre-incubated in 170 microL of mixture including 0.1 mg protein/mL human liver microsomes, 100 mM potassium phosphate buffer (pH 7.4), 1 mM MgCl$_2$ and probes as substrate for 5 min. Reaction was started by adding a 20 microL of 10 mM NADPH (20 microL of NADPH generating system, which consist of 10 mM NADP$^+$, 50 mM DL-Isocitric acid and 10 U/ml Isocitric Dehydrogenase, was also used). The assay plate was incubated at 37° C. Acetonitril was added to the incubate solution at appropriate time (e.g. 8 min).

The metabolites' concentration in the supernatant was measured by LC/MS/MS system.

The degree of drug drug interaction was interpreted based on generation % of metabolites in the presence or absence of test compound.

The compounds of this invention showed preferable results, which show the above-mentioned practical use.

Plasma Protein Binding Assay

Plasma protein binding of the test compound (1 microM) was measured by the method of equilibrium dialysis using 96-well plate type equipment. HTD96a(registered trademark), regenerated cellulose membranes (molecular weight cut-off 12,000-14,000, 22 mm×120 mm) were soaked for over night in distilled water, then for 15 minutes in 30% ethanol, and finally for 20 minutes in dialysis buffer (Dulbecco's phosphate buffered saline, pH7.4). Frozen plasma of human, Sprague-Dawley rats, and Beagle dogs were used. The dialysis equipment was assembled and added 150 microL of compound-fortified plasma to one side of each well and 150 microL of dialysis buffer to the other side of each well. After 4 hours incubation at 37° C. for 150 r.p.m, aliquots of plasma and buffer were sampled. The compound in plasma and buffer were extracted with 300 microL of acetonitrile containing internal standard compounds for analysis. The concentration of the compound was determined with LC/MS/MS analysis.

The fraction of the compound unbound was calculated by the following equation (A) or (B):

$$(A) fu = 1 - \{([plasma]_{eq} - [buffer]_{eq})/([plasma]_{eq})\} \quad \text{[Math.4]}$$

wherein $[plasma]_{eq}$ and $[buffer]_{eq}$ are the concentrations of the compound in plasma and buffer, respectively.

[Math. 5]

$$fu(\%) = \frac{Cb/Cis, b \times 4}{Cp/Cis, p \times 4/3} \times 100. \quad (B)$$

wherein Cp is the peak area of the compound in plasma sample;

Cis,p is the peak area of the internal standard in plasma sample;

Cb is the peak area of the compound in buffer sample;

Cis,b is the peak area of the internal standard in buffer sample;

4 and 4/3 is the reciprocal of the dilution rate in plasma and buffer, respectively.

The compounds of this invention showed preferable plasma protein binding, which show the above-mentioned practical use.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A compound of formula (I)

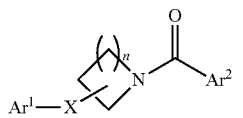

wherein
Ar¹ is phenyl which may be optionally substituted with 1 to 5 substituents independently selected from the group consisting of
(1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$— (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C$(=O)—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, Ar² is selected from; 3-benzofuranyl, 4-benzofuranyl, 5-benzofuranyl, 6-benzofuranyl, 7-benzofuranyl, benzofurazanyl, benzimidazolonyl, 3-benzoimidazolyl, 4-benzoimidazolyl, 5-benzoimidazolyl, 6-benzoimidazolyl, 7-benzoimidazolyl, benzoisothiazolyl, benzoisoxazolyl, benzothiadiazolyl, 3-benzothiazolyl, 4-benzothiazolyl, 5-benzothiazolyl, 6-benzothiazolyl, 7-benzothiazolyl, benzoxadiazolyl, benzoxazolonyl, 3-benzoxazolyl, 4-benzoxazolyl, 5-benzoxazolyl, 6-benzoxazolyl, 7-benzoxazolyl, 3-benzothiophenyl, 4-benzothiophenyl, 5-benzothiophenyl, 6-benzothiophenyl, 7-benzothiophenyl, benzotriazolyl, chromanyl, cinnolinyl, 2,3-dioxoindolyl, furanyl, furopyridyl, furopyrrolyl, imidazolyl, imidazopyrazinyl, imidazopyridinyl, imidazopyrimidinyl, imidazothiazolyl, indazolyl, indolinyl, 4-indolyl, 5-indolyl, 6-indolyl, 7-indolyl, isochromanyl, isoquinolyl, isoxazolopyridyl, isoxazolyl, isothiazolyl, naphthyridinyl, oxadiazolyl, oxazolyl, 2-oxoindolyl, oxoisoindolyl, phthalazyl, pyrazolyl, pyrazolopyridyl, pyrazolopyrimidinyl, pyrazinyl, pyridopyrimidinyl, 2-pyridyl, 3-pyridyl, 5-pyridyl, 6-pyridyl, pyrimidyl, pyridazinyl, pyrrolopyridyl, pyrrolyl, quinazolinyl, quinolyl, quinoxalinyl, thiazolyl, thiophenyl, thienopyrazinyl, thienopyrazolyl, thienopyridyl, thienopyrrolyl, triazolopyrimidinyl, triazolyl, 3,4-dihydro-2H-pyrido[3,2-b][1,4]oxazinyl, 1-methyl-4-oxo-1,4-dihydroquinolyl, 4-oxo-1,4-dihydropyrimidyl, 2-oxo-1,2-dihydroquinolyl, 4-oxo-4H-pyrido[1,2-a]pyrimidyl, 2-oxo-2,5,6,7-tetrahydro-1H-cyclopentapyridyl, 4,5,6,7-tetrahydro-indazolyl, 4-oxo-1,4-dihydro-1,8-naphthyridyl, and 5,6,7,8-tetrahydro-1,6-naphthyridyl wherein said 3-benzofuranyl, 4-benzofuranyl, 5-benzofuranyl, 6-benzofuranyl, 7-benzofuranyl, benzofurazanyl, benzimidazolonyl, 3-benzoimidazolyl, 4-benzoimidazolyl, 5-benzoimidazolyl, 6-benzoimidazolyl, 7-benzoimidazolyl, benzoisothiazolyl, benzoisoxazolyl, benzothiadiazolyl, 3-benzothiazolyl, 4-benzothiazolyl, 5-benzothiazolyl, 6-benzothiazolyl, 7-benzothiazolyl, benzoxadiazolyl, benzoxazolonyl, 3-benzoxazolyl, 4-benzoxazolyl, 5-benzoxazolyl, 6-benzoxazolyl, 7-benzoxazolyl, 3-benzothiophenyl, 4-benzothiophenyl, 5-benzothiophenyl, 6-benzothiophenyl, 7-benzothiophenyl, benzotriazolyl, chromanyl, cinnolinyl, 2,3-dioxoindolyl, furanyl, furopyridyl, furopyrrolyl, imidazolyl, imidazopyrazinyl, imidazopyridinyl, imidazopyrimidinyl, imidazothiazolyl, indazolyl, indolinyl, 4-indolyl, 5-indolyl, 6-indolyl, 7-indolyl, isochromanyl, isoquinolyl, isoxazolopyridyl, isoxazolyl, isothiazolyl, naphthyridinyl, oxadiazolyl, oxazolyl, 2-oxoindolyl, oxoisoindolyl, phthalazyl, pyrazolyl, pyrazolopyridyl, pyrazolopyrimidinyl, pyrazinyl, pyridopyrimidinyl, 2-pyridyl, 3-pyridyl, 5-pyridyl, 6-pyridyl, pyrimidyl, pyridazinyl, pyrrolopyridyl, pyrrolyl, quinazolinyl, quinoxalinyl, thiazolyl, thiophenyl, thienopyrazinyl, thienopyrazolyl, thienopyridyl, thienopyrrolyl, triazolopyrimidinyl, triazolyl, 3,4-dihydro-2H-pyrido[3,2-b][1,4]oxazinyl, 1-methyl-4-oxo-1,4-dihydroquinolyl, 4-oxo-1,4-dihydropyrimidyl, 2-oxo-1,2-dihydroquinolyl, 4-oxo-4H-pyrido[1,2-a]pyrimidyl, 2-oxo-2,5,6,7-tetrahydro-1H-cyclopentapyridyl, 4,5,6,7-tetrahydro-indazolyl, 4-oxo-1,4-dihydro-1,8-naphthyridyl, and 5,6,7,8-tetrahydro-1,6-naphthyridyl may be optionally substituted with 1 to 5 substituents independently selected from the group consisting of (1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$— (10) cyano, (11) hydroxy $C_1$-$C_4$ alkyl-$O_i$—, (12) $C_1$-$C_4$ alkyl-$O_i$, (15) $C_1$-$C_4$ alkyl C(=O)—, (16) HO—C(=O)—, (17) $C_1$-$C_4$ alkyl-O—C(=O)—, (18) $R^1N(R^2)C$(=O)—$C_{0-4}$ alkyl-$O_i$—, (19) $C_1$-$C_4$ alkyl-$SO_2$—NH—$C_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C$(=O)NH—, (23) phenyl-$O^i$—$C_0$-$C_4$ alkyl-$O_k$—; wherein said phenyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl)amino, $C_1$-$C_4$ alkylthio, $C_1$-$C_4$ alkylsulfonyl, $R^1N(R^2)C$(=O)—, $C_1$-$C_4$ alkyl-$SO_2$—NH—, and nitro;

said quinolyl may be optionally substituted with 1 to 4 substituents independently selected from the group consisting of
(1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) 2-hydroxyl, (6) 3-hydroxyl, (7) 5-hydroxyl, (8) 6-hydroxyl, (9) 7-hydroxyl, (10) 8-hydroxyl, (11) $C_3$-$C_8$ cycloalkyl-$C_1$-$C_4$ alkyl-$O_i$—, (12) $C_1$-$C_4$ alkylthio, (13) nitro, (14) $R^1N(R^2)$—$C_{0-4}$ alkyl-$O_i$— (15) cyano, (16) hydroxy $C_1$-$C_4$ alkyl-$O_i$—, (17) $C_1$-$C_4$ alkyl-$O_i$—, (20) $C_1$-$C_4$ alkyl C(=O)—, (21) HO—C(=O)—, (22) $C_1$-$C_4$ alkyl-O—C(=O)—, (23) $R^1N(R^2)C$(=O)—$C_{0-4}$ alkyl-$O_i$—, (24) $C_1$-$C_4$ alkyl-$SO_2$—NH—$C_{0-4}$ alkyl-$O_i$—, (25) $R^1$—O, —C(=O)N($R^2$)—$C_{0-4}$ alkyl-$O_k$—, (26) $NH_2$(HN=)C—, (27) $NH_2C$(=O)NH—, (28) phenyl-$O_i$—$C_0$-$C_4$ alkyl-$O_k$—; wherein said phenyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl) amino, $C_1$-$C_4$ alkylthio, $C_1$-$C_4$ alkylsulfonyl, $R^1N(R^2)C(=O)$—, $C_1$-$C_4$ alkyl-$SO_2$—NH—;

n is 3;

i is 0 or 1;

k is 0 or 1;

$R^1$ and $R^2$ are independently selected from the group consisting of:
(1) hydrogen, (2) $C_{1-6}$ alkyl, (3) hydroxy $C_1$-$C_4$ alkyl, (4) $C_1$-$C_4$ alkoxy $C_1$-$C_4$ alkyl, (5) amino $C_1$-$C_4$ alkyl, (6) $C_1$-$C_4$ haloalkyl, (7) $C_1$-$C_4$ haloalkoxy, (8) $C_{3-6}$ alkenyl, (9) $C_{3-8}$ cycloalkyl $C_{0-6}$ alkyl, (10) phenyl, which is unsubstituted or substituted with $R^3$, and (11) phenyl $C_0$-$C_4$ alkyl; wherein said phenyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl) amino, $C_1$-$C_4$ alkylthio, and nitro;

or $R^1$ and $R^2$ taken together with the nitrogen atom to which they are attached form a 3 to 8 membered ring, where the ring may contain one to four heteroatom(s) independently selected from nitrogen, oxygen, and sulfur; where the ring may be saturated or partially saturated or unsaturated; and the ring is unsubstituted or substituted one or more substituents selected from $R^3$;

$R^3$ is selected from the group consisting of:
(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocyclic group, (10) —$CO_2H$, and (11) —CN;

X is —O—, —S—, —SO—, or —$SO_2$—;

or a pharmaceutically acceptable salt thereof.

2. A compound of formula (I)

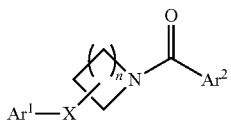

(I)

wherein $Ar^1$ is phenyl which is substituted with chloro, trifluoromethyl, trifluoromethoxy, trifluoroethoxy or ethoxy; and which may be substituted with 1 to 2 substituents independently selected from:
(1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (13) $C_1$-$C_4$ alkylsulfonyl, (14) $R^1N(R^2)$—$SO_2$—$C_{0-4}$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C(=O)$—C(=O)—$C_{0-4}$ alkyl-$O_i$—, (19) $C_1$-$C_4$ alkyl-$SO_2$—NH—$O_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C$(=O)NH—;

$Ar^2$ is 4-pyridyl which may be optionally substituted with 1 to 5 substituents independently selected from the group consisting of
(1) halogen, (2) $C_1$-$C_4$ alkyl-$O_i$—, (3) $C_3$-$C_8$ cycloalkyl-$O_i$—, (4) $C_1$-$C_4$ haloalkyl-$O_i$—, (5) hydroxy, (6) $C_3$-$C_8$ cycloalkyl-$C_1$-$C_4$ alkyl-$O_i$—, (7) $C_1$-$C_4$ alkylthio, (8) nitro, (9) $R^1N(R^2)$—$C_{0-4}$ alkyl-$O_i$—, (10) cyano, (11) hydroxy $C_1$-$C_4$ alkyl-$O_i$—, (12) $C_1$-$C_4$ alkyl-O—$C_1$-$C_4$ alkyl-$O_i$—, (15) $C_1$-$C_4$ alkyl C(=O)—, (16) HO—C(=O)—, (17) $C_1$-$C_4$ alkyl-O—C(=O)—, (18) $R^1N(R^2)C(=O)$—$O_{0-4}$ alkyl-$O_i$—, (19) $C_1$-$C_4$ alkyl-$SO_2$—NH—$O_{0-4}$ alkyl-$O_i$—, (20) $R^1$—$O_i$—C(=O)N($R^2$)—$C_{0-4}$ alkyl-$O_k$—, (21) $NH_2$(HN=)C—, (22) $NH_2C$(=O)NH—, (23) phenyl-$O_i$—$C_0$-$C_4$ alkyl-$O_k$—; wherein said phenyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl) amino, $C_1$-$C_4$ alkylthio, $C_1$-$C_4$ alkylsulfonyl, $R^1N(R^2)C(=O)$—, $C_1$-$C_4$ alkyl-$SO_2$—NH—, and nitro;

n is 3;

i is 0 or 1;

k is 0 or 1;

$R^1$ and $R^2$ are independently selected from the group consisting of:
(1) hydrogen, (2) $C_{1-6}$ alkyl, (3) hydroxy $C_1$-$C_4$ alkyl, (4) $C_1$-$C_4$ alkoxy $C_1$-$C_4$ alkyl, (5) amino $C_1$-$C_4$ alkyl, (6) $C_1$-$C_4$ haloalkyl, (7) $C_1$-$C_4$ haloalkoxy, (8) $C_{3-6}$ alkenyl, (9) $C_{3-8}$ cycloalkyl $C_0$-6 alkyl, (10) phenyl, which is unsubstituted or substituted with $R^3$, and (11) phenyl $C_0$-$C_4$ alkyl; wherein said phenyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl $C_{0-6}$ alkyl, amino, $C_1$-$C_4$ alkylamino, di($C_1$-$C_4$ alkyl) amino, $C_1$-$C_4$ alkylthio, and nitro;

or $R^1$ and $R^2$ taken together with the nitrogen atom to which they are attached form a 3 to 8 membered ring, where the ring may contain one to four heteroatom(s) independently selected from nitrogen, oxygen, and sulfur; where the ring may be saturated or partially saturated or unsaturated; and the ring is unsubstituted or substituted one or more substituents selected from $R^3$;

$R^3$ is selected from the group consisting of:
(1) hydroxy, (2) halogen, (3) $C_{1-6}$ alkyl, (4) —$C_{3-8}$ cycloalkyl, (5) —O—$C_{1-6}$ alkyl, (6) —O(C=O)—$C_{1-6}$ alkyl, (7) —NH—$C_{1-6}$ alkyl, (8) phenyl, (9) heterocyclic group, (10) —$CO_2H$, and (11) —CN;

X is —O—, —S—, —SO—, or —$SO_2$—;

or a pharmaceutically acceptable salt thereof.

3. A compound which is selected from:

(4-(4-chlorophenoxyl)piperidin-1-yl)(8-hydroxyquinolin-2-yl)methanone;

(4-(2-chlorophenoxy)piperidin-1-yl)(8-hydroxyquinolin-2-yl)methanone;

(4-(3-chlorophenoxy)piperidin-1-yl)(8-hydroxyquinolin-2-yl)methanone;

(8-hydroxyquinolin-2-yl)(4-(o-tolyloxy)piperidin-1-yl) methanone;

(8-hydroxyquinolin-2-yl)(4-(m-tolyloxy)piperidin-1-yl) methanone;

(8-hydroxyquinolin-2-yl)(4-(p-tolyloxy)piperidin-1-yl)methanone;
(4-(4-chlorophenoxyl)piperidin-1-yl)(quinolin-2-yl)methanone;
(4-(4-chlorophenoxyl)piperidin-1-yl)(4-hydroxyquinolin-2-yl)methanone;
(4-(4-chlorophenoxyl)piperidin-1-yl)(quinolin-6-yl)methanone;
(4-(4-chlorophenoxyl)piperidin-1-yl)(quinolin-3-yl)methanone;
(4-(4-chlorophenoxyl)piperidin-1-yl)(isoquinolin-3-yl)methanone;
(4-(4-chlorophenoxyl)piperidin-1-yl)(1,6-naphthyridin-2-yl)methanone;
(4-(4-chlorophenoxyl)piperidin-1-yl)(isoquinolin-1-yl)methanone;
(4-(4-chlorophenoxyl)piperidin-1-yl)(quinolin-4-yl)methanone;
(4-(4-chlorophenoxyl)piperidin-1-yl)(6-(2,2,2-trifluoroethoxyl)pyridin-3-yl)methanone;
(4-(4-chlorophenoxyl)piperidin-1-yl)(6-methylpyridin-2-yl)methanone;
(4-(4-chlorophenoxyl)piperidin-1-yl)(3,5-difluoropyridin-2-yl)methanone;
(4-(4-chlorophenoxyl)piperidin-1-yl)(5-methylpyridin-3-yl)methanone;
(4-(4-chlorophenoxyl)piperidin-1-yl)(quinoxalin-6-yl)methanone;
(4-(4-chlorophenoxyl)piperidin-1-yl)(6-phenoxypyridin-3-yl)methanone;
(4-(4-chlorophenoxyl)piperidin-1-yl)(quinolin-8-yl)methanone;
benzo[c]isoxazol-3-yl(4-(4-chlorophenoxyl)piperidin-1-yl)methanone;
(4-(4-chlorophenoxyl)piperidin-1-yl)(1-isopropyl-1H-benzo[d][1,2,3]triazol-5-yl)methanone;
(4-(4-chlorophenoxyl)piperidin-1-yl)(5-fluoro-1H-indol-2-yl)methanone;
(4-(4-chlorophenoxyl)piperidin-1-yl)(6-fluoro-1H-indol-2-yl)methanone;
(4-(4-chlorophenoxyl)piperidin-1-yl)(5-isobutylisoxazol-3-yl)methanone;
(4-(4-chlorophenoxyl)piperidin-1-yl)(2-methyl-5-phenylfuran-3-yl)methanone;
(4-(4-chlorophenoxyl)piperidin-1-yl)(3-(2-methylthiazol-4-yl)phenyl)methanone;
(4-(4-chlorophenoxyl)piperidin-1-yl)(5-methoxy-1H-indol-2-yl)methanone;
(4-(4-chlorophenoxyl)piperidin-1-yl)(1H-indol-4-yl)methanone;
(3-(1H-pyrazol-1-yl)phenyl)(4-(4-chlorophenoxyl)piperidin-1-yl)methanone;
(4-(1H-1,2,4-triazol-1-yl)phenyl)(4-(4-chlorophenoxyl)piperidin-1-yl)methanone;
(4-(4-chlorophenoxyl)piperidin-1-yl)(5-methyl-2-phenyl-2H-1,2,3-triazol-4-yl)methanone;
(4-(4-chlorophenoxyl)piperidin-1-yl)(4,5-dichloroisothiazol-3-yl)methanone;
benzofuran-2-yl(4-(4-chlorophenoxyl)piperidin-1-yl)methanone;
benzo[b]thiophen-2-yl(4-(4-chlorophenoxyl)piperidin-1-yl)methanone;
(8-hydroxyquinolin-2-yl)(4-(2-methoxyphenoxyl)piperidin-1-yl)methanone;
(4-(4-chlorophenoxyl)piperidin-1-yl)(4-methyl-2-phenylpyrimidin-5-yl)methanone;
(4-(4-chlorophenoxyl)piperidin-1-yl)(6-phenylpyrimidin-4-yl)methanone;
(4-(4-chlorophenoxyl)piperidin-1-yl)(4-methoxyquinolin-2-yl)methanone;
(4-(4-chlorophenoxyl)piperidin-1-yl)(quinoxalin-2-yl)methanone;
benzo[d]thiazol-6-yl(4-(4-chlorophenoxyl)piperidin-1-yl)methanone;
(4-(4-chlorophenoxyl)piperidin-1-yl)(1H-indol-3-yl)methanone;
(4-(4-chlorophenoxyl)piperidin-1-yl)(1H-indol-2-yl)methanone;
(4-(4-chlorophenoxyl)piperidin-1-yl)(1-methyl-1H-indol-3-yl)methanone;
(4-(4-chlorophenoxyl)piperidin-1-yl)(1-methyl-1H-indol-2-yl)methanone;
(4-(4-chlorophenoxyl)piperidin-1-yl)(2,3-dimethyl-1H-indol-5-yl)methanone;
(4-(4-chlorophenoxyl)piperidin-1-yl)(1H-indol-6-yl)methanone;
(4-(4-chlorophenoxyl)piperidin-1-yl)(2-methyl-1H-benzo[d]imidazol-5-yl)methanone;
(4-(4-chlorophenoxyl)piperidin-1-yl)(imidazo[1,2-a]pyridin-2-yl)methanone;
(4-(4-chlorophenoxyl)piperidin-1-yl)(2-methylimidazo[1,2-a]pyridin-3-yl)methanone;
(4-(4-chlorophenoxyl)piperidin-1-yl)(5-methyl-1-phenyl-1H-pyrazol-4-yl)methanone;
(4-(tert-butyl)phenyl)(4-(4-chlorophenoxyl)piperidin-1-yl)methanone;
(4-(4-chlorophenoxyl)piperidin-1-yl)(4-chlorophenyl)methanone;
(4-(4-chlorophenoxyl)piperidin-1-yl)(4-fluorophenyl)methanone;
(4-(4-chlorophenoxyl)piperidin-1-yl)(3-(5-fluoro-1H-benzo[d]imidazol-2-yl)phenyl)methanone;
(4-(4-chlorophenoxyl)piperidin-1-yl)(3-(1-methyl-1H-benzo[d]imidazol-2-yl)phenyl)methanone;
(4-(2-fluorophenoxyl)piperidin-1-yl)(8-hydroxyquinolin-2-yl)methanone;
(4-(3-fluorophenoxyl)piperidin-1-yl)(8-hydroxyquinolin-2-yl)methanone;
(4-(4-fluorophenoxyl)piperidin-1-yl)(8-hydroxyquinolin-2-yl)methanone;
(8-hydroxyquinolin-2-yl)(4-(3-methoxyphenoxyl)piperidin-1-yl)methanone;
2-((1-(8-hydroxyquinoline-2-carbonyl)piperidin-4-yl)oxy)benzonitrile;
4-((1-(8-hydroxyquinoline-2-carbonyl)piperidin-4-yl)oxy)benzonitrile;
3-((1-(8-hydroxyquinoline-2-carbonyl)piperidin-4-yl)oxy)benzonitrile;
(4-(4-chlorophenoxyl)piperidin-1-yl)(8-methoxyquinolin-2-yl)methanone;
(4-(4-chlorophenoxyl)piperidin-1-yl)(1-methyl-1H-indol-7-yl)methanone;
(4-(4-chlorophenoxyl)piperidin-1-yl)(1-methyl-1H-indol-4-yl)methanone;
(4-(4-chlorophenoxyl)piperidin-1-yl)(1,8-naphthyridin-2-yl)methanone;
(8-hydroxyquinolin-2-yl)(4-phenoxypiperidin-1-yl)methanone;
(8-hydroxyquinolin-2-yl)(4-(2-(trifluoromethyl)phenoxy)piperidin-1-yl)methanone;
(8-hydroxyquinolin-2-yl)(4-(3-(trifluoromethyl)phenoxy)piperidin-1-yl)methanone;

(5-(tert-butyl)isoxazol-3-yl)(4-(4-chlorophenoxyl)piperidin-1-yl)methanone;
(4-(4-chlorophenoxyl)piperidin-1-yl)(5-phenylisoxazol-3-yl)methanone;
(4-(4-chlorophenoxyl)piperidin-1-yl)(5-cyclopropylisoxazol-3-yl)methanone;
(4-(4-chlorophenoxyl)piperidin-1-yl)(3,5-dimethylisoxazol-4-yl)methanone;
(4-(4-chlorophenoxyl)piperidin-1-yl)(1-methyl-1H-indazol-3-yl)methanone;
(4-(4-chlorophenoxyl)piperidin-1-yl)(2-methyl-2H-indazol-3-yl)methanone;
(4-(4-chlorophenoxyl)piperidin-1-yl)(cinnolin-4-yl)methanone;
(4-(4-chlorophenoxyl)piperidin-1-yl)(2-methyl-4-phenylpyrimidin-5-yl)methanone;
(4-(4-chlorophenoxyl)piperidin-1-yl)(6-methylpyridin-3-yl)methanone;
(4-(4-chlorophenoxyl)piperidin-1-yl)(pyridin-4-yl)methanone;
[1,2,4]triazolo[1,5-a]pyrimidin-2-yl(4-(4-chlorophenoxyl)piperidin-1-yl)methanone;
(4-(4-chlorophenoxyl)piperidin-1-yl)(1,2,3-trimethyl-1H-indol-5-yl)methanone;
(4-(4-chlorophenoxyl)piperidin-1-yl)(1-methyl-1H-indol-6-yl)methanone;
(4-(4-chlorophenoxyl)piperidin-1-yl)(2-methylthiazol-4-yl)methanone;
(4-(4-chlorophenoxyl)piperidin-1-yl)(6-methoxypyridin-3-yl)methanone;
(4-(4-chlorophenoxyl)piperidin-1-yl)(2-phenoxypyridin-3-yl)methanone;
(4-(4-chlorophenoxyl)piperidin-1-yl)(1H-indol-7-yl)methanone;
7-(4-(4-chlorophenoxy)piperidine-1-carbonyl)indoline-2,3-dione;
(4-(4-chlorophenoxyl)piperidin-1-yl)(3-methylpyridin-2-yl)methanone;
(4-(4-chlorophenoxyl)piperidin-1-yl)(6-hydroxypyridin-2-yl)methanone;
(4-(4-chlorophenoxyl)piperidin-1-yl)(2,4-dimethylthiazol-5-yl)methanone;
(4-(4-chlorophenoxyl)piperidin-1-yl)(5-methyl-1,3,4-oxadiazol-2-yl)methanone;
(4-(4-chlorophenoxyl)piperidin-1-yl)(1H-indazol-3-yl)methanone;
(4-(4-chlorophenoxyl)piperidin-1-yl)(4,5,6,7-tetrahydro-1H-indazol-3-yl)methanone;
(4-(4-chlorophenoxyl)piperidin-1-yl)(6-methoxypyridin-2-yl)methanone;
(4-(4-chlorophenoxyl)piperidin-1-yl)(2-methyl-4,5,6,7-tetrahydro-2H-indazol-3-yl)methanone;
(4-(4-chlorophenoxyl)piperidin-1-yl)(isoquinolin-4-yl)methanone;
(4-(4-chlorophenoxyl)piperidin-1-yl)(4-methylpyridin-2-yl)methanone;
(4-(4-chlorophenoxyl)piperidin-1-yl)(6-methoxyquinolin-2-yl)methanone;
(4-(4-chlorophenoxyl)piperidin-1-yl)(6-methoxy-2-methylquinolin-3-yl)methanone;
benzo[d]isoxazol-3-yl(4-(4-chlorophenoxyl)piperidin-1-yl)methanone;
(4-(4-chlorophenoxyl)piperidin-1-yl)(2-(trifluoromethyl)-1H-benzo[d]imidazol-5-yl)methanone;
(4-(4-chlorophenoxyl)piperidin-1-yl)(1,5-naphthyridin-2-yl)methanone;
(4-(4-chlorophenoxyl)piperidin-1-yl)(2-methyl-6-phenylpyridin-3-yl)methanone;
(4-(4-chlorophenoxyl)piperidin-1-yl)(1,5-dimethyl-1H-indol-3-yl)methanone;
(4-(4-chlorophenoxyl)piperidin-1-yl)(5-fluoro-1-methyl-1H-indol-3-yl)methanone;
(5-chloro-1-methyl-1H-indol-3-yl)(4-(4-chlorophenoxyl)piperidin-1-yl)methanone;
(4-(4-chlorophenoxyl)piperidin-1-yl)(5-methoxy-1-methyl-1H-indol-3-yl)methanone;
(4-(4-chlorophenoxyl)piperidin-1-yl)(1,6-dimethyl-1H-indol-3-yl)methanone;
(4-(4-chlorophenoxyl)piperidin-1-yl)(6-fluoro-1-methyl-1H-indol-3-yl)methanone;
(6-chloro-1-methyl-1H-indol-3-yl)(4-(4-chlorophenoxyl)piperidin-1-yl)methanone;
(4-(4-chlorophenoxyl)piperidin-1-yl)(6-methoxy-1-methyl-1H-indol-3-yl)methanone;
(4-(4-chlorophenoxyl)piperidin-1-yl)(5-fluoro-1-methyl-1H-indol-2-yl)methanone;
(4-(4-chlorophenoxyl)piperidin-1-yl)(5-methoxy-1-methyl-1H-indol-2-yl)methanone;
(4-(4-chlorophenoxyl)piperidin-1-yl)(3-fluorophenyl)methanone;
(4-(4-chlorophenoxyl)piperidin-1-yl)(p-tolyl)methanone;
(4-(4-chlorophenoxyl)piperidin-1-yl)(4-methoxyphenyl)methanone;
4-(4-(4-chlorophenoxy)piperidine-1-carbonyl)benzonitrile;
(4-(4-chlorophenoxyl)piperidin-1-yl)(6-methylimidazo[1,2-a]pyridin-2-yl)methanone;
(6-chloroimidazo[1,2-a]pyridin-2-yl)(4-(4-chlorophenoxy)piperidin-1-yl)methanone;
(4-(4-chlorophenoxyl)piperidin-1-yl)(2-methylpyridin-3-yl)methanone;
(4-(4-chlorophenoxyl)piperidin-1-yl)(4-isopropoxyphenyl)methanone;
(4-(4-chlorophenoxyl)piperidin-1-yl)(4-(trifluoromethoxy)phenyl)methanone;
(4-(4-chlorophenoxyl)piperidin-1-yl)(4-(methylsulfonyl)phenyl)methanone;
(4-(4-chlorophenoxyl)piperidin-1-yl)(3-methoxyphenyl)methanone;
(4-(4-chlorophenoxyl)piperidin-1-yl)(pyridin-2-yl)methanone;
(4-(4-chlorophenoxyl)piperidin-1-yl)(5-methylisoxazol-3-yl)methanone;
(4-(4-chlorophenoxyl)piperidin-1-yl)(oxazol-4-yl)methanone;
(4-(4-chlorophenoxyl)piperidin-1-yl)(4-methylthiazol-5-yl)methanone;
(4-(4-chlorophenoxyl)piperidin-1-yl)(5-methylpyrazin-2-yl)methanone;
(4-(4-chlorophenoxyl)piperidin-1-yl)(6-fluoro-1-methyl-1H-indol-2-yl)methanone;
4-(4-(4-chlorophenoxy)piperidine-1-carbonyl)-N,N-dimethylbenzenesulfonamide;
4-(4-(4-chlorophenoxy)piperidine-1-carbonyl)benzamide;
(4-(4-chlorophenoxyl)piperidin-1-yl)(5-fluoro-1H-indazol-3-yl)methanone;
(5-chloro-1H-indazol-3-yl)(4-(4-chlorophenoxyl)piperidin-1-yl)methanone;
(6-chloro-1H-indazol-3-yl)(4-(4-chlorophenoxyl)piperidin-1-yl)methanone;
(4-(4-chlorophenoxyl)piperidin-1-yl)(4-(2-hydroxypropan-2-yl)phenyl)methanone;

(4-(4-chlorophenoxyl)piperidin-1-yl)(2,6-dimethoxypyridin-3-yl)methanone;
(4-(4-chlorophenoxyl)piperidin-1-yl)(6-methoxy-1-methyl-1H-indol-2-yl)methanone;
(4-(4-chlorophenoxyl)piperidin-1-yl)(1-methyl-5-(trifluoromethoxy)-1H-indol-2-yl)methanone;
2-(4-(4-chlorophenoxy)piperidine-1-carbonyl)-1-methyl-1H-indole-5-carbonitrile;
(4-(4-chlorophenoxyl)piperidin-1-yl)(1-methyl-5-(methylsulfonyl)-1H-indol-2-yl)methanone;
(4-(4-chlorophenoxyl)piperidin-1-yl)(4-methylpyridin-3-yl)methanone;
3-(4-(4-chlorophenoxy)piperidine-1-carbonyl)-5,6-dimethylpyridin-2(1H)-one;
(4-(4-chlorophenoxyl)piperidin-1-yl)(quinolin-5-yl)methanone;
(4-(4-fluorophenoxyl)piperidin-1-yl)(2-methyl-2H-indazol-3-yl)methanone;
(4-(4-fluorophenoxyl)piperidin-1-yl)(6-methoxypyridin-3-yl)methanone;
(4-(4-chlorophenoxyl)piperidin-1-yl)(3-methoxy-4-methylphenyl)methanone;
(5-chloro-4-methoxythiophen-3-yl)(4-(4-chlorophenoxyl)piperidin-1-yl)methanone;
(4-phenoxypiperidin-1-yl)(quinolin-8-yl)methanone;
(4-(4-fluorophenoxyl)piperidin-1-yl)(imidazo[1,2-a]pyridin-2-yl)methanone;
(4-(4-fluorophenoxyl)piperidin-1-yl)(quinolin-8-yl)methanone;
(6-aminopyridin-3-yl)(4-(4-chlorophenoxy)piperidin-1-yl)methanone;
(5-bromopyridin-3-yl)(4-(4-chlorophenoxyl)piperidin-1-yl)methanone;
(5-bromopyridin-2-yl)(4-(4-chlorophenoxyl)piperidin-1-yl)methanone;
1-(4-(4-(4-chlorophenoxy)piperidine-1-carbonyl)phenyl)ethanone;
(4-(4-chlorophenoxyl)piperidin-1-yl)(3,4-dimethoxyphenyl)methanone;
(4-(4-chlorophenoxyl)piperidin-1-yl)(isoquinolin-5-yl)methanone;
(4-(4-chlorophenoxyl)piperidin-1-yl)(phenyl)methanone;
(4-(4-chlorophenoxyl)piperidin-1-yl)(m-tolyl)methanone;
(4-(4-chlorophenoxyl)piperidin-1-yl)(2-methoxyphenyl)methanone;
(4-(4-chlorophenoxyl)piperidin-1-yl)(3-(trifluoromethoxy)phenyl)methanone;
(1H-benzo[d]imidazol-5-yl)(4-(4-chlorophenoxyl)piperidin-1-yl)methanone;
(4-(4-chlorophenoxyl)piperidin-1-yl)(1,5-dimethyl-1H-pyrazol-3-yl)methanone;
(4-(4-chlorophenoxyl)piperidin-1-yl)(1,3-dimethyl-1H-pyrazol-5-yl)methanone;
(3-(tert-butyl)-1-methyl-1H-pyrazol-5-yl)(4-(4-chlorophenoxyl)piperidin-1-yl)methanone;
(4-(4-chlorophenoxyl)piperidin-1-yl)(1-methyl-5-(trifluoromethyl)-1H-pyrazol-3-yl)methanone;
(4-(4-chlorophenoxyl)piperidin-1-yl)(1-(4-methoxyphenyl)-5-methyl-1H-pyrazol-4-yl)methanone;
(4-(4-chlorophenoxyl)piperidin-1-yl)(1-(2-methoxyphenyl)-1H-pyrazol-4-yl)methanone;
(4-(4-chlorophenoxyl)piperidin-1-yl)(3,5-dimethyl-1H-pyrazol-4-yl)methanone;
(4-(4-chlorophenoxyl)piperidin-1-yl)(1H-1,2,4-triazol-3-yl)methanone;
(4-(4-chlorophenoxyl)piperidin-1-yl)(5-isopropyl-1H-pyrazol-3-yl)methanone;
(4-(4-chlorophenoxyl)piperidin-1-yl)(imidazo[2,1-b]thiazol-6-yl)methanone;
(4-(3-methoxyphenoxyl)piperidin-1-yl)(quinolin-8-yl)methanone;
imidazo[1,2-a]pyridin-2-yl(4-(3-methoxyphenoxyl)piperidin-1-yl)methanone;
(4-(3-fluorophenoxyl)piperidin-1-yl)(quinolin-8-yl)methanone;
(4-(3-fluorophenoxyl)piperidin-1-yl)(imidazo[1,2-a]pyridin-2-yl)methanone;
(4-(4-chlorophenoxyl)piperidin-1-yl)(5-chloropyridin-3-yl)methanone;
(4-(4-chlorophenoxyl)piperidin-1-yl)(5-methoxypyridin-3-yl)methanone;
3-(4-(4-chlorophenoxy)piperidine-1-carbonyl)benzonitrile;
(4-(4-chlorophenoxyl)piperidin-1-yl)(2-ethoxypyridin-3-yl)methanone;
(4-(4-chlorophenoxyl)piperidin-1-yl)(2-methoxypyridin-4-yl)methanone;
(4-(4-chlorophenoxyl)piperidin-1-yl)(isoquinolin-8-yl)methanone;
(4-(4-chlorophenoxyl)piperidin-1-yl)(2-methylthiazol-5-yl)methanone;
(4-((4-chlorophenyl)thio)piperidin-1-yl)(quinolin-8-yl)methanone;
(4-((4-chlorophenyl)thio)piperidin-1-yl)(6-methylpyridin-3-yl)methanone;
(4-((4-chlorophenyl)sulfonyl)piperidin-1-yl)(quinolin-8-yl)methanone;
1-(3-((1-(quinoline-8-carbonyl)piperidin-4-yl)oxy)phenyl)ethanone;
(4-(3,5-dimethoxyphenoxyl)piperidin-1-yl)(quinolin-8-yl)methanone;
quinolin-8-yl(4-(3-(trifluoromethoxy)phenoxy)piperidin-1-yl)methanone;
(4-(4-chlorophenoxyl)piperidin-1-yl)(3-methylisoxazol-5-yl)methanone;
(4-(4-chlorophenoxyl)piperidin-1-yl)(1-isopropyl-1H-pyrazol-4-yl)methanone;
5-(4-(4-chlorophenoxy)piperidine-1-carbonyl)picolinonitrile;
(4-(4-chlorophenoxyl)piperidin-1-yl)(2-hydroxyquinolin-4-yl)methanone;
(4-(4-chlorophenoxyl)piperidin-1-yl)(5-(trifluoromethyl)-1H-pyrazol-3-yl)methanone;
(4-(4-chlorophenoxyl)piperidin-1-yl)(5-cyclopropyl-1H-pyrazol-3-yl)methanone;
(4-(4-chlorophenoxyl)piperidin-1-yl)(5-(2-methoxyphenyl)-1H-pyrazol-3-yl)methanone;
(4-(4-chlorophenoxyl)piperidin-1-yl)(3-isopropyl-1-methyl-1H-pyrazol-5-yl)methanone;
(4-(4-chlorophenoxyl)piperidin-1-yl)(3-ethyl-1-methyl-1H-pyrazol-5-yl)methanone;
(4-(4-chlorophenoxyl)piperidin-1-yl)(1-ethyl-3-methyl-1H-pyrazol-5-yl)methanone;
(4-(4-chlorophenoxyl)piperidin-1-yl)(2-methyloxazol-4-yl)methanone;
(4-(4-chlorophenoxyl)piperidin-1-yl)(thieno[3,2-b]pyridin-2-yl)methanone;
(4-(4-chlorophenoxyl)piperidin-1-yl)(imidazo[1,2-a]pyridin-6-yl)methanone;
(4-(4-chlorophenoxyl)piperidin-1-yl)(1-methyl-1H-indazol-6-yl)methanone;

(4-(4-chlorophenoxyl)piperidin-1-yl)(6-(trifluoromethoxy)-1H-indazol-3-yl)methanone;
(4-(4-chlorophenoxyl)piperidin-1-yl)(1-methyl-6-(trifluoromethoxy)-1H-indazol-3-yl)methanone;
(4-(4-chlorophenoxyl)piperidin-1-yl)(2,4-dimethyloxazol-5-yl)methanone;
(4-(4-chlorophenoxyl)piperidin-1-yl)(5-methoxypyridin-2-yl)methanone;
(4-(4-chlorophenoxyl)piperidin-1-yl)(imidazo[1,2-a]pyridin-7-yl)methanone;
(4-(4-chlorophenoxyl)piperidin-1-yl)(imidazo[1,2-a]pyrazin-2-yl)methanone;
(4-(4-chlorophenoxyl)piperidin-1-yl)(2-methyl-2H-indazol-6-yl)methanone;
(4-(4-chlorophenoxyl)piperidin-1-yl)(6-(pyrrolidin-1-yl)pyridin-2-yl)methanone;
(4-(4-chlorophenoxyl)piperidin-1-yl)(5-(pyrrolidin-1-yl)pyridin-2-yl)methanone;
(4-(4-chlorophenoxyl)piperidin-1-yl)(4-fluoro-3-methoxyphenyl)methanone;
(4-(4-chlorophenoxyl)piperidin-1-yl)(4-methyl-3,4-dihydro-2H-pyrido[3,2-b][1,4]oxazin-7-yl)methanone;
(4-(4-chlorophenoxyl)piperidin-1-yl)(6-(piperidin-1-yl)pyridin-3-yl)methanone;
3-(4-(4-chlorophenoxy)piperidine-1-carbonyl)quinolin-2(1H)-one;
(4-(4-chlorophenoxyl)piperidin-1-yl)(imidazo[1,2-a]pyridin-8-yl)methanone;
(4-(4-chlorophenoxyl)piperidin-1-yl)(pyrazolo[1,5-a]pyridin-7-yl)methanone;
(4-(4-chlorophenoxyl)piperidin-1-yl)(4-(trifluoromethyl)pyridin-3-yl)methanone;
(4-(4-chlorophenoxyl)piperidin-1-yl)(1-methyl-1H-imidazol-2-yl)methanone;
(4-(4-chlorophenoxyl)piperidin-1-yl)(1-(2-(trifluoromethyl)phenyl)-1H-imidazol-2-yl)methanone;
3-(4-(4-chlorophenoxy)piperidine-1-carbonyl)-1-methylquinolin-4(1H)-one;
(4-(4-chlorophenoxyl)piperidin-1-yl)(pyrimidin-4-yl)methanone;
(4-(4-chlorophenoxyl)piperidin-1-yl)(5-chloropyridin-2-yl)methanone;
(4-(4-chlorophenoxyl)piperidin-1-yl)(2-methoxyquinolin-4-yl)methanone;
(4-(4-chlorophenoxyl)piperidin-1-yl)(5-hydroxypyridin-3-yl)methanone;
(4-(4-chlorophenoxyl)piperidin-1-yl)(6-(trifluoromethyl)pyridin-3-yl)methanone;
(5-aminopyridin-3-yl)(4-(4-chlorophenoxy)piperidin-1-yl)methanone;
(4-(4-chlorophenoxyl)piperidin-1-yl)(imidazo[1,2-a]pyrimidin-2-yl)methanone;
N-(5-(4-(4-chlorophenoxy)piperidine-1-carbonyl)pyridin-3-yl)acetamide;
(4-(4-chlorophenoxyl)piperidin-1-yl)(chroman-6-yl)methanone;
(4-(4-chlorophenoxyl)piperidin-1-yl)(1-methyl-1H-pyrazolo[3,4-b]pyridin-3-yl)methanone;
(4-(4-chlorophenoxyl)piperidin-1-yl)(1-methyl-1H-indol-5-yl)methanone;
(4-(4-chlorophenoxyl)piperidin-1-yl)(3-(pyridin-2-yloxy)phenyl)methanone;
(4-(4-chlorophenoxyl)piperidin-1-yl)(1-methyl-1H-benzo[d]imidazol-5-yl)methanone;
(4-(4-chlorophenoxyl)piperidin-1-yl)(4-((tetrahydro-2H-pyran-4-yl)oxy)phenyl)methanone;
(4-(4-chlorophenoxyl)piperidin-1-yl)(pyrazolo[1,5-a]pyridin-2-yl)methanone;
1-(3-(4-(4-chlorophenoxy)piperidine-1-carbonyl)-1H-pyrazol-5-yl)ethanone;
(4-(4-chlorophenoxyl)piperidin-1-yl)(1,3,5-trimethyl-1H-pyrazol-4-yl)methanone;
(4-(4-chlorophenoxyl)piperidin-1-yl)(1H-pyrrolo[2,3-b]pyridin-2-yl)methanone;
4-(4-(4-chlorophenoxy)piperidine-1-carbonyl)-1-methylquinolin-2(1H)-one;
5-(4-(4-chlorophenoxy)piperidine-1-carbonyl)-1H-benzo[d]imidazol-2(3H)-one;
(4-(4-chlorophenoxyl)piperidin-1-yl)(5-methoxypyrazin-2-yl)methanone;
5-(4-(4-chlorophenoxy)piperidine-1-carbonyl)-1,3-dimethyl-1H-benzo[d]imidazol-2(3H)-one;
(4-(4-chlorophenoxyl)piperidin-1-yl)(1-methyl-1H-imidazol-4-yl)methanone;
(4-(4-chlorophenoxyl)piperidin-1-yl)(2-phenyl-1H-imidazol-4-yl)methanone;
(4-(4-chlorophenoxyl)piperidin-1-yl)(1,3-dimethyl-1H-pyrazol-4-yl)methanone;
(4-(4-chlorophenoxyl)piperidin-1-yl)(1,5-dimethyl-1H-pyrazol-4-yl)methanone;
(4-(4-chlorophenoxyl)piperidin-1-yl)(3-isobutyl-1-methyl-1H-pyrazol-5-yl)methanone;
(4-chloro-5-methyl-1H-pyrazol-3-yl)(4-(4-chlorophenoxy)piperidin-1-yl)methanone;
3-(4-(4-chlorophenoxy)piperidine-1-carbonyl)-1-isopropyl-6,7-dihydro-1H-cyclopenta[b]pyridin-2(5H)-one;
5-(4-(4-chlorophenoxy)piperidine-1-carbonyl)-2-methoxybenzonitrile;
(4-(4-chlorophenoxyl)piperidin-1-yl)(2-isopropylthiazol-4-yl)methanone;
(4-(4-chlorophenoxyl)piperidin-1-yl)(5,6-dimethoxy-1H-indol-2-yl)methanone;
(4-(4-chlorophenoxyl)piperidin-1-yl)(2,7-dimethylpyrazolo[1,5-a]pyrimidin-6-yl)methanone;
(4-(4-chlorophenoxyl)piperidin-1-yl)(1H-pyrrolo[2,3-b]pyridin-3-yl)methanone;
(4-(4-chlorophenoxyl)piperidin-1-yl)(1-methyl-1H-pyrrolo[2,3-b]pyridin-2-yl)methanone;
(4-(4-chlorophenoxyl)piperidin-1-yl)(5,6-dimethoxy-1-methyl-1H-indol-2-yl)methanone;
(4-(4-chlorophenoxyl)piperidin-1-yl)(1-methyl-1H-pyrrolo[2,3-b]pyridin-3-yl)methanone;
3-(4-(4-chlorophenoxy)piperidine-1-carbonyl)-1-isopropyl-4-methylquinolin-2(1H)-one;
(4-(4-chlorophenoxyl)piperidin-1-yl)(4-methyl-4H-furo[3,2-b]pyrrol-5-yl)methanone;
(4-(4-chlorophenoxyl)piperidin-1-yl)(4-methyl-4H-thieno[3,2-b]pyrrol-5-yl)methanone;
(4-(4-chlorophenoxyl)piperidin-1-yl)(1,3-dimethyl-1H-thieno[2,3-c]pyrazol-5-yl)methanone;
2-(4-(4-chlorophenoxy)piperidine-1-carbonyl)-6,7-dihydropyrido[3,2,1-ij]quinolin-3(5H)-one;
5-(4-(4-chlorophenoxy)piperidine-1-carbonyl)-1H-pyrrolo[3,2,1-ij]quinolin-4(2H)-one;
3-(4-(4-chlorophenoxy)piperidine-1-carbonyl)-1-ethyl-7-methyl-1,8-naphthyridin-4(1H)-one;
(4-(4-chlorophenoxyl)piperidin-1-yl)(isoquinolin-6-yl)methanone;
(4-(4-chlorophenoxyl)piperidin-1-yl)(5-methylpyridin-2-yl)methanone;
(4-(4-chlorophenoxyl)piperidin-1-yl)(5-(2,2,2-trifluoroethoxyl)pyridin-3-yl)methanone;

(4-(4-chlorophenoxyl)piperidin-1-yl)(3-methylisoxazolo[5,4-b]pyridin-5-yl)methanone;
(4-(4-chlorophenoxyl)piperidin-1-yl)(1,3,6-trimethyl-1H-pyrazolo[3,4-b]pyridin-4-yl)methanone;
(4-(4-chlorophenoxyl)piperidin-1-yl)(thieno[2,3-b]pyridin-2-yl)methanone;
(4-(4-chlorophenoxyl)piperidin-1-yl)(thieno[2,3-b]pyrazin-6-yl)methanone;
(4-(4-chlorophenoxyl)piperidin-1-yl)(pyrazolo[1,5-a]pyrimidin-3-yl)methanone;
(4-(4-chlorophenoxyl)piperidin-1-yl)(2-(pyrrolidin-1-yl)pyrimidin-5-yl)methanone;
(1H-benzo[d]imidazol-4-yl)(4-(4-chlorophenoxyl)piperidin-1-yl)methanone;
benzo[d][1,2,3]thiadiazol-7-yl(4-(4-chlorophenoxyl)piperidin-1-yl)methanone;
3-(4-(4-chlorophenoxy)piperidine-1-carbonyl)-1-methylquinolin-2(1H)-one;
(4-(4-chlorophenoxyl)piperidin-1-yl)(1-methyl-1H-benzo[d]imidazol-2-yl)methanone;
(4-(4-chlorophenoxyl)piperidin-1-yl)(pyrazolo[1,5-a]pyrimidin-2-yl)methanone;
(4-(4-chlorophenoxyl)piperidin-1-yl)(2-methoxypyrimidin-5-yl)methanone;
(1H-benzo[d][1,2,3]triazol-4-yl)(4-(4-chlorophenoxyl)piperidin-1-yl)methanone;
(4-(4-chlorophenoxyl)piperidin-1-yl)(6-methylimidazo[2,1-b]thiazol-5-yl)methanone;
benzo[c][1,2,5]thiadiazol-4-yl(4-(4-chlorophenoxyl)piperidin-1-yl)methanone;
(4-(4-chlorophenoxyl)piperidin-1-yl)(1-(2-methoxyethyl)-1H-indol-5-yl)methanone;
(4-(4-chlorophenoxyl)piperidin-1-yl)(1-(2-methoxyethyl)-1H-indol-6-yl)methanone;
(3-amino-1-methyl-1H-pyrazol-5-yl)(4-(4-chlorophenoxyl)piperidin-1-yl)methanone;
(4-(4-chlorophenoxyl)piperidin-1-yl)(5-cyclopropyl-1-methyl-1H-pyrazol-3-yl)methanone;
(4-(4-chlorophenoxyl)piperidin-1-yl)(3-cyclopropyl-1-methyl-1H-pyrazol-5-yl)methanone;
1-benzyl-3-(4-(4-chlorophenoxy)piperidine-1-carbonyl)pyridin-2(1H)-one;
(1-benzyl-1H-pyrazol-4-yl)(4-(4-chlorophenoxyl)piperidin-1-yl)methanone;
(4-(4-chlorophenoxyl)piperidin-1-yl)(1-(2-methoxyethyl)-1H-indol-2-yl)methanone;
(4-(4-chlorophenoxyl)piperidin-1-yl)(1-(2-methoxyethyl)-1H-indol-4-yl)methanone;
(4-(4-chlorophenoxyl)piperidin-1-yl)(3,6-dimethylisoxazolo[5,4-b]pyridin-4-yl)methanone;
4-(4-(4-chlorophenoxy)piperidine-1-carbonyl)-1-methylpyridin-2(1H)-one;
3-(4-(4-chlorophenoxy)piperidine-1-carbonyl)-4H-pyrido[1,2-a]pyrimidin-4-one;
3-(4-(4-chlorophenoxy)piperidine-1-carbonyl)isoquinolin-1(2H)-one;
(4-(4-chlorophenoxyl)piperidin-1-yl)(2-(3,5-dimethyl-1H-pyrazol-4-yl)phenyl)methanone;
benzo[c][1,2,5]oxadiazol-5-yl(4-(4-chlorophenoxyl)piperidin-1-yl)methanone;
(6-aminopyridin-2-yl)(4-(4-chlorophenoxy)piperidin-1-yl)methanone;
3-(4-(4-chlorophenoxy)piperidine-1-carbonyl)-1,6-dimethylpyridin-2(1H)-one;
(4-(4-chlorophenoxyl)piperidin-1-yl)(3-propoxypyridin-2-yl)methanone;
(4-(4-chlorophenoxyl)piperidin-1-yl)(6-((tetrahydro-2H-pyran-4-yl)oxy)pyridin-3-yl)methanone;
(4-(4-chlorophenoxyl)piperidin-1-yl)(6-((tetrahydro-2H-pyran-4-yl)oxy)pyridin-2-yl)methanone;
(4-(4-chlorophenoxyl)piperidin-1-yl)(5-((tetrahydro-2H-pyran-4-yl)oxy)pyridin-3-yl)methanone;
(4-(4-chlorophenoxyl)piperidin-1-yl)(3-hydroxy-4-methoxyphenyl)methanone;
(4-chloro-2-hydroxyphenyl)(4-(4-chlorophenoxyl)piperidin-1-yl)methanone;
(4-(4-chlorophenoxyl)piperidin-1-yl)(4-hydroxy-3-methylphenyl)methanone;
(4-(4-chlorophenoxyl)piperidin-1-yl)(6-morpholinopyridin-2-yl)methanone;
(4-(4-chlorophenoxyl)piperidin-1-yl)(2-morpholinopyridin-4-yl)methanone;
(4-(4-chlorophenoxyl)piperidin-1-yl)(1-methyl-3-(trifluoromethyl)-1H-pyrazol-5-yl)methanone;
(4-(4-chlorophenoxyl)piperidin-1-yl)(2-hydroxy-4-(trifluoromethyl)phenyl)methanone;
(4-(4-chlorophenoxyl)piperidin-1-yl)(3-hydroxy-4-methylphenyl)methanone;
tert-butyl ((2-(4-(4-chlorophenoxyl)piperidine-1-carbonyl)pyridin-4-yl)methyl)carbamate;
(4-(aminomethyl)pyridin-2-yl)(4-(4-chlorophenoxyl)piperidin-1-yl)methanone;
N-((2-(4-(4-chlorophenoxy)piperidine-1-carbonyl)pyridin-4-yl)methyl)pivalamide;
N-((2-(4-(4-chlorophenoxy)piperidine-1-carbonyl)pyridin-4-yl)methyl)-4-fluorobenzamide;
N-((2-(4-(4-chlorophenoxy)piperidine-1-carbonyl)pyridin-4-yl)methyl)-4-fluorobenzenesulfonamide;
tert-butyl 2-(4-(4-chlorophenoxyl)piperidine-1-carbonyl)-7,8-dihydro-1,6-naphthyridine-6(5H)-carboxylate;
(4-(4-chlorophenoxyl)piperidin-1-yl)(6-(methylsulfonyl)-5,6,7,8-tetrahydro-1,6-naphthyridin-2-yl)methanone;
N-(tert-butyl)-4-(4-(4-chlorophenoxyl)piperidine-1-carbonyl)benzamide;
N-(tert-butyl)-4-(4-(4-chlorophenoxyl)piperidine-1-carbonyl)-N-methylbenzamide;
4-(4-(4-chlorophenoxy)piperidine-1-carbonyl)-N-(2,2,2-trifluoroethyl)benzamide;
(4-(4-chlorophenoxyl)piperidin-1-yl)(4-(2-methoxyethoxyl)phenyl)methanone;
(4-(4-chlorophenoxyl)piperidin-1-yl)(4-(2-hydroxyethoxyl)phenyl)methanone;
N-(4-(4-(4-chlorophenoxy)piperidine-1-carbonyl)benzyl)pivalamide;
4-(4-(4-chlorophenoxy)piperidine-1-carbonyl)picolinamide;
(4-(4-chlorophenoxyl)piperidin-1-yl)(5-morpholinopyridin-3-yl)methanone;
(4-(4-chlorophenoxyl)piperidin-1-yl)(6-(piperidin-1-yl)pyrimidin-4-yl)methanone;
(3-(1H-imidazol-1-yl)phenyl)(4-(4-chlorophenoxyl)piperidin-1-yl)methanone;
(2-(1H-pyrazol-1-yl)phenyl)(4-(4-chlorophenoxyl)piperidin-1-yl)methanone;
(4-(4-chlorophenoxyl)piperidin-1-yl)(2-(2-methyl-1H-imidazol-1-yl)phenyl)methanone;
(4-(4-chlorophenoxyl)piperidin-1-yl)(2-(3-methyl-1,2,4-oxadiazol-5-yl)phenyl)methanone;
(4-(4-chlorophenoxyl)piperidin-1-yl)(3-methyl-1H-pyrazol-5-yl)methanone;
(4-(4-chlorophenoxyl)piperidin-1-yl)(6-(piperidine-1-carbonyl)pyridin-2-yl)methanone;

(4-(4-chlorophenoxyl)piperidin-1-yl)(2-hydroxy-4-methoxyphenyl)methanone;
(4-(4-chlorophenoxyl)piperidin-1-yl)(4-hydroxy-3-methoxyphenyl)methanone;
N-(5-chloro-2-(4-(4-chlorophenoxyl)piperidine-1-carbonyl)phenyl)methanesulfonamide;
N-(4-chloro-2-(4-(4-chlorophenoxyl)piperidine-1-carbonyl)phenyl)methanesulfonamide;
(4-(4-chlorophenoxyl)piperidin-1-yl)(2'-(hydroxymethyl)-[1,1'-biphenyl]-4-yl)methanone;
(4-(4-chlorophenoxyl)piperidin-1-yl)(2'-(methylsulfonyl)-[1,1'-biphenyl]-4-yl)methanone;
(3-chloro-4-hydroxyphenyl)(4-(4-chlorophenoxyl)piperidin-1-yl)methanone;
3-(tert-butyl)-5-(4-(4-chlorophenoxyl)piperidine-1-carbonyl)benzamide;
3-(tert-butyl)-5-(4-(4-chlorophenoxyl)piperidine-1-carbonyl)-N,N-dimethylbenzamide;
(3-(tert-butyl)-5-(4-(4-chlorophenoxy)piperidine-1-carbonyl)phenyl)(morpholino)methanone;
4'-(4-(4-chlorophenoxy)piperidine-1-carbonyl)-[1,1'-biphenyl]-3-carboxamide;
(4-(4-chlorophenoxyl)piperidin-1-yl)(1-(2-morpholinoethyl)-1H-indol-5-yl)methanone;
2-(5-(4-(4-chlorophenoxy)piperidine-1-carbonyl)-1H-indol-1-yl)-N,N-dimethylacetamide;
(4-(4-chlorophenoxyl)piperidin-1-yl)(1-(2-hydroxyethyl)-1H-indol-5-yl)methanone;
(4-(4-chlorophenoxyl)piperidin-1-yl)(4-morpholinopyridin-2-yl)methanone;
(4-(4-chlorophenoxyl)piperidin-1-yl)(4-(piperidin-1-yl)pyridin-2-yl)methanone;
2-(3-(4-(4-chlorophenoxy)piperidine-1-carbonyl)-1H-indol-1-yl)-N,N-dimethylacetamide;
(4-(4-chlorophenoxyl)piperidin-1-yl)(1-(2-hydroxyethyl)-1H-indol-3-yl)methanone;
(4-(4-chlorophenoxyl)piperidin-1-yl)(1-(2-morpholinoethyl)-1H-indol-3-yl)methanone;
(4-(4-chlorophenoxyl)piperidin-1-yl)(1-(2-(piperidin-1-yl)ethyl)-1H-indol-3-yl)methanone;
2-(4-(4-(4-chlorophenoxy)piperidine-1-carbonyl)phenyl)-2-methylpropanenitrile;
(4-(4-chlorophenoxyl)piperidin-1-yl)(3-fluoro-4-hydroxyphenyl)methanone;
2-chloro-5-(4-(4-chlorophenoxyl)piperidine-1-carbonyl)benzenesulfonamide;
4'-(4-(4-chlorophenoxy)piperidine-1-carbonyl)-[1,1'-biphenyl]-4-carboxamide;
4'-(4-(4-chlorophenoxy)piperidine-1-carbonyl)-[1,1'-biphenyl]-2-carboxamide;
(5-chloro-2-hydroxyphenyl)(4-(4-chlorophenoxyl)piperidin-1-yl)methanone;
(4-(4-chlorophenoxyl)piperidin-1-yl)(2-hydroxy-4-methylphenyl)methanone;
(4-(4-chlorophenoxyl)piperidin-1-yl)(5-fluoro-2-hydroxyphenyl)methanone;
(4-(4-chlorophenoxyl)piperidin-1-yl)(2-hydroxy-3-methylphenyl)methanone;
(4-(4-chlorophenoxyl)piperidin-1-yl)(2-hydroxy-3-isopropylphenyl)methanone;
(4-(4-chlorophenoxyl)piperidin-1-yl)(2-hydroxy-6-methoxyphenyl)methanone;
(4-(4-chlorophenoxyl)piperidin-1-yl)(2-fluoro-6-hydroxyphenyl)methanone;
(4-(4-chlorophenoxyl)piperidin-1-yl)(3-hydroxy-2-methylphenyl)methanone;
(2-chloro-4-hydroxyphenyl)(4-(4-chlorophenoxyl)piperidin-1-yl)methanone;
(4-(4-chlorophenoxyl)piperidin-1-yl)(2-fluoro-4-hydroxyphenyl)methanone;
N-(4-(4-(4-chlorophenoxy)piperidine-1-carbonyl)-2-methylphenyl)methanesulfonamide;
(4-(4-chlorophenoxyl)piperidin-1-yl)(4-fluoro-3-hydroxyphenyl)methanone;
(4-(4-chlorophenoxyl)piperidin-1-yl)(2-hydroxy-5-methylphenyl)methanone;
(4-(4-chlorophenoxyl)piperidin-1-yl)(2-hydroxy-3-methoxyphenyl)methanone;
(4-(4-chlorophenoxyl)piperidin-1-yl)(4-fluoro-2-hydroxyphenyl)methanone;
(4-(4-chlorophenoxyl)piperidin-1-yl)(3,5-dihydroxyphenyl)methanone;
N-(3-(4-(4-chlorophenoxy)piperidine-1-carbonyl)phenyl)acetamide;
(4-(4-chlorophenoxyl)piperidin-1-yl)(1-((4-hydroxytetrahydro-2H-pyran-4-yl)methyl)-1H-indol-5-yl)methanone;
(1-(2-aminoethyl)-1H-indol-5-yl)(4-(4-chlorophenoxyl)piperidin-1-yl)methanone;
N-(2-(5-(4-(4-chlorophenoxyl)piperidine-1-carbonyl)-1H-indol-1-yl)ethyl)acetamide;
N-(2-(5-(4-(4-chlorophenoxyl)piperidine-1-carbonyl)-1H-indol-1-yl)ethyl)methanesulfonamide;
2-(5-(4-(4-chlorophenoxy)piperidine-1-carbonyl)-1H-indol-1-yl)-1-morpholinoethanone;
(4-(4-chlorophenoxyl)piperidin-1-yl)(3'-(methylsulfonyl)-[1,1'-biphenyl]-4-yl)methanone;
(4-(4-chlorophenoxyl)piperidin-1-yl)(3'-(hydroxymethyl)-[1,1'-biphenyl]-4-yl)methanone;
N-(4'-(4-(4-chlorophenoxy)piperidine-1-carbonyl)-[1,1'-biphenyl]-2-yl)methanesulfonamide;
N-(4'-(4-(4-chlorophenoxy)piperidine-1-carbonyl)-[1,1'-biphenyl]-3-yl)methanesulfonamide;
4'-(4-(4-chlorophenoxy)piperidine-1-carbonyl)-N-methyl-[1,1'-biphenyl]-3-carboxamide;
4'-(4-(4-chlorophenoxy)piperidine-1-carbonyl)-N,N-dimethyl-[1,1'-biphenyl]-3-carboxamide;
(4-(4-chlorophenoxyl)piperidin-1-yl)(3'-(morpholine-4-carbonyl)-[1,1'-biphenyl]-4-yl)methanone;
(4-chloro-3-hydroxyphenyl)(4-(4-chlorophenoxyl)piperidin-1-yl)methanone;
N-(5-(4-(4-chlorophenoxy)piperidine-1-carbonyl)-2-methylphenyl)methanesulfonamide;
1-(3-(4-(4-chlorophenoxy)piperidine-1-carbonyl)phenyl)ethanone;
(4-(4-chlorophenoxyl)piperidin-1-yl)(1-(2-hydroxyethyl)-2-methyl-1H-benzo[d]imidazol-5-yl)methanone;
(4-(4-chlorophenoxyl)piperidin-1-yl)(6-ethoxypyridin-2-yl)methanone;
(4-(4-chlorophenoxyl)piperidin-1-yl)(4-hydroxy-7-methyl-1,8-naphthyridin-3-yl)methanone;
N-(6-(4-(4-chlorophenoxy)piperidine-1-carbonyl)pyridin-2-yl)acetamide;
N-(4-(4-(4-chlorophenoxy)piperidine-1-carbonyl)pyridin-2-yl)acetamide;
N-(5-(4-(4-chlorophenoxy)piperidine-1-carbonyl)pyridin-2-yl)acetamide;
(4-(4-chlorophenoxyl)piperidin-1-yl)(3-hydroxypyridin-2-yl)methanone;
(4-bromo-1-methoxynaphthalen-2-yl)(4-(4-chlorophenoxyl)piperidin-1-yl)methanone;

6-(4-(4-chlorophenoxy)piperidine-1-carbonyl)isoindolin-1-one;
(4-(4-chlorophenoxyl)piperidin-1-yl)(quinoxalin-5-yl)methanone;
(4-(4-chlorophenoxyl)piperidin-1-yl)(1,6-naphthyridin-5-yl)methanone;
(4-(4-chlorophenoxyl)piperidin-1-yl)(4-hydroxyphenyl)methanone;
(4-(4-chlorophenoxyl)piperidin-1-yl)(4-ethoxy-2-hydroxyphenyl)methanone;
(4-(4-chlorophenoxyl)piperidin-1-yl)(3-hydroxyphenyl)methanone;
(4-(4-chlorophenoxyl)piperidin-1-yl)(2-hydroxyphenyl)methanone;
(4-(4-chlorophenoxyl)piperidin-1-yl)(4-hydroxy-3,5-dimethoxyphenyl)methanone;
(4-(4-chlorophenoxyl)piperidin-1-yl)(4-hydroxy-2-methylphenyl)methanone;
(4-(4-chlorophenoxyl)piperidin-1-yl)(5-hydroxy-2-methylphenyl)methanone;
(3-chloro-2-hydroxyphenyl)(4-(4-chlorophenoxyl)piperidin-1-yl)methanone;
(4-(4-chlorophenoxyl)piperidin-1-yl)(3-fluoro-2-hydroxyphenyl)methanone;
2-(5-(4-(4-chlorophenoxy)piperidine-1-carbonyl)-2-methylphenoxy)acetamide;
2-(2-(4-(4-chlorophenoxy)piperidine-1-carbonyl)-5-methylphenoxy)acetamide;
(4-(4-chlorophenoxyl)piperidin-1-yl)(2,6-dihydroxyphenyl)methanone;
(4-(4-chlorophenoxyl)piperidin-1-yl)(2-fluoro-3-hydroxyphenyl)methanone;
(4-(4-chlorophenoxyl)piperidin-1-yl)(2-fluoro-5-hydroxyphenyl)methanone;
(2-chloro-5-hydroxyphenyl)(4-(4-chlorophenoxyl)piperidin-1-yl)methanone;
(3-(tert-butyl)-1-methyl-1H-pyrazol-5-yl)(4-(4-fluorophenoxyl)piperidin-1-yl)methanone;
(4-fluoro-3-methoxyphenyl)(4-(4-fluorophenoxyl)piperidin-1-yl)methanone;
(4-((4-chlorophenyl)sulfonyl)piperidin-1-yl)(2-methyl-2H-indazol-3-yl)methanone;
(4-(4-fluorophenoxyl)piperidin-1-yl)(4-fluorophenyl)methanone;
(5-(tert-butyl)isoxazol-3-yl)(4-(4-fluorophenoxyl)piperidin-1-yl)methanone;
(4-(4-fluorophenoxyl)piperidin-1-yl)(1-methyl-5-(trifluoromethyl)-1H-pyrazol-3-yl)methanone;
(4-(4-fluorophenoxyl)piperidin-1-yl)(1-methyl-1H-indazol-3-yl)methanone;
(4-(4-fluorophenoxyl)piperidin-1-yl)(quinoxalin-2-yl)methanone;
(4-(4-fluorophenoxyl)piperidin-1-yl)(4-methoxyquinolin-2-yl)methanone;
(4-(4-fluorophenoxyl)piperidin-1-yl)(6-methoxyquinolin-2-yl)methanone;
(4-(4-fluorophenoxyl)piperidin-1-yl)(isoquinolin-1-yl)methanone;
(4-(4-fluorophenoxyl)piperidin-1-yl)(isoquinolin-4-yl)methanone;
(4-(4-fluorophenoxyl)piperidin-1-yl)(quinolin-4-yl)methanone;
(5-aminopyridin-2-yl)(4-(4-chlorophenoxyl)piperidin-1-yl)methanone;
(6-(tert-butyl)pyridin-3-yl)(4-(4-chlorophenoxyl)piperidin-1-yl)methanone;
(6-(tert-butyl)pyridin-3-yl)(4-(4-fluorophenoxyl)piperidin-1-yl)methanone;
N-(6-(4-(4-chlorophenoxy)piperidine-1-carbonyl)pyridin-3-yl)acetamide;
(6-methylpyridin-3-yl)(4-(3-(trifluoromethoxy)phenoxy)piperidin-1-yl)methanone;
(1,3-dimethyl-1H-pyrazol-5-yl)(4-(3-(trifluoromethoxy)phenoxy)piperidin-1-yl)methanone;
(3,5-dimethylisoxazol-4-yl)(4-(3-(trifluoromethoxy)phenoxy)piperidin-1-yl)methanone;
(6-hydroxypyridin-2-yl)(4-(3-(trifluoromethoxy)phenoxy)piperidin-1-yl)methanone;
(3-methylpyridin-2-yl)(4-(3-(trifluoromethoxy)phenoxy)piperidin-1-yl)methanone;
(5-methoxypyridin-3-yl)(4-(3-(trifluoromethoxy)phenoxy)piperidin-1-yl)methanone;
(5-aminopyridin-3-yl)(4-(3-(trifluoromethoxy)phenoxy)piperidin-1-yl)methanone;
(6-methoxypyridin-3-yl)(4-(3-(trifluoromethoxy)phenoxy)piperidin-1-yl)methanone;
4-(4-(3-(trifluoromethoxy)phenoxy)piperidine-1-carbonyl)picolinamide;
(3-methylisoxazol-5-yl)(4-(3-(trifluoromethoxy)phenoxy)piperidin-1-yl)methanone;
(2-methylthiazol-5-yl)(4-(3-(trifluoromethoxy)phenoxy)piperidin-1-yl)methanone;
(1-methyl-1H-imidazol-4-yl)(4-(3-(trifluoromethoxy)phenoxy)piperidin-1-yl)methanone;
(2-hydroxy-6-methoxyphenyl)(4-(3-(trifluoromethoxy)phenoxy)piperidin-1-yl)methanone;
(2,4-dimethylthiazol-5-yl)(4-(3-(trifluoromethoxy)phenoxy)piperidin-1-yl)methanone;
(2-methyl-2H-indazol-3-yl)(4-(3-(trifluoromethoxy)phenoxy)piperidin-1-yl)methanone;
(2-methyl-2H-indazol-6-yl)(4-(3-(trifluoromethoxy)phenoxy)piperidin-1-yl)methanone;
imidazo[1,2-a]pyridin-8-yl(4-(3-(trifluoromethoxy)phenoxy)piperidin-1-yl)methanone;
(1,8-naphthyridin-2-yl)(4-(3-(trifluoromethoxy)phenoxy)piperidin-1-yl)methanone;
(1,5-naphthyridin-2-yl)(4-(3-(trifluoromethoxy)phenoxy)piperidin-1-yl)methanone;
(2-hydroxyquinolin-4-yl)(4-(3-(trifluoromethoxy)phenoxy)piperidin-1-yl)methanone;
1,6-dimethyl-3-(4-((3-(trifluoromethoxy)phenoxy)piperidine-1-carbonyl)pyridin-2(1H)-one;
benzo[d]thiazol-6-yl(4-(4-fluorophenoxyl)piperidin-1-yl)methanone;
(4-(4-fluorophenoxyl)piperidin-1-yl)(2-methyl-1H-benzo[d]imidazol-5-yl)methanone;
(4-(4-fluorophenoxyl)piperidin-1-yl)(1-methyl-1H-benzo[d]imidazol-5-yl)methanone;
(4-(4-fluorophenoxyl)piperidin-1-yl)(5-methoxypyridin-2-yl)methanone;
(4-(4-fluorophenoxyl)piperidin-1-yl)(4-methyl-2-phenylpyrimidin-5-yl)methanone;
(4-(4-fluorophenoxyl)piperidin-1-yl)(1-methyl-1H-benzo[d]imidazol-2-yl)methanone;
(4-(4-chlorophenoxyl)piperidin-1-yl)(6-ethoxypyridin-3-yl)methanone;
(4-(4-chlorophenoxyl)piperidin-1-yl)(6-(dimethylamino)pyridin-3-yl)methanone;
(4-((4-chlorophenyl)sulfonyl)piperidin-1-yl)(quinolin-2-yl)methanone;
(4-((4-chlorophenyl)sulfonyl)piperidin-1-yl)(quinolin-3-yl)methanone;

(4-((4-chlorophenyl)sulfonyl)piperidin-1-yl)(5-methyl-1-phenyl-1H-pyrazol-4-yl)methanone;
(4-((4-chlorophenyl)sulfonyl)piperidin-1-yl)(4-methoxyquinolin-2-yl)methanone;
(4-((4-chlorophenyl)sulfonyl)piperidin-1-yl)(6-ethoxypyridin-2-yl)methanone;
(6-methoxypyridin-2-yl)(4-(3-(trifluoromethoxy)phenoxy)piperidin-1-yl)methanone;
(5-methoxypyrazin-2-yl)(4-(3-(trifluoromethoxy)phenoxy)piperidin-1-yl)methanone;
(2-hydroxy-3-methoxyphenyl)(4-(3-(trifluoromethoxy)phenoxy)piperidin-1-yl)methanone;
(2-methyloxazol-4-yl)(4-(3-(trifluoromethoxy)phenoxy)piperidin-1-yl)methanone;
(4-(2-hydroxypropan-2-yl)phenyl)(4-(3-(trifluoromethoxy)phenoxy)piperidin-1-yl)methanone;
(6-ethoxypyridin-2-yl)(4-(3-(trifluoromethoxy)phenoxy)piperidin-1-yl)methanone;
(1H-benzo[d]imidazol-6-yl)(4-(3-(trifluoromethoxy)phenoxy)piperidin-1-yl)methanone;
imidazo[1,2-a]pyrazin-2-yl(4-(3-(trifluoromethoxy)phenoxy)piperidin-1-yl)methanone;
(4-hydroxy-7-methyl-1,8-naphthyridin-3-yl)(4-(3-(trifluoromethoxy)phenoxy)piperidin-1-yl)methanone;
N-(4-(4-(3-(trifluoromethoxy)phenoxy)piperidine-1-carbonyl)pyridin-2-yl)acetamide;
N-(6-(4-(3-(trifluoromethoxy)phenoxy)piperidine-1-carbonyl)pyridin-2-yl)acetamide;
(4-((4-chlorophenyl)sulfonyl)piperidin-1-yl)(p-tolyl)methanone;
(4-((4-chlorophenyl)sulfonyl)piperidin-1-yl)(4-methoxyphenyl)methanone;
(4-chlorophenyl)(4-((4-chlorophenyl)sulfonyl)piperidin-1-yl)methanone;
(4-((4-chlorophenyl)sulfonyl)piperidin-1-yl)(1,5-naphthyridin-2-yl)methanone;
(4-((4-chlorophenyl)sulfonyl)piperidin-1-yl)(6-methoxy-1-methyl-1H-indol-2-yl)methanone;
quinolin-8-yl(4-((3-(trifluoromethyl)phenyl)sulfonyl)piperidin-1-yl)methanone;
quinolin-8-yl(4-tosylpiperidin-1-yl)methanone;
(4-((4-chlorophenyl)sulfonyl)piperidin-1-yl)(isoquinolin-3-yl)methanone;
4-(4-(3-(trifluoromethoxy)phenoxy)piperidine-1-carbonyl)benzamide;
3-(4-(3-(trifluoromethoxy)phenoxy)piperidine-1-carbonyl)benzamide;
3-(4-(4-chlorophenoxy)piperidine-1-carbonyl)benzamide;
3-(4-(4-chlorophenoxy)piperidine-1-carbonyl)-N-methylbenzamide;
4-(4-(4-chlorophenoxy)piperidine-1-carbonyl)-N-methylbenzamide;
(4-hydroxyquinolin-2-yl)(4-(3-(trifluoromethoxy)phenoxy)piperidin-1-yl)methanone;
(3-hydroxyquinoxalin-2-yl)(4-(3-(trifluoromethoxy)phenoxy)piperidin-1-yl)methanone;
(6-(hydroxymethyl)pyridin-2-yl)(4-(3-(trifluoromethoxy)phenoxy)piperidin-1-yl)methanone;
(1-(2-hydroxyethyl)-2-methyl-1H-benzo[d]imidazol-5-yl)(4-(3-(trifluoromethoxy)phenoxy)piperidin-1-yl)methanone;
(2-hydroxy-6-methylpyridin-4-yl)(4-(3-(trifluoromethoxy)phenoxy)piperidin-1-yl)methanone;
1-methyl-4-(4-(3-(trifluoromethoxy)phenoxy)piperidine-1-carbonyl)pyridin-2(1H)-one;
(2-hydroxy-6-methylpyridin-3-yl)(4-(3-(trifluoromethoxy)phenoxy)piperidin-1-yl)methanone;
3-(4-(3-(trifluoromethoxy)phenoxy)piperidine-1-carbonyl)quinolin-2(1H)-one;
(1H-1,2,4-triazol-3-yl)(4-(3-(trifluoromethoxy)phenoxy)piperidin-1-yl)methanone;
2-cyclopropyl-6-methyl-5-(4-((3-(trifluoromethoxy)phenoxy)piperidine-1-carbonyl)pyrimidin-4(1H)-one;
5,6-dimethyl-3-(4-((3-(trifluoromethoxy)phenoxy)piperidine-1-carbonyl)pyridin-2(1H)-one;
(4-(3-(trifluoromethoxy)phenoxy)piperidin-1-yl)(1,3,6-trimethyl-1H-pyrazolo[3,4-b]pyridin-4-yl)methanone;
4-(4-(3-(trifluoromethoxy)phenoxy)piperidine-1-carbonyl)-1H-benzo[d]imidazol-2(3H)-one;
(4-(4-chloro-2-methoxyphenoxy)piperidin-1-yl)(quinolin-8-yl)methanone;
1-(5-chloro-2-((1-(quinoline-8-carbonyl)piperidin-4-yl)oxy)phenyl)ethanone;
5-chloro-2-((1-(quinoline-8-carbonyl)piperidin-4-yl)oxy)benzonitrile;
(4-((4-chlorophenyl)sulfonyl)piperidin-1-yl)(quinoxalin-2-yl)methanone;
(4-((4-chlorophenyl)sulfonyl)piperidin-1-yl)(6-methoxyquinolin-2-yl)methanone;
(4-((4-chlorophenyl)sulfonyl)piperidin-1-yl)(4-methyl-2-phenylpyrimidin-5-yl)methanone;
(4-((4-chlorophenyl)sulfonyl)piperidin-1-yl)(6-(pyrrolidin-1-yl)pyridin-2-yl)methanone;
(5-(tert-butyl)isoxazol-3-yl)(4-((4-chlorophenyl)sulfonyl)piperidin-1-yl)methanone;
(4-((4-chlorophenyl)sulfonyl)piperidin-1-yl)(6-(2,2,2-trifluoroethoxy)pyridin-3-yl)methanone;
(4-((4-chlorophenyl)sulfonyl)piperidin-1-yl)(1-methyl-1H-indol-5-yl)methanone;
(4-((4-chlorophenyl)sulfonyl)piperidin-1-yl)(1-methyl-1H-indol-2-yl)methanone;
(4-(3-fluorophenoxyl)piperidin-1-yl)(4-fluorophenyl)methanone;
(4-((4-chlorophenyl)sulfonyl)piperidin-1-yl)(1-methyl-1H-indol-6-yl)methanone;
3-(4-(3-(trifluoromethyl)phenoxy)piperidine-1-carbonyl)benzamide;
4-(4-(3-(trifluoromethyl)phenoxy)piperidine-1-carbonyl)benzamide;
4-(4-(3-(trifluoromethyl)phenoxy)piperidine-1-carbonyl)picolinamide;
(4-((4-chlorophenyl)sulfonyl)piperidin-1-yl)(2-methoxyquinolin-4-yl)methanone;
(4-((4-chlorophenyl)sulfonyl)piperidin-1-yl)(6-phenoxypyridin-3-yl)methanone;
3-(4-((4-chlorophenyl)sulfonyl)piperidine-1-carbonyl)quinolin-2(1H)-one;
3-(4-((4-chlorophenyl)sulfonyl)piperidine-1-carbonyl)-1-methylquinolin-2(1H)-one;
(4-(4-fluorophenoxyl)piperidin-1-yl)(5-methyl-1-phenyl-1H-pyrazol-4-yl)methanone;
4-(4-(4-chlorophenoxy)piperidine-1-carbonyl)-N-(2-methoxyethyl)-N-methylbenzamide;
4-(4-(4-chlorophenoxy)piperidine-1-carbonyl)-N-(2-methoxyethyl)benzamide;
4-(4-(4-chlorophenoxy)piperidine-1-carbonyl)-N-(1-((1-hydroxycyclohexyl)methyl)piperidin-4-yl)benzamide;
(S)-4-(4-(4-chlorophenoxyl)piperidine-1-carbonyl)-N-(2-hydroxy-1-phenylethyl)benzamide;
(S)-4-(4-(4-chlorophenoxyl)piperidine-1-carbonyl)-N-(2-hydroxy-2-phenylethyl)benzamide;

(S)-4-(4-(4-chlorophenoxyl)piperidine-1-carbonyl)-N-(1-hydroxy-3-phenylpropan-2-yl)benzamide;
(S)—N-(1-amino-1-oxo-3-phenylpropan-2-yl)-4-(4-(4-chlorophenoxy)piperidine-1-carbonyl)benzamide;
(4-((4-chlorophenyl)sulfonyl)piperidin-1-yl)(1-methyl-1H-indol-4-yl)methanone;
4-(4-((4-chlorophenyl)thio)piperidine-1-carbonyl)picolinamide;
6-(4-(3-(trifluoromethoxy)phenoxy)piperidine-1-carbonyl)picolinamide;
4-(4-(4-chlorophenoxy)piperidine-1-carbonyl)-N-(2-oxo-2-phenyl ethyl)benzamide;
(2-(methylsulfonyl)phenyl)(4-(3-(trifluoromethoxy)phenoxy)piperidin-1-yl)methanone;
(3-(methylsulfonyl)phenyl)(4-(3-(trifluoromethoxy)phenoxy)piperidin-1-yl)methanone;
(4-((4-chlorophenyl)sulfonyl)piperidin-1-yl)(5-fluoro-1-methyl-1H-indol-2-yl)methanone;
(4-((4-chlorophenyl)sulfonyl)piperidin-1-yl)(6-fluoro-1-methyl-1H-indol-2-yl)methanone;
(4-(3-ethoxyphenoxyl)piperidin-1-yl)(quinolin-8-yl)methanone;
(4-((4-chlorophenyl)sulfonyl)piperidin-1-yl)(3-(2-methylthiazol-4-yl)phenyl)methanone;
N-methyl-3-(4-(3-(trifluoromethoxy)phenoxy)piperidine-1-carbonyl)benzamide;
3-(4-(3-(trifluoromethoxy)phenoxy)piperidine-1-carbonyl)benzenesulfonamide;
4-(4-(3-(trifluoromethoxy)phenoxy)piperidine-1-carbonyl)benzenesulfonamide;
(4-(4-fluorophenoxyl)piperidin-1-yl)(1,5-naphthyridin-2-yl)methanone;
(4-(4-fluorophenoxyl)piperidin-1-yl)(quinolin-2-yl)methanone;
(4-(3-fluorophenoxyl)piperidin-1-yl)(4-methoxyquinolin-2-yl)methanone;
(1H-benzo[d][1,2,3]triazol-7-yl)(4-(3-(trifluoromethoxy)phenoxy)piperidin-1-yl)methanone;
2-(2-(4-(4-chlorophenoxy)piperidine-1-carbonyl)phenoxy)acetamide;
2-(4-(4-chlorophenoxy)piperidine-1-carbonyl)phenoxy)acetamide;
2-(2-(4-(3-(trifluoromethoxy)phenoxy)piperidine-1-carbonyl)phenoxy)acetamide;
2-(3-(4-(3-(trifluoromethoxy)phenoxy)piperidine-1-carbonyl)phenoxy)acetamide;
2-(4-(4-(3-(trifluoromethoxy)phenoxy)piperidine-1-carbonyl)phenoxy)acetamide;
(8-hydroxyquinolin-2-yl)(4-((3-(trifluoromethoxy)phenyl)sulfonyl)piperidin-1-yl)methanone;
quinolin-8-yl(4-((3-(trifluoromethoxy)phenyl)sulfonyl)piperidin-1-yl)methanone;
quinolin-2-yl(4-((3-(trifluoromethoxy)phenyl)sulfonyl)piperidin-1-yl)methanone;
(4-((4-chlorophenyl)sulfonyl)piperidin-1-yl)(5-phenyl-isoxazol-3-yl)methanone;
(6-methoxyquinolin-2-yl)(4-((3-(trifluoromethoxy)phenyl)sulfonyl)piperidin-1-yl)methanone;
(5-methyl-2-phenyl-2H-1,2,3-triazol-4-yl)(4-((3-(trifluoromethoxy)phenyl)sulfonyl)piperidin-1-yl)methanone;
(5-fluoro-1-methyl-1H-indol-2-yl)(4-((3-(trifluoromethoxy)phenyl)sulfonyl)piperidin-1-yl)methanone;
(6-fluoro-1-methyl-1H-indol-2-yl)(4-((3-(trifluoromethoxy)phenyl)sulfonyl)piperidin-1-yl)methanone;
(4-hydroxyquinolin-8-yl)(4-(3-(trifluoromethoxy)phenoxy)piperidin-1-yl)methanone;
(1,8-naphthyridin-4-yl)(4-(3-(trifluoromethoxy)phenoxy)piperidin-1-yl)methanone;
(1,6-naphthyridin-8-yl)(4-(3-(trifluoromethoxy)phenoxy)piperidin-1-yl)methanone;
[1,2,4]triazolo[1,5-a]pyrimidin-2-yl(4-(3-(trifluoromethoxy)phenoxy)piperidin-1-yl)methanone;
(5-methyl-1H-pyrazol-3-yl)(4-(3-(trifluoromethoxy)phenoxy)piperidin-1-yl)methanone;
2-chloro-5-(4-(3-(trifluoromethoxy)phenoxy)piperidine-1-carbonyl)benzenesulfonamide;
(S)-3-(4-(4-chlorophenoxyl)piperidine-1-carbonyl)-N-(2-hydroxy-2-phenylethyl)benzamide;
(S)-3-(4-(4-chlorophenoxyl)piperidine-1-carbonyl)-N-(2-hydroxy-1-phenylethyl)benzamide;
(S)-3-(4-(4-chlorophenoxyl)piperidine-1-carbonyl)-N-(1-hydroxy-3-phenylpropan-2-yl)benzamide;
(S)—N-(1-amino-1-oxo-3-phenylpropan-2-yl)-3-(4-(4-chlorophenoxy)piperidine-1-carbonyl)benzamide;
(4-((3-ethoxyphenyl)sulfonyl)piperidin-1-yl)(8-hydroxyquinolin-2-yl)methanone;
(4-((4-chlorophenyl)sulfonyl)piperidin-1-yl)(4-methyl-2-phenylthiazol-5-yl)methanone;
(4-((4-chlorophenyl)sulfonyl)piperidin-1-yl)(2-phenylthiazol-4-yl)methanone;
(4-chloro-2-(methylsulfonyl)phenyl)(4-(3-(trifluoromethoxy)phenoxy)piperidin-1-yl)methanone;
(5-fluoro-2-(methylsulfonyl)phenyl)(4-(3-(trifluoromethoxy)phenoxy)piperidin-1-yl)methanone;
N,N-dimethyl-4-(4-(3-(trifluoromethoxy)phenoxy)piperidine-1-carbonyl)benzenesulfonamide;
N-(2-(4-(4-(3-(trifluoromethoxy)phenoxy)piperidine-1-carbonyl)phenoxy)ethyl)acetamide;
(2-phenyl-1H-imidazol-5-yl)(4-((3-(trifluoromethoxy)phenyl)sulfonyl)piperidin-1-yl)methanone;
(3-(2-methylthiazol-4-yl)phenyl)(4-((3-(trifluoromethoxy)phenyl)sulfonyl)piperidin-1-yl)methanone;
N-(4-(4-(3-ethoxyphenoxyl)piperidine-1-carbonyl)pyridin-2-yl)acetamide;
(4-(3-ethoxyphenoxyl)piperidin-1-yl)(2-(methylsulfonyl)phenyl)methanone;
3-(4-(3-ethoxyphenoxy)piperidine-1-carbonyl)benzenesulfonamide;
N-(6-(4-(3-ethoxyphenoxyl)piperidine-1-carbonyl)pyridin-2-yl)acetamide;
(4-(3-ethoxyphenoxyl)piperidin-1-yl)(2-methyl-2H-indazol-3-yl)methanone;
(4-(3-ethoxyphenoxyl)piperidin-1-yl)(1,5-naphthyridin-2-yl)methanone;
(8-hydroxyquinolin-2-yl)(4-((4-(trifluoromethoxy)phenyl)sulfonyl)piperidin-1-yl)methanone;
quinolin-8-yl(4-((4-(trifluoromethoxy)phenyl)sulfonyl)piperidin-1-yl)methanone;
quinolin-2-yl(4-((4-(trifluoromethoxy)phenyl)sulfonyl)piperidin-1-yl)methanone;
N-(3-(4-(3-(trifluoromethoxy)phenoxy)piperidine-1-carbonyl)phenyl)methanesulfonamide;
(2-(ethylsulfonyl)phenyl)(4-(3-(trifluoromethoxy)phenoxy)piperidin-1-yl)methanone;
(3-fluoro-4-(methylsulfonyl)phenyl)(4-(3-(trifluoromethoxy)phenoxy)piperidin-1-yl)methanone;
ethyl (4-(4-(3-(trifluoromethoxy)phenoxy)piperidine-1-carbonyl)pyridin-2-yl)carbamate;
2-(4-(3-(trifluoromethoxy)phenoxy)piperidine-1-carbonyl)thiazole-4-carboxamide;
N,N-dimethyl-2-(4-(3-(trifluoromethoxy)phenoxy)piperidine-1-carbonyl)benzenesulfonamide;

(4-(4-(3-(trifluoromethoxy)phenoxy)piperidine-1-carbonyl)phenyl)methanesulfonamide;
4-methoxy-3-(4-(3-(trifluoromethoxy)piperidine-1-carbonyl)benzenesulfonamide;
2-((2-(4-(3-(trifluoromethoxy)phenoxy)piperidine-1-carbonyl)pyridin-3-yl)oxy)acetamide;
(4-(aminomethyl)pyridin-2-yl)(4-(3-(trifluoromethoxy)phenoxy)piperidin-1-yl)methanone;
N-((2-(4-(3-(trifluoromethoxy)phenoxy)piperidine-1-carbonyl)pyridin-4-yl)methyl)methanesulfonamide;
ethyl ((2-(4-(3-(trifluoromethoxy)phenoxy)piperidine-1-carbonyl)pyridin-4-yl)methyl)carbamate;
N-(2-(4-(3-(trifluoromethoxy)phenoxy)piperidine-1-carbonyl)benzyl)acetamide;
N-(2-(4-(3-(trifluoromethoxy)phenoxy)piperidine-1-carbonyl)benzyl)methanesulfonamide;
ethyl 2-(4-(3-(trifluoromethoxy)phenoxy)piperidine-1-carbonyl)benzylcarbamate;
(2-(methylsulfonyl)phenyl)(4-(3-(2,2,2-trifluoroethoxy)phenoxy)piperidin-1-yl)methanone;
N-(4-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)picolinamide;
3-(4-(3-(2,2,2-trifluoroethoxy)phenoxy)piperidine-1-carbonyl)benzamide;
3-(4-(3-(2,2,2-trifluoroethoxy)phenoxy)piperidine-1-carbonyl)benzenesulfonamide;
2-(2-(4-(3-(2,2,2-trifluoroethoxy)phenoxy)piperidine-1-carbonyl)phenoxy)acetamide;
quinolin-8-yl(4-(3-(2,2,2-trifluoroethoxyl)phenoxy)piperidin-1-yl)methanone;
(1,5-naphthyridin-2-yl)(4-(3-(2,2,2-trifluoroethoxyl)phenoxy)piperidin-1-yl)methanone;
(2-methyl-2H-indazol-3-yl)(4-(3-(2,2,2-trifluoroethoxyl)phenoxy)piperidin-1-yl)methanone;
(1,3-dimethyl-1H-pyrazol-5-yl)(4-(3-(2,2,2-trifluoroethoxy)phenoxy)piperidin-1-yl)methanone;
N-(6-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)benzamide;
(3,5-dimethylisoxazol-4-yl)(4-(3-(2,2,2-trifluoroethoxy)phenoxy)piperidin-1-yl)methanone;
(3-(methylsulfonyl)phenyl)(4-(3-(2,2,2-trifluoroethoxy)phenoxy)piperidin-1-yl)methanone;
(1,6-naphthyridin-8-yl)(4-(3-(2,2,2-trifluoroethoxyl)phenoxy)piperidin-1-yl)methanone;
(3-methyl-1H-pyrazol-5-yl)(4-(3-(2,2,2-trifluoroethoxyl)phenoxy)piperidin-1-yl)methanone;
2-(3-(4-(3-(2,2,2-trifluoroethoxy)phenoxy)piperidine-1-carbonyl)phenoxy)acetamide;
(5-((tetrahydro-2H-pyran-4-yl)oxy)pyridin-3-yl)(4-(3-(trifluoromethoxy)phenoxy)piperidin-1-yl)methanone;
1-(3-(4-(3-(trifluoromethoxy)phenoxy)piperidine-1-carbonyl)phenyl)urea;
1-(4-(4-(3-(trifluoromethoxy)phenoxy)piperidine-1-carbonyl)phenyl)urea;
(1H-1,2,4-triazol-3-yl)(4-(3-(2,2,2-trifluoroethoxyl)phenoxy)piperidin-1-yl)methanone;
(4-(3-ethoxyphenoxyl)piperidin-1-yl)(3-(methylsulfonyl)phenyl)methanone;
(4-(3-ethoxyphenoxyl)piperidin-1-yl)(3-methyl-1H-pyrazol-5-yl)methanone;
N,N-dimethyl-3-(4-((3-(trifluoromethoxy)phenoxy)piperidine-1-carbonyl)benzenesulfonamide;
N-(2-(4-(3-(trifluoromethoxy)phenoxy)piperidine-1-carbonyl)phenyl)methanesulfonamide;
(6-aminopyridin-2-yl)(4-(3-(trifluoromethoxy)phenoxy)piperidin-1-yl)methanone;
2-(methyl(3-(4-(3-(trifluoromethoxy)piperidine-1-carbonyl)benzyl)amino)acetamide;
2-(methyl(4-(4-(3-(trifluoromethoxy)piperidine-1-carbonyl)benzyl)amino)acetamide;
N,N-dimethyl-2-(2-(4-(3-(trifluoromethoxy)phenoxy)piperidine-1-carbonyl)phenoxy)acetamide;
(1,3-dimethyl-1H-pyrazol-5-yl)(4-(3-(trifluoromethyl)phenoxy)piperidin-1-yl)methanone;
(2-(methylsulfonyl)phenyl)(4-(3-(trifluoromethyl)phenoxy)piperidin-1-yl)methanone;
N-(6-(4-(3-(trifluoromethyl)phenoxy)piperidine-1-carbonyl)pyridin-2-yl)acetamide;
3-(4-(3-(trifluoromethyl)phenoxy)piperidine-1-carbonyl)benzenesulfonamide;
(3,5-dimethylisoxazol-4-yl)(4-(3-(trifluoromethyl)phenoxy)piperidin-1-yl)methanone;
(1,6-naphthyridin-8-yl)(4-(3-(trifluoromethyl)phenoxy)piperidin-1-yl)methanone;
(3-methyl-1H-pyrazol-5-yl)(4-(3-(trifluoromethyl)phenoxy)piperidin-1-yl)methanone;
2-(2-(4-(3-(trifluoromethyl)phenoxy)piperidine-1-carbonyl)phenoxy)acetamide;
2-(4-(4-(3-(trifluoromethyl)phenoxy)piperidine-1-carbonyl)phenoxy)acetamide;
2-(3-(4-(3-(trifluoromethyl)phenoxy)piperidine-1-carbonyl)phenoxy)acetamide;
(1H-1,2,4-triazol-3-yl)(4-(3-(trifluoromethyl)phenoxy)piperidin-1-yl)methanone;
N-(2-(2-(4-(3-(trifluoromethoxy)phenoxy)piperidine-1-carbonyl)phenoxy)ethyl)acetamide;
N-(2-(2-(4-(3-(trifluoromethoxy)phenoxy)piperidine-1-carbonyl)phenoxy)ethyl)methanesulfonamide;
ethyl (2-(2-(4-(3-(trifluoromethoxy)phenoxy)piperidine-1-carbonyl)phenoxy)ethyl)carbamate;
N-(2-(2-(4-(3-(trifluoromethoxy)phenoxy)piperidine-1-carbonyl)phenoxy)ethyl)cyclopropane-1,1-dicarboxamide;
(3-(2-aminoethoxy)phenyl)(4-(3-(trifluoromethoxy)phenoxy)piperidin-1-yl)methanone;
N-(2-(3-(4-(3-(trifluoromethoxy)phenoxy)piperidine-1-carbonyl)phenoxy)ethyl)acetamide;
N-(2-(3-(4-(3-(trifluoromethoxy)phenoxy)piperidine-1-carbonyl)phenoxy)ethyl)methanesulfonamide;
ethyl (2-(3-(4-(3-(trifluoromethoxy)phenoxy)piperidine-1-carbonyl)phenoxy)ethyl)carbamate;
N-(2-(3-(4-(3-(trifluoromethoxy)phenoxy)piperidine-1-carbonyl)phenoxy)ethyl)cyclopropane-1,1-dicarboxamide;
N-(3-(4-(3-(trifluoromethoxy)phenoxy)piperidine-1-carbonyl)pyridin-2-yl)acetamide;
N-(1-methyl-5-(4-(3-(trifluoromethoxy)phenoxy)piperidine-1-carbonyl)-1H-pyrazol-3-yl)acetamide;
(2-(ethylsulfonyl)phenyl)(4-(3-(trifluoromethyl)phenoxy)piperidin-1-yl)methanone;
(4-(3-ethoxyphenoxyl)piperidin-1-yl)(2-(ethylsulfonyl)phenyl)methanone;
(2-(ethylsulfonyl)phenyl)(4-(3-(2,2,2-trifluoroethoxy)phenoxy)piperidin-1-yl)methanone;
N-(2-(4-(3-(trifluoromethoxy)phenoxy)piperidine-1-carbonyl)pyridin-3-yl)acetamide;
2-(4-(4-(3-chlorophenoxy)piperidine-1-carbonyl)phenoxy)acetamide;

2-(2-(4-((4-chlorophenyl)thio)piperidine-1-carbonyl)phenoxy)acetamide;
2-(3-(4-((4-chlorophenyl)thio)piperidine-1-carbonyl)phenoxy)acetamide;
(4-((4-chlorophenyl)thio)piperidin-1-yl)(2-(methylsulfonyl)phenyl)methanone;
2-(methyl(2-(4-(3-(trifluoromethoxy)phenoxy)piperidine-1-carbonyl)benzyl)amino)acetamide;
1-morpholino-2-(2-(4-(3-(trifluoromethoxy)phenoxy)piperidine-1-carbonyl)phenoxy)ethanone;
1-(piperidin-1-yl)-2-(2-(4-(3-(trifluoromethoxy)phenoxy)piperidine-1-carbonyl)phenoxy)ethanone;
(2-(2-methoxyethoxyl)phenyl)(4-(3-(trifluoromethoxy)phenoxy)piperidin-1-yl)methanone;
(3-(methylsulfonyl)phenyl)(4-(3-(trifluoromethyl)phenoxy)piperidin-1-yl)methanone;
(4-(3-chlorophenoxyl)piperidin-1-yl)(3-(methylsulfonyl)phenyl)methanone;
(4-(4-chlorophenoxyl)piperidin-1-yl)(3-(methylsulfonyl)phenyl)methanone;
(4-(4-chlorophenoxyl)piperidin-1-yl)(2-(ethylsulfonyl)phenyl)methanone;
N,N-dimethyl-3-(4-(3-(trifluoromethyl)phenoxy)piperidine-1-carbonyl)benzenesulfonamide;
3-(4-(4-chlorophenoxy)piperidine-1-carbonyl)-N,N-dimethylbenzenesulfonamide;
N,N-dimethyl-3-(4-(3-(2,2,2-trifluoroethoxy)phenoxy)piperidine-1-carbonyl)benzenesulfonamide;
N,N-dimethyl-2-(4-(3-(trifluoromethyl)phenoxy)piperidine-1-carbonyl)benzenesulfonamide;
2-(4-(4-chlorophenoxy)piperidine-1-carbonyl)-N,N-dimethylbenzenesulfonamide;
N,N-dimethyl-2-(4-(3-(2,2,2-trifluoroethoxy)phenoxy)piperidine-1-carbonyl)benzenesulfonamide;
(4-(3-(2-methoxyethoxyl)phenoxy)piperidin-1-yl)(quinolin-8-yl)methanone;
(4-(3-(2-methoxyethoxyl)phenoxy)piperidin-1-yl)(quinolin-2-yl)methanone;
(4-(3-(2-methoxyethoxyl)phenoxy)piperidin-1-yl)(2-methyl-2H-indazol-3-yl)methanone;
2-((2-(4-(3-(trifluoromethoxy)phenoxy)piperidine-1-carbonyl)phenyl)thio)acetamide;
2-((2-(4-(4-chlorophenoxyl)piperidine-1-carbonyl)phenyl)thio)acetamide;
4-(4-(3-(2,2,2-trifluoroethoxy)phenoxy)piperidine-1-carbonyl)-1H-benzo[d]imidazol-2(3H)-one;
(4-(3-ethoxyphenoxyl)piperidin-1-yl)(1-methyl-1H-benzo[d]imidazol-2-yl)methanone;
(4-(3-fluorophenoxyl)piperidin-1-yl)(1-methyl-1H-benzo[d]imidazol-2-yl)methanone;
(1H-pyrrolo[2,3-b]pyridin-2-yl)(4-(3-(2,2,2-trifluoroethoxy)phenoxy)piperidin-1-yl)methanone;
(4-(3-ethoxyphenoxyl)piperidin-1-yl)(1H-pyrrolo[2,3-b]pyridin-2-yl)methanone;
(1H-pyrrolo[2,3-b]pyridin-2-yl)(4-(3-(trifluoromethoxy)phenoxy)piperidin-1-yl)methanone;
(4-(3-ethoxyphenoxyl)piperidin-1-yl)(1-methyl-1H-pyrazolo[3,4-b]pyridin-3-yl)methanone;
(4-(3-ethoxyphenoxyl)piperidin-1-yl)(1H-pyrrolo[2,3-b]pyridin-3-yl)methanone;
(4-(3-ethoxyphenoxyl)piperidin-1-yl)(pyrazolo[1,5-a]pyrimidin-3-yl)methanone;
(1,3-dimethyl-1H-thieno[2,3-c]pyrazol-5-yl)(4-(3-ethoxyphenoxyl)piperidin-1-yl)methanone;
(4-(3-fluorophenoxyl)piperidin-1-yl)(4-methyl-3,4-dihydro-2H-pyrido[3,2-b][1,4]oxazin-7-yl)methanone;
(3,5-dimethyl-1H-pyrazol-4-yl)(4-(3-(2,2,2-trifluoroethoxy)phenoxy)piperidin-1-yl)methanone;
N-(2-hydroxyethyl)-N-methyl-2-(4-(3-(trifluoromethoxy)phenoxy)piperidine-1-carbonyl)benzenesulfonamide;
N-(2-methoxyethyl)-N-methyl-2-(4-(3-(trifluoromethoxy)phenoxy)piperidine-1-carbonyl)benzenesulfonamide;
(2-(morpholinosulfonyl)phenyl)(4-(3-(trifluoromethoxy)phenoxy)piperidin-1-yl)methanone;
2-(N-methyl-2-(4-(3-(trifluoromethoxy)phenoxy)piperidine-1-carbonyl)phenylsulfonamido)acetamide;
N-methyl-3-(4-(3-(2,2,2-trifluoroethoxy)phenoxy)piperidine-1-carbonyl)benzenesulfonamide;
3-(4-(3-ethoxyphenoxy)piperidine-1-carbonyl)-N-methylbenzenesulfonamide;
N-methyl-3-(4-((3-(trifluoromethoxy)phenoxy)piperidine-1-carbonyl)benzenesulfonamide;
(1,5-naphthyridin-2-yl)(4-(3-(trifluoromethyl)phenoxy)piperidin-1-yl)methanone;
3-(4-((4-chlorophenyl)thio)piperidine-1-carbonyl)benzenesulfonamide;
(4-((4-chlorophenyl)thio)piperidin-1-yl)(1,5-naphthyridin-2-yl)methanone;
N-(6-(4-((4-chlorophenyl)thio)piperidine-1-carbonyl)pyridin-2-yl)acetamide;
(4-((4-chlorophenyl)thio)piperidin-1-yl)(1,6-naphthyridin-8-yl)methanone;
2-(4-(4-(3,4-difluorophenoxy)piperidine-1-carbonyl)phenoxy)acetamide;
(4-(3,4-difluorophenoxyl)piperidin-1-yl)(1,5-naphthyridin-2-yl)methanone;
2-(4-(4-(2,4-difluorophenoxy)piperidine-1-carbonyl)phenoxy)acetamide;
N-(4-(4-(3-(trifluoromethoxy)phenoxy)piperidine-1-carbonyl)pyridin-2-yl)pivalamide;
(2-(1H-imidazol-1-yl)pyridin-4-yl)(4-(3-(trifluoromethoxy)phenoxy)piperidin-1-yl)methanone;
N-(4-(4-(3-ethoxyphenoxyl)piperidine-1-carbonyl)pyridin-2-yl)pivalamide;
1-(3-(4-(3-(trifluoromethoxy)phenoxy)piperidine-1-carbonyl)phenyl)pyrrolidin-2-one;
1-(3-(4-(3-(trifluoromethoxy)phenoxy)piperidine-1-carbonyl)phenyl)imidazolidin-2-one;
(5-amino-1H-pyrazol-3-yl)(4-(3-(trifluoromethoxy)phenoxy)piperidin-1-yl)methanone;
or a pharmaceutically acceptable salt thereof.

4. A compound which is selected from:
(4-(4-chlorophenoxyl)piperidin-1-yl)(quinoxalin-6-yl)methanone;
(4-(4-chlorophenoxyl)piperidin-1-yl)(quinolin-8-yl)methanone;
(4-(1H-1,2,4-triazol-1-yl)phenyl)(4-(4-chlorophenoxyl)piperidin-1-yl)methanone;
(4-(4-chlorophenoxyl)piperidin-1-yl)(3,5-dimethylisoxazol-4-yl)methanone;
(4-(4-chlorophenoxyl)piperidin-1-yl)(2-methyl-2H-indazol-3-yl)methanone;
(4-(4-chlorophenoxyl)piperidin-1-yl)(6-methylpyridin-3-yl)methanone;
(4-(4-chlorophenoxyl)piperidin-1-yl)(6-methoxypyridin-3-yl)methanone;
(4-(4-chlorophenoxyl)piperidin-1-yl)(3-methylpyridin-2-yl)methanone;
(4-(4-chlorophenoxyl)piperidin-1-yl)(2,4-dimethylthiazol-5-yl)methanone;

(4-(4-chlorophenoxyl)piperidin-1-yl)(4,5,6,7-tetrahydro-1H-indazol-3-yl)methanone;
(4-(4-chlorophenoxyl)piperidin-1-yl)(6-methoxypyridin-2-yl)methanone;
(4-(4-chlorophenoxyl)piperidin-1-yl)(2-methyl-4,5,6,7-tetrahydro-2H-indazol-3-yl)methanone;
(4-(4-chlorophenoxyl)piperidin-1-yl)(1,5-naphthyridin-2-yl)methanone;
4-(4-(4-chlorophenoxy)piperidine-1-carbonyl)benzamide;
(4-(4-chlorophenoxyl)piperidin-1-yl)(4-(2-hydroxypropan-2-yl)phenyl)methanone;
(4-(4-chlorophenoxyl)piperidin-1-yl)(quinolin-5-yl)methanone;
(4-(4-fluorophenoxyl)piperidin-1-yl)(2-methyl-2H-indazol-3-yl)methanone;
(4-phenoxypiperidin-1-yl)(quinolin-8-yl)methanone;
(4-(4-fluorophenoxyl)piperidin-1-yl)(quinolin-8-yl)methanone;
(4-(4-chlorophenoxyl)piperidin-1-yl)(phenyl)methanone;
(1H-benzo[d]imidazol-5-yl)(4-(4-chlorophenoxyl)piperidin-1-yl)methanone;
(4-(4-chlorophenoxyl)piperidin-1-yl)(1,3-dimethyl-1H-pyrazol-5-yl)methanone;
(4-(3-methoxyphenoxyl)piperidin-1-yl)(quinolin-8-yl)methanone;
(4-(3-fluorophenoxyl)piperidin-1-yl)(quinolin-8-yl)methanone;
(4-(4-chlorophenoxyl)piperidin-1-yl)(2-methylthiazol-5-yl)methanone;
1-(3-((1-(quinoline-8-carbonyl)piperidin-4-yl)oxy)phenyl)ethanone;
(4-(4-chlorophenoxyl)piperidin-1-yl)(3-methylisoxazol-5-yl)methanone;
(4-(4-chlorophenoxyl)piperidin-1-yl)(1-isopropyl-1H-pyrazol-4-yl)methanone;
(4-(4-chlorophenoxyl)piperidin-1-yl)(3-isopropyl-1-methyl-1H-pyrazol-5-yl)methanone;
(4-(4-chlorophenoxyl)piperidin-1-yl)(3-ethyl-1-methyl-1H-pyrazol-5-yl)methanone;
(4-(4-chlorophenoxyl)piperidin-1-yl)(imidazo[1,2-a]pyrazin-2-yl)methanone;
(4-(4-chlorophenoxyl)piperidin-1-yl)(4-methyl-3,4-dihydro-2H-pyrido[3,2-b][1,4]oxazin-7-yl)methanone;
(4-(4-chlorophenoxyl)piperidin-1-yl)(pyrazolo[1,5-a]pyridin-7-yl)methanone;
(4-(4-chlorophenoxyl)piperidin-1-yl)(1-methyl-1H-imidazol-2-yl)methanone;
(4-(4-chlorophenoxyl)piperidin-1-yl)(1-methyl-1H-imidazol-4-yl)methanone;
(4-chloro-5-methyl-1H-pyrazol-3-yl)(4-(4-chlorophenoxy)piperidin-1-yl)methanone;
(4-(4-chlorophenoxyl)piperidin-1-yl)(4-methyl-4H-furo[3,2-b]pyrrol-5-yl)methanone;
(4-(4-chlorophenoxyl)piperidin-1-yl)(pyrazolo[1,5-a]pyrimidin-3-yl)methanone;
(4-(4-chlorophenoxyl)piperidin-1-yl)(2-(pyrrolidin-1-yl)pyrimidin-5-yl)methanone;
(1H-benzo[d][1,2,3]triazol-4-yl)(4-(4-chlorophenoxyl)piperidin-1-yl)methanone;
3-(4-(4-chlorophenoxy)piperidine-1-carbonyl)-1,6-dimethylpyridin-2(1H)-one;
(4-(4-chlorophenoxyl)piperidin-1-yl)(1-methyl-3-(trifluoromethyl)-1H-pyrazol-5-yl)methanone;
(4-(4-chlorophenoxyl)piperidin-1-yl)(4-(2-hydroxyethoxyl)phenyl)methanone;
(4-(4-chlorophenoxyl)piperidin-1-yl)(2-hydroxy-4-methoxyphenyl)methanone;
2-(3-(4-(4-chlorophenoxy)piperidine-1-carbonyl)-1H-indol-1-yl)-N,N-dimethylacetamide;
(4-(4-chlorophenoxyl)piperidin-1-yl)(3-fluoro-4-hydroxyphenyl)methanone;
2-chloro-5-(4-(4-chlorophenoxyl)piperidine-1-carbonyl)benzenesulfonamide;
(4-(4-chlorophenoxyl)piperidin-1-yl)(2-hydroxy-6-methoxyphenyl)methanone;
(4-(4-chlorophenoxyl)piperidin-1-yl)(2-fluoro-4-hydroxyphenyl)methanone;
(4-(4-chlorophenoxyl)piperidin-1-yl)(4-fluoro-3-hydroxyphenyl)methanone;
(4-(4-chlorophenoxyl)piperidin-1-yl)(2-hydroxy-3-methoxyphenyl)methanone;
N-(3-(4-(4-chlorophenoxy)piperidine-1-carbonyl)phenyl)acetamide;
(4-(4-chlorophenoxyl)piperidin-1-yl)(1-((4-hydroxytetrahydro-2H-pyran-4-yl)methyl)-1H-indol-5-yl)methanone;
N-(6-(4-(4-chlorophenoxy)piperidine-1-carbonyl)pyridin-2-yl)acetamide;
N-(4-(4-(4-chlorophenoxy)piperidine-1-carbonyl)pyridin-2-yl)acetamide;
(4-(4-chlorophenoxyl)piperidin-1-yl)(1,6-naphthyridin-5-yl)methanone;
(4-(4-chlorophenoxyl)piperidin-1-yl)(3-hydroxyphenyl)methanone;
(4-(4-chlorophenoxyl)piperidin-1-yl)(2-fluoro-3-hydroxyphenyl)methanone;
(3-(tert-butyl)-1-methyl-1H-pyrazol-5-yl)(4-(4-fluorophenoxyl)piperidin-1-yl)methanone;
(4-fluoro-3-methoxyphenyl)(4-(4-fluorophenoxyl)piperidin-1-yl)methanone;
(4-((4-chlorophenyl)sulfonyl)piperidin-1-yl)(2-methyl-2H-indazol-3-yl)methanone;
(4-(4-fluorophenoxyl)piperidin-1-yl)(1-methyl-1H-indazol-3-yl)methanone;
(4-(4-fluorophenoxyl)piperidin-1-yl)(4-methoxyquinolin-2-yl)methanone;
(4-(4-fluorophenoxyl)piperidin-1-yl)(isoquinolin-1-yl)methanone;
(5-aminopyridin-2-yl)(4-(4-chlorophenoxyl)piperidin-1-yl)methanone;
(1,3-dimethyl-1H-pyrazol-5-yl)(4-(3-(trifluoromethoxy)phenoxy)piperidin-1-yl)methanone;
(3,5-dimethylisoxazol-4-yl)(4-(3-(trifluoromethoxy)phenoxy)piperidin-1-yl)methanone;
(3-methylpyridin-2-yl)(4-(3-(trifluoromethoxy)phenoxy)piperidin-1-yl)methanone;
4-(4-(3-(trifluoromethoxy)phenoxy)piperidine-1-carbonyl)picolinamide;
(1-methyl-1H-imidazol-4-yl)(4-(3-(trifluoromethoxy)phenoxy)piperidin-1-yl)methanone;
(2-hydroxy-6-methoxyphenyl)(4-(3-(trifluoromethoxy)phenoxy)piperidin-1-yl)methanone;
(2,4-dimethylthiazol-5-yl)(4-(3-(trifluoromethoxy)phenoxy)piperidin-1-yl)methanone;
(2-methyl-2H-indazol-3-yl)(4-(3-(trifluoromethoxy)phenoxy)piperidin-1-yl)methanone;
1,6-dimethyl-3-(4-((3-(trifluoromethoxy)phenoxy)piperidine-1-carbonyl)pyridin-2(1H)-one;
benzo[d]thiazol-6-yl(4-(4-fluorophenoxyl)piperidin-1-yl)methanone;
(4-(4-fluorophenoxyl)piperidin-1-yl)(1-methyl-1H-benzo[d]imidazol-2-yl)methanone;

(2-methyloxazol-4-yl)(4-(3-(trifluoromethoxy)phenoxy)piperidin-1-yl)methanone;
N-(4-(4-(3-(trifluoromethoxy)phenoxy)piperidine-1-carbonyl)pyridin-2-yl)acetamide;
N-(6-(4-(3-(trifluoromethoxy)phenoxy)piperidine-1-carbonyl)pyridin-2-yl)acetamide;
3-(4-(3-(trifluoromethoxy)phenoxy)piperidine-1-carbonyl)benzamide;
(6-(hydroxymethyl)pyridin-2-yl)(4-(3-(trifluoromethoxy)phenoxy)piperidin-1-yl)methanone;
5,6-dimethyl-3-(4-((3-(trifluoromethoxy)phenoxy)piperidine-1-carbonyl)pyridin-2(1H)-one;
4-(4-(3-(trifluoromethoxy)phenoxy)piperidine-1-carbonyl)-1H-benzo[d]imidazol-2(3H)-one;
(4-(4-chloro-2-methoxyphenoxy)piperidin-1-yl)(quinolin-8-yl)methanone;
3-(4-(3-(trifluoromethyl)phenoxy)piperidine-1-carbonyl)benzamide;
4-(4-(3-(trifluoromethyl)phenoxy)piperidine-1-carbonyl)picolinamide;
(4-(4-fluorophenoxyl)piperidin-1-yl)(5-methyl-1-phenyl-1H-pyrazol-4-yl)methanone;
4-(4-chlorophenoxyl)piperidine-1-carbonyl)-N-(2-methoxyethyl)-N-methylbenzamide;
(S)-4-(4-(4-chlorophenoxyl)piperidine-1-carbonyl)-N-(2-hydroxy-2-phenylethyl)benzamide;
4-(4-((4-chlorophenyl)thio)piperidine-1-carbonyl)picolinamide;
6-(4-(3-(trifluoromethoxy)phenoxy)piperidine-1-carbonyl)picolinamide;
(2-(methylsulfonyl)phenyl)(4-(3-(trifluoromethoxy)phenoxy)piperidin-1-yl)methanone;
(4-(3-ethoxyphenoxyl)piperidin-1-yl)(quinolin-8-yl)methanone;
N-methyl-3-(4-(3-(trifluoromethoxy)phenoxy)piperidine-1-carbonyl)benzamide;
3-(4-(3-(trifluoromethoxy)phenoxy)piperidine-1-carbonyl)benzenesulfonamide;
4-(4-(3-(trifluoromethoxy)phenoxy)piperidine-1-carbonyl)benzenesulfonamide;
(4-(4-fluorophenoxyl)piperidin-1-yl)(1,5-naphthyridin-2-yl)methanone;
(4-(4-fluorophenoxyl)piperidin-1-yl)(quinolin-2-yl)methanone;
(4-(3-fluorophenoxyl)piperidin-1-yl)(4-methoxyquinolin-2-yl)methanone;
(1H-benzo[d][1,2,3]triazol-7-yl)(4-(3-(trifluoromethoxy)phenoxy)piperidin-1-yl)methanone;
2-(2-(4-(4-chlorophenoxy)piperidine-1-carbonyl)phenoxy)acetamide;
2-(2-(4-(3-(trifluoromethoxy)phenoxy)piperidine-1-carbonyl)phenoxy)acetamide;
(4-((4-chlorophenyl)sulfonyl)piperidin-1-yl)(5-phenyl-isoxazol-3-yl)methanone;
(4-hydroxyquinolin-8-yl)(4-(3-(trifluoromethoxy)phenoxy)piperidin-1-yl)methanone;
(1,8-naphthyridin-4-yl)(4-(3-(trifluoromethoxy)phenoxy)piperidin-1-yl)methanone;
(1,6-naphthyridin-8-yl)(4-(3-(trifluoromethoxy)phenoxy)piperidin-1-yl)methanone;
[1,2,4]triazolo[1,5-a]pyrimidin-2-yl(4-(3-(trifluoromethoxy)phenoxy)piperidin-1-yl)methanone;
(5-methyl-1H-pyrazol-3-yl)(4-(3-(trifluoromethoxy)phenoxy)piperidin-1-yl)methanone;
2-chloro-5-(4-(3-(trifluoromethoxy)phenoxy)piperidine-1-carbonyl)benzenesulfonamide;
(S)-3-(4-(4-chlorophenoxyl)piperidine-1-carbonyl)-N-(2-hydroxy-2-phenylethyl)benzamide;
(S)—N-(1-amino-1-oxo-3-phenylpropan-2-yl)-3-(4-(4-chlorophenoxy)piperidine-1-carbonyl)benzamide;
(4-((4-chlorophenyl)sulfonyl)piperidin-1-yl)(2-phenylthiazol-4-yl)methanone;
(5-fluoro-2-(methylsulfonyl)phenyl)(4-(3-(trifluoromethoxy)phenoxy)piperidin-1-yl)methanone;
N,N-dimethyl-4-(4-(3-(trifluoromethoxy)phenoxy)piperidine-1-carbonyl)benzenesulfonamide;
N-(2-(4-(4-(3-(trifluoromethoxy)phenoxy)piperidine-1-carbonyl)phenoxy)ethyl)acetamide;
N-(4-(4-(3-ethoxyphenoxyl)piperidine-1-carbonyl)pyridin-2-yl)acetamide;
3-(4-(3-ethoxyphenoxy)piperidine-1-carbonyl)benzenesulfonamide;
N-(6-(4-(3-ethoxyphenoxyl)piperidine-1-carbonyl)pyridin-2-yl)acetamide;
(4-(3-ethoxyphenoxyl)piperidin-1-yl)(1,5-naphthyridin-2-yl)methanone;
quinolin-8-yl(4-((4-(trifluoromethoxy)phenyl)sulfonyl)piperidin-1-yl)methanone;
quinolin-2-yl(4-((4-(trifluoromethoxy)phenyl)sulfonyl)piperidin-1-yl)methanone;
(2-(ethylsulfonyl)phenyl)(4-(3-(trifluoromethoxy)phenoxy)piperidin-1-yl)methanone;
2-(4-(3-(trifluoromethoxy)phenoxy)piperidine-1-carbonyl)thiazole-4-carboxamide;
(4-(4-(3-(trifluoromethoxy)phenoxy)piperidine-1-carbonyl)phenyl)methanesulfonamide;
4-methoxy-3-(4-(3-(trifluoromethoxy)phenoxy)piperidine-1-carbonyl)benzenesulfonamide;
2-((2-(4-(3-(trifluoromethoxy)phenoxy)piperidine-1-carbonyl)pyridin-3-yl)oxy)acetamide;
(4-(aminomethyl)pyridin-2-yl)(4-(3-(trifluoromethoxy)phenoxy)piperidin-1-yl)methanone;
N-((2-(4-(3-(trifluoromethoxy)phenoxy)piperidine-1-carbonyl)pyridin-4-yl)methyl)methanesulfonamide;
ethyl ((2-(4-(3-(trifluoromethoxy)phenoxy)piperidine-1-carbonyl)pyridin-4-yl)methyl)carbamate;
N-(2-(4-(3-(trifluoromethoxy)phenoxy)piperidine-1-carbonyl)benzyl)acetamide;
N-(2-(4-(3-(trifluoromethoxy)phenoxy)piperidine-1-carbonyl)benzyl)methanesulfonamide;
(2-(methylsulfonyl)phenyl)(4-(3-(2,2,2-trifluoroethoxy)phenoxy)piperidin-1-yl)methanone;
N-(4-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)picolinamide;
3-(4-(3-(2,2,2-trifluoroethoxy)phenoxy)piperidine-1-carbonyl)benzamide;
2-(2-(4-(3-(2,2,2-trifluoroethoxy)phenoxy)piperidine-1-carbonyl)phenoxy)acetamide;
(1,5-naphthyridin-2-yl)(4-(3-(2,2,2-trifluoroethoxyl)phenoxy)piperidin-1-yl)methanone;
(2-methyl-2H-indazol-3-yl)(4-(3-(2,2,2-trifluoroethoxyl)phenoxy)piperidin-1-yl)methanone;
(1,3-dimethyl-1H-pyrazol-5-yl)(4-(3-(2,2,2-trifluoroethoxy)phenoxy)piperidin-1-yl)methanone;
N-(6-(4-(3-(2,2,2-trifluoroethoxy)phenoxy)piperidine-1-carbonyl)pyridin-2-yl)acetamide;
4-(4-(3-(2,2,2-trifluoroethoxy)phenoxy)piperidine-1-carbonyl)benzamide;
(3,5-dimethylisoxazol-4-yl)(4-(3-(2,2,2-trifluoroethoxy)phenoxy)piperidin-1-yl)methanone;

(3-(methylsulfonyl)phenyl)(4-(3-(2,2,2-trifluoroethoxy)phenoxy)piperidin-1-yl)methanone;
(1,6-naphthyridin-8-yl)(4-(3-(2,2,2-trifluoroethoxyl)phenoxy)piperidin-1-yl)methanone;
(3-methyl-1H-pyrazol-5-yl)(4-(3-(2,2,2-trifluoroethoxyl)phenoxy)piperidin-1-yl)methanone;
2-(3-(4-(3-(2,2,2-trifluoroethoxy)phenoxy)piperidine-1-carbonyl)phenoxy)acetamide;
1-(4-(4-(3-(trifluoromethoxy)phenoxy)piperidine-1-carbonyl)phenyl)urea;
(1H-1,2,4-triazol-3-yl)(4-(3-(2,2,2-trifluoroethoxyl)phenoxy)piperidin-1-yl)methanone;
(4-(3-ethoxyphenoxyl)piperidin-1-yl)(3-(methylsulfonyl)phenyl)methanone;
(4-(3-ethoxyphenoxyl)piperidin-1-yl)(3-methyl-1H-pyrazol-5-yl)methanone;
N,N-dimethyl-3-(4-((3-(trifluoromethoxy)phenoxy)piperidine-1-carbonyl)benzenesulfonamide;
N-(2-(4-(3-(trifluoromethoxy)phenoxy)piperidine-1-carbonyl)phenyl)methanesulfonamide;
(6-aminopyridin-2-yl)(4-(3-(trifluoromethoxy)phenoxy)piperidin-1-yl)methanone;
N,N-dimethyl-2-(2-(4-(3-(trifluoromethoxy)phenoxy)piperidine-1-carbonyl)phenoxy)acetamide;
(1,3-dimethyl-1H-pyrazol-5-yl)(4-(3-(trifluoromethyl)phenoxy)piperidin-1-yl)methanone;
(2-(methylsulfonyl)phenyl)(4-(3-(trifluoromethyl)phenoxy)piperidin-1-yl)methanone;
N-(6-(4-(3-(trifluoromethyl)phenoxy)piperidine-1-carbonyl)pyridin-2-yl)acetamide;
3-(4-(3-(trifluoromethyl)phenoxy)piperidine-1-carbonyl)benzenesulfonamide;
(3,5-dimethylisoxazol-4-yl)(4-(3-(trifluoromethyl)phenoxy)piperidin-1-yl)methanone;
(1,6-naphthyridin-8-yl)(4-(3-(trifluoromethyl)phenoxy)piperidin-1-yl)methanone;
(3-methyl-1H-pyrazol-5-yl)(4-(3-(trifluoromethyl)phenoxy)piperidin-1-yl)methanone;
2-(2-(4-(3-(trifluoromethyl)phenoxy)piperidine-1-carbonyl)phenoxy)acetamide;
2-(3-(4-(3-(trifluoromethyl)phenoxy)piperidine-1-carbonyl)phenoxy)acetamide;
(1H-1,2,4-triazol-3-yl)(4-(3-(trifluoromethyl)phenoxy)piperidin-1-yl)methanone;
N-(2-(2-(4-(3-(trifluoromethoxy)phenoxy)piperidine-1-carbonyl)phenoxy)ethyl)methanesulfonamide;
N-(2-(2-(4-(3-(trifluoromethoxy)phenoxy)piperidine-1-carbonyl)phenoxy)ethyl)cyclopropane-1,1-dicarboxamide;
N-(2-(3-(4-(3-(trifluoromethoxy)phenoxy)piperidine-1-carbonyl)phenoxy)ethyl)methanesulfonamide;
N-(3-(4-(3-(trifluoromethoxy)phenoxy)piperidine-1-carbonyl)pyridin-2-yl)acetamide;
N-(1-methyl-5-(4-(3-(trifluoromethoxy)phenoxy)piperidine-1-carbonyl)-1H-pyrazol-3-yl)acetamide;
(2-(ethylsulfonyl)phenyl)(4-(3-(trifluoromethyl)phenoxy)piperidin-1-yl)methanone;
(2-(ethylsulfonyl)phenyl)(4-(3-(2,2,2-trifluoroethoxy)phenoxy)piperidin-1-yl)methanone;
N-(2-(4-(3-(trifluoromethoxy)phenoxy)piperidine-1-carbonyl)pyridin-3-yl)acetamide;
(3-(methylsulfonyl)phenyl)(4-(3-(trifluoromethyl)phenoxy)piperidin-1-yl)methanone;
(4-(3-chlorophenoxyl)piperidin-1-yl)(3-(methylsulfonyl)phenyl)methanone;
(4-(4-chlorophenoxyl)piperidin-1-yl)(3-(methylsulfonyl)phenyl)methanone;
(4-(4-chlorophenoxyl)piperidin-1-yl)(2-(ethylsulfonyl)phenyl)methanone;
N,N-dimethyl-3-(4-(3-(trifluoromethyl)phenoxy)piperidine-1-carbonyl)benzenesulfonamide;
3-(4-(4-chlorophenoxyl)piperidine-1-carbonyl)-N,N-dimethylbenzenesulfonamide;
(4-(3-(2-methoxyethoxyl)phenoxy)piperidin-1-yl)(quinolin-8-yl)methanone;
(4-(3-(2-methoxyethoxyl)phenoxy)piperidin-1-yl)(quinolin-2-yl)methanone;
(4-(3-(2-methoxyethoxyl)phenoxy)piperidin-1-yl)(2-methyl-2H-indazol-3-yl)methanone;
2-((2-(4-(3-(trifluoromethoxy)phenoxy)piperidine-1-carbonyl)phenyl)thio)acetamide;
2-((2-(4-(4-chlorophenoxyl)piperidine-1-carbonyl)phenyl)thio)acetamide;
4-(4-(3-(2,2,2-trifluoroethoxyl)phenoxy)piperidine-1-carbonyl)-1H-benzo[d]imidazol-2(3H)-one;
(4-(3-ethoxyphenoxyl)piperidin-1-yl)(1-methyl-1H-benzo[d]imidazol-2-yl)methanone;
(4-(3-fluorophenoxyl)piperidin-1-yl)(1-methyl-1H-benzo[d]imidazol-2-yl)methanone;
(4-(3-ethoxyphenoxyl)piperidin-1-yl)(1-methyl-1H-pyrazolo[3,4-b]pyridin-3-yl)methanone;
(4-(3-ethoxyphenoxyl)piperidin-1-yl)(pyrazolo[1,5-a]pyrimidin-3-yl)methanone;
(4-(3-fluorophenoxyl)piperidin-1-yl)(4-methyl-3,4-dihydro-2H-pyrido[3,2-b][1,4]oxazin-7-yl)methanone;
(3,5-dimethyl-1H-pyrazol-4-yl)(4-(3-(2,2,2-trifluoroethoxyl)phenoxy)piperidin-1-yl)methanone;
N-(2-hydroxyethyl)-N-methyl-2-(4-(3-(trifluoromethoxy)phenoxy)piperidine-1-carbonyl)benzenesulfonamide;
(2-(morpholinosulfonyl)phenyl)(4-(3-(trifluoromethoxy)phenoxy)piperidin-1-yl)methanone;
2-(N-methyl-2-(4-(3-(trifluoromethoxy)phenoxy)piperidine-1-carbonyl)phenylsulfonamido)acetamide;
N-methyl-3-(4-(3-(2,2,2-trifluoroethoxyl)phenoxy)piperidine-1-carbonyl)benzenesulfonamide;
3-(4-(3-ethoxyphenoxyl)piperidine-1-carbonyl)-N-methylbenzenesulfonamide;
N-methyl-3-(4-(3-(trifluoromethoxy)phenoxy)piperidine-1-carbonyl)benzenesulfonamide;
(4-((4-chlorophenyl)thio)piperidin-1-yl)(1,5-naphthyridin-2-yl)methanone;
N-(6-(4-((4-chlorophenyl)thio)piperidine-1-carbonyl)pyridin-2-yl)acetamide;
2-(4-(4-(3,4-difluorophenoxy)piperidine-1-carbonyl)phenoxy)acetamide;
(4-(3,4-difluorophenoxyl)piperidin-1-yl)(1,5-naphthyridin-2-yl)methanone;
2-(4-(4-(2,4-difluorophenoxy)piperidine-1-carbonyl)phenoxy)acetamide;
N-(4-(4-(3-(trifluoromethoxy)phenoxy)piperidine-1-carbonyl)pyridin-2-yl)pivalamide; and
(5-amino-1H-pyrazol-3-yl)(4-(3-(trifluoromethoxy)phenoxy)piperidin-1-yl)methanone;
or a pharmaceutically acceptable salt thereof.

5. A pharmaceutical composition comprising the compound or the pharmaceutically acceptable salt thereof, as claimed in claim 1, and a pharmaceutically acceptable carrier.

6. A pharmaceutical composition as claimed in claim 5, further comprising another pharmacologically active agent.

* * * * *